(12) United States Patent
Kobayashi et al.

(10) Patent No.: US 8,653,067 B2
(45) Date of Patent: *Feb. 18, 2014

(54) PHARMACEUTICAL COMPOSITION FOR TREATING ALZHEIMER'S DISEASE

(75) Inventors: Naotake Kobayashi, Osaka (JP); Kazuo Ueda, Osaka (JP); Naohiro Itoh, Osaka (JP); Gaku Sakaguchi, Shiga (JP); Akira Kato, Shiga (JP); Akihiro Hori, Osaka (JP); Hidekazu Haraguchi, Tokyo (JP); Ken Yasui, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 577 days.

This patent is subject to a terminal disclaimer.

(21) Appl. No.: 12/597,470

(22) PCT Filed: Apr. 23, 2008

(86) PCT No.: PCT/JP2008/057842
§ 371 (c)(1),
(2), (4) Date: Nov. 24, 2009

(87) PCT Pub. No.: WO2008/133273
PCT Pub. Date: Nov. 6, 2008

(65) Prior Publication Data
US 2010/0160290 A1 Jun. 24, 2010

(30) Foreign Application Priority Data
Apr. 24, 2007 (JP) .................. 2007-114764

(51) Int. Cl.
| | | |
|---|---|---|
| A61K 31/554 | (2006.01) | |
| A61K 31/541 | (2006.01) | |
| A61K 31/426 | (2006.01) | |
| A61K 31/506 | (2006.01) | |
| C07D 417/02 | (2006.01) | |
| C07D 279/06 | (2006.01) | |
| C07D 277/18 | (2006.01) | |
| C07D 239/02 | (2006.01) | |

(52) U.S. Cl.
USPC ............... 514/227.2; 514/211.01; 514/370; 514/275; 544/54; 544/330; 548/199; 540/544

(58) Field of Classification Search
USPC ........... 514/227.2, 211.01, 370, 275; 544/54, 544/330; 548/199; 540/544
See application file for complete search history.

(56) References Cited

U.S. PATENT DOCUMENTS

| | | |
|---|---|---|
| 3,115,494 A | 12/1963 | Joseph et al. |
| 3,227,713 A | 1/1966 | Behner et al. |
| 3,235,551 A | 2/1966 | Schubert et al. |
| 3,636,116 A | 1/1972 | Trepanier |
| 3,719,674 A | 3/1973 | Trepanier |
| 3,775,409 A | 11/1973 | Harsanyi et al. |
| 4,311,840 A | 1/1982 | Condon |
| 4,895,841 A | 1/1990 | Sugimoto et al. |
| 4,906,626 A | 3/1990 | Amrein et al. |
| 5,100,901 A | 3/1992 | Sugimoto et al. |
| 5,236,942 A | 8/1993 | Miller |
| 5,328,915 A | 7/1994 | Long et al. |
| 5,880,147 A | 3/1999 | Yoshida et al. |
| 5,952,374 A | 9/1999 | Clarkson, Jr. et al. |
| 6,096,753 A | 8/2000 | Spohr et al. |
| 6,590,123 B2 | 7/2003 | Bekesi et al. |
| 6,713,276 B2 | 3/2004 | Cordell et al. |
| 7,183,070 B2 | 2/2007 | Cordell et al. |
| 7,309,706 B2 * | 12/2007 | Rupp et al. ............. 514/269 |
| 7,326,792 B2 * | 2/2008 | Shum et al. ............. 548/331.5 |
| 7,414,050 B2 * | 8/2008 | Illig et al. ............. 514/222.5 |
| 7,763,609 B2 * | 7/2010 | Zhu et al. ............. 514/229.2 |
| 7,902,238 B2 * | 3/2011 | Galley et al. ............. 514/374 |
| 8,173,642 B2 * | 5/2012 | Kobayashi et al. ....... 514/227.2 |

(Continued)

FOREIGN PATENT DOCUMENTS

| | | |
|---|---|---|
| DE | 140144 | 2/1980 |
| EP | 0798 292 | 10/1995 |

(Continued)

OTHER PUBLICATIONS

Co-pending U.S. Appl. No. 13/260,103, entitled Isothiourea Derivatives or Isourea Derivatives Having BACEI Inhibitory Activity, filed Sep. 23, 2011.

(Continued)

*Primary Examiner* — Jennifer M Kim
(74) *Attorney, Agent, or Firm* — Hamre, Schumann, Mueller & Larson, P.C.

(57) ABSTRACT

A pharmaceutical composition for treating Alzheimer's disease containing a compound represented by the general formula (I);

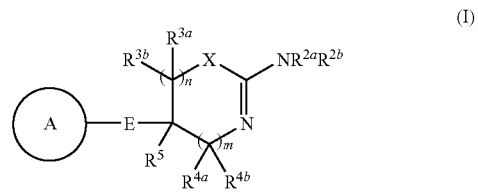

(I)

wherein ring A is an optionally substituted carbocyclic group or an optionally substituted heterocyclic group;
E is lower alkylene, etc.;
X is S, O, or $NR^1$;
$R^1$ is a hydrogen atom or lower alkyl;
$R^{2a}$, $R^{2b}$, $R^{3a}$, $R^{3b}$, $R^{4a}$ and $R^{4b}$ are each independently a hydrogen atom, halogen, hydroxy, etc.;
n and m are each independently an integer of 0 to 3;
n+m is an integer of 1 to 3; and
$R^5$ is a hydrogen atom, optionally substituted lower alkyl, etc.;
its pharmaceutically acceptable salt, or a solvate thereof as an active ingredient.

9 Claims, No Drawings

(56) References Cited

U.S. PATENT DOCUMENTS

| | | |
|---|---|---|
| 2002/0019427 A1 | 2/2002 | Carry et al. |
| 2005/0165080 A1 | 7/2005 | Rupp et al. |
| 2006/0173006 A1 | 8/2006 | Sun et al. |
| 2006/0183790 A1 | 8/2006 | Cole et al. |
| 2006/0183792 A1 | 8/2006 | Fobare et al. |
| 2006/0183943 A1 | 8/2006 | Hu et al. |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1 | 8/2008 | Zhu et al. |
| 2009/0023729 A1 | 1/2009 | Nakamuta et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1 | 5/2010 | Holenz et al. |
| 2010/0234365 A1* | 9/2010 | Liu et al. ............... 514/227.8 |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258962 A1 | 10/2012 | Hilpert et al. |
| 2012/0295900 A1 | 11/2012 | Hilpert et al. |
| 2013/0158260 A1 | 6/2013 | Kobayashi et al. |

FOREIGN PATENT DOCUMENTS

| | | |
|---|---|---|
| EP | 0713704 | 5/1996 |
| EP | 0717040 | 6/1996 |
| EP | 0718294 | 6/1996 |
| EP | 1043312 | 10/2000 |
| EP | 1283039 | 2/2003 |
| EP | 1 577 294 | 9/2005 |
| EP | 1 942 105 | 7/2008 |
| EP | 1942105 | 7/2008 |
| EP | 2147914 | 1/2010 |
| EP | 2151435 | 2/2010 |
| EP | 2 233 474 | 9/2010 |
| EP | 2305672 | 4/2011 |
| EP | 2332943 | 6/2011 |
| EP | 2 360 155 | 8/2011 |
| EP | 2415756 | 2/2012 |
| GB | 1001093 | 8/1965 |
| JP | 62-120374 | 6/1987 |
| JP | 8-231521 | 9/1996 |
| JP | 09-067355 | 3/1997 |
| JP | 10-505862 | 12/1999 |
| JP | 11/349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| WO | 94/012165 | 6/1994 |
| WO | 95/09619 | 4/1995 |
| WO | 96/09286 | 3/1996 |
| WO | 96/14842 | 5/1996 |
| WO | 96/18608 | 6/1996 |
| WO | 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | 01/19788 | 3/2001 |
| WO | 01/078709 | 10/2001 |
| WO | WO 01/87293 | 11/2001 |
| WO | 2002/062766 | 8/2002 |
| WO | 02/088101 | 11/2002 |
| WO | 02/096897 | 12/2002 |
| WO | 03/039446 | 5/2003 |
| WO | 03/040096 | 5/2003 |
| WO | 03/040115 | 5/2003 |
| WO | 03/040142 | 5/2003 |
| WO | 03/082191 | 10/2003 |
| WO | 2004/009549 | 1/2004 |
| WO | 2004/014843 | 2/2004 |
| WO | 2004/031154 | 4/2004 |
| WO | 2004/039404 | 5/2004 |
| WO | 2004/043916 | 5/2004 |
| WO | 2004/096795 | 11/2004 |
| WO | 2005/014555 | 2/2005 |
| WO | 2005/032493 | 4/2005 |
| WO | 2005/058311 | 6/2005 |
| WO | 2005/097767 | 10/2005 |
| WO | WO2005/111031 A2 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | 2006/041404 | 4/2006 |
| WO | 2006/041405 | 4/2006 |
| WO | 2006/065204 | 6/2006 |
| WO | 2006/065277 | 6/2006 |
| WO | 2006/076284 | 7/2006 |
| WO | 2006/099379 | 9/2006 |
| WO | 2006/138265 | 12/2006 |
| WO | 2006/138304 | 12/2006 |
| WO | WO 2006/138192 | 12/2006 |
| WO | WO 2006/138217 | 12/2006 |
| WO | 2007/002220 | 1/2007 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | 2007/049532 | 5/2007 |
| WO | 2007/058580 | 5/2007 |
| WO | WO 2007/058582 | 5/2007 |
| WO | WO 2007/058583 | 5/2007 |
| WO | WO 2007/058601 | 5/2007 |
| WO | WO 2007/058602 | 5/2007 |
| WO | 2007/073284 | 6/2007 |
| WO | WO 2007/078813 | 7/2007 |
| WO | 2007/092846 | 8/2007 |
| WO | 2007/092854 | 8/2007 |
| WO | 2007/114771 | 10/2007 |
| WO | 2007/120096 | 10/2007 |
| WO | 2007/146225 | 12/2007 |
| WO | 2008/011560 | 1/2008 |
| WO | 2008/022024 | 2/2008 |
| WO | 2008/073365 | 6/2008 |
| WO | WO 2008/073370 | 6/2008 |
| WO | 2008/103351 | 8/2008 |
| WO | WO 2008/133273 | 11/2008 |
| WO | WO2008/133274 A1 | 11/2008 |
| WO | 2009/010454 | 1/2009 |
| WO | 2009/064418 | 5/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | WO 2009/134617 | 11/2009 |
| WO | 2009/151098 | 12/2009 |
| WO | 2010/019392 | 2/2010 |
| WO | 2010/019393 | 2/2010 |
| WO | WO 2010/013302 | 2/2010 |
| WO | WO 2010/013794 | 2/2010 |

(56) References Cited

FOREIGN PATENT DOCUMENTS

| WO | 2010/047372 | 4/2010 |
|---|---|---|
| WO | 2010/056194 | 5/2010 |
| WO | 2010/056195 | 5/2010 |
| WO | 2010/056196 | 5/2010 |
| WO | 2010/113848 | 10/2010 |
| WO | 2010/128058 | 11/2010 |
| WO | 2010/129864 | 11/2010 |
| WO | 2011/005738 | 1/2011 |
| WO | 2011/009897 | 1/2011 |
| WO | 2011/009898 | 1/2011 |
| WO | 2011/009943 | 1/2011 |
| WO | 2011/020806 | 2/2011 |
| WO | 2011/029803 | 3/2011 |
| WO | 2011/044181 | 4/2011 |
| WO | 2011/044184 | 4/2011 |
| WO | 2011/044185 | 4/2011 |
| WO | 2011/044187 | 4/2011 |
| WO | 2011/058763 | 5/2011 |
| WO | 2011/060207 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | 2011/080176 | 7/2011 |
| WO | 2011/138293 | 11/2011 |
| WO | 2011/154374 | 12/2011 |
| WO | 2011/154431 | 12/2011 |
| WO | 2012/000933 | 1/2012 |
| WO | 2012/006953 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095469 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).

Clark, et al., "Antitumor Imidazotetrazines, 32,1 Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.

Congreve, et al., "Application of Fragment Screening by X-ray Crystallography to the Discovery of Aminopyridines as Inhibitors of β-Secretase§", J. Med. Chem., vol. 50, 2007, pp. 1124-1132.

Huang, et al., "Progress in the Development of Nonpeptidomimetic BACE 1 Inhibitors for Alzheimer's Disease", Current Medicinal Chemistry, vol. 16, 2009, pp. 1806-1820.

Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.

Siddiqui et al., "Some extensions of Von Bruan (BrCN) reaction on organic bases," Proc. Pakistan Acad. Sci., 1988, vol. 25, No. 3, pp. 231-240.

Ozawa et al., Pharmacological actions of 2-Aminoethylisothiuronium (AET) derivatives. I1), Yakugaku Zasshi, 1968, vol. 88, No. 2, pp. 156-162 (with English language abstract).

Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp. 2193-2196.

Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65(and International Search Report issued in PCT/JP2010/055528, which corresponds to co-pending U.S. Appl. No. 13/260,103).

Desai et al., "The condensation of thiocarbamides with monochloroacetic acid and the conversion of arylformamidinethiolacetic acids into pseudothiohydantoin derivatives," Recuil des Travaux Chimiques des Pays-Bas et de la Belgique, 1935, pp. 118-121.

Cole et al., "Acylguanidines as small-molecule beta-secretase inhibitors," J. Med. Chem., 2006, pp. 6158-6161.

Co-pending U.S. Appl. No. 13/417,786, entitled Aminodihydrothiazine Derivatives Substituted With a Cyclic Group, filed Mar. 12, 2012.

Hünig et al., "Azofarbstoffe Durch Oxydative Kupplung, XVII[1])Synthese von 3-substituierten Thiazolon-(2)-hydrazonen und Thiazolon-(2)-benzolsulfonylhydrazonen", 1961, vol. 647, pp. 66-76 (with English abstract).

Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.

Fujisawa et al., "Switchover of diastereofacial selectivity in the condensation reaction of optically active N-sulfinimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "N-Alkylidenesulfinamides," Sulfur Reports, vol. 21, 1999, pp. 211-239.

Vippagunta et al. "Crystalline Solids". Advanced Drug Delivery Reviews, vol. 48, 2001, pp. 3-26.

Gavezzotti. "Are Crystal Structures Predictable". Accounts of Chemical Research, vol. 27, 1994, pp. 309-314.

Savoca et al., "1,5-Diazabicyclo[4.3.0]non-5-ene[1]," Encyclopedia of Reagents for Organic Synthesis, 2006, 10 pages total.

Creeke et al., "Synthesis and elaboration of heterocycles via iodocyclisation of unsaturated thioureas," Tetrahedron Letters, 1989, vol. 30, No. 33, pp. 4435-4438.

Mellor et al.,"A general route to spirocycles by radical additions to exocyclic unsaturated sulphides and related compounds," Tetrahedron Letters, 1991, vol. 32, No. 48, pp. 7111-7114.

Murai et al., "Indo-cyclization of N-homoallyl thioamides leading to 2,4-diaryl-5,6-dihydro-4H-1,3-thiazines," Chemistry Letters, 2004, vol. 33, No. 5, pp. 508-509.

Singh et al., "Synthesis of heterocyclic compounds via enamines. Part 8.[1] Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.

(56) References Cited

OTHER PUBLICATIONS

International Search Report for PCT/JP2006/321015.
Specification for co-pending U.S. Appl. No. 12/997,802 entitled Sulfur-Containing Heterocyclic Derivative Having Beta Secretase Inhibitory Activity.
Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.
Schubert et al., "Neue synthesen von 2-Amino-5,6-dihydro-4H-1,3-thiazinen," Archiv der Pharmazie, 1968, vol. 301, No. 10, pp. 750-762.
Huang et al., "Pharmacophore model construction of βsecretase inhibitors," 2008, Acta Chimica Sinica, vol. 66, No. 16, pp. 1889-1897 (English language abstract provided).
Specification for co-pending U.S. Appl. No. 12/997,802, filed Dec. 13, 2010 entitled Sulfur-Containing Heterocyclic Derivative Having Beta Secretase Inhibitory Activity.
Co-pending U.S. Appl. No. 13/518,285, entitled 4-Amino-1,3-Thiazine or Oxazine Derivative, filed Jun. 21, 2012.
Bol'but et al., Heterocyclizations of Functionalized Heterocumulenes with C,N- and C,O-Dinucleophiles: III. Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 29, No. 2, pp. 1789-1791.
Trepanier et al,, "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.
Sayed et al., "α-Enones in heterocyclic synthesis of indazole, thiazine, chromene and quinolone derivatives with their antimicrobial activities," Journal of Chemical Research, 2009, vol. 12, pp. 726-728.
Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 abstract Accessed Jul. 13, 2012.
Bol'but et al., "Synthesis of 4-imino-2-trifluoromethyl-3,4-dihydro-2h-Benzo-[1,3]Thiazines," Chemistry of Heterocyclic Compounds, 2001, vol. 37, No. 4, pp. 522-523.
Vovk et al., "Intramolecular thermal cyclization of N-(1-Aryl-1-aryloxy-2,2,2-trifluoroethyl)-N'-arylcarbodiimides," Russian Journal of Organic Chemistry, 2000, vol. 36, No. 12, pp. 1739-1742.
Vovk et al., "Regioselective cyclization of 1-chloroalkylcarbodiimides with 1,1- and 1,2-bifunctional nucleophilic reagents," Russian Journal of Organic Chemistry, 1997, vol. 22, No. 1, pp. 96-102.
Potts et al., "N-Acyl-β-enamino Ketones: Versatile Heterocyclic Synthons," J. Org. Chem., 1983, 48, pp. 625-626.
Rivkin et al., "Piperazinyl pyrimidine derivatives as potent γ-secretase modulators," Bioorganic & Medicinal Chemistry Letters, 2010, 20, pp. 1269-1271.
Rivkin et al., "Purine derivatives as potent γ-secretase modulators," Bioorganic & Medicinal Chemistry Letters, 2010, 20, pp. 2279-2282.
Edwards et al. "Application of Fragment-Based Lead Generation to the Discovery of Novel, Cyclic Amidine β-Secretase Inhibitors with Nanomolar Potency, Cellular Activity, and High Ligand Efficiency", Journal of Medicinal Chemistry, vol. 50, No. 24, 2007, pp. 5912-5925.
Cohen et al., "Synthesis of 2-Amino-5,6-dihydro-4H-1,3-thiazines and Related Compounds by Acid Catalyzed Cyclization of Allylic Isothiuronium Salts", J. Heterocyclic Chem., vol. 14, Aug. 1977, pp. 717-723.
Kuo et al., "A Synthesis of Estrone via Novel Intermediates. Mechanism of the Coupling Reaction of a Vinyl Carbinol with a β Diketone", The Journal of Organic Chemistry, vol. 33, No. 8, Aug. 1968, pp. 3126-3132.
Liebscher et al., "2-arylimino-3-thiazolines—Formation of Unusual Tautomers of 2-arylamino-thiazolines—A Revision", Tetrahedron Letters, vol. 26, No. 35, 1985, pp. 4179-4180.
Garcia et al., "Syntheses and Spectral Properties of β-Iodoureas and 2-Amino-4,4-diphenyl-2-oxazolines", J. Heterocyclic Chem., vol. 28, 1991, pp. 777-780.
Schaumann et al. "Cycloadditionsreaktionen von Heterokumulenen, XIII[1])Stickstoffhaltige Fünfring-Heterocyclen aus Carbodiimiden oder Keteniminen mit 3-Dimethylamino-2H-azirinen", Liebigs Ann. Chem, 1981, pp. 290-305 (with English language abstract).
Fernandez et al., "Syntheses of β-iodourea derivatives of carbohydrates and glycosylamino-oxazolines", Carbohydrate Research, vol. 216, 1991, pp. 21-32.
Cambie et al., "vic-Iodothiocyanates and Iodoisothiocyanates. Part 2.[1,2] New Syntheses of Thiazolidin-2-ones and 2-Amino-2-thiazolines", J.C.S. Perkin I, 1979, pp. 765-770.
Hünig et al., "Azofarbstoffe Durch Oxydative Kupplung, XVIII[1]) Synthese von 3-substituierten Thiazolon-(2)-hydrazonen and Thiazolon-(2)-benzolsulfonylhydrazonen", 1961, vol. 647, pp. 66-76.
STN a the Web, RN 79005-45-1, 1964.
Zhu et al., Two novel Diastereoselective Three-Component Reactions of Alkenes or 3,4-Dihydro-(2H)-pyran with Urea/Thiourea-Aldehyde Mixtures: [4+2] Cycloaddition vs Biginelli-Type Reaction, Organic Letters, 2006, vol. 8, No. 12, pp. 2599-2602.
Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).
Kavya et al. "Nitric oxide synthase regulation and diversity: Implications in Parkinson's Disease", Nitric Oxide: Biology and Chemistry, vol. 15, No. 4, pp. 280-294 (2006).
Chiou et al. "Review: Effects of Nitric Oxide on Eye Diseases and Their Treatment". Journal of Ocular Pharmacology and Therapeutics, vol. 17, No. 2, pp. 189-198 (2001).
Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).
Pak et al. "Morphine via nitric oxide modulates β-amyloid metabolism: a novel protective mechanism for Alzheimer's disease", Medical Science Monitor, vol. 11, No. 10, pp. BR357-BR366 (2005).
Kiselyov et al., "Design and chemical synthesis of [1,2,4]triazol[1,5-c]pyrimidin-5-y1 amines, a novel class of VEGFR-2 kinase inhibitors," 2009, Tetrahedron Letters, vol. 50, pp. 3809-3812.
Mulcahy et al., "A stereoselective synthesis of (+)-Gonyautoxin 3," Journal of the American Chemical Society, 2008, vol. 130, pp. 12630-12631.
"Diphenyl Cyanocarbonimidate," e-EROS Encyclopedia of Reagents for Organic Synthesis, 2001, 2 pages total.
Shafik et al., "Synthesis of novel 2-[2-(substituted amino)phenethyl]-1H-benzimidazoles; 3,4-dihydro and 1,2,3,4-tetrahydropyrimido[1,6-a]-benzimidazoles as potential antiulcer agents," 2004, Pharmazie, vol. 59, No. 12, pp. 899-905.
Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.
Buschauer et al., "Isohistamine and Homologe als Bausteine von $H_2$-Antagonisten,"Arzneimittel-Forschung, 1985, vol. 35, pp. 1025-1029 (English language abstract provided).
Buschauer et al., "7,8-Dihydroimidazo[1,2-c]pyrimidin-5(6H)-one, -5(6H)-thione and -5(6H1)-ylidencyanamide," Chemische Berichte, 1984, vol. 117, pp. 2597-2614.
Borchers et al., "$H_2$-Antihystaminika, 19. Mitt, [1]) Syntheses and $H_2$-antihistaminische Wirkung $N^\alpha$-substituierter Histamine," Archie der Pharmazie (Weinheim, Germany), 1984, vol.317, pp. 455-459.
Cheong et al., "Pharmacophore elucidation for a new series of 2-aryl-pyrazolo-triazolo-pyrimidines as potent human $A_3$ adenosine receptor antagonists," Bioorganic & Medicinal Chemistry Letters, 2011, vol. 21, pp. 2898-2905.

(56) References Cited

OTHER PUBLICATIONS

Xu et al., "Copper-catalyzed cascade synthesis of benzimidazoquinazoline derivatives under mild condition," Chemical Communications, 2011, vol,47, pp. 5596-5598.

Kishore et al., "QSAR of adenosine receptor antagonists: exploring physicochemical requirements for binding of pyrazolo[4,3-e]-1,2,4-triazolo[1,5-c]pyrimidine derivatives with human adenosine A3 receptor subtype," Bioorganic & Medicinal Chemistry Letters, 2011, vol. 21, No. 2, pp. 818-823.

Dolzhenko et al., "8-methyl-2-[4-(trifluoromethyl)phenyl]-8H-pyrazolo[4,3-e][1,2,4]triazolo[1,5-c]-pyrimidin-5-amine methanol disolvate," Acta Crystallographica, Section E: Structure Reports Online, 2010, E66(7), 12 pages total.

Beaton et al., "3,4-dihydro-l-isoquinolinamines: a novel class of nitric oxide synthase inhibitors with a range of isoform selectivity and potency," Bioorganic & Medicinal Chemistry Letters, 2001, vol. 11, pp. 1023-1026.

Beaton et al., "The synthesis of 1-aminodihydroisoquinolines by an imine addition cyclisation reaction," 1998, Tetrahedron Letters, vol. 39, pp. 1227-1230.

Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. I, pp. 49-53.

Weinhardt et al, "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.

Meschino et al., "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med, Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbony)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

Co-pending U.S.Appl. No. 13/881,112, entitled Fused Aminodihydropyrimidine Derivative, filed Apr. 23, 2013.

Co-pending U.S. Appl. No. 13/881,250, entitled Naphthyridine Derivative, filed Apr. 24, 2013.

Co-pending U.S. Appl. No. 13/877,745, entitled Aminodihydrothiazine Derivtives Substituted with a Cycle Group, filed May 6, 2013.

Co-pending U.S. Appl. No. 13/941,082, entitled Aminodihydrothiazine Derivatives, filed Jul. 12, 2013.

Co-pending U.S. Appl. No. 13/952,073, entitled Sulfur-Containing Heterocyclic Derivative Having Beta Secretase Inhibitory Activity, filed Jul. 26, 2013.

Dörwald, "Side reactions in organic synthesis: a guide to successful synthesis design" 2005 Wiley-VCH Verlag GmbH & Co., KGaA, Wienheim, chapter 1, 32 pages total.

Wermuth; Practice of Medicinal Chemistry, Third Ed., 2008, Elsevier, chapter 15, 54 pages total.

Co-pending U.S. Appl. No. 14/112,400, entitled Pyridine Derivatives and a Pharmaceutical Composition for Inhibiting BACE1 Containing Them, filed Oct. 17, 2013.

Co-pending U.S. Appl. No. 14/113,327, entitled Oxazine Derivatives and a Pharmaceutical Composition for Inhibiting BACE1 Containing Them, filed Oct. 22, 2013.

Co-pending U.S. Appl. No. 14/070,202, entitled A Pharmaceutical Composition for Treating Alzheimer's Disease, filed Nov. 1, 2013.

\* cited by examiner

PHARMACEUTICAL COMPOSITION FOR TREATING ALZHEIMER'S DISEASE

TECHNICAL FIELD

The present invention relates to a pharmaceutical composition which has reducing effect to produce amyloid β protein and is useful as an agent for treating disease induced by production, secretion and/or deposition of amyloid β protein, especially Alzheimer's disease.

BACKGROUND ART

In the brain of Alzheimer's patient, the peptide composed of about 40 amino acids residue as is called amyloid β protein, that accumulates to form insoluble specks (senile specks) outside nerve cells is widely observed. It is concerned that this senile specks kill nerve cells to cause Alzheimer's disease. The therapeutic agents for Alzheimer's disease, such as decomposition agents of amyloid β protein and amyloid β vaccine, are under investigation.

Secretase is an enzyme which cleaves amyloid βprecursor protein (APP) in cell and produce amyloid β protein. The enzyme which controls the production of N terminus of amyloid β protein is called as BACE 1 (beta-site APP-cleaving enzyme 1, β-secretase). It is thought that inhibition of this enzyme leads to reduction of producing amyloid β protein and that the therapeutic agent for Alzheimer's disease will be created by the inhibition.

Patent Literature 1 describes the compounds which are similar to those of the compounds contained in the pharmaceutical composition of the present invention, and the compounds have NO synthase enzyme inhibitory activity and are useful for dementia.

Patent. Literature 2 to 10 describes the compounds which are known as BACE 1 inhibitor, however, have different structures from the compounds contained in the pharmaceutical composition of the present invention.
[Patent Literature 1] International Patent Application Publication WO96/014842
[Patent Literature 2] International Patent Application Publication WO02/96897
[Patent Literature 3] International Patent Application Publication WO04/043916
[Patent Literature 4] International Patent Application Publication WO2005/058311
[Patent Literature 5] international Patent Application Publication WO2005/097767
[Patent Literature 6] International Patent Application Publication WO2006/041404
[Patent Literature 7] International Patent Application Publication WO2006/041405
[Patent Literature 8] US Patent Application Publication US2007/0004786
[Patent Literature 9] US Patent Application Publication US2007/0004730
[Patent Literature 10] US Patent Application Publication US2007/27199
[Patent Literature 11] International Patent Application Publication WO2007/049532

DISCLOSURE OF INVENTION

Problems to be Solved by the Invention

The present invention provides pharmaceutical compositions which have reducing effects to produce amyloid β protein, especially BACE 1 inhibitory activity, and which are useful as an agent for treating disease induced by production, secretion and/or deposition of amyloid β protein.

Means to Solve the Problems

The present invention provides:
(a) a pharmaceutical composition for treating Alzheimer's disease containing a compound represented by the general formula (I):

[Chemical formula 1]

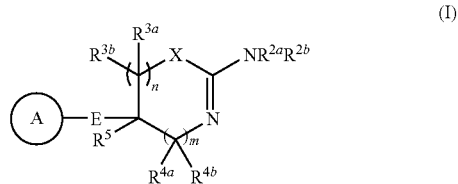

wherein ring A is an optionally substituted carbocyclic group or an optionally substituted heterocyclic group;

[Chemical formula 2]

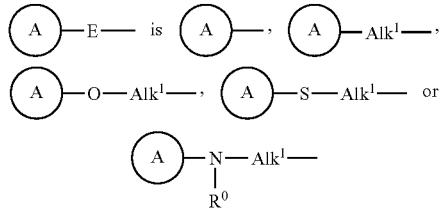

wherein $Alk^1$ is lower alkylene or lower alkenylene;
$R^0$ is a hydrogen atom, lower alkyl or acyl;
X is S, O, or $NR^1$;
$R^1$ is a hydrogen atom or lower alkyl;
$R^{2a}$ and $R^{2b}$ are each independently a hydrogen atom, hydroxy, optionally substituted lower alkyl, optionally substituted lower alkenyl, optionally substituted amino, optionally substituted amidino, optionally substituted acyl, optionally substituted carbamoyl, optionally substituted carbamoylcarbonyl, optionally substituted lower alkylsulfonyl, optionally substituted arylsulfonyl, an optionally substituted carbocyclic group or an optionally substituted heterocyclic group;
$R^{3a}$, $R^{4a}$ and $R^{4b}$ are each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group;
n and m are each independently an integer of 0 to 3;
n+m is an integer of 1 to 3;
each $R^{3a}$, each $R^{3b}$, each $R^{4a}$, and each $R^{4b}$ may be independently different;
$R^5$ is a hydrogen atom, optionally substituted lower alkyl, optionally substituted lower alkenyl, optionally substituted lower alkynyl, an optionally substituted carbocyclic group or an optionally substituted heterocyclic group;

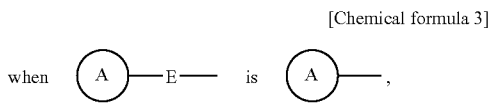

[Chemical formula 3]

$R^5$ and ring A can be taken together to form

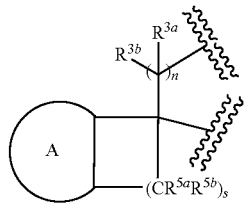

wherein $R^{5a}$ and $R^{5b}$ are each independently a hydrogen atom or lower alkyl;

s is an integer of 1 to 4;

each $R^{5a}$ and each $R^{5b}$ may be different;

with the proviso that the compound wherein n+m is 2; $R^5$ is a hydrogen atom; and ring A is non-substituted phenyl is excluded, its pharmaceutically acceptable salt, or a solvate thereof as an active ingredient, (a1) a pharmaceutical composition for treating Alzheimer's disease containing a compound represented by the general formula (I):

[Chemical formula 4]

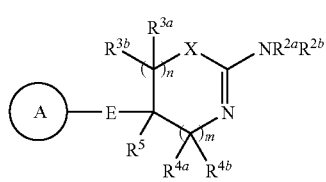

(I)

wherein ring A is an optionally substituted carbocyclic group or an optionally substituted heterocyclic group;

[Chemical formula 5]

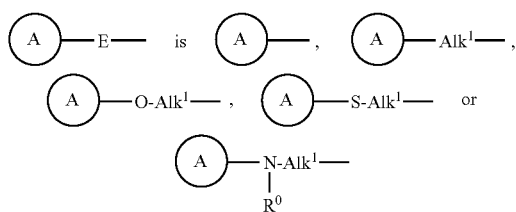

wherein $Alk^1$ is lower alkylene;

$R^0$ is a hydrogen atom, lower alkyl or acyl;

X is S, O, or $NR^1$;

$R^1$ is a hydrogen atom or lower alkyl;

$R^{2a}$ and $R^{2b}$ are each independently a hydrogen atom, hydroxy, optionally substituted lower alkyl, optionally substituted lower alkenyl, optionally substituted amino, optionally substituted amidino, optionally substituted acyl, optionally substituted carbamoyl, optionally substituted lower alkylsulfonyl, optionally substituted arylsulfonyl, an optionally substituted carbocyclic group or an optionally substituted heterocyclic group;

$R^{3a}$, $R^{3b}$, $R^{4a}$, and $R^{4b}$ are each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group;

n and m are each independently an integer of 0 to 3;

n+m is an integer of 1 to 3;

each $R^{3a}$, each $R^{3b}$, each $R^{4a}$, and each $R^{4b}$ may be independently different;

$R^5$ is a hydrogen atom, optionally substituted lower alkyl, optionally substituted lower alkenyl, optionally substituted lower alkynyl, an optionally substituted carbocyclic group or an optionally substituted heterocyclic group;

[Chemical formula 6]

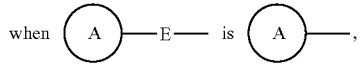

$R^5$ and ring A can be taken together to form

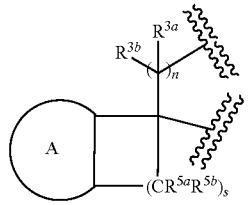

wherein $R^{5a}$ and $R^{5b}$ are each independently a hydrogen atom or lower alkyl;

s is an integer of 1 to 4;

each $R^{5a}$ and each $R^{5b}$ may be different;

with the proviso that the compound wherein n+m is 2; $R^3$ is a hydrogen atom; and ring A is non-substituted phenyl is excluded, its pharmaceutically acceptable salt, or a solvate thereof as an active ingredient, (b) the pharmaceutical composition for treating Alzheimer's disease according to (a), wherein X is S, (c) the pharmaceutical composition for treating Alzheimer's disease according to (a), wherein n is 2, and m is 0, (d) the pharmaceutical composition for treating Alzheimer's disease according to (a), wherein E is a bond, (e) a pharmaceutical composition for treating Alzheimer's disease containing a compound represented by the general formula (I):

[Chemical formula 7]

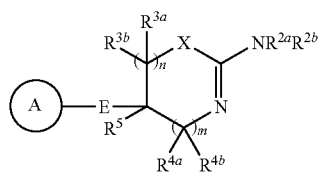
(I)

wherein each symbols are the same as described in (a), with the proviso that the compounds as shown below;
i) wherein n+m is 2, $R^3$ is a hydrogen atom, and ring A is non-substituted phenyl;
ii) wherein n is 2, m is 0, $R^{2a}$ is a hydrogen atom, $R^{2b}$ is a hydrogen atom or acetyl, $R^5$ is methyl, and ring A is phenyl or 4-methoxyphenyl;
iii) wherein n is 2, m is 0, $R^{2a}$ is a hydrogen atom, $R^{2b}$ is a hydrogen atom or acetyl,
$R^5$ is ethyl, and ring A is 3,4-dimethoxyphenyl;
iv) wherein n is 2, in is 0, $R^{2a}$ is a hydrogen atom, $R^{2b}$ is a hydrogen atom or acetyl, and $R^5$ and ring A is phenyl;
v) wherein n is 2, m is 0, $R^{2a}$ and $R^{2b}$ is a hydrogen atom, $R^5$ and ring A are taken together to form

[Chemical formula 8]

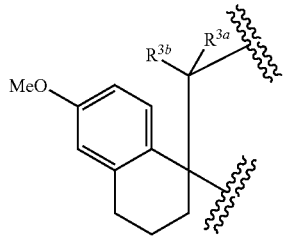

wherein Me is methyl, and each symbols are the same as described above; and
vi) wherein n+m is 2,
$R^5$ is a hydrogen atom, and
ring A is phenyl substituted with one or two substituent(s) selected from the group of hydroxy, halogen, lower alkyl, lower alkoxy, nitro, amino, lower alkylcarbonylamino, mercapto, lower alkylthio, and carbamoyl, non-substituted phenyl,
or non-substituted naphthyl; are excluded,
its pharmaceutically acceptable salt, or a solvate thereof as an active ingredient,
(f) the pharmaceutical composition for treating Alzheimer's disease according to (e), wherein X is S,
(g) the pharmaceutical composition for treating Alzheimer's disease according to (e) or (f), wherein n is 2, and m is 0,
(h) the pharmaceutical composition for treating Alzheimer's disease according to any one of (e) to (g), wherein $R^5$ is optionally substituted lower alkyl, optionally substituted lower alkenyl, optionally substituted lower alkynyl, an optionally substituted carbocyclic group or an optionally substituted heterocyclic group,
(i) the pharmaceutical composition for treating Alzheimer's disease according to any one of (e) to (h), wherein $R^{1a}$ is a hydrogen atom; $R^{2b}$ is a hydrogen atom, optionally substituted lower alkyl, optionally substituted acyl, optionally substituted lower alkylsulfonyl, or optionally substituted amidino,
(j) the pharmaceutical composition for treating Alzheimer's disease according to any one of (e) to (h), wherein $NR^{2a}R^{2b}$ is represented by the formula:

[Chemical formula 9]

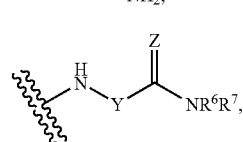
(a)

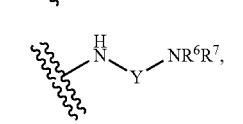
(b)

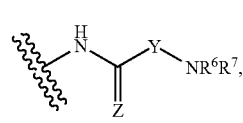
(c)

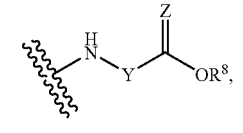
(d)

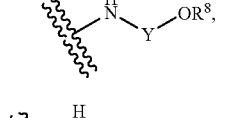
(e)

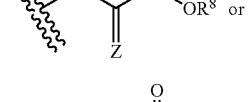
(f)

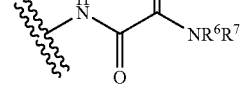
(g)

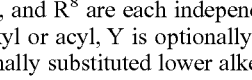
(h)

wherein $R^6$, $R^7$, and $R^8$ are each independently a hydrogen atom, lower alkyl or acyl, Y is optionally substituted lower alkylene, optionally substituted lower alkenylene or optionally substituted lower alkynylene;
Z is O or S;
(k) the pharmaceutical composition for treating Alzheimer's disease according to any one of (e) to (j), wherein ring A is substituted phenyl,
(l) the pharmaceutical composition for treating Alzheimer's disease according to any one of (e) to (j), wherein ring A is represented by the formula:

[Chemical formula 10]

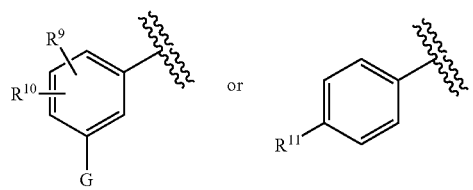

wherein $R^9$, $R^{10}$ and $R^{11}$ are hydrogen atom or G;

G is halogen, hydroxy, cyano, nitro, mercapto, optionally substituted lower alkyl, optionally substituted lower alkoxy, optionally substituted lower alkenyl, optionally substituted lower alkynyl, optionally substituted acyl, optionally substituted acyloxy, carboxy, optionally substituted lower alkoxycarbonyl, optionally substituted lower alkoxycarbonyloxy, optionally substituted aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl, optionally substituted lower alkylsulfinyl, optionally substituted arylsulfinyl, optionally substituted lower alkylsulfonyloxy, optionally substituted arylsulfonyloxy, an optionally substituted carbocyclic group, optionally substituted carbocyclicoxy, an optionally substituted heterocyclic group or optionally substituted heterocyclicoxy;

each G may be independently different, (m) the pharmaceutical composition for treating Alzheimer's disease according to (l), wherein G is represented by the formula:

[Chemical formula 11]

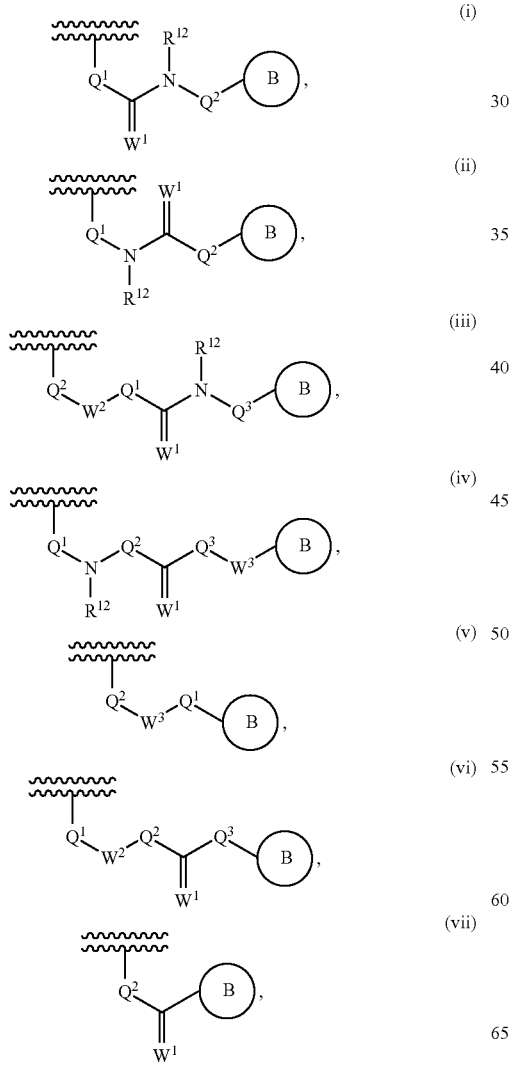

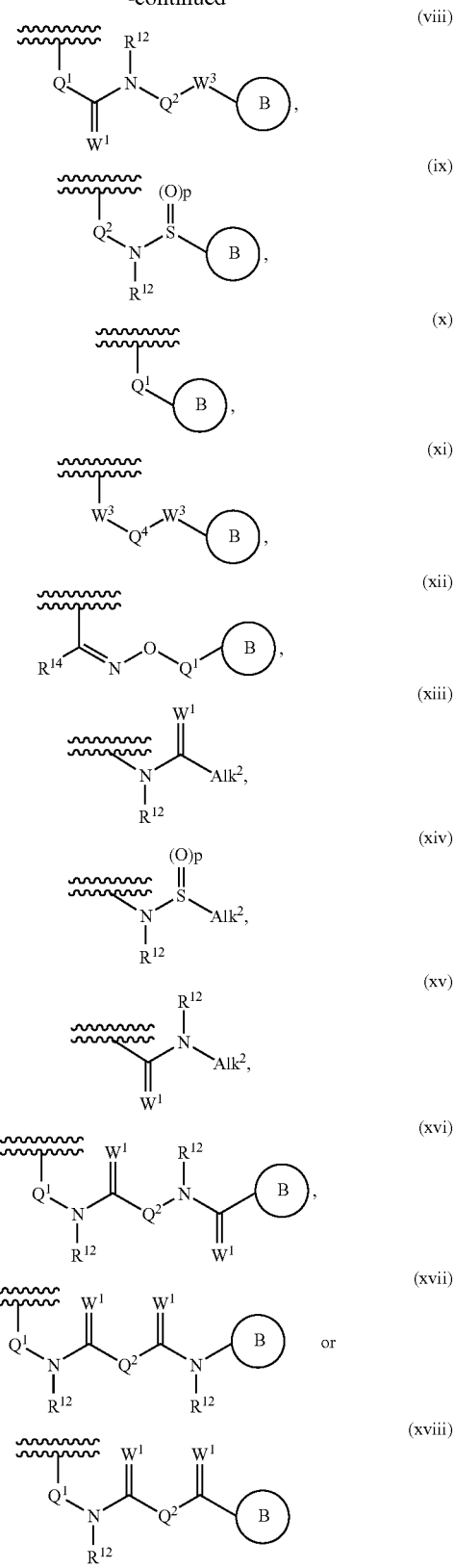

wherein $Q^1$, $Q^2$, and $Q^3$ are each independently a bond, optionally substituted lower alkylene, or optionally substituted lower alkenylene;

$Q^4$ is optionally substituted lower alkylene or optionally substituted lower alkenylene;

$W^1$ and $W^2$ are each independently O or S;

$W^3$ is O, S or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl or acyl;

$R^{14}$ is a hydrogen atom or lower alkyl;

ring B is an optionally substituted carbocyclic group or an optionally substituted heterocyclic group;

$Alk^2$ is optionally substituted lower alkyl;

p is 1 or 2;

if there are multiple $W^1$, multiple $W^3$, and multiple $R^{12}$, each may be independently different;

in (xii), the position of an oxygen atom may be cis or trans to a substituent $R^{14}$, (n) the pharmaceutical composition for treating Alzheimer's disease according to (m), wherein ring B is aryl optionally substituted with one or more substituents selected from the group of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy and an optionally substituted heterocyclic group, or heteroaryl optionally substituted with one or more substituents selected from the group of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy and an optionally substituted heterocyclic group, (o) the pharmaceutical composition for treating Alzheimer's disease according to (m), wherein G is represented by the formula:

[Chemical formula 12]

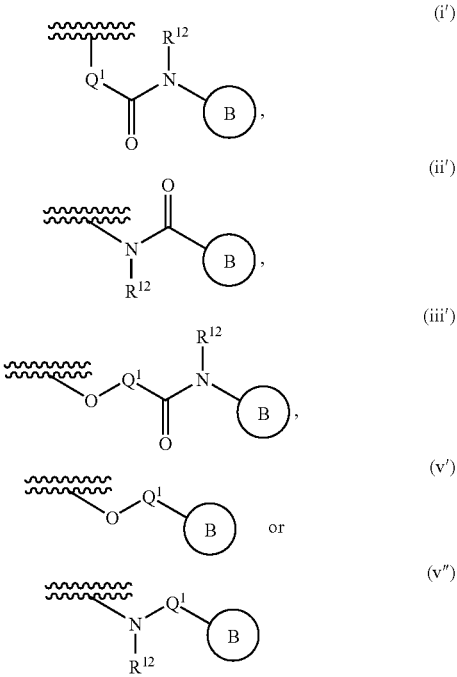

wherein, each symbols are the same as described above, (p) the pharmaceutical composition for treating Alzheimer's disease according to any one of (e) to (o), wherein $R^5$ is C1 to C3 alkyl, (q) the pharmaceutical composition for treating Alzheimer's disease according to any one of (e) to (o), wherein $R^5$ is methyl, (r) the pharmaceutical composition for treating Alzheimer's disease according to any one of (e) to (q), wherein $R^{3a}$ and $R^{3b}$ are each independently a hydrogen atom, halogen, hydroxy, optionally substituted lower a optionally substituted lower alkoxy or optionally substituted aryl, (s) the pharmaceutical composition for treating Alzheimer's disease according to any one of (e) to (q), wherein $R^{3a}$ and $R^{3b}$ are both hydrogen atoms, (t) the pharmaceutical composition according to any one of (a) to (d) which is the composition for reducing amyloid β production, its pharmaceutically acceptable salt, or a solvate thereof as an active ingredient, (u) the pharmaceutical composition according to any one of (a) to (d) or (d) which is the composition for treating disease induced by production, secretion and/or deposition of amyloid β protein, (v) a method for treating disease induced by production, secretion and/or deposition of amyloid β protein (for example, Alzheimer's disease) comprising administering the compound as defined in any one of formula (I) in above (a), its pharmaceutically acceptable salt, or a solvate thereof, (w) use of the compound as defined in any one of formula (I) in above (a), its pharmaceutically acceptable salt, or a solvate thereof, in the manufacture of a medicament for the treatment of disease induced by production, secretion and/or deposition of amyloid β protein (for example, Alzheimer's disease), (x) a method for treating Alzheimer's disease characterizing in administering the compound as defined in any one of formula (I) in above (a), its pharmaceutically acceptable salt, or a solvate thereof, (y) use of the compound as defined in any one of formula (I) in above (a), its pharmaceutically acceptable salt, or a solvate thereof, in the manufacture of a medicament for the treatment of Alzheimer's disease.

Effect of the Invention

The composition of the present invention is useful as an agent for treating disease such as Alzheimer's disease induced by production, secretion and/or deposition of amyloid β protein.

Additionally, because the pharmaceutical composition of the present invention comprises the compound which has the characteristics: it has high inhibitory activity against BACE-1, it has high selectivity against other enzymes, and the like; as an active ingredient, it can be a medicament whose side effects are reduced. The pharmaceutical composition of the present invention can be a medicament which possess a great safety margin in side effect by comprising an optical active compound which has a suitable conformation as an active ingredient. The pharmaceutical composition of the present invention can be an excellent medicament because it comprises the compound which has the following characteristics as an active ingredient: high metabolic stability, high dissolubility, high oral absorbability, high bioavailability, preferable clearance, high transfer to brain, long half-life, high proteinunbound fraction, low inhibitory activity to hERG channel, low inhibitory activity to CYPs, and/or negative activity in Ames assay.

BEST MODE FOR CARRYING OUT THE INVENTION

As used herein, the "halogen" includes fluorine, chlorine, bromine, and iodine. A halogeno part of the "halogeno lower alkyl", the "halogeno lower alkoxy", the "halogeno acyl", the "halogeno lower alkylthio" and the "halogeno lower alkoxycarbonyl" is the same.

The "lower alkyl" includes a straight or branched alkyl of a carbon number of 1 to 15, preferably a carbon number of 1 to 10, further preferably a carbon number of 1 to 6, and more further preferably a carbon number of 1 to 3, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

A lower alkyl part of the "carbocyclic lower alkyl", the "lower alkoxy", the "halogeno lower alkyl", the "halogeno lower alkoxy", the "halogeno lower alkylthio", the "hydroxy lower alkyl", the "lower alkoxycarbonyl", the "halogeno lower alkoxycarbonyl", the "lower alkoxycarbonyl lower alkyl", the "lower alkoxycarbonyloxy", the "lower alkylamino", the "lower alkylcarbonylamino", the "lower alkoxycarbonylamino", the "lower alkoxy lower alkyl", the "lower alkylcarbamoyl", the "hydroxy lower alkylcarbamoyl", the "amino lower alkyl", the "hydroxy imino lower alkyl", the "lower alkoxy imino lower alkyl", the "lower alkylthio", the "lower alkylsulfonyl", the "lower alkyl sulfamoyl", the "lower alkylsulfinyl", the "lower alkylsulfonyloxy", the "lower alkoxycarbonyl lower alkynyl", the "lower alkylthio lower alkyl", the "aryl lower alkyl", the "aryl lower alkylamino", the "aryl lower alkoxycarbonyl", the "aryl lower alkylcarbamoyl", the "heterocyclic group lower alkylamino" and the "heterocyclic group lower alkylcarbamoyl" is the same as that of the aforementioned "lower alkyl".

The example of the "optionally substituted lower alkyl" as a substituent of ring A is lower alkyl optionally substituted with one or more substituents selected from the "substituent group α", "hydroxyimino" and "lower alkoxyimino"; the group defined as above (i), (iv), (vi), (x) (wherein each $Q^1$ is optionally substituted lower alkylene); the group defined as (v), (vii), (ix) (wherein $Q^2$ is optionally substituted lower alkylene); and the group (xii).

In other "optionally substituted lower alkyl" is optionally substituted with one or more substituents selected from the "substituent group α".

The "substituent group α" is selected from the group of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group.

Especially as a substituent of the "optionally substituted lower alkyl" in $Alk^2$, halogen, hydroxy, lower alkoxy, lower alkoxy lower alkoxy, lower alkoxycarbonyl, amino, acylamino, lower alkylamino and/or lower alkylthio are preferable.

The example of the "optionally substituted lower alkoxy" as a substituent of ring A is lower alkoxy optionally substituted with one or more substituents selected from the above "substituent group α"; above (iii) wherein $Q^1$ is optionally substituted lower alkylene. $Q^2$ is a bond, $W^2$ is O; above (v) wherein $Q^1$ is optionally substituted lower alkylene, $Q^2$ is a bond. $W^3$ is O; above (vi) wherein $Q^1$ is a bond, $Q^2$ is optionally substituted lower alkylene, $W^2$ is O; or above (xi) wherein $Q^4$ is optionally substituted lower alkylene, $W^2$ is O.

In other case, the substituents of the "optionally substituted lower alkoxy", the "optionally substituted lower alkoxycarbonyl", the "optionally substituted lower alkoxycarbonyloxy", the "optionally substituted lower alkylsulfonyl", the "optionally substituted lower alkylsulfinyl", the "optionally substituted lower alkylsulfonyloxy" and the "optionally substituted lower alkylthio" are one or more substituents selected from the "substituent group α".

The "lower alkenyl" includes a straight or branched alkenyl of a carbon number of 2 to 15, preferably a carbon number of 2 to 10, further preferably a carbon number of 2 to 6 and more further preferably a carbon number of 2 to 4 having one or more double bonds at an arbitrary position. Specifically examples include vinyl, allyl, propenyl, isopropenyl, butenyl, isobutenyl, prenyl, butadienyl, pentenyl, isopentenyl, hexenyl, isohexenyl, hexadienyl, heptenyl, octenyl, nonenyl, decenyl, undecenyl, dodenyl, tridecenyl, tetradecenyl, and pentadecenyl.

The "lower alkynyl" includes a straight or branched alkynyl of a carbon number of 2 to 10, preferably a carbon number of 2 to 8, further preferably a carbon number of 3 to 6, having one or more triple bonds at an arbitrary position. Specifically, examples include ethynyl, propenyl, butynyl, pentynyl, hexynyl, heptynyl, octynyl, nonynyl, and decynyl. These may further have a double bond at an arbitrary position.

A lower alkynyl part of the "lower alkoxycarbonyl lower alkynyl" is the same as that of above "lower alkynyl".

The example of the "optionally substituted lower alkenyl" as a substituent of ring A is lower alkenyl optionally substituted with one or more substituents selected from the above "substituent group α"; above (i), (ii), (iv), (vi), (viii) or (x), wherein $Q^1$ is optionally substituted lower alkenylene; (v), (vii) or (ix), wherein $Q^2$ is optionally substituted lower alkenylene.

In other case, the substituents of the "optionally substituted lower alkenyl" and the "optionally substituted lower alkynyl" are one or more substituents selected from the "substituent group α".

The example of the "optionally substituted lower amino" as a substituent of ring A is amino optionally substituted with one or more substituents selected from the group of lower alkyl, acyl, hydroxy, lower alkoxy, lower alkoxyl carbonyl, a carbocyclic group and a heterocyclic group; (ii), wherein $Q^1$ is a bond; (iv), wherein $Q^1$ is a bond; (v), wherein $Q^2$ is a bond, $W^3$ is $NR^{12}$; (ix), wherein $Q^2$ is a bond; (xiii); or (xiv).

The example of the "optionally substituted carbamoyl" as a substituent of ring A is carbamoyl optionally substituted with one or more substituents selected from the group of lower alkyl, acyl, hydroxy, lower alkoxy, lower alkoxycarbonyl, a carbocyclic group and a heterocyclic group; (i), (viii), wherein each $Q^1$ is bond; or (xv).

In other case, the substituents of the "optionally substituted amino", the "optionally substituted amidino", the "optionally substituted carbamoyl", the "optionally substituted carbamoylcarbonyl", and the "optionally substituted carbamoyloxy" are one or two substituents selected from the group of lower alkyl, acyl, hydroxy, lower alkoxy, lower alkoxycarbonyl, a carbocyclic group and a heterocyclic group, and the like.

The "acyl" includes aliphatic acyl of a carbon number of 1 to 10, carbocyclic carbonyl and heterocyclic carbonyl. Specifically, formyl, acetyl, propyonyl, butylyl, isobutylyl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolcarbonyl, pyradinecarbonyl, piperidinecarbonyl, thiomorpholinocarbonyl, and the like.

The part of the acyl of the "halogenoacyl", the "acylamino" and the "acyloxy" is the same as the aforementioned "acyl".

The substituent of the "optionally substituted acyl" and "optionally substituted acyloxyl" is one or more substituents selected from the group of the "substituent group α". The ring part of the "carbocyclic carbonyl" and the "heterocyclic carbonyl" is optionally substituted with one or more substituents selected from the group of "lower alkyl"; the "substituent group α"; and "lower alkyl substituted with one or more substituents selected from the group of the substituent α".

The "carbocyclic group" includes cycloalkyl, cycloalkenyl, aryl and non-aromatic fused carbocyclic group.

The "cycloalkyl" includes a carbocyclic group of a carbon number of 3 to 10, preferably a carbon number of 3 to 8, further preferably a carbon number of 4 to 8, and examples include, cyclopropyl, cyclobutyl, cyclopentyl, cyclohexyl, cycloheptyl, cyclooctyl, cyclononyl, and cyclodecyl, and the like.

The "cycloalkenyl" includes cycloalkenyl having one or more double bonds at an arbitrary position in a ring of the aforementioned cycloalkyl, and examples include cyclopropenyl, cyclobutenyl, cyclopentenyl, cyclohexenyl, cycloheptynyl, cyclooctynyl, and cyclohexadienyl, and the like.

The "aryl" includes phenyl, naphthyl, anthryl, and phenanthryl, and the like, and phenyl is particularly preferable.

The "non-aromatic fused a carbocyclic group" includes group fused with two or more ring groups selected from the group of the above "cycloalkyl", the "cycloalkenyl" and the "aryl". Specifically, examples include indanyl, indenyl, tetrahydronaphthyl, and fluorenyl, and the like.

The carbocyclic part of the "carbocyclicoxy", and the "carbocyclic lower alkyl" is the same as the aforementioned "carbocyclic group".

The aryl part of the "aryl lower alkyl", the "aryloxy", the "aryloxycarbonyl", the "aryloxycarbonyloxy", the "aryl lower alkoxycarbonyl", the "arylthio", the "arylamino", the "aryl lower alkylamino", the "arylsulfonyl", the "arylsulfonyloxy", the "arylsulfinyl", the "arylsulfamoyl", the "arylcarbamoyl" and the "aryl lower alkylcarbamoyl" is the same as the aforementioned "aryl".

The "heterocyclic group" includes a heterocyclic group having one or more heteroatoms arbitrary selected from O, S, and N in a ring, specifically includes a 5- to 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, isothiazolyl, furyl and thienyl; a bicyclic fused heterocyclic group such as indolyl, isoindolyl, indazolyl, indolidinyl, indolinyl, isoindolinyl, quinolyl, isoquinolyl, cinnolinyl, phthalazinyl, quinazolinyl, naphthyridinyl, purinyl, pteridinyl, benzopyranyl, benzimidazolyl, benzioxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridyl, triazolopyridyl, itnidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl; a tricyclic fused heterocyclic group such as carbazolyl, acridinyl, xanthenyl, phenothiazinyl, phenoxathiinyl, phenoxazinyl, dibenzofuryl, and imidazoquinolyl; a non-aromatic heterocyclic group such as dioxanyl, thiiranyl, oxyranyl, oxathioranyl, azethidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, dihydrobenzoimidazolyl, tetrahydropyridyl, tetrahydrofuryl, tetrahydropyranyl, tetrahydrothiazolyl, tetrahydroisothiazolyl, dihydroxadinyl, hexahydroazepinyl, tetrahydroazepyinyl. Preferable is a 5- to 6-membered heteroaryl, or a non-aromatic heterocyclic group.

The heterocyclic part of the "heterocyclicoxy", the "heterocyclic thio", the "heterocyclic carbonyl", the "heterocyclic amino", the "heterocyclic carbonylamino", the "heterocyclic sulfamoyl", the "heterocyclic sulfonyl", the "heterocyclic carbamoyl", the "heterocyclicoxycarbonyl", the "heterocyclic lower alkylamino" and the "heterocyclic lower alkyl carbamoyl" is the same as the aforementioned "heterocyclic group".

The example of the substituent of the "optionally substituted carbocyclic group" and the "optionally substituted heterocyclic group" in ring A is;

the substituent α, wherein preferable is for example, halogen, hydroxy, acyl, acyloxy, carboxy, lower alkoxycarbonyl, carbamoyl, amino, lower alkylamino, lower alkylthio; lower alkyl optionally substituted with one or more substituents selected from the group of substituent α, wherein preferable is halogen, hydroxy, lower alkoxy, lower alkoxycarbonyl, and the like;

amino lower alkyl substituted with one or more substituents selected from the group of substituent α, wherein preferable is acyl, lower alkyl and for lower alkoxy, and the like; hydroxyimino lower alkyl; lower alkoxyimino lower alkyl;

lower alkenyl optionally substituted with one or more substituents selected from the group of substituent α, wherein preferable is lower alkoxycarbonyl, halogen and /or halogeno lower alkoxycarbonyl, and the like;

lower alkynyl optionally substituted with one or more substituents selected from the group of substituent α, wherein preferable is for example, lower alkoxycarbonyl, lower alkoxy optionally substituted with one or more substituents selected from the group of substituent α, wherein preferable is for example, lower alkyl carbamoyl and for hydroxy lower alkyl carbamoyl, lower alkylthio optionally substituted with one or more substituents selected from the group of substituent α, lower alkylamino substituted with one or more substituents selected from the group of substituent α, lower alkylsulfonyl optionally substituted with one or more substituents selected from the group of substituent α, aryl lower alkoxycarbonyl optionally substituted with one or more substituents selected from the group of substituent α, azido, and lower alkyl, acyl substituted with one or more substituents selected from the group of substituent α, cycloalkyl optionally substituted with one or more substituents selected from the group of substituent α, azido, and lower alkyl, lower alkylsulfinyl optionally substituted with one or more substituents selected from the group of substituent α, sulfamoyl, aryl optionally substituted with one or more substituents selected from the group of substituent α, azido, and lower alkyl, heterocyclic optionally group substituted with one or more substituents selected from the group of substituent α, azido, and lower alkyl, aryloxy optionally substituted with one or more substituents selected from the group of substituent α, azido, and lower alkyl, heterocyclicoxy optionally substituted with one or more substituents selected from the group of substituent α, azido, and lower alkyl, arylthio optionally substituted with one or more substituents selected from the group of substituent α, azido, and lower alkyl, heterocyclicthio optionally substituted with one or more substituents selected from the group of substituent α, azido, and lower alkyl, arylamino optionally substituted with one or more substituents selected from the group of substituent α, azido, and lower alkyl, heterocyclicamino optionally substituted with one or more substituents selected from the group of substituent α, azido, and lower alkyl, aryl lower alkylamino optionally substituted with one or more substituents selected from the group of substituent α, azido, and lower alkyl, heterocyclic lower alkylamino optionally substituted with one or more substituents selected from the group of substituent α, azido, and lower alkyl, lower alkyl sulfamoyl optionally substituted with one or more substituents selected from the group of substituent α, aryl sulfamoyl optionally substituted with one or more substituents selected from the group of substituent α, azido, and lower alkyl, heterocyclic sulfamoyl optionally substituted with one or more substituents selected from the group of substituent α, azido, and lower alkyl, arylsulfonyl optionally substituted with one or more substituents selected from the group of substituent α, azido, and lower alkyl, heterocyclic sulfomyl optionally substituted with one or more substituents selected from the group of substituent α, azido, and lower alkyl, aryl carbamoyl optionally substituted with one or more substituents selected from the group of substituent α, azido, and lower alkyl, heterocyclic carbamoyl optionally substituted with one or more substituents selected from the group of substituent α, azido, and lower alkyl, aryl lower alkylcarbamoyl optionally substituted with one or more substituents selected from the group of substituent α, azido, and lower alkyl, heterocyclic lower alkylcarbamoyl optionally substituted with one or more substituents selected from the group of substituent α, azido, and lower alkyl, aryloxycarbonyl optionally substituted with one or more substituents selected from the group of substituent α, azido, and lower alkyl, heterocyclicoxycarbonyl optionally substituted with one or more substituents selected from the group of substituent α, azido, and lower alkyl, lower alkylenedioxy optionally substituted with halogen; oxo; azido;

[Chemical formula 13]

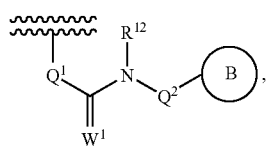
(i)

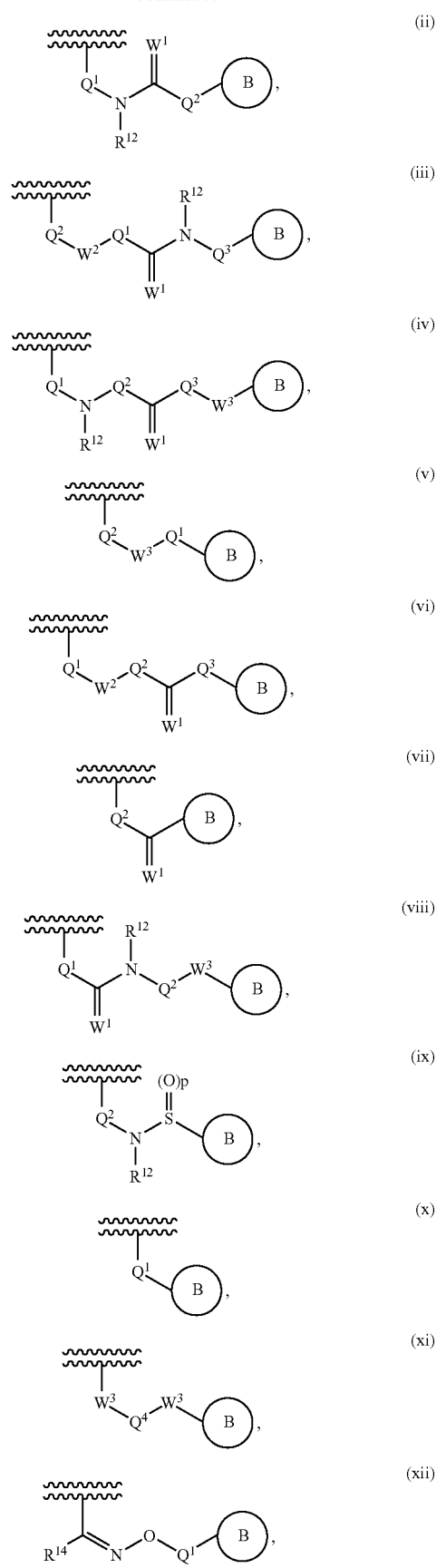

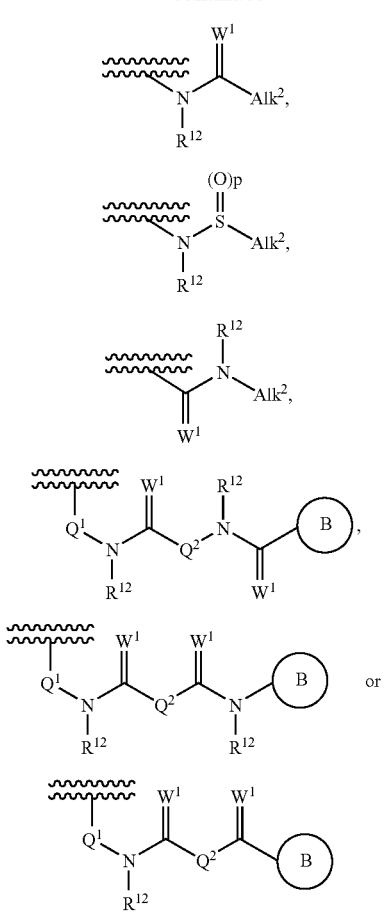

wherein $Q^1$, $Q^2$ and $Q^3$ are each independently a bond, optionally substituted lower alkylene or optionally substituted lower alkenylene;
$Q^4$ is optionally substituted lower alkylene or optionally substituted lower alkenylene;
$W^1$ and $W^2$ are each independently O or S;
$W^3$ is O, S or $NR^{12}$;
$R^{12}$ is a hydrogen atom, lower alkyl, hydroxy lower alkyl, lower alkoxy lower alkyl, lower alkoxycarbonyl lower alkyl, carbocyclic group lower alkyl or acyl;
$R^{14}$ is a hydrogen atom or lower alkyl;
ring B is an optionally substituted carbocyclic group or an optionally substituted heterocyclic group;
$Alk^2$ is optionally substituted lower alkyl;
and the ring A is optionally substituted with one or more substituents selected from these groups.
If there are multiple $W^1$, multiple $W^3$, and multiple $R^{12}$, each may be independently different.
In addition, an oxygen atom in (xii) may be cis or trans position to the substituent $R^{14}$.
The substituent of the "substituted phenyl" is, in the same way, phenyl substituted with one or two substituents selected preferably from the group of the substituent α or (i) to (xv).
The substituent of the "optionally substituted carbocyclic group" or the "optionally substituted heterocyclic group" in ring B is optionally substituted with one or more substituents selected from the following group of, for example;
the substituent α, wherein preferable is halogen, hydroxy, lower alkoxy, carboxy, lower alkoxycarbonyl, acyl, amino, lower alkylamino, acylamino, carbamoyl, lower alkylcarbamoyl, cyano, and nitro, and the like;
lower alkyl optionally substituted with one or more substituents selected from the group of the substituent α, wherein preferable is halogen, hydroxy, and lower alkoxy, and the like; amino lower alkyl substituted with one or more substituents selected from the group of substituent α,
hydroxyimino lower alkyl;
lower alkoxyimino lower alkyl;
lower alkenyl optionally substituted with one or more substituents selected from the group of substituent α;
lower alkynyl optionally substituted with one or more substituents selected from the group of substituent α;
lower alkoxy optionally substituted with one or more substuents selected from the group of substituent α, wherein preferable is halogen, hydroxy, and the like;
lower alkylthio optionally substituted with one or more substituents selected from the group of substituent α, wherein preferable is halogen;
lower alkylamino substituted with one or more substituents selected from the group of substituent α, wherein preferable is amino;
lower alkylsulfonyl optionally substituted with one or more substituents selected from the group of substituent α;
aryl lower alkoxycarbonyl optionally substituted with one or more substituents selected from the group of substituent α and lower alkyl;
acyl substituted with one or more substituents selected from the group of substituent α, wherein preferable is halogen;
lower alkylsulfonyl optionally substituted with one or more substituents selected from the group of substituent α;
sulfamoyl;
lower alkyl sulfamoyl optionally substituted with one or more substituents selected from the group of substituent α;
cycloalkyl optionally substituted with one or more substituents selected from the group of substituent α, azido and lower alkyl;
aryl optionally substituted with one or more substituents selected from the group of substituent αazido and lower alkyl;
heterocyclic group optionally substituted with one or more substituents selected from the group of substituent α, azido and lower alkyl, wherein preferable is halogen, lower alkyl, and the like; aryloxy optionally substituted with one or more substituents selected from the group of substituent α, azido and lower alkyl;
heterocyclicoxy optionally substituted with one or more substituents selected from the group of substituent α, azido and lower alkyl;
arylthio optionally substituted with one or more substituents selected from the group of substituent α, azido and lower alkyl, wherein preferable is halogen, hydroxy, lower alkoxy, acyl, and the like;
heterocyclic thio optionally substituted with one or more substituents selected from the group of substituent α, azido and lower alkyl;
arylamino optionally substituted with one or more substituents selected from the group of substituent α, azido and lower alkyl, wherein preferable is halogen, hydroxy, lower alkoxy, acyl;
heterocyclic amino optionally substituted with one or more substituents selected from the group of substituent α, azido and lower alkyl;
aryl lower alkylamino optionally substituted with one or more substituents selected from the group of substituent α, azido and lower alkyl, wherein preferable is halogen, hydroxy, lower alkoxy, acyl;

heterocyclic lower alkylamino optionally substituted with one or more substituents selected from the group of substituent α, azido and lower alkyl;
arylsulfamoyl optionally substituted with one or more substituents selected from the group of substituent αazido and lower alkyl;
heterocyclic sulfamoyl optionally substituted with one or more substituents selected from the group of substituent α, azido and lower alkyl;
arylsulfonyl optionally substituted with one or more substituents selected from the group of substituent α, azido and lower alkyl;
heterocyclic sulfonyl optionally substituted with one or more substituents selected from the group of substituent α, azido and lower alkyl;
arylcarbamoyl optionally substituted with one or more substituents selected from the group of substituent α, azido and lower alkyl;
heterocyclic carbamoyl optionally substituted with one or more substituents selected from the group of substituent α, azido and lower alkyl;
aryl lower alkylcarbamoyl optionally substituted with one or more substituents selected from the group of substituent α, azido and lower alkyl;
heterocyclic lower alkylcarbamoyl optionally substituted with one or more substituents selected from the group of substituent α, azido and lower alkyl;
aryloxy carbonyl optionally substituted with one or more substituents selected from the group of substituent α, azido and lower alkyl;
heterocyclicoxycarbonyl optionally substituted with one or more substituents selected from the group of substituent α, azido and lower alkyl;
lower alkylenedioxy optionally substituted with halogen; oxo; and the like.

In other case, the substituent of the "optionally substituted carbocyclic group", the "optionally substituted heterocyclic group", the "optionally substituted carbocyclicoxy", the "optionally substituted arylsulfonyl", the "optionally substituted aryloxycarbonyloxy", the "optionally substituted heterocyclicoxy", the "optionally substituted arylsulfinyl", the "optionally substituted arylsulfonyloxy", the "optionally substituted arylthio" is one or more substituents selected from the group of "lower alkyl" and the "substituent α".

"heteroaryl" include aromatic ring group in the aforementioned "heterocyclic group".

The substituent of the "optionally substituted 5- to 6-membered heteroaryl" is the same as the substituent of the "optionally substituted heterocyclic group" in the aforementioned "ring B". Preferable is one or more substituent selected from lower alkyl and a substituent α.

The "lower alkylene" includes a straight or branched bivalent carbon chain of a carbon number of 1 to 10, preferably a carbon number of 1 to 6, further preferably a carbon number of 1 to 3, Specifically, examples include methylene, dimethylene, trimethylene, tetramethylene, and methyltrimethylene, and the like.

The part of lower alkylene of the "lower alkylenedioxy" is the same as the aforementioned "lower alkylene".

The "lower alkenylene" includes a straight or branched bivalent carbon chain of a carbon number of 2 to 10, preferably a carbon number of 2 to 6, further preferably a carbon number of 2 to 4 having double bond at an arbitrary position. Specifically, examples include vinylene, propenylene, butenylene, butadienylene, methylpropenylene, pentenylene, and hexenylene, and the like.

The "lower alkynylene" includes a straight or branched bivalent carbon chain of a carbon number of 2 to 10, preferably a carbon number of 2 to 6, further preferably a carbon number of 2 to 4 having triple bond at an arbitrary position. Specifically, examples include ethynylene, propynylene, butynylene, pentynylene, and hexynylene, and the like.

The substituent of the "optionally substituted lower alkylene", the "optionally substituted lower alkenylene", the "optionally substituted lower alkynylene" is the substituent α, preferable is halogen, hydroxy and the like.

The "each $R^{3a}$, each $R^{3b}$, each $R^{4a}$, and each $R^{4b}$ may be independently different" means when n is 2 or 3, two or three $R^{3a}$ may be independently different, and two or three $R^{3b}$ may be independently different. In the same way, when in is 2 or 3, two or three $R^{4a}$ may be independently different, and two or three $R^{4b}$ may be independently different.

[Chemical formula 14]

The case that 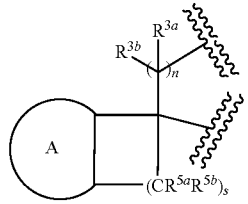 is ⓐ—, $R^5$ and ring A can be taken together to form

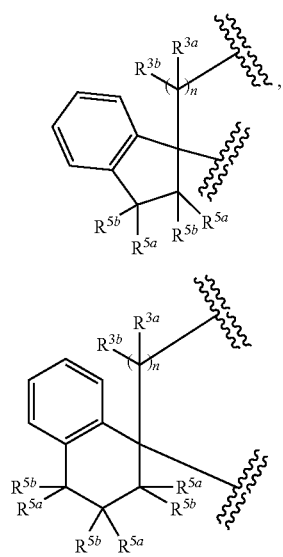

means for example, include the following structures.

[Chemical formula 15]

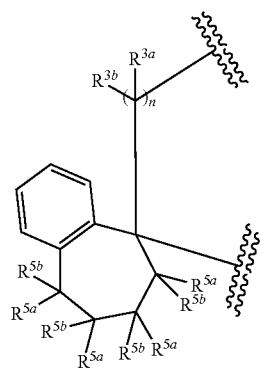

wherein each symbols are the same as described above;
preferably, $R^{5a}$ and $R^{5b}$ are all hydrogen atoms.

In this description, "solvate" includes, for example, a solvate with an organic solvent and a hydrate, and the like. When hydrate is formed, arbitrary number of water molecules may be coordinated.

The compound (I) includes a pharmaceutically acceptable salt. Examples include salts with alkali metals (lithium, sodium or potassium, and the like), alkaline earth metals (magnesium or calcium, and the like), ammonium, organic bases or amino acids, and salts with inorganic acids (hydrochloric acid, sulfuric acid, nitric acid, hydrobromic acid, phosphoric acid or hydroiodic acid, and the like), and organic acid (acetic acid, trifluoroacetic acid, citric acid, lactic acid, tartaric acid, oxalic acid, maleic acid, fumaric acid, manderic acid, glutaric acid, malic acid, benzoic acid, phthalic acid, benzenesulfonic acid, p-toluenesulfonic acid, methanesulfonic acid, or ethanesulfonic acid, and the like). Particularly, hydrochloric acid, phosphoric acid, tartaric acid, or methanesulfonic acid is preferable. These salts can be formed by a conventional method.

In addition, the compound (I) is not limited to a specific isomer, but includes all possible isomers (keto-enol isomer, imine-enamine isomer, diastereo isomer, optical isomer, and rotational isomer, and the like) and racemates. For example, the compound (I), wherein $R^{2a}$ is a hydrogen atom, includes following tautomer.

[Chemical formula 16]

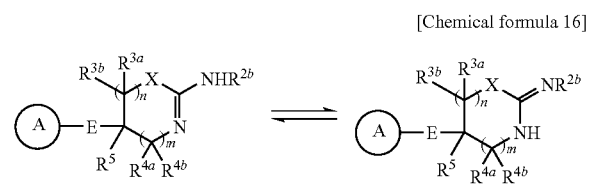

The compound (I) in this invention can be prepared by the process described in, for example Non-patent Document 1 or following process.

The synthesis of aminodihydrothiazine ring; Method A

[Chemical formula 17]

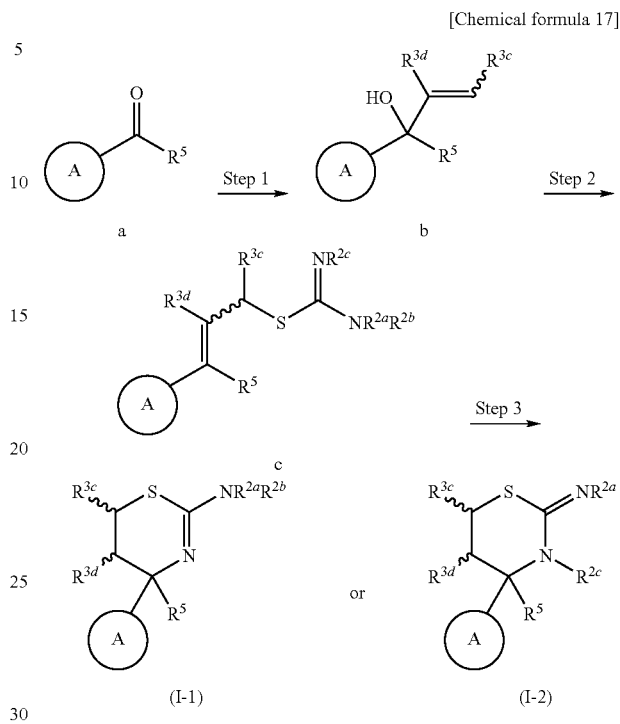

In formula, at least either $R^{2b}$ or $R^{2c}$ is a hydrogen atom, either $R^{3c}$ or $R^{3d}$ is each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group. Other symbols are the same as described above.

(Step 1)
To a solution of compound (a), which is commercially available or prepared by known method, in appropriate solvent or mixture of solvents, such as ether, tetrahydrofuran, and the like is added the Grignard reagent having substituent corresponds to the target compound; for example vinylmagnesium chloride, vinylmagnesium bromide, or propenylmagnesium bromide, and the like; at −100° C. to 50° C., preferably −80° C. to 0° C. The mixture is reacted for 0.2 to 24 hours, preferably 0.5 to 5 hours, to obtain compound (b).

(Step 2)
The compound (b) in solvent, such as toluene or absence of solvent is treated with thiourea derivatives having substituent corresponds to the target compound, such as thiourea, N-methylthiourea, N,N'-dimethylthiourea, and the like in the presence of an acid or mixture of acids, such as acetic acid, trifluoroacetic acid, hydrochloric acid, or sulfuric acid, and the like. The mixture is reacted at −20° C. to 100° C., preferably 0° C. to 50° C. for 0.5 to 120 hours, preferably 1 to 72 hours, to obtain the compound (c).

(Step 3)
The compound (c) in solvent, such as toluene or absence of solvent is treated with an acid or mixture of acids, such as trifluoroacetic acid, methanesulfonic acid, trifluoromethanesulfonic acid, and the like. The mixture is reacted at −20° C. to 100° C., preferably 0° C. to 50° C. for 0.5 to 120 hours, preferably 1 to 72 hours, to obtain the compound (I-2), wherein $R^{2b}$ is a hydrogen atom, or the compound (I-1), wherein $R^{2c}$ is a hydrogen atom.

The synthesis of aminodihydrothiazine ring; Method B

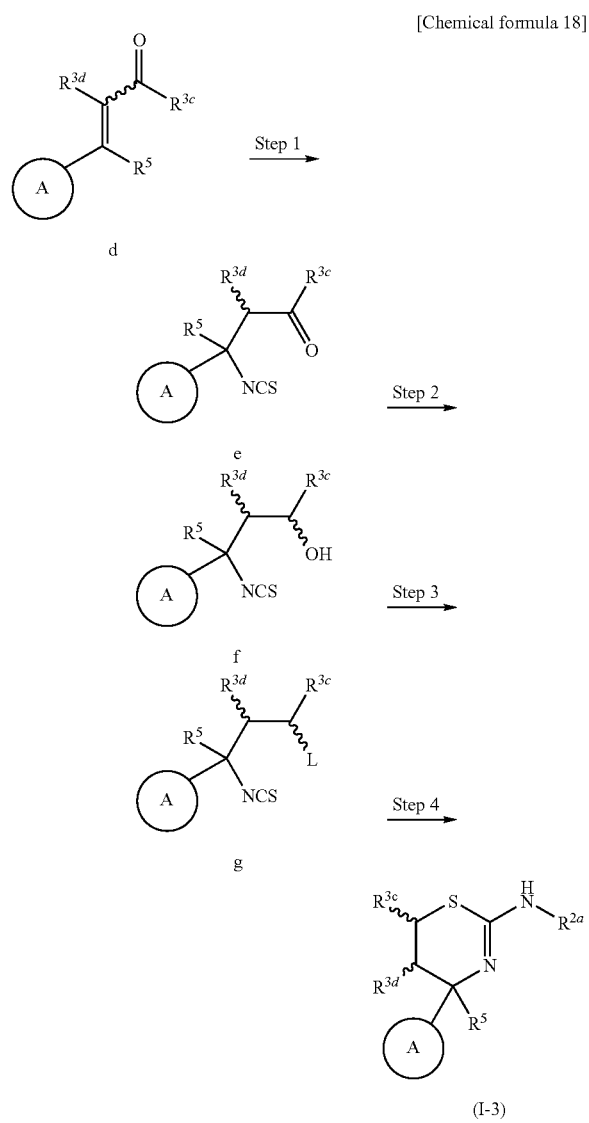

[Chemical formula 18]

In formula, L is leaving group such as halogen or sulfonyloxy, and the like. Other symbols are the same as described above.

(Step 1)

The compound (d) which is commercially available or prepared by known method is reacted with thiocyanic acid; for example, sodium thiocyanic acid, ammonium thiocyanic acid, and the like; in solvent; for example, toluene, chloroform, tetrahydrofuran, and the like; in the presence of acid; for example, water, hydrochloric acid, sulfuric acid, and the like; at 0° C. to 150° C., preferably 20° C. to 100° C. for 0.5 to 24 hours, preferably 1 to 12 hours, to obtain the compound (e), (Step 2)

To the compound (e) in solvent or mixture of solvents; for example, tetrahydrofuran, methanol, ethanol, water, and the like; in the presence or the absence of buffer like sodium dihydorgen phosphate, and the like; reducing agent; for example sodium borohydride, and the like; is added and the mixture is reacted at −80° C. to 50° C., preferably −20° C. to 20° C. for 0.1 to 24 hours, preferably 0.5 to 12 hours, to obtain the compound (f).

(Step 3)

The compound (f) in the presence or the absence of solvent; for example, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, to obtain the compound (g). Alternatively, the compound (f) in the presence or the absence of solvent; for example, toluene, dichloromethane, and the like; under base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours, to obtain the compound (g).

(Step 4)

To the compound (g) in solvent or mixture of solvents, for example methanol, ethanol, water, and the like; is reacted with primary amine; for example, ammonia or methylamine, and the like; at −20° C. to 80° C., preferably 0° C. to 40° C. for 0.5 to 48 hours, preferably 1 to 24 hours, to obtain the compound (I-3).

The synthesis of aminodihydrothiazine ring; Method C

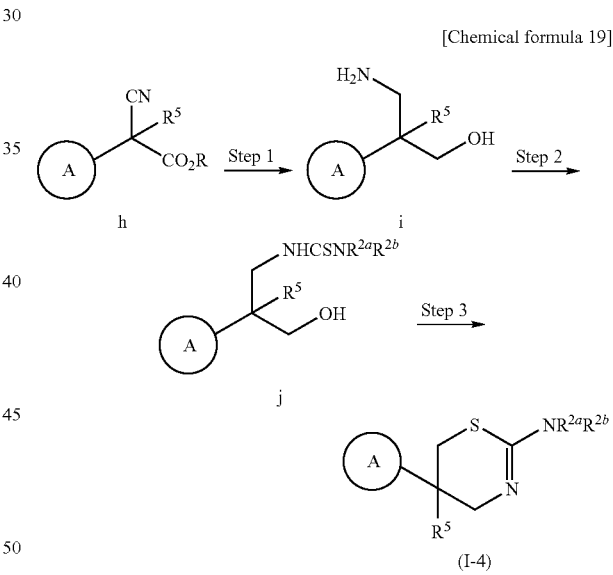

[Chemical formula 19]

In formula, R is a hydrogen atom or protective groups of carboxyl group. Other symbols are the same as described above.

(Step 1)

The compound (h) which is commercially available or prepared by known method is reacted with reducing agent; for example, lithium aluminium hydride, diisobutyl aluminium hydride, and the like; in solvent; for example tetrahydrofuran, ether, and the like; at −80° C. to 150° C., preferably 25° C. to 100° C. for 0.1 to 24 hours, preferably 0.5 to 12 hours, to obtain the compound (i).

(Step 2)

The compound (i) in solvent; for example, toluene, chloroform, tetrahydrofuran, and the like; in the presence or the absence of base; for example, diisopropylethylamine, triethylamine, pyridine, sodium hydroxide, and the like; is reacted with corresponding isothiocyanate; for example, 4-methoxybenzylisothiocyanate, t-butylisothiocyanate, and the like; or corresponding thiocarbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (j).

(Step 3)

The compound (j) in solvent; for example, acetonitrile, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, or alternatively, the compound (j) in solvent; for example, toluene, dichloromethane, and the like; in the presence of base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-4).

The synthesis of aminodihydrothiazine ring; Method D

The synthesis of aminothiazoline ring; Method A

The synthesis of tetrahydrothiazepine ring; Method A

[Chemical formula 20]

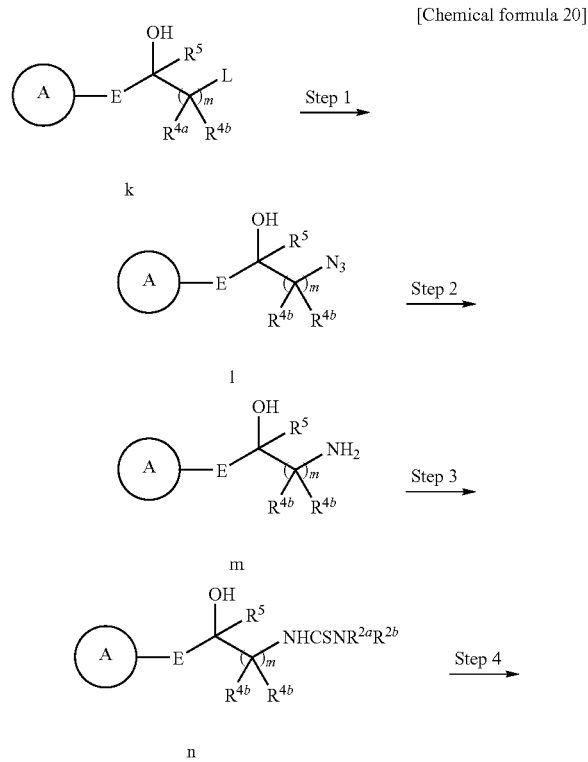

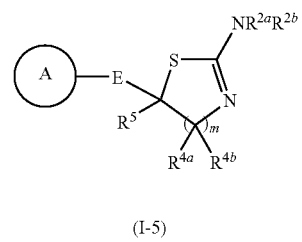

(I-5)

In formula, L is leaving group such as halogen or sulfonyloxy, and the like; m is an integer of 1 to 3; and the other symbols are the same as described above.

(Step 1)

The compound (k) which is commercially available or prepared by known method is reacted with azide reagent; for example, sodium azide, and, the like; in solvent; for example N,N-dimethylformamide, tetrahydrofuran, and the like; at 0° C. to 200° C., preferably 40° C. to 150° C. for 0.5 to 24 hours, preferably 1 to 12 hours, to obtain the compound (l).

(Step 2)

The compound 0) is reacted with reducing agent; for example, lithium aluminium hydride, diisobutyl aluminium hydride, and the like; in solvent; for example tetrahydrofuran, ether, and the like; at −80° C. to 150° C., preferably 25° C. to 100° C. for 0.1 to 24 hours, preferably 0.5 to 12 hours, to obtain the compound (m).

(Step 3)

The compound (m) in solvent; for example, toluene, chloroform, tetrahydrofuran, and the like; is reacted with corresponding isothiocyanate; for example, methylisothiocyanate, ethylisothiocyanate, and the like; or corresponding thiocarbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (n).

(Step 4)

The compound (n) in solvent; for example, acetonitrile, toluene, dichloromethane and the like; is reacted with halogenating agent; for example thionyl chloride, phosphorus oxychloride, carbon tetrabromide-triphenylphosphine, and the like; at −80° C. to 50° C., preferably −20° C. to 20° C. for 0,1 to 24 hours, preferably 0.5 to 12 hours, or alternatively, the compound (n) in solvent; for example, toluene, dichloromethane, and the like; in the presence of base; for example diisopropylethylamine, triethylamine, and the like; is reacted with sulfonating agent; for example, methanesulfonyl chloride, p-toluenesulfonylchloride, and the like; at −80° C. to 50° C., preferably -20° C. to 20° C. for 0,1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-5).

The synthesis of aminodihydrothiazine ring; Method E
The synthesis of aminothiazoline ring; Method B
The synthesis of tetrahydrothiazepine ring; Method B mixture is reacted at −20° C. to 100° C., preferably 0° C. to 50° C. for 0.5 to 200 hours, preferably 1 to 150 hours, to obtain the compound (I-6)(wherein $R^{2c}$ is H), or the compound (I-7)(wherein $R^{2b}$ is H).

The synthesis of aminodihydrothiazine ring; Method F

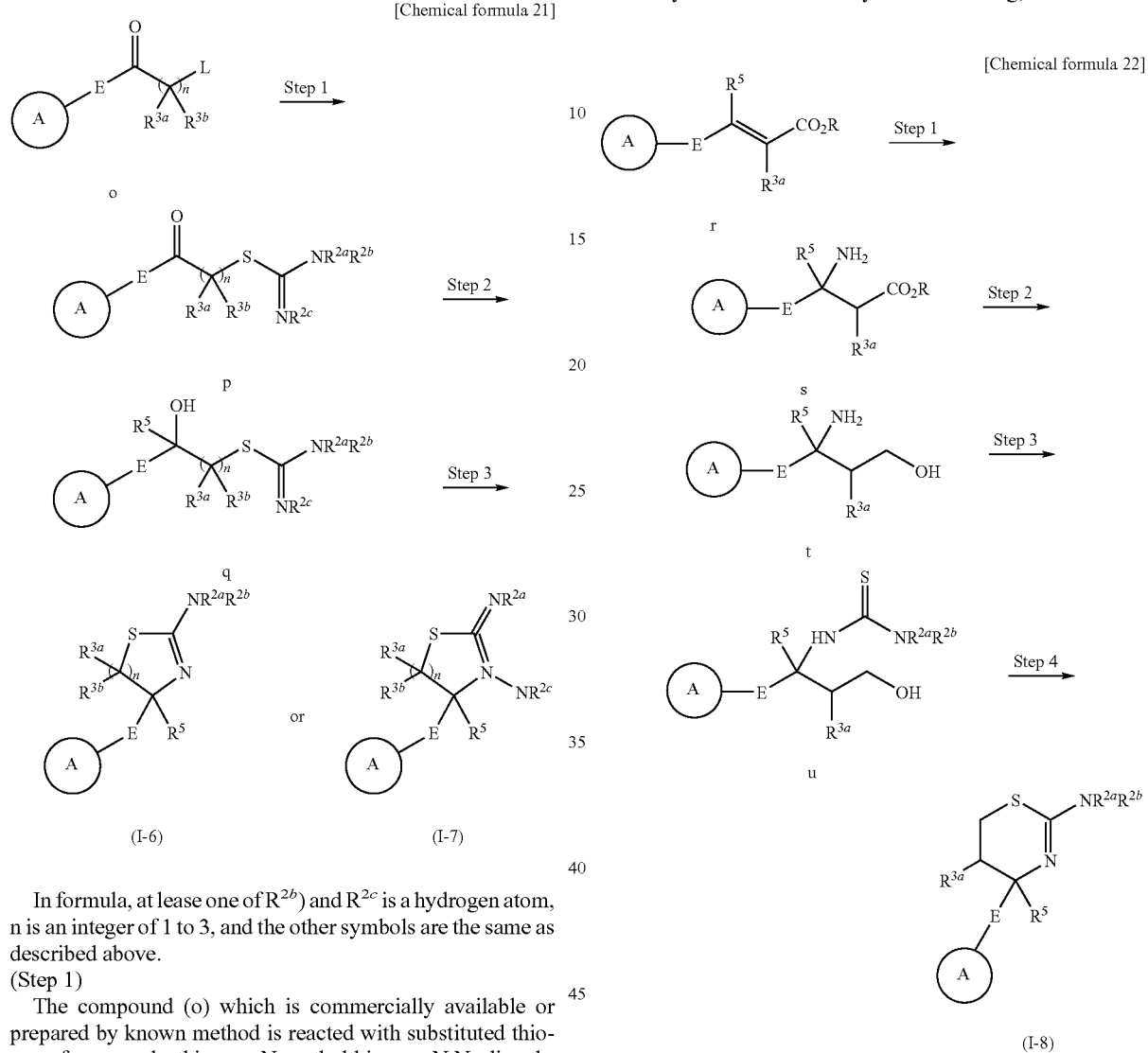

In formula, at lease one of $R^{2b}$) and $R^{2c}$ is a hydrogen atom, n is an integer of 1 to 3, and the other symbols are the same as described above.

(Step 1)

The compound (o) which is commercially available or prepared by known method is reacted with substituted thiourea; for example, thiourea, N-methylthiourea, N,N,-dimethylthiourea, N,N'-dimethylthiourea, and the like; in solvent; for example, ethanol, methanol, tetrahydrofuran, toluene, and the like; at −20° C. to 200° C., preferably 0° C. to 150° C. for 0.5 to 200 hours, preferably 1 to 120 hours, to obtain the compound (p).

(Step 2)

To the compound (p) in solvent or mixture of solvents; for example, ether, tetrahydrofuran, and the like; the Grignard reagent having substituent corresponding to target compound; for example methylmagnesium chloride, ethylmagnesium bromide, or benzylmagnesium bromide, and the like; is added at −100° C. to 50° C., preferably −80° C. to 30° C., and the mixture is reacted for 0.2 to 24 hours, preferably 0.5 to 5 hours, to obtain the compound (q).

(Step 3)

To the compound (q) in the presence or the absence of solvent; for example, toluene, and the like; acid or mixture of acids, such as trifluoroacetic acid, methanesulfonic acid, trifluoromethanesulfonic acid, and the Like; is added and the In formula, each symbols are the same as described above.
(Step 1)

The compound (r) which is commercially available or prepared by known method is reacted with ammonium chloride in solvent; for example, acetic acid, and the like; at 0° C. to 200° C., preferably 10° C. to 100° C. for 0.1 to 100 hours, preferably 0.5 to 24 hours, to obtain the compound (s).

(Step 2)

The compound (s) is reacted with reducing agent; for example, lithium aluminium hydride, diisobutyl aluminium hydride, and the like; in solvent; for example tetrahydrofuran, ether, and the like; at −80° C. to 150° C., preferably 0° C. to 100° C. for 0.1 to 24 hours, preferably 0.5 to 12 hours, to obtain the compound (t).

(Step 3)

The compound (t) in solvent; for example, toluene, chloroform, tetrahydrofuran, and the like; in the presence or the absence of base; for example, diisopropylethylamine, triethylamine, pyridine, sodium hydroxide, and the like; is reacted with corresponding isothiocyanate; for example, 4-methoxybenzylisothiocyanate, t-butylisothiocyanate, and the like; or corresponding carbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (u).

(Step 4)

The compound (u) in solvent; for example, acetonitrile, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hour preferably 0.5 to 12 hours, or alternatively, the compound (u) in solvent; for example, toluene, dichloromethane, and the like; in the presence of base; for example triethylamine, and the like; is reacted with sulfonating agent; for example, methanesulfonyl chloride, p-toluenesulfonylchloride, and the like; at −80° C. to 50° C. preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-8).

The synthesis of aminodihydrooxazine ring; Method A
The synthesis of aminotetrahydrooxazepine ring; Method A

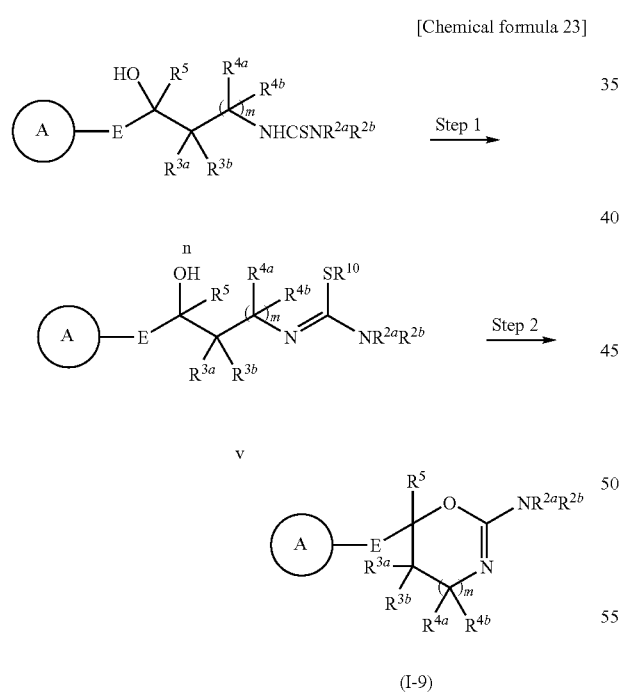

In formula, each symbols are the same as described above.

(Step 1)

The compound (n) which is obtained by Step 3(the compound (m) to the compound (n)) of "The synthesis of aminodihydrothiazine ring; Method D", in solvent; for example, methanol, ethanol, N,N-dimethylformamide, tetrahydrofuran, and the like; in the presence or the absence of base; for example, diisopropylethylamine, triethylamine, pyridine, sodium hydroxide, and the like; is reacted with alkylating agent; for example, methyl iodide, dimethyl sulfate, benzyl bromide, and the like; at 0° C. to 200° C., preferably 40° C. to 150° C. for 0.1 to 48 hours, preferably 0.5 to 24 hours, to obtain the compound (v).

(Step 2)

The compound (v) in solvent; for example, N,N-dimethylformamide, tetrahydrofuran, dichloromethane, and the like; in the presence or the absence of base; for example, diisopropylethylamine, triethylamine, pyridine, sodium hydroxide, and the like; is reacted with metallic oxide; for example, silver oxide, mercury oxide, manganese dioxide, and the like; at 0° C. to 200° C., preferably 10° C. to 150° C. for 1 to 120 hours, preferably 0.5 to 100 hours, to obtain the compound (I-9).

The synthesis of aminodihydrooxazine ring; Method B
The synthesis of aminoxazoline ring
The synthesis of aminotetrahydrooxazepine ring; Method B

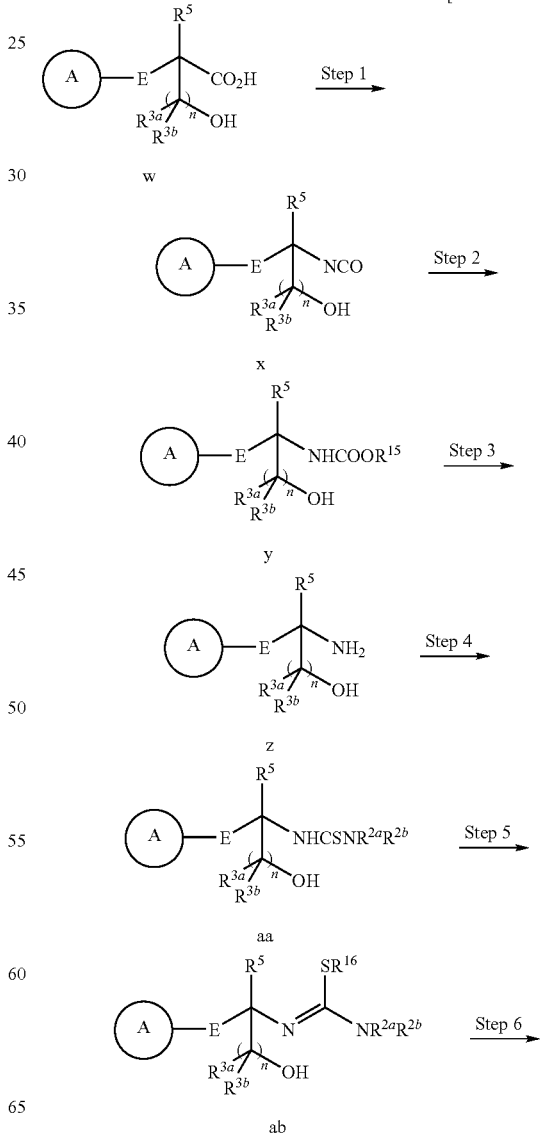

-continued

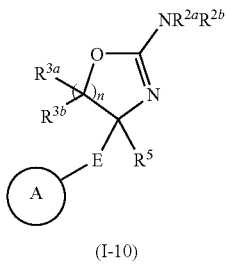

(I-10)

In formula, $R^{15}$ is optionally substituted lower alkyl; for example, t-butyl, benzyl, and the like; $R^{16}$ is hydrogen atom or lower alkyl; n is an integer of 1 to 3, and the other symbols are the same as described above.

(Step 1)

The compound (w) which is commercially available or prepared by known method in solvent; for example, toluene, t-butylalcohol, tetrahydrofuran, and the like; in the presence of base; for example, diisopropylethylamine, triethylamine, pyridine, and the like; is reacted with azide reagent; for example, diphenyl phosphoryl azide, and the like; at 0° C. to 200° C., preferably 40° C. to 150° C. for 1 to 48 hours, preferably 0.5 to 24 hours, to obtain the compound (x).

(Step 2)

The compound (x) in solvent; for example, toluene, xylene, N,N-dimethylformamide, tetrahydrofuran, and the like; is reacted with alcohol; for example, t-butylalcohol, 3,4-dimethoxybenzylalcohol, 4-methoxybenzylalcohol, and the like; at 0° C. to 300° C., preferably 50° C. to 200° C. for 1 to 800 hours, preferably 5 to 500 hours, to obtain the compound (y).

(Step 3)

The compound (y) in the presence or the absence of solvent; for example, water, toluene, dichloromethane, methanol, 1,4-dioxane, acetic acid, ethyl acetate, and the like; in the presence of acid; for example, hydrochloric acid, sulfuric acid, hydrobromic acid, trifluoroacetic acid, and the like; at 0° C. to 200° C., preferably 25° C. to 150° C. for 0.1 to 48 hours, preferably 0.5 to 24 hours, to obtain the compound (z).

(Step 4)

The compound (z) in solvent; for example, toluene, chloroform, tetrahydrofuran, and the like; in the presence of base; for example, diisopropylethylamine, triethylamine, pyridine, and the like; is reacted with corresponding isothiocyanate, or thiocarbamoylhalide corresponding to target compound; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (aa).

(Step 5)

The compound (aa) in solvent; for example, methanol, ethanol, N,N-dimethylformamide, tetrahydrofuran, and the like; in the presence or the absence of base; for example, diisopropylethylamine, triethylamine, pyridine, sodium hydroxide, and the like; is reacted with alkylating agent; for example, methyl iodide, dimethyl sulfate, benzyl bromide, and the like; at 0° C. to 200° C., preferably 40° C. to 150° C. for 1 to 48 hours, preferably 0.5 to 24 hours, to obtain the compound (ab).

(Step 6)

The compound (ab) in solvent; for example, N,N-dimethylformamide, tetrahydrofuran, dichloromethane, and the like; in the presence of base; for example, diisopropylethylamine, triethylamine, pyridine, sodium hydroxide, and the like; is reacted with metallic oxide; for example, silver oxide, mercury oxide, manganese dioxide, and the like; at 0° C. to 200° C., preferably 10° C. to 150° C. for 1 to 120 hours, preferably 0.5 to 100 hours, to obtain the compound (O-10).

The synthesis of aminotetrahydropyrimidine ring

[Chemical formula 25]

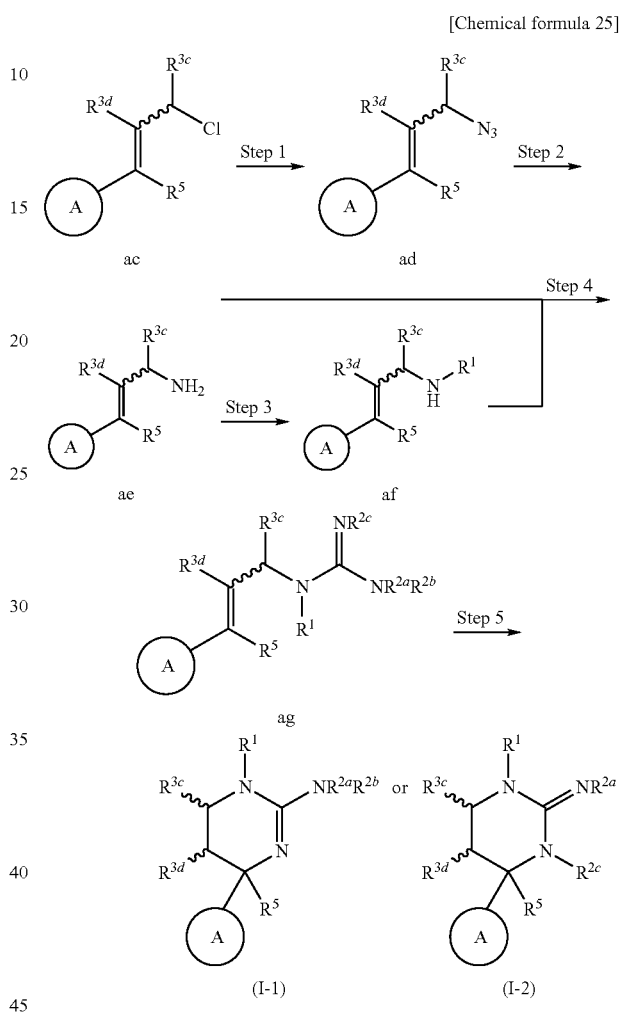

In formula, each symbols are the same as described above.

(Step 1)

To the compound (ac) prepared by known method in solvent; for example, N,N-dimethylformamide, methanol, and the like; is reacted with azide reagent; for example, sodium azide, lithium azide, and the like; at 20° C. to 150° C., preferably 50° C. to 100° C. for 0.5 to 120 hours, preferably 1 to 72 hours, to obtain the compound (ad).

(Step 2)

To the suspension of lithium aluminium hydride in solvent; for example, tetrahydrofuran, or ether, and the like; the compound (ad) dissolved in solvent; for example, tetrahydrofuran, or diethyl ether, and the like; is added under nitrogen atmosphere, at −80° C. to 20° C., preferably −30° C. to 0° C., and the mixture is reacted for 1 minute to 10 hours, preferably 10 minutes to 1 hour, or alternatively to the compound (ad) in solvent; for example, ethanol, isopropanol, or n-butanol, and the like; Raney-Nickel is added at 10° C. to 110° C., preferably 50° C. to 80° C., and reacted for 1 minute to 10 hours, preferably 10 minutes to 1 hour, to obtain the compound (ae).

(Step 3)

The compound (ae) in solvent; for example, tetrahydrofuran, dichloromethane, and the like; in the presence of acid; for example, acetic acid, or propionic acid, and the like; is reacted with reducing agent; for example, sodium cyanoborohydride, sodium triacetoxyborohydride, and the like; at −50° C. to 100° C., preferably 0° C. to 50° C., for 0.1 to 48 hours, preferably 0.5 to 24 hours, or the compound (ae) in solvent; for example, tetrahydrofuran, N,N-dimethylformamide, and the like; in the presence of dehydrating agent; for example, 1-ehthyl-3-(3-dimethylaminopropyl)carbodiimide-N-hydroxybenzotriazole, carbonyldiimidazole, and the like; or in the presence of base; for example, triethylamine, potassium carbonate, and the like; is reacted with carboxylic acid; for example, formic acid, acetic acid, and the like; at −50° C. to 100° C., preferably 0° C. to 50° C. for 0.1 to 48 hours, preferably 0.5 to 16 hours, to obtain the compound (af). And next, to the suspension of lithium aluminium hydride in solvent; for example, tetrahydrofuran, or diethyl ether, and the like; the aforementioned amide compound dissolved in solvent; for example, tetrahydrofuran, or ether, and the like; is added at −50° C. to 60° C., preferably 0° C. to 50° C., and the mixture is reacted for 1 minute to 48 hours, preferably 10 minutes to 10 hours, to obtain the compound (af).

(Step 4)

The compound (ae) or the compound (af) in solvent; for example, acetonitrile, tetrahydrofuran, N,N-dimethylformamide, and the like; is reacted with 3,5-dimethylpyrazole-1-carboxyamidine or S-methylthiourea at 0° C. to 150° C., preferably 20° C. to 100° C., and the mixture is reacted for 0.5 to 120 hours, preferably 1 to 24 hours, to obtain the compound (ag).

(Step 5)

To the compound (ag) (wherein at least either $R^{2b}$ or $R^{2c}$ is a hydrogen atom) in the presence or the absence of solvent; for example, toluene, and the like; acid; for example, trifluoroacetic acid, methanesulfonic acid, trifluoromethanesulfonic acid, and the like, or the mixture thereof; is added and the mixture is reacted at −20° C. to 100° C., preferably 0° C. to 50° C., and the mixture is reacted for 0.5 to 120 hours, preferably 1 to 72 hours, to obtain the compound (I-2) (wherein $R^{2b}$ is a hydrogen atom) or the compound (I-1) (wherein $R^{2c}$ is a hydrogen atom) respectively, Proviso, if $R^{2a}$, $R^{2b}$, and $R^{2c}$ have fragile structure under acidic condition; for example, t-butyloxycarbonyl, and the like; $R^{2a}$, $R^{2b}$, and $R^{2c}$ in the compound (I-1) or the compound (I-2) may be transformed into a hydrogen atom.

The synthesis of aminothiazoline ring; Method C

[Chemical formula 26]

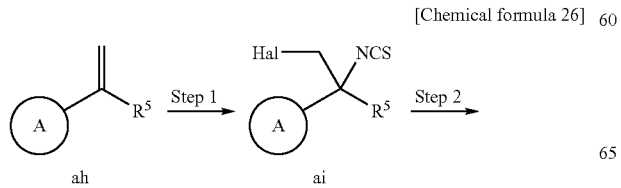

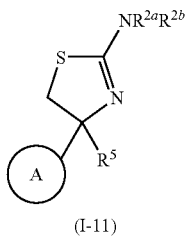

(I-11)

In formula, Hal is halogen, and other symbols are the same as described above.

(Step 1)

The compound (ah) which is commercially available or prepared by known method in solvent; for example, toluene, chloroform, tetrahydrofuran, and the like; or in mixed-solvent; for example, chloroform-water, and the like; is reacted with halogen; for example, including iodine, bromine, chorine; phase transfer catalyst; for example, sodium thiocyanic acid, ammonium thiocyanic acid, and the like; at 0° C. to 150° C., preferably 20° C. to 100° C., for 0.5 to 48 hours, preferably 1 to 24 hours, to obtain the compound (ai).

(Step 2)

The compound (ai) in solvent; for example, toluene, chloroform, tetrahydrofuran, and the like; is reacted with amine having substituent corresponding to target compound; for example ammonia, methylamine, diethylamine, and the like; at 0° C. to 150° C., preferably 20° C. to 100° C., for 0.5 to 48 hours, preferably 1 to 24 hours, to obtain the compound (I-11).

The aminoacyl derivative-1

[Chemical formula 27]

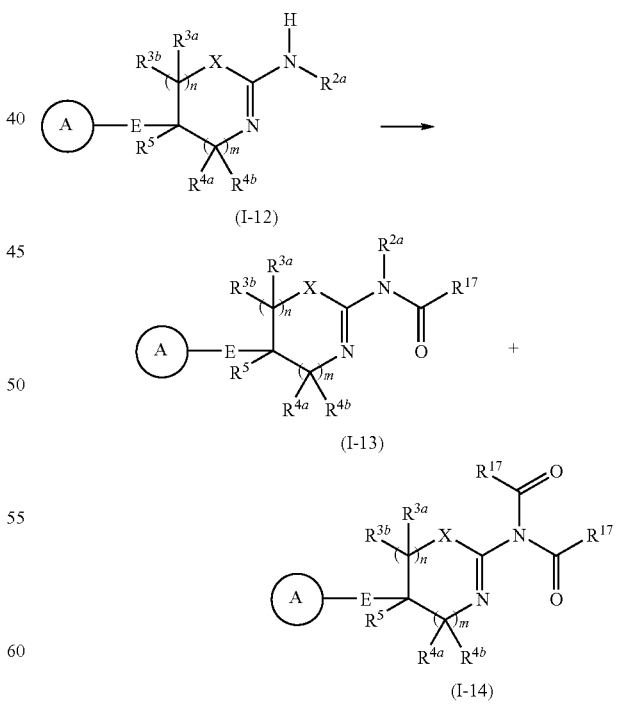

In formula, $R^{17}$ is optionally substituted lower alkyl, an optionally substituted carbocyclic group or an optionally substituted heterocyclic group, and the other symbols are the same as described above.

The compound (I-12) wherein $R^{2b}$ is a hydrogen atom in the presence or the absence of solvent; for example, tetrahydrofuran, dichloromethane, and the like; in the presence of base; for example, pyridine, triethylamine, and the like; is reacted with acylating agent having substituent corresponding to target compound; for example, benzoyl chloride, 2-furoyl chloride, acetic anhydride, and the like; at −80° C. to 100° C., preferably −20° C. to 40° C., for 0.1 to 24 hours, preferably 1 to 12 hours, or alternatively, the compound (I-12) in solvent; for example, N,N-dimethylformamide, tetrahydrofuran, dichloromethane, and the like; in the presence of dehydrating agent; for example, dicyclohexylcarbodiimide, carbonyldiimidazole, and the like; is reacted with carboxylic acid having substituent corresponding to target compound; for example, amino acid, glycolic acid, and the like; at −80° C. to 100° C., preferably −20° C. to 40° C., for 0.1 to 24 hours, preferably 1 to 12 hours, to obtain the compound (I-13) and/or the compound (I-14) (wherein $R^{2a}$ is a hydrogen atom).

The guanidino derivatives

[Chemical formula 28]

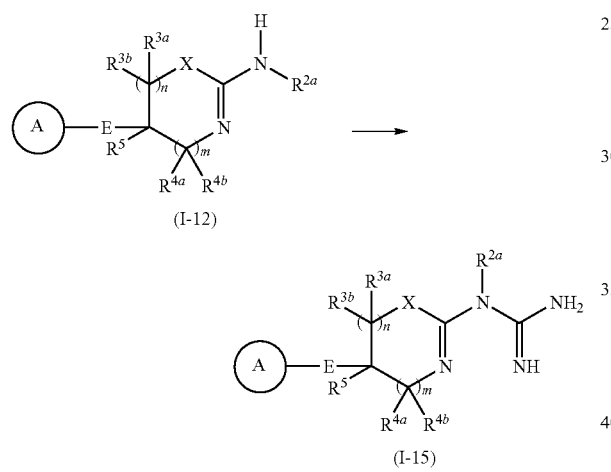

(I-12)

(I-15)

In formula, each symbols are the same as described above,

The compound (I-12) wherein $R^{2b}$ is a hydrogen atom in solvent; for example, acetonitrile, tetrahydrofuran. N,N-dimethylformamide, and the like; in the presence or the absence of base; for example, triethylamine, sodium hydrogencarbonate, and the like; is reacted with 3,5-dimethylpyrazole-1-carboxyamidine, or S-methylisothiourea etc. at 0° C. to 150° C., preferably 20° C. to 100° C., for 0.5 to 120 hours, preferably 1 to 24 hours, to obtain the compound (I-15).

The carbamoyl derivatives

[Chemical formula 29]

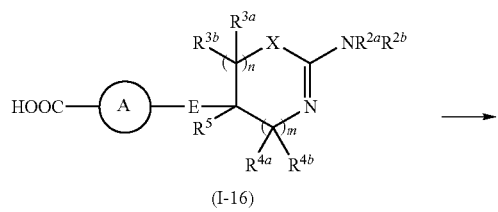

(I-16)

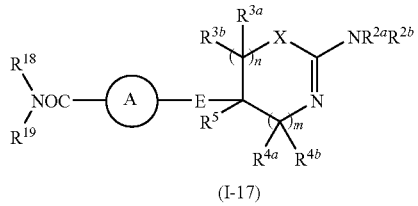

(I-17)

In formula, $CONR^{18}R^{19}$ is optionally substituted carbamoyl, and the other symbols are the same as described above.

The compound (I-16) having a carboxyl group as substituent of ring A in solvent; for example, N,N-dimethylformamide, tetrahydrofuran, dichloromethane, and the like; in the presence of dehydrating agent; for example, dicyclohexylcarbodiimide, carbonyldiimidazole, dicyclohexylcarbodiimide-N-hydroxybenzotriazole, and the like; is reacted with primary amine or secondary amine (aniline, 2-aminopyridine, dimethylamine etc.) at −80° C. to 100° C., preferably −20° C. to 40° C., for 0.1 to 24 hours, preferably 1 to 12 hours, to obtain the compound (I-17).

The acylamino derivative-2

[Chemical formula 30]

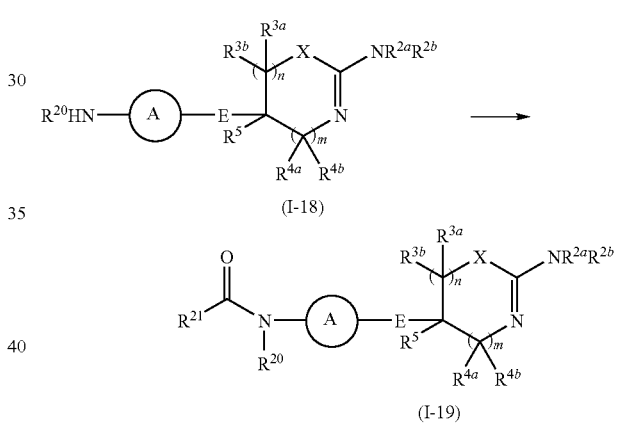

(I-18)

(I-19)

In formula, $NHR^{20}$ is optionally substituted amino; $NR^{20}COR^{21}$ is optionally substituted acyl amino, optionally substituted ureido, carboxy amino having substituent on oxygen atom, and the other symbols are the same as described above.

The compound (I-18) having an optionally substituted amino group on ring A in the presence or the absence of solvent; for example, tetrahydrofuran, dichloromethane, and the like; in the presence or the absence of base; for example, pyridine, triethylamine, and the like; is reacted with reagent including acid chloride, acid anhydride, chloroformate ester derivatives, isocyanate derivatives (benzoyl chloride, 2-furoyl chloride, acetic anhydride, benzyl chloroformate, di-t-butyl dicarbonate, phenyl isocyanate etc.), at −80° C. to 100° C., preferably −20° C. to 40° C., for 0.1 to 24 hours, preferably 1 to 12 hours. Or alternatively, the compound (I-18) having an optionally substituted amino group on ring A in solvent; for example, N,N-dimethylformamide, tetrahydrofuran, dichloromethane, and the like; in the presence of dehydrating agent; for example, dicyclohexylcarbodiimide, carbonyldiimidazole, dicyclohexylcarbodiimide-N-hydroxybenzotriazole, and the like; is reacted with carboxylic acid having substituent corresponding to target compound;

for example, benzoic acid, 2-pyridinecarboxylic acid, and the like; at 80° C. to 100° C., preferably −20° C. to 40° C., for 0.1 to 24 hours, preferably 1 to 12 hours, to obtain the compound (I-19).

The alkylamino derivatives

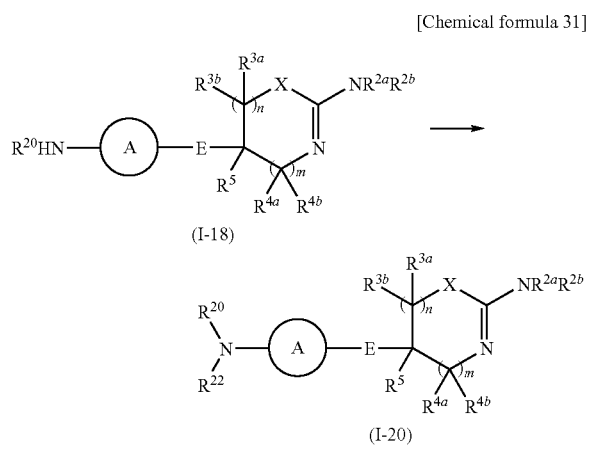

In formula, NHR$^{20}$ is optionally substituted amino, R$^{22}$ is lower alkyl.

The compound(I-18) having an amino group on ring A in solvent; for example, dichloromethane, tetrahydrofuran, and the like; in the presence or the absence of acid; for example, acetic acid, and the like; is reacted with aldehyde having substituent corresponding to target compound; for example, benzaldehyde, pyridine-2-carboaldehyde, and the like; and reducing agent; for example, sodium borohydride, sodium triacetoxyborohydride, and the like; at −80° C. to 100° C., preferably 0° C. to 40° C., for 0.5 to 150 hours, preferably 1 to 24 hours, to obtain the compound (I-20).

The substituted alkoxy derivatives

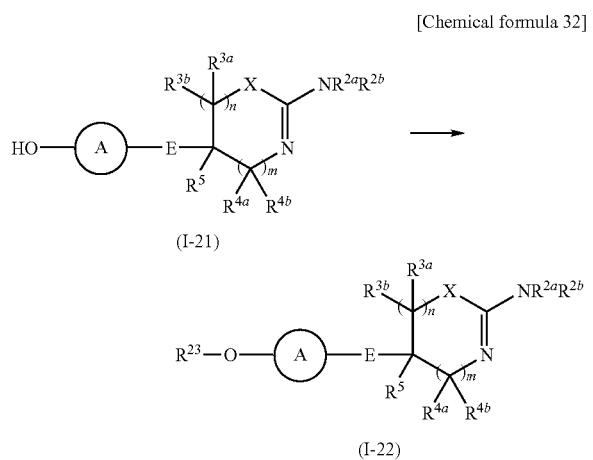

In formula, R$^{23}$ is optionally substituted lower alkyl, an optionally substituted carbocyclic group or an optionally substituted heterocyclic group, etc., and the other symbols are the same as described above.

The compound (I-21) having a hydroxy group as substituent of A ring in solvent; for example, N,N-dimethylformamide, tetrahydrofuran, and the like; in the presence of base; for example potassium carbonate, sodium hydroxide, sodium hydride, and the like; is reacted with alkylating agent having substituent corresponding to target compound; for example, benzylchloride, methyl iodide, and the like; at −80° C. to 100° C., preferably 0° C. to 40° C., for 0.5 to 150 hours, preferably 1 to 24 hours, or alternatively, the compound (I-18) in solvent; for example, N,N-dimethylformamide, tetrahydrofuran, and the like; under Mitsunobu reagent; for example triphenylphosphine-azodicarboxylic acid ethyl ester, and the like; is reacted with alcohol; for example, 2-aminoethanol, and the like; at −80° C. to 100° C., preferably 0° C. to 40° C., for 0.5 to 72 hours, preferably 1 to 24 hours, to obtain the compound (I-22).

The introduction of substituent with palladium coupling reaction

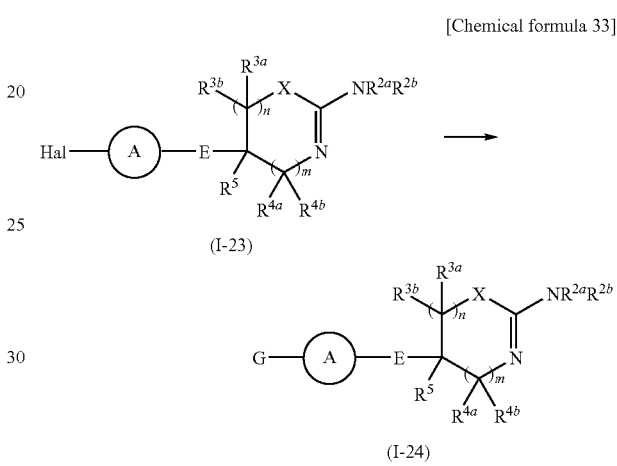

In formula, Hal is halogen, G is optionally substituted lower alkenyl, optionally substituted lower alkynyl, optionally substituted lower alkoxycarbonyl, an optionally substituted carbocyclic group or an optionally substituted heterocyclic group etc., and the other symbols are the same as described above.

The compound (I-23) having halogen as substituent of A ring in solvent; for example, tetrahydrofuran, N,N-dimethylformamide, 1,2dimethoxyethane, methanol, and the like; in the presence of base; for example, triethylamine, sodium carbonate, and the like; palladium catalyst; for example, palladium acetate, palladium chloride, and the like; and ligand; for example triphenylphosphine, and the like; is reacted with compound having substituent corresponding to target compound(styrene, propargyl alcohol, aryl boronic acid, carbon monoxide), with or without microwave irradiation, at −80° C. to 150° C., preferably 0° C. to 100° C., for 0.5 to 72 hours, preferably 1 to 24 hours, to obtain the compound (I-24).

The oxime derivatives

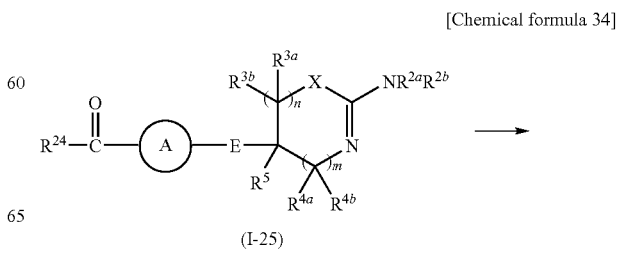

-continued

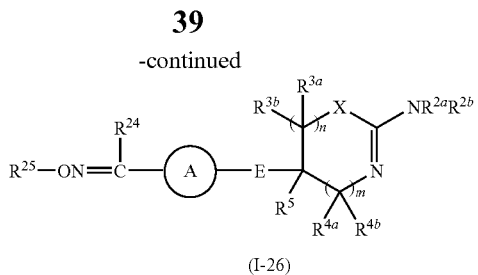

(I-26)

In formula, in $R^{24}$ is a hydrogen atom or optionally substituted lower alkyl etc., $R^{25}$ is a hydrogen atom, optionally substituted lower alkyl, optionally substituted lower alkenyl or an optionally substituted carbocyclic group or an optionally substituted heterocyclic group etc., and the other symbols are the same as described above.

The compound (I-25) having an acyl group as substituent of A ring in solvent; for example, methanol, ethanol, and the like; in the presence or the absence of additives; for example, potassium acetate, and the like; is reacted with hydroxylamine having substituent corresponding to target compound (hydroxylamine, methoxylamine, O-benzylhydroxylamine, etc.) or the salt thereof, at 0° C. to 100° C., preferably 0° C. to 40° C., for 0.5 to 150 hours, preferably 1 to 72 hours, to obtain the compound (I-26).

Production of optical active compounds

For example, Optical active compound aq, one embodiment of the pharmaceutical composition of the present invention can be synthesized in the following method.

1) n=2
1-1) X=S

[Chemical formula 35]

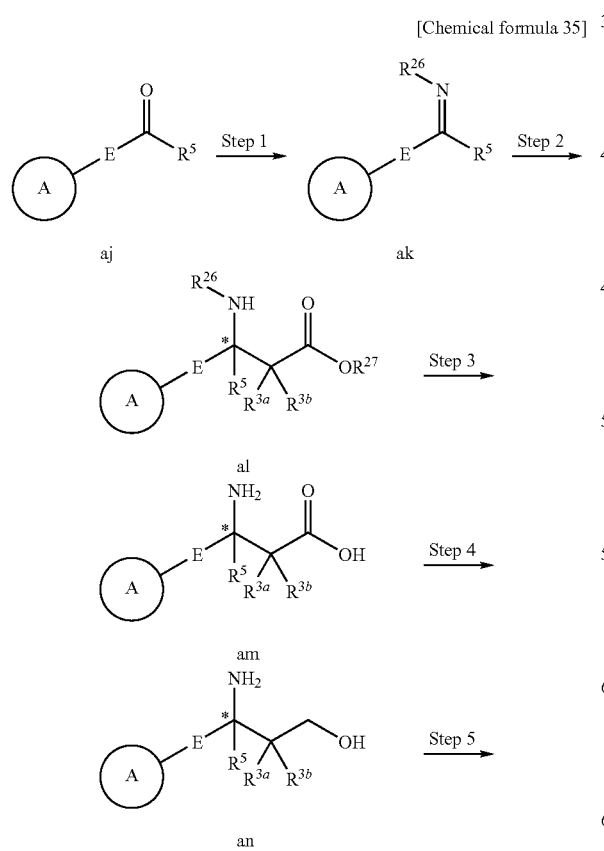

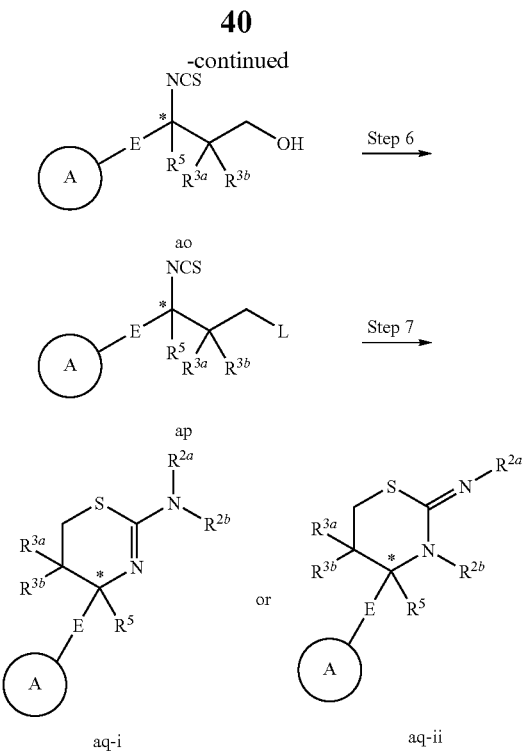

wherein $R^5$ is hydrogen, optionally substituted lower alkyl, optionally substituted lower alkenyl, optionally substituted lower alkynyl, lower alkoxycarbonyl, optionally substituted carbamoyl, an optionally substituted cabocyclic group or an optionally substituted heterocyclic group, $R^{25}$ is a chiral sulfoxide having optionally substituted lower alkyl, optionally substituted lower alkenyl, optionally substituted carbocyclic group or optionally substituted hetererocyclic group, $R^{3a}$ and $R^{3b}$ are each independently hydrogen, halogen, hydroxy, optionally substituted lower alkyl, optionally substituted lower alkenyl, optionally substituted lower alkoxycarbonyl, optionally substituted carbamoyl, an optionally substituted carbocyclic group or an optionally substituted heterocyclic group, optionally substituted acyl, carboxy or optionally substituted amino, $R^{27}$ is optionally substituted lower alkyl, optionally substituted lower alkenyl, $R^{2a}$ and $R^{2b}$ are each independently hydrogen, hydroxy, optionally substituted lower alkyl, optionally substituted lower alkenyl, optionally substituted amino, optionally substituted amidino, optionally substituted acyl, optionally substituted carbamoyl, optionally substituted carbamoylcarbonyl, optionally substituted lower alkylsulfonyl, optionally substituted arylsulfonyl, an optionally substituted carbocyclic group or an optionally substituted heterocyclic group, L is an leaving group such as halogen, methanesulfonyloxy, trifluoromethylsulfonyloxy and the like, and other symbols are the same as described above.

The above compounds ak and al can be synthesized according to the method described in (1)T, Fujisawa et al., Tetrahedron Lett., 37, 3881-3884 (1996), (2)D. H. Hua et al, Sulfur Reports, vol. 21, pp. 211-239 (1999), (3)Y. Koriyama et al., Tetrahedron, 58, 9621-9628 (2002), (4)T. Vilavan et al, Cuuent Organic Chemistry, 9, 1315-1392 (2005) and the like, or by optical resolution of each intermediate or final compound, or by the method described below. Examples of methods for optical resolution are separation of optical isomers using an optically active column, kinetic resolution by an enzyme reaction or the like, crystallization of diastereomers by salt formulation using a chiral acid or a chiral base, and a preferential crystallization etc.

Step 1

Compound ak can be obtained by reacting Compound aj, which is commercially available or can be prepared by a known method, with a chiral reagent having a substituent corresponding to the target compound such as para-toluene, tert-butylsulfine amide or the like at 60° C. to 120° C., preferably 80° C. to 100° C. in a solvent such as ether, tetrahydrofuran, toluene, benzene or the like or a mixed solvent such as ether-tetrahydrofuran or the like for 0.5 to 24 hours, preferably 0.5 to 5 hours in the presence of moleculer sieves or magnesium sulfate or the like, under continuous evaporation by Dean-Stark apparatus, or in the presence of a chiral reagent having a substituent corresponding to the target compound such as para-toluene, tert-butylsulfine amide ane the like according to the method described in the above literatures.

Step 2

Compound al can be diastereoselectively obtained by reacting compound ak with a metal, which is lithium, aluminum, zinc, titanium or the like, enolate of acetate ester or the like possessing a substituent corresponding to the target compound which is commercially available or prepared by a known method, at −100° C. to 0° C., preferably −80° C. to −50° C. for 0.5 to 24 hours, preferably 0.5 hours in a solvent such as ether, tetrahydrofuran, toluene, methylene chloride or a mixed solvent of ethertetrahydrofuran or the like, or obtained according to the method described in the above literature (1) or (3). Alternatively, ketenesilyl acetate of acetate ester which is prepared from ester acetate or the like possessing a substituent corresponding to the target compound can be used.

Step 3

Compound am can be obtained by reacting Compound al in a solvent such as methanol, ethanol ether, tetrahydrofuran, 1,4-dioxane, methylene chloride, ethyl acetate or the like, which contains hydrogen chloride, trifluoroacetic acid or the like, or in trifluoroacetcic acid without a solvent, or at −30° C. to 100° C., preferably −10° C. to 90° C. for 0.5 to 12 hours, preferably 0.5 to 5 hours.

Step 4

To a solution of Compound am in a solvent such as ether, tetrahydrofuran, toluene or the like or a mixed solvent such as ether-tetrahydrofuran is added a reductant such as a borantetrahydrofuran complex, a boran-dimethylsulfide complex, a boran-triethylamine complex, a boran-pyridine complex or the like, or ether of tetrahydrofuran solution of them at −30° C. to 30° C., preferably −10° C. to 20° C. and the mixture is reacted for 0.5 to 12 hours, preferably 0.5 to 5 hours to obtain Compound an.

Step 5

To a solution of Compound an in a solvent such as methylene chloride, toluene or the like or a mixed solvent of methylene chloride-water or the like is added calcium carbonate, potassium carbonate or the like, and added thiophosgene at −30° C. to 50° C., preferably −10° C. to 25° C., followed by reacting for 0.5 to 12 hours, preferably 0.5 to 5 hours to obtain Compound ao.

Step 6

To a solution of Compound ao in a solvent such as methylene chloride, tetrahydrofuran, toluene or the like are added oxalyl chloride, thionyl chloride or the like and a catalytic amount of N,N-dimethylformamide at −30° C. to 50° C., preferably −10° C. to 20° C. The mixture is reacted at 0° C. to 100° C., preferably 20° C. to 90° C. for 0.5 to 12 hours, preferably 0.5 to 5 hours to obtain Compound ap. Alternatively, Compound ap can be obtained by halogenation according to the method described in Comprehensive Organic Transformations, Richard C Larock (Mcgraw-Hill) or by reacting Compound ao with a sulfonylation reagent such as methanesulfonyl chloride, p-toluene sulfonyl chloride or the like in the presence of a base such as diisopropylethylamine, triethylamine or the like in a solvent such as toluene, dichloromethane or the like at −80° C. to 50° C., preferably −20° C. to 20° C. for 0.1 to 24 hours, preferably 0.5 to 12 hours.

Step 7

To a solution of Compound ap in a solvent such as ethyl acetate, methylene chloride, tetrahydrofuran, toluene or the like is added 15 to 30% aqueous ammonia or a reagent having a substituent corresponding to the target compound such as tert-butyl amine at −30° C. to 50° C., preferably −10° C. to 30° C. The mixture is reacted at −10° C. to 30° C., preferably 0° C. to 30° C. for 0.5 to 72 hours to obtain Compound aq-i or Compound aq-ii.

In the case that thus-obtained Compound aq-i or Compound aq-ii is a compound wherein $R^{2a}$ and/or $R^{2b}$ is hydrogen, the target substituent $R^{2a}$ or $R^{2b}$ can be introduced by the usual method, if necessary.

1-2) Introduction of $R^{3a}$ and $R^{3b}$

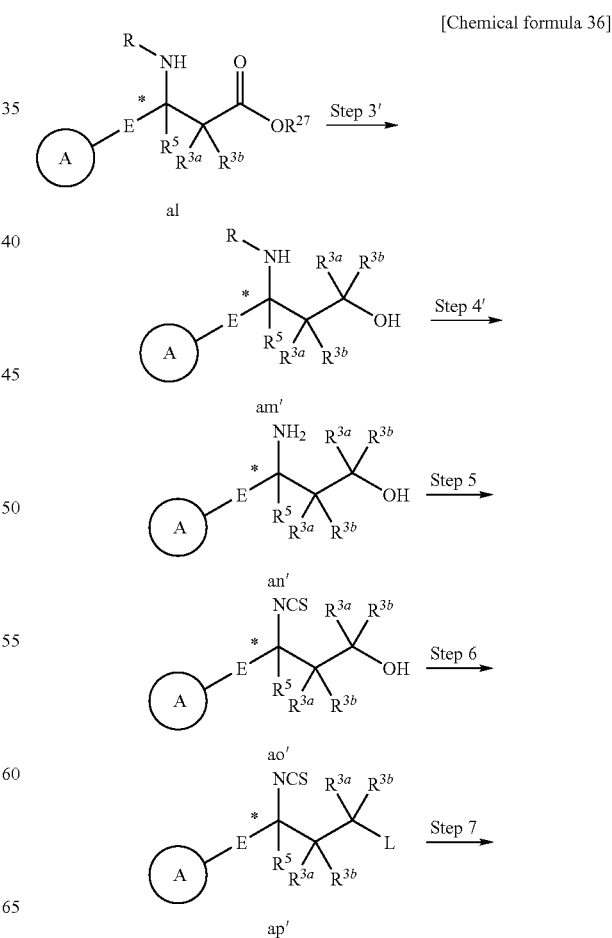

[Chemical formula 36]

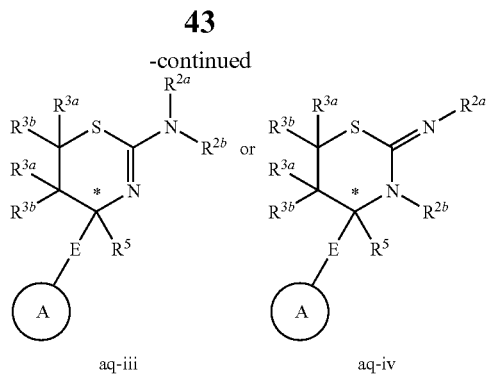

aq-iii          aq-iv wherein each symbols are the same as described above.

To obtain Compound aq-iii or aq-iv wherein $R^{3a}$ and $R^{3b}$ are substituted at the carbon atom neighboring to X, $R^{3a}$ and $R^{3b}$ may be introduced by conducting Step 3' and Step 4' instead of Step 3 and Step4.

Step 3'

To a solution of Compound al in a solvent such as ether, tetrahydrofuran or the like or a mixed solvent such as ether-tetrahydrofuran or the like is added a Grignard reagent having a substituent corresponding to the target compound such as methyl magnesium chloride, ethyl magnesium bromide or the like at −100° C. to 50° C., preferably −80° C. to 30° C. to obtain Compound am'. Alternatively, after conversion of Compound al to Weinreb amide thereof, the compound is reacted sequentially with a Grignard reagent having a substituent corresponding to the target compound such as $R^{3\ a}$ MgBr, $R^{3\ b}$ MgBr or the like to obtain Compound am', The reaction may be conducted for 0.2 to 24 hours, preferably 0.2 to 5 hours.

Step 4'

Compound an' can be synthesized according to the above-mentioned Step 3. Compound an can be obtained by reacting Compound am' in a solvent such as methanol, ethanol, ether, tetrahydrofuran, 1,4-dioxane, methylene chloride, ethyl acetate or the like which includes hydrogen chloride, trifluoroacetic acid or the like, without a solvent, or in trifluoroacetic acid without a solvent at −30° C. to 100° C., preferably −10° C. to 90° C. for 0.5 to 12 hours, preferably 0.5 to 5 hours.

Then, the target Compound aq-iii or aq-iv can be obtained by conducting the similar methods to Steps 5 to 7 mentioned in the above 1-1), 1-3) X=O

[Chemical formula 37]

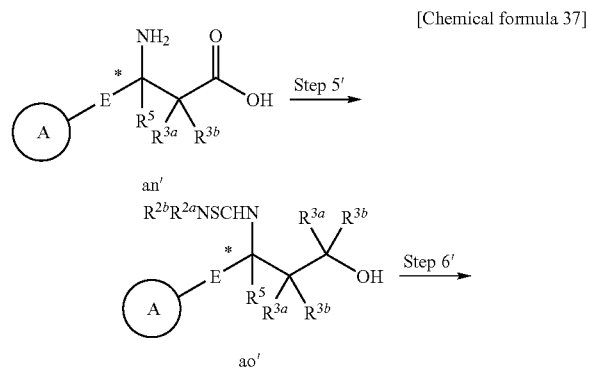

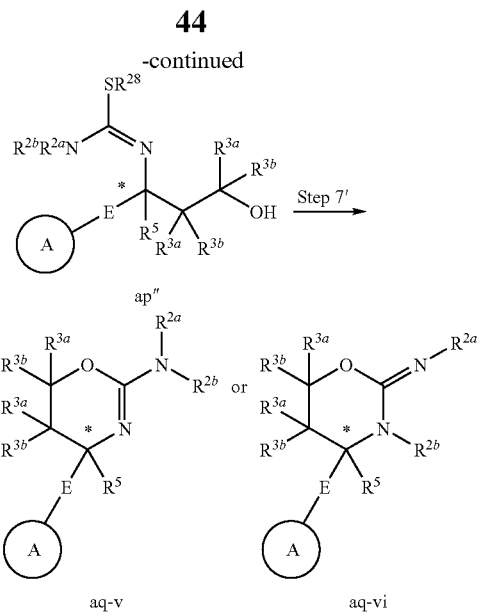

aq-v          aq-vi wherein $R^{28}$ is alkyl or optionally substituted alkylsulfonyl, optionally substituted carbocyclic sulfonyl or optionally substituted heterocyclic sulfonyl and other symbols are the same as described above.

The target compound can be obtained by conducting the following steps instead of Steps 5 to 7 described in the above 1-1).

Step 5'

Compound ao' can be obtained by reacting Compound an' with an isothiocyanate having the substituent corresponding to the target compound such as ally isothiocyanate, tert-butylisothiocyanate or the like or a thiocarbamoyl halide having the substituent corresponding to the target compound such as N,N-dimethylthiocarbamoyl chloride, N,N-diethylthiocarbamoyl chloride or the like in a solvent such as toluene, chloroform, tetrahydrofuran or the like at 0° C. to 150° C., preferably 20° C. to 100° C. for 0.5 to 120 hours, preferably 1 to 72 hours.

Step 6'

Compound ap" can be obtained by reacting Compound ao' with an alkylating agent such as methyl iodide, diethyl sulfate, benzylbromide or the like or a sulfonating agent such as p-toluensulfonyl chloride in the presence or absence of a base such as diisopropylethylamine, triethylamine, pyridine, sodium hydroxide or the like in a solvent such as methanol, ethanol, dimethylformamide, tetrahydrofuran or the like at 0° C. to 200° C., preferably 40° C. to 150° C. for 0.1 to 48 hours, preferably 0.5 to 24 hours.

Step 7

Compound aq-v or aq-vi can be obtained by reacting Compound ap' in the presence or absence of a base such as diisopropylethylamine, triethylamine, pyridine, sodium hydroxide or the like, in the presence or absence of a metallic oxide such as silver oxide, mercury oxide, manganese dioxide or the like, in a solvent such as dimethylformamide, tetrahydrofuran, dichloromethane or the like at 0° C. to 200° C., preferably 10° C. to 150° C. for 1 to 120 hours, preferably 0.5 to 100 hours.

1-4) X=N

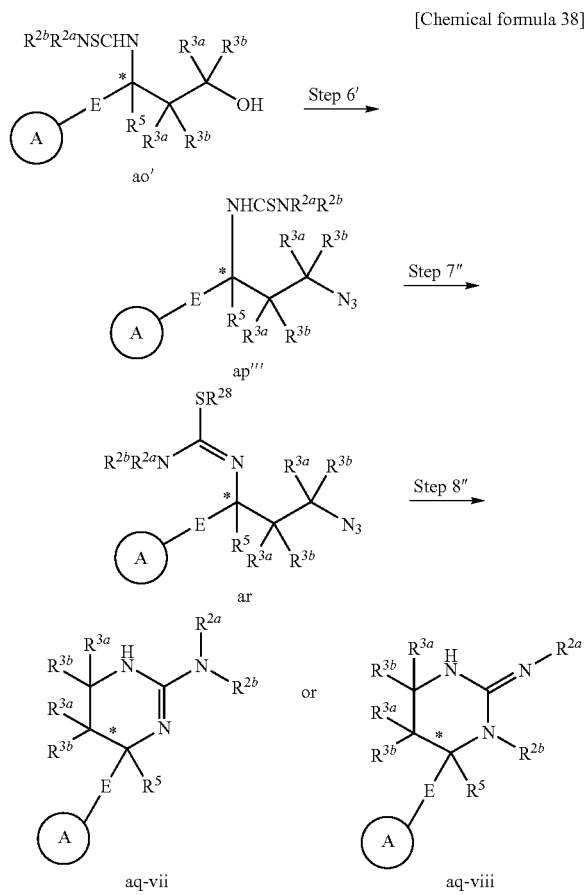

[Chemical formula 38]

wherein each symbols are the same as described above.
Step 6"

Compound ap'" can be obtained by reacting Compound ao' with an azidation agent such as sodium azide, trimethylsillylazide or the like in the presence or absence of an acid such as trifluoroacetic acid or the like in a solvent such as chloroform, tetrahydrofuran or the like at −10° C. to 200° C., preferably 0° C. to 100° C. for 0.1 to 48 hours, preferably 0.5 to 24 hours.
Step 7'

Compound ar can be obtained by reacting Compound ap'" with an alkylating agent such as methyl iodide, diethyl sulfate, benzylbromide or the like or a sulfonating agent such as p-toluensulfonyl chloride in the presence or absence of a base such as diisopropylethylamine, triethylamine, pyridine, sodium hydroxide or the like in a solvent such as methanol, ethanol, dimethylformamide, tetrahydrofuran or the like at 0° C. to 200° C., preferably 40° C. to 150° C. for 0.1 to 48 hours, preferably 0.5 to 24 hours.
Step 8"

To a solution of Compound ar in a solvent such as tetrahydrofuran, ethyl acetate, methanol or the like is added a catalytic reduction catalyst such as 10% Pd/C, and the mixture is reacted under hydrogen atmosphere at normal pressures to 5 atm, preferably at normal pressure to 2 atm at 10° C. to 100° C., preferably 20° C. to 80° C. for 0.5 to 48 hours, preferably 6 to 20 hours to obtain Cyclized Compound aq-vii or aq-viii. Alternatively, Cyclized Compound aq-vii or aq-viii can be obtained by reducing a azide group of Compound or by the method described in "Comprehensive Organic Transformations, Richard C Larock (Mcgraw-Hill)". If necessary, the compound obtained by reduction may be treated with a base such as triethylamine, sodium hydroxide or the like to obtain Compound aq-vii or aq-viii.

2) n=3

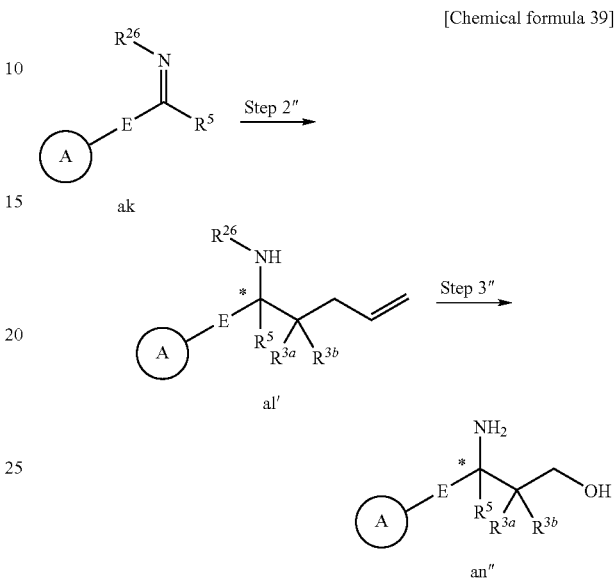

[Chemical formula 39]

wherein the each symbols are the same as defined above.
Step 2"

Compound al' can be obtained by reacting Compound ak with a Grignard reagent having a substituent corresponding to the target compound such as an allyl Grignard reagent in a solvent such as ether, tetrahydrofuran, toluene or the like or a mixed solvent such as ether-tetrahydrofuran at −80° C. to 50° C., preferably −40° C. to 30° C. for 0.5 to 12 hours, preferably 0.5 to 8 hours.
Step 3"

Compound an" can be obtained by hydroboration, wherein Compound al' is reacted with a reductant such as a boran-tetrahydrofuran complex, a boran-dimethylsulfide complex, a boran-triethylamine complex, a boran-pyridine complex or the like or an ether or tetrahydrofuran solution of them in a solvent such as ether, tetrahydrofuran, toluene or the like or a mixed solvent such as ether-tetrahydrofuran or the like at −30° C. to 30° C., preferably −15° C. to 20° C. for 0.5 to 12 hours, preferably 0.5 to 5 hours.

Substituents $R^{3a}$ and $R^{3b}$ can be introduced into thus-obtained Compound an" by the method according to the above-mentioned 1-2).

3) Conversion of Substituents (1)

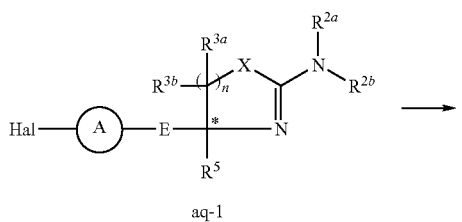

[Chemical formula 40]

-continued

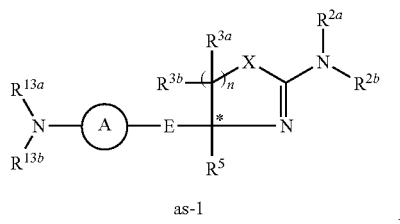

as-1 wherein $R^{13a}$ and $R^{13b}$ are amino-protecting groups and the other symbols are the same as defined above.

Synthesis of Compound as-1

To a solution of Compound aq-1 in a solvent such as tetrahydrofuran, toluene, xylene or the like are added tris-dibenzyliden acetone dipalladium, palladium acetate or palladium(0) prepared in situ and a phosphine ligand such as tri-tert-butylphosphine, dicyclohexylbiphenyl phosphine or the like, and further added a reagent having the substituent corresponding to the target compound such as lithium hexamethyl disilazide at −10° C. to 30° C., followed by reacting at 30° C. to 120° C., preferably 50° C. to 100° C. for 0.5 to 48 hours, preferably 3 to 20 hours to obtain Compound as-1.

An amino protecting group may be a group which is deprotected by the method described in "Protective Groups in Organic Synthesis, Theodora W Green (John Wiley & Sons)" etc. and the examples are lower alkoxy-carbonyl, lower alkenyloxycarbonyl, trialkylsillyl, acyl, methansulfonyl, trifluoroethansulfonyl, toluensulfonyl and the like.

4) Conversion of Substituent (2)

[Chemical formula 41]

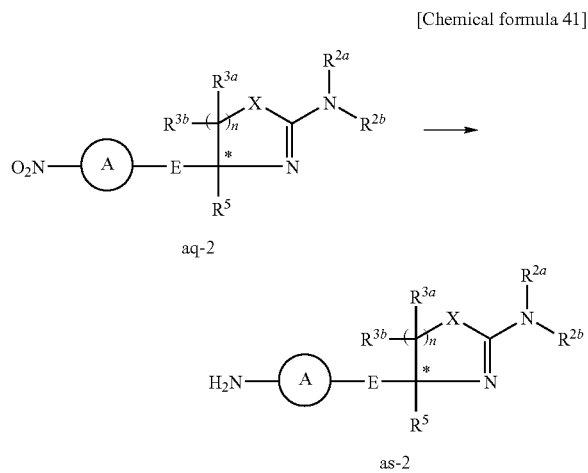

as-2

Synthesis of Compound as-2

To a solution of aq-2 in a solvent such as tetrahydrofuran, ethyl acetate, methanol or the like is added a catalytic reduction catalyst such as 10% Pd/C, and then the mixture is reacted at normal pressure to 5 atm, preferably normal pressure to 2 atm under hydrogen atmosphere for 0.5 to 48 hours, preferably 6 to 20 hours to obtain Compound as-2. Alternatively. Compound as-2 can be obtained by the method described in "Comprehensive Organic Transformations, Richard C Larock (McGraw-Hill)".

5) Conversion of Substituent (3)

[Chemical formula 42]

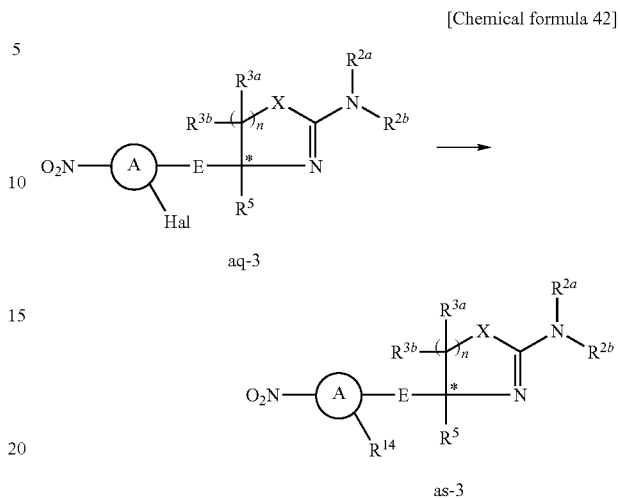

as-3 wherein $R^{14}$ is hydroxy, optionally substituted lower alkyl, optionally substituted lower alkoxy, optionally substituted lower alkylthio, optionally substituted lower amino, optionally substituted aromatic carbocyclicoxy or heterocyclic oxy, optionally substituted aromatic carbocyclicamino or heterocyclic amino, optionally substituted aromatic carbocyclicthio or heterocyclicthio, cyano, azide, optionally substituted carbocyclic group, optionally substituted heterocyclic group, optionally substituted carbamoyl or the like and the other symbols are the same as defined above.

Synthesis of Compound as-3

To a solution of Compound aq-3 in a solvent such as tetrahydrofuran, ethanol or the like is added a reagent having the substituent corresponding to the target compound such as ethanol, methanethiol, dimethyl amine or the like at −10° C. to 30° C. and the mixture is reacted for 0.5 to 12 hours, preferably 1 to 8 hours to obtain Compound as-3.

Then, the similar reaction described in the above "4) Conversion of substituent (2)" may be conducted, and further a coupling reaction may be conducted according to the above-mentioned method for producing Compound (I-19), if necessary.

In all of above mentioned steps, if a compound having substituent which interrupts the reaction; (for example, hydroxy, mercapto, amino, formyl, carbonyl, carboxyl, etc.), the substituent of the compound is protected by methods described in Protective Groups in Organic Synthesis, Theodora W Green (John Wiley & Sons) beforehand, and is deprotected at preferable step.

The compound (I) in this invention presented below; in particular, X is S, and E is a bond or methylene; is preferable.

1) A Compound represented by the general formula (I'),

[Chemical formula 43]

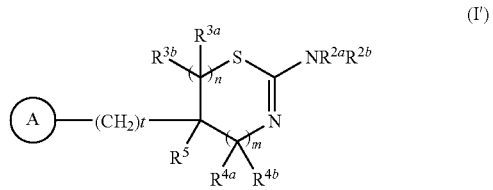

(I')

wherein, t is 0 or 1, the other symbols are the same as above (a), with the proviso that the compounds represented below;
i) wherein n+m is 2, $R^5$ is a hydrogen atom, and ring A is non-substituted phenyl;
ii) wherein n is 2, no is 0, $R^{2a}$ is a hydrogen atom, $R^{2b}$ is a hydrogen atom or acetyl, $R^5$ is methyl, and ring A is phenyl or 4-methoxyphenyl;
iii) wherein n is 2, m is 0, $R^{2a}$ is a hydrogen atom, $R^{2b}$ is a hydrogen atom or acetyl, $R^5$ is ethyl, and ring A is 3,4-dimethoxyphenyl;
iv) wherein n is 2, m is 0, $R^{2a}$ is a hydrogen atom, $R^{2b}$ is a hydrogen atom or acetyl, and $R^5$ and ring A are phenyl;
v) wherein n is 2, m is 0, $R^{2a}$ and $R^{2b}$ are a hydrogen atom, $R^5$ and ring A are taken together to form

[Chemical formula 44]

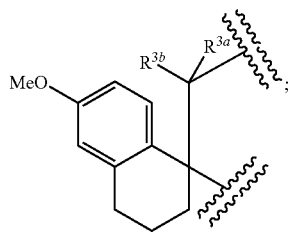

and
vi) wherein n+m is 1 or 2; $R^5$ is a hydrogen atom; and ring A is phenyl substituted by one or two substituent selected from hydroxy, halogen, lower alkyl, lower alkoxy, nitro, amino, lower alkyl carbonylamino, mercapto, lower alkylthio, carbamoyl, lower alkylamino, lower alkyl carbamoyl and lower alkoxycarbonyl; non-substituted phenyl, or non-substituted naphthyl; are excluded.

In addition, in formula (I'), preferable is the compound represented below.
2) The compound, wherein n is 1 and m is 0 (this compound is represented by nm-1),
3) the compound, wherein n is 2 and m is 0 (this compound is represented by nm-2),
4) the compound, wherein n is 3 and m is 0 (this compound is represented by nm-3),
5) the compound, wherein $R^{2a}$ is a hydrogen atom: $R^{2b}$ is a hydrogen atom, optionally substituted lower alkyl, optionally substituted acyl, optionally substituted lower alkylsulfonyl, or optionally substituted amidino (this compound is represented by R2-1),
6) the compound, wherein $R^{2a}$ is a hydrogen atom; $R^{2b}$ is a hydrogen atom, optionally substituted lower alkyl or optionally substituted acyl (this compound is represented by R2-2),
7) the compound, wherein $NR^{2a}R^{2b}$ is represented by the following formula:

[Chemical formula 45]

(a) —$NH_2$, (b) 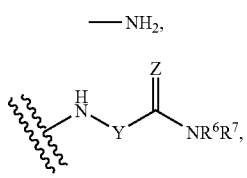

(c) 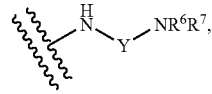

(d) 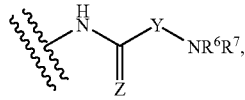

(e) 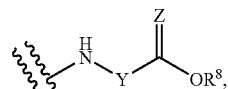

(f) 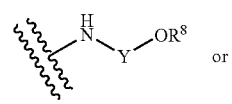

or (g) 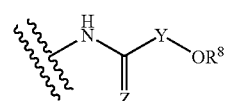

wherein each symbols are the same as described above,
$R^6$, $R^7$ and $R^8$ are each independently a hydrogen atom, lower alkyl or acyl,
Y is optionally substituted lower alkylene, optionally substituted lower alkenylene or optionally substituted lower alkynylene,
Z is O or S (this compound is represented by R2-3),
8) the compound, wherein $NR^{2a}R^{2b}$ is $NH_2$ (this compound is represented by R2-4),
9) the compound, wherein ring A is substituted phenyl or substituted pyridyl (this compound is represented by A-1),
10) the compound, wherein ring A is represented by the following formula:

[Chemical formula 46]

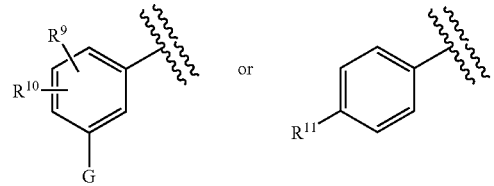

wherein $R^9$, $R^{10}$ and $R^{11}$ is a hydrogen atom or G,
G is halogen, hydroxy, cyano, nitro, mercapto, optionally substituted lower alkyl, optionally substituted lower alkoxy, optionally substituted lower alkenyl, optionally substituted lower alkynyl, optionally substituted acyl, optionally substituted acyloxy, carboxy, optionally substituted lower alkoxycarbonyl, optionally substituted lower alkoxycarbonyloxy; optionally substituted aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl, optionally substituted lower alkylsulfinyl, optionally substituted arylsulfinyl, optionally substituted lower alkylsulfonyloxy, optionally substituted arylsulfonyloxy, optionally substituted sulfamoyl, an optionally substituted carbocyclic group, optionally substituted carbocyclicoxy, an optionally substituted heterocyclic group or optionally substituted heterocyclicoxy, each G may be different (this compound is represented by A-2), 11) the compound, wherein ring A is represented by the following formula:

[Chemical formula 47]

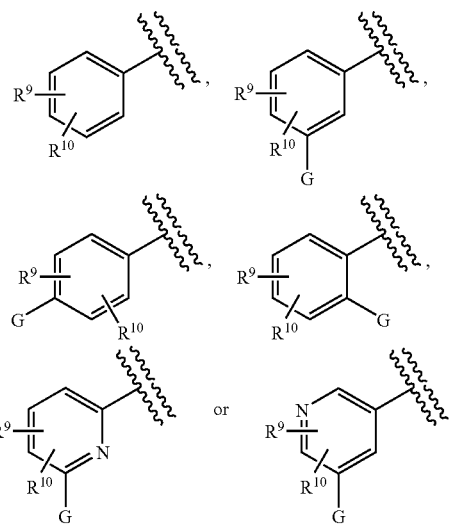

wherein $R^9$ and $R^{10}$ are each independently a hydrogen atom, halogen, hydroxy, optionally substituted lower alkyl, cyano, nitro, optionally substituted lower alkoxy, optionally substituted acyl, optionally substituted amino, optionally substituted carbamoyl, optionally substituted carbamoyloxy, optionally substituted lower alkylsulfonyl, optionally substituted arylsulfonyl, optionally substituted lower alkylsulfonyloxy, optionally substituted arylsulfonyloxy, an optionally substituted carbocyclic group, optionally substituted carbocyclicoxy, an optionally substituted heterocyclic group or optionally substituted heterocyclicoxy, G is the same as described above 10) (this compound is represented by A-3), 12) the compound, wherein ring A is represented by the following formula:

[Chemical formula 48]

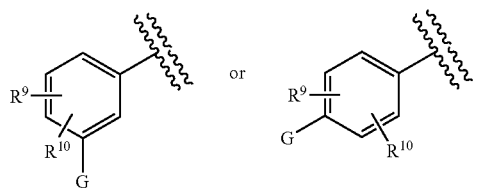

wherein $R^9$ and $R^{10}$ is the same as described in 11), G is the same as described in 10) (this compound is represented by A-4), 13) the compound, wherein ring A, $R^9$, and $R^{10}$ are defined in 11), G is optionally substituted amino (this compound is represented by A-5), 14) the compound, wherein ring A, $R^9$ and $R^{10}$ are defined in 11), G is optionally substituted arylcarbonylamino or optionally substituted heterocyclic carbonylamino, 15) the compound, wherein ring A, $R^9$ and $R^{10}$ are defined in 11), G is optionally substituted heterocyclic carbonylamino (this compound is represented by A-6), 16) the compound, wherein ring A is defined in 11), G is represented by the following formula:

[Chemical formula 49]

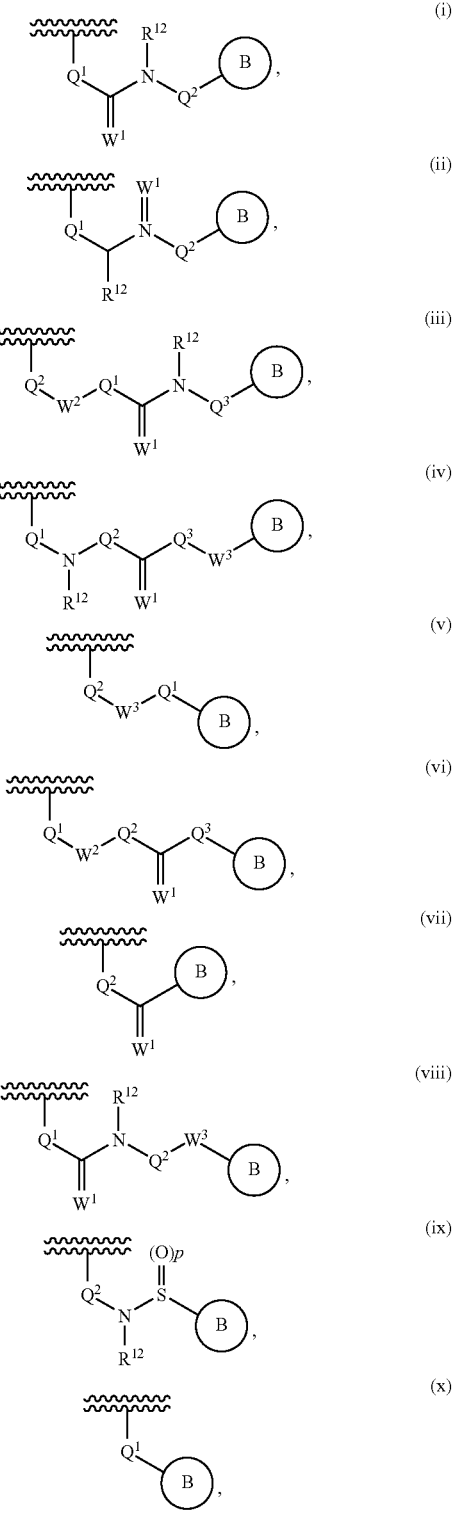

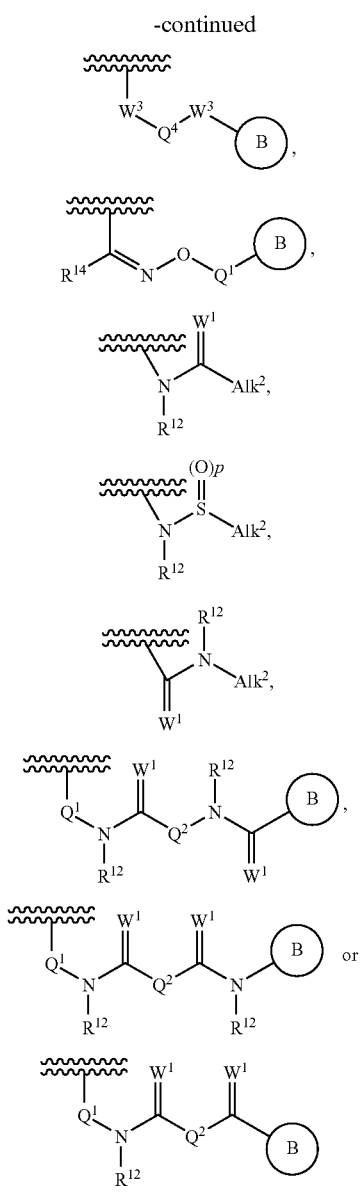

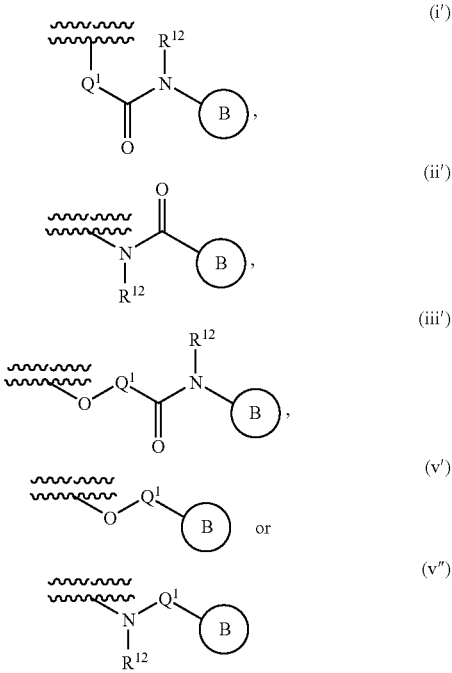

lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group or heteroaryl optionally substituted with one or more substituents selected from halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group;

and the other symbols are the same as described in 16) (this compound is represented by A-8), 18) the compound, wherein ring A, $R^9$ and $R^{10}$ are defined in 11), G is represented by the following formula;

[Chemical formula 50]

wherein each symbols are the same as described in 16) (this compound is represented by A-9), 19) the compound, wherein ring A is represented by the following formula:

[Chemical formula 51]

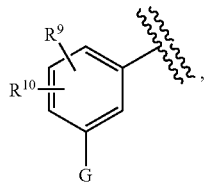

wherein G is defined in 16), ring B is optionally substituted aryl or optionally substituted heteroaryl, either $R^9$ or $R^{10}$ is a hydrogen atom; and the other is a hydrogen atom, halogen, optionally substituted lower alkyl, cyano, nitro, optionally substituted lower alkoxy, optionally substituted wherein $Q^1$, $Q^2$ and $Q^3$ are each independently a bond, optionally substituted lower alkylene or optionally substituted lower alkenylene;

$Q^4$ is optionally substituted lower alkylene or optionally substituted lower alkenylene;

$W^1$ and $W^2$ are each independently O or S;

$W^3$ is O, S or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl or acyl;

$R^{14}$ is a hydrogen atom or lower alkyl;

ring B is an optionally substituted carbocyclic group or an optionally substituted heterocyclic group;

$Alk^2$ is optionally substituted lower alkyl; and $R^9$ and $R^{10}$ are the same as described in 11) (this compound is represented by A-7), 17) the compound, wherein ring A, $R^9$ and $R^{10}$ are the group defined in 11); G is the group defined in 16); ring B is aryl optionally substituted with one or more substituents selected from halogen, hydroxy, optionally substituted amino, optionally substituted carbamoyl, optionally substituted lower alkylsulfonyl, an optionally substituted carbocyclic group or an optionally substituted heterocyclic group (this compound is represented by A-10), 20) the compound, wherein ring A is represented by the following formula:

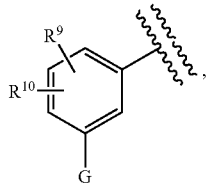
[Chemical formula 52]

wherein G is defined in 18), the other symbols are the same as described in 19) (this compound is represented by A-11), 21) the compound, wherein ring A is represented by the following formula:

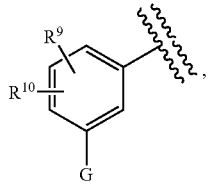
[Chemical formula 53]

wherein G is defined in 16), ring B is optionally substituted phenyl, optionally substituted 5- to 6-membered heteroaryl, optionally substituted benzothiazolyl or optionally substituted benzothienyl, and $R^9$ and $R^{10}$ are the same as described in 19) (this compound is represented by A-12), 22) the compound, wherein ring A is represented by the following formula:

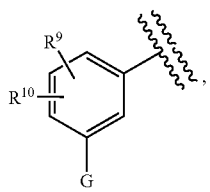
[Chemical formula 54]

wherein G is defined in 18), ring B is defined in 21), $R^9$ and $R^{10}$ are the same as described in 19) (this compound is represented by A-13), 23) the compound, wherein ring A is represented by the following formula:

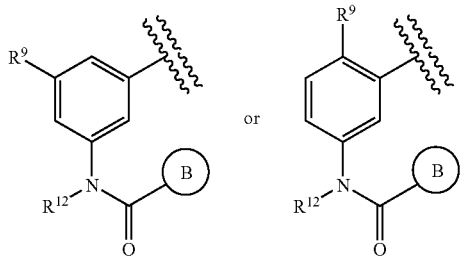
[Chemical formula 55]

wherein $R^9$ is a hydrogen atom, halogen, optionally substituted lower alkyl, cyano, nitro, optionally substituted lower alkoxy, optionally substituted amino, optionally substituted carbamoyl, optionally substituted lower alkylsulfonyl, an optionally substituted carbocyclic group or an optionally substituted heterocyclic group, ring B is the same as described in 21): and $R^{12}$ is a hydrogen atom or lower alkyl (this compound is represented by A-14), 24) the compound, wherein $R^5$ is a hydrogen atom or C1 to C3 alkyl (this compound is represented by R5-1), 25) the compound, wherein $R^5$ is C1 to C3 alkyl (this compound is represented by R5-2), 26) the compound, wherein $R^5$ is methyl (this compound is represented by R5-3), 27) the compound, wherein $R^{3a}$ and $R^{3b}$ are each independently a hydrogen atom, halogen, hydroxy, optionally substituted lower alkyl, optionally substituted lower alkoxy or optionally substituted aryl (this compound is represented by R3-1), 28) the compound wherein, $R^{3a}$ is a hydrogen atom, halogen, hydroxy, optionally substituted lower alkyl, optionally substituted lower alkoxy or optionally substituted aryl, $R^{3b}$ is a hydrogen atom, one $R^3$ is a hydrogen atom when n is 2, one or two $R^{2a}$ is (are) a hydrogen atom(s) when n is 3 (this compound is represented by R3-2), 29) the compound, wherein $R^{3a}$ and $R^{3b}$ are all hydrogen atoms (this compound is represented by R3-3), and in a compound represented by the general formula (I'), a compound, wherein the combination of n, m, $R^{2a}$, $R^{2b}$, ring A, $R^{3a}$, and $R^{3b}$ (nm, $R^2$, A, $R^5$, $R^3$) is the following compound.

(nm, $R^2$, A, $R^5$ $R^3$)=(nm-1,R2-1,A-1,R5-1,R3-1),(nm-1,R2-1,A-1,R5-1,R3-2),(nm-1,R2-1,A-1,R5-2,R3-1),(nm-1,R2-1,A-1,R5-2,R3-2),(nm-1,R2-1,A-1,R5-3,R3-1),(nm-1,R2-1,A-1,R5-3,R3-2),(nm -1,R2-1,A-2,R5-1,R3-1),(nm-1,R2-1,A-2,R5-1,R3-2),(nm-1,R2-1,A-2,R5-2,R3-1),(nm-1,R2-1,A-2,R5-2,R3-2),(nm-1,R2-1,A-2,R5-3,R3-1),(nm-1,R2-1,A-2,R5-3,R3-2),(nm-1,R 2-1,A-3,R5-1,R3-1),(nm-1,R2-1,A-3,R5-1,R3-2),(nm-1,R2-1,A-3,R5-2,R3-1),(nm-1,R2-1,A-3,R5-2,R3-2),(nm-1,R2-1,A-3,R5-3,R3-1),(nm-1,R2-1,A-3,R5-3,R3-2),(nm-1,R2-1,A-4,R5-1,R3-1),(nm-1,R2-1,A-4,R5-1,R3-2),(nm-1,R2-1,A-4,R5-2,R3-1),(nm-1,R2-1,A-4,R5-2,R3-2),(nm-1,R2-1,A-4,R5-3,R3-1),(nm-1,R2-1,A-4,R5-3,R3-2),(nm-1,R2-1,A-5,R5-1,R3-1),(nm-1,R2-1,A-5,R5-1,R3-2), (nm-1,R2-1,A-5,R5-2,R3-1),(nm-1,R2-1,A5,R 5-2,R3-2),(nm-1,R2-1,A-5,R5-3,R3-1),(nm-1,R2-1,A-5,R5-3,R3-2),(nm1,R2-1,A-6,R5-1,R3-1),(nm-1,R2-1,A-6,R5-1,R3-2),(nm-1,R2-1,A-6,R5-2,R3-1,),(nm-1,R2-1,A-6,R5-2,R3-2),(nm-1,R2-1,A-6,R5-3,R3-1),(nm-1,R2-1,A-6,R5-3,R3-2),(nm-1,R2-1,A-7,R5-1,R3-1),(nm-1,R2-1,A-7,R5-1,R3-2),(nm-1,R2-1,A-7,R5-2,R3-1),(nm-1,R2-1,A-7,R5-2,R3-2),(nm-1,R2-1,A-7,R5-3,R3-1),(nm-1,R2-1,

A-7,R5-3,R3-2),(nm-1,R2-1,A-8,R5-1,R3-1), (nm-1,R2-1,A-8,R5-1,R3-2),(nm-1,R2-1,A-8,R5-2,R3-1),(nm-1,R2-1,A-8,R5-2,R3-2),(nm-1,R2-1,A-8,R5-3,R3-1),(nm-1,R2-1,A-8,R5-3,R3-2),(nm-1,R2-1,A-9,R5-1,R3-1), (nm-1,R2-1,A-9,R5-1,R3-2),(nm-1,R2-1,A-10,R5-2,R3-1),(nm-1,R2-1,A-10,R5-2,R3-2),nm -1,R2-1,A-9,R5-3,R3-1(nm-1,R2-1,A-9,R5-3,R3-2),(nm-1,R2-1,A-10,R5-1,R3-1),(nm-1,R2-1,A-10,R5-1,R3-2),(nm-1,R2-1,A-10,R5-2,R3-1),(nm-1,R2-1,A-10,R5-2,R3-2),(nm-1,R2-1,A-10,R5-3,R3-1),(nm-1,R2-1,A-10,R5-2,R3-1),(nm-1,R2-1,A-10,R5-1,R3-1),(nm-1,R2-1,A-11,R5-1,R3-2), (nm-1,R2-1,A-11,R5-2,R3-1),(nm-1,R2-1,A-11,R5-2,R3-2), (nm-1,R2-1,A-11,R5-3,R3-1),(nm-1,R2-1,A-10,R5-3,R3-2),(nm-1,R2-1,A-12,R5-1,R3-1),(nm-1,R2-1,A-12,R5-1,R3-2),(nm-1,R2-1,A-12,R5-2,R3-1),(nm-1,R2-1,A-12,R5-2,R3-2),(nm-1,R2-1,A-12,R5-3,R3-1),(nm-1,R2-1,A-12,R5-3,R3-2),(nm-1,R2-1,A-13,R5-1,R3-1), (nm-1,R2-1,A-13,R5-1,R3-2),(nm-1,R2-1,A-13,R5-2,R3-1),(nm-1,R2-1,A-13,R5-2,R 3-2),(nm-1,R2-1,A-13,R5-3,R3-1),(nm-1,R2-1,A-13,R5-3,R3-2),(nm-1,R2-1,A-14,R5-1,R3-1),(nm-1,R2-1,A-14,R5-1,R3-2),(nm-1,R2-1,A-14,R5-2,R3-1),(nm-1,R2-1,A-14,R5-2,R3-2),(nm-1,R2-1,A-14,R5-3,R3-1),(nm-1,R2-1,A-14,R5-3,R3-2), (nm-1,R2-2,A-1,R5-1,R3-1),(nm-1,R2-2,A-1,R5-1,R3-2),(nm-1,R2-2,A-1,R5-2,R3-1),(nm-1,R2-2,A-1,R5-2,R3-2),(nm-1,R2-2,A-1,R5-3,R3-1),(nm-1,R2-2,A-1,R5-3,R3-2),(nm-1,R2-2,A-2,R5-1,R3-1),(nm-1,R2-2,A-2,R5-1,R3-2),(nm-1,R2-2,A-2,R5-2,R3-1),(nm-1,R2-2,A-2,R5-2,R3-2),(nm-1,R2-2,A-2,R5-3,R3-1),(nm-1,R2-2,A-2,R5-3,R3-2),(nm-1,R2-2,A-3,R5-1,R3-1),(nm-1,R2-2,A-3,R5-1,R3-2),(nm-1,R2-2,A-3,R5-2,R3-1),(nm-1,R2-2,A-3,R5-2,R3-2),(nm-1,R2-2,A-3,R5-3,R3-1),(nm-1,R2-2,A-3,R5-3,R3-2),(nm-1,R2-2,A-4,R5-1,R3-1), (nm-1,R2-2,A-4,R5-3,R3-1),(nm-1,R2-2,A-4,R5-3,R3-2),(nm-1,R2-2,A-5,R5-1,R3-1),(nm-1,R2-2,A-5,R5-1,R3-2),(nm-1,R2-2,A-5,R5-2,R3-1),(nm-1,R2-2,A-5,R5-2,R3-2),(nm-1,R2-2,A-5,R5-1,R3-2),(nm-1,R2-2,A-5,R5-2,R3-1),(nm-1,R2-2,A-5,R5-2,R3-2),(nm -1,R2-2,A-5,R5-3,R3-1),(nm-1,R2-2,A-5,R5-3,R3-2),(nm-1,R2-2,A-6,R5-1,R3-1),(nm-1,R2-2,A-6,R5-1,R3-2),(nm-1,R2-2,A-6,R5-2,R3-1),(nm-1,R2-2,A-6,R5-2,R3-2),(nm-1,R2-2,A-6,R5-3,R3-1),(nm-1,R2-2,A-6,R5-3,R3-2),(nm-1,R2-2,A-7,R5-1,R3-1),(nm-1,R2-2,A-7,R5-1,R3-2), (nm-1,R2-2,A-7,R5-2,R3-1),(nm-1,R2-2,A-7,R5-R2,R3-2),(nm-1,R2-2,A-7,R5-3,R3-1),(nm-1,R2-2,A-7,R5-3,R3-2),(nm-1,R2-2,A-8,R5-1,R3-1),(nm-1,R2-2,A-8,R5-1,R3-2),(nm-1,R2-2,A-8,R5-2,R3-1),(nm-1,R2-2,A-8,R5-2,R3-2),(nm-1,R2-2,A-8,R5-3,R3-1),(nm-1,R2-2,A-8R5-3,R3-2,(nm-1,R2-2,A-9,R5-1),R3-1),(nm-1,R2-2,A-9,R5-1,R3-2),(nm-1,R2-2,A-9,R5-2,R3-1),(nm-1,R2-2,A-9,R5-2,R3-2),(nm-1,R2-2,A-9,R5-3,R3-1),(nm-1,R2-2,A-9,R5-3,R3-2),(nm-10,R2-2,A-10,R5-1,R3-1),(nm-1,R2-2,A-10,R5-1,R3-2),(nm-1,R2-2,A-10,R5-2,R3-1), (nm-1,R2-2,A-10,R5-2,R3-2),(nm-1,R2-2,A-10,R5-3,R3-1),(nm-1,R2-2,A-10,R5-3,R3-2),(nm-1,R2-2,A-11,R5-1,R3-1),(nm-1,R2-2,A-1 1,R5-1,R3-2),(nm-1,R2-2,A-11,R5-2,R3-1),(nm-1,R2-2,A-11,R5-2,R3-2),(nm-1,R2-2,A -11,R5-3,R3-1),(nm-1,R2-2,A-11,R5-3,R3-2), (nm-1,R2-2,A-12,R5-1,R3-1),(nm-1,R2-2,A-12,R5-1,R3-2),(nm-1,R2-2,A-12,R5-2,R3-1),(nm-1,R2-2,A-12,R5-2,R3-2),(nm-1,R2-2,A-12,R5-3,R3-1),(nm-1,R2-2,A-12,R5-3,R3-2),(nm-1,R2-2,A-13,R5-1,R3-1),(nm-1,R2-2,A-13,R5-1,R3-2),(nm-1,R2-2,A-13,R5-2,R3-1),(nm-1,R2-2,A-13,R5-2,R3-2),(nm-1,R2-2,A-13,R5-3,R3-1),(nm-1,R2-2,A-13,R5-3,R3-2), (nm-1,R2-2,A-13,R5-3,R3-2),(nm-1,R2-2,A-14,R5-1,R3-1),(nm-1,R2-2,A-14,R5-1,R3-2),(nm-1,R2-2,A-14,R5-2,R3-1),(nm-1,R2-2,A-14,R5-2,R3-2),(nm-1,R2-2,A-14,R5-3,R3-1),(nm-1,R2-2,A-14,R5-3,R3-2),(nm-1,R2-3,A-1,R5-1,R3-1),(nm-1,R2-3,A-1,R5-1,R3-2),(nm-1,R2-3,A-1,R5-2,R3-1),(nm-1,R2-3,A-1,R5-2,R3-2),(nm-1,R2-3,A-1,R5-3,R3-1),(nm-1,R2-3,A-1,R5-3,R3-2), (nm-1,R2-3,A-2,R5-1,R3-1),(nm -1,R2-3,A-2,R5-1,R3-2),(nm-1,R2-3,A-2,R5-2,R3-1),(nm-1,R2-3,A-2,R5-2,R3-2),(nm-1,R2-3,A-2,R5-3,R3-1),(nm-1,R2-3,A-2,R5-3,R3-2),(nm-1,R2-3,A-3,R5-1,R3-1),(nm-1,R2-3,A-3,R5-1,R3-2),(nm-1,R2-3,A-3,R5-2,R3-1),(nm-1,R2-3,A-3,R5-2,R3-2),(nm-1,R2-3,A-3,R5-3,R3-1),(nm-1,R2-3,A-3,R5-3,R3-2),(nm-1,R2-3,A-4,R5-1,R3-1),(nm-1,R2-3,A-4,R5-1,R3-2),(nm-1,R2-3,A-4,R5-2,R3-1),(nm-1,R2-3,A-4,R5-2,R3-2),(nm-1,R2-3,A-4,R5-3,R3-1),(nm-1,R2-3,A-4,R5-3,R3-2),(nm-1,R2-3,A-5,R5-1,R3-1), (nm-1,R2-3,A-5,R5-1,R3-2),(nm-1,R2-3,A-5,R5-2,R3-1),(nm-1,R2-3,A-5,R5-2,R3-2),(nm-1,R2-3,A-5,R5-3,R3-1),(nm-1,R2-3,A-5,R5-3,R3-2),(nm-1,R2-3,A-6,R5-1,R3-1),(nm-1,R2-3,A-6,R5-1,R3-2),(nm-1,R2-3,A-6,R5-2,R3-1),(nm-1,R2-3,A-6,R5-2,R3-2),(nm-1,R2-3,A-6,R5-3,R3-1),(nm-1,R2-3,A-6,R5-3,R3-2),(nm-1,R2-3,A-7,R5-1,R3-1),(nm-1,R2-3,A-7,R5-1,R3-2),(nm-1,R2-3,A-7,R5-2,R3-1),(nm-1,R2-3,A-7,R5-2,R3-2),(nm-1,R2-3,A-7,R5-3,R3-1),(nm-1,R2-3,A-7,R5-3,R3-2),(nm-1,R2-3,A-8,R5-1,R3-1),(nm-1,R2-3,A-8,R5-1,R3-2), (nm-1,R2-3,A-8,R5-2,R3-1),(nm-1,R2-3,A-8,R5-2,R3-2),(nm-1,R2-3,A-8,R5-3,R3-1),(nm-1,R2-3,A-8,R5-3,R3-2),(nm-1,R2-3,A-9,R5-1,R3-1),(nm-1,R2-3,A-9,R5-1,R3-2),(nm-1,R2-3,A-9,R5-2,R3-1),(nm-1,R2-3,A-9,R5-2,R3-2),(nm-1,R2-3,A-9,R5-3,R3-1),(nm -1,R2-3,A-9,R5-3,R3-2),(nm-1,R2-3,A-10,R5-1,R3-1),(nm-1,R2-3,A-10,R5-1,R3-2),(nm-1,R2-3,A-10,R5-2,R3-1),(nm-1,R2-3,A-10,(R5-2,R3-2),(nm-1,R2-3,A-10,R5-3,R3-1),(nm-1,R2-3,A-10,R5-3,R3-2),(nm-1,R2-3,A-11,R5-1,R3-1),(nm-1,R2-3,A-11,R5-1,R3-2), (nm-1,R2-3,A-11,R5-2,R3-1),(nm-1,R2-3,A-11,R5-2,R3-2),(nm-1,R2-3,A-11,R5-3,R3-1),(nm-1,R2-3,A-11,R5-3,R3-2),(nm-1,R2-3,A-12,R5-1,R3-1),(nm-1,R2-3,A-12,R5-1,R3-2),(nm-1,R2-3,A-12,R5-2,R3-1),(nm-1,R2-3,A-12,R5-2,R3-2), (nm-1,R2-3,A-12,R5-3,R3-1),(nm-1,R2-3,A-12,R5-3,R3-2),(nm-1,R2-3,A-13,R5-1,R3-1),(nm-1,R2-3,A-13,R5-1,R3-2),(nm-1,R2-3,A-13,R5-2,R3-1),(nm-1,R2-3,A-13,R5-2,R3-2),(nm-1,R2-3,A-13,R5-3,R3-1),(nm-1,R2-3,A-13,R5-3,R3-2),(nm-1,R2-3,A-14,R5-1,R3-1),(nm-1,R2-3,A-14,R5-1,R3-2),(nm-1,R2-3,A-14,R5-2,R3-1),(nm-1,R2-3,A-14,R5-2,R3-2),(nm-1,R2-3,A-1 4,R5-3,R3-1),(nm-1,R2-3,A-14,R5-3,R3-2),(nm-1,R2-4,A-1,R5-1,R3-1),(nm-1,R2-4,A-1,R5-1,R3-2),(nm-1,R2-4,A-1,R5-2,R3-1),(nm-1,R2-4,A-1,R5-2,R3-2),(nm-1,R2-4,A-1,R5-3,R3-1),(nm-1,R2-4,A-1,R5-3,R3-2),(nm-1,R2-4,A-2,R5-1,R3-1),(nm-1,R2-4,A-2,R5-1,R3-2),(nm-1,R2-4,A-2,R5-2,R3-1),(nm-1,R2-4,A-2,R5-2,R3-2),(nm-1,R2-4,A-2,R5-3,R3-1),(nm-1,R2-4,A-2,R5-3,R3-2),(nm-1,R2-4,A-3,R5-1,R3-1),(nm-1,R2-4,A-3,R5-1,R3-2), (nm-1,R2-4,A-3,R5-2,R3-1),(nm-1,R2-4,A-3,R5-2,R3-2),(nm-1,R2-4,A-3,R5-3,R3-1),(nm-1,R2-4,A-3,R5-3,R3-2),(nm-1,R2-4,A-4,R5-1,R3-1),(nm-1,R2-4,A-4,R5-1,R3-2),(nm-1,R2-4,A-4,R5-2,R3-1),(nm-1,R2-4,A-4,R5-2,R3-2),(nm-1,R2-4,A-4,R5-3,R3-1), (nm-1,R2-4,A-4,R5-3,R3-2),(nm-1,R2-4,A-5,R5-1,R3-1),(nm-1,R2-4,A-5,R5-1,R3-2),(nm-1,R2-4,A-5,R5-2,R3-1),(nm-1,R2-4,A-5,R5-2,R3-2),(nm-1,R2-4,A-5,R5-3,R3-1),(nm-1,R2-4,A-5,R5-3,R3-2),(nm-1,R2-4,A-6,R5-1,R3-1),(nm-1,R2-4,A-6,R5-1,R3-2),(nm -1,R2-4,A-6,R5-2,R3-1),(nm-1,R2-4,A-6,R5-2,R3-2),(nm-1,R2-4,A-6,R5-3,R3-1),(nm-1,R2-4,A-6,R5-3,R3-2),(nm-1,R2-4,A-7,R5-1,R3-1),(nm-1,R2-4,A-7,R5-1,R3-2),(nm-1,R2-4,A-7,R5-2,R3-1),(nm-1,R2-4A-7,R5-2,R3-2),(nm-1,R2-4,A-7,R5-

3,R3-1),(nm-1,R2-4,A-7,R5-3,R3-2),(nm-1,R2-4,A-8, R5-1,R3-1),(nm-1,R2-4,A-8,R5-1,R3-2),(nm-1,R2-4,A-8,R5-2,R3-1),(nm-1,R2-4,A-8,R5-2,R3-2),(nm-1,R2-4, A-8,R5-3,R3-1),(nm-1,R2-4,A-8,R5-3,R3-2),(nm-1,R2-4,A-9,R5-1,R3-1),(nm-1,R2-4,A-9,R5-1,R3-2),(nm-1, R2-4,A-9,R5-2,R3-1),(nm-1,R2-4,A-9,R5-2,R3-2),(nm-1,R2-4,A-9,R5-3,R3-1),(nm-1,R2-4,A-9,R5-3,R3-2), (nm-1,R2-4,A-10,R5-1,R3-1),(nm-1,R2-4,A-10,R5-1, R3-2),(nm-1,R2-4,A-10,R5-2,R3-1),(nm-1,R2-4,A-10, R5-2,R3-2),(nm-1,R2-4,A-10,R5-3,R3-1),(nm-1,R2-4, A-1 0,R5-3,R3-2),(nm-1,R2-4,A-11,R5-1,R3-1),(nm-1, R2-4,A-11,R5-1,R3-2),(nm-1,R2-4,A -11,R5-2,R3-1), (nm-1,R2-4,A-11,R5-2,R3-2),(nm-1,R2-4,A-11,R5-3, R3-1),(nm-1,R2-4,A-11,R5-3,R3-2),(nm-1,R2-4,A-12, R5-1,R3-1),(nm-1,R2-4,A-12,R5-1,R3-2),(nm-1,R2-4,A-12,R5-2,R3-1),(nm-1,R2-4,A-12,R5-2,R3-2),(nm-1,R2-4,A-12,R5-3,R3-1),(nm-1,R2-4,A-12,R5-3,R3-2),(nm-1, R2-4,A-13,R5-1,R3-1),(nm-1,R2-4,A-13,R5-1,R3-2), (nm-1,R2-4,A-13,R5-2,R3-1),(nm-1,R2-4,A-13,R5-2, R3-2),(nm-1,R2-4,A-13,R5-3,R3-1),(nm-1,R2-4,A-13, R5-3,R3-2),(nm-1,R2-4,A-14,R5-1,R3-1),(nm-1,R2-4,A-14,R5-1,R3-2),(nm-1,R2-4,A-14,R5-2,R3-1),(nm-1,R2-4,A-14,R5-2,R3-2),(nm-1,R2-4,A-14,R5-3,R3-1),(nm-1, R2-4,A-14,R5-3,R3-2), (nm-2,R2-1,A-1,R5-1,R3-1),(nm-2,R2-1,A-1,R5-1,R3-2), (nm-2,R2-1,A-1,R5-2,R3-1),(nm-2,R2-1,A-1,R5-2,R3-2),(nm-2,R2-1,A-1,R5-3,R3-1),(nm-2,R2-1,A-1,R5-3, R3-2),(nm-2,R2-1,A-2,R5-1,R3-1),(nm-2,R2-1,A-2,R5-1,R3-2),(nm-2,R2-1,A-2,R5-2,R3-1),(nm-2,R2-1,A-2, R5-2,R3-2),(nm-2,R2-1,A-2,R5-3,R3-1),(nm-2,R2-1,A-2,R5-3,R3-2),nm-2,R2-1,A-3,R5-1,R3-1),(nm-2,R2-1,A-3,R5-1,R3-2),(nm-2,R2-1,A-3,R5-2,R3-1),(nm-2,R2-1, A-3,R5-2,R3-2),(nm-2,R2-1,A-3,R5-3,R3-1),(nm-2,R2-1,A-3,R5-3,R3-2),(nm-2,R2-1,A-4,R5-1,R3-1),(nm-2, R2-1,A-4,R5-1,R3-2),(nm-2,R2-1,A-4,R5-2,R3-1),(nm-2,R2-1,A-4,R5-2,R3-2),(nm-2,R2-1,A-4,R5-3,R3-1), (nm-2,R2-1,A-4,R5-3,R3-2),(nm-2,R2-1,A-5,R5-1,R3-1),(nm-2,R2-1,A-5,R5-1,R3-2),(nm-2,R2-1,A-5,R5-2, R3-1),(nm-2,R2-1,A-5,R5-2,R3-2),(nm-2,R2-1,A-5,R5-3,R3-1),(nm-2,R2-1,A-5,R5-3,R3-2),(nm-2,R2-1,A-6, R5-1,R3-1),(nm-2,R2-1,A-6,R5-1,R3-2),(nm-2,R2-1,A-6,R5-2,R3-1),(nm-2,R2-1,A-6,R5-2,R3-2),(nm-2,R2-1, A-6,R5-3,R3-1),(nm-2,R2-1,A-6,R5-3,R3-2),(nm-2,R2-1,A-7,R5-1,R3-1),(nm-2,R2-1,A-7,R5-1,R3-2),(nm-2, R2-1,A-7,R5-2,R3-1),(nm-2,R2-1,A-7,R5-2,R3-2),(nm-2,R2-1,A-7,R5-3,R3-1),(nm-2,R2-1,A-7,R5-3,R3-2), (nm-2,R2-1,A-8,R5-1,R3-1), (nm-2,R2-1,A-8,R5-1,R3-2),(nm-2,R2-1,A-8,R5-2,R3-1),(nm-2,R2-1,A-8,R5-2, R3-2),(nm-2,R2-1,A-8,R5-3,R3-1),(nm-2,R2-1,A-8,R5-3,R3-2),(nm-2,R2-1,A-9,R5-1,R3-1),(nm-2,R2-1,A-9, R5-1,R3-2),(nm-2,R2-1,A-9,R5-2,R3-1),(nm-2,R2-1,A-9,R5-2,R3-2),(nm -2,R2-1,A-9,R5-3,R3-1),(nm-2,R2-1, A-9,R5-3,R3-2),(nm-2,R2-1,A-10,R5-1,R3-1),(nm-2,R2-1,A-10,R5-1,R3-2),(nm-2,R2-1,A-10,R5-2,R3-1),(nm-2, R2-1,A-10,R5-2,R3-1),(nm-2,R2-1,A-10,R5-3,R3-1), (nm-2,R2-1,A-10,R5-3,R3-2),(nm-2,R2-1,A-11,R5-1, R3-1),(nm-2,R2-1,A-11,R5-1,R3-2),(nm-2,R2-1,A-11, R5-2,R3-1),(nm-2,R2-1,A-11,R5-2,R3-2), (nm-2,R2-1, A-11,R5-3,R3-1),(nm-2,R2-1,A-11,R5-3,R3-2),(nm-2, R2-1,A-12,R5-1,R3-1),(nm-2,R2-1,A-12,R5-1,R3-2), (nm-2,R2-1,A-12,R5-2),(R3-1),(nm-2,R2-1,A-12,R5-2, R3-2),(nm-2,R2-1,A-12,R5-3,R3-1),(nm-2,R2-1,A-12, R5-3,R3-2),(nm-2,R2-1,A-13,R5-1,R3-1),(nm-2,R2-1,A-13,R5-1,R3-2),(nm-2,R2-1,A-13,R5-2,R3-1),(nm-2,R2-1,A-13,R5-2,R3-2),(nm-2,R2-1,A-13,R5-3,R3-1),(nm-2, R2-1,A-13,R5-3,R3-2),(nm-2,R2-1,A-14,R5-1,R3-1), (nm-2,R2-1,A-14,R5-1,R3-2),(nm-2,R2-1,A-14,R5-2, R3-1),(nm-2,R2-1,A-14,R5-2,R3-2),(nm-2,R2-1,A-14, R5-3,R3-1),(nm-2,R2-1,A-14,R5-3,R3-2),(nm-2,R2-2,A-1,R5-1,R3-1),(nm-2,R2-2,A-1,R5-1,R3-2),(nm-2,R2-2, A-1,R5-2,R3-1),(nm-2,R2-2,A-1,R5-2,R3-2),(nm-2,R2-2,A-1,R5-3,R3-1),(nm-2,R2-2,A-1,R5-3,R3-2),(nm-2, R2-2,A-2,R5-1,R3-1),(nm-2,R2-2,A-2,R5-1,R3-2),(nm-2,R2-2,A-2,R5-2,R3-1),(nm-2,R2-2,A-2,R5-2,R3-2), (nm-2,R2-2,A-2,R5-3,R3-1),(nm-2,R2-2,A-2,R5-3,R3-2),(nm-2,R2-2,A-3,R5-1,R3-1),(nm-2,R2-2,A-3,R5-1, R3-2),(nm-2,R2-2,A-3,R5-2,R3-1),(nm-2,R2-2,A-3,R5-2,R3-2),(nm-2,R2-2,A-3,R5-3,R3-1),(nm-2,R2-2,A-3, R5-3,R3-2),(nm-2,R2-2,A-4,R5-1,R3-1), (nm-2,R2-2,A-4,R5-1,R3-2),(nm-2,R2-2,A-4,R5-2,R3-1),(nm-2,R2-2, A-4,R5-2,R3-2),(nm-2,R2-2,A-4,R5-3,R3-1),(nm-2,R2-2,A-4,R5-3,R3-2),(nm-2,R2-2,A-5,R5-1,R3-1),(nm-2, R2-2,A-5,R5-1,R3-2),(nm-2,R2-2,A-5,R5-2,R3-1),(nm-2,R2-2,A-5,R5-2,R3-2),(nm -2,R2-2,A-5,R5-3,R3-1), (nm-2,R2-2,A-5,R5-3,R3-2),(nm-2,R2-2,A-6,R5-1,R3-1),(nm-2,R2-2,A-6,R5-1,R3-2),(nm-2,R2-2,A-6,R5-2, R3-1),(nm-2,R2-2,A-6,R5-2,R3-2),(nm-2,R2-2,A-6,R5-3,R3-1),(nm-2,R2-2,A-6,R5-3,R3-2),(nm-2,R2-2,A-7, R5-1,R3-1),(nm-2,R2-2,A-7,R5-1,R3-2),(nm-2,R2-2,A-7,R5-2,R3-1),(nm-2,R2-2,A-7,R5-2,R3-2),(nm-2,R2-2, A-7,R5-3,R3-1),(nm-2,R2-2,A-7,R5-3,R3-2),(nm-2,R2-2,A-8,R5-1,R3-1),(nm-2,R2-2,A-8,R5-1,R3-2),(nm-2, R2-2,A-8,R5-2,R3-1),(nm-2,R2-2,A-8,R5-2,R3-2),(nm-2,R2-2,A-8,R5-3,R3-1),(nm-2,R2-2,A-8,R5-3,R3-2), (nm-2,R2-2,A-9,R5-1,R3-1),(nm-2,R2-2,A-9,R5-1,R3-2),(nm-2,R2-2,A-9,R5-3,R3-1),(nm-2,R2-2,A-9,R5-2, R-2),(nm-2,R2-2,A-9,R3,R3-1),(nm-2,R2-2,A-9,R5-3, R3-2),(nm-2,R2-2,A-10,R5-1,R3-1),(nm-2,R2-2,A-10, R5-1,R3-2),(nm-2,R2-2,A-10,R5-2,R3-1),(nm-2,R2-2,A-10,R5-2,R3-2),(nm-2,R2-2,A-10,R5-3,R3-1),(nm-2,R2-2,A-10,R5-3,R3-2),(nm-2,R2-2,A-11,R5-1,R3-1),(nm-2, R2-2,A-1 1,R5-1,R3-2),(nm-2,R2-2,A-11,R5-2,R3-1), (nm-2,R2-2,A-11,R5-2,R3-2),(nm-2,R2-2,A -11,R5-3, R3-1),(nm-2,R2-2,A-11,R5-3,R3-2),(nm-2,R2-2,A-12, R5-1,R3-1),(nm-2,R2-2,A-12,R5-1,R3-2),(nm-2,R2-2,A-12,R5-2,R3-1),(nm-2,R2-2,A-12,R5-2R3-2),(nm-2,R2-2, A-12,R5-3,R3-1),(nm-2,R2-2A-12,R5-3,R3-2),(nm-2, R2-2,A-13,R5-1,R3-1),(nm-2,R2-2,A-13,R5-1,R3-2), (nm-2,R2-2,A-13,R5-2,R3-1),(nm-2,R2-2,A-13,R5-2, R3-2),(nm-2,R2-2,A-13,R5-3,R3-1),(nm-2,R2-2,A-13, R5-3,R3-2),(nm-2,R2-2,A-14,B5-1,R3-1),(nm-2,R2-2,A-14,R5-1,R3-2),(nm-2,R2-2,A-14,R5-2,R3-1),(nm-2,R2-2,A-14,R5-2,R3-2),(nm-2,R2-2,A-14,R5-3,R3-1),(nm-2, R2-2,A-14,R5-3,R3-2),(nm-2,R2-3,A-1,R5-1,R3-1),(nm-2,R2-3,A-1,R5-1,R3-2),(nm-2,R2-3,A-1,R5-2,R3-1), (nm-2,R2-3,A-1,R5-2,R3-2),(nm-2,R2-3,A-1,R5-3,R3-1),(nm-2,R2-3,A-1,R5-3,R3-2),(nm-2,R2-3,A-2,R5,-1, R3-1),(nm -2,R2-3,A-2,R5-1,R3-2),(nm-2,R2-3,A-2,R5-2,R3-1),(nm-2,R2-3,A-2,R5-2,R3-2),(nm-2,R2-3,A-2, R5-3,R3-1),(nm-2,R2-3,A-2,R5-3,R3-2),(nm-2,R2-3,A-3,R5-1,R3-1),(nm-2,R2-3,A-3,R5-1,R3-2),(nm-2,R2-3, A-3,R5-2,R3-1),(nm-2,R2-3,A-3,R5-2,R3-2),(nm-2,R2-3,A-3,R5-3,R3-1),(nm-2,R2-3,A-3,R5-3,R3-2),(nm-2, R2-3,A-4,R5-1,R3-1),(nm-2,R2-3,A-4,R5-1,R3-2),(nm-2,R2-3,A-4,R5-2,R3-1),(nm-2,R2-3,A-4,R5-2,R3-2), (nm-2,R2-3,A-4,R5-3,R3-1),(nm-2,R2-3,A-4,R5-3,R3-2),(nm-2,R2-3,A-5,R5-1,R3-1),(nm-2,R2-3,A-5,R5-1, R3-2),(nm-2,R2-3,A-5,R5-2,R3-1),(nm-2,R2-3,A-5,R5-2,R3-2),(nm-2,R2-3,A-5,R5-3,R3-1),(nm-2,R2-3,A-5, R5-3,R3-2),(nm-2,R2-3,A-6,R5-1,R3-1),(nm-2,R2-3,A-6,R5-1,R3-2),(nm-2,R2-3,A-6,R5-2,R3-1),(nm-2,R2-3, A6,R5-2,R3-2),(nm-2,R2-3,A-6,R5-3,R3-1),(nm-2,R2-3, A-6,R5-3,R3-2),(nm-2,R2-3,A-7,R5-1,R3-1),(nm-2,R2-3,A-7,R5-1,R3-2),(nm-2,R2-3,A-7,R5-2,R3-1),(nm-2,

R2-3,A-7,R5-2,R3-2),(nm-2,R2-3,A-7,R5-3,R3-1),(nm-2,R2-3,A-7,R5-3,R3-2),(nm-2,R2-3,A-8,R5-1,R3-1),(nm-2,R2-3,A-8,R5-1,R3-2), (nm-2,R2-3,A-8,R5-2,R3-1),(nm-2,R2-3,A-8,R5-2,R3-2),(nm-2,R2-3,A-8,R5-3,R3-1),(nm-2,R2-3,A-8,R5-3,R3-2),(nm-2,R2-3,A-9,R5-1,R3-1),(nm-2,R2-3,A-9,R5-1,R3-2),(nm-2,R2-3,A-9,R5-2,R3-1),(nm-2,R2-3,A-9,R5-2,R3-2),(nm-2,R2-3,A-9,R5-3,R3-1),(nm -2,R2-3,A-9,R5-3,R3-2),(nm-2,R2-3,A-10,R5-1,R3-1),(nm-2,R2-3,A-10,R5-1,R3-2),(nm-2,R2-3,A-10,R5-2,R3-1),(nm-2,R2-3,A-10,R5-2,R3-2),(nm-2,R2-3,A-10,R5-3,R3-1),(nm-2,R2-3,A-10,R5-3,R3-2),(nm-2,R2-3,A-11,R5-1,R3-1),(nm-2,R2-3,A-11,R5-1,R3-2), (nm-2,R2-3,A-11,R5-2,R3-1),(nm-2,R2-3,A-11,R5-2,R3-2),(nm-2,R2-3,A-11,R5-3,R3-1),(nm-2,R2-3,A-11,R5-3,R3-2),(nm-2,R2-3,A-12,R5-1,R3-1),(nm-2,R2-3,A-12,R5-1,R3-2),(nm-2,R2-3,A-12,R5-2,R3-1),(nm-2,R2-3,A-12,R5-2,R3-2),(nm-2,R2-3,A-12,R5-3,R3-1),(nm-2,R2-3,A-12,R5-3,R3-2),(nm-2,R2-3,A-13,R5-1,R3-1),(nm-2,R2-3,A-13,R5-1,R3-2),(nm-2,R2-3,A-13,R5-2,R3-1),(mn-2,R2-3,A-13,R5-2,R3-2),(nm-2,R2-3,A-13,R5-3,R3-1),(nm-2,R2-3,A-13,R5-3,R3-2),(nm-2,R2-3,A-14,R5-1,R3-1),(nm-2,R2-3,A-14,R5-1,R3-2),(nm-2,R2-3,A-14,R5-2,R3-1),(nm-2,R2-3,A-1 4,R5-3,R3-1),(nm-2,R2-3,A-14,R5-3,R3-2),(nm-2,R2-4,A-1,R5-1,R3-1),(nm-2,R2-4,A-1,R5-1,R3-2),(nm-2,R2-4,A-1,R5-2,R3-1),(nm-2,R2-4,A-1,R5-2,R3-2),(nm-2,R2-4,A-1,R5-3,R3-1),(nm-2,R2-4,A-1,R5-3,R3-2),(nm-2,R2-4,A-2,R5-1,R3-1),(nm-2,R2-4,A-2,R5-1,R3-2),(nm-2,R2-4,A-2,R5-2,R3-1),(nm-2,R2-4,A-2,R5-2,R3-2),(nm-2,R2-4,A-2,R5-3,R3-1),(nm-2,R2-4,A-2,R5-3,R3-2),(nm-2,R2-4,A-3,R5-1,R3-1),(nm-2,R2-4,A-3,R5-1,R3-2),(nm-2,R2-4,A-3,R5-2,R3-1),(nm-2,R2-4,A-3,R5-2,R3-2),(nm-2,R2-4,A-3,R5-3,R3-1),(nm-2,R2-4,A-3,R5-3,R3-2),(nm-2,R2-4,A-4,R5-1,R3-1),(nm-2,R2-4,A-4,R5-1,R3-2),(nm-2,R2-4,A-4,R5-2,R3-1),(nm-2,R2-4,A-4,R5-2,R3-2),(nm-2,R2-4,A-4,R5-3,R3-1), (nm-2,R2-4,A-4,R5-3,R3-2),(nm-2,R2-4,A-5,R5-1,R3-1),(nm-2,R2-4,A-5,R5-1,R3-2),(nm-2,R2-4,A-5,R5-2,R3-1),(nm-2,R2-4,A-5,R5-2,R3-2),(nm-2,R2-4,A-5,R5-3,R3-1),(nm-2,R2-4,A-5,R5-3,R3-2),(nm-2,R2-4,A-6,R5-1,R3-1),(nm-2,R2-4,A-6,R5-1,R3-2),(nm -2,R2-4,A-6,R5-2,R3-1),(nm-2,R2-4,A-6,R5-2,R3-2),(nm-2,R2-4,A-6,R5-3,R3-1),(nm-2,R2-4,A-6,R5-3,R3-2),(nm-2,R2-4,A-7,R5-1,R3-1),(nm-2,R2-4,A-7,R5-1,R3-2),(nm-2,R2-4,A-7,R5-2,R3-1),(nm-2,R2-4,A-7,R5-2,R3-2),(nm-2,R2-4,A-7,R5-3,R3-1),(nm-2,R2-4,A-7,R5-3,R3-2),(nm-2,R2-4,A-8,R5-1,R3-1),(nm-2,R2-4,A-8,R5-1,R3-2),(nm-2,R2-4,A-8,R5-2,R3-1),(nm-2,R2-4,A-8,R5-2,R3-2),(nm-2,R2-4,A-8,R5-3,R3-1),(nm-2,R2-4,A-8,R5-3,R3-2),(nm-2,R2-4A-9,R5-1,R3-1),(nm-2,R2-4,A-9,R5-1,R3-2),(nm-2,R2-4,A-9,R5-2,R3-1),(nm-2,R2-4,A-9,R5-2,R3-2),(nm-2,R2-4,A-9,R5-3,R3-1),(nm-2,R2-4,A-9,R5-3,R3-2),(nm-2,R2-4,A-10,R5-1,R3-1),(nm-2,R2-4,A-10,R5-1,R3-2),(nm2,R2-4,A-10,R5-2,R3-1),(nm-2,R2-4,A-10,R5-2,R3-2),(nm-2,R2-4,A-10,R5-3,R3-1),(nm-2,R2-4,A-1 0,R5-3,R3-2),(nm-2,R2-4,A-11,R5-1,R3-1),(nm-2,R2-4,A-11,R5-1,R3-2),(nm-2,R2-4,A -11,R5-2,R3-1),(nm-2,R2-4,A-11,R5-2,R3-2),(nm-2,R2-4,A-11,R5-3,R3-1),(nm-2,R2-4,A-11,R5-3,R3-2),(nm-2,R2-4,A-12,R5-1,R3-1),(nm-2,R2-4,A-12,R5-1,R3-2),(nm-2,R2-4,A-12,R5-2,R3-1),(nm-2,R2-4,A-12,R5-2,R3-2),(nm-2,R2-4,A-12,R5-3,R3-1),(nm-2,R2-4,A-12,R5-3,R3-2),(nm-2,R2-4,A-13,R5-1,R3-1),(nm-2,R2-4,A-13,R5-1,R3-2),(nm-2,R2-4,A-13,R5-2,R3-1),(nm-2,R2-4,A-13,R5-2,R3-2),(nm-2,R2-4,A-13,R5-3,R3-1),(nm-2,R2-4,A-13,R5-3,R3-2),(nm-2,R2-4,A-14,R5-1,R3-1),(nm-2,R2-4,A-14,R5-1,R3-2),(nm-2,R2-4,A-14,R5-2,R3-1),(nm-2,R2-4,A-14,R5-2,R3-2),(nm-2,R2-4,A-14,R5-3,R3-1),(nm-2,R2-4,A-14,R5-3,R3-2), (nm-3,R2-1,A-1,R5-1,R3-1),(nm-3,R2-1,A-1,R5-1,R3-2),(nm-3,R2-1,A-1,R5-2,R3-1),(nm-3,R2-1,R5-2,R3-2),(nm-3,R2-1,A-1,R5-3,R3-1),(nm-3,R2-1,A-1,R5-3,R3-2),(nm -3,R2-1,A-2,R5-1,R3-1),(nm-3,R2-1,A-2,R5-1,R3-2),(nm-3,R2-1,A-2,R5-2,R3-1),(nm-3,R2-1,A-2,R5-2,R3-2),(nm-3,R2-1,A-2,R5-3,R3-1),(nm-3,R2-1,A-2,R5-3,R3-2),(nm-3,R2-1,A-3,R5-1,R3-1),(nm-3,R2-1,A-3,R5-1,R3-2),(nm-3,R2-1,A-3,R5-2,R3-1),(nm-3,R2-1,A-3,R5-2,R3-2),(nm-3,R2-1,A-3,R5-3,R3-1),(nm-3,R2-1,A-3,R5-3,R3-2),(nm-3,R2-1,A-4,R5-1,R3-1),(nm-3,R2-1,A-4,R5-1,R3-2),(nm-3,R2-1,A-4,R5-2,R3-1),(nm-3,R2-1,A-4,R5-2,R3-2),(nm-3,R2-1,A-4,R5-3,R3-1), (nm-3,R2-1,A-4,R5-3,R3-2),(nm-3,R2-1,A-5,R5-1,R3-1),(nm-3,R2-1,A-5,R5-1,R3-2),(nm-3,R2-1,A-5,R5-2,R3-1),(nm-3,R2-1,A-5,R5-2,R3-2),(nm-3,R2-1,A-5,R5-3,R3-1),(nm-3,R2-1,A-5,R5-3,R3-2),(nm-3,R2-1,A-6,R5-1,R3-1),(nm-3,R2-1,A-6,R5-1,R3-2),(nm-3,R2-1,A6,R5-2,R3-1),(nm-3,R2-1,A-6,R5-2,R3-2),(nm-3,R2-1),A-6,R5-3,R3-1,(nm-3,R2-1,A-6,R5-3,R3-2),(nm-3,R2-1,A-7,R5-1,R3-1),(nm-3,R2-1,A-7,R5-1,R3-2),(nm-3,R2-1,A-7,R5-2,R3-1),(nm-3,R2-1,A-7,R5-2,R3-2),(nm-3,R2-1,A-7,R5-3,R3-1),(nm-3,R2-1,A-7,R5-3,R3-2),(nm-3,R2-1,A-8,R5-1,R3-1), (nm-3,R2-1,A-8,R5-1,R3-2),(nm-3,R2-1,A-8,R5-2,R3-1),(nm-3,R2-1,A-8,R5-2,R3-2),(nm-3,R2-1,A-8,R5-3,R3-1),(nm-3,R2-1,A-8,R5-3,R3-2),(nm-3,R2-1,A-9,R5-1,R3-1),(n m-3,R2-1,A-9,R5-1,R3-2),(nm-3,R2-1,A-9,R5-2,R3-1),(nm-3,R2-1,A-9,R5-2,R3-2),(nm -3,R2-1,A-9,R5-3,R3-1),(nm-3,R2-1,A-9,R5-3,R3-2),(nm-3,R2-1,A-10,R5-1,R3-1),(nm-3,R2-1,A-10,R5-1,R3-2),(nm-3,R2-1,A-10,R5-2,R3-1),(nm-3,R2-1,A-10,R5-2,R3-2),(nm-3,R2-1,A-10,R5-3,R3-1),(nm-3,R2-1,A-10,R5-3,R3-2),(nm-3,R2-1,A-11,R5-1,A-11,R5-1,R3-1),(nm3,R2-1,A-11,R5-1,R3-2),(nm-3,R2-1,A-11,R5-2,R3-1),(nm-3,R2-1,A-11,R5-2,R3-2), (nm-3,R2-1,A-11,R5-3,R3-1),(nm-3,R2-1,A-11,R5-3,R3-2),(nm-3,R2-1,A-12,R5-1,R3-1),(nm-3,R2-1,A-12,R5-1,R3-2), (nm-3,R2-1,A-12,R5-2,R3-1),(nm-3,R2-1,A-12,R5-2,R3-2),(nm-3,R2-1,A-12,R5-3,R3-1),(nm-3,R2-1,A-12,R5-3,R3-2),(nm-3,R2-1,A-13,R5-1,R3-1),(nm-3,R2-1,A-13,R5-1,R3-2),(nm-3,R2-1,A-13,R5-2,R3-1),(nm-3,R2-1,A-13,R5-2,R3-2),(nm-3,R2-1,A-13,R5-3,R3-1),(nm-3,R2-1,A-13,R5-3,R3-2),(nm-3,R2-1,A-14,R5-1,R3-1), (nm-3,R2-1,A-14,R5-1,R3-2),(nm-3,R2-1,A-14,R5-2,R3-1),(nm-3,R2-1,A-14,R5-2,R3-2),(nm-3,R2-1,A-14,R5-3,R3-1),(nm-3,R2-1,A-14,R5-3,R3-2),(nm-3,R2-2,A-1,R5-1,R3-1),(nm-3,R2-2,A-1,R5-1,R3-2),(nm-3,R2-2,A-1,R5-2,R3-1),(nm-3,R2-2,A-1,R5-2,R3-2),(nm-3,R2-2,A-1,R5-3,R3-1),(nm-3,R2-2,A-1,R5-3,R3-2),(nm-3,R2-2,A-2,R5-1,R3-1),(nm-3,R2-2,A-2,R5-1,R3-2),(nm-3,R2-2,A-2,R5-2,R3-1),(nm-3,R2-2,A-2,R5-2,R3-2), (nm-3,R2-2,A-2,R5-3,R3-1),(nm-3,R2-2,A-2,R5-3,R3-2),(nm-3,R2-2,A-3,R5-1,R3-1),(nm-3,R2-2,A-3,R5-1,R3-2),(nm-3,R2-2,A-3,R5-2,R3-1),(nm-3,R2-2,A-3,R5-2,R3-2),(nm-3,R2-2,A-3,R5-3,R3-1),(nm-3,R2-2,A-3,R5-3,R3-2),(nm-3,R2-2,A-4,R5-1,R3-1), (nm-3,R2-2,A-4,R5-1,R3-2),(nm-3,R2-2,A-4,R5-2,R3-1),(nm-3,R2-2,A-4,R5-2,R3-2),(nm-3,R2-2,A-4,R5-3,R3-1),(nm-3,R2-2,A-4,R5-3,R3-2),(nm-3,R2-2,A-5,R5-1,R3-1),(nm-3,R2-2,A-5,R5-1,R3-2),(nm-3,R2-2,A-5,R5-2,R3-1),(nm-3,R2-2,A-5,R5-2,R3-2),(nm -3,R2-2,A-5,R5-3,R3-1),(nm-3,R2-2,A-5,R5-3,R3-2),(nm-3,R2-2,A-6,R5-1,R3-1),(nm-3,R2-2,A-6,R5-1,R3-2),(nm-3,R2-2,A-6,R5-2,R3-1),(nm-3,R2-2,A-6,R5-2,R3-2),(nm-3,R2-2,A-6,R5-3,R3-1),(nm-3,R2-2,A-6,R5-3,R3-2),(nm-3,R2-2,A-7,R5-1,R3-1),(nm-3,R2-2,A-7,R5-1,R3-2),(nm-3,R2-2,A-

7,R5-2,R3-1),(nm-3,R2-2,A-7,R5-2,R3-2),(nm-3,R2-2,A-7,R5-3,R3-1),(nm-3,R2-2,A-7,R5-3,R3-2),(nm-3,R2-2,A-8,R5-1,R3-1),(nm-3,R2-2,A-8,R5-1,R3-2),(nm-3,R2-2,A-8,R5-2,R3-1),(nm-3,R2-2,A-8,R5-2,R3-2),(nm-3,R2-2,A-8,R5-3,R3-1),(nm-3,R2-2,A-8,R5-3,R3-2),(nm-3,R2-2,A-9,R5-1,R3-1),(nm-3,R2-2,A-9,R5-1,R3-2),(nm-3,R2-2,A-9,R5-2,R3-1),(nm-3,R2-2,A-9,R5-2,R3-2),(nm-3,R2-2,A-9,R5-3,R3-1),(nm-3,R2-2,A-9,R5-3,R3-2),(nm-3,R2-2,A-10,R5-1,R3-1),(nm-3,R2-2,A-10,R5-1,R3-2),(nm-3,R2-2,A-10,R5-2,R3-1),(nm-3,R2-2,A-10,R5-2,R3-2),(nm-3,R2-2,A-10,R5-3,R3-1),(nm-3,R2-2,A-10,R5-3,R3-2),(nm-3,R2-2,A-11,R5-1,R3-1),(nm-3,R2-2,A-1 1,R5-1,R3-2),(nm-3,R2-2,A-11,R5-2,R3-1),(nm-3,R2-2,A-11,R5-2,R3-2),(nm-3,R2-2,A -11,R5-3,R3-1),(nm-3,R2-2,A-11,R5-3,R3-2),(nm-3,R2-2,A-12,R5-1,R3-1),(nm-3,R2-2,A-12,R5-1,R3-2),(nm-3,R2-2,A-12,R5-2,R3-1),(nm-3,R2-2,A-12,R5-2,R3-2),(nm-3,R2-2,A-12,R5-3,R3-1),(nm-3,R2-2,A-12,R5-3,R3-2),(nm-3,R2-2,A-13,R5-1,R3-1),(nm-3,R2-2,A-13,R5-1,R3-2),(nm-3,R2-2,A-13,R5-2,R3-1),(nm-3,R2-2,A-13,R5-2,R3-2),(nm-3,R2-2,A-13,R5-3,R3-1),(nm-3,R2-2,A-13,R5-3,R3-2),(nm-3,R2-2,A-14,R5-1,R3-1),(nm-3,R2-2,A-14,R5-1,R3-2),(nm-3,R2-2,A-14,R5-2,R3-1),(nm-3,R2-2,A-14,R5-2,R3-2),(nm-3,R2-2,A-14,R5-3,R3-1),(nm-3,R2-2,A-14,R5-3,R3-2),(nm-3,R2-3,A-1,R5-1,R3-1),(nm-3,R2-3,A-1,R5-1,R3-2),(nm-3,R2-3,A-1,R5-2,R3-1),(nm-3,R2-3,A-1,R5-2,R3-2),(nm-3,R2-3,A-1,R5-3,R3-1),(nm-3,R2-3,A-1,R5-3,R3-2),(nm-3,R2-3,A-2,R5-1,R3-1),(nm-3,R2-3,A-2,R5-1,R3-2),(nm-3,R2-3,A-2,R5-2,R3-1),(nm-3,R2-3,A-2,R5-2,R3-2),(nm-3,R2-3,A-2,R5-3,R3-1),(nm-3,R2-3,A-2,R5-3,R3-2),(nm-3,R2-3,A-3,R5-1,R3-1),(nm-3,R2-3,A-3,R5-1,R3-2),(nm-3,R2-3,A-3,R5-2,R3-1),(nm-3,R2-3,A-3,R5-2,R3-1),(nm-3,R2-3,A-3,R5-3,R3-1),(nm-3,R2-3,A-3,R5-3,R3-2),(nm-3,R2-3,A-4,R5-1,R3-1),(nm-3,R2-3,A-4,R5-1,R3-2),(nm-3,R2-3,A-4,R5-2,R3-1),(nm-3,R2-3,A-4,R5-2,R3-2),(nm-3,R2-3,A-4,R5-3,R3-1),(nm-3,R2-3,A-4,R5-3,R3-2),(nm-3,R2-3,A-5,R5-1,R3-1),(nm-3,R2-3,A-5,R5-1,R3-2),(nm-3,R2-3,A-5,R5-2,R3-1),(nm-3,R2-3,A-5,R5-2,R3-2),(nm-3,R2-3,A-5,R5-3,R3-1),(mn-3,R2-3,A-5,R5-3,R3-2),(nm-3,R2-3,A-6,R5-1,R3-1),(nm-3,R2-3,A-6,R5-1,R3-2),(nm-3,R2-3,A-6,R5-2,R3-1),(nm-3,R2-3,A-6,R5-2,R3-2),(nm-3,R2-3,A-6,R5-3,R3-1),(nm-3,R2-3),A-6,R5-3,R3-2),(nm-3,R2-3,A-7,R5-1,R3-1),(nm-3,R2-3,A-7,R5-1,R3-2),(nm-3,R2-3,A-7,R5-2,R3-1),(nm-3,R2-3,A-7,R5-2,R3-2),(nm-3,R2-3,A-7,R5-3,R3-1),(nm-3,R2-3,A-7,R5-3,R3-2),(nm-3,R2-3,A-8,R5-1,R3-1),(nm-3,R2-3,A-8,R5-1,R3-2), (nm-3,R2-3,A-8,R5-2,R3-1),(nm-3,R2-3,A-8,R5-2,R3-2),(nm-3,R2-3,A-8,R5-3,A-8,R5-3,R3-1),(nm-3,R2-3,A-8,R5-3,R3-2),(nm-3,R2-3,A-9,R5-1,R3-1),(nm-3,R2-3,A-9,R5-1,R3-2),(nm-3,R2-3,A-9,R5-2,R3-1),(nm-3,R2-3,A-9,R5-2,R3-2),(nm-3,R2-3,A-9,R5-3,R3-1),(nm -3,R2-3,A-9,R5-3,R3-2),(nm-3,R2-3,A-10,R5-1,R3-1),(nm-3,R2-3,A-10,R5-1,R3-2),(nm-3,R2-3,A-10,R5-2,R3-1),(nm-3,R2-3,A-10,R5-2,R3-2),(nm-3,R2-3,A-10,R5-3,R3-1),(nm-3,R2-3,A-10,R5-3,R3-2),(nm-3,R2-3,A-11,R5-1,R3-1),(nm-3,R2-3,A-11,R5-1,R3-2), (nm-3,R3-3,A-11,R5-2,R3-1),(nm-3,R2-3,A-11,R5-2,R3-2),(nm-3,R2-3,A-11,R5-3,R3-1),(nm-3,R2-3,A-11,R5-3,R3-2),(nm-3,R2-3,A-12,R5-1,R3-1),(nm-3,R2-3,A-12,R5-1,R3-2),(nm-3,R2-3,A-12,R5-2,R3-1),(nm-3,R2-3,A-12,R5-2,R3-2),(nm-3,R2-3,A-12,R5-3,R3-1),(nm-3,R2-3,A-12,R5-3,R3-2),(nm-3,R2-3,A-13,R5-1,R3-1),(nm-3,R2-3,A-13,R5-1,R3-2),(nm-3,R2-3,A-13,R5-2,R3-1),(nm-3,R2-3,A-13,R5-2,R3-2),(nm-3,R2-3,A-13,R5-3,R3-1),(nm-3,R2-3,A-13,R5-3,R3-2),(nm-3,R2-3,A-14,R5-1,R3-1),(nm-3,R2-3,A-14,R5-1,R3-2),(nm-3,R2-3,A-14,R5-2,R3-1),(nm-3,R2-3,A-14,R5-2,R3-2),(nm-3,R2-3,A-1 4,R5-3,R3-1),(nm-3,R2-3,A-14,R5-3,R3-2),(nm-3,R2-4,A-1,R5-1,R3-1),(nm-3,R2-4,A-1,R5-1,R3-2),(nm-3,R2-4,A-1,R5-2,R3-1),(nm-3,R2-4,A-1,R5-2,R3-2),(nm-3,R2-4,A-1,R5-3,R3-1),(nm-3,R2-4,A-1,R5-3,R3-2),(nm-3,R2-4,A-2,R5-1,R3-1),(nm-3,R2-4,A-2,R5-1,R3-2),(nm-3,R2-4A-2,R5-2,R3-1),(nm-3,R2-4,A-2,R5-2,R3-2),(nm-3,R2-4,A-2,R5-3,R3-1),(nm-3,R2-4,A-2,R5-3,R3-2),(nm-3,R2-4,A-3,R5-1,R3-1),(nm-3,R2-4,A-3,R5-1,R3-2),(nm-3,R2-4,A-3,R5-2,R3-1),(nm-3,R2-4,A-3,R5-2,R3-2),(nm-3,R2-4,A-3,R5-3,R3-1),(nm-3,R2-4,A-3,R5-3,R3-2),(nm-3,R2-4,A-4,R5-1,R3-1),(nm-3,R2-4,A-4,R5-1,R3-2),(nm-3,R2-4,A-4,R5-2,R3-1),(nm-3,R2-4,A-4,R5-2),(nm-3,R2-4,A-4,R5-3,R3-1), (nm-3,R2-4,A-4,R5-3,R3-2),(nm-3,R2-4,A-5,R5-1,R3-1),(nm-3,R2-4,A-5,R5-1,R3-2),(nm-3,R2-4,A-5,R5-2,R3-1),(nm-3,R2-4,A-5,R5-2,R3-2),(nm-3,R2-4,A-5,R5-3,R3-1),(nm-3,R2-4,A-5,R5-3,R3-2),(nm-3,R2-4,A-6,R5-1,R3-1),(nm-3,R2-4,A-6,R5-1,R3-2),(nm-3,R2-4,A-6,R5-2,R3-1),(nm-3,R2-4,A-6,R5-2,R3-2),(nm-3,R2-4,A-6,R5-3,R3-1),(nm-3,R2-4,A-6,R5-3,R3-2),(nm-3,R2-4,A-7,R5-1,R3-1),(nm-3,R2-4,A-7,R5-1,R3-2),(nm-3,R2-4,A-7,R5-2,R3-1),(nm-3,R2-4,A-7,R5-2,R3-2),(nm-3,R2-4,A-7,R5-3,R3-1),(nm-3,R2-4,A-7,R5-3,R3-2),(nm-3,R2-4,A-8R5-1,R3-1),(nm-3,R2-4,A-8,R5-1,R3-2),(nm-3,R2-4,A-8,R5-2,R3-1),(nm-3,R2-4,A-8,R5-2,R3-2),(nm-3,R2-4,A-8,R5-3,R3-1),(nm-3,R2-4,A-8,R5-3,R3-2),(nm-3,R2-4,A-9,R5-1,R3-1),(nm-3,R2-4,A-9,R5-1,R3-2),(nm-3,R2-4,A-9,R5-2,R3-1),(nm-3,R2-4,A-9,R5-2,R3-2),(nm-3,R2-4,A-9,R5-3,R3-1),(nm-3,R2-4,A-9,R5-3,R3-2),(nm-3,R2-4,A-10,R5-1,R3-1),(nm-3,R2-4,A-10,R5-1,R3-2),(nm-3,R2-4,A-10,R5-2,R3-1),(nm-3,R2-4,A-10,R5-2,R3-2),(nm-3,R2-4,A-10,R5-3,R3-1),(nm-3,R2-4,A-1 0,R5-3,R3-2),(nm-3,R2-4,A-11,R5-1,R3-1),(nm-3,R2-4,A-11,R5-1,R3-2),(nm-3,R2-4,A -11,R5-2,R3-1),(nm-3,R2-4,A-11,R5-2,R3-2),(nm-3,R2-4,A-11,R5-3,R3-1),(nm-3,R2-4,A-11,R5-3,R3-2),(nm-3,R2-4,A-12,R5-1,R3-1),(nm-3,R2-4,A-12,R5-1,R3-2),(nm-3,R2-4,A-12,R5-2,R3-1),(nm-3,R2-4,A-12,R5-2,R3-2),(nm-3,R2-4,A-12,R5-3,R3-1),(nm-3,R2-4,A-12,R5-3,R3-2),(nm-3,R2-4,A-13,R5-1,R3-1),(nm-3,R2-4,A-13,R5-1,R3-2),(nm-3,R2-4,A-13,R5-2,R3-1),(nm-3,R2-4,A-13,R5-2,R3-2),(nm-3,R2-4,A-13,R5-3,R3-1),(nm-3,R2-4,A-13,R5-3,R3-2),(nm-3,R2-4,A-14,R5-1,R3-1),(nm-3,R2-4,A-14,R5-1,R3-2),(nm-3,R2-4,A-14,R5-2,R3-1),(nm-3,R2-4,A-14,R5-2,R3-2),(nm-3,R2-4,A-14,R5-3,R3-1),(nm-3,R2-4,A-14,R5-3,R3-2), and (nm-3,R2-4,A-14,R5-3,R3-3).

In the compound represented by the general formula (I'), a compound, wherein the combination of n, m, $R^{2a}$, $R^{2b}$, ring A, $R^5$, $R^{3a}$, and $R^{3b}$ (nm, $R^2$, A, $R^5$, $R^3$) is one of the above compound, and E is a bond.

The compounds of the invention can be employed in the treatment and/or prevention of disease associated with the generation, secretion or deposition of β-amyloid protein, such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, amyloid angiopathy and so on.

The compounds of the invention can be administered in combination with other pharmaceutical agents such as other therapeutic drugs for Alzheimer's disease, acetylcholinesterase inhibitors and so on. The compounds of the invention can be treated with concomitantly with the anti-dementia agents such as Donepezil Hydrochloride, Tacrine, Galantamine, Rivastigmine, Zanapezil, Memantine, Vinpocetine.

When the present compound is administered to a human, it can be administered orally as powders, granules, tablets, capsules, pills, solutions, or the like, or parenterally as injectables, suppositories, transdermal absorbable agents, absorbable agents, or the like. In addition, the present compound can be formulated into pharmaceutical preparations by adding pharmaceutical additives such as excipients, binders, wetting agents, disintegrating agents, lubricants and the like, which are suitable for formulations and an effective amount of the present compound, A dose is different depending on state of disease, an administration route, and an age and a weight of a patient, and is usually 0.1 μg to 1 g/day, preferably 0.01 to 200 mg/day when orally administered to an adult, and is usually 0.1 μg to 10 g/day, preferably 0.1 to 2 g/day when parenterally administered, Following examples and test examples illustrate the present invention in more detail, but the present invention is not limited by these examples, In example, the meaning of each abbreviation is following.
Me methyl
Et ethyl
iPr or Pr$^i$ isopropyl
Ph phenyl
Bn benzyl
Boc t-butoxycarbonyl
TBDPS t-butyldiphenylsilyl

EXAMPLE

Reference Example 1

The Synthesis of Compound 588

[Chemical formula 56]

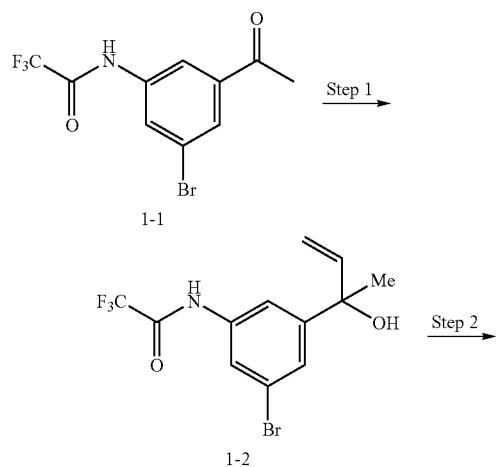

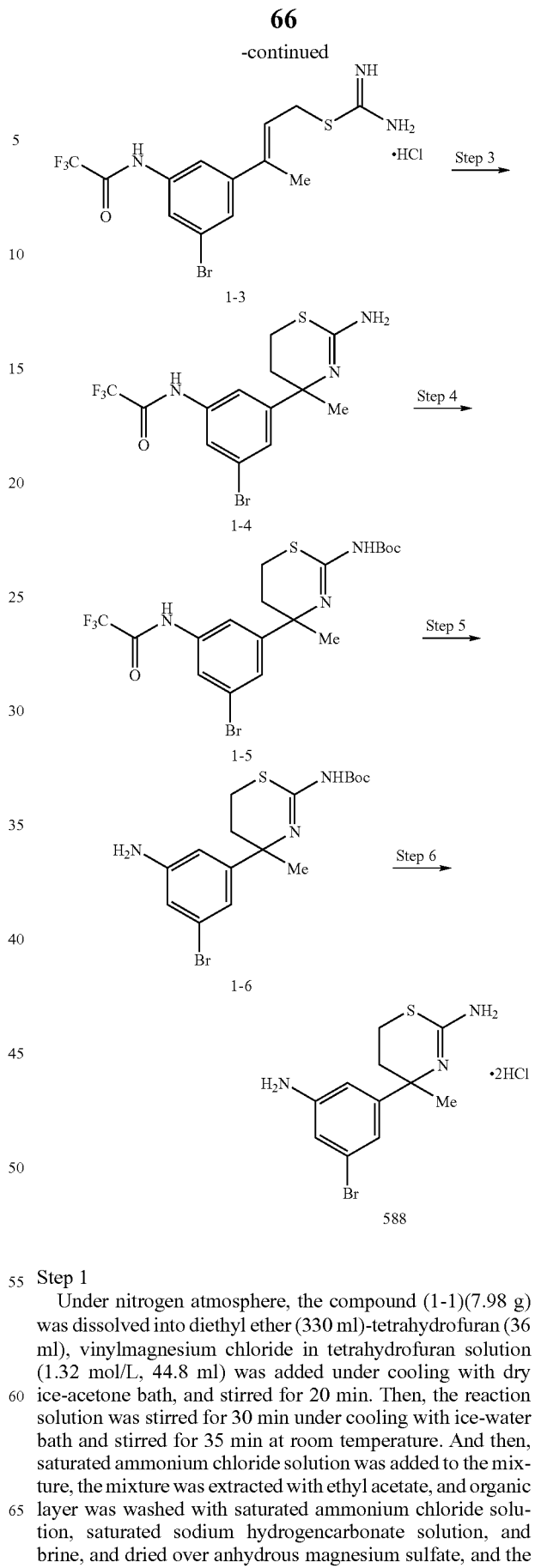

Step 1
Under nitrogen atmosphere, the compound (1-1)(7.98 g) was dissolved into diethyl ether (330 ml)-tetrahydrofuran (36 ml), vinylmagnesium chloride in tetrahydrofuran solution (1.32 mol/L, 44.8 ml) was added under cooling with dry ice-acetone bath, and stirred for 20 min. Then, the reaction solution was stirred for 30 min under cooling with ice-water bath and stirred for 35 min at room temperature. And then, saturated ammonium chloride solution was added to the mixture, the mixture was extracted with ethyl acetate, and organic layer was washed with saturated ammonium chloride solution, saturated sodium hydrogencarbonate solution, and brine, and dried over anhydrous magnesium sulfate, and the solvent was evaporated. Then, the residue was purified by silica gel column chromatography to afford the compound (1-2)(6.00 g).

$^1$H-NMR(CDCl$_3$): 1.63(3H, s), 2.08(1H, br), 5.20(1H, dd, J=10.6, 1.6 Hz), 5.31(1H, dd, J=17.1, 1.6 Hz), 6.09(1H, m), 7.46(1H, m), 7.52(1H, dd, J=3,4, 2.6 Hz), 7.80(1H, dd, J=3.9, 2.6 Hz), 8,06(1H, br)

Step 2

The compound (1-2)(6.36 g) was dissolved into acetic acid (30 ml), and added thiourea (1.50 g), 1 mol/L hydrochloride-acetic acid solution (20.7 ml). The reaction mixture was stirred at room temperature for 3 hours, then stirred at 40° C. for 3 hours, then stirred at room temperature for 66 hours, and at 40° C. for 19 hours. Thiourea (0.450 g), and 1 mol/L hydrochloric acid-acetic acid solution (7.53 ml) was added, and stirred at 40° C. for 23 hours. After the consumption of the compound (1-2), the solvent was evaporated under reduced pressure, then the obtained residue was crystallized from methanol-diethyl ether to afford the compound (1-3)(5.23 g) as crystal. On the other hand, filtrate was evaporated under reduced pressure, and the compound (1-3)(3,00 g) was obtained as a crude solid product.

$^1$H-NMR(DMSO-d$_6$): 2.09(3H, s), 4.10(2H, d, J=7.3 Hz), 5.94(1H, t, J=7.7 Hz), 7.50(1H, s), 7.75(1H, s), 7.87(1H, s), 9.17(3H, br), 11.46(1H, s)

Step 3

The compound (1-3)(5.23 g) dissolved in trifluoroacetic acid (25 ml) was added methanesulfonic acid (2.14 ml) dropwise under cooling with ice-water bath. After addition, the reaction mixture was stirred at room temperature for 3.5 hours. After the consumption of the compound (1-3), the solvent was evaporated under reduced pressure. To the residue obtained was added water and sodium carbonate and then extracted with ethyl acetate. The organic layer was washed with saturated sodium hydrogencarbonate solution, and was dried over anhydrous magnesium sulfate, and the solvent was evaporated under reduced pressure to afford the compound (1-4)(4.90 g) as a crude product.

$^1$H-NMR(CDCl3): 1.53(3H, s), 1.90(1H, m), 2.09(1H, m), 2.74(1H, m), 2.97(1H, m), 4.32(2H, br), 7.34(1H, t, J=1.6 Hz), 7.37(1H, t, J=1.8 Hz), 7.86(1H, t, J=1.8 Hz)

Step 4

Under nitrogen atmosphere, the compound (1-4)(4.90 g) dissolved in tetrahydrofuran was added di-t-butyl-dicarbonate (2.97 g) and triethylamine (1.89 ml) under cooling with ice-water bath and then stirred for 2 hours. The reaction mixture was stirred at room temperature for 3 hours. The reaction mixture was added water, and then extracted with ethyl acetate. The organic layer was washed with water, and dried over anhydrous magnesium sulfate, then the solvent was evaporated under reduced pressure. Then the obtained residue was crystallized from ethyl acetate-diethyl ether to afford the compound (1-5)(4.62 g) as crystal.

$^1$H-NMR(CDCl$_3$): 1.36(9H, s), 1.72(3H, s), 2.10(1H, m), 2.41(1H, m),2.62(1H, m), 2.75(1H, m), 7.22(1H, s), 7.48(1H, s), 8.29(1H, s)

Step 5

The compound (1-5)(1.00 g) was dissolved into tetrahydrofuran (8.7 ml), and 1 mol/L lithium hydroxide (4.43 ml) was added and stirred at 50° C. for 4 hours. Water was added to the reaction mixture, and the mixture was extracted with ethyl acetate, and the organic layer was washed with water, brine successively, and dried over anhydrous magnesium sulfate, and the solution was evaporated under reduced pressure. The obtained residue was purified by medium-pressured silica gel column chromatography to afford the compound (1-6)(0.668 g).

$^1$H-NMR(CDCl$_3$): 1.51(9H, s), 1.63(3H, s), 2.06(1H, m), 2.40(1H, m), 2.68-2.74(2H, m), 3.83(2H, br), 6.51(1H, t, J=1.8 Hz), 6.72-6.74(2H, m)

Step 6

The compound (1-6)(20.0 mg) was dissolved into 4 mol/L hydrochloric acid in 1,4-dioxane, and the mixture was stirred for 16 hours. The reaction solvent was evaporated under reduced pressure and the obtained residue was crystallized from methanol-diethyl ether to afford the compound (588) (14.7 mg).

$^1$H-NMR(DMSO-d$_6$): 1.59(3H, s), 2.09-2.76(4H, m), 6.44 (1H, t, J=1.6 Hz), 6.60(1H, t J=1.9 Hz), 6.71(1H, t, J=2.0 Hz), 10.4(1H, s)

Reference Example 2

The Synthesis of Compound 835

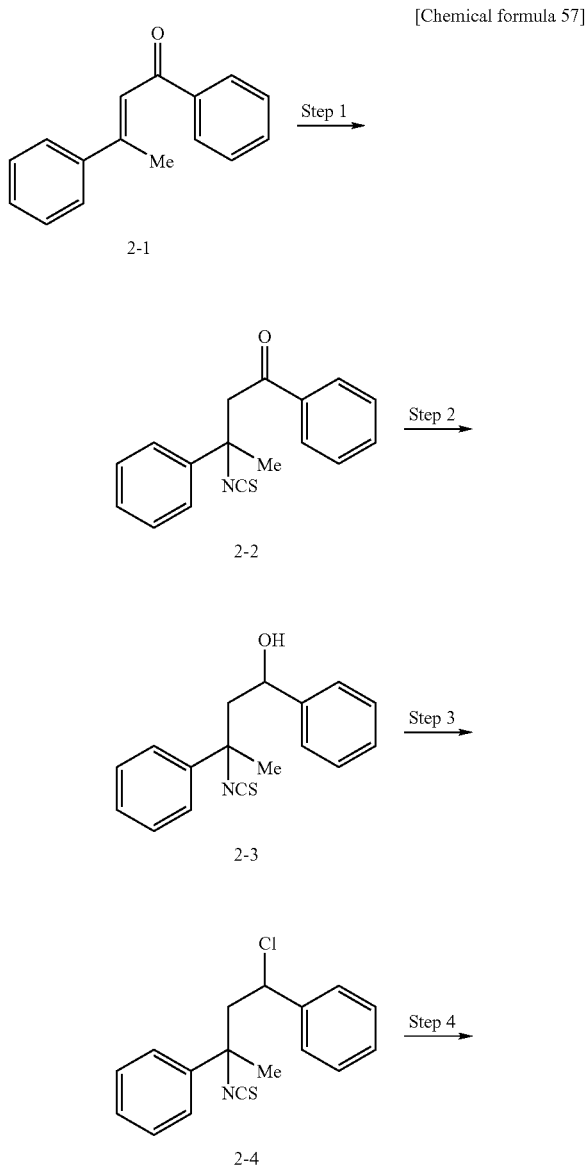

[Chemical formula 57]

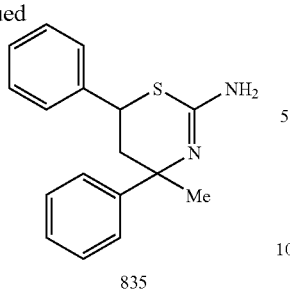

835

Step 1

The compound (2-1)(2020 mg) was dissolved into chloroform (20 ml), then water(4 ml) and sodium thiocyanate (1470 mg) were added at room temperature with stirring, and then sulfuric acid (1.94 ml) was added dropwise under cooling with ice-water bath. After an addition was complete, the reaction mixture was warmed to room temperature and then stirred for 345 minutes, then stirred at 60 ° C. overnight. Because the compound (2-1) was remained(checked by TLC), the reaction mixture was cooled to room temperature, then sodium thiocyanate (1470 mg), water (5 ml) and sulfuric acid (1.94 ml) were added successively. After the reaction mixture was warmed to 60° C., the mixture was stirred for 1 day. Saturated sodium bicarbonate solution was added to the reaction mixture to be basic condition under cooling with ice-water bath, and then the reaction mixture was extracted with ethyl acetate. The organic layer was washed with brine, then dried over anhydrous magnesium sulfate. The solvent was evaporated and the obtained residue was purified by silica gel column chromatography to afford the compound (2-2) (968 mg).

$^1$H-NMR(CDCl$_3$, 270 MHz): 1.99 (3H, s), 3.55 (1H, d, J=16.1 Hz), 3.69(1H, d, J=16.1 Hz), 7.12-7.64 (8H, m), 7.82-7.95 (2H, m)

Step 2

The compound (2-2)(842 mg) was dissolved into ethano (8.4 ml), sodium dihydrogen phosphate and an aqueous solution of sodium borohydride (113.2 mg) in water (2.8 ml) were added successively under cooling with ice-water bath with stirring, and the mixture was stirred for 30 minutes. After the consumption of the compound (2-2)(checked by TLC), ethyl acetate and water were added to the reaction mixture under cooling with ice-water bath, and then stirred for a few minutes. The reaction mixture was extracted with ethyl acetate. The organic layer was washed with water, brine successively, and dried over anhydrous magnesium sulfate. The solvent was evaporated to afford the compound (2-3)(904.8 mg) as a crude product.

Step 3

To a solution of compound (23)(900 mg) in toluene (10 ml) was added a solution of thionyl chloride (0.7 ml) in toluene (5 ml) under cooling with ice-water bath with stirring, and then stirred for 1 hour at the same temperature. After the consumption of the compound (2-3)(checked by TLC), the reaction solvent was evaporated under reduced pressure to afford the compound (2-4)(1076.8 mg) as a crude product.

Step 4

The compound. (2-4)(1070 mg) was dissolved into about 7 mol/L ammonia in methanol (20 ml) at room temperature, then the mixture was stirred for 1 day. After the consumption of the compound (2-4)(checked by TLC), the reaction solvent was evaporated under reduced pressure to afford the compound (835)(2633 mg) as a crude product.

Reference Example 3

The Synthesis of Compound 561

[Chemical formula 58]

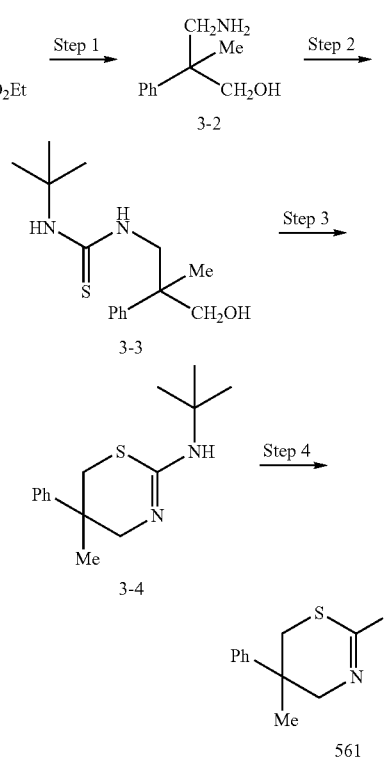

Step 1

To tetrahydrofuran (30 ml) under cooling with ice-water bath with stirring, lithium aluminum hydride (0.63 g) was added portionwise, then a solution of compound (3-1)(1.94 g) in tetrahydrofuran (40 ml) was added dropwise. The reaction mixture was reacted for 20 minutes at room temperature, then reacted for 3 hours under reflux. Then ice was added in small portions under cooling, and then stirred for 1 day at room temperature. The reaction mixture was filtered and the filtrate was evaporated under reduced pressure, and the residue was purified by silica gel column chromatography to afford the compound (3-2)(0.90 g).

$^1$H-NMR(CDCl$_3$): 1.22(3H, s), 3.08(1H, d, J=12.5 Hz), 3.34(1H, d, J=12.5 Hz), 3.85(1H, d, J=11.0 Hz), 4.11(1H, d, J=11.0 Hz), 7.21-7.25(1H, m), 7.34-7.40(2H, m), 7.46-7.50 (2H, m).

Step 2

The compound (3-2)(0.90 g) was dissolved into tetrahydrofuran (15 ml), t-butylisothiocyanate (0.69 g) in tetrahydrofuran (5 ml) was added under cooling with ice-water bath with stirring. The reaction mixture was stirred for 3 days at room temperature, water was added and extracted with dichloromethane. The organic layer,was dried over anhydrous magnesium sulfate, then the solvent was evaporated under reduced pressure. The residue was purified by silica gel column chromatography to afford the compound (3-3)(1.33 g).

$^1$H-NMR(CDCl$_3$): 1.12(9H, s), 1.34(3H, s), 3.15(1H, br), 3.76(1H, d, J=11.2 Hz), 3.87(1H, dd, J=14.2, 4.6 Hz), 4.13 (1H, d, J=11.2 Hz), 4.23(1H, dd, J=14,2, 6.6 Hz), 5.18(1H ,br), 6.01(1H, br), 7.23-7.28(1H, m), 7.34-7.41(4H, m).

Step 3

The compound (3-3)(315 mg) was dissolved into acetonitrile (3 ml), triphenylphosphine (440 mg), and carbon tetrachloride (520 mg) in acetonitrile 3 ml) were added under cooling with ice-water bath with stirring. The reaction mixture was stirred for 1 hour at room temperature, and then potassium carbonate (460 mg) was added and stirred for 2 days at room temperature. Then water was added to the reaction mixture and the mixture was extracted with dichloromethane. The organic layer was dried over anhydrous magnesium sulfate, and then the solvent was evaporated under reduced pressure. The residue was purified by silica gel column chromatography to afford the compound (3-4)(0.23 g).

$^1$H-NMR(CDCl3): 1.30(9H, s), 1.36(3H, s), 3.13(1H, d, J=12.2 Hz), 3.24(1H, dd, J=12.2, 2.3 Hz), 3.51(1H, br), 3.53 (1H, d, J=15.2 Hz), 3.99(1H, dd, J=15.2, 2.3 Hz), 7.20-7.25 (1H, m), 7.30-7.36(2H, m), 7.39-7.43(2H, m).

Step 4

To the compound (3-4)(0.22 g), conc. hydrochloric acid (4.5 ml) was added, then stirred for 2 hours under reflux, and then the reaction solvent was evaporated under reduced pressure. The obtained residue was crystallized from methanol-diethyl ether to afford the compound (561)(0.16 g).

$^1$H-NMR,(DMSO-d$_6$): 1.33(3H, s), 3.33-3.49(2H, m), 3.65-3.96(2H, m), 7.29(1H, t, J=7.6 Hz), 7.40(2H, t, J=7.6 Hz), 7.48(2H, t, J=7.6 Hz).

Reference Example 4

The Synthesis of Compound 534

[Chemical formula 59]

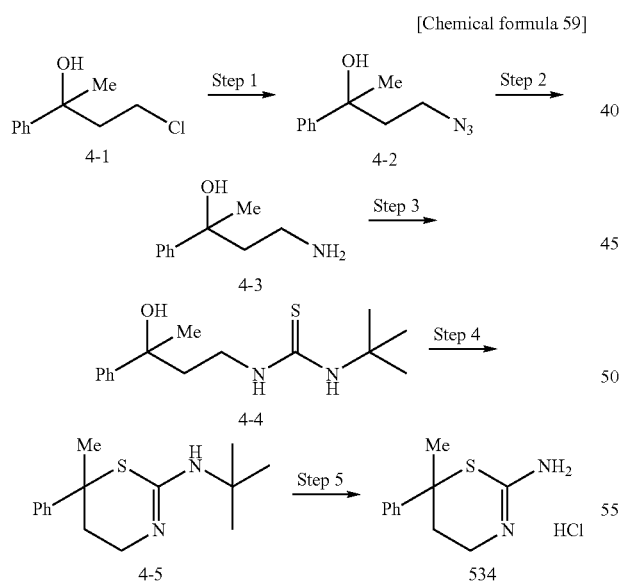

Step 1

The compound (4-1)(0.72 g) was dissolved into N,N-dimethylformamide (15 ml), then sodium azide (0.31 g) was added. The reaction mixture was stirred at 100° C. for 13 hours, then water was added and the mixture was extracted with diethyl ether, the organic layer was dried over anhydrous magnesium sulfate to afford the compound (4-2)(0.71 g) as a crude product.

Step 2

To a solution of the compound (4-2)(0.71 g) in tetrahydrofuran (10 ml), lithium aluminum hydride (0.14 g) was added portionwise under cooling with ice-water bath with stirring, then stirred for 2 hours at room temperature. After the consumption of the starting material, ice was added in small portions, then stirred for 18 hours at room temperature. The reaction mixture was filtered then filtrate was evaporated under reduced pressure to afford the compound (4-3)(0.89 g) as a crude product.

Step 3

The compound (4-3)(0.89 g) was dissolved into tetrahydrofuran (10 ml), then t-butylisothiocyanate (0.56 g) in tetrahydrofuran (5 ml) was added under cooling with ice-water bath with stirring. The reaction mixture was stirred for 4 hours at room temperature, and water was added, and then extracted with dichloromethane, and the organic layer was dried over anhydrous magnesium sulfate. Then the residue was purified by silica gel column chromatography to afford the compound (4-4)(0.72 g).

$^1$H-NMR(CDCl$_3$): 1.39(9H, s), 2.08(3H, s), 2.09-2.15(2H, m), 3.37-3.44(1H, m), 3.80-3.87(1H, m), 5.97(1H, br.), 6.86 (1H, br.), 7.28-7.43(5H, m).

Step 4

The compound (4-4)(120 mg) was dissolved into acetonitrile (2 ml), triphenylphosphine (170 mg), and carbon tetrachloride (200 mg) in acetonitrile (1 ml) were added under cooling with ice-water bath with stirring. The reaction mixture was stirred for 5 hours at room temperature, and then potassium carbonate (177 mg) was added and stirred for 5 days at room temperature. Then water was added to the reaction mixture and the mixture was extracted with dichloromethane, the organic layer was dried over anhydrous magnesium sulfate, then the solvent was evaporated under reduced pressure. The residue was purified by silica gel column chromatography to afford the compound (4-5)(0.06 g), $^1$H-NMR(CDCl$_3$): 1.35(9H, s), 1.59(3H, s), 1.91(1H, ddd, J=13.5, 8.8, 5.0 Hz), 2.06(1H, dt, J=13.5, 5.0 Hz), 3.00(1H, ddd, J=15.1, 8.8, 5.0 Hz), 3.30(1H, dt, J=15.1, 5.0 Hz), 7.24-7.38(5H, m).

Step 5

To the compound (4-5)(0.06 g), conc. hydrochloric acid (3 ml) was added, then the mixture was stirred for 1 hour under reflux, and the solvent was evaporated under reduced pressure. The obtained residue was crystallized from methanol-water to afford the compound (534)(0.02 g).

$^1$H-NMR(DMSO-d$_6$): 1.43(3H, s), 1.77(1H, dt. J=8.4, 3.4 Hz), 2.11(1H, d, J=9.2 Hz), 2.48-2.50(1H, m), 2.83-2.99 (1H,), 6.12(1H, br), 6,65(1H, br), 7.21-7.24(1H, m), 7.31-7,37(4H, m).

Reference Example 5

The Synthesis of Compound 1008

[Chemical formula 60]

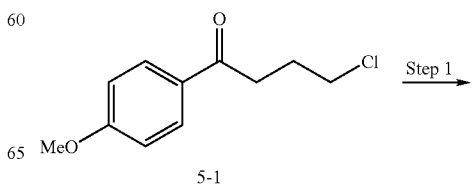

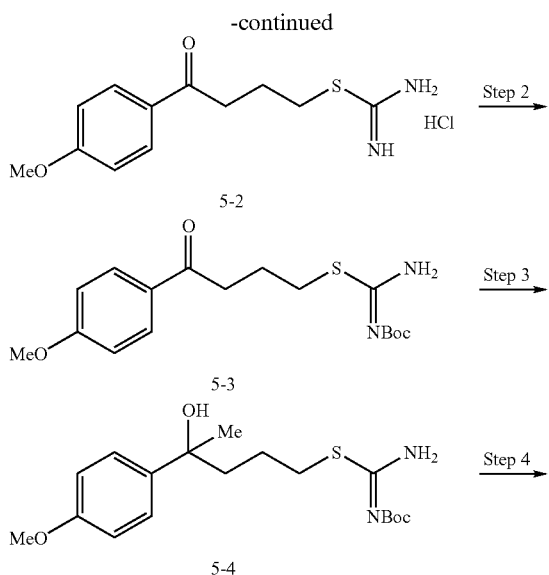

reduced pressure. The obtained residue was purified by silica gel column chromatography to afford the compound (5-4) (0.39 g), $^1$H-NMR(CDCl$_3$): 1.51(9H, s), 1.63(3H, s), 1.55-1.65(2H, m), 1.87-1.91(2H, m), 2.96-3.12(2H, m), 6.86(2H, d, J=8.9 Hz), 7.36(2H, d, J=8.9 Hz).

Step 4

The compound (5-4)(0.24 g) was dissolved into trifluoroacetic acid (6 ml), and stirred for 20 hours at room temperature, then the reaction solvent was evaporated under reduced pressure. To the residue, water and saturated sodium hydrogencarbonate was added, and then extracted with dichloromethane. The organic layer was dried over anhydrous sodium sulfate, and then the solvent was evaporated under reduced pressure. The residue was purified by silica gel column chromatography to afford the compound (1008)(0.06 g).

$^1$H-NMR(CDCl$_3$): 1.54(3H, s), 1.77-1.87(1H, m), 1.90-1.97(1H, m), 2.20-2.36(2H, m), 2.67-2.79(2H, m), 3.81(3H, s), 5.30(2H, br), 6.87(2H, d, J=9.0 Hz), 7.33(2H, d, J=9.0 Hz).

Reference Example 6

The Synthesis of Compound 783

[Chemical formula 61]

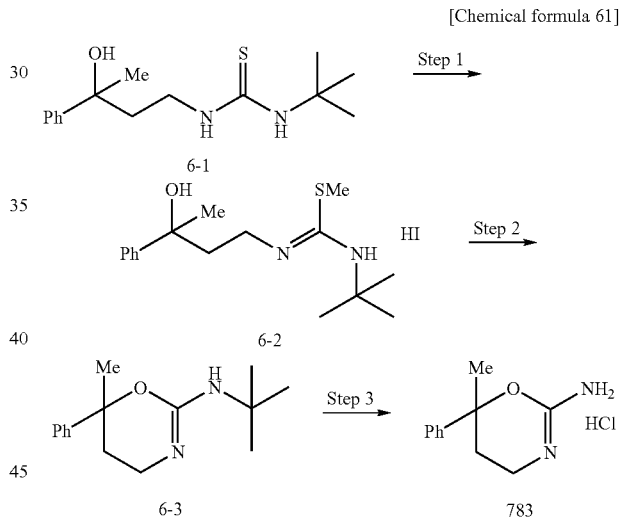

Step 1

The compound (6-1)(0.55 g) was dissolved into methanol (7 ml), and methyl iodide (0.36 g) was added at room temperature with stirring. The mixture was stirred at room temperature for 18 hours, then the reaction solvent was evaporated under reduced pressure to afford the compound (6-2) (0.92 g) as a crude product.

Step 2

The compound (6-2)(0.92 g) was dissolved into tetrahydrofuran (7 ml), then triethylamine (0.24 g) and silver oxide (1.1 g) was added. The mixture was stirred at room temperature for 3 days, then the insolubles was removed by filtration, then the filtrate was evaporated under reduced pressure, and then the obtained residue was purified by silica gel column chromatography to afford the compound (6-3)(0.31 g).

$^1$H-NMR(CDCl$_3$): 1.35(9H, s), 1.60(3H, s), 1.92(1H, ddd, J=9.2, 5.8, 3.4 Hz), 2,07(1H, dt, J=9.2, 3.4 Hz), 3.00(1H, ddd, J=9.2, 5.8, 3.4 Hz), 3.30(1H, dt, J=9.2, 3.4 Hz), 7.24-7.38(5H, m).

Step 1

The compound (5-1)(3.00 g) was dissolved into ethanol (30 ml), and thiourea (1.13 g) was added, and then the mixture was refluxed for 26 hours, and the solvent was evaporated under reduced pressure. The obtained residue was crystallized from ethyl acetate/hexane to afford the compound (5-2) (4.03 g).

$^1$H-NMR(DMSO-d$_6$): 1.95(2H, quint, J=6.8 Hz), 3.13(2H, t, J=6.8 Hz), 3.21(2H, t, J=6.8 Hz), 3.85(3H, s), 7.06(2H, d, J=8.8 Hz), 7.95(2H, d, J=8.8 Hz), 9.18(4H, br).

Step 2

The compound (5-2)(1.00 g) was dissolved into tetrahydrofuran (25 ml), then di-t-butyl-dicarbonate (1.74 g), and triethylamine (0.88 g) were added, and then the mixture was stirred for 3 hours at room temperature. Water was added to the reaction mixture, and the mixture was extracted with dichloromethane. The organic layer was dried over anhydrous magnesium sulfate, and then the solvent was evaporated, under reduced pressure. The residue was purified by silica gel column chromatography to afford the compound (5-3)(1.24 g).

$^1$H-NMR(CDCl$_3$): 1.50(9H, 5), 2.07-2.17(2H, m), 2.98 (2H, t, J=7.8 Hz), 3.09(2H, t, J=6.3 Hz), 6.95(2H, d, J=8.9 Hz), 7.95(2H, d, J=8.9 Hz),

Step 3

The compound (5-3)(1.18 g) was dissolved into tetrahydrofuran (12 ml), then 0.9 mol/L methylmagnesium bromide in tetrahydrofuran solution (10.1 ml) was added under cooling with acetonitrile-dry ice bath with stirring, and then reaction mixture was stirred for 1 hour, then stirred for 30 minutes at room temperature. After the reaction, saturated ammonium chloride solution was added under cooling with ice-water bath with stirring, then the mixture was extracted with diethyl ether, and the organic layer was dried over anhydrous magnesium sulfate, and then the solvent was evaporated under Step 3

To the compound (6-3)(0.22 g), conc. hydrochloric acid (3 ml) was added, then the mixture was stirred for 1 hour under reflux, and then the reaction solvent was evaporated under reduced pressure. The obtained residue was crystallized from water to afford the compound (783)(0.13 g).

$^1$H-NMR(DMSO-d$_6$): 1.44(3H, s), 1.78(1H, dt, J=12.4, 4.2 Hz), 2.12(1H, d, J=8.9 Hz), 2.51-2.52(1H, m), 2.96(1H, d, J=4.2 Hz), 6.12(1H, br), 6.66(1H, br), 7.21-7.24(1H, m), 7.32-7.37(4H, m).

Reference Example 7

The Synthesis of Compound 69

[Chemical formula 62]

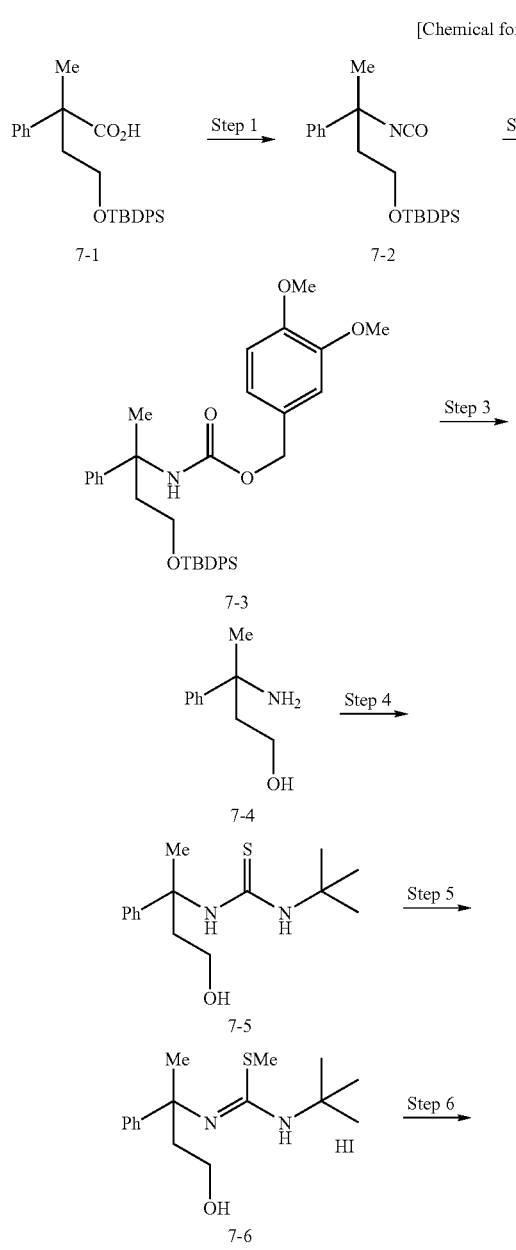

Step 1

A solution of the compound (7-1)(1.93 g), diphenylphosphoryl azide (1.60 g), and triethylamine (0.59 g) in toluene (20 ml) was stirred at 80° C. for 3 hours, and water was added, and then the mixture was extracted with diethyl ether. The organic layer was dried over anhydrous sodium sulfate, and then the solvent was evaporated under reduced pressure. The obtained residue was purified by silica gel column chromatography to afford the compound (7-2)(1.69 g).

$^1$H-NMR(CDCl$_3$): 1.00(9H, s), 1.72(3H, s), 2.17-2.22(2H, m), 3.49-3.58(1H, m), 3.70-3.80(1H, m), 7.20-7.42(10H, m), 7.58-7.63(5H, m).

Step 2

The compound (7-2)(1.68 g) was dissolved into toluene (9 ml), and 3,4-dimethoxybenzylalcohol (0.79 g) was added, the mixture was refluxed for 8 hours. To the reaction mixture, water was added, then the mixture was extracted with dichloromethane, and the organic layer was dried over anhydrous sodium sulfate, and the solvent was evaporated under reduced pressure. The obtained residue was purified by silica gel column chromatography to afford the compound (7-3)(2.09 g).

$^1$H-NMR(CDCl$_3$): 1.03(9H, s), 1.87(3H, s), 2.04(2H, m), 3.48(1H, m), 3.51(1H, m), 3.62(3H, s), 3.65(3H, s), 4.95(1H, d, J=12.2 Hz), 5.03(1H, d, J=12.2 Hz), 6.80-7.09(3H, m), 7.22-7.42(10H, m), 7.56-7.64(5H, m).

Step 3

The compound (7-3)(2.09 g) was dissolved into 1,4-dioxane (15 ml), and 4 mol/L hydrochloric acid-1,4-dioxane (15 ml) solution was added, then stirred at room temperature for 24 hours. To the reaction mixture, water and 1 mol/L—sodium hydroxide solution were added and extracted with dichloromethane, then the organic layer was dried over anhydrous sodium sulfate, and then the solvent was evaporated under reduced pressure. The obtained residue was purified by silica gel column chromatography to afford the compound (7-4)(0.45 g).

$^1$H-NMR(CDCl$_3$): 1.57(3H, s), 1.07-1.98(2H,), 3.48-3.56 (1H, 3.72-3.86(1H, m), 7.23-7.45(15H, m).

Step 4

The compound (7-4)(0.44 g) was dissolved into tetrahydrofuran (15 ml), t-butylisothiocyanate (0.41 g) and diisopropylethylamine (0.46 g) were added. After the mixture was stirred at room temperature for 3 days, water was added, and extracted with dichloromethane, then the organic layer was dried over anhydrous sodium sulfate, and then the solvent was evaporated under reduced pressure. The obtained residue was purified by silica gel column chromatography to afford the compound (7-5)(0.17 g).

$^1$H-NM(CDCl$_3$): 1.79(3H, s), 1.82-2.20(2H, 3.71-3.81 (2H, m), 5.09(1H, br), 7.30-7.52(5H, m).

Step 5

The compound (7-5)(0.17 g) was dissolved into tetrahydrofuran (3.4 ml), then methyl iodide (0.11 g) was added at room temperature with stirring. The mixture was stirred for 23 hours, the reaction solvent was evaporated under reduced pressure to afford the compound (7-6)(0.28 g) as a crude product.

Step 6

The compound (7-6)(0.28 g) was dissolved into tetrahydrofuran (5 ml), then triethylamine (74 mg) and silver oxide (0.34 g) were added. The mixture was stirred at room temperature for 20 hours, then insolubles were removed by filtration, and then the filtrate was evaporated under reduced pressure. The obtained residue was purified by silica gel column chromatography to afford the compound (7-7)(0.14 g).

$^1$H-NMR(CDCl$_3$): 1.36(9H, s), 1.49(3H, s), 1.96-2.09(2H, m), 2.77-3.83(1H, m), 4.05-4.10(1H, m), 7.19(1H, t, J=7.3 Hz), 7.31(2H, t, J=7.3 Hz), 7.44(2H, d, J=7.3 Hz).

Step 7

To the compound (7-7)(0.12 g) conc. hydrochloric acid (9 ml) was added, then stirred for 1 hour under reflux, and then the reaction solvent was evaporated under reduced pressure. The obtained residue was crystallized from methanol-water to afford the compound (69)(0.10 g).

$^1$H-NMR(DMSO-d$_6$): 1.65(3H, s), 2.28-2.35(1H, m), 2.39-2.44(1H, m), 3.97(1H, dt, J=7.8, 3.0 Hz), 4.53(1H, dt, J=7.8, 3.0 Hz), 7.32-7.44(5H, m), 8.44(2H, br), 10.33(1H, s).

Reference Example 8

The Synthesis of Compound 256

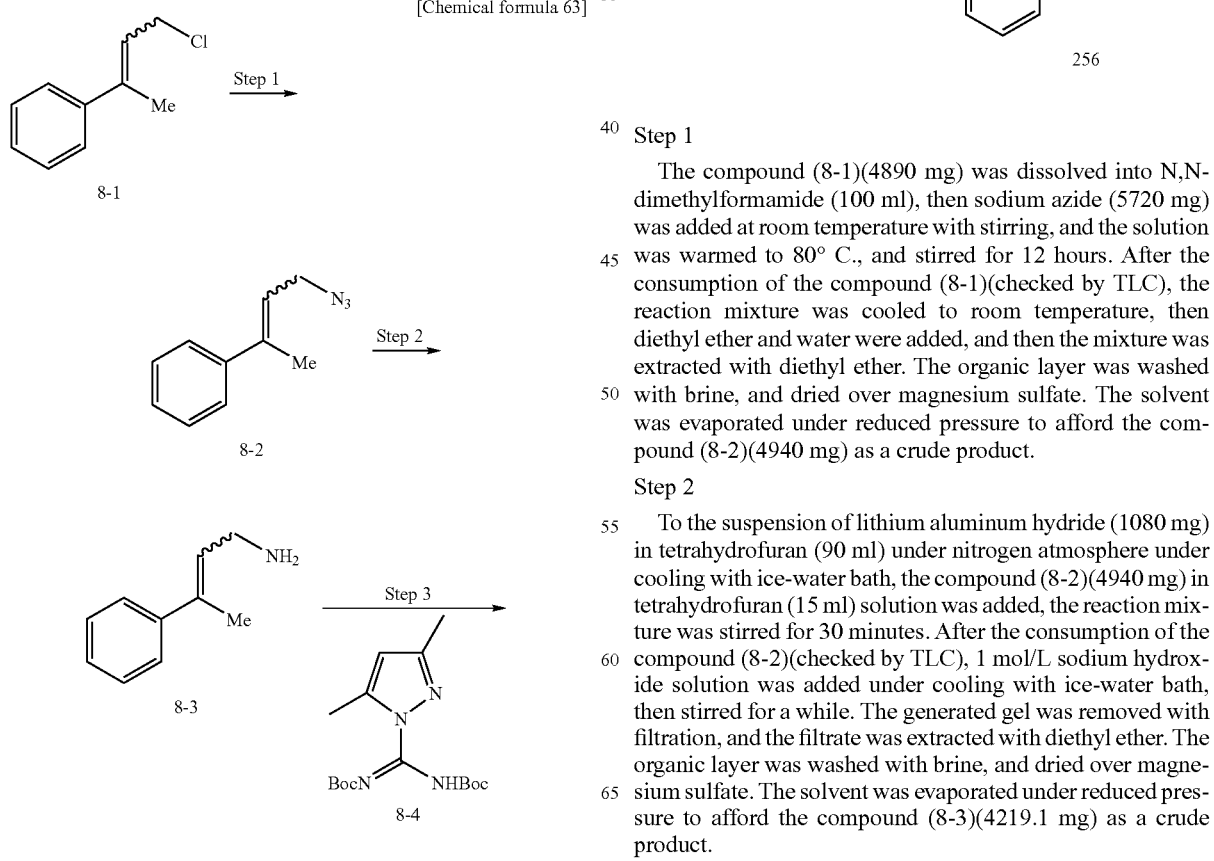

[Chemical formula 63]

Step 1

The compound (8-1)(4890 mg) was dissolved into N,N-dimethylformamide (100 ml), then sodium azide (5720 mg) was added at room temperature with stirring, and the solution was warmed to 80° C., and stirred for 12 hours. After the consumption of the compound (8-1)(checked by TLC), the reaction mixture was cooled to room temperature, then diethyl ether and water were added, and then the mixture was extracted with diethyl ether. The organic layer was washed with brine, and dried over magnesium sulfate. The solvent was evaporated under reduced pressure to afford the compound (8-2)(4940 mg) as a crude product.

Step 2

To the suspension of lithium aluminum hydride (1080 mg) in tetrahydrofuran (90 ml) under nitrogen atmosphere under cooling with ice-water bath, the compound (8-2)(4940 mg) in tetrahydrofuran (15 ml) solution was added, the reaction mixture was stirred for 30 minutes. After the consumption of the compound (8-2)(checked by TLC), 1 mol/L sodium hydroxide solution was added under cooling with ice-water bath, then stirred for a while. The generated gel was removed with filtration, and the filtrate was extracted with diethyl ether. The organic layer was washed with brine, and dried over magnesium sulfate. The solvent was evaporated under reduced pressure to afford the compound (8-3)(4219.1 mg) as a crude product.

Step 3

The compound (8-3)(800 mg) was dissolved into acetonitrile (16 ml), the compound (8-4)(1840 mg) was added with stirring at room temperature, and stirred for 13 hours. After the consumption of the compound (8-3)(checked by TLC), the reaction solvent was evaporated under reduced pressure, the obtained residue was purified by silica gel column chromatography to afford the compound (8-5)(1550.7 mg).

8-5-(Z): $^1$H-NMR(CDCl$_3$, 270 MHz): 1.49 (18H, s), 2.06 (3H, d, J=1.4 Hz), 3.91-4.00 (2H, m), 5.54 (1H, td, 7.1, 1.4 Hz), 7.12-7.41 (5H, m), 8.17-8.25 (1H, m), 11.47 (1H, s)

8-5-(E): $^1$H-NMR(CDCl$_3$, 270 MHz): 1.49 (9H, s), 1.52 (9H,s), 2.09 (3H, d, J=1.5 Hz), 4.24 (2H, dd, J=6.6, 5.3 Hz), 5.80 (1H, td, J=6.6, 1.5 Hz), 7.21-7.48 (5H, m), 8.28-8.38 (1H, m), 11.51 (1H, s)

Step 4

The compound (8-5)(474.1 mg) was dissolved into trifluoroacetic acid (4.5 ml) under cooling with ice-water bath, then warmed to room temperature, and stirred for 4 hours. After the consumption of the compound (8-5)(checked by NMR), the reaction mixture was poured into floating ice—1 mol/L sodium hydroxide solution to be neutralized, then the mixture was extracted with ethyl acetate. The organic layer was washed with brine, and dried over magnesium sulfate. The solvent was evaporated under reduced pressure to afford the compound (8-6)(326.4 mg) as a crude product, Step 5

The compound (8-6)(326.4 mg) was dissolved into 1,4-dioxane (2.4 ml), sodium hydroxide (195 mg) and water (1.2 ml) were added successively, then di-t-butyl dicarbonate (0.84 ml) was added under cooling with ice-water bath. The reaction mixture was warmed to room temperature, and stirred for 15 hours, then the consumption of the compound (8-6) was checked by LC-MS. After added water to the reaction mixture, the mixture was extracted with ethyl acetate. The organic layer was washed with brine, and dried over magnesium sulfate. The solvent was evaporated under reduced pressure, and the obtained residue was purified by silica gel column chromatography to afford the compound (8-7)(113.6 mg).

$^1$H-NMR(CDCl$_3$, 400 MHz): 1.46 (9H, s), 1.51 (9H, s), 1.64 (3H, s), 2.06 (1H, ddd, J=13.4, 11.4, 5.0 Hz), 2.27 (1H, dt, J=13.4, 4.6 Hz), 3.15 (1H, ddd, J=12.9, 11.3, 4.6 Hz), 3,70 (1H, dt, J=12.9, 4.7 Hz), 7.23-7.29 (1H, m), 7.33-7.38 (4H, m)

Step 6

The compound (8-7)(110 mg) was dissolved into 4 mol/L hydrochloric acid-1,4-dioxane solution (1 ml) under cooling ice-water bath, the mixture was warmed to room temperature, and stirred for 2 days, then the consumption of the compound (8-7) was checked by LC-MS, and diethyl ether and water were added at room temperature. After separation of diethyl ether layer, water layer was evaporated under reduced pressure. To the obtained residue, methanol was added, then the generated crystal was filtered. The methanol in the filtrate was evaporated under reduced pressure to afford the compound (256)(69 mg).

$^1$H-NMR(DMSO-d$_6$, 400 MHz): 1.57 (3H, s), 1.87-1.96 (1H, m), 2.30 (1H, dt, J=13.6, 3.8 Hz), 2.60 (1H, td, J=12.0, 3.7 Hz), 3.25 (1H, ddd, J=12.8, 8.2, 4.4 Hz), 6.93 (2H,s), 7.27-7.44 (5H, m), 7.94 (1H, s), 8.63 (1H,s)

Reference Example 9

The Synthesis of Compound 24

[Chemical formula 64]

Step 1

The compound (9-1)(0.39 g) was dissolved into chloroform (20 ml), iodine (1.53 g), potassium thiocyanate (1.25 g), catalytic amount of tetrabutylammonium chloride, and water (1 ml) were added at room temperature, then stirred for 15 hours. To the reaction mixture, 10% thiosodium sulfate solution and water were added, and the mixture was extracted with dichloromethane. The organic layer was dried over anhydrous sodium sulfate, the solvent was evaporated under reduced pressure. The obtained residue was purified by silica gel column chromatography to afford the compound (9-2) (0.56 g).

$^1$H-NMR(CDCl$_3$): 1.95(3H, s), 3.62(2H, s), 7.30-7.40(4H, m).

Step 2

To a solution of the compound (9-2)(0.56 g) in tetrahydrofuran (10 ml), t-butylamine (0.24 g) was added and stirred at room temperature for 18 hours. The reaction solvent was evaporated under reduced pressure, then the obtained residue was purified by silica gel column chromatography to afford the compound (9-3)(190 mg).

$^1$H-NMR(CDCl3): 1.43(9H, s), 1.56(3H, s), 3.27(1H, d, J=10.6 Hz), 3.36(1H, d, J=10.6 Hz), 7.28(2H, d, J=8.2 Hz), 7.43(2H, d, J=8.2 Hz).

Step 3

To the compound (9-3)(190 mg), conc. hydrochloric acid (3 ml) was added, then stirred at 100° C. for 3 hours. To the reaction mixture, 6 mol/L sodium hydroxide was added to neutralize, the mixture was extracted with dichloromethane. The organic layer was dried with anhydrous sodium sulfate, and the solvent was evaporated under reduced pressure. The obtained residue was purified by silica gel column chromatography, then crystallized from dichloromethane/n-hexane to afford the compound (24)(110 mg).

¹H-NMR(CDCl₃): 1.62(3H, s), 3.47(1H, d, J=10.6 Hz), 3.52(1H, d, J=10.6 Hz), 4.59(2H, br), 7.29(2H, d, J=8.6 Hz), 7.39(2H, d, J=8.6 Hz).

Reference Example 10

The Synthesis of Compound 48

[Chemical formula 65]

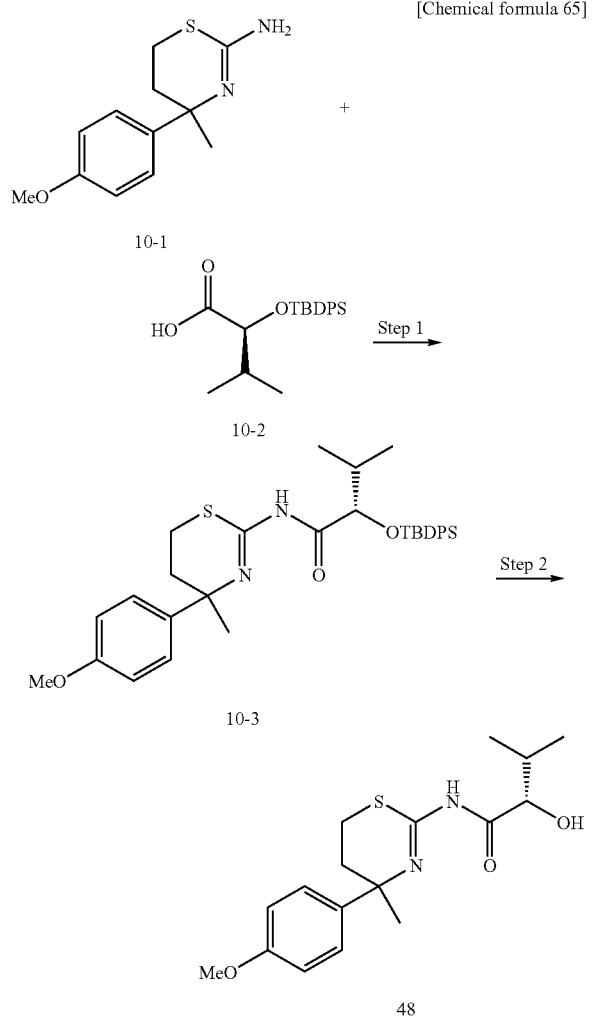

Step 1

The compound (10-1)(79.6 mg) and (10-2)(120 mg) were dissolved into N,N-dimethylformamide (3 ml), then 1-hydroxybenzotriazole (54.6 mg) and N,N'-diisopropylcarbodiimide (0.063 ml) were added, then the reaction mixture was stirred overnight at room temperature. Then after the consumption of the compound (10-1), water was added, and the mixture was extracted with ethyl acetate. The organic layer was washed with brine, and dried over magnesium sulfate, and the solvent was evaporated under reduced pressure. The obtained residue was purified by silica gel column chromatography to afford the compound (10-3)(110.2 mg) as a crude product of diastereomer.

¹H-NMR(CDCl₃): 0.78-1.00 (6H, m), 1.14 (9/2H, s), 1.16 (9/2H, s) 1.52 (3/2H, s), 1.54 (3/2H, s) 1.86-2.28 (3H, m), 2.56-2.89 (2H, m), 3.80 (3/2H, s), 3.81 (3/2H, s) 4.04-4.14 (1H, m), 6.80-6.91 (2H, 7.08-7.22 (2H, m), 7.30-7.51 (6H, m), 7.61-7.76 (4H, m)

Step 2

The compound (10-3)(100 mg) was dissolved into tetrahydrofuran (3 ml) under nitrogen atmosphere, then 1 mol/L tetrabutylammonium fluoride in tetrahydrofuran (0.18 ml) was added at 0° C. with stirring, then the reaction mixture was stirred at 0° C. for 5 minutes. After the consumption of the compound (10-3), water was added, and the mixture was extracted with ethyl acetate. The organic layer was washed with brine, and dried over magnesium sulfate, then the solvent was evaporated under reduced pressure. The obtained residue was purified by silica gel column chromatography to afford the compound (48)(40.7 mg) as a mixture of diastereomers.

¹H-NMR(CDCl₃): 0.80-0.90 (3H, m) 1.01-1.12(3H, m) 1.70 (3H, m), 2.02-2.31(2H, m) 2.39--2.55 (1H, m), 2.61-2.90 (2H,) 3.53-3.70 (1H, m) 3.81 (3H, m), 3.96-4.08(1H, m) 6.87-6.96 (2H, m), 7.13-7.22 (2H, m)

Reference Example 11

The Synthesis of Compound 707

[Chemical formula 66]

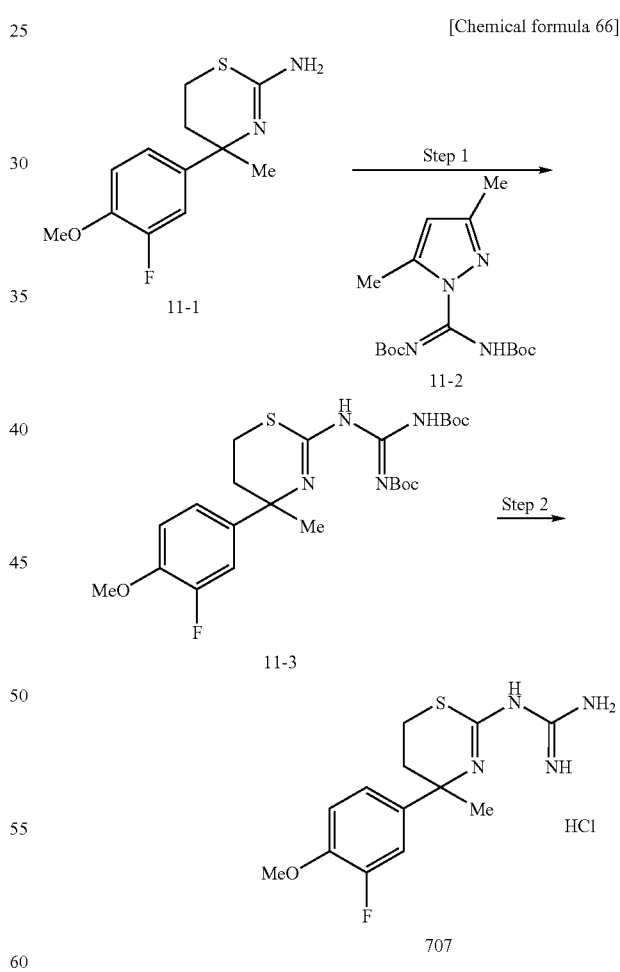

Step 1

The compound (11-1)(150 mg) was dissolved into acetonitrile (5 ml), then the compound (11-2)(219.6 mg) was added at room temperature with stirring, and then the reaction mixture was warmed to 60° C., and stirred for 25 hours. The compound (11-1) was remained (checked by TLC). The reaction solvent was evaporated under reduced pressure, then the obtained residue was purified by silica gel column chromatography to afford the compound (11-1)(211.4 mg). $^1$H-NMR (CDCl$_3$, 400 MHz): 1.46 (9H, s), 1.50 (9H, s), 1.57 (3H, s), 1.90 (1H, ddd, J=13.7, 10.0, 3.8 Hz) 2.11 (1H, ddd, J=13.7, 6.5, 3.7 Hz) 2.68-2.76 (1H, m), 2.86-2.93 (1H, m), 3.88 (3H, s), 6.91 (1H, t, J=8.6 Hz) 6.99-7.03 (1H,), 7.06 (1H, dd, J=13.0, 2.2 Hz), 10.14 (1H, s), 13.93 (1H, s)

Step 2

The compound (11-3)(210 mg) was dissolved into 4 mol/L hydrochloric acid in 1,4-dioxane (4 ml) under cooling with ice-water bath, then the mixture was warmed to room temperature and stirred for 67 hours. After the consumption of the compound (11-3)(checked by LC/MS), the reaction solvent was evaporated under reduced pressure. The obtained residue was crystallized from methanol-diethyl ether, and crystal was collected by filtration and washed with diethyl ether to afford compound (707)(140.2 mg).

$^1$H-NMR(DMSO-d$_6$, 400 MHz): 1.56 (3H, s), 1.90-2.01 (1H, m), 2.43-2.62 (2H, m), 2.95-3.03 (1H,), 3.84 (3H, s), 7.10-7.27 (3H, m), 7.76 (3H, br s), 8.26 (1H, br s), 9.42 (1H, s)

Reference Example 12

The Synthesis of Compound 845

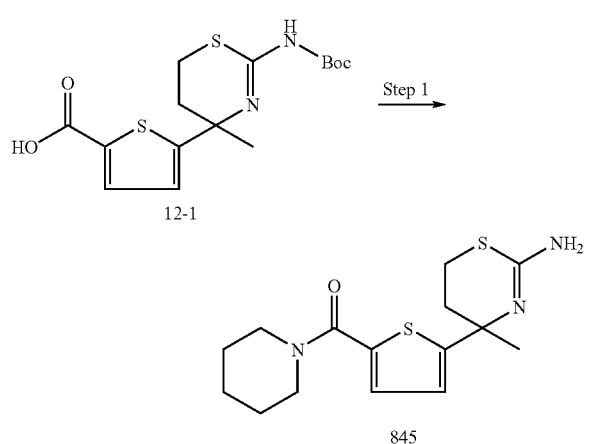

Step 1

The compound (12-1)(50 mg) and piperidine (17,9 mg) were dissolved into N,N-dimethylformamide (2 ml), then O-(7-azabenzotriazo-1-yl)-1,1,3,3-tetramethyluronium-hexafluorophosphate (79.8 mg) was added, and then the mixture was stirred at room temperature for 40 hours. After the consumption of the compound (12-1), the solvent was evaporated under reduced pressure with heating. To the obtained residue, saturated sodium hydrogencarbonate solution was added, and extracted with ethyl acetate. The organic layer was washed with brine, and dried over magnesium sulfate, then the solvent was evaporated under reduced pressure. The obtained residue was purified by silica gel column chromatography to afford the compound (845)(30.7 mg).

$^1$H-NMR(CDCl$_3$): 1.60 (3H, s), 1.51-1.82 (6H, m), 1.87-1.98 (1H, m), 2.09-2.19(1H, m), 2.91-2.97 (2H, m), 3.64-3.68 (4H,), 6.73 (1H, d, J=4.05 Hz), 7.14(1H, d, J=4.05 Hz)

Reference Example 13

The Synthesis of Compound 1262

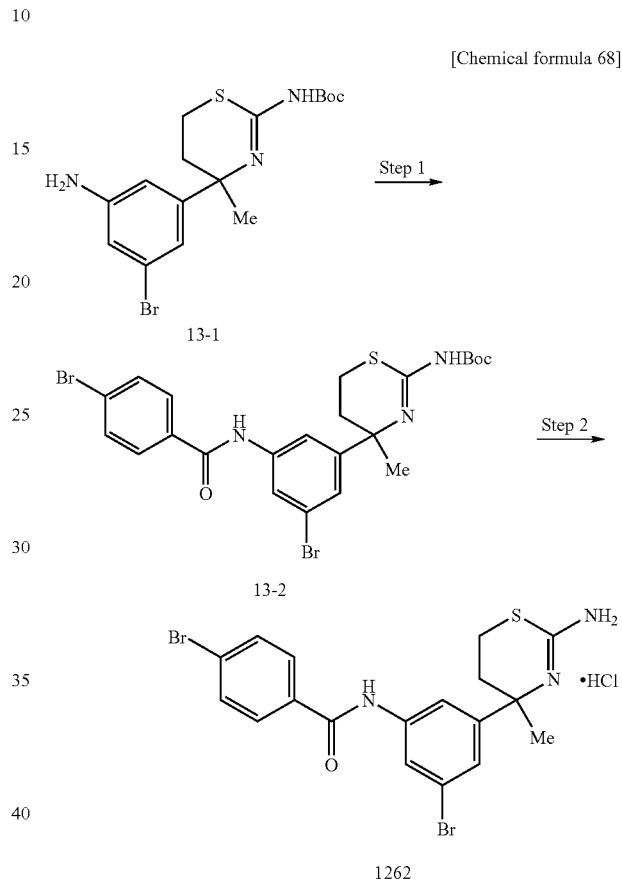

Step 1

The compound (13-1)(50.0 mg) was dissolved into tetrahydrofuran (1 ml) under nitrogen atmosphere, then triethylamine (19 μl), and 4-bromobenzoyl chloride (30.1 mg) were added under cooling with ice-water bath, and stirred for 40 minutes. The reaction solvent was evaporated under reduced pressure, and then the obtained residue was dissolved into ethyl acetate. The solution was washed with saturated sodium hydrogencarbonate solution, and dried over magnesium sulfate, and then the solvent was evaporated under reduced pressure. The generated crystal was collected by filtration to afford the compound (13-2)(57.2 mg).

$^1$H-NMR(CDCl$_3$): 1.48(9H, s), 1.68(3H, s), 2.08(1H, m), 2.44(1H, m), 2.65(1H, m), 2.76(1H, m), 7.18(1H, s), 7.32 (1H, s), 7.64(2H, d, J=8.2 Hz), 7.78(2H, d, J=8.2 Hz), 8.15 (1H, s), 8.25(1H, br)

Step 2

The compound (13-2)(62.3 mg) was dissolved into 4 mol/L hydrochloric acid-1,4-dioxane and stirred for 24 hours. The reaction solvent was evaporated under reduced pressure. The obtained residue was crystallized from methanol/diethyl ether to afford the compound (1262)(44.7 mg).

¹H-NMR(DMSO-d₆): 1.67(3H, s), 2.10(1H, m), 2.50-2.61 (3H, m), 7.33(1H, s), 7.74(1H, s), 7.77(2H, d, J=8,6 Hz), 7.91(2H, d, J=8.6 Hz), 8.08(1H, s), 10.6(1H, s)

Reference Example 14

The Synthesis of Compound 753

[Chemical formula 69]

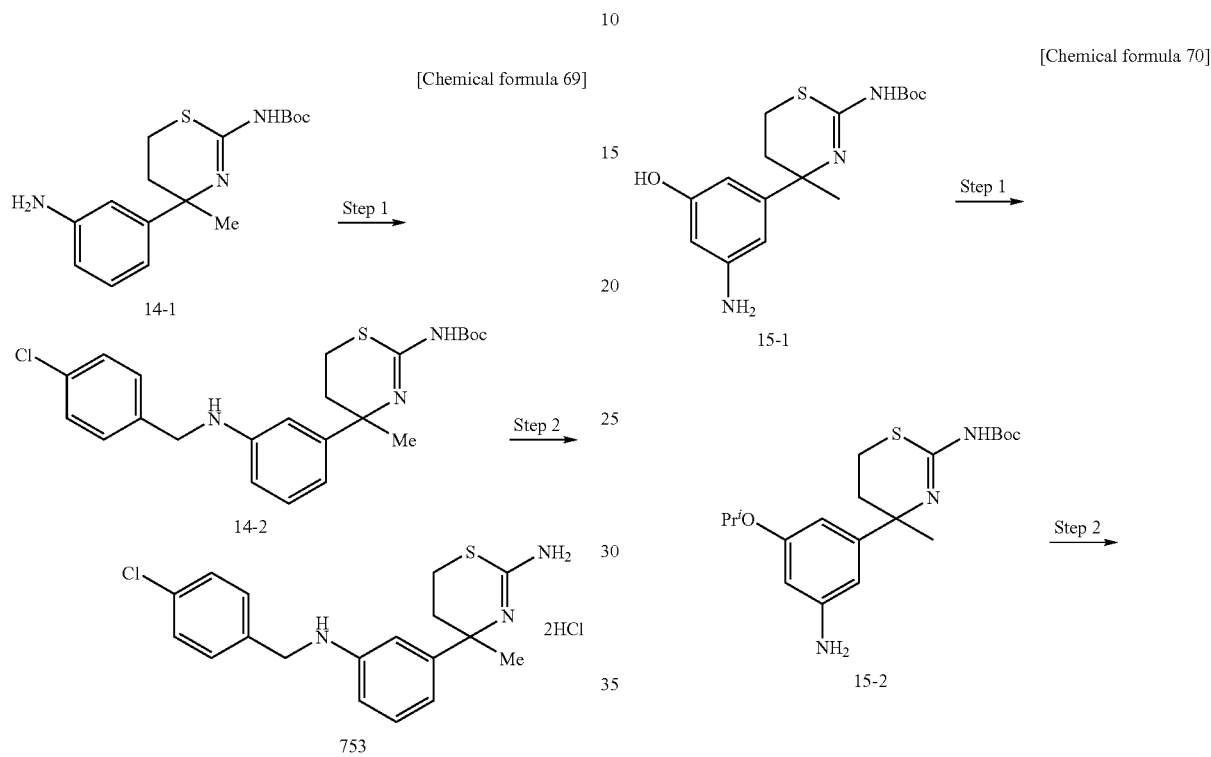

Step 1

The compound (14-1)(46 mg) was dissolved into dichloromethane (2 ml), then 4-chlorobenzaldehyde (20 mg) and acetic acid (17 mg) was added at room temperature, and then stirred for 20 minutes, and then sodium triacetoxyborohydride (45 mg) was added under cooling with ice-water bath. The mixture was stirred at room temperature for 14 hours, and then water was added and extracted with dichloromethane. The organic layer was dried over sodium sulfate, and then the solvent was evaporated under reduced pressure. The obtained residue was purified by silica gel column chromatography to afford the compound (14-2)(52 mg).

¹H-NMR(CDCl₃): 1.50(9H, s), 1.64(3H, s), 2.02-2.10(1H, m), 2.40(1H, dt, J=14.0 4.1 Hz), 2.62-2.74(2H, m), 4.30(2H, s), 6.49(1H, ddd, J=7.8, 2.0, 0.8 Hz), 6.52(1H, t, J=2.0 Hz), 6.60(1H, ddd, J=7.8, 2.0, 0.8 Hz), 7.16(1H, t, J=7.8 Hz), 7.18-7.33(4H, m).

Step 2

To the compound (14-2)(52 mg), 4 mol/L hydrochloric acid in 1,4-dioxane solution (4 ml) was added, then the mixture was stirred at room temperature for 4 days, and then the reaction solvent was evaporated under reduced pressure. The obtained residue was crystallized from methanol/diethyl ether to afford the compound (753)(42 mg), ¹H-NMR(DMSO-d₆): 1.58(3H, s), 2.00(1H, ddd, J=14.3, 11.3, 3.3 Hz),2.49-2.57(2H, m), 3.07(1H, dt, J=12.7, 3.3 Hz), 4.27(2H, s), 6.47(1H, d, J=8.2 Hz), 6.51-6.53(2H, m), 7.08 (1H, t, J=8.2 Hz), 7.37(4H, s), 8.80(2H, br).

Reference Example 15

The Synthesis of Compound 1135

[Chemical formula 70]

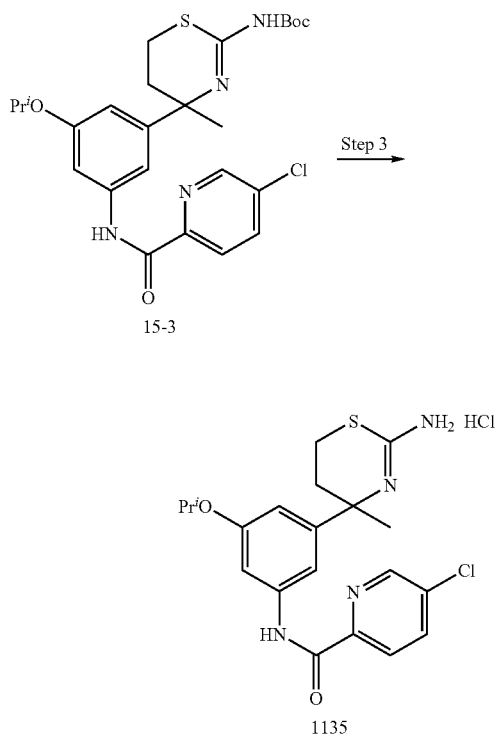

Step 1

To a solution of the compound (15-1)(101 mg), 2-propanol (56 μl), and triphenylphosphine (189 mg) in tetrahydrofuran (2 ml), diethyl azodicarboxylate (2.2 mol/L) in toluene (328 μl) was added dropwise, then stirred for 1 hour at room temperature. After the consumption of the compound (15-1), the solvent was evaporated under reduced pressure. The obtained residue was purified by silica gel column chromatography to afford the compound (15-2)(280 mg) as a mixture of triphenylphosphine oxide and diethyl hydrazodicarboxylate.

Step 2

To the suspension of 5-chloropyridine-2-carboxylic acid (47 mg) in toluene (1 ml), N,N-dimethylformamide (1 drop) and thionylchloride (91 μl) were added and stirred at. 100° C. for 1 hour. The solvent was evaporated under reduced pressure, then the obtained residue was dissolved into tetrahydrofuran (1 ml), and then the mixture of the compound (15-2) (280 mg), and pyridine (194 μl) in tetrahydrofuran (0.5 ml) were added dropwise at 0° C. and stirred for 10 minutes. After the consumption of the compound (15-2), water was added and the mixture was extracted with ethyl acetate. The organic layer, was washed with water, and then the solvent was evaporated under reduced pressure. The obtained residue was purified by silica gel column chromatography to afford the compound (15-3)(68 mg) as a mixture of diethyl hydrazodicarboxylate.

Step 3

To the compound (15-3)(68 mg) as a mixture of diethyl hydrazodicarboxylate, 4 mol/L in hydrochloric acid in 1,4-dioxane solution (1 ml) was added, then the mixture was stirred at room temperature for 16 hours. After the consumption of the compound (44), the reaction solvent was evaporated under reduced pressure. The obtained residue was crystallized from 2-propanol/diethyl ether to afford the compound (1135)(36 mg).

$^1$H-NMR(DMSO-$d_6$): 1.30(3H, d, J=6.4 Hz), 1.31(3H, d, J=6.4 Hz), 1.65(3H, s), 2.04-2.11(1H, m), 2.50-2.64(2H, m), 3.12-3.16(1H, m), 4.61(1H, sep, J=6.4 Hz), 6.66(1H, t, J=2.0 Hz), 7.48(1H, t, J=2.0 Hz), 7.60(1H, t, J=2.0 Hz), 8.16 (1H, dd, J=8.4, 0.8 Hz), 8.22(1H, dd, J=8.4, 2.4 Hz), 8.79(1H, dd, J=2.4, 0.8 Hz), 10.33(1H, s), 10.72(1H, s).

Reference Example 16

The Synthesis of Compound 161

[Chemical formula 71]

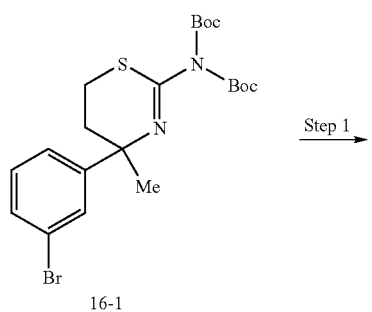

16-1

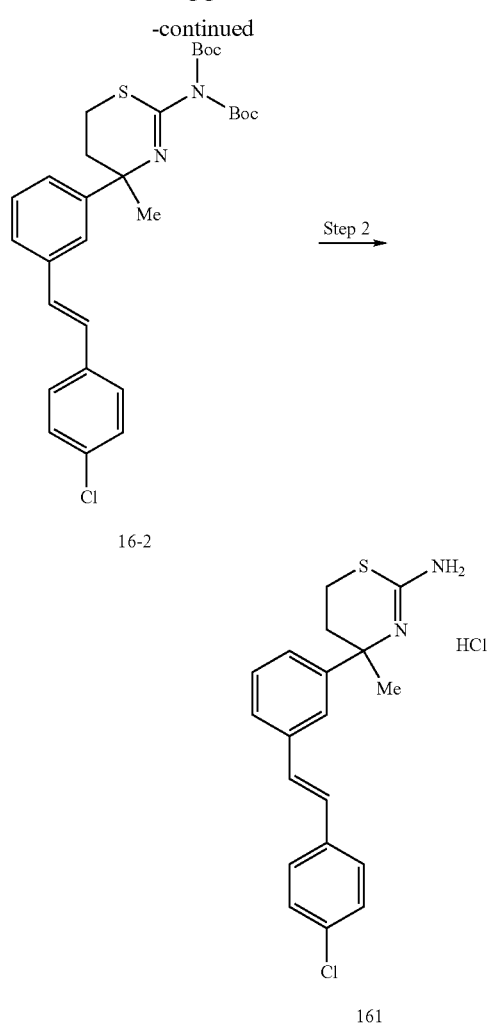

Step 1

The compound (16-1)(200 mg), palladium acetate (4.7 mg), and tri-(o-tolyl)phosphine (12.5 mg), were dissolved into N,N-dimethylformamide (2 ml) under nitrogen atmosphere, then n-butylamine (0.196 ml), and p-chlorostyrene (0.074 ml) were added at room temperature with stirring, then the solution was warmed to 80° C., and stirred for 3 hours. After the consumption of the compound (16-1)(checked by TLC), the reaction mixture was cooled to room temperature, and saturated ammonium chloride solution was added to the mixture. The mixture was extracted with ethyl acetate, the organic layer was washed with water and brine, and dried over magnesium sulfate, and then the solvent was evaporated under reduced pressure. The obtained residue was purified by silica gel column chromatography to afford the compound (16-2)(213.1 mg).

$^1$H-NMR(CDCl$_3$, 400 MHz): 1.54 (18H, s), 1.64 (3H, s), 1.96 (1H, ddd, J=13.7, 9.1, 4.0 Hz) 2.10 (1H, ddd, J=13.7, 8.1, 3.4 Hz) 2.86 (1H, ddd, J=12.3, 9.1, 3.4 Hz), 3.03 (1H, ddd, J=12.3, 8.1, 4.0 Hz), 7.08 (1H, d, J=16.4 Hz) 7.15 (1H, d, J=16.4 Hz), 7.27-7.40 (5H, m) 7.44 (2H, d, J=8.8 Hz), 7.58 (1H, s)

Step 2

The compound (16-2)(213 mg) was dissolved into 4 mol/L, hydrochloric acid in 1,4-dioxane (5 ml) under cooling with ice-water bath, then the mixture was warmed to room temperature and stirred for 63 hours. After the consumption of the compound (16-2)(checked by LC/MS), the reaction mixture was diluted with diethyl ether. The generated crystal was collected by filtration, and washed with diethyl ether to afford the compound (161)(108.6 mg).

$^1$H-NMR(DMSO-$d_6$, 400 MHz): 1.69 (3H, s), 2.08-2.18 (1H, m), 2.56-2.70 (2H, m), 3.13-3.20 (1H, m), 7.23 (1H, d, J=8.0 Hz), 7.31 (1H, d, J=17.0 Hz), 7.35 (1H, d, J=17.0 Hz), 7.45 (2H, d, J=8.6 Hz), 7.46 (1H, t, 7.6 Hz), 7.59 (1H, d, J=2.0 Hz), 7.61-7.64 (1H, m), 7.64 (2H, d, J=8.6 Hz), 8.53-9.50 (2H, br), 10.67 (1H, br s)

Reference Example 17

The Synthesis of Compound 597

[Chemical formula 72]

$^1$H-NMR(DMSO-$d_6$): 1.67(3H, s), 2.08-2.15(1H, m), 2.20 (3H, s), 2.56-2.64(2H, m), 3.14-3.17(1H, m), 3.92(3H, s), 7.37(1H, d, J=8.0 Hz), 7.48(1H, d, J=8.0 Hz), 7.56(1H, s), 7.62(1H, d, J=8.0 Hz).

Reference Example 18

The Synthesis of Compounds 134 and 135

[Chemical formula 73]

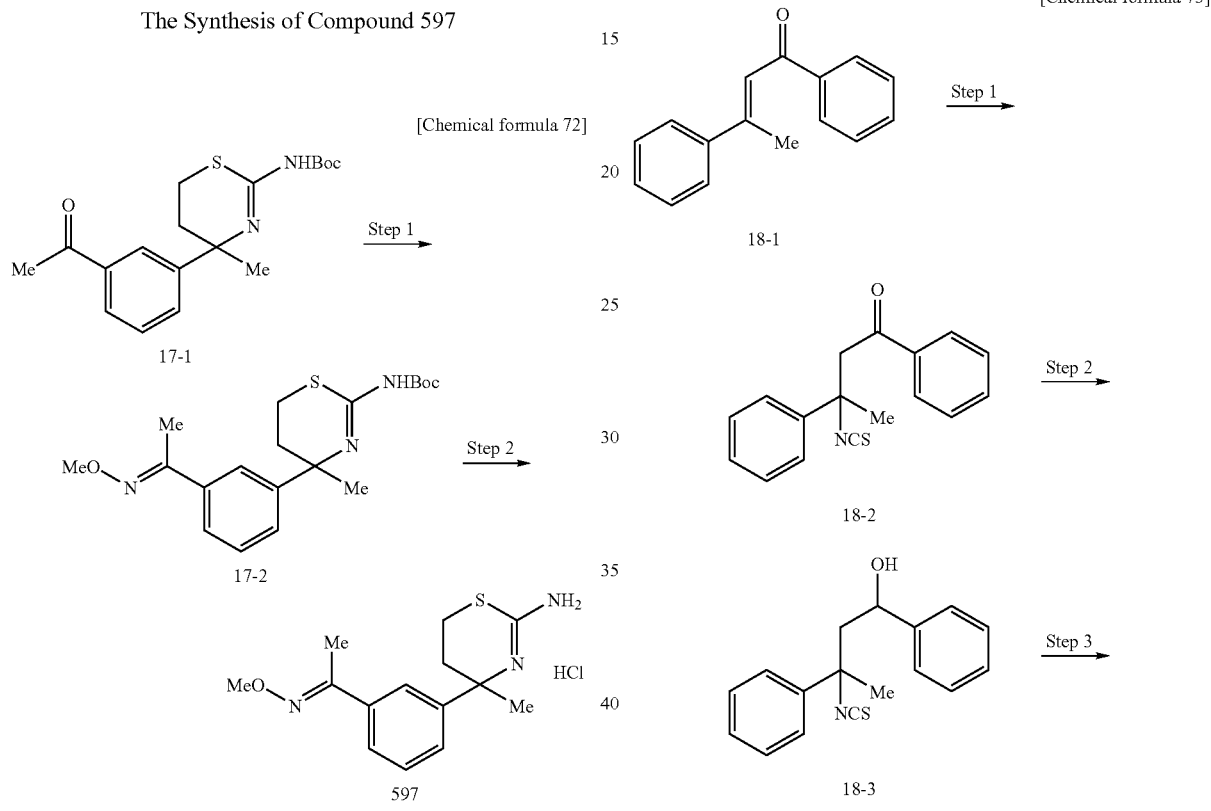

Step 1

The solution of compound (17-1)(135 mg), O-metbxylhydroxylamine hydrochloride (39 mg), and potassium acetate (27 mg) in methanol (3 ml) was stirred at room temperature for 16 hours, then water was added. The mixture was extracted with dichloromethane, the organic layer was dried over anhydrous sodium sulfate, then the solvent was evaporated under reduced pressure. The obtained residue was purified by silica gel column chromatography to afford the compound (17-2)(110 mg).

$^1$H-NMR(CDCl$_3$): 1.51(9H, s), 1.70(3H, s), 2.14(1H, ddd, J=14.4, 11.4, 3.4 Hz), 2.22(3H, s), 2.48(1H, m), 2.65(1H, dt, J=12.6, 11.4 Hz), 2.78(1H, ddd, J=12.6, 5.6, 3.4 Hz), 4.00 (3H, s), 7.30(1H, d, J=7.8 Hz), 7.38(1H, d, J=7.8 Hz), 7.54-7.57(2H, m).

Step 2

To the compound (17-2)(110 mg), 4 mol/L hydrochloric acid in 1,4-dioxane (4.5 ml) solution was added and stirred for 4 days at room temperature, then the reaction solvent was evaporated under reduced pressure. The obtained residue was crystallized from methanol/diethyl ether to afford compound (597)(65 mg).

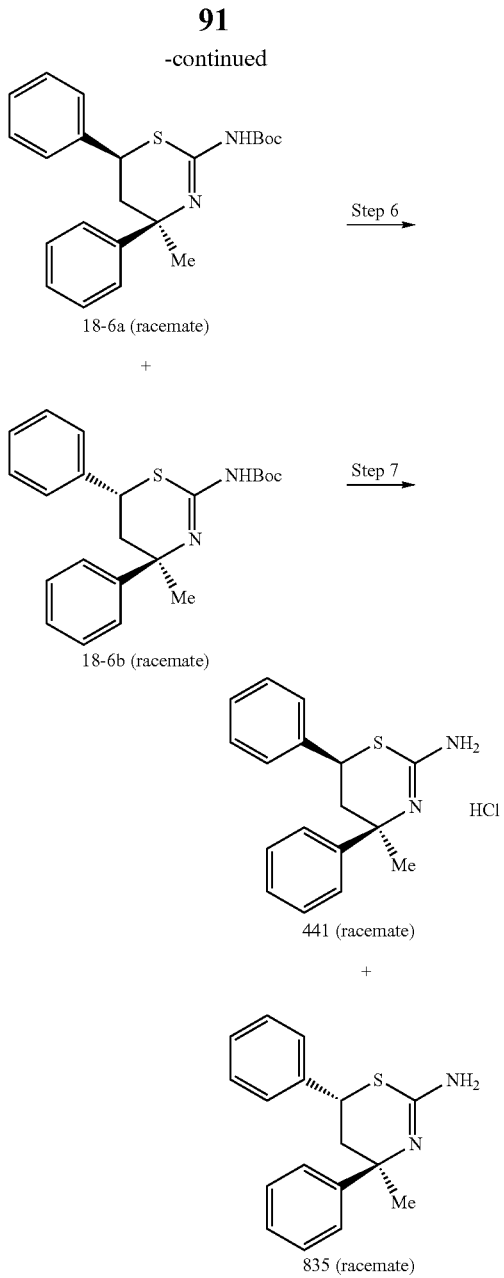

18-6a (racemate)

+

18-6b (racemate)

441 (racemate) · HCl

+

835 (racemate)

Step 1

The compound (18-1) (2020 mg) was dissolved into chloroform (20 ml), and water (4 ml) and sodium thiocyanate (1470 mg) were added to the solution with stirring at room temperature. Sulfuric acid (1.94 ml) was added dropwise to the reaction mixture under cooling with ice-water bath. After the addition was completed, the reaction mixture was warmed to room temperature and then stirred for 345 minutes, then stirred at 60° C. for overnight. Because the compound (18-1) was remained (checked by TLC), the reaction mixture was cooled to room temperature, then sodium thiocyanate (1470 mg), water (5 ml) and sulfuric acid (1.94 ml) were added successively. After the reaction mixture was warmed to 60° C., the mixture was stirred for 1 day. A saturatedسodium bicarbohydrate solution was added to the reaction mixture to be basic condition under cooling with ice-water bath, and then the reaction mixture was extracted with ethyl acetate. The organic layer was washed with brine, then dried over anhydrous magnesium sulfate. The solvent was evaporated under reduced pressure and the obtained residue was subjected to silica gel chromatography to afford the compound (18-2) (968 mg).

$^1$H-NMR(CDCl$_3$, 270 MHz): 1.99 (3H, s), 3.55 (1H, d, J=16.1 Hz), 3.69 (1H, d, J=16.1 Hz), 7.12-7.64 m), 7.82-7.95 (2H, m)

Step 2

The compound (18-2) (842 mg) was dissolved into ethanol (8.4 ml). Sodium dihydrogen phosphate(1600 mg) and sodium borohydride (113.2 mg) in water (2.8 ml) were added to the solution successively under cooling with ice-water bath with stirring, and the mixture was stirred for 30 minutes at the same temperature. After the consumption of the compound (18-2) (checked by TLC), ethyl acetate and water were added to the mixture under cooling with ice-water bath, and then stirred for a few minutes. The reaction mixture was extracted with ethyl acetate. The organic layer was washed with water and brine successively, and dried over anhydrous magnesium sulfate. The solvent was evaporated under reduced pressure to afford the compound (18-3) (904.8 mg) as a crude product.

Step 3

To a stirring solution of the compound (18-3) (900 mg) in toluene (10 ml) was added a solution of thionyl chloride (0.7 ml) in toluene (5 ml) under cooling with ice-water bath, and stirred for 1 hour at the same temperature. After the consumption of the compound (18-3)(checked by TLC), the reaction solution was concentrated under reduced pressure to afford the compound (18-4)(1076.8 mg) as a crude product.

Step 4

The compound (18-4) (1070 mg) was dissolved into ca. 7 mol/L ammonia in methanol (20 ml) at room temperature, then the mixture was stirred for 1 day. After the consumption of the compound (18-4)(checked by TLC), the reaction solution was concentrated under reduced pressure to afford the compound (18-5) (2633 mg) as a crude product.

Step 5

The compound (18-5)(2633 mg) was dissolved into tetrahydrofuran (10 ml), and 4-dimethylaminopyridine (43.2 mg) and di-t-butyl dicarbonate (0.976 ml) were added to the solution successively under cooling with ice-water bath with stirring. The reaction mixture was warmed to room temperature and then stirred for 260 minutes. Because the compound (18-5) was remained (checked by TLC) in the reaction solution, di-t-butyl dicarbonate (0.488 ml) was added to the reaction mixture at room temperature and then stirred at the same temperature for overnight. After, addition of water, the reaction mixture was extracted with ethyl acetate. The organic layer was washed with brine, then dried over anhydrous magnesium sulfate. The solvent was evaporated under reduced pressure and the obtained residue was subjected to silica gel column chromatography to afford the compound (18-6a) (99.6 mg) and the compound (18-6b) (183.2 mg).

18-6a: $^1$H-NMR(CDCl$_3$, 400 MHz): 1.49 (9H, s), 1.80 (3H, s), 2.22 (1H, t, J=13.6 Hz), 2.36 (1H, dd, J=14.2, 3.4 Hz), 4.63 (1H, dd, J=12.6, 3.4 Hz), 7.27-7.47 (10H, m)

18-6b: $^1$H-NMR(CDCl$_3$, 400 MHz): 1.53 (9H, s), 1.72 (3H, s), 2.34 (1H, t, J=13.0 Hz), 2.66 (1H, dd, J=14.0, 2.5 Hz), 3.86 (1H, dd, J=12.4, 2.5 Hz), 7.20-7.45 (10H, m)

Step 6

The compound (18-6a) (99.6 mg) was dissolved into a 4 mol/L hydrogen chloride in 1,4-dioxane solution (4 ml) on ice bath, and the mixture was warmed to room temperature and then stirred for 6 days. After the consumption of the compound (18-6a) (checked by LC-MS), the reaction mixture was concentrated under reduced pressure. The obtained residue was crystallized from dichloromethane-ethyl acetate, and the crystals were collected by filtration and washed with ethyl acetate to afford the compound (441) (52.4 mg).

$^1$H-NMR(DMSO-d$_6$, 400 MHz): 1.83 (3H, s), 2.43 (1H, t, J=13.2 Hz), 2.55 (1H, dd, J=14.0, 2.8 Hz), 5.10 (1H, dd, J=12.4, 2.8 Hz), 7.34-7.48 (6H, m), 7.53-7.57 (4H,

Step 7

The compound (18-6b) (183 mg) was dissolved into a 4 mol/L of hydrogen chloride in 1,4-dioxane solution (8 ml) on ice bath, and the mixture was warmed to room temperature and then stirred for 6 days. Because the compound (18-6b) was remained. (checked by LC-MS), 4 mol/L of hydrogen chloride in 1,4-dioxanesolution (2 ml) was added to the reaction mixture at room temperature, and then the mixture was stirred at 40° C. for overnight. The reaction mixture was concentrated under reduced pressure, a saturated sodium bicarbonate aqueous solution was added to be basic condition, and the reaction mixture was extracted with ethyl acetate. The organic layer was washed with brine, and then dried over anhydrous magnesium sulfate. After the solvent was evaporated under reduced pressure, the obtained residue was subjected to silica gel column chromatography and crystallized from dichloromethane-diisopropyl ether. The crystals were collected by filtration and washed with diisopropyl ether to afford the compound (835) (32,2. mg).

$^1$H-NMR(CDCl$_3$, 400 MHz): 1.64 (3H, s), 1.95 (1H, t, J=13.2 Hz), 2.52 (1H, dd, J=13.8, 3.0 Hz), 3.84 (1H, dd, J=12.6, 3.0 Hz), 4.16-4.76 (2H, br), 7.20-7.39 (10H, m)

Reference Example 19

[Chemical formula 74]

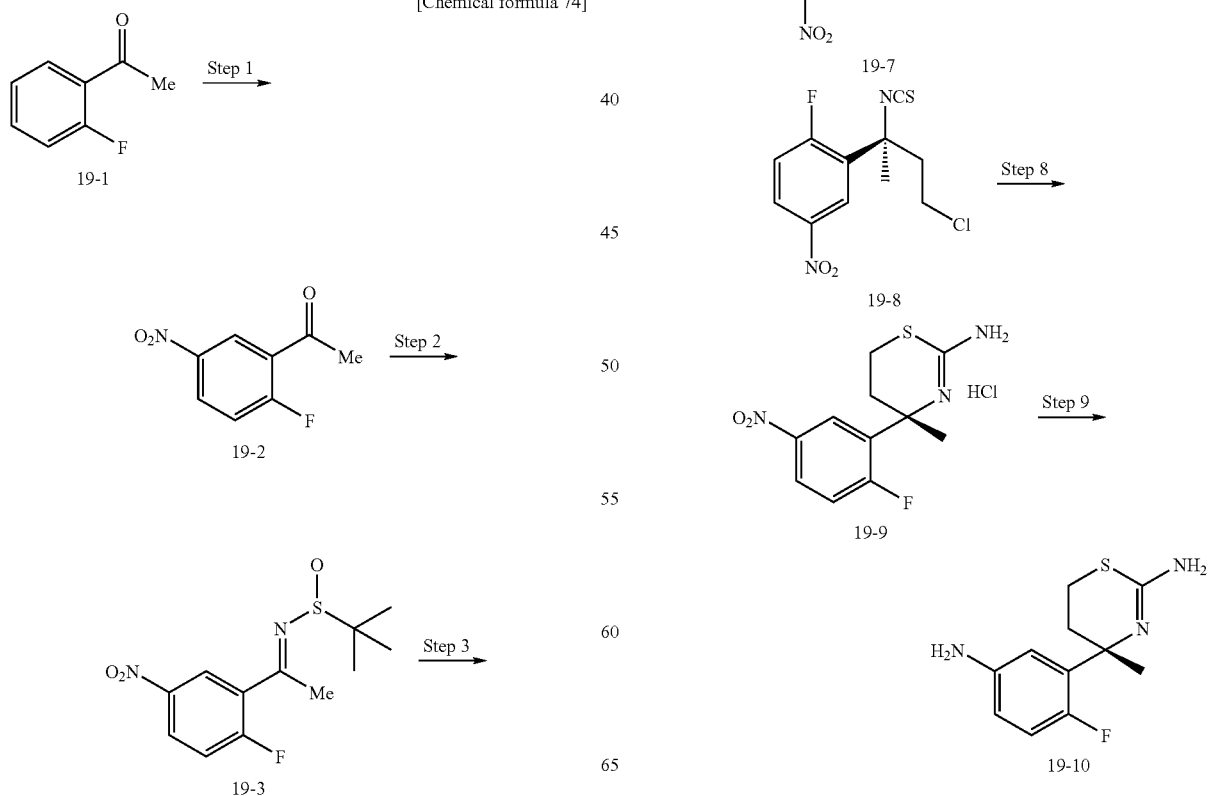

Step 1

After the compound (19-1) was added dropwise to sulfuric acid (279 ml) under cooling on acetonitrile/dry ice bath with stirring, the mixture of fuming nitric acid (42 ml) and sulfuric acid (98 ml) was added dropwise to the mixture. After stirred for 16 minutes, the reaction mixture was gradually added into ice. The precipitated crystals were collected by filtration and dried to afford the compound (19-2) (77.79 g).

$^1$H-NMR (CDCl$_3$) δ: 2.71 (3H, d, J=4.9 Hz), 7.34 (1H, t, J=9.3 Hz), 8.40 (1H, ddd, J=9.3, 6.2, 3.0 Hz), 8.78 (1H, dd, J=6.2, 3.0 Hz).

Step 2

After the mixed solution of the compound (19-2) (73.94 g), (R)-(+)-2-methyl-2-propane sulfinamide (53.82 g) and tetraethyl orthotitanate (230.20 g) in tetrahydrofuran (500 ml) was heated and refluxed for 2.5 hours. The reaction mixture was gradually poured into ice and the precipitated insoluble was removed by filtration. The filtrate was extracted with ethyl acetate, and the organic layer was dried over anhydrous magnesium sulfate. The solvent was evaporated under reduced pressure and the obtained residue was crystallized from ethyl acetate/ n-hexane to afford the compound (19-3) (85.44 g).

$^1$H-NMR. (CDCl$_3$) δ: 1.34 (9H, s), 2.81 (3H, d, J=3.5 Hz), 7.29 (1H, t, J=8.9 Hz), 8.31 (1H, dt, J=8.9, 2.9 Hz), 8.55 (1H, dd, J=6.3, 2.9 Hz).

Step 3

A solution of t-butyl acetate (6.08 g) in tetrahydrofuran (10 ml) was added dropwise to a solution of 2M lithium diisopropylamide in tetrahydrofuran/n-heptane/ethyl benzene (27.9 ml) under cooling on acetone/dry ice bath with stirring. After stirred for 20 minutes, a solution of chlorotitanium triisopropoxide (17.5 ml) in tetrahydrofuran (30 ml) was added dropwise to the mixture. The mixture was stirred for 1 hour and a solution of the compound (19-3) (5.00 g) in tetrahydrofuran (10 ml) was added dropwise to the mixture. After reacted for 1 hour, the mixture was gradually poured into an aqueous solution of ammonium chloride under cooling on ice-water bath with stirring, and the precipitated insoluble was removed by filtration. The filtrate was extracted with ethyl acetate, and the organic layer was dried over anhydrous sodium sulfate, and the solvent was evaporated under reduced pressure. The residue was subjected to silica gel chromatography to afford the compound (19-4) (5.49 g).

$^1$H-NMR (CDCl$_3$) δ: 1.30 (9H, s), 1.35 (9H, s), 1.86 (3H, s), 3.11 (1H, dd, J=16.2, 2.1 Hz), 3.26 (1H, dd, J=16.2, 2.1 Hz), 5.55 (1H, s), 7.18 (1H, dd, J=11.1, 8.9 Hz), 8.18 (1H, ddd, J=8.9, 4.0, 2.9 Hz), 8.53 (1H, dd, J=7.0, 2.9 Hz).

Ration of diastereomers: S:R97/3, HPLC Column: AS-RH, Detection: 254 nm: Column temp.: 25° C., Mobile phase: 40% MeCNaq., Flow rate: 0.5 ml/min.

It is known that stereochemistry of the obtained compound (19-4) is preferentially afforded (S) isomer as described in Literature A, and each of diastereomers can be arbitrarily synthesized by using appropriate metal species or reaction conditions.

Literature A
(1) T. Fujisawa et al., Tetrahedron Lett., 37, 3881-3884 (1996), (2) D. H. Hua et al, Sulfur Reports, vol. 21., pp. 211-239 (1999), (3) Y. Kori ouzo et al., Tetrahedron, 58, 9621-9628 (2002), (4) Yong Qin et al., J. Org. Chem., 71, 1588-1591 (2006)

Step 4

To the compound (19-4) (12.74 g) was added a solution of 4M hydrochloric acid in 1,4-dioxane (50 ml). After the mixture was stirred at 80° C. for 1 hour, diethyl ether (50 ml) was added to the mixture. The precipitated crystals were collected by filtration, and dried to afford the compound (19-5) (7.67 g), $^1$H-NMR (DMSO-d$_6$) δ: 1.76 (3H, s), 3.25 (2H, s), 7.62 (1H, dd, J=11.4, 9.4 Hz), Step 5

To a stirred solution of the compound (19-5) (141.32 g) in tetrahydrofuran (707 ml) was added dropwise a solution of 1M boran tetrahydrofuran complex in tetrahydrofuran (2029 ml) under cooling on ice-water bath. After reacted for 3 hours 6 minutes, the mixture was added into the mixture of sodium bicarbonate (511 g), ice (1500 g) and ethyl acetate (3000 ml) at room temperature with stirring. The mixture was extracted with ethyl acetate, and the organic layer was dried over anhydrous magnesium sulfate, and the solvent was evaporated under reduced pressure to afford the compound (19-6) (115.46 g) as a crude product.

Step 6

To the compound (19-6) (3.76 g) obtained in Step 5 was added toluene (25 ml) and water (12.5 ml), Potassium carbonate (7.97 g) and thiophosgene (2.85 g) was added to the stirring mixture subsequently under cooling on ice-water bath After reacted for 3 hours, water was added to the mixture and extracted with toluene, and the organic layer was dried over anhydrous magnesium sulfate, and a part of the solvent was removed under reduced pressure to afford the compound (19-7) as a crude product.

Step 7

To a stirred solution of the compound (19-7) obtained in Step 6 in toluene (17.4 ml) was added thionyl chloride (6.67 g) and N,N-dimethylformamide (0.128 ml) at room temperature. After stirred for 2 hours at 80° C., water was added to the mixture and extracted with toluene. Solvent was evaporated under reduced pressure to afford the compound (19-8) (4.03 g).

Step 8

To a stirred solution of the compound (19-8) (4.03 g) from Step 7 in tetrahydrofuran (23.8 ml) was added,28% aqueous ammonia (23.8 ml) on ice bath, and the mixture was stirred at room temperature for 3 days. The solvent of the reaction mixture was evaporated under reduced pressure, and then ethyl acetate was added. Hydrochloric acid (6 ml) was added to the stirred mixture under cooling with ice-water bath, and the precipitated crystals were washed with ethyl acetate and water, then dried to afford the compound (19-9) (2.14 g).

$^1$H-NMR. (DMSO-d$_6$) δ: 1.76 (3H, s), 2.13-2.24 (1H, m), 2.68-2.74 (2H, m), 3.19-3.25 (1H, m), 7.63 (1H, dd, 11.4, 8.9 Hz), 8.07 (1H, dd, J=7.0, 3.5 Hz), 8.36 (1H, dt, J=8.9, 3.5 Hz), 11.22 (1H, s).

Step 9

The compound (19-9) (100 mg) was dissolved into methanol (2 ml), 10% palladium carbon powder (50 mg) was added and then stirred at room temperature for 18 hours. The insoluble was removed by filtration, the solvent of the filtrate was removed under reduced pressure. Sodium carbonate and water were added to the mixture. The mixture was extracted with ethyl acetate, and the organic layer was dried over anhydrous sodium sulfate, and a solvent was evaporated under reduced pressure to afford the compound (19-10) (68 mg).

Reference Example 20

[Chemical formula 75]

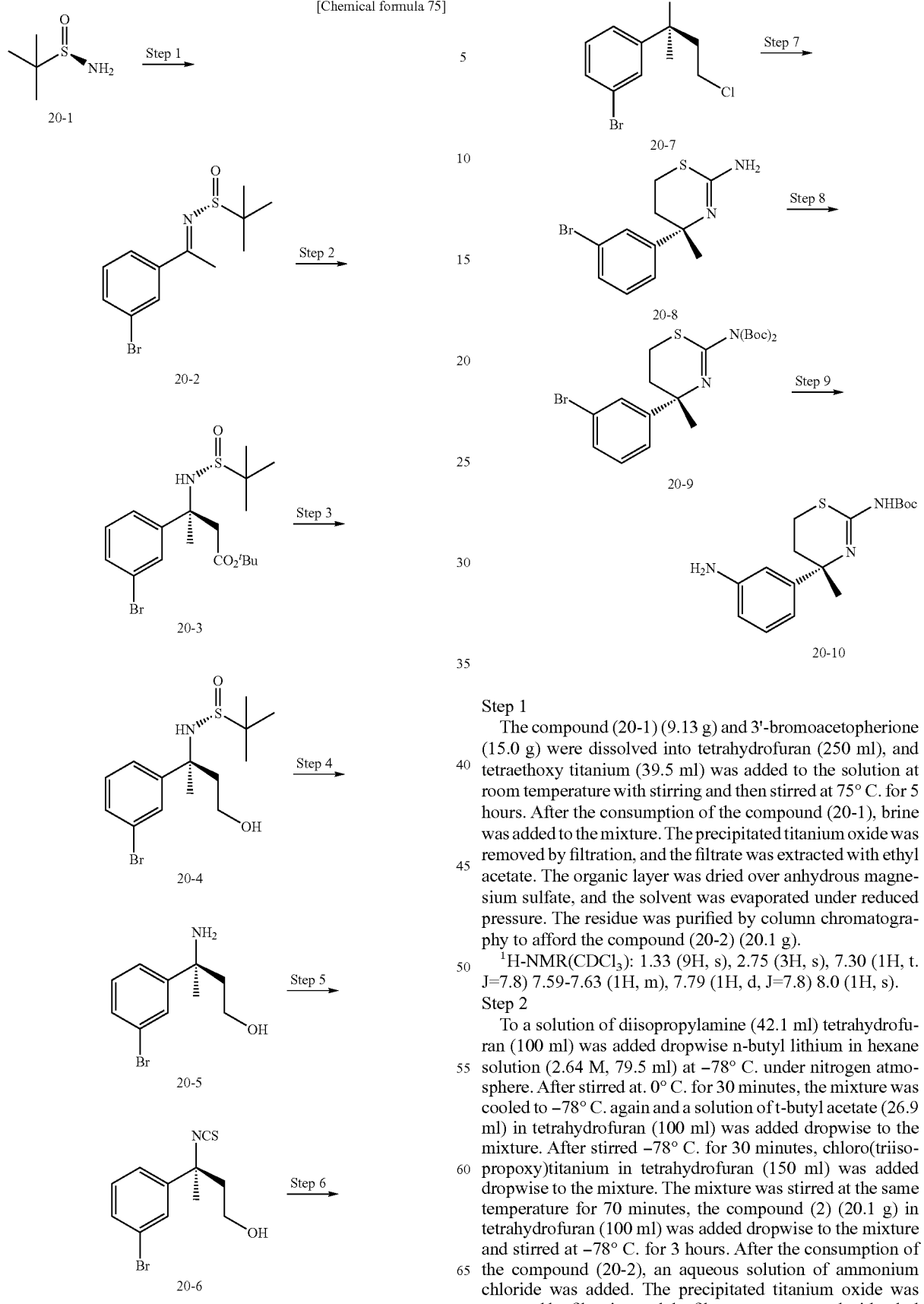

Step 1

The compound (20-1) (9.13 g) and 3'-bromoacetopherione (15.0 g) were dissolved into tetrahydrofuran (250 ml), and tetraethoxy titanium (39.5 ml) was added to the solution at room temperature with stirring and then stirred at 75° C. for 5 hours. After the consumption of the compound (20-1), brine was added to the mixture. The precipitated titanium oxide was removed by filtration, and the filtrate was extracted with ethyl acetate. The organic layer was dried over anhydrous magnesium sulfate, and the solvent was evaporated under reduced pressure. The residue was purified by column chromatography to afford the compound (20-2) (20.1 g).

$^1$H-NMR(CDCl$_3$): 1.33 (9H, s), 2.75 (3H, s), 7.30 (1H, t. J=7.8) 7.59-7.63 (1H, m), 7.79 (1H, d, J=7.8) 8.0 (1H, s).

Step 2

To a solution of diisopropylamine (42.1 ml) tetrahydrofuran (100 ml) was added dropwise n-butyl lithium in hexane solution (2.64 M, 79.5 ml) at −78° C. under nitrogen atmosphere. After stirred at. 0° C. for 30 minutes, the mixture was cooled to −78° C. again and a solution of t-butyl acetate (26.9 ml) in tetrahydrofuran (100 ml) was added dropwise to the mixture. After stirred −78° C. for 30 minutes, chloro(triisopropoxy)titanium in tetrahydrofuran (150 ml) was added dropwise to the mixture. The mixture was stirred at the same temperature for 70 minutes, the compound (2) (20.1 g) in tetrahydrofuran (100 ml) was added dropwise to the mixture and stirred at −78° C. for 3 hours. After the consumption of the compound (20-2), an aqueous solution of ammonium chloride was added. The precipitated titanium oxide was removed by filtration and the filtrate was extracted with ethyl acetate. The organic layer was washed with brine, then dried over anhydrous magnesium sulfate. The solvent was removed under reduced pressure to afford the compound (20-3) as a crude product (26.4 g).

Step 3

The crude product of the compound (20-3) (26.4 g) was dissolved into toluene (80 ml) and added dropwise to a 1.0 M diisobuty aluminum hydride in toluene (253 ml) with stirring at 0° C. The reaction mixture was stirred at room temperature for 1.5 hours. After the consumption of the compound (20-3), a 1M hydrochloric acid aqueous solution was added. The mixture was extracted with ethyl acetate, the organic layer was washed with brine, then dried over anhydrous magnesium sulfate, and the solvent was evaporated under reduced pressure. The residue was purified by crystallization to afford the compound (20-4) (18.1 g), $^1$H-NMR(CDCl$_3$):1.28(9H,s,),1.71(3H,s),2.19-2.24(2H, m),3.27-3.32(1H,m),3.54-3.66(1H, m), 3.87-3.97 (1H, m), 5.10-5.11(1H, m), 7.22 (1H, t, 7.32-7.41 (2H, m), 7.56-7.58 (1H, m)

Step 4

The compound (20-4) (18.1 g) was dissolved into methanol (130 ml) and a 10% hydrochloric acid-methanol solution (130 ml) was added to the solution with stirring at room temperature. Then, the reaction mixture was stirred at room temperature for 4 hours. After consumption of the compound (20-4), a 1M hydrochloric acid aqueous solution was added. The mixture was washed with ethyl acetate, the aqueous layer was neutralized with a 2M sodium hydroxide aqueous solution and extracted with ethyl acetate. The organic layer was dried over anhydrous magnesium sulfate, and the solvent was evaporated under reduced pressure to afford the crude product of the compound (20-5) (14.1 g).

Step 5

The crude product of the compound (20-5) (32.8 g) and potassium carbonate (37.1 g) were dissolved into a mixed solvent of toluene (450 ml) and water (225 ml), and thiophosgene (15.3 ml) was added dropwise to the mixture with stirring at 0° C. The reaction mixture was stirred at 0° C. for 1 hour. After consumption of the compound (20-5), water was added. After the mixture was extracted with ethyl acetate, the organic layer was washed with brine, and dried over anhydrous magnesium sulfate. The solvent was evaporated under reduced pressure to afford the crude product of the compound (20-6) (38.4 g).

Step 6

The crude product of the compound (20-6) (38.4 g) was dissolved into toluene (384 ml), and thionyl chloride (29.4 ml) and N,N-dimethylformamide (1.04 ml) were added dropwise to the solution with stirring at 0° C. The reaction mixture was stirred at 80° C. for 5 hours. After consumption of the compound (6), the solvent was evaporated under reduced pressure to afford the crude product of the compound (20-7) (40.9 g).

Step 7

The crude product of the compound (20-7) (40.9 g) was dissolved into tetrahydrofuran (250 ml), and 25% aqueous ammonia (250 ml) was added dropwise to the solution at 0° C. The reaction mixture was stirred at room temperature for 16 hours. After consumption of the compound (6), a saturated solution of sodium hydrogencarbonate was added. The organic layer was separated and the aqueous solution was extracted with dichloromethane. The combined organic layer was dried over anhydrous magnesium sulfate, and the solvent was evaporated under reduced pressure to afford the crude product of the compound (20-8) (38.3 g).

Step 8

The crude product of the compound (20-8) (38.3 g) was dissolved into tetrahydrofuran (383 ml), and di-t-butyl dicarbonate (61.5 g) and N,N-dimethylaminopyridine (1.64 g) were added to the solution, and the mixture was stirred at room temperature for 72 hours. After consumption of the compound (20-8), the solvent was evaporated under reduced pressure and the residue was subjected to silica gel chromatography to afford the compound (20-9) (45.3 g).

$^1$H-NMR(CDCl$_3$): 1.54 (9H, s,), 1.57 (3H, s), 1.96 (2H, t, 2.80-2.92(1H, m), 3.00-3.13 (1H, m), 7.21 (1H, t, J=8.1) 7.28-7.41 (2H, m), 7.52-7.55 (1H, m).

Step 9

The compound (20-9) (12.1 g), tris dibenzylidene acetone dipalladium (1.14 g) and dicyclohexyl biphenyl phosphine (0.88 g) were dissolved into toluene (125 ml) under nitrogen atmosphere, and a solution of 1.6M lithium hexamethyl disilazide in tetrahydrofuran (46.9 ml) was added with stirring at room temperature. The reaction mixture was warmed to 80° C. and then stirred for 16 hours. After consumption of the compound (20-9), the mixture was cooled to 0° C. and diethyl ether and a 1M hydrochloric acid aqueous solution were added. After stirring at 0° C. for 10 minutes, the mixture was neutralized by the addition of a saturated aqueous solution of sodium carbonate. The mixture was extracted with ethyl acetate, the organic layer was washed with brine, and dried over anhydrous magnesium sulfate. The solvent was evaporated under reduced pressure and the residue was subjected to silica gel chromatography to afford the compound (20-10) (6.84 g).

$^1$H-NMR(CDCl$_3$): 1.51 (9H, s,), 1.69 (3H, s), 2.01-2.12 (1H, m), 2.40-2.51(1H, m), 2.67-2.76 (2H, m), 6.55-6.67 (3H, m), 7.15 (1H, t, J=8.1)

Reference Example

The Synthesis of Compound 241

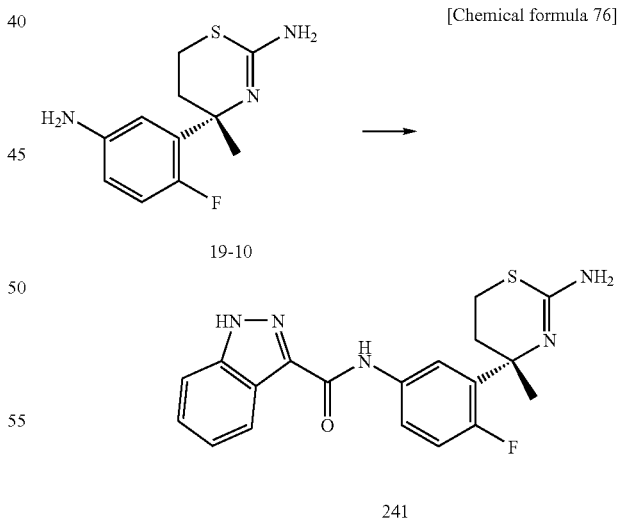

Indazole-3-carboxylic acid (71 mg) and the compound (19-10) (100 mg) were dissolved into methanol (5 ml), and 4-(4,6-dimethoxy-1,3,5-triazine-2-yl)-4-methylnmorpholinium chloride (173 mg) was added to the mixture with stirring at room temperature. The mixture was stirred for 5 hours. The reaction was quenched by the addition of brine, and the reaction mixture was extracted with ethyl acetate, dried over anhydrous magnesium sulfate and then concentrated. The crude product was purified by silica gel chromatography (NH₂-silica gel, 2-8% MeOH/CHCl₃) to afford the compound (241) (66 mg).

¹H-NMR (DMSO-d6) δ: 1.49 (3H, s), 1.78-1.86 (1H, m), 2.13-2.21 (1H, m), 2.59-2.67 (1H, m), 2.96-3.02 (1H, m), 7.11 (1H, t, J=10.7 Hz), 7.29 (1H, t, J=7.8 Hz), 7.45 (1H, t, J=7.5 Hz), 7.66 (1H, d, J=8.8 Hz), 7.74-7.78 (1H, m), 7.80-7.83 (1H, m), 8.21 (1H, d, J=8.6 Hz), 10.25 (1H, s).

Reference Example 22

The Synthesis of Compound 702

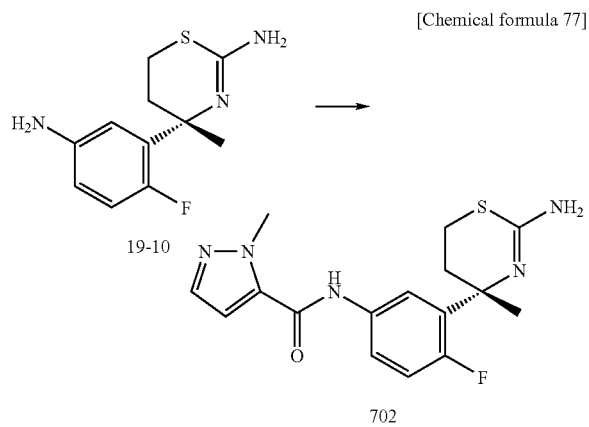

[Chemical formula 77]

702

1-methylpyrazole-5-carboxylic acid (80 mg) and the compound (19-10) (145 mg) were dissolved into methanol (3 ml), and 4-(4,6-dimethoxy-1,3,5-triazine-2-yl)-4-methylmorpholinium chloride (251 mg) was added to the mixture with stirring at room temperature, and the mixture was stirred for 5 hours. The reaction was quenched by addition of brine, and the mixture was extracted with ethyl acetate, dried over anhydrous magnesium sulfate and concentrated. The crude product was purified by silica gel chromatography (NH₂-silica gel, 0-4% MeOH/CHCl₃) to afford the compound (702) (146 mg).

¹H-NMR (CDCl₃) δ: 1.65 (3H, s), 1.91-1.98 (1H, m), 2.57-2.62 (1H, m), 2.68-2.75 (1H, m), 2.92-2.97 (1H, m), 4.18 (3H, s), 6.82 (1H, br s), 7.02-7.08 (1H, m), 7.28-7.32 (1H, m), 7.44 (1H, s), 7.92-7.96 (1H, m).

Reference Example 23

The Synthesis of the Compound 737

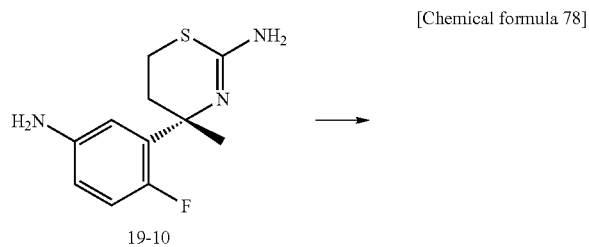

[Chemical formula 78]

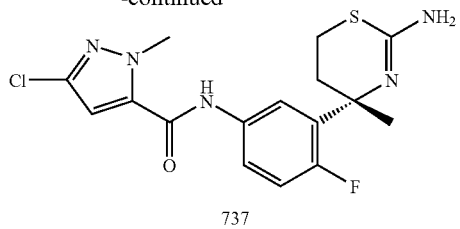

737

3-chloro-1-methylpyrazole-5-carboxylic acid (102 mg) and the compound (19-10) (145 mg) were dissolved into methanol (3 ml), and 4-(4,6-dimethoxy-1,3,5-triazine-2-yl)-4-methylmorpholinium chloride (251 mg) was added to the mixture with stirring at room temperature, and the mixture was stirred for 5 hours. The reaction was quenched by addition of brine, and the mixture was extracted with ethyl acetate, dried over anhydrous magnesium sulfate and concentrated to afford crude product. The crude product was purified by silica gel chromatography (NH₂-silica gel, 33-78% AcOEt/Hexane) to afford the compound (737) (51 mg).

¹H-NMR (CDCl₃) δ: 1.59 (3H, s), 1.87-1.94 (1H, m), 2.47-2.53 (1H, m), 2.67-2.73 (1H, m), 2.93-2.99 (1H, m), 4.10 (3H, s), 6.62 (1H, s), 7.04 (1H, t, J=10.2 Hz), 7.33 (1H, d, J=4.3 Hz), 7.85 (1H, s).

Reference Example 24

The Synthesis of the Compound 949

[Chemical formula 79]

949

5-fluoro-2-pyridine carboxylic acid (70.7 mg) was dissolved into methanol (2 ml), and 4-(4,6-dimethoxy-1,3,5-triazine-2-yl)-4-methylmorpholinium chloride (180.1 mg) was added to the mixture with stirring at room temperature. The mixture was stirred for 5 minutes and a solution of the compound (19-10) (119.9 mg) in methanol (2 ml) was added to the reaction solution with stirring under cooling with ice-water bath. After stirred for 3 hours, a 0.5M aqueous solution of sodium hydroxide was added to the mixture with stirring under cooling with ice-water bath, and the mixture was extracted with ethyl acetate. The organic layer was washed with brine, and dried over anhydrous magnesium sulfate. The solvent was evaporated under reduced pressure and the obtained residue was subjected to silica gel chromatography to afford the compound (949) (149.4 mg).

¹H-NMR (CDCl₃) δ: 1.63 (3H, s), 1.82-2.00 (1H, m), 2.43-2.58 (1H, m), 2.72-2.82 (1H, m), 2.95-3.02 (1H, m), 7.06 (1H, dd, J=11,7, 9.0 Hz), 7.43-7.48 (1H, m), 7.97-8.03 (1H, m), 8.15-8.18 (1H, m), 8.42 (1H, d, J=8.1 Hz), 8.72 (1H, s), 9.91 (1H, br s)

Reference Example 25

The Synthesis of the Compound 943

[Chemical formula 80]

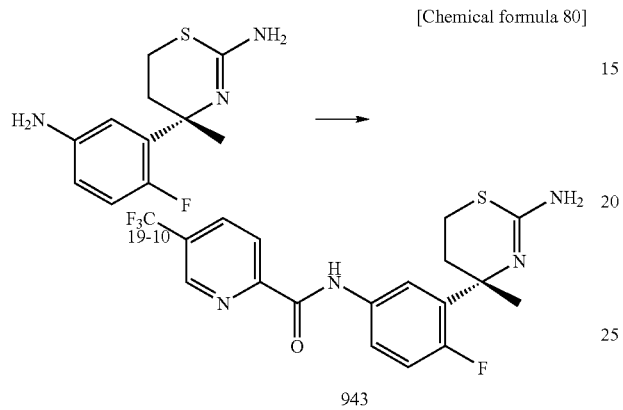

5-trifluoromethyl-2-pyridine carboxylic acid (95.7 mg) was dissolved into methanol (2 ml), and 4-(4,6-dimethoxy-1,3,5-triazine-2-yl)-4-methylmorpholinium chloride (180.1 mg) was added to the solution with stirring at room temperature. After stirring for 5 minutes, a solution of the compound (19-10) (119.9 mg) in methanol (2 ml) was added to the reaction mixture with stirring under cooling with ice-water bath. After stirring for 3 hours, a 0.5N aqueous solution of sodium hydroxide was added with stirring under cooling with ice-water bath, and the mixture was extracted with ethyl acetate. The organic layer was washed with brine, and dried over anhydrous magnesium sulfate. The solvent was evaporated under reduced pressure, and the obtained residue was subjected to silica gel chromatography to afford the compound (943) (174.5 mg).

¹H-NMR (CDCl₃) δ: 1.63 (3H, s), 1.82-2.00 (1H, m), 2.36-2.52 (1H, m), 2.72-2.82 (1H, m), 2.95-3.02 (1H, m), 7.07 (1H, dd, J=11.7, 8.1 Hz), 7.39-7.42 (1H, m), 7.55-7.63 (1H, m), 7.96-8.02 (1H,), 8.33 (1H, dd, J=4.8, 9.0 Hz), 8.45 (1H, d, J=2.4 Hz), 9.78 (1H, s).

Reference Example 26

The Synthesis of the Compound 578

[Chemical formula 81]

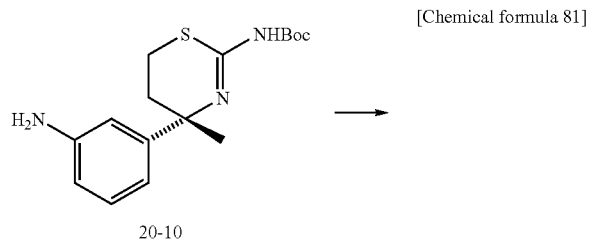

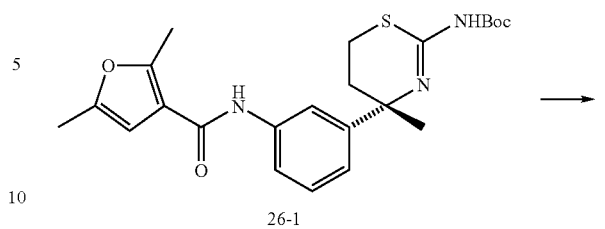

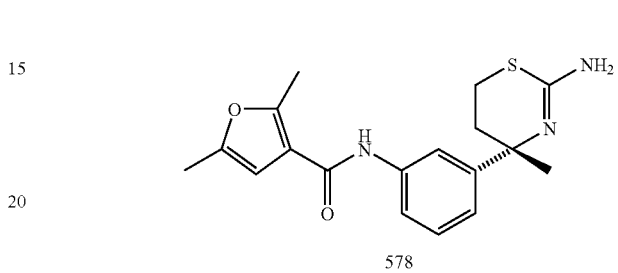

Step 1

To a stirred solution of 2,5-dimethylfuran carboxylic acid (115 mg) and the compound (20-10) (290 mg) in methanol (2 ml) was added 4-(4,6-dimethoxy-1,3,5-triazine-2-yl)-4-methylmorpholinium chloride (273 mg) at room temperature. After stirring for 2 hours, the reaction was quenched by addition of a saturated aqueous solution of sodium hydrogencarbonate, and the mixture was extracted with ethyl acetate. The mixture was washed with water and brine successively, dried and concentrated to afford crude product (300 mg). The crude product was purified by silica gel chromatography (silica gel, 50-66% AcOEt/hexane) to afford the compound (26-1) (221 mg).

¹H-NMR (CDCl₃) δ: 7.64-7.60 (1.0H, m), 7.43-7.41 (2.0H, m), 7.35 (1.0H, t, J=7.93 Hz), 7.04-7.02 (1.0H, m), 6.17 (1.0H, s), 2.80-2.61 (2.0H, m), 2.59(3.0H, s), 2.56-2.52 (1.0H, m), 2.30 (3.0H, s), 2.19-2.06 (1.0H, m), 1.71 (3.0H, s), 1.52 (9.0H, s).

Step 2

The compound (26-1) (221 mg) was dissolved into dichloroethane (1 ml) and trifluoroacetic acid (1 ml) was added to the solution with stirring at room temperature. After stirring for 1 hour 10 minutes, the solvent was evaporated. Ethyl acetate and an aqueous solution of sodium carbonate were added to the residue and the mixture was stirred for 1 hour. The mixture was extracted with ethyl acetate and washed with an aqueous solution of sodium carbonate, water and brine successively. The organic layer was dried, and concentrated to afford crude product (154 mg). The crude product was purified by recrystallization (hexane/AcOEt) to afford the compound (578) (24 mg).

(1H-NMR (CDCl₃) δ: 7.79 (1.0H, br s), 7.65-7.64 (1.0H, m), 7.48-7.41 (1.0H, m), 7.31 (1.0H, t, J=8.01 Hz), 7.04-7.01 (1.0H, m), 6.23 (1.0H, br s), 2.93-2.65 (2.0H, m), 2.57 (3.0H, br s), 2.40 (1.0H, ddd, J=14.11, 5.34, 3.43 Hz), 2.27 (3.0H, br s), 2.09-1.92 (1.0H, m), 1.67 (3.01H, s).

Reference Example 27

The Synthesis of the Compound 472

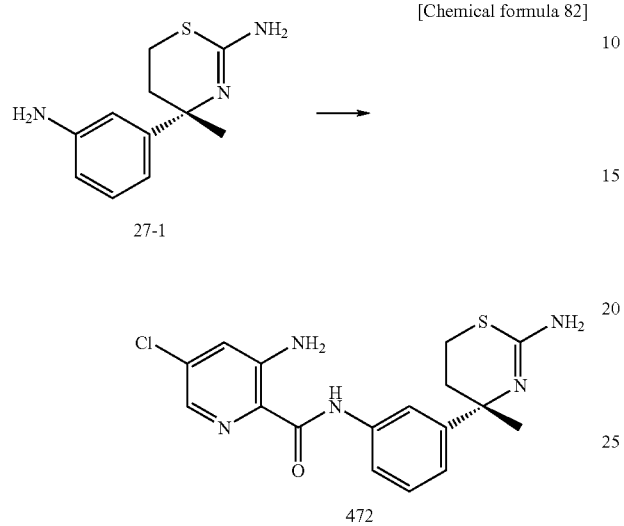

[Chemical formula 82]

The compound (27-1) (256 mg) and 3-amino-5-chloropicolinic acid hydrochloride (266 mg) were suspended in methanol (2.6 ml), and N-methylmorpholine (153 μl) was added to the suspension, and the mixture was stirred at room temperature. After stirred for 6 minutes, 4-(4,6-dimethoxy-1,3,5-triazine-2-yl)-4-methylmorpholinium chloride (385 mg) was added to the mixture, and stirred for 1 hour 10 minutes, and left to stand for 13 hours 20 minutes additionally. The solvent was evaporated, and ethyl acetate, methanol and an aqueous solution of sodium carbonate were added to the residue and stirred for 40 minutes. The aqueous layer was removed, the organic layer was washed with a saturated aqueous solution of sodium hydrogencarbonate and brine, and dried over magnesium sulfate. The magnesium sulfate was removed by filtration, the filtrate was concentrated under reduced pressure, and the obtained residue was purified by silica gel chromatography (Yamazen HI-FLASH column NH2-40W-M, ethyl acetate:hexane=1:1). The obtained fraction was concentrated and the residue was crystallized from ethyl acetate. The crystals were collected by filtration, washed with diethyl ether and dried to afford the compound (472) (82.0 mg).

$^1$H-NMR (DMSO-$d_6$) δ: 1.41 (3H, s), 1.72 (1H, ddd, J=13.7, 10.2, 3.6 Hz), 2.02 (1H, m), 2.58 (1H, m), 2.90 (1H, ddd, J=11.9, 6,6, 3.6 Hz), 5.77 (2H, brs), 7.09 (1H, dt, J=7.9, 1.3 Hz), 7.13 (2H, brs), 7.27 (1H, t, J=8.0 Hz), 7.33 (1H, d, J=2.2 Hz), 7.68-7.72 (2H, m), 7.85 (1H, d, J=2.0 Hz), 10.23 (1H, s).

The other compounds were synthesized in the same way. The structural formulas and physical constants are shown below.

TABLE 1

| No. | Structure |
|---|---|
| 1 | 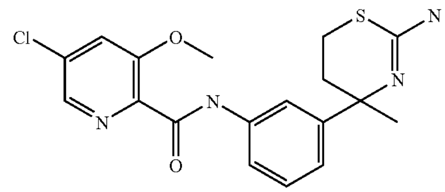 [SMILES: COc1cc(Cl)cnc1C(=O)Nc1cccc(C2(C)CCSC(N)=N2)c1] |
| 2 | 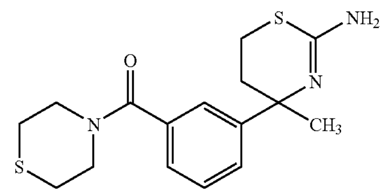 [SMILES: CC1(c2cccc(C(=O)N3CCSCC3)c2)CCSC(N)=N1] |
| 3 | 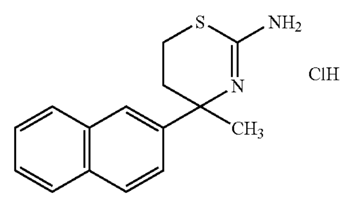 [SMILES: CC1(c2ccc3ccccc3c2)CCSC(N)=N1 ; Cl] |
| 4 | 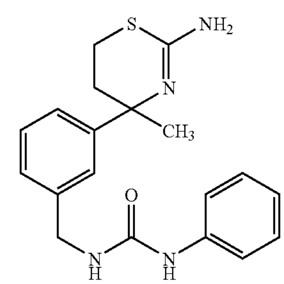 [SMILES: CC1(c2cccc(CNC(=O)Nc3ccccc3)c2)CCSC(N)=N1] |
| 5 | 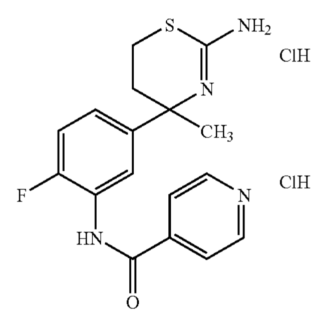 [SMILES: CC1(c2ccc(F)c(NC(=O)c3ccncc3)c2)CCSC(N)=N1 ; Cl ; Cl] |
| 6 | 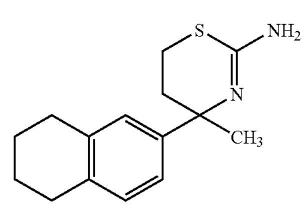 [SMILES: CC1(c2ccc3c(c2)CCCC3)CCSC(N)=N1] |

TABLE 1-continued
| No. | Structure |
|---|---|
| 7 | 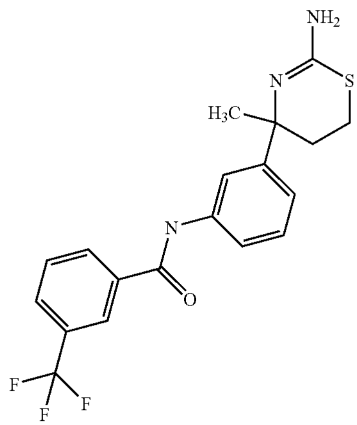 [SMILES: CC1(c2cccc(NC(=O)c3cccc(C(F)(F)F)c3)c2)CCSC(N)=N1] |
| 8 | 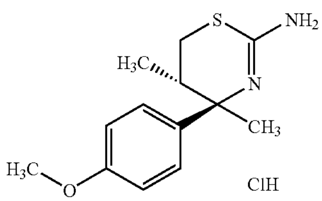 [SMILES: COc1ccc([C@]2(C)N=C(N)SC[C@H]2C)cc1 ; Cl] |
| 9 | 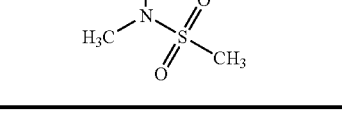 |
TABLE 2
| No. | Structure |
|---|---|
| 10 | 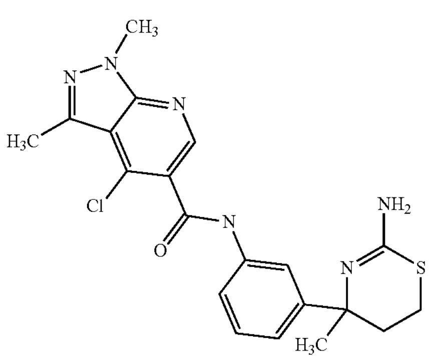 [SMILES: Cc1nn(C)c2ncc(C(=O)Nc3cccc(C4(C)CCSC(N)=N4)c3)c(Cl)c12] |
TABLE 2-continued
| No. | Structure |
|---|---|
| 11 | 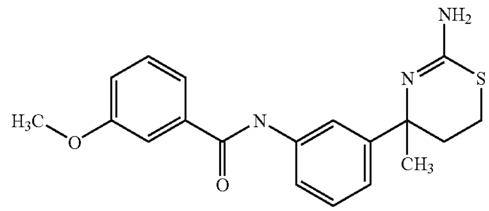 [SMILES: COc1cccc(C(=O)Nc2cccc(C3(C)CCSC(N)=N3)c2)c1] |
| 12 | 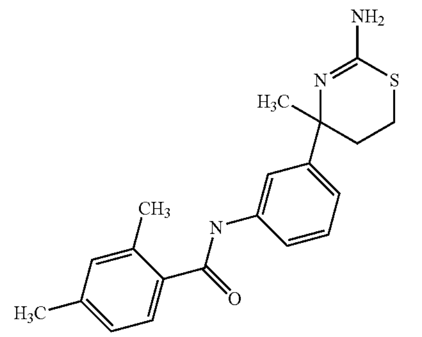 [SMILES: Cc1ccc(C(=O)Nc2cccc(C3(C)CCSC(N)=N3)c2)c(C)c1] |
| 13 | 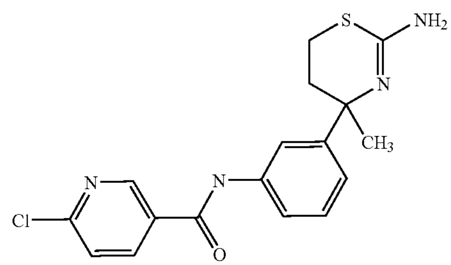 [SMILES: CC1(c2cccc(NC(=O)c3ccc(Cl)nc3)c2)CCSC(N)=N1] |
| 14 | 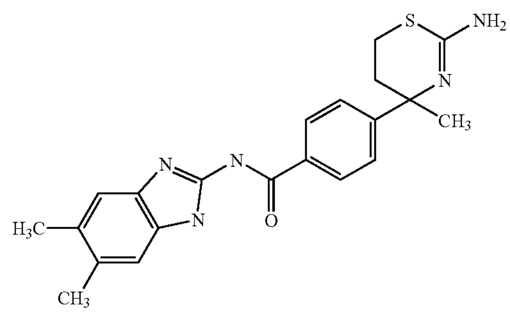 [SMILES: Cc1cc2nc(NC(=O)c3ccc(C4(C)CCSC(N)=N4)cc3)[nH]c2cc1C] |
| 15 | 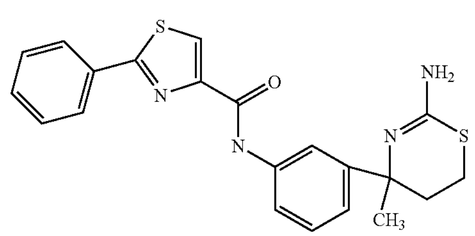 [SMILES: CC1(c2cccc(NC(=O)c3csc(-c4ccccc4)n3)c2)CCSC(N)=N1] |
| 16 | 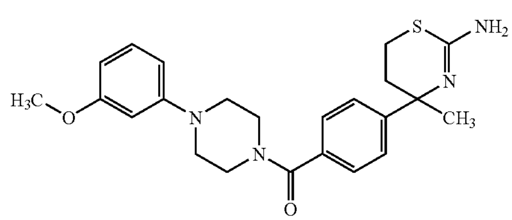 [SMILES: COc1cccc(N2CCN(C(=O)c3ccc(C4(C)CCSC(N)=N4)cc3)CC2)c1] |

TABLE 2-continued

| No. | Structure |
|---|---|
| 17 | (2-amino-4-methyl-5,6-dihydro-4H-1,3-thiazin-4-yl)phenyl linked via NH-C(=O)-CH2-O-(4-fluorophenyl) |
| 18 | 2-amino-4-methyl-5,6-dihydro-4H-1,3-thiazine substituted with 2,3-dihydro-1,4-benzodioxin-6-yl |

TABLE 3

| No. | Structure |
|---|---|
| 19 | 4-chloro-N-phenyl benzamide with 3-(2-amino-4-methyl-5,6-dihydro-4H-1,3-thiazin-4-yl) substituent |
| 20 | 3-(trifluoromethyl)cinnamide N-linked to 2-fluoro-5-(2-amino-4-methyl-5,6-dihydro-4H-1,3-thiazin-4-yl)phenyl |
| 21 | 2-fluoro-6-chloro-N-[3-(2-amino-4-methyl-5,6-dihydro-4H-1,3-thiazin-4-yl)phenyl]benzamide |
| 22 | 4-chloro-N-[2-fluoro-5-(2-amino-4-methyl-5,6-dihydro-4H-1,3-thiazin-4-yl)phenyl]benzamide |
| 23 | N-(5-chloropyridin-2-yl)-N'-[3-(2-imino-4-methyl-1,3-thiazinan-4-yl)phenyl]thiourea |
| 24 | 2-amino-4-(4-chlorophenyl)-4-methyl-4,5-dihydro-1,3-thiazole |
| 25 | N-benzyl-N-methyl-4-(2-amino-4-methyl-5,6-dihydro-4H-1,3-thiazin-4-yl)benzamide |
| 26 | 4-(trifluoromethyl)-N-[3-(2-amino-4-methyl-5,6-dihydro-4H-1,3-thiazin-4-yl)phenyl]benzamide |

TABLE 3-continued
| No. | Structure |
|---|---|
| 27 | 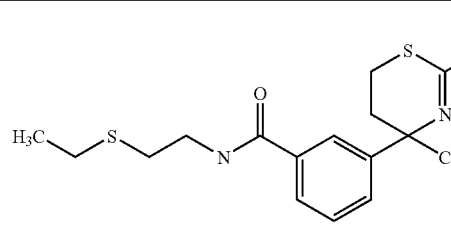 |
| 28 | 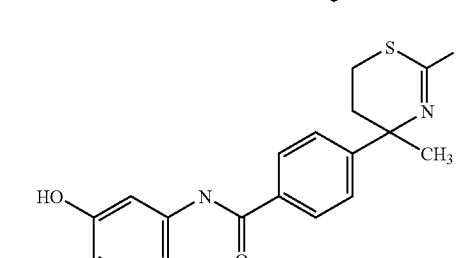 |
TABLE 4
| No. | Structure |
|---|---|
| 29 | 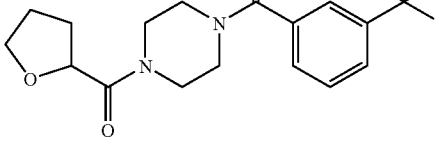 |
| 30 | 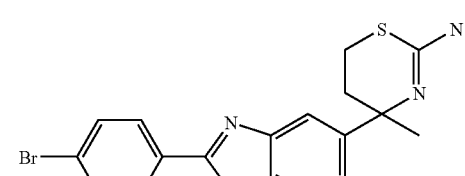 |
| 31 | 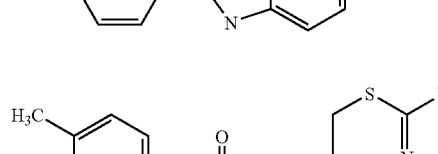 |
| 32 | 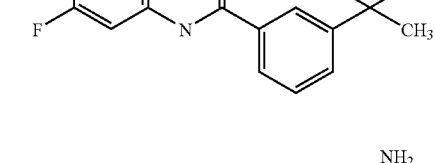 |
| 33 | 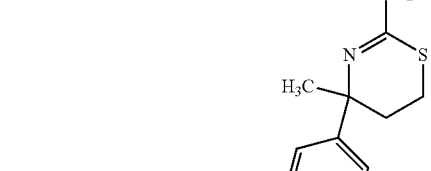 |
| 34 | 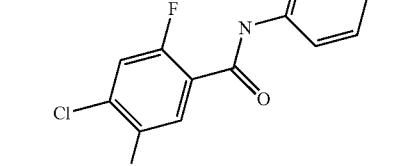 |
| 35 | 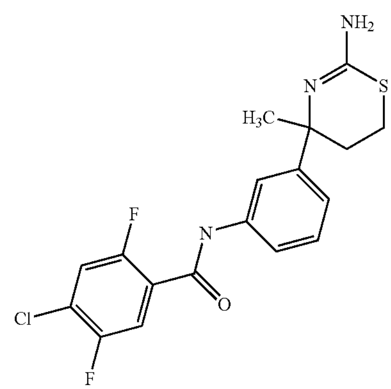 [SMILES: CC1(c2cccc(NC(=O)c3cc(F)c(Cl)cc3F)c2)CCSC(N)=N1] |
| 36 | 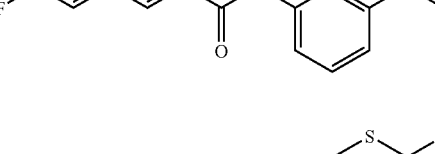 |
| 37 | 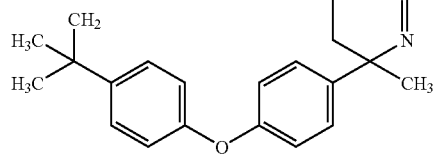 |

TABLE 4-continued
| No. | Structure |
|---|---|
| 38 | 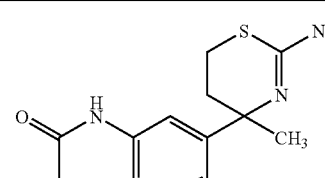 |
| 39 | 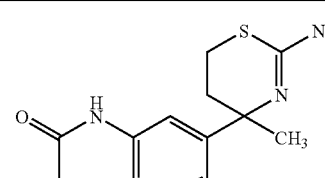 |
TABLE 5
| No. | Structure |
|---|---|
| 40 | 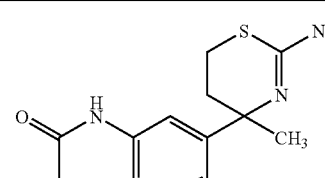 |
| 41 | 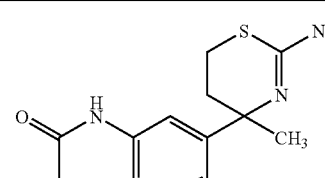 |
| 42 | 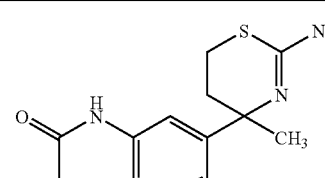 |
| 43 | 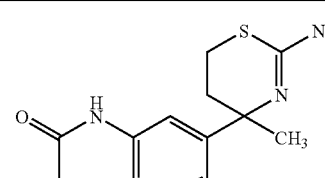 |
TABLE 5-continued
| No. | Structure |
|---|---|
| 44 | 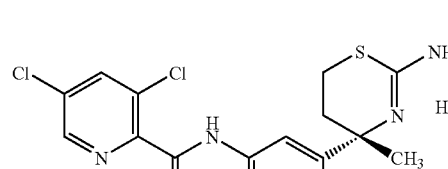 |
| 45 | 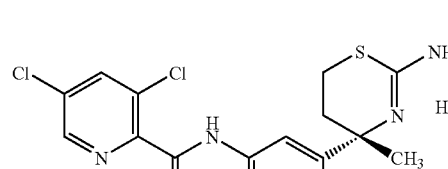 |
| 46 | 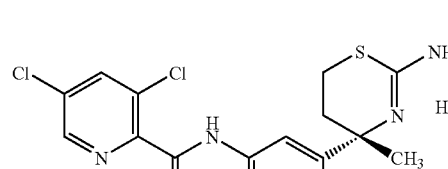 |
| 47 | 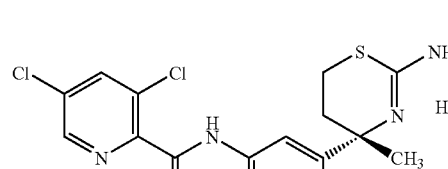 |

TABLE 6
| No. | Structure |
|---|---|
| 48 | 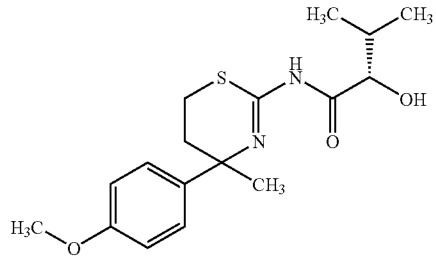 |
| 49 | 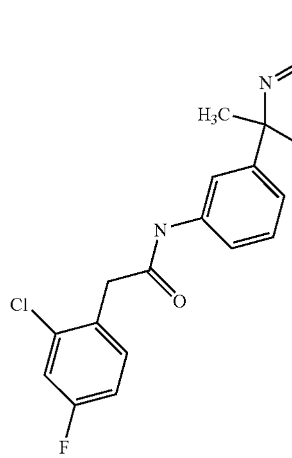 |
| 50 | 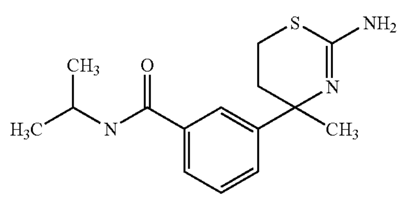 [SMILES: CC(C)NC(=O)c1cccc(C2(C)CCSC(N)=N2)c1] |
| 51 | 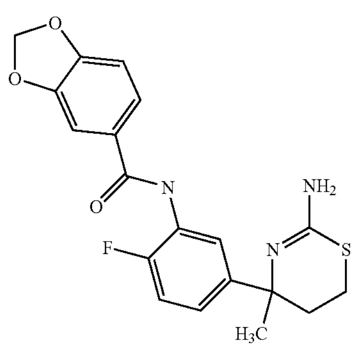 [SMILES: CC1(c2ccc(F)c(NC(=O)c3ccc4c(c3)OCO4)c2)CCSC(N)=N1] |
| 52 | 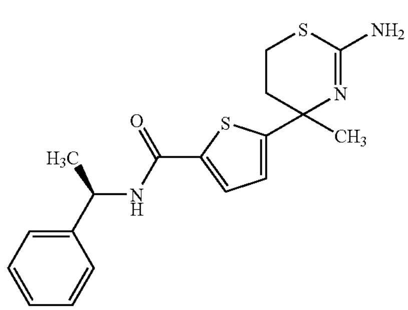 |
TABLE 6-continued
| No. | Structure |
|---|---|
| 53 |  |
| 54 |  |
| 55 |  |
TABLE 7
| No. | Structure |
|---|---|
| 56 | 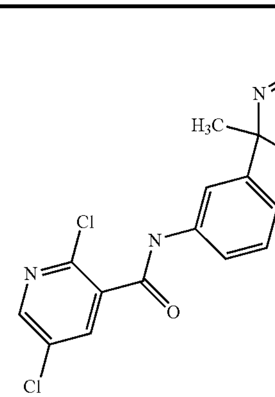 |
| 57 | 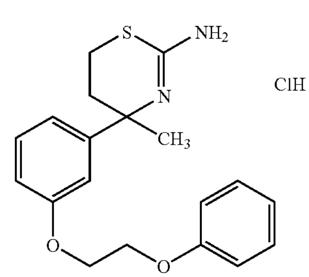 [SMILES: CC1(c2cccc(OCCOc3ccccc3)c2)CCSC(N)=N1 ; Cl] |

TABLE 7-continued
| No. | Structure |
|---|---|
| 58 | 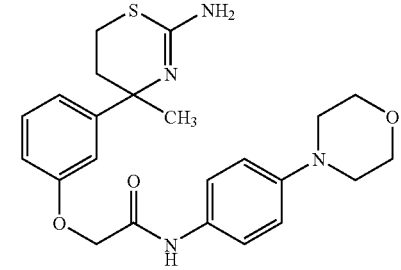 |
| 59 | 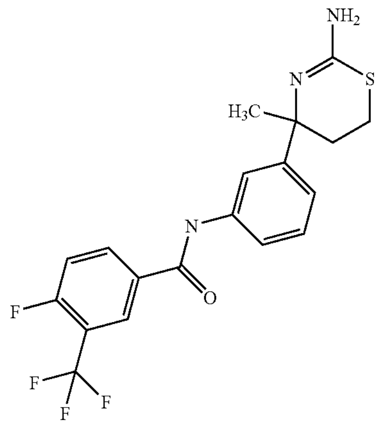 [SMILES: CC1(c2cccc(NC(=O)c3ccc(F)c(C(F)(F)F)c3)c2)CCSC(N)=N1] |
| 60 | 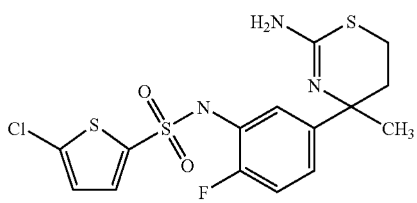 [SMILES: CC1(c2ccc(F)c(NS(=O)(=O)c3ccc(Cl)s3)c2)CCSC(N)=N1] |
| 61 | 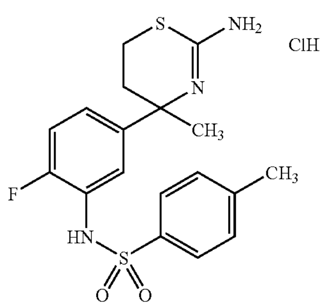 [SMILES: Cc1ccc(S(=O)(=O)Nc2cc(C3(C)CCSC(N)=N3)ccc2F)cc1 ; Cl] |
| 62 | 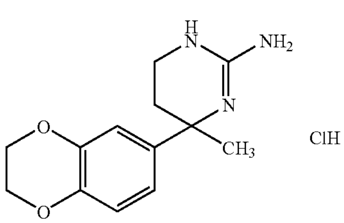 [SMILES: CC1(c2ccc3c(c2)OCCO3)CCNC(N)=N1 ; Cl] |
| 63 | 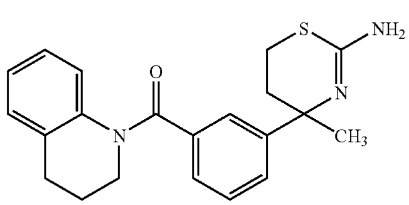 [SMILES: CC1(c2cccc(C(=O)N3CCCc4ccccc43)c2)CCSC(N)=N1] |
TABLE 7-continued
| No. | Structure |
|---|---|
| 64 | 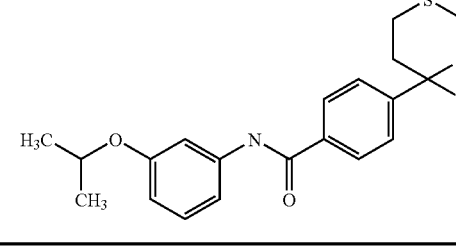 |
| 65 | |
TABLE 8
| No. | Structure |
|---|---|
| 66 | 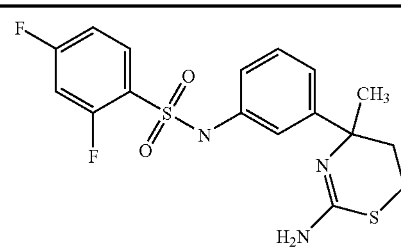 |
| 67 | 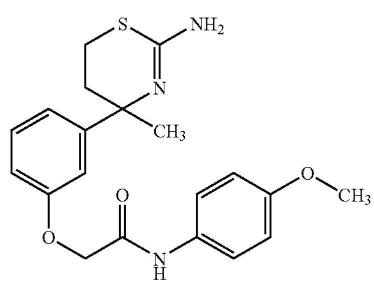 [SMILES: COc1ccc(NC(=O)COc2cccc(C3(C)CCSC(N)=N3)c2)cc1] |
| 68 | 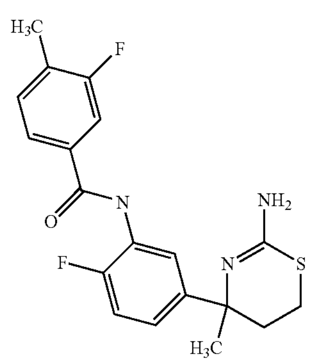 [SMILES: Cc1ccc(C(=O)Nc2cc(C3(C)CCSC(N)=N3)ccc2F)cc1F] |

TABLE 8-continued

| No. | Structure |
|---|---|
| 69 | 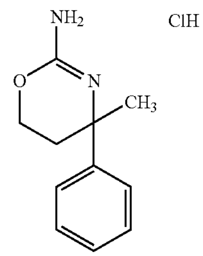 |
| 70 | 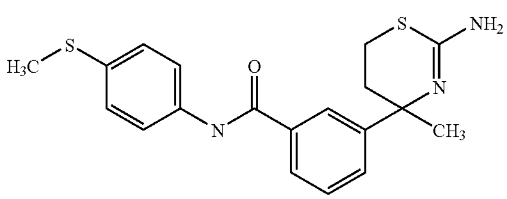 [SMILES: CSc1ccc(NC(=O)c2cccc(C3(C)CCSC(N)=N3)c2)cc1] |
| 71 | 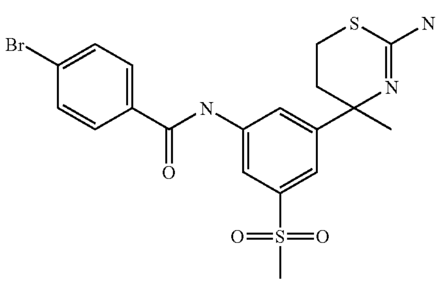 [SMILES: CC1(c2cc(NC(=O)c3ccc(Br)cc3)cc(S(C)(=O)=O)c2)CCSC(N)=N1] |
| 72 | 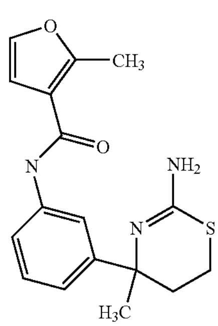 [SMILES: Cc1occc1C(=O)Nc1cccc(C2(C)CCSC(N)=N2)c1] |
| 73 | 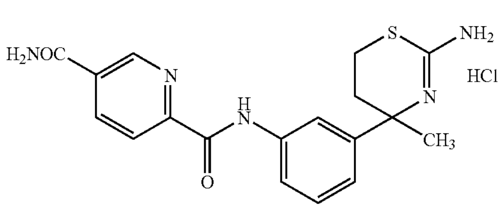 [SMILES: CC1(c2cccc(NC(=O)c3ccc(C(N)=O)cn3)c2)CCSC(N)=N1 ; Cl] |
| 74 | 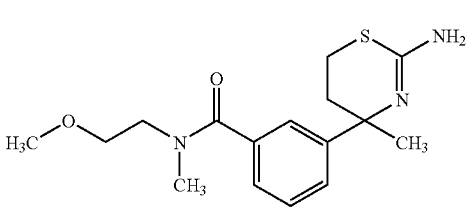 [SMILES: COCCN(C)C(=O)c1cccc(C2(C)CCSC(N)=N2)c1] |

TABLE 9

| No. | Structure |
|---|---|
| 75 | 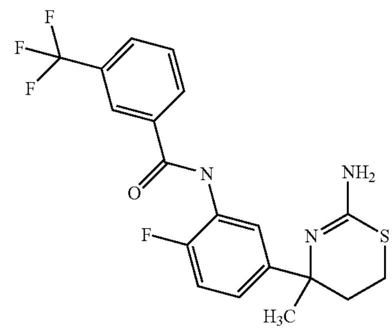 |
| 76 | 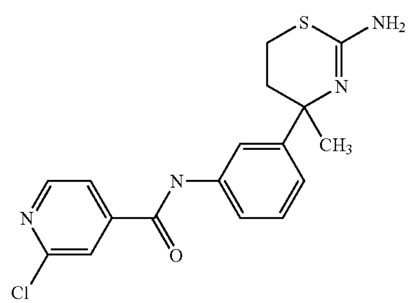 |
| 77 | 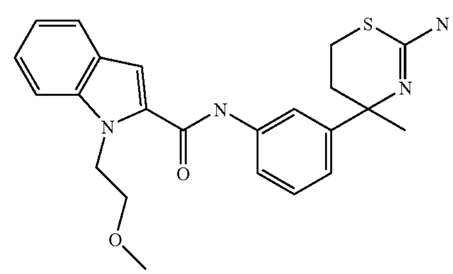 [SMILES: COCCn1c(C(=O)Nc2cccc(C3(C)CCSC(N)=N3)c2)cc2ccccc21] |
| 78 | 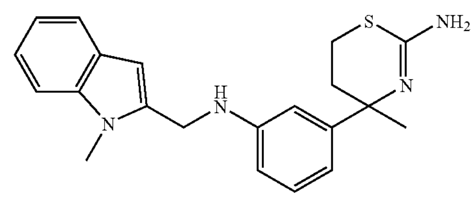 [SMILES: Cn1c(CNc2cccc(C3(C)CCSC(N)=N3)c2)cc2ccccc21] |
| 79 | 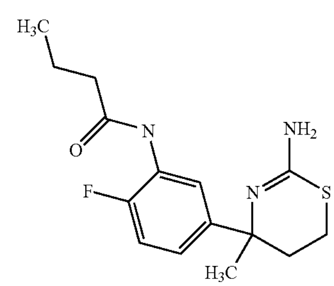 [SMILES: CCCC(=O)Nc1cc(C2(C)CCSC(N)=N2)ccc1F] |
| 80 | 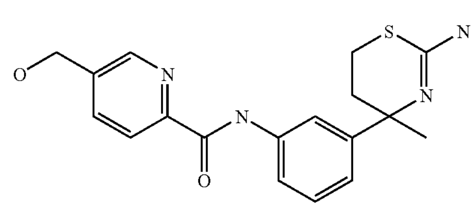 [SMILES: CC1(c2cccc(NC(=O)c3ccc(CO)cn3)c2)CCSC(N)=N1] |

TABLE 9-continued
| No. | Structure |
|---|---|
| 81 | 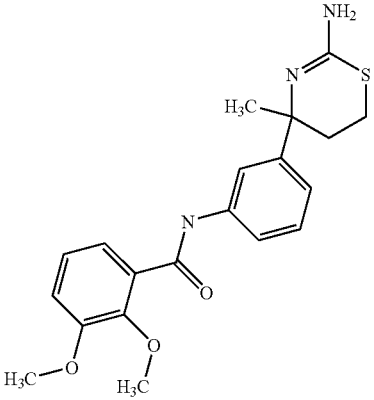 [SMILES: COc1cccc(C(=O)Nc2cccc(C3(C)CCSC(N)=N3)c2)c1OC] |
| 82 | 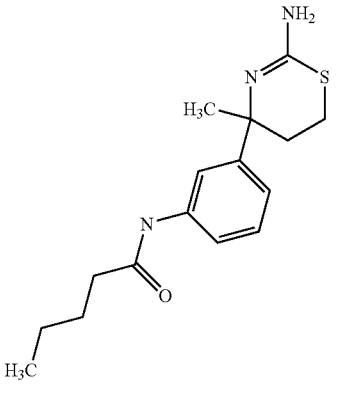 [SMILES: CCCCC(=O)Nc1cccc(C2(C)CCSC(N)=N2)c1] |
TABLE 10
| No. | Structure |
|---|---|
| 83 | 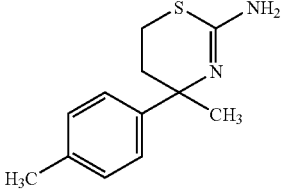 |
| 84 | 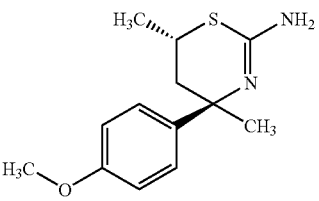 [SMILES: COc1ccc([C@@]2(C)C[C@H](C)SC(N)=N2)cc1] |
| 85 | 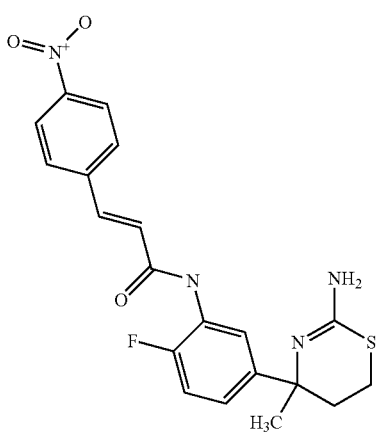 |
| 86 | 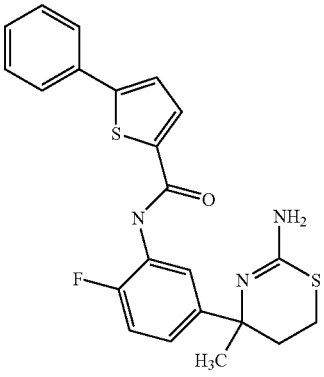 [SMILES: CC1(c2ccc(F)c(NC(=O)c3ccc(-c4ccccc4)s3)c2)CCSC(N)=N1] |
| 87 | 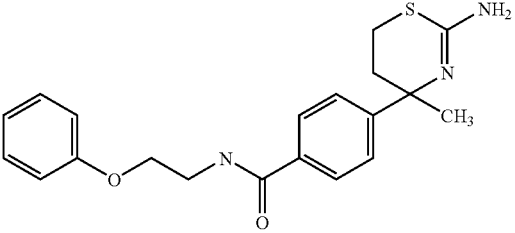 [SMILES: CC1(c2ccc(C(=O)NCCOc3ccccc3)cc2)CCSC(N)=N1] |
| 88 | 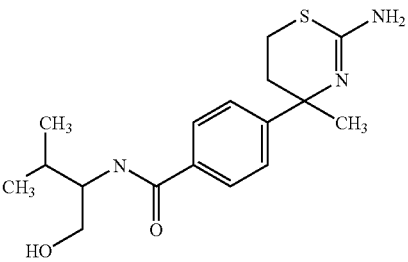 |
| 89 | 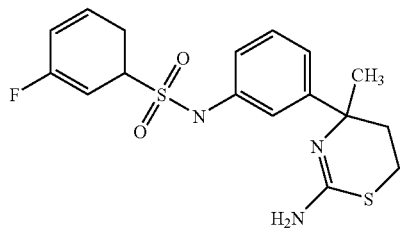 |

TABLE 10-continued

| No. | Structure |
|---|---|
| 90 | (structure) |
| 91 | (structure) Chiral |

TABLE 11

| No. | Structure |
|---|---|
| 92 | (structure) |
| 93 | (structure) |
| 94 | (structure) Chiral |

TABLE 11-continued

| No. | Structure |
|---|---|
| 95 | (structure) |
| 96 | (structure) |
| 97 | (structure) |
| 98 | (structure) |
| 99 | (structure) |
| 100 | (structure) |

TABLE 11-continued
| No. | Structure |
|---|---|
| 101 | 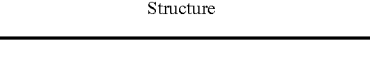 |
TABLE 12
| No. | Structure |
|---|---|
| 102 | 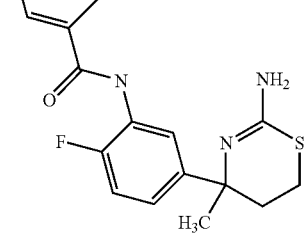 |
| 103 | 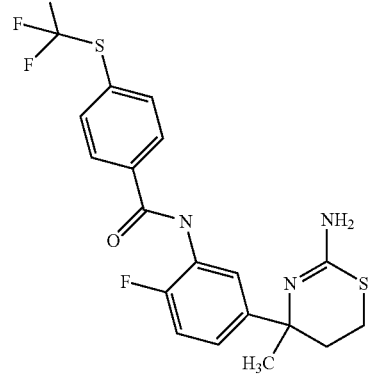 |
| 104 | 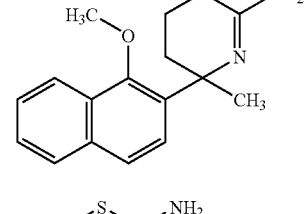 |
| 105 | 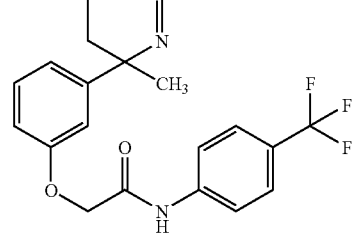 |
TABLE 12-continued
| No. | Structure |
|---|---|
| 106 | 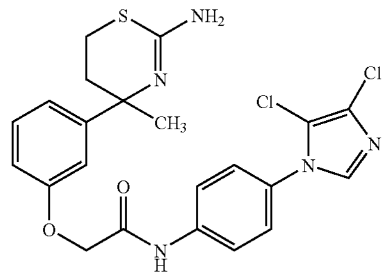 [SMILES: CC1(c2cccc(OCC(=O)Nc3ccc(-n4cnc(Cl)c4Cl)cc3)c2)CCSC(N)=N1] |
| 107 | 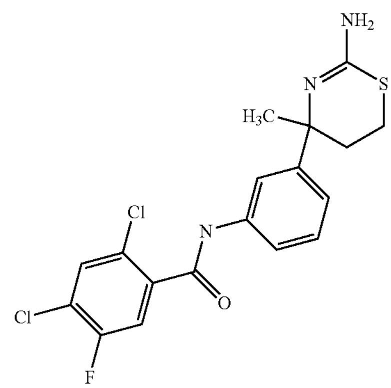 [SMILES: CC1(c2cccc(NC(=O)c3cc(F)c(Cl)cc3Cl)c2)CCSC(N)=N1] |
| 108 | 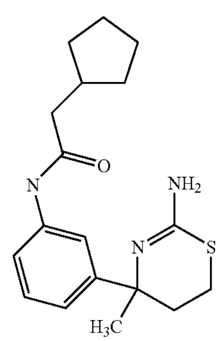 [SMILES: CC1(c2cccc(NC(=O)CC3CCCC3)c2)CCSC(N)=N1] |
| 109 | 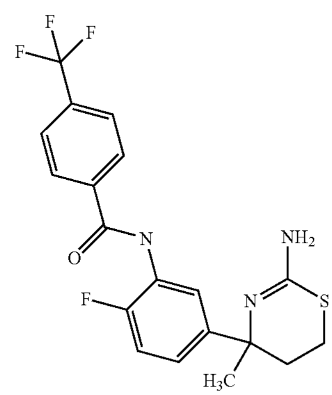 [SMILES: CC1(c2ccc(F)c(NC(=O)c3ccc(C(F)(F)F)cc3)c2)CCSC(N)=N1] |

TABLE 13

| No. | Structure |
|-----|-----------|
| 110 | 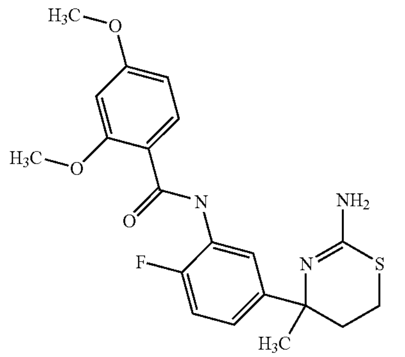 [SMILES: COc1ccc(C(=O)Nc2cc(C3(C)CCSC(N)=N3)ccc2F)c(OC)c1] |
| 111 | 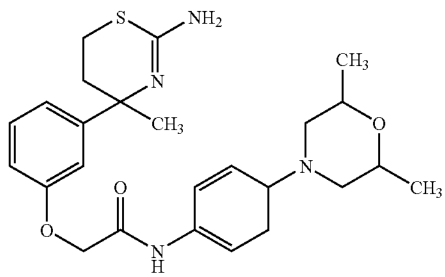 [SMILES: CC1CN(C2C=CC(NC(=O)COc3cccc(C4(C)CCSC(N)=N4)c3)=CC2)CC(C)O1] |
| 112 | 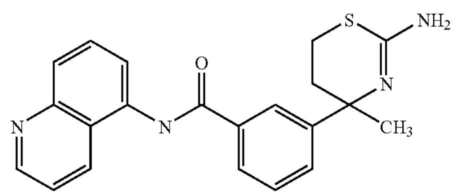 [SMILES: CC1(c2cccc(C(=O)Nc3cccc4ncccc34)c2)CCSC(N)=N1] |
| 113 | 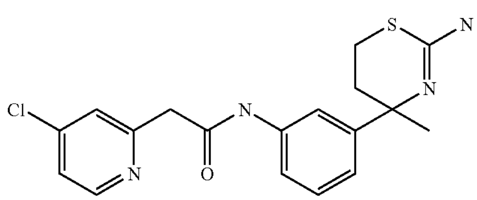 [SMILES: CC1(c2cccc(NC(=O)Cc3cc(Cl)ccn3)c2)CCSC(N)=N1] |
| 114 | 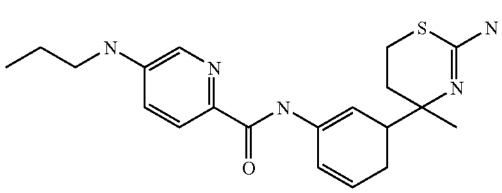 [SMILES: CCCNc1ccc(C(=O)NC2=CC(C3(C)CCSC(N)=N3)CC=C2)nc1] |
| 115 | 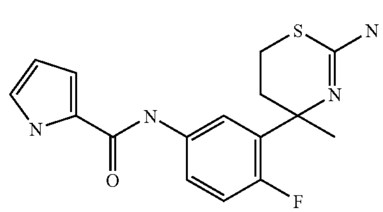 [SMILES: CC1(c2cc(NC(=O)c3ccc[nH]3)ccc2F)CCSC(N)=N1] |

TABLE 13-continued

| No. | Structure |
|-----|-----------|
| 116 | 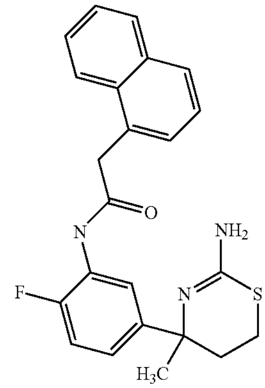 [SMILES: CC1(c2ccc(F)c(NC(=O)Cc3cccc4ccccc34)c2)CCSC(N)=N1] |
| 117 | 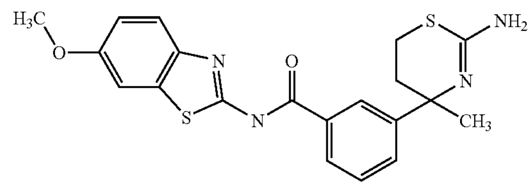 [SMILES: COc1ccc2nc(NC(=O)c3cccc(C4(C)CCSC(N)=N4)c3)sc2c1] |
| 118 | 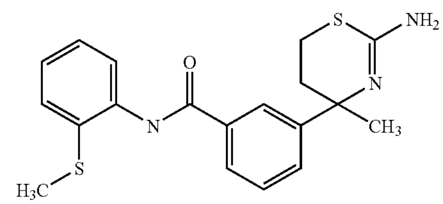 [SMILES: CSc1ccccc1NC(=O)c1cccc(C2(C)CCSC(N)=N2)c1] |
| 119 | 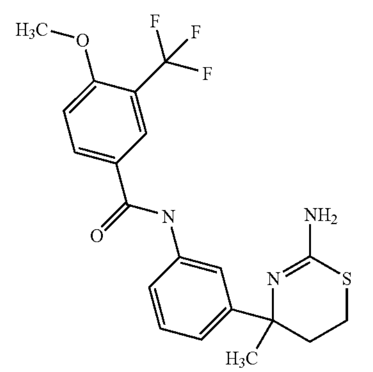 [SMILES: COc1ccc(C(=O)Nc2cccc(C3(C)CCSC(N)=N3)c2)cc1C(F)(F)F] |

TABLE 14

| No. | Structure |
|-----|-----------|
| 120 | 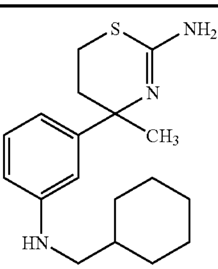 |

TABLE 14-continued
| No. | Structure |
|---|---|
| 121 | 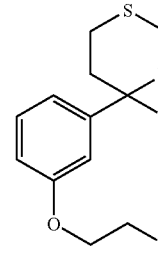 ClH |
| 122 | 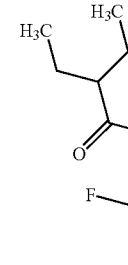 |
| 123 | 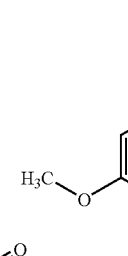 |
| 124 | 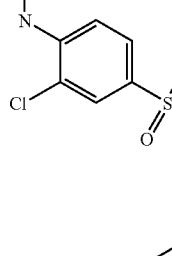 |
| 125 | 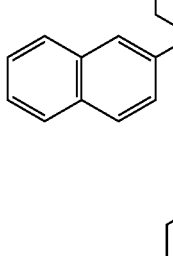 |
| 126 | 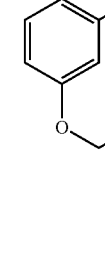 |
TABLE 14-continued
| No. | Structure |
|---|---|
| 127 | 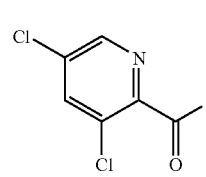 ClH |
| 128 | 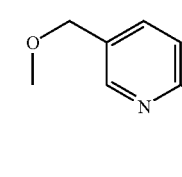 |
| 129 | 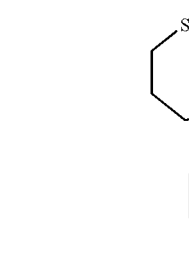 ClH |
TABLE 15
| No. | Structure |
|---|---|
| 130 | 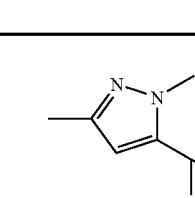 |
| 131 | 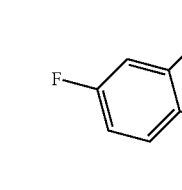 |
| 132 | 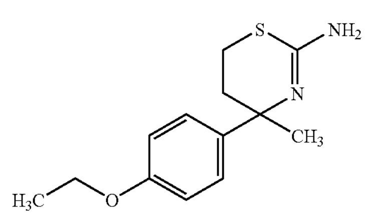 [SMILES: CCOc1ccc(C2(C)CCSC(N)=N2)cc1] |

TABLE 15-continued

| No. | Structure |
|---|---|
| 133 | (chiral structure) |
| 134 | (structure) |
| 135 | (structure) |
| 136 | (structure) |
| 137 | (structure) |
| 138 | (structure) |
| 139 | (structure) |

TABLE 16

| No. | Structure |
|---|---|
| 140 | (structure) |
| 141 | (structure) |
| 142 | (structure) |
| 143 | (structure) |
| 144 | (structure) |

TABLE 16-continued
| No. | Structure |
|-----|-----------|
| 145 | 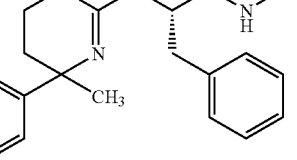 |
| 146 | 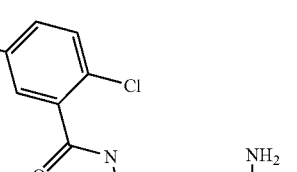 |
| 147 | 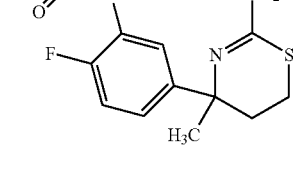 |
TABLE 17
| No. | Structure |
|-----|-----------|
| 148 | 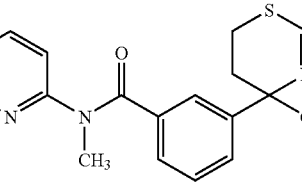 |
| 149 | 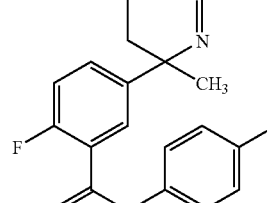 |
TABLE 17-continued
| No. | Structure |
|-----|-----------|
| 150 | 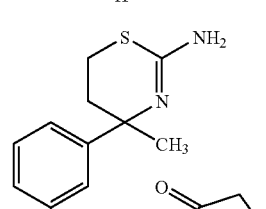 Chiral |
| 151 | 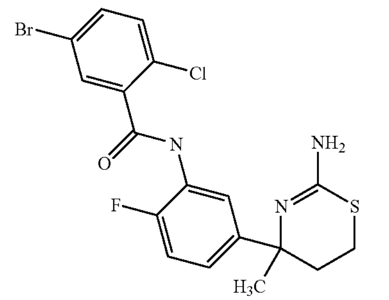 [SMILES: CC1(c2ccc(F)c(NC(=O)c3cc(Br)ccc3Cl)c2)CCSC(N)=N1] |
| 152 | 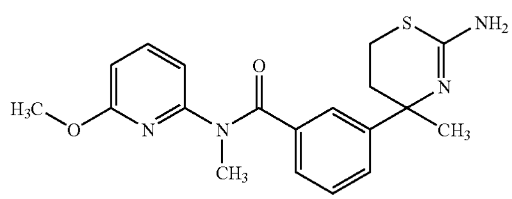 [SMILES: COc1cccc(N(C)C(=O)c2cccc(C3(C)CCSC(N)=N3)c2)n1] |
| 153 | 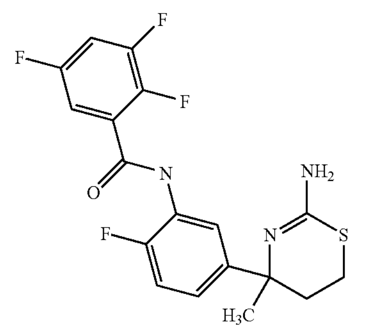 [SMILES: CC1(c2ccc(F)c(NC(=O)c3cc(F)cc(F)c3F)c2)CCSC(N)=N1] |
| 154 | 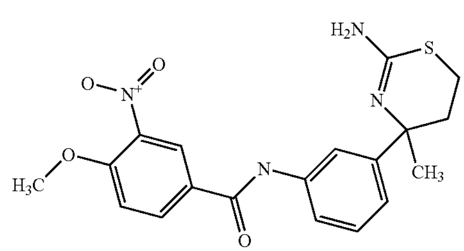 |
| 155 | 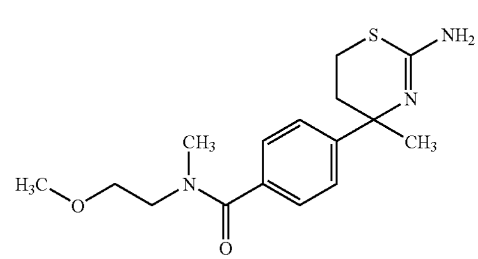 [SMILES: COCCN(C)C(=O)c1ccc(C2(C)CCSC(N)=N2)cc1] |

TABLE 17-continued

| No. | Structure |
|---|---|
| 156 | 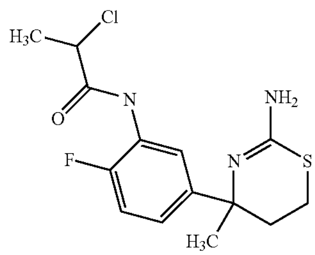 [SMILES: CC(Cl)C(=O)Nc1cc(C2(C)CCSC(N)=N2)ccc1F] |
| 157 | 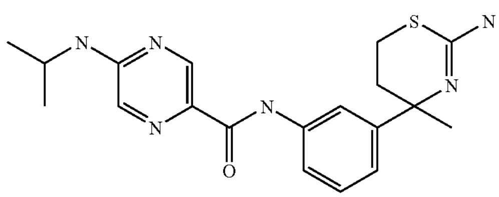 [SMILES: CC(C)Nc1cnc(C(=O)Nc2cccc(C3(C)CCSC(N)=N3)c2)cn1] |

TABLE 18

| No. | Structure |
|---|---|
| 158 | 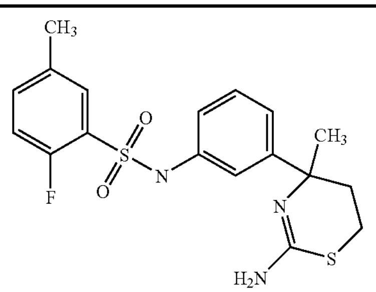 |
| 159 | 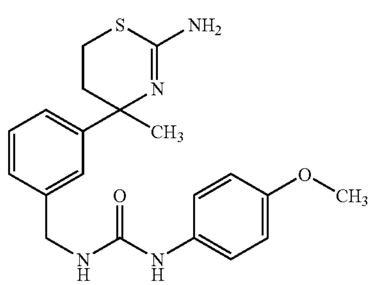 [SMILES: COc1ccc(NC(=O)NCc2cccc(C3(C)CCSC(N)=N3)c2)cc1] |
| 160 | 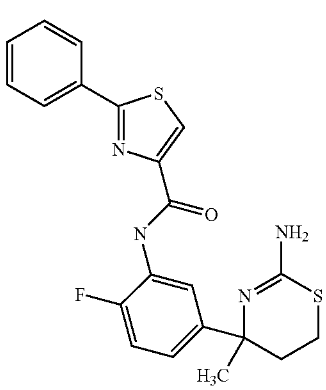 [SMILES: CC1(c2ccc(F)c(NC(=O)c3csc(-c4ccccc4)n3)c2)CCSC(N)=N1] |

TABLE 18-continued

| No. | Structure |
|---|---|
| 161 | 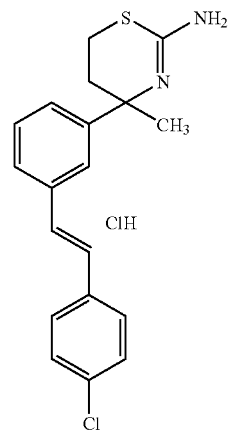 [SMILES: CC1(c2cccc(/C=C/c3ccc(Cl)cc3)c2)CCSC(N)=N1 ; Cl] |
| 162 | 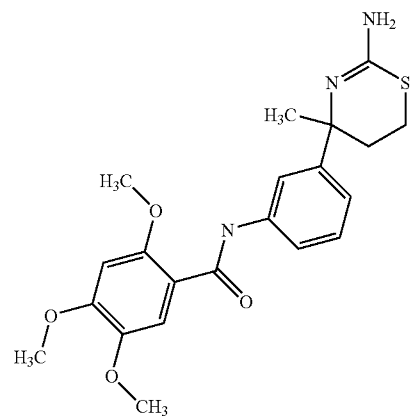 [SMILES: COc1cc(OC)c(C(=O)Nc2cccc(C3(C)CCSC(N)=N3)c2)cc1OC] |
| 163 | 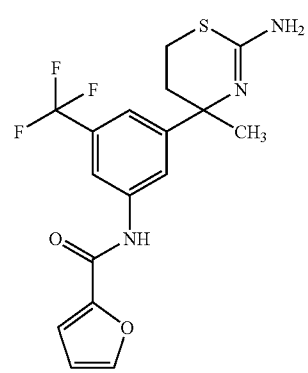 [SMILES: CC1(c2cc(NC(=O)c3ccco3)cc(C(F)(F)F)c2)CCSC(N)=N1] |

TABLE 19

| No. | Structure |
|---|---|
| 164 | 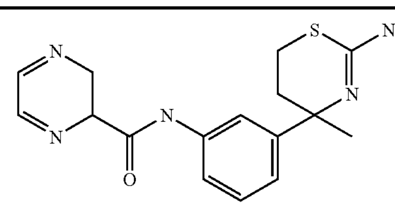 |

TABLE 19-continued

| No. | Structure |
|---|---|
| 165 | 5-chloro-N-(3-bromo-5-(2-amino-4-methyl-5,6-dihydro-4H-1,3-thiazin-4-yl)phenyl)picolinamide · ClH |
| 166 | 4-(3-(3-cyclohexylpropoxy)phenyl)-4-methyl-5,6-dihydro-4H-1,3-thiazin-2-amine · HCl |
| 167 | 3-chloro-4-methoxy-N-(4-(2-amino-4-methyl-5,6-dihydro-4H-1,3-thiazin-4-yl)benzamide) |
| 168 | 3-chloro-4-fluoro-N-(3-(2-amino-4-methyl-5,6-dihydro-4H-1,3-thiazin-4-yl)phenyl)benzamide |
| 169 | 5-(aminomethyl)-N-(3-(2-imino-4-methyl-1,3-thiazinan-4-yl)phenyl)isoxazole-3-carboxamide |
| 170 | N-(3-hydroxy-4-methylphenyl)-3-(2-amino-4-methyl-5,6-dihydro-4H-1,3-thiazin-4-yl)benzamide |
| 171 | N-(1,3,4-thiadiazol-2-yl)-4-(2-amino-4-methyl-5,6-dihydro-4H-1,3-thiazin-4-yl)benzamide |
| 172 | 4-chloro-3-methyl-N-(3-(2-amino-4-methyl-5,6-dihydro-4H-1,3-thiazin-4-yl)phenyl)benzamide |
| 173 | 4-bromo-N-(2-fluoro-5-(2-amino-4-methyl-5,6-dihydro-4H-1,3-thiazin-4-yl)phenyl)benzamide |
| 174 | N-ethyl-N-(pyridin-4-ylmethyl)-4-(2-amino-4-methyl-5,6-dihydro-4H-1,3-thiazin-4-yl)benzamide |

TABLE 20

| No. | Structure |
|---|---|
| 175 | (structure) |
| 176 | (structure) |
| 177 | (structure) |
| 178 | (structure) |
| 179 | (structure) |

TABLE 20-continued

| No. | Structure |
|---|---|
| 180 | (structure) |
| 181 | (structure) |
| 182 | (structure) |
| 183 | (structure) |
| 184 | (structure) |

TABLE 20-continued
| No. | Structure |
|---|---|
| 185 | 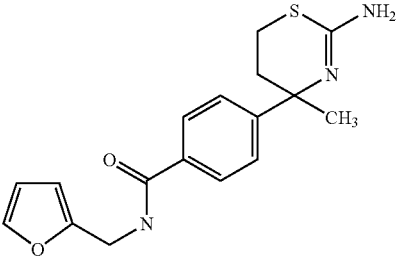 [SMILES: CC1(c2ccc(C(=O)NCc3ccco3)cc2)CCSC(N)=N1] |
TABLE 21
| No. | Structure |
|---|---|
| 186 | 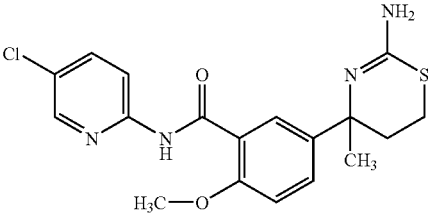 [SMILES: COc1ccc(C2(C)CCSC(N)=N2)cc1C(=O)Nc1ccc(Cl)cn1] |
| 187 | 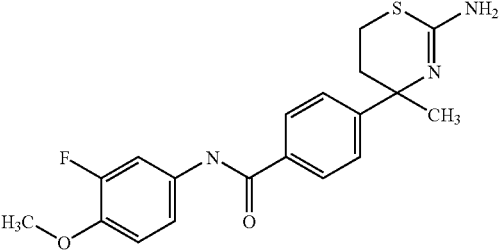 |
| 188 | 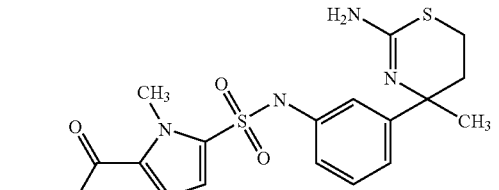 |
| 189 | 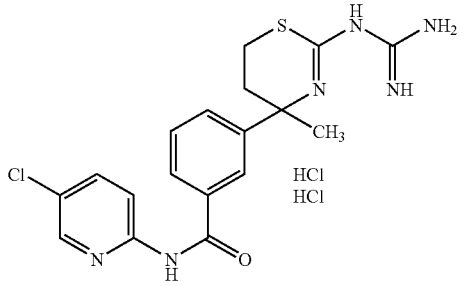 [SMILES: CC1(c2cccc(C(=O)Nc3ccc(Cl)cn3)c2)CCSC(NC(=N)N)=N1 ; Cl ; Cl] |
TABLE 21-continued
| No. | Structure |
|---|---|
| 190 | 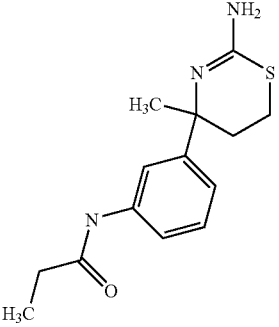 [SMILES: CCC(=O)Nc1cccc(C2(C)CCSC(N)=N2)c1] |
| 191 | 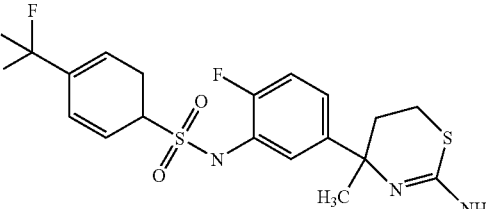 |
| 192 | 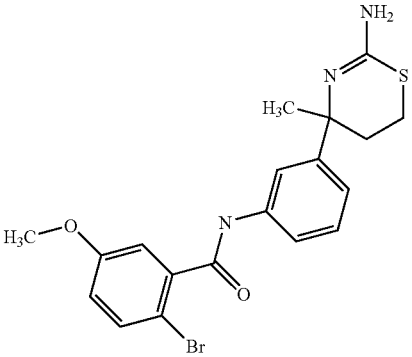 [SMILES: COc1ccc(Br)c(C(=O)Nc2cccc(C3(C)CCSC(N)=N3)c2)c1] |
| 193 | 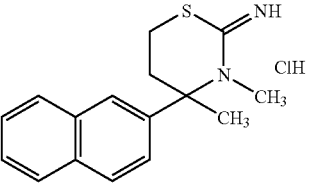 [SMILES: CN1C(=N)SCCC1(C)c1ccc2ccccc2c1 ; Cl] |
| 194 | 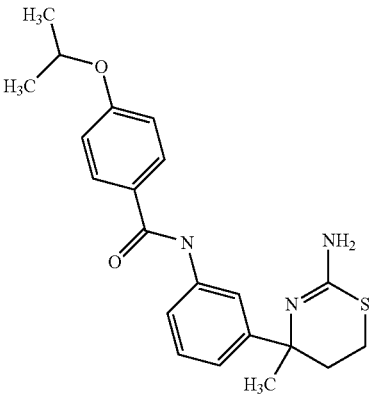 [SMILES: CC(C)Oc1ccc(C(=O)Nc2cccc(C3(C)CCSC(N)=N3)c2)cc1] |

TABLE 22
| No. | Structure |
|---|---|
| 195 | 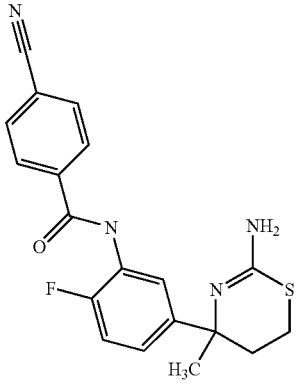 [SMILES: CC1(c2ccc(F)c(NC(=O)c3ccc(C#N)cc3)c2)CCSC(N)=N1] |
| 196 | 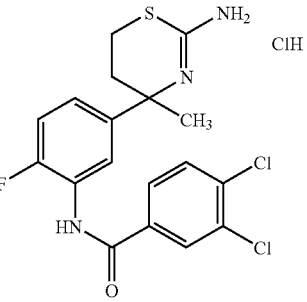 |
| 197 | 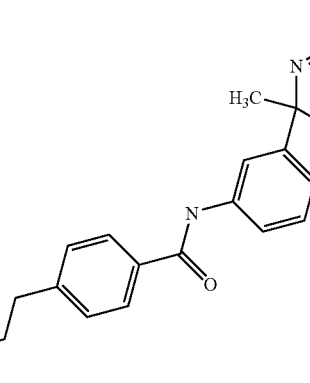 |
| 198 | 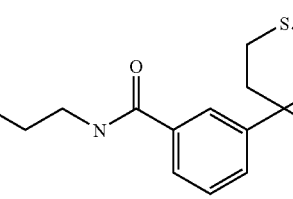 |
| 199 | 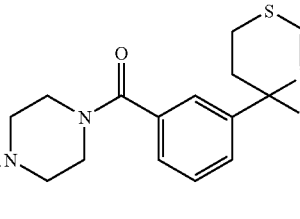 |
TABLE 22-continued
| No. | Structure |
|---|---|
| 200 | 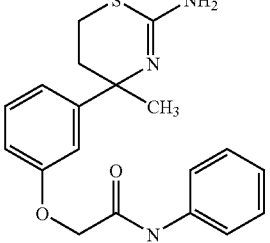 |
| 201 | 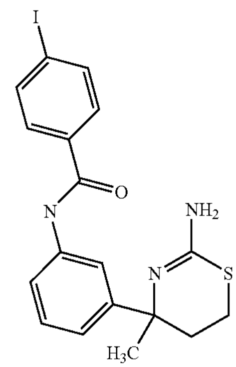 [SMILES: CC1(c2cccc(NC(=O)c3ccc(I)cc3)c2)CCSC(N)=N1] |
| 202 | 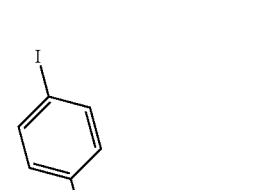 |
| 203 | 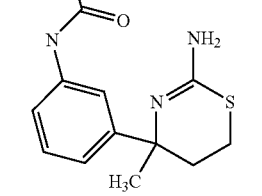 |
| 204 | 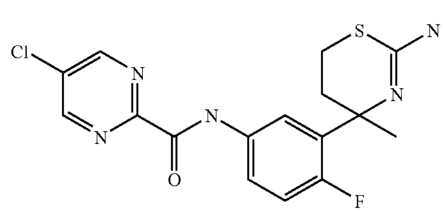 [SMILES: CC1(c2cc(NC(=O)c3ncc(Cl)cn3)ccc2F)CCSC(N)=N1] |

TABLE 23
| No. | Structure |
|---|---|
| 205 | 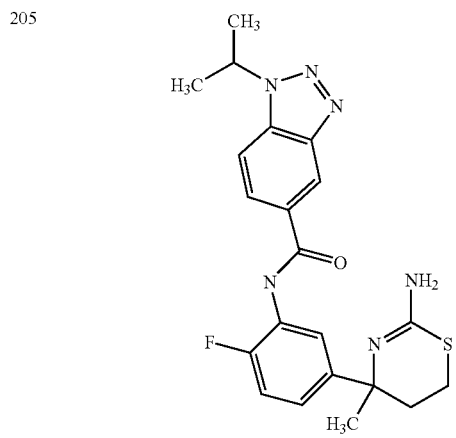 |
| 206 | 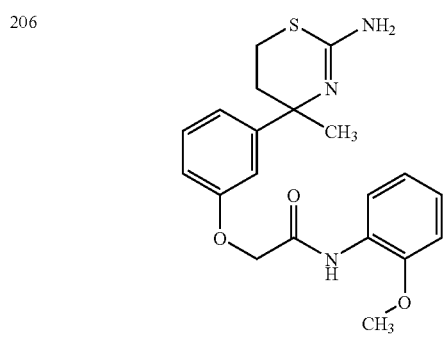 |
| 207 | 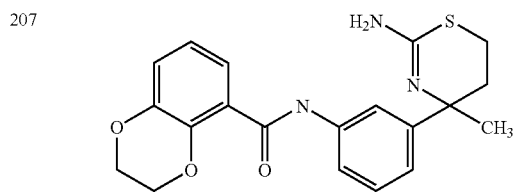 |
| 208 | 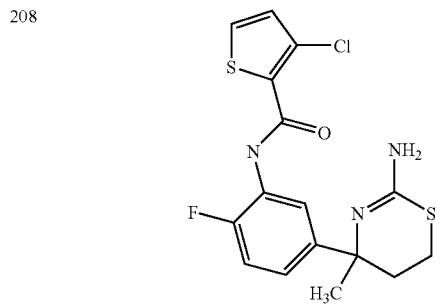 |
TABLE 23-continued
| No. | Structure |
|---|---|
| 209 | 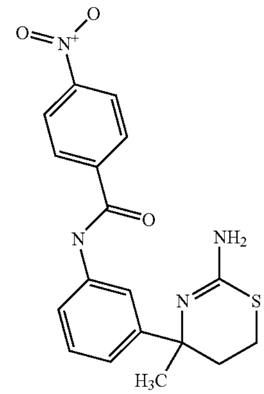 |
| 210 | 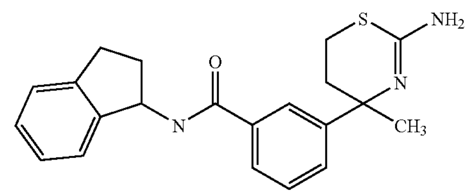 [SMILES: CC1(c2cccc(C(=O)NC3CCc4ccccc43)c2)CCSC(N)=N1] |
| 211 | 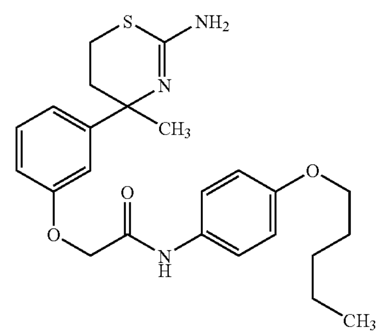 [SMILES: CCCCCOc1ccc(NC(=O)COc2cccc(C3(C)CCSC(N)=N3)c2)cc1] |
| 212 | 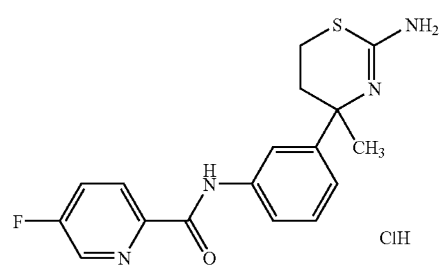 [SMILES: CC1(c2cccc(NC(=O)c3ccc(F)cn3)c2)CCSC(N)=N1 ; Cl] |
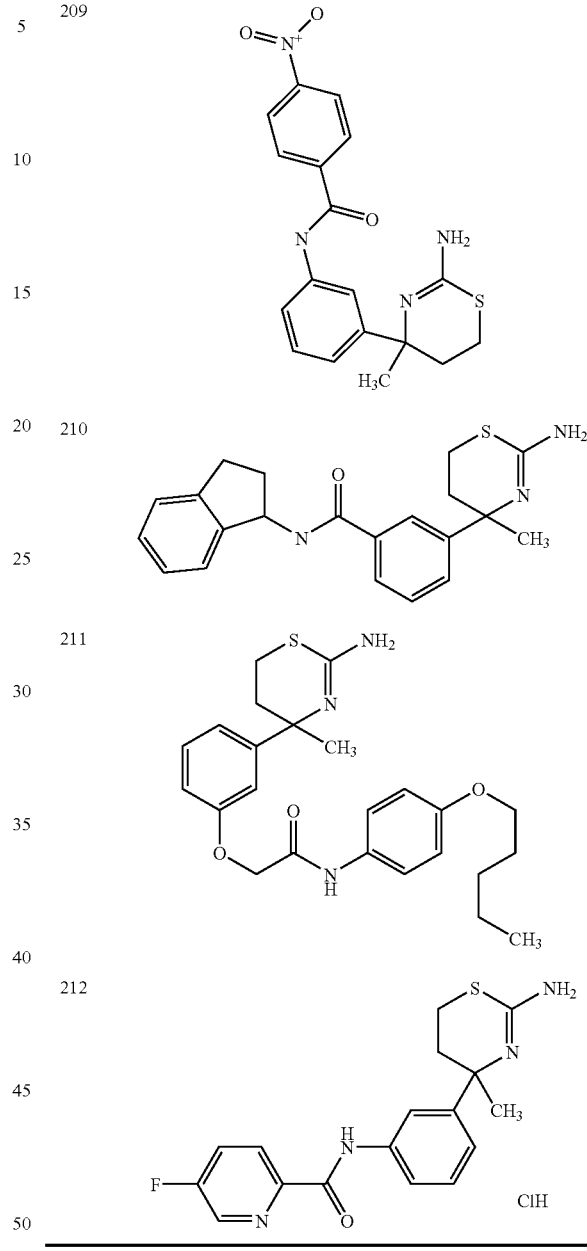
TABLE 24
| No. | Structure |
|---|---|
| 213 | 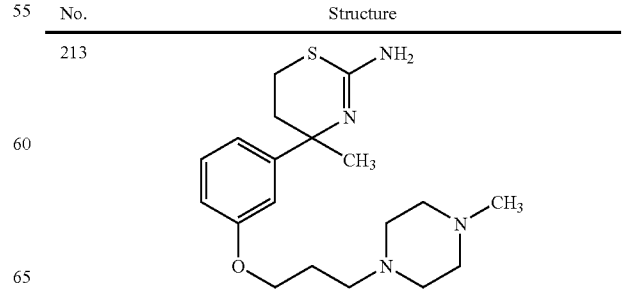 |

TABLE 24-continued
| No. | Structure |
|---|---|
| 214 | 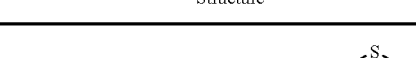 |
| 215 | 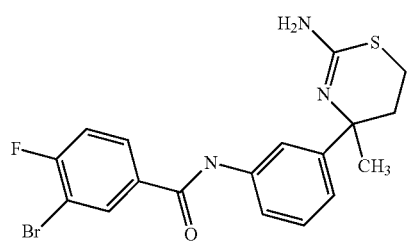 [SMILES: CC1(c2cccc(NC(=O)c3ccc(F)c(Br)c3)c2)CCSC(N)=N1] |
| 216 | 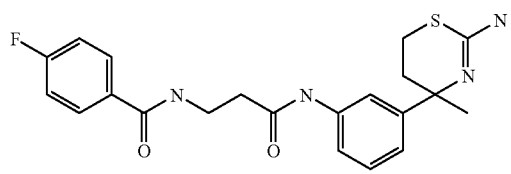 |
| 217 | 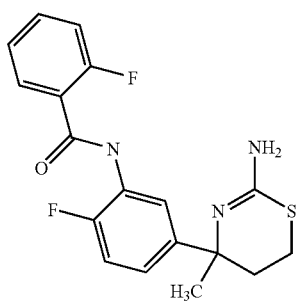 |
| 218 | 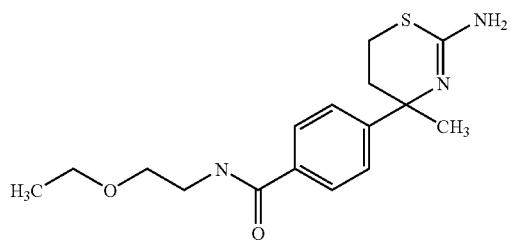 [SMILES: CCOCCNC(=O)c1ccc(C2(C)CCSC(N)=N2)cc1] |
| 219 | 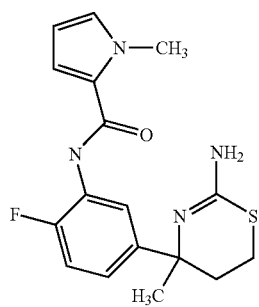 [SMILES: Cn1cccc1C(=O)Nc1cc(C2(C)CCSC(N)=N2)ccc1F] |
TABLE 24-continued
| No. | Structure |
|---|---|
| 220 | 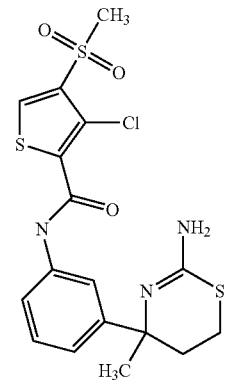 ClH ClH |
| 221 | 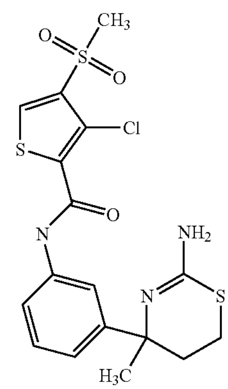 [SMILES: CC1(c2cccc(NC(=O)c3scc(S(C)(=O)=O)c3Cl)c2)CCSC(N)=N1] |
| 222 | 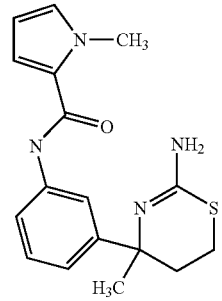 [SMILES: Cn1cccc1C(=O)Nc1cccc(C2(C)CCSC(N)=N2)c1] |
TABLE 25
| No. | Structure |
|---|---|
| 223 | 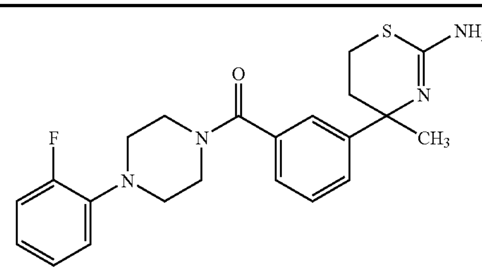 |
| 224 | 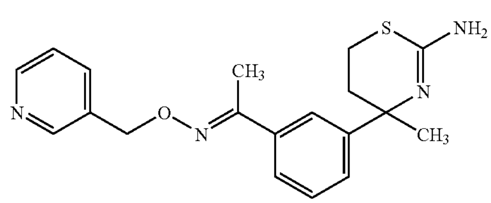 |

TABLE 25-continued
| No. | Structure |
|---|---|
| 225 | 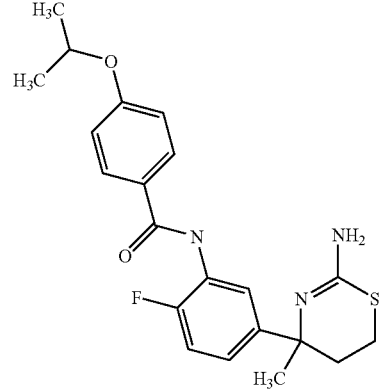 [SMILES: CC(C)Oc1ccc(C(=O)Nc2cc(C3(C)CCSC(N)=N3)ccc2F)cc1] |
| 226 | 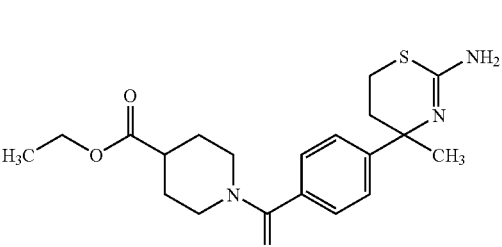 |
| 227 | 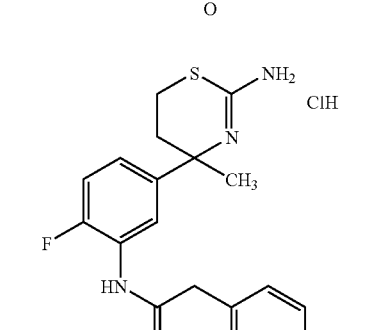 |
| 228 | 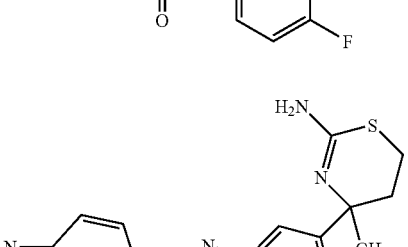 |
| 229 | 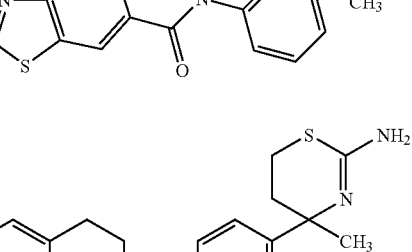 |
TABLE 25-continued
| No. | Structure |
|---|---|
| 230 | |
| 231 | |
| 232 | |
TABLE 26
| No. | Structure |
|---|---|
| 233 | 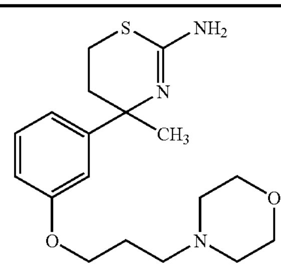 |
| 234 | 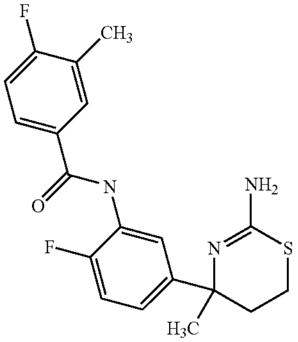 |

TABLE 26-continued
| No. | Structure |
|---|---|
| 235 | 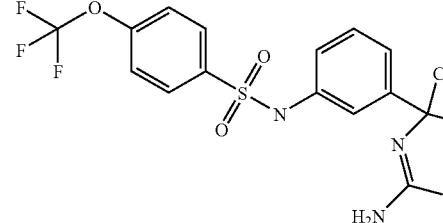 |
| 236 | 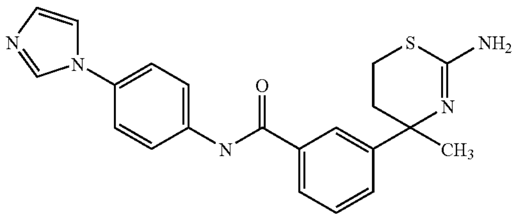 [SMILES: CC1(c2cccc(C(=O)Nc3ccc(-n4ccnc4)cc3)c2)CCSC(N)=N1] |
| 237 | 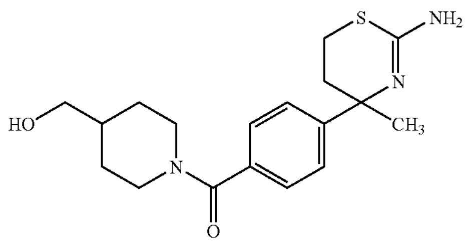 [SMILES: CC1(c2ccc(C(=O)N3CCC(CO)CC3)cc2)CCSC(N)=N1] |
| 238 | 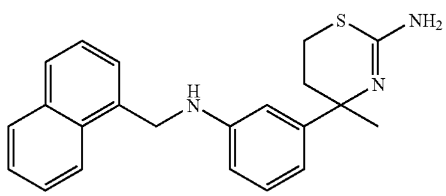 [SMILES: CC1(c2cccc(NCc3cccc4ccccc34)c2)CCSC(N)=N1] |
| 239 | 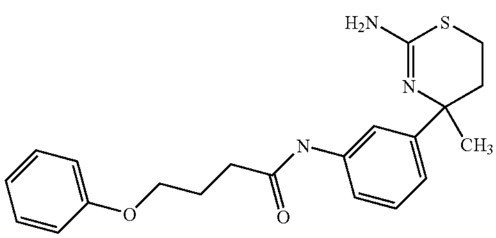 [SMILES: CC1(c2cccc(NC(=O)CCCOc3ccccc3)c2)CCSC(N)=N1] |
| 240 | 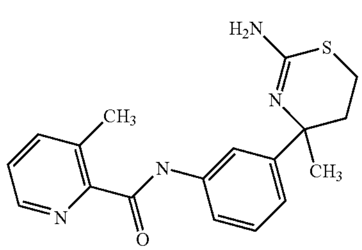 [SMILES: Cc1cccnc1C(=O)Nc1cccc(C2(C)CCSC(N)=N2)c1] |
| 241 | 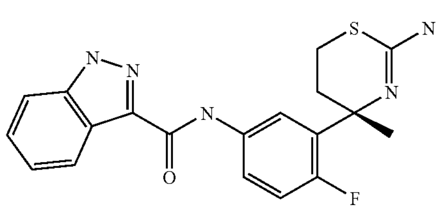 |
TABLE 26-continued
| No. | Structure |
|---|---|
| 242 | 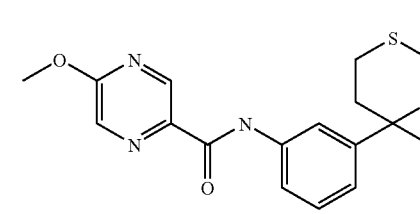 |
| 243 | |
TABLE 27
| No. | Structure |
|---|---|
| 244 | 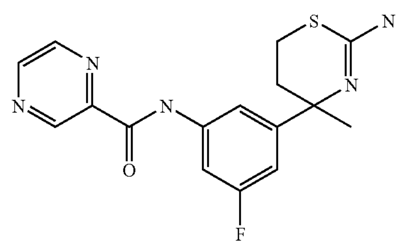 [SMILES: CC1(c2cc(F)cc(NC(=O)c3cnccn3)c2)CCSC(N)=N1] |
| 245 | 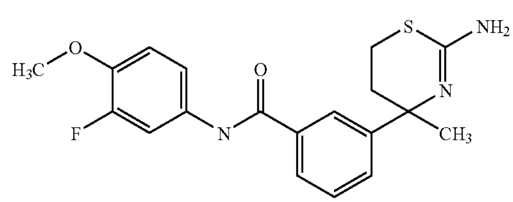 [SMILES: COc1ccc(NC(=O)c2cccc(C3(C)CCSC(N)=N3)c2)cc1F] |
| 246 | 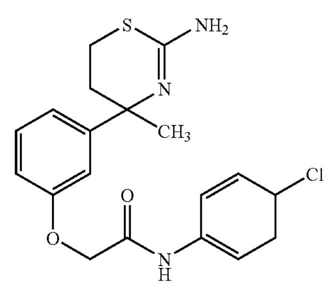 [SMILES: CC1(c2cccc(OCC(=O)NC3=CCC(Cl)C=C3)c2)CCSC(N)=N1] |

TABLE 27-continued
| No. | Structure |
|---|---|
| 247 | 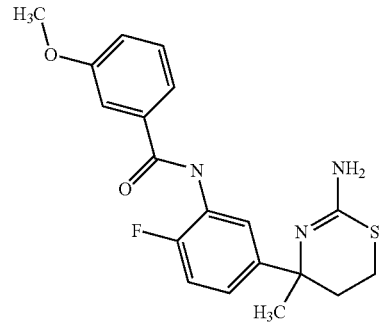 [SMILES: COc1cccc(C(=O)Nc2cc(C3(C)CCSC(N)=N3)ccc2F)c1] |
| 248 | 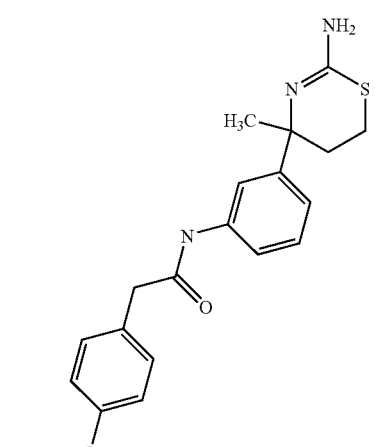 |
| 249 | 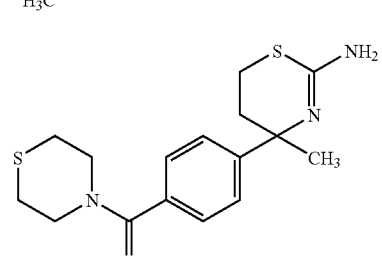 |
| 250 | 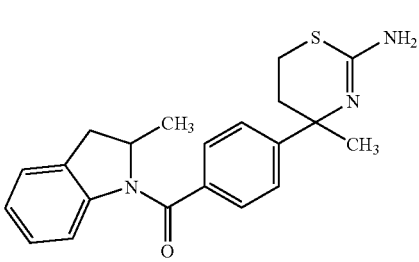 [SMILES: CC1Cc2ccccc2N1C(=O)c1ccc(C2(C)CCSC(N)=N2)cc1] |
| 251 | 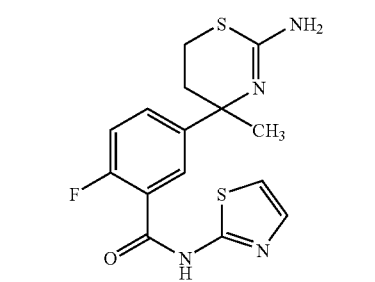 [SMILES: CC1(c2ccc(F)c(C(=O)Nc3nccs3)c2)CCSC(N)=N1] |
| 252 | 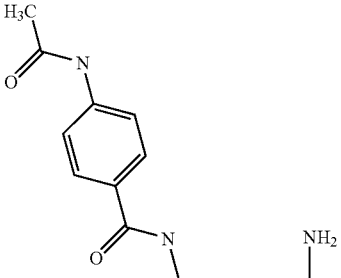 |
| 253 | 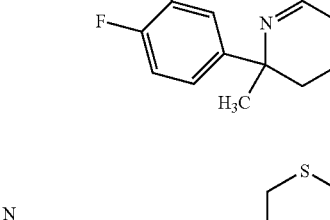 |
TABLE 28
| No. | Structure |
|---|---|
| 254 | 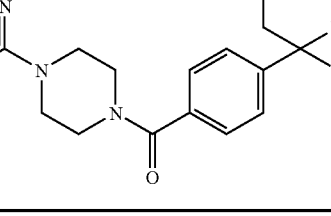 |
| 255 | 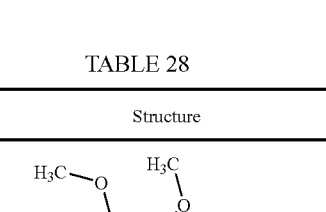 |

TABLE 28-continued
| No. | Structure |
|---|---|
| 256 | 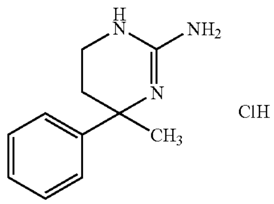 |
| 257 | 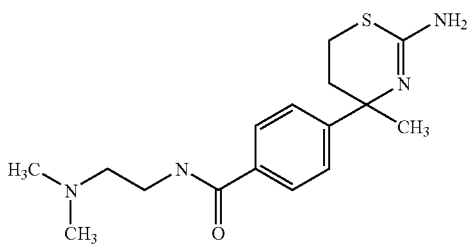 [SMILES: CN(C)CCNC(=O)c1ccc(C2(C)CCSC(N)=N2)cc1] |
| 258 | 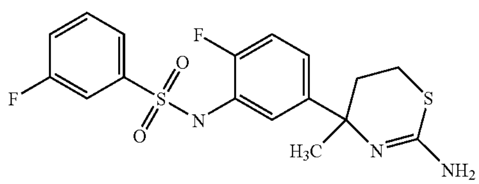 [SMILES: CC1(c2ccc(F)c(NS(=O)(=O)c3cccc(F)c3)c2)CCSC(N)=N1] |
| 259 | 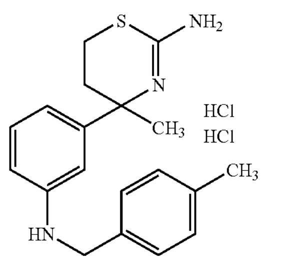 [SMILES: Cc1ccc(CNc2cccc(C3(C)CCSC(N)=N3)c2)cc1 ; Cl ; Cl] |
| 260 | 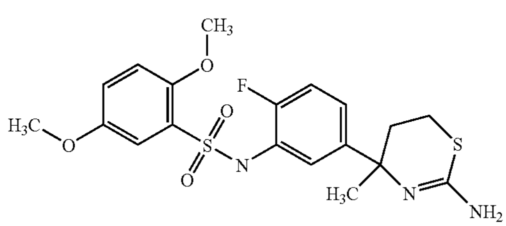 [SMILES: COc1ccc(OC)c(S(=O)(=O)Nc2cc(C3(C)CCSC(N)=N3)ccc2F)c1] |
| 261 | 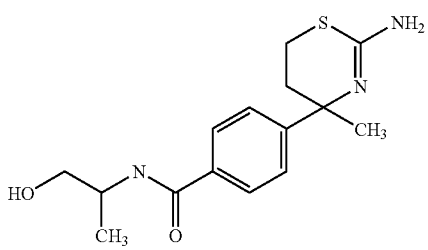 [SMILES: CC(CO)NC(=O)c1ccc(C2(C)CCSC(N)=N2)cc1] |
TABLE 28-continued
| No. | Structure |
|---|---|
| 262 |  |
| 263 | |
| 264 | |
TABLE 29
| No. | Structure |
|---|---|
| 265 | 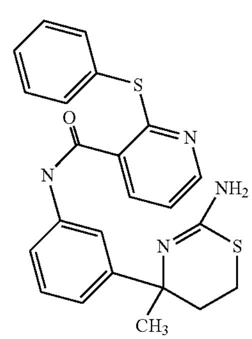 [SMILES: CC1(c2cccc(NC(=O)c3cccnc3Sc3ccccc3)c2)CCSC(N)=N1] |

TABLE 29-continued
| No. | Structure |
|---|---|
| 266 | 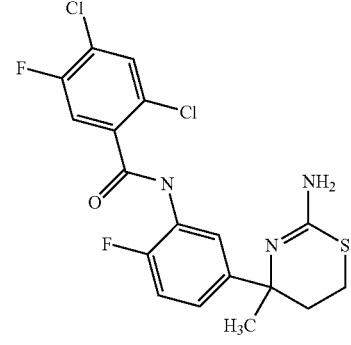 [SMILES: CC1(c2ccc(F)c(NC(=O)c3cc(F)c(Cl)cc3Cl)c2)CCSC(N)=N1] |
| 267 | 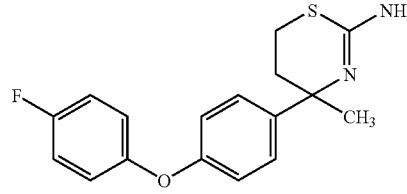 |
| 268 | 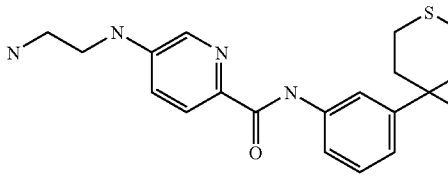 |
| 269 | 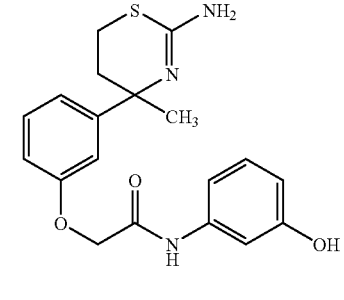 [SMILES: CC1(c2cccc(OCC(=O)Nc3cccc(O)c3)c2)CCSC(N)=N1] |
| 270 | 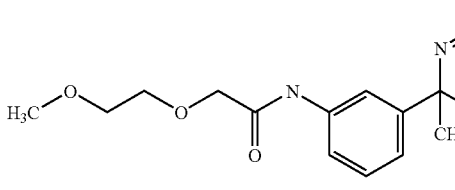 |
| 271 | 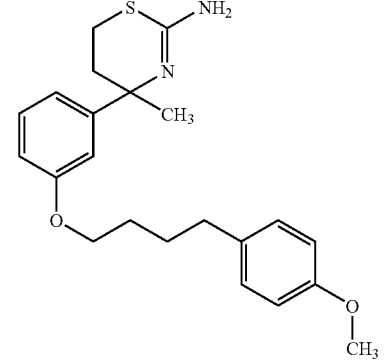 [SMILES: COc1ccc(CCCCOc2cccc(C3(C)CCSC(N)=N3)c2)cc1] |
TABLE 29-continued
| No. | Structure |
|---|---|
| 272 | 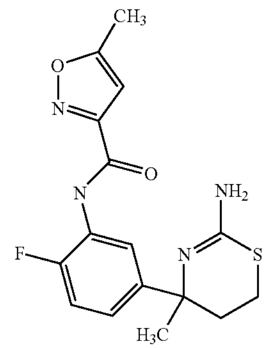 [SMILES: Cc1cc(C(=O)Nc2cc(C3(C)CCSC(N)=N3)ccc2F)no1] |
| 273 | 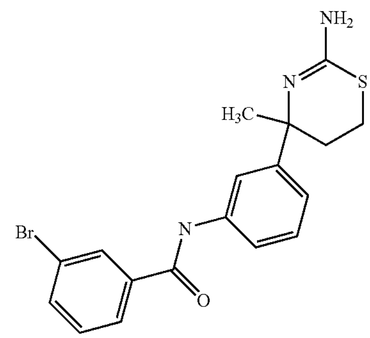 |
TABLE 30
| No. | Structure |
|---|---|
| 274 | 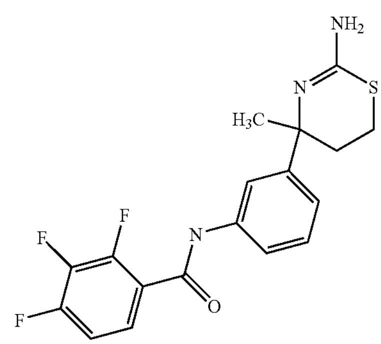 [SMILES: CC1(c2cccc(NC(=O)c3ccc(F)c(F)c3F)c2)CCSC(N)=N1] |
| 275 | 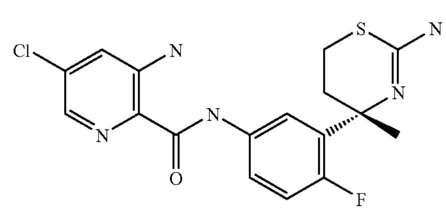 |

TABLE 30-continued

| No. | Structure |
|---|---|
| 276 | 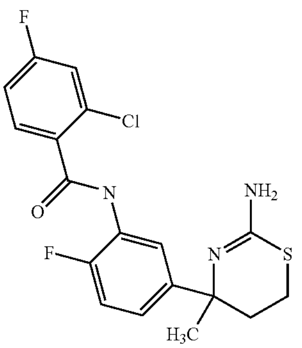 |
| 277 | 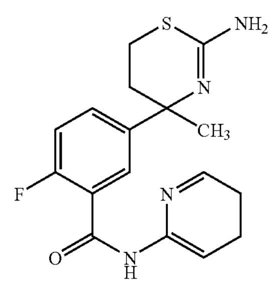 [SMILES: CC1(c2ccc(F)c(C(=O)NC3=CCCC=N3)c2)CCSC(N)=N1] |
| 278 | 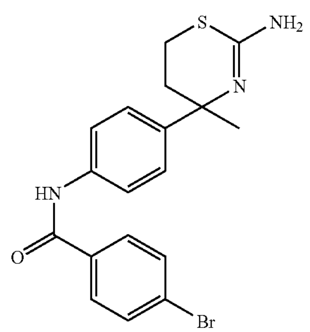 [SMILES: CC1(c2ccc(NC(=O)c3ccc(Br)cc3)cc2)CCSC(N)=N1] |
| 279 | 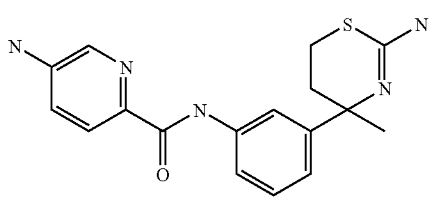 [SMILES: CC1(c2cccc(NC(=O)c3ccc(N)cn3)c2)CCSC(N)=N1] |
| 280 | 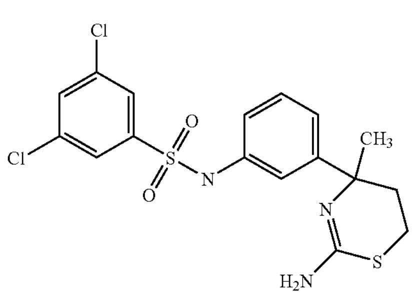 [SMILES: CC1(c2cccc(NS(=O)(=O)c3cc(Cl)cc(Cl)c3)c2)CCSC(N)=N1] |

TABLE 30-continued

| No. | Structure |
|---|---|
| 281 | |

TABLE 31

| No. | Structure |
|---|---|
| 282 | 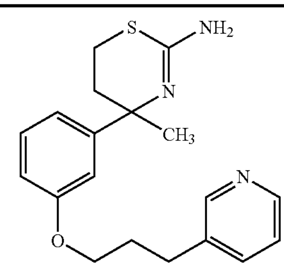 |
| 283 | 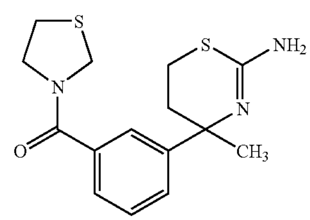 [SMILES: CC1(c2cccc(C(=O)N3CCSC3)c2)CCSC(N)=N1] |
| 284 | 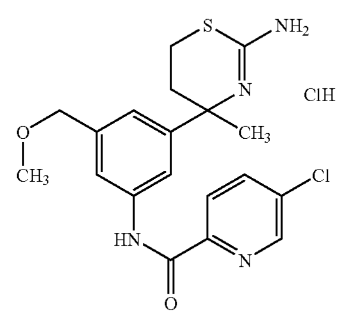 [SMILES: COCc1cc(NC(=O)c2ccc(Cl)cn2)cc(C2(C)CCSC(N)=N2)c1 ; Cl] |
| 285 | 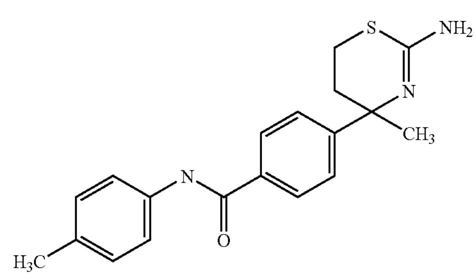 [SMILES: Cc1ccc(NC(=O)c2ccc(C3(C)CCSC(N)=N3)cc2)cc1] |

TABLE 31-continued
| No. | Structure |
|---|---|
| 286 | 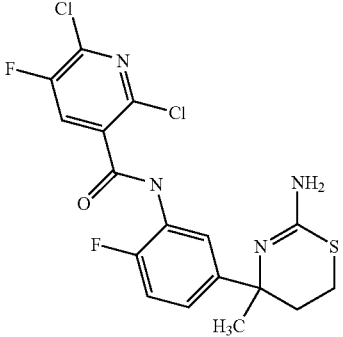 |
| 287 | 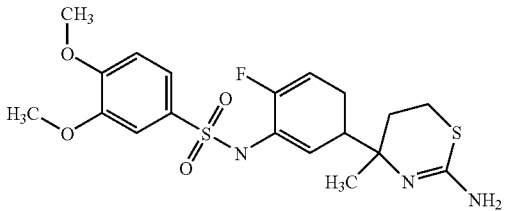 [SMILES: COc1ccc(S(=O)(=O)NC2=CC(C3(C)CCSC(N)=N3)CC=C2F)cc1OC] |
| 288 | 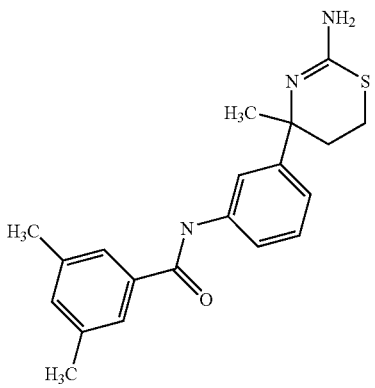 [SMILES: Cc1cc(C)cc(C(=O)Nc2cccc(C3(C)CCSC(N)=N3)c2)c1] |
| 289 | 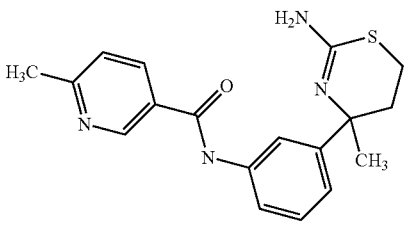 [SMILES: Cc1ccc(C(=O)Nc2cccc(C3(C)CCSC(N)=N3)c2)cn1] |
| 290 | 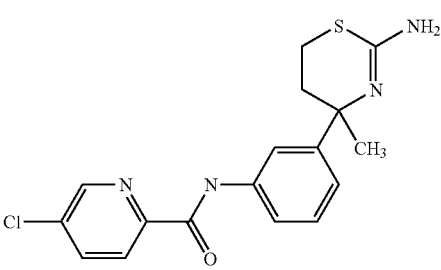 [SMILES: CC1(c2cccc(NC(=O)c3ccc(Cl)cn3)c2)CCSC(N)=N1] |
| 291 | 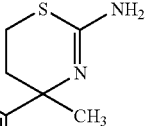 |
TABLE 32
| No. | Structure |
|---|---|
| 292 | 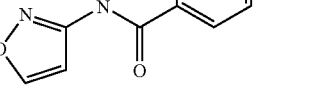 |
| 293 | 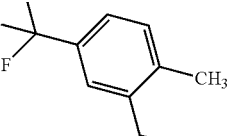 |
| 294 | 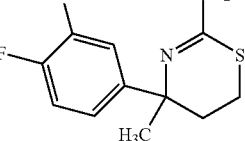 |
| 295 | 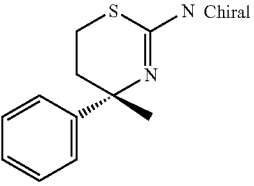 |

TABLE 32-continued
| No. | Structure |
|---|---|
| 296 | 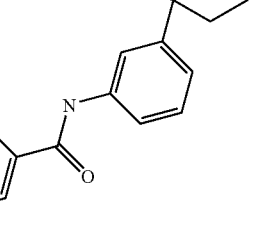 |
| 297 | 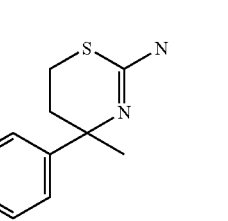 |
| 298 | 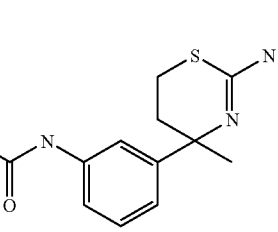 |
| 299 | 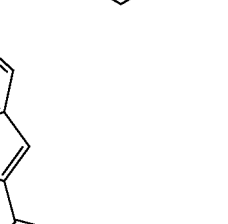 |
TABLE 33
| No. | Structure |
|---|---|
| 300 | 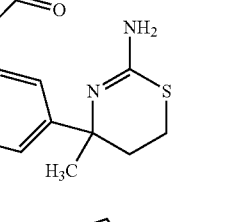 |
| 301 | 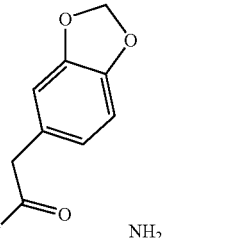 |
| 302 | 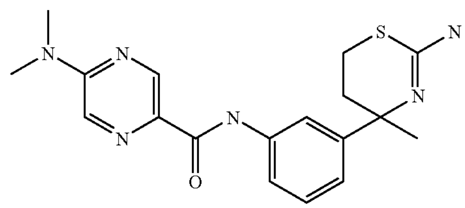 [SMILES: CN(C)c1cnc(C(=O)Nc2cccc(C3(C)CCSC(N)=N3)c2)cn1] |
| 303 | 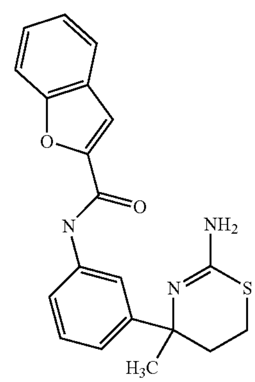 [SMILES: CC1(c2cccc(NC(=O)c3cc4ccccc4o3)c2)CCSC(N)=N1] |
| 304 | 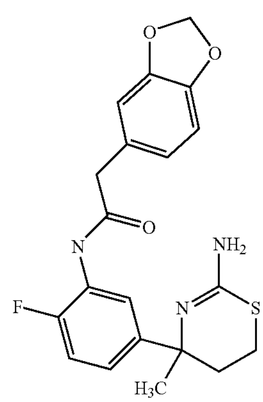 [SMILES: CC1(c2ccc(F)c(NC(=O)Cc3ccc4c(c3)OCO4)c2)CCSC(N)=N1] |

TABLE 33-continued
| No. | Structure |
|---|---|
| 305 | 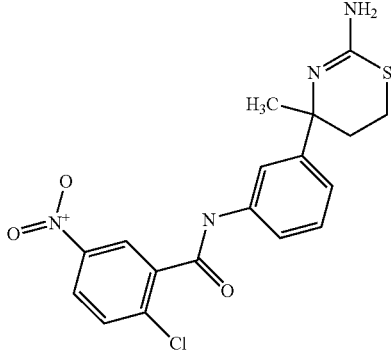 |
| 306 | 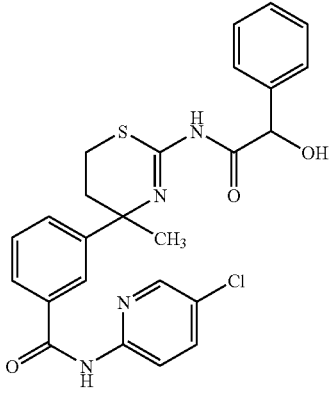 [SMILES: CC1(c2cccc(C(=O)Nc3ccc(Cl)cn3)c2)CCSC(NC(=O)C(O)c2ccccc2)=N1] |
| 307 | 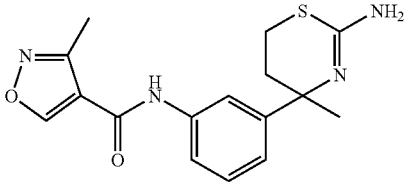 [SMILES: Cc1nocc1C(=O)Nc1cccc(C2(C)CCSC(N)=N2)c1] |
| 308 | 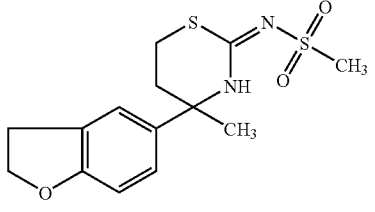 [SMILES: CC1(c2ccc3c(c2)CCO3)CCS/C(=N/S(C)(=O)=O)N1] |
| 309 | 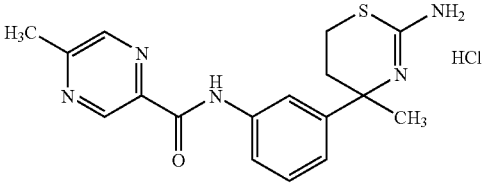 [SMILES: Cc1cnc(C(=O)Nc2cccc(C3(C)CCSC(N)=N3)c2)cn1 ; Cl] |
TABLE 34
| No. | Structure |
|---|---|
| 310 | 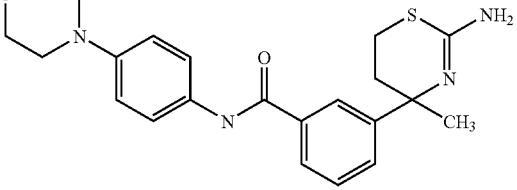 |
| 311 | 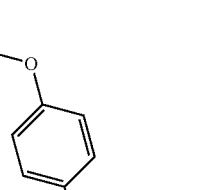 |
| 312 | 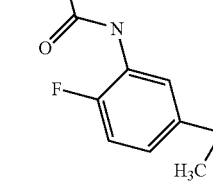 |
| 313 | 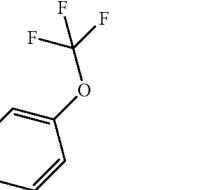 |
| 314 | 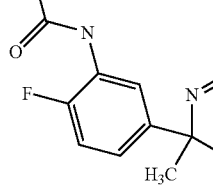 |

TABLE 34-continued
| No. | Structure |
|---|---|
| 315 | 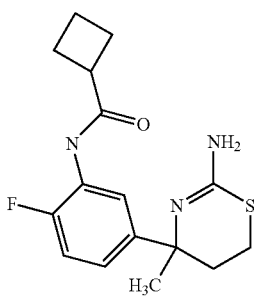 [SMILES: CC1(c2ccc(F)c(NC(=O)C3CCC3)c2)CCSC(N)=N1] |
| 316 | 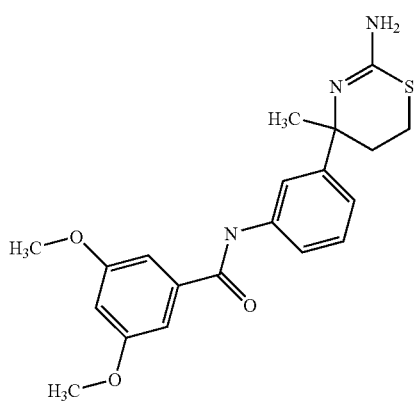 [SMILES: COc1cc(OC)cc(C(=O)Nc2cccc(C3(C)CCSC(N)=N3)c2)c1] |
| 317 | 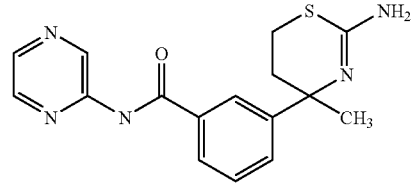 [SMILES: CC1(c2cccc(C(=O)Nc3cnccn3)c2)CCSC(N)=N1] |
TABLE 35
| No. | Structure |
|---|---|
| 318 | 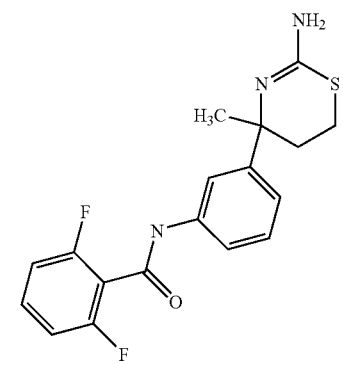 [SMILES: CC1(c2cccc(NC(=O)c3c(F)cccc3F)c2)CCSC(N)=N1] |
| 319 | 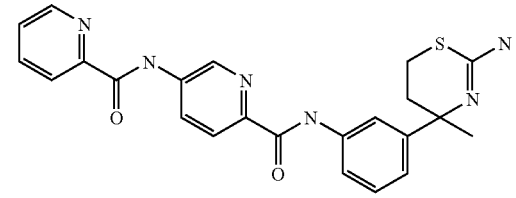 [SMILES: CC1(c2cccc(NC(=O)c3ccc(NC(=O)c4ccccn4)cn3)c2)CCSC(N)=N1] |
| 320 | 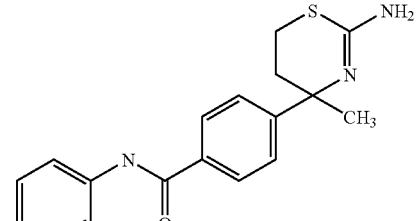 |
| 321 | 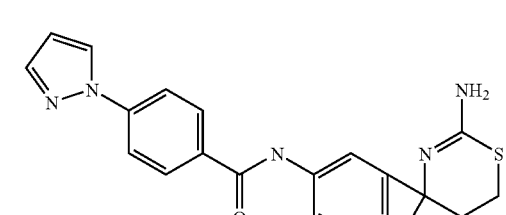 |
| 322 | 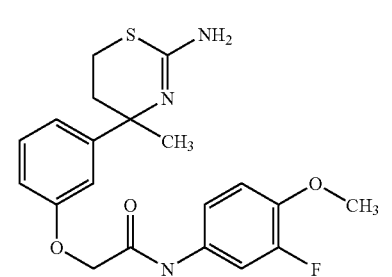 |
| 323 | 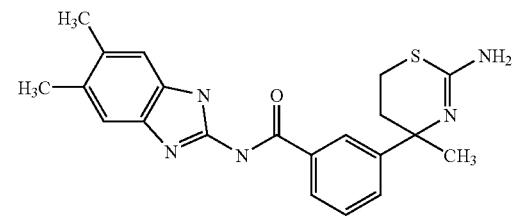 [SMILES: Cc1cc2nc(NC(=O)c3cccc(C4(C)CCSC(N)=N4)c3)[nH]c2cc1C] |
| 324 | 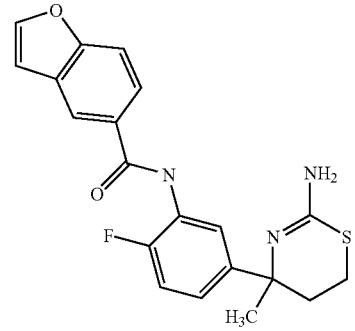 [SMILES: CC1(c2ccc(F)c(NC(=O)c3ccc4occc4c3)c2)CCSC(N)=N1] |

TABLE 35-continued
| No. | Structure |
|---|---|
| 325 | 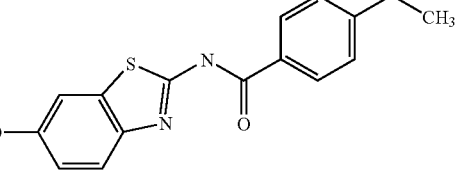 |
| 326 | 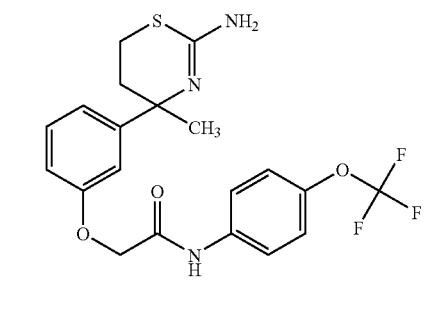 [SMILES: CC1(c2cccc(OCC(=O)Nc3ccc(OC(F)(F)F)cc3)c2)CCSC(N)=N1] |
| 327 | 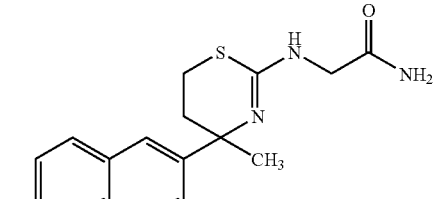 |
| 328 | 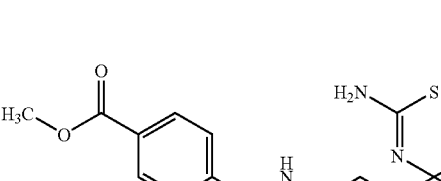 |
TABLE 36
| No. | Structure |
|---|---|
| 329 | 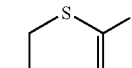 |
| 330 | 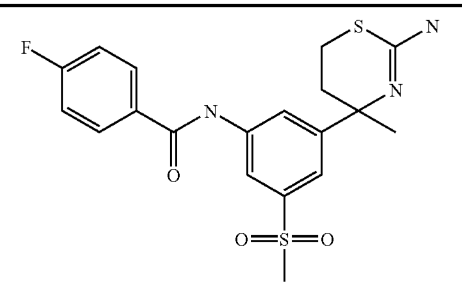 |
| 331 | 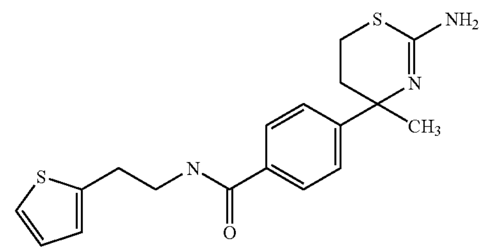 [SMILES: CC1(c2ccc(C(=O)NCCc3cccs3)cc2)CCSC(N)=N1] |
| 332 | 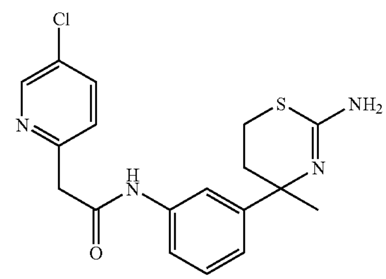 [SMILES: CC1(c2cccc(NC(=O)Cc3ccc(Cl)cn3)c2)CCSC(N)=N1] |
| 333 | 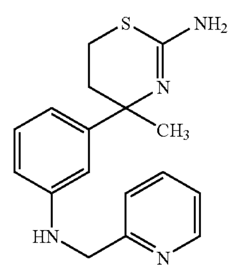 [SMILES: CC1(c2cccc(NCc3ccccn3)c2)CCSC(N)=N1] |
| 334 | 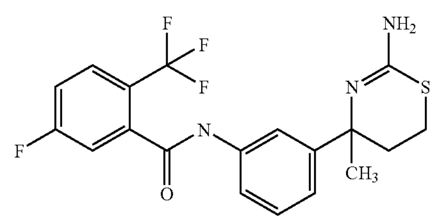 [SMILES: CC1(c2cccc(NC(=O)c3cc(F)ccc3C(F)(F)F)c2)CCSC(N)=N1] |
| 335 | 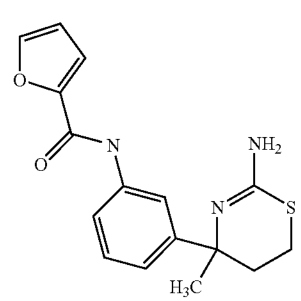 [SMILES: CC1(c2cccc(NC(=O)c3ccco3)c2)CCSC(N)=N1] |

TABLE 36-continued

| No. | Structure |
|---|---|
| 336 | 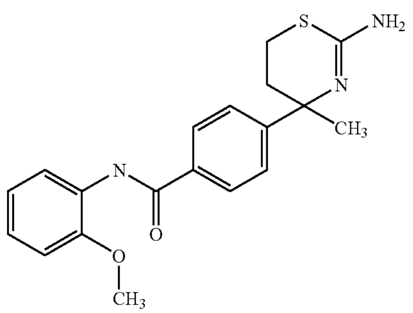 [SMILES: COc1ccccc1NC(=O)c1ccc(C2(C)CCSC(N)=N2)cc1] |
| 337 | 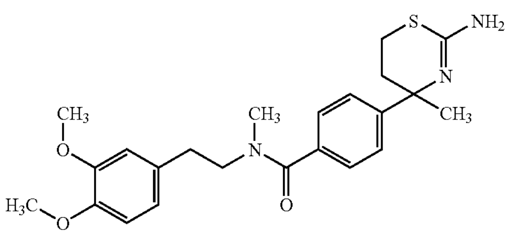 [SMILES: COc1ccc(CCN(C)C(=O)c2ccc(C3(C)CCSC(N)=N3)cc2)cc1OC] |
| 338 | 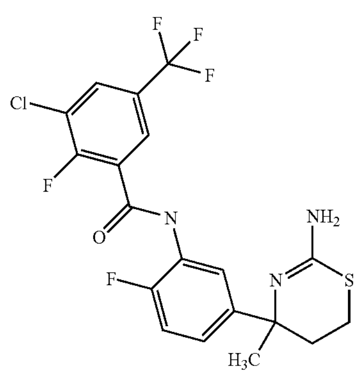 [SMILES: CC1(c2ccc(F)c(NC(=O)c3cc(C(F)(F)F)cc(Cl)c3F)c2)CCSC(N)=N1] |
| 339 | 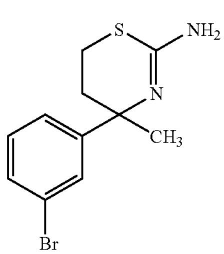 |

TABLE 37

| No. | Structure |
|---|---|
| 340 | 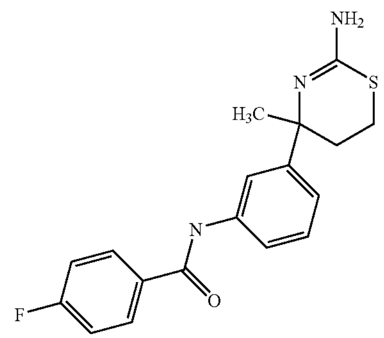 [SMILES: CC1(c2cccc(NC(=O)c3ccc(F)cc3)c2)CCSC(N)=N1] |
| 341 | 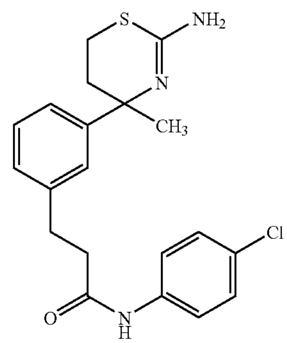 [SMILES: CC1(c2cccc(CCC(=O)Nc3ccc(Cl)cc3)c2)CCSC(N)=N1] |
| 342 | 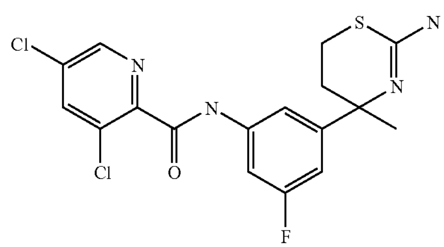 [SMILES: CC1(c2cc(F)cc(NC(=O)c3ncc(Cl)cc3Cl)c2)CCSC(N)=N1] |
| 343 | 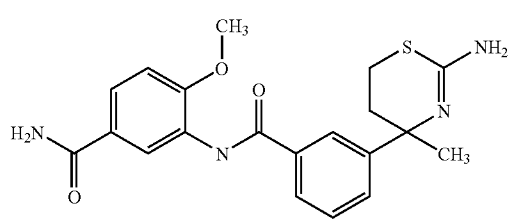 [SMILES: COc1ccc(C(N)=O)cc1NC(=O)c1cccc(C2(C)CCSC(N)=N2)c1] |
| 344 | 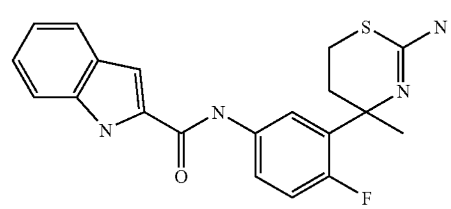 [SMILES: CC1(c2cc(NC(=O)c3cc4ccccc4[nH]3)ccc2F)CCSC(N)=N1] |

TABLE 37-continued

| No. | Structure |
|---|---|
| 345 | 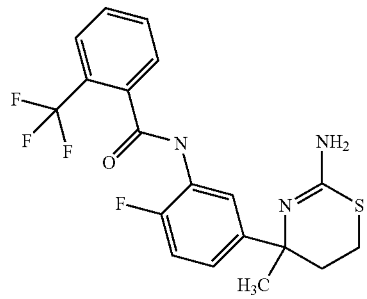 [SMILES: CC1(c2ccc(F)c(NC(=O)c3ccccc3C(F)(F)F)c2)CCSC(N)=N1] |
| 346 | 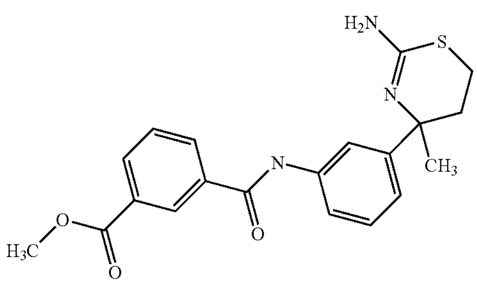 [SMILES: COC(=O)c1cccc(C(=O)Nc2cccc(C3(C)CCSC(N)=N3)c2)c1] |
| 347 | 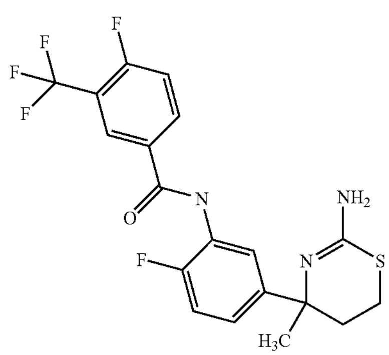 [SMILES: CC1(c2ccc(F)c(NC(=O)c3ccc(F)c(C(F)(F)F)c3)c2)CCSC(N)=N1] |
| 348 | 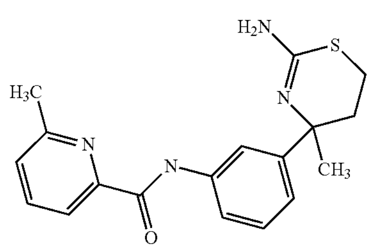 [SMILES: Cc1cccc(C(=O)Nc2cccc(C3(C)CCSC(N)=N3)c2)n1] |

TABLE 38

| No. | Structure |
|---|---|
| 349 | 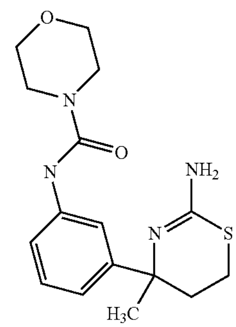 [SMILES: CC1(c2cccc(NC(=O)N3CCOCC3)c2)CCSC(N)=N1] |
| 350 | 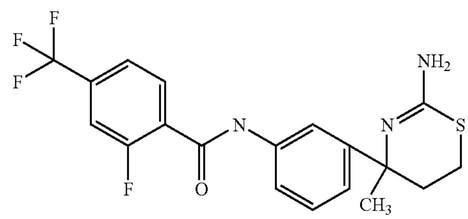 [SMILES: CC1(c2cccc(NC(=O)c3ccc(C(F)(F)F)cc3F)c2)CCSC(N)=N1] |
| 351 | 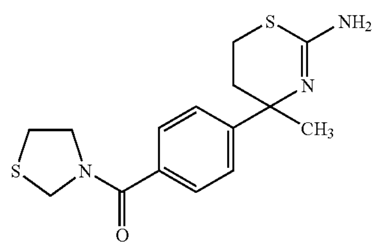 [SMILES: CC1(c2ccc(C(=O)N3CCSC3)cc2)CCSC(N)=N1] |
| 352 | 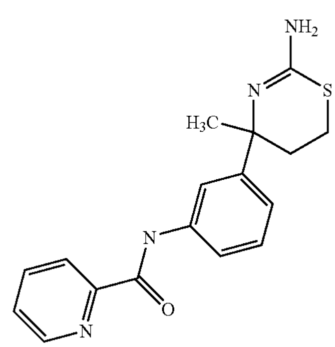 [SMILES: CC1(c2cccc(NC(=O)c3ccccn3)c2)CCSC(N)=N1] |
| 353 | 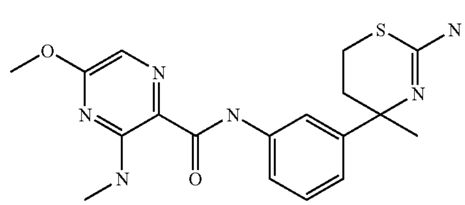 [SMILES: CNc1nc(OC)cnc1C(=O)Nc1cccc(C2(C)CCSC(N)=N2)c1] |

TABLE 38-continued
| No. | Structure |
|-----|-----------|
| 354 | 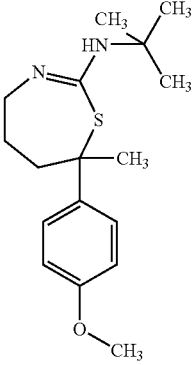 [SMILES: COc1ccc(C2(C)CCCN=C(NC(C)(C)C)S2)cc1] |
| 355 | 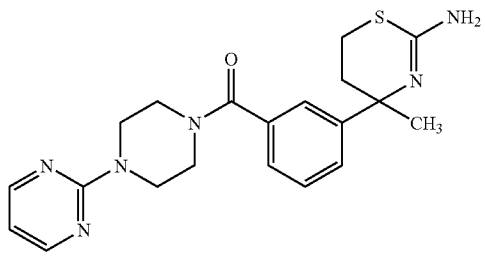 [SMILES: CC1(c2cccc(C(=O)N3CCN(c4ncccn4)CC3)c2)CCSC(N)=N1] |
| 356 | 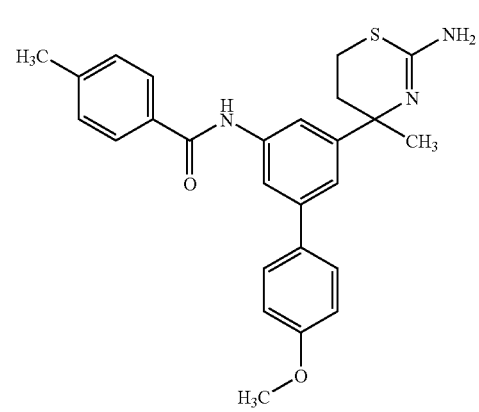 [SMILES: COc1ccc(-c2cc(NC(=O)c3ccc(C)cc3)cc(C3(C)CCSC(N)=N3)c2)cc1] |
| 357 | 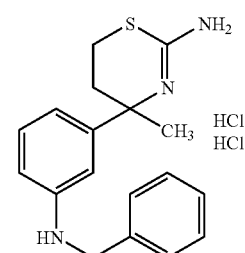 |
TABLE 39
| No. | Structure |
|-----|-----------|
| 358 | 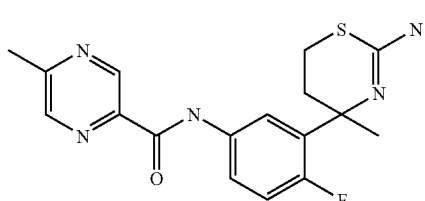 |
| 359 | 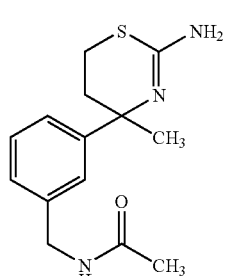 |
| 360 | 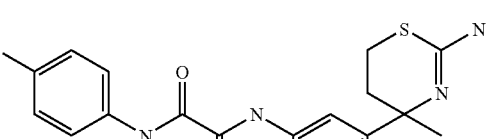 |
| 361 | 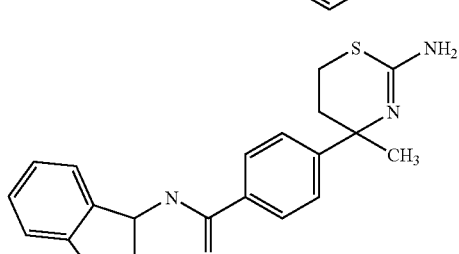 |
| 362 | 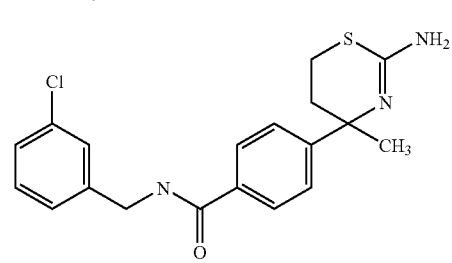 [SMILES: CC1(c2ccc(C(=O)NCc3cccc(Cl)c3)cc2)CCSC(N)=N1] |
| 363 | 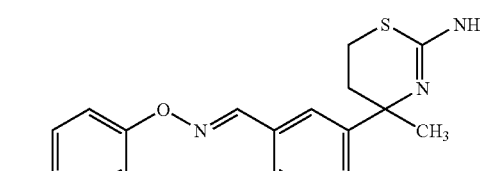 |
| 364 | 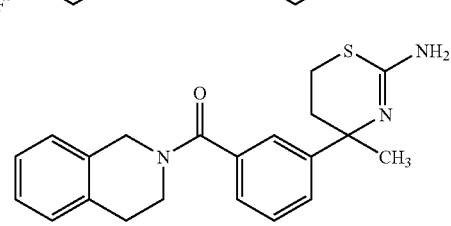 |
| 365 | 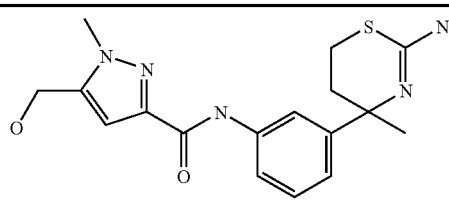 |

TABLE 39-continued

| No. | Structure |
|---|---|
| 366 | 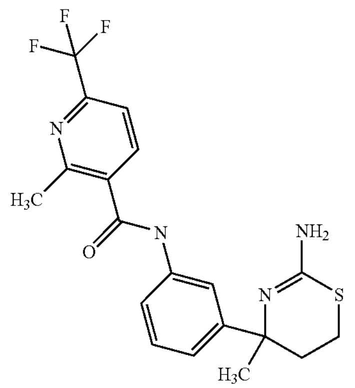 [SMILES: Cc1nc(C(F)(F)F)ccc1C(=O)Nc1cccc(C2(C)CCSC(N)=N2)c1] |
| 367 | 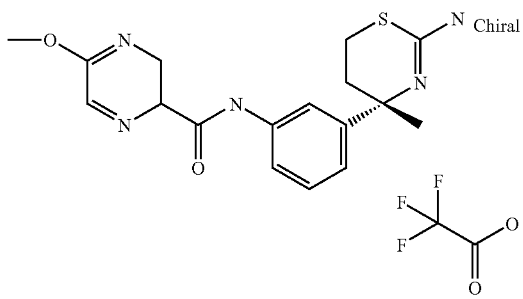 |
| 368 | 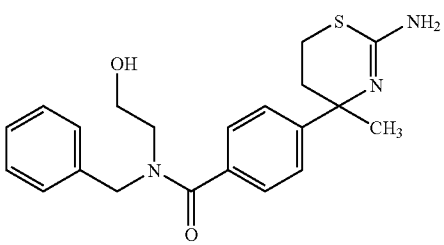 [SMILES: CC1(c2ccc(C(=O)N(CCO)Cc3ccccc3)cc2)CCSC(N)=N1] |
| 369 | 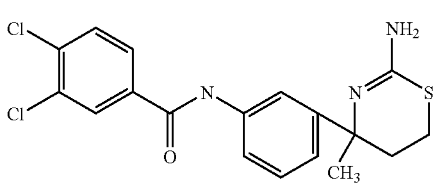 [SMILES: CC1(c2cccc(NC(=O)c3ccc(Cl)c(Cl)c3)c2)CCSC(N)=N1] |

TABLE 40

| No. | Structure |
|---|---|
| 370 | 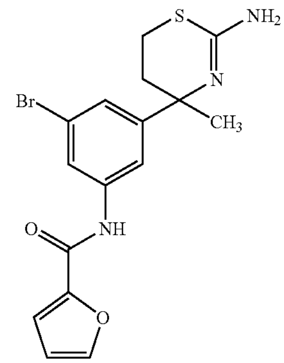 [SMILES: CC1(c2cc(Br)cc(NC(=O)c3ccco3)c2)CCSC(N)=N1] |
| 371 | 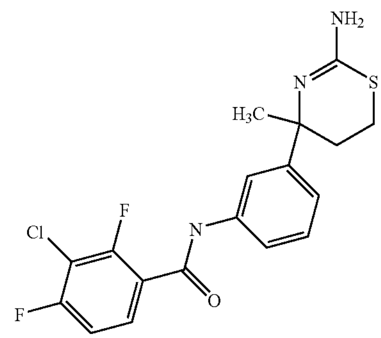 [SMILES: CC1(c2cccc(NC(=O)c3ccc(F)c(Cl)c3F)c2)CCSC(N)=N1] |
| 372 | 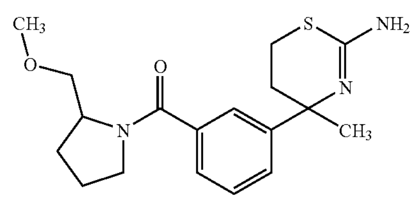 [SMILES: COCC1CCCN1C(=O)c1cccc(C2(C)CCSC(N)=N2)c1] |
| 373 | 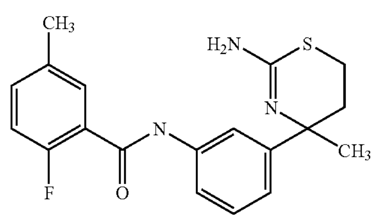 [SMILES: Cc1ccc(F)c(C(=O)Nc2cccc(C3(C)CCSC(N)=N3)c2)c1] |
| 374 | 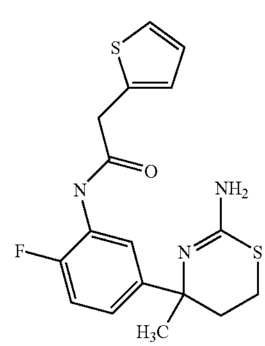 [SMILES: CC1(c2ccc(F)c(NC(=O)Cc3cccs3)c2)CCSC(N)=N1] |

TABLE 40-continued

| No. | Structure |
|---|---|
| 375 | (structure with 2-amino-thiazine, methyl, fluorophenyl, NH-C(O)-phenyl-tert-butyl, ClH salt) |
| 376 | (2-amino-thiazine with methyl, phenyl, NH-C(O)-phenyl with F and CF₃ substituents) |
| 377 | (5-methyl-3-phenyl-isoxazole-4-carboxamide linked to fluorophenyl-methyl-thiazine-amine) |
| 378 | (2-amino-thiazine-methyl-phenyl-NH-C(O)-phenyl with F and Cl) |

TABLE 41

| No. | Structure |
|---|---|
| 379 | (isoquinoline-NH-C(O)-phenyl-methyl-thiazine-amine) |
| 380 | (5-chloropyridine-C(O)-NH-phenyl-ethyl-thiazine) |
| 381 | (piperidine-phenyl-NH-C(O)-phenyl-methyl-thiazine-amine) |
| 382 | (2-amino-thiazine-methyl-phenyl-NH-C(O)-m-tolyl) |
| 383 | (phenoxy-imine-phenyl-methyl-thiazine-amine) |
| 384 | (2-ethoxybenzamide-N-(fluorophenyl-methyl-thiazine-amine)) |

TABLE 41-continued
| No. | Structure |
|---|---|
| 385 | 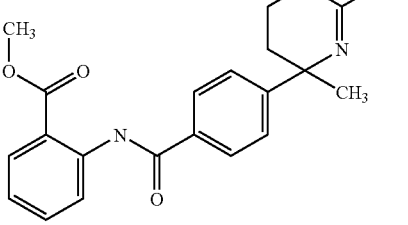 |
| 386 | 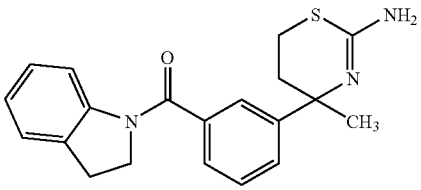 [SMILES: CC1(c2cccc(C(=O)N3CCc4ccccc43)c2)CCSC(N)=N1] |
| 387 | 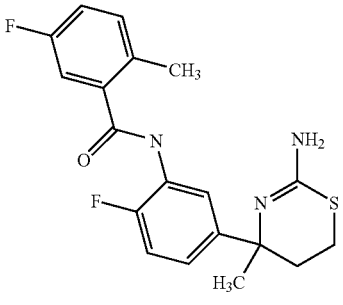 [SMILES: Cc1ccc(F)cc1C(=O)Nc1cc(C2(C)CCSC(N)=N2)ccc1F] |
| 388 | 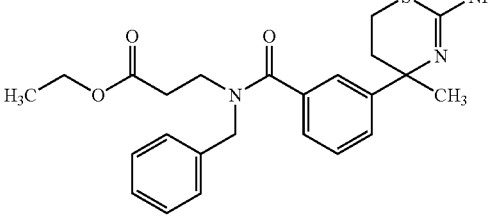 |
| 389 | 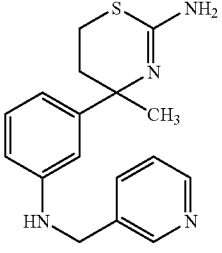 [SMILES: CC1(c2cccc(NCc3cccnc3)c2)CCSC(N)=N1] |
TABLE 42
| No. | Structure |
|---|---|
| 390 | 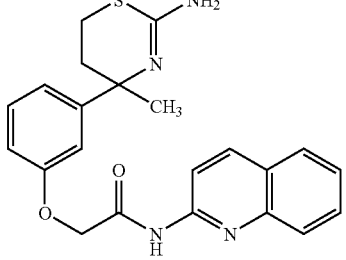 |
| 391 | 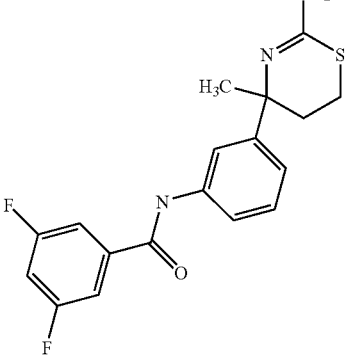 |
| 392 | 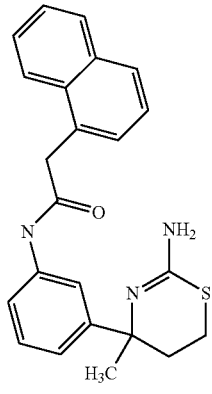 [SMILES: CC1(c2cccc(NC(=O)Cc3cccc4ccccc34)c2)CCSC(N)=N1] |
| 393 | 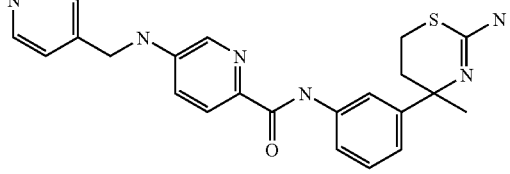 |
| 394 | 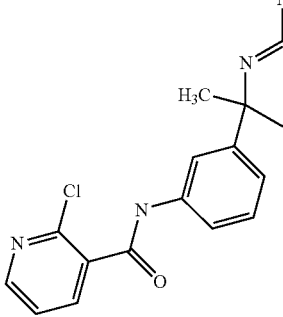 |

TABLE 42-continued
| No. | Structure |
|---|---|
| 395 | 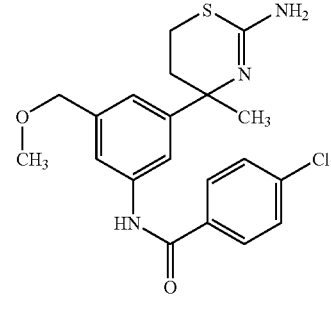 [SMILES: COCc1cc(NC(=O)c2ccc(Cl)cc2)cc(C2(C)CCSC(N)=N2)c1] |
| 396 | 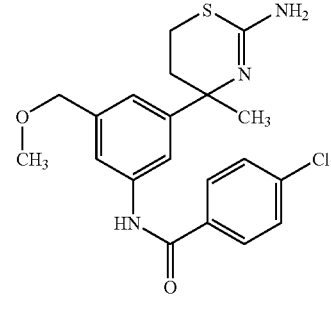 [SMILES: COCc1cc(NC(=O)c2ccc(Cl)cc2)cc(C2(C)CCSC(N)=N2)c1] |
| 397 | 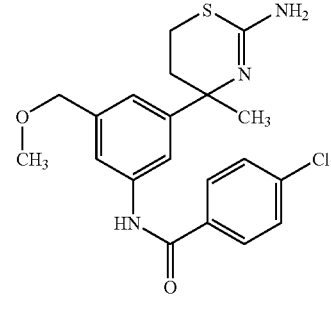 [SMILES: COCc1cc(NC(=O)c2ccc(Cl)cc2)cc(C2(C)CCSC(N)=N2)c1] |
TABLE 43
| No. | Structure |
|---|---|
| 398 | 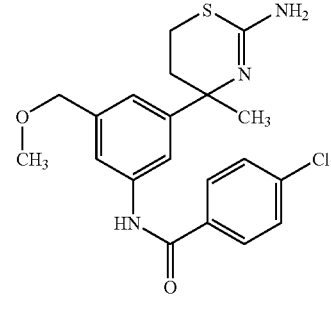 [SMILES: COCc1cc(NC(=O)c2ccc(Cl)cc2)cc(C2(C)CCSC(N)=N2)c1] |
TABLE 43-continued
| No. | Structure |
|---|---|
| 399 | 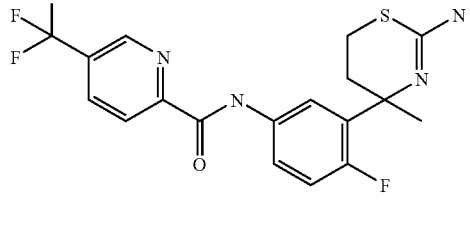 |
| 400 | 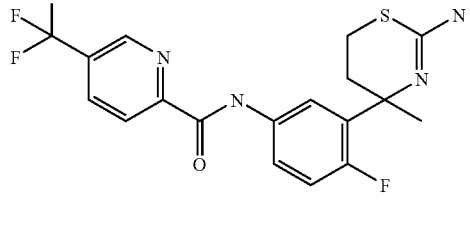 |
| 401 | 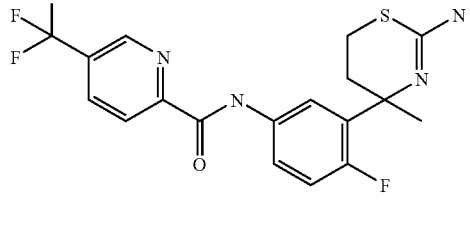 |
| 402 | 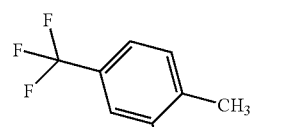 |
| 403 | 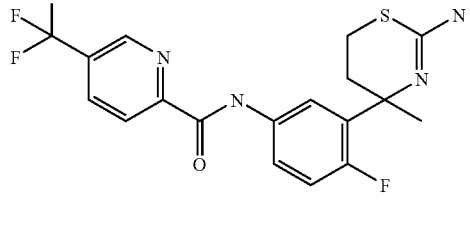 |

TABLE 43-continued

| No. | Structure |
|---|---|
| 404 | 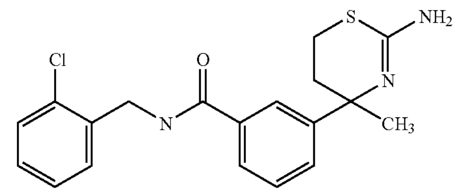 [SMILES: CC1(c2cccc(C(=O)NCc3ccccc3Cl)c2)CCSC(N)=N1] |
| 405 | 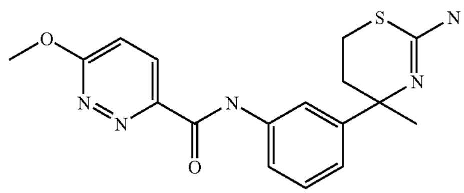 [SMILES: COc1ccc(C(=O)Nc2cccc(C3(C)CCSC(N)=N3)c2)nn1] |
| 406 | 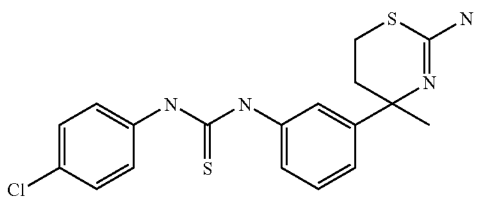 [SMILES: CC1(c2cccc(NC(=S)Nc3ccc(Cl)cc3)c2)CCSC(N)=N1] |
| 407 | 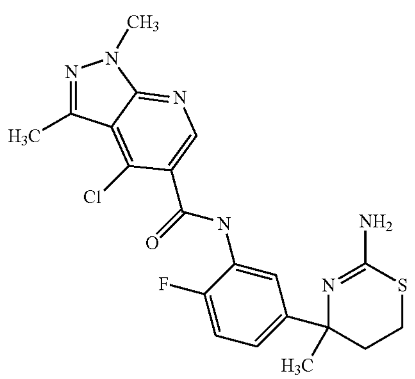 [SMILES: Cc1nn(C)c2ncc(C(=O)Nc3cc(C4(C)CCSC(N)=N4)ccc3F)c(Cl)c12] |

TABLE 44

| No. | Structure |
|---|---|
| 408 | |
| 409 | |
| 410 | 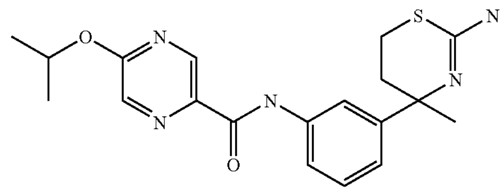 [SMILES: CC(C)Oc1cnc(C(=O)Nc2cccc(C3(C)CCSC(N)=N3)c2)cn1] |
| 411 | 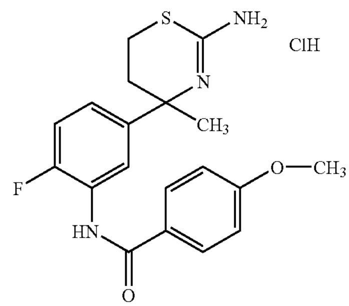 [SMILES: COc1ccc(C(=O)Nc2cc(C3(C)CCSC(N)=N3)ccc2F)cc1 ; Cl] |
| 412 | 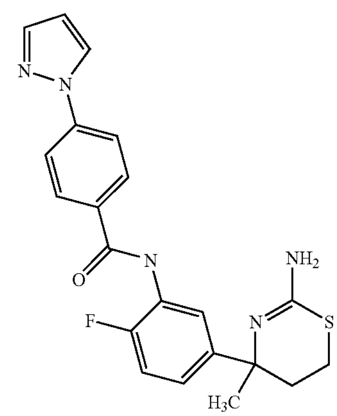 [SMILES: CC1(c2ccc(F)c(NC(=O)c3ccc(-n4cccn4)cc3)c2)CCSC(N)=N1] |
| 413 | 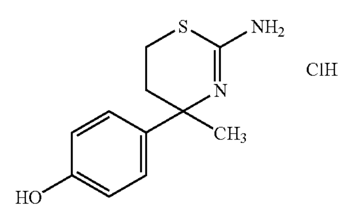 |
| 414 | 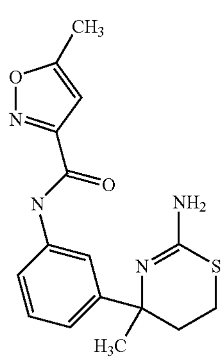 [SMILES: Cc1cc(C(=O)Nc2cccc(C3(C)CCSC(N)=N3)c2)no1] |

TABLE 44-continued
| No. | Structure |
|---|---|
| 415 | 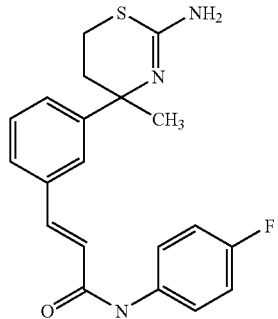 |
| 416 | 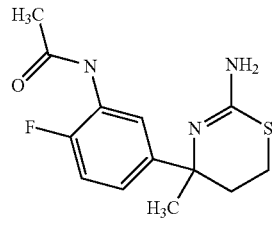 [SMILES: CC(=O)Nc1cc(C2(C)CCSC(N)=N2)ccc1F] |
TABLE 45
| No. | Structure |
|---|---|
| 417 | 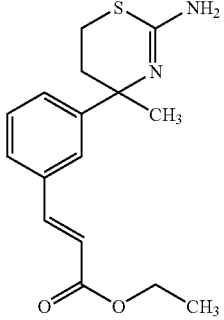 [SMILES: CCOC(=O)/C=C/c1cccc(C2(C)CCSC(N)=N2)c1] |
| 418 | 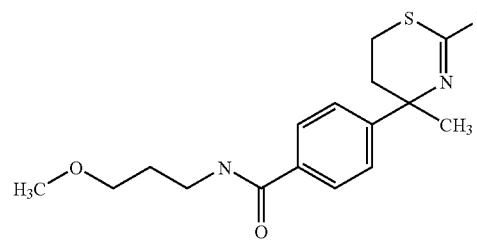 |
| 419 | 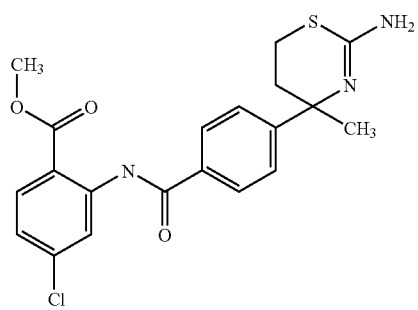 [SMILES: COC(=O)c1ccc(Cl)cc1NC(=O)c1ccc(C2(C)CCSC(N)=N2)cc1] |
| 420 | 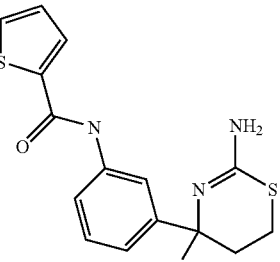 |
| 421 | 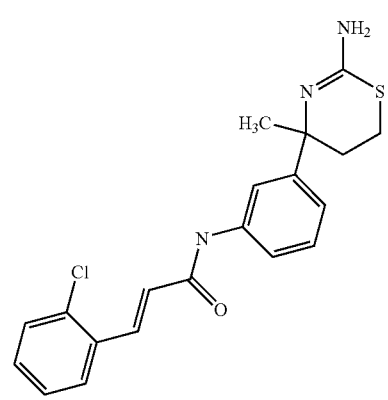 [SMILES: CC1(c2cccc(NC(=O)/C=C/c3ccccc3Cl)c2)CCSC(N)=N1] |
| 422 | 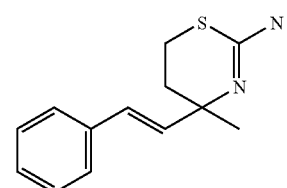 |
| 423 | 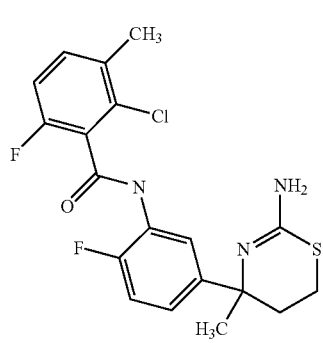 [SMILES: Cc1ccc(F)c(C(=O)Nc2cc(C3(C)CCSC(N)=N3)ccc2F)c1Cl] |
| 424 | 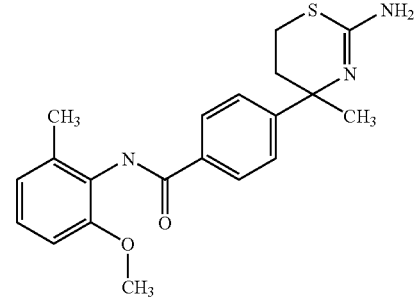 [SMILES: COc1cccc(C)c1NC(=O)c1ccc(C2(C)CCSC(N)=N2)cc1] |

TABLE 46
| No. | Structure |
|-----|-----------|
| 425 | 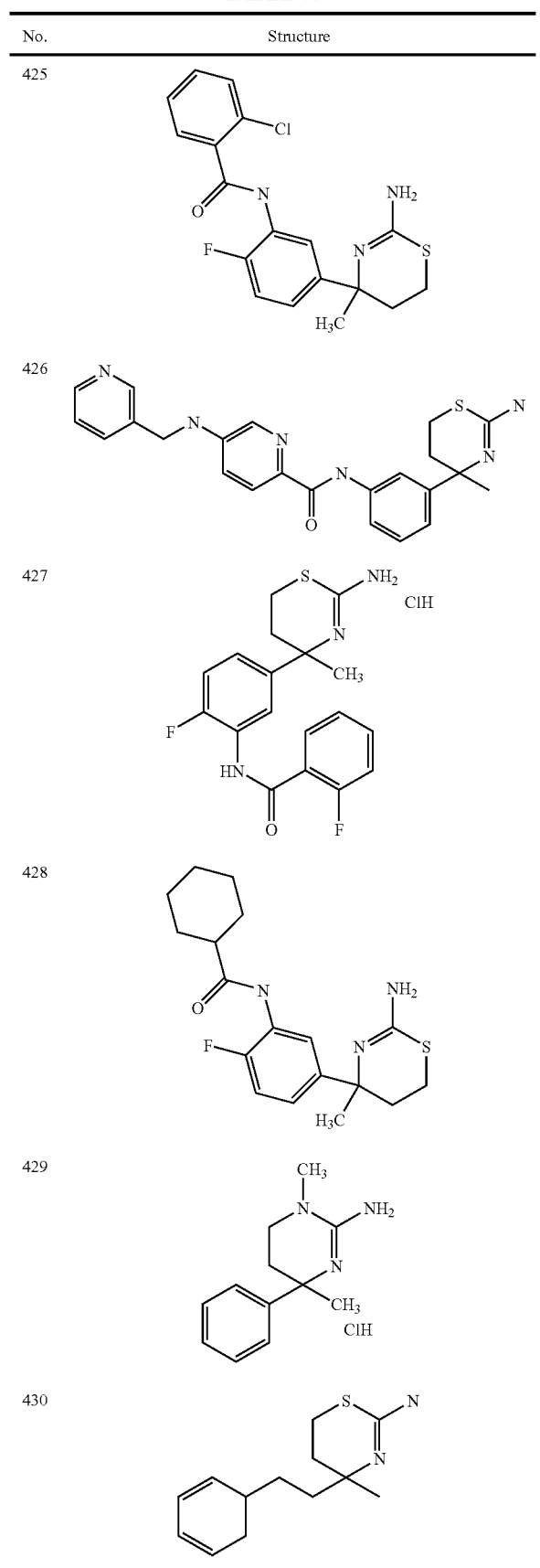 |
| 426 | 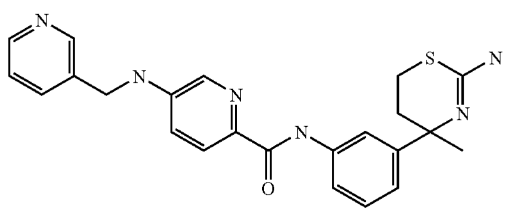 [SMILES: CC1(c2cccc(NC(=O)c3ccc(NCc4cccnc4)cn3)c2)CCSC(N)=N1] |
| 427 | 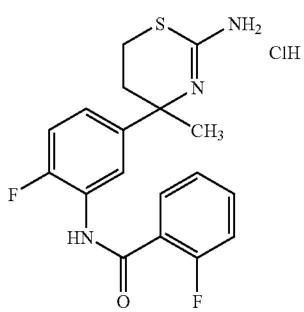 [SMILES: CC1(c2ccc(F)c(NC(=O)c3ccccc3F)c2)CCSC(N)=N1 ; Cl] |
| 428 | 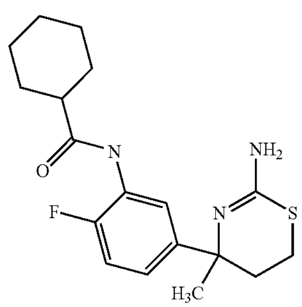 [SMILES: CC1(c2ccc(F)c(NC(=O)C3CCCCC3)c2)CCSC(N)=N1] |
| 429 | 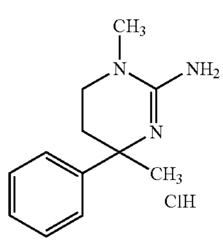 |
| 430 | 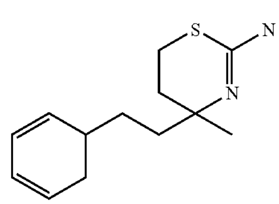 [SMILES: CC1(CCC2C=CC=CC2)CCSC(N)=N1] |
TABLE 46-continued
| No. | Structure |
|-----|-----------|
| 431 | 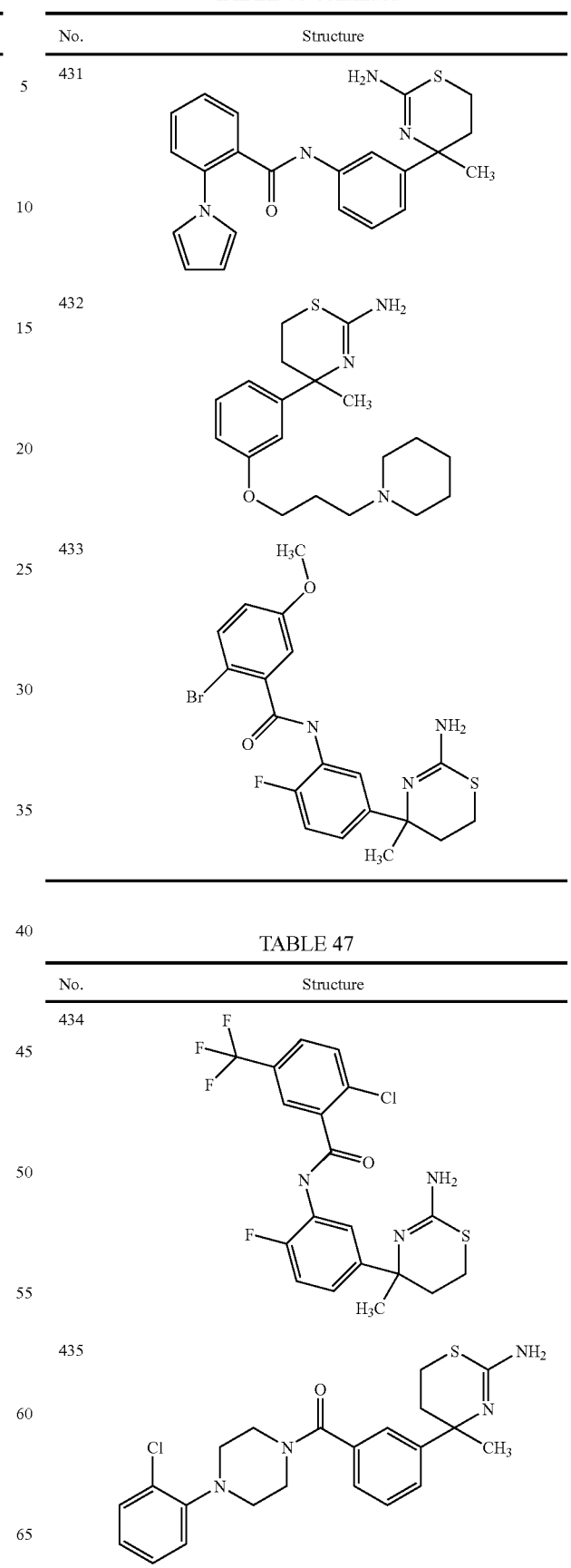 |
| 432 | 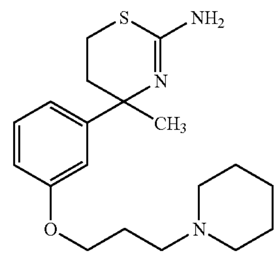 [SMILES: CC1(c2cccc(OCCCN3CCCCC3)c2)CCSC(N)=N1] |
| 433 | 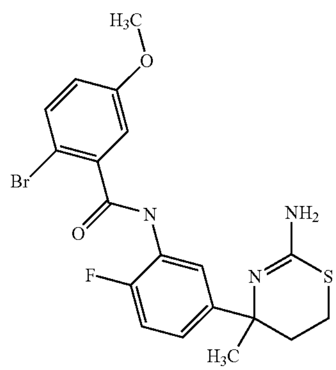 [SMILES: COc1ccc(Br)c(C(=O)Nc2cc(C3(C)CCSC(N)=N3)ccc2F)c1] |
TABLE 47
| No. | Structure |
|-----|-----------|
| 434 | 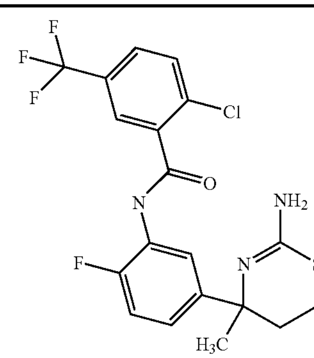 |
| 435 | 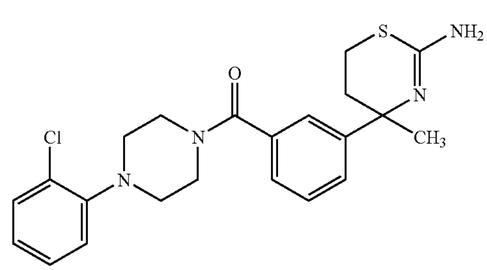 [SMILES: CC1(c2cccc(C(=O)N3CCN(c4ccccc4Cl)CC3)c2)CCSC(N)=N1] |

TABLE 47-continued

| No. | Structure |
|---|---|
| 436 | (2,5-dimethylfuran-3-yl)-N-(3-bromo-5-(2-amino-4-methyl-5,6-dihydro-4H-1,3-thiazin-4-yl)phenyl)carboxamide · HCl |
| 437 | benzothiophene-3-carboxylic acid N-[3-(2-amino-4-methyl-5,6-dihydro-4H-1,3-thiazin-4-yl)phenyl]amide |
| 438 | 2-[3-(2-amino-4-methyl-5,6-dihydro-4H-1,3-thiazin-4-yl)phenoxy]-N-(3-ethoxyphenyl)acetamide |
| 439 | 3,4-difluoro-N-[2-fluoro-5-(2-amino-4-methyl-5,6-dihydro-4H-1,3-thiazin-4-yl)phenyl]benzamide |
| 440 | 4-(2-amino-4-methyl-5,6-dihydro-4H-1,3-thiazin-4-yl)-N-(3-fluoro-4-methylphenyl)benzamide |

TABLE 47-continued

| No. | Structure |
|---|---|
| 441 (racemate) | 2-amino-4-methyl-4,6-diphenyl-5,6-dihydro-4H-1,3-thiazine · HCl |
| 442 | 5-(2-amino-4-methyl-5,6-dihydro-4H-1,3-thiazin-4-yl)-N-[2-(4-chlorophenyl)ethyl]thiophene-2-carboxamide |

TABLE 48

| No. | Structure |
|---|---|
| 443 | 4-[3-(naphthalen-2-ylmethylamino)phenyl]-2-amino-4-methyl-5,6-dihydro-4H-1,3-thiazine |
| 444 | 5-methyl-N-[3-(2-amino-4-methyl-5,6-dihydro-4H-1,3-thiazin-4-yl)phenyl]pyrazine-2-carboxamide |
| 445 | 2-amino-spiro[(5,6-dihydro-4H-1,3-thiazine)-4,1'-(1',2',3',4'-tetrahydronaphthalene)] |
| 446 | 1-[3-(2-amino-4-methyl-5,6-dihydro-4H-1,3-thiazin-4-yl)phenyl]ethanone O-(4-methylbenzyl)oxime |

TABLE 48-continued
| No. | Structure |
|-----|-----------|
| 447 | 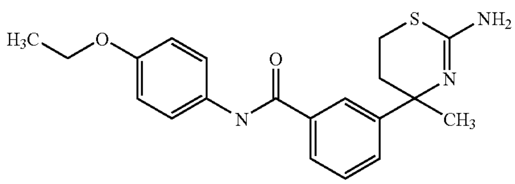 [SMILES: CCOc1ccc(NC(=O)c2cccc(C3(C)CCSC(N)=N3)c2)cc1] |
| 448 | 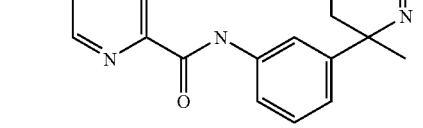 |
| 449 | 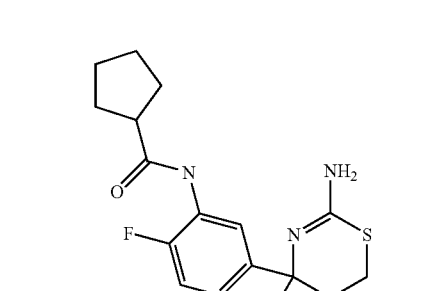 |
| 450 | 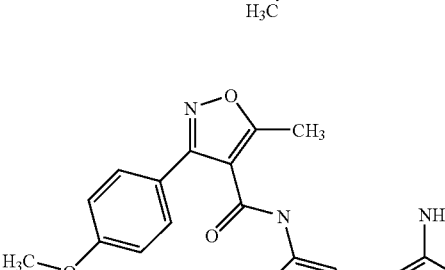 |
| 451 | 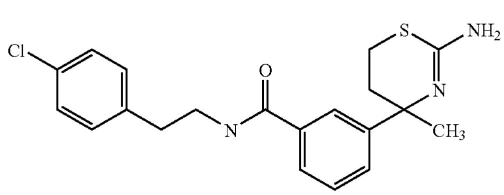 [SMILES: CC1(c2cccc(C(=O)NCCc3ccc(Cl)cc3)c2)CCSC(N)=N1] |
| 452 | 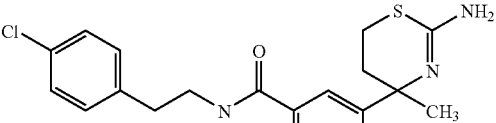 |
| 453 | 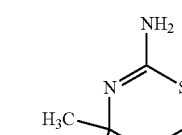 |
TABLE 49
| No. | Structure |
|-----|-----------|
| 454 | 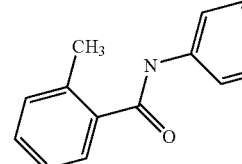 |
| 455 | 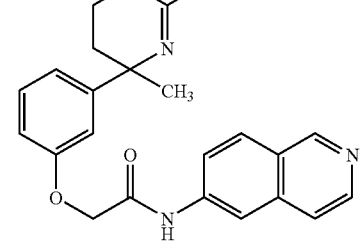 |
| 456 | 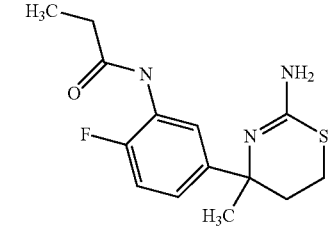 [SMILES: CCC(=O)Nc1cc(C2(C)CCSC(N)=N2)ccc1F] |
| 457 | 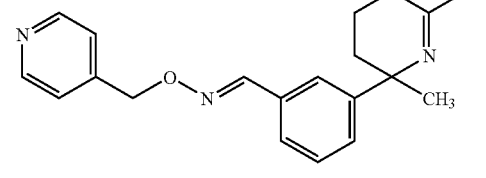 |

TABLE 49-continued

| No. | Structure |
|---|---|
| 458 | (chemical structure) |
| 459 | (chemical structure) |
| 460 | (chemical structure) |
| 461 | (chemical structure) |
| 462 | (chemical structure) |

TABLE 49-continued

| No. | Structure |
|---|---|
| 463 | (chemical structure) |
| 464 | (chemical structure) |

TABLE 50

| No. | Structure |
|---|---|
| 465 | (chemical structure) |
| 466 | (chemical structure) |
| 467 | (chemical structure) |

TABLE 50-continued

| No. | Structure |
|-----|-----------|
| 468 | 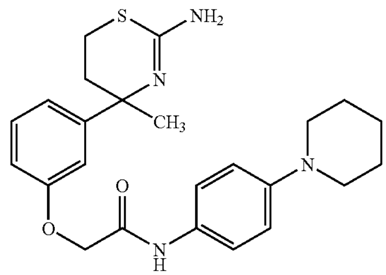 [SMILES: CC1(c2cccc(OCC(=O)Nc3ccc(N4CCCCC4)cc3)c2)CCSC(N)=N1] |
| 469 | 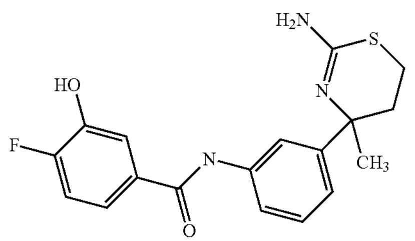 [SMILES: CC1(c2cccc(NC(=O)c3ccc(F)c(O)c3)c2)CCSC(N)=N1] |
| 470 | 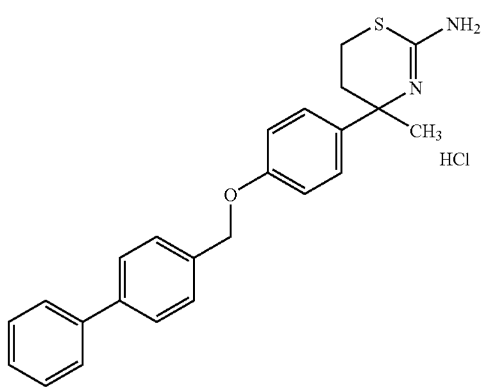 [SMILES: CC1(c2ccc(OCc3ccc(-c4ccccc4)cc3)cc2)CCSC(N)=N1 ; Cl] |
| 471 | 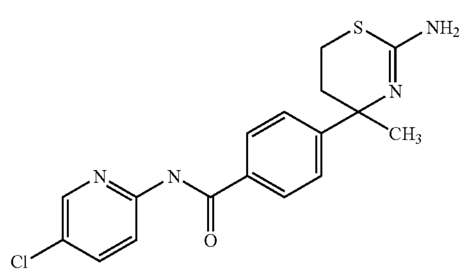 [SMILES: CC1(c2ccc(C(=O)Nc3ccc(Cl)cn3)cc2)CCSC(N)=N1] |
| 472 | 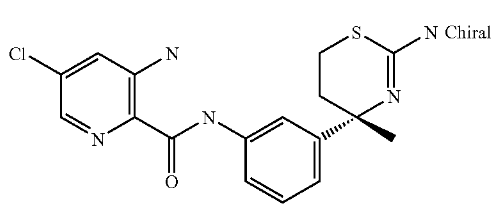 [SMILES: C[C@@]1(c2cccc(NC(=O)c3ncc(Cl)cc3N)c2)CCSC(N)=N1] |

TABLE 50-continued

| No. | Structure |
|-----|-----------|
| 473 | |
| 474 | |

TABLE 51

| No. | Structure |
|-----|-----------|
| 475 | 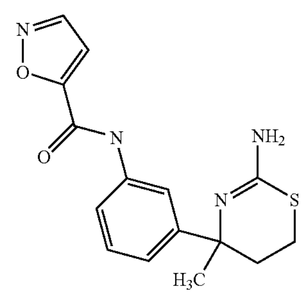 [SMILES: CC1(c2cccc(NC(=O)c3ccno3)c2)CCSC(N)=N1] |
| 476 | 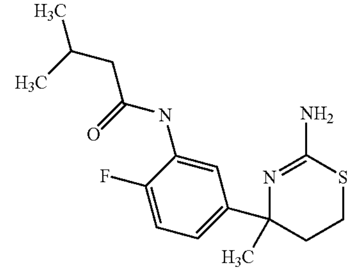 [SMILES: CC(C)CC(=O)Nc1cc(C2(C)CCSC(N)=N2)ccc1F] |

TABLE 51-continued

| No. | Structure |
|---|---|
| 477 | (structure) |
| 478 | (structure) |
| 479 | (structure) |
| 480 | (structure) |
| 481 | (structure) |

TABLE 51-continued

| No. | Structure |
|---|---|
| 482 | (structure) |
| 483 | (structure) |

TABLE 52

| No. | Structure |
|---|---|
| 484 | (structure) |
| 485 | (structure) |
| 486 | (structure) |

TABLE 52-continued
| No. | Structure |
|-----|-----------|
| 487 | 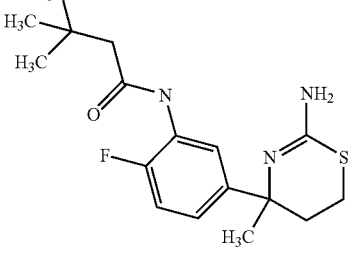 |
| 488 | 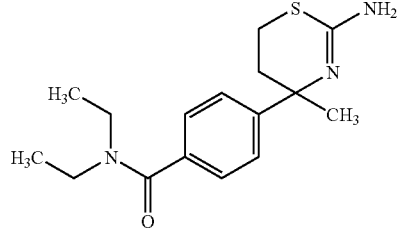 [SMILES: CCN(CC)C(=O)c1ccc(C2(C)CCSC(N)=N2)cc1] |
| 489 | 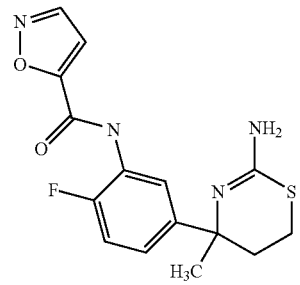 [SMILES: CC1(c2ccc(F)c(NC(=O)c3ccno3)c2)CCSC(N)=N1] |
| 490 | 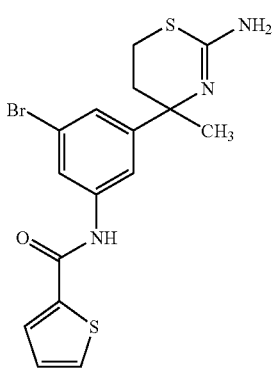 |
| 491 | 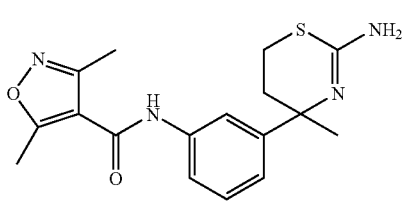 [SMILES: Cc1noc(C)c1C(=O)Nc1cccc(C2(C)CCSC(N)=N2)c1] |
TABLE 52-continued
| No. | Structure |
|-----|-----------|
| 492 | 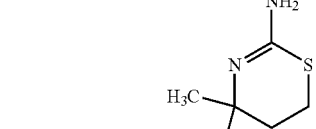 |
TABLE 53
| No. | Structure |
|-----|-----------|
| 493 | 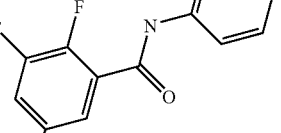 |
| 494 | 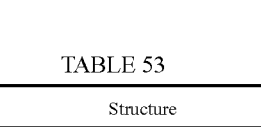 |
| 495 | 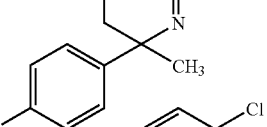 |
| 496 | 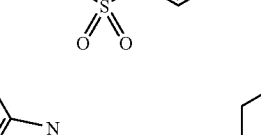 |
| 497 | 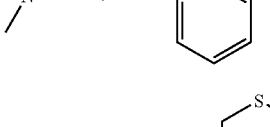 |

TABLE 53-continued

| No. | Structure |
|---|---|
| 498 | 4-cyano-N-(3-(2-amino-4-methyl-5,6-dihydro-4H-1,3-thiazin-4-yl)phenyl)benzamide |
| 499 | N-(4-methoxybenzyl)-4-(2-amino-4-methyl-5,6-dihydro-4H-1,3-thiazin-4-yl)benzamide |
| 500 | N-(5-chloropyridin-2-yl)-5-(2-amino-4-methyl-5,6-dihydro-4H-1,3-thiazin-4-yl)thiophene-2-carboxamide |
| 501 | 2-amino-4-(3-(hydroxymethyl)phenyl)-4-methyl-5,6-dihydro-4H-1,3-thiazine |
| 502 | 2-amino-4-(3-((4-methoxyphenoxy)methyl)phenyl)-4-methyl-5,6-dihydro-4H-1,3-thiazine |
| 503 | 4-(trifluoromethyl)-N-(4-fluoro-3-(2-imino-4-methyl-1,3-thiazinan-4-yl)phenyl)benzamide |

TABLE 54

| No. | Structure |
|---|---|
| 504 | cinnamamide derivative · 2HCl |
| 505 | N-(2-chloropyridin-4-yl)-3-(2-amino-4-methyl-5,6-dihydro-4H-1,3-thiazin-4-yl)benzamide |
| 506 | N-(2,3-dimethoxyphenyl)-4-(2-amino-4-methyl-5,6-dihydro-4H-1,3-thiazin-4-yl)benzamide |
| 507 | methyl 3-hydroxy-4-(4-(2-amino-4-methyl-5,6-dihydro-4H-1,3-thiazin-4-yl)benzamido)benzoate |
| 508 | N-(1-(4-fluorophenyl)ethyl)-4-(2-amino-4-methyl-5,6-dihydro-4H-1,3-thiazin-4-yl)benzamide |

TABLE 54-continued

| No. | Structure |
|---|---|
| 509 | 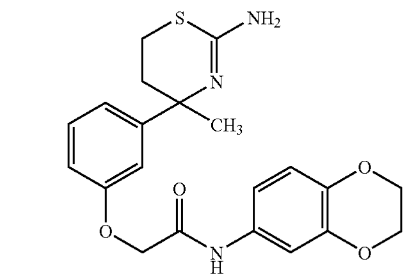 [SMILES: CC1(c2cccc(OCC(=O)Nc3ccc4c(c3)OCCO4)c2)CCSC(N)=N1] |
| 510 | 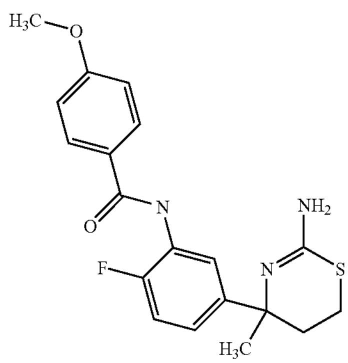 |
| 511 | 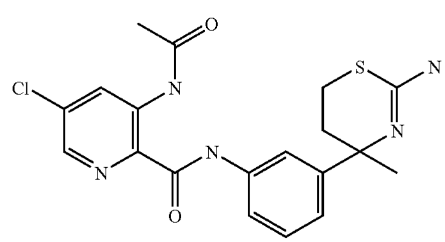 [SMILES: CC(=O)Nc1cc(Cl)cnc1C(=O)Nc1cccc(C2(C)CCSC(N)=N2)c1] |
| 512 | 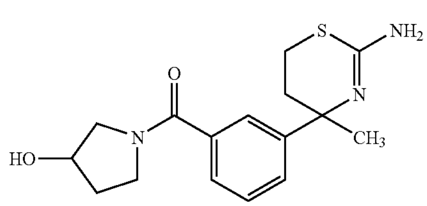 [SMILES: CC1(c2cccc(C(=O)N3CCC(O)C3)c2)CCSC(N)=N1] |
| 513 | 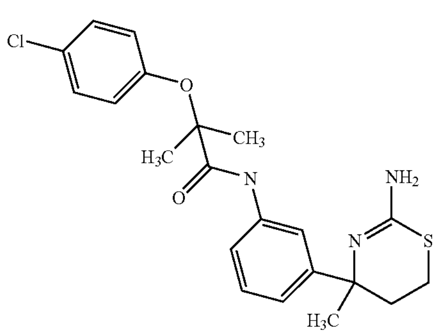 [SMILES: CC(C)(Oc1ccc(Cl)cc1)C(=O)Nc1cccc(C2(C)CCSC(N)=N2)c1] |

TABLE 54-continued

| No. | Structure |
|---|---|
| 514 | |

TABLE 55

| No. | Structure |
|---|---|
| 515 | 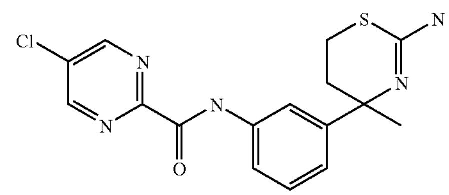 [SMILES: CC1(c2cccc(NC(=O)c3ncc(Cl)cn3)c2)CCSC(N)=N1] |
| 516 | 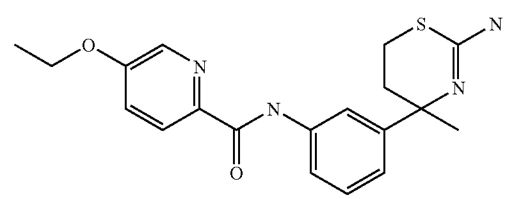 [SMILES: CCOc1ccc(C(=O)Nc2cccc(C3(C)CCSC(N)=N3)c2)nc1] |
| 517 | 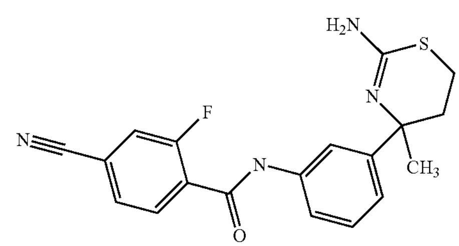 [SMILES: CC1(c2cccc(NC(=O)c3ccc(C#N)cc3F)c2)CCSC(N)=N1] |
| 518 | 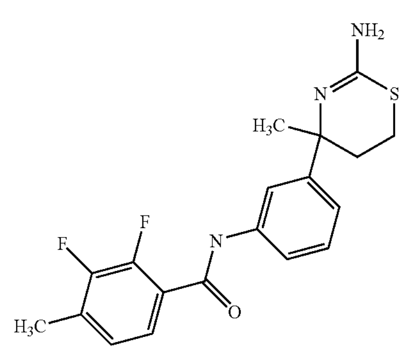 [SMILES: Cc1ccc(C(=O)Nc2cccc(C3(C)CCSC(N)=N3)c2)c(F)c1F] |

TABLE 55-continued
| No. | Structure |
|---|---|
| 519 | 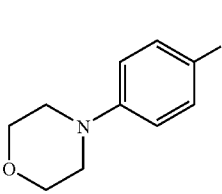 |
| 520 | 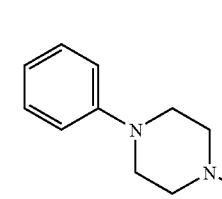 |
| 521 | 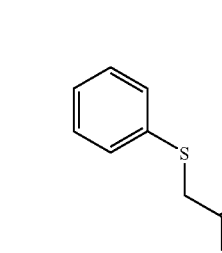 |
| 522 | 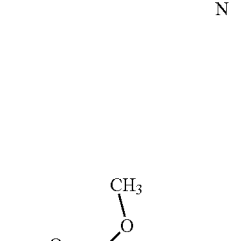 |
| 523 | 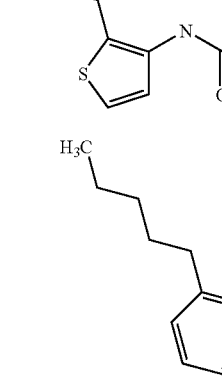 |
TABLE 55-continued
| No. | Structure |
|---|---|
| 524 | 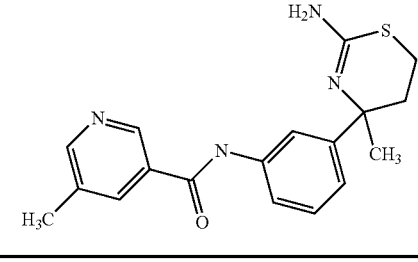 |
TABLE 56
| No. | Structure |
|---|---|
| 525 | 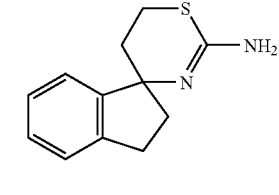 [SMILES: NC1=NC2(CCS1)CCc1ccccc12] |
| 526 | 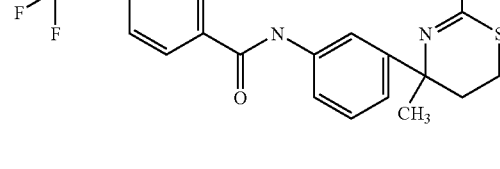 |
| 527 | 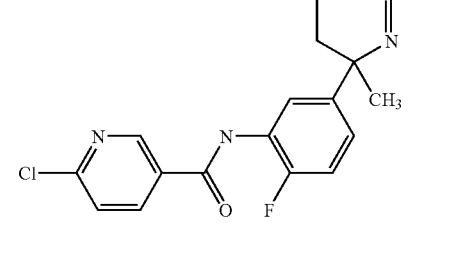 |
| 528 | 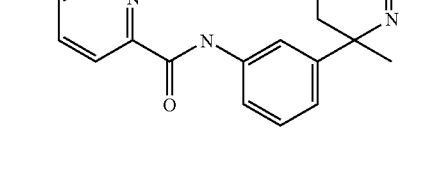 |
| 529 | 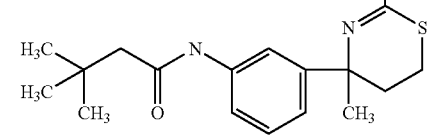 |

TABLE 56-continued

| No. | Structure |
|---|---|
| 530 | 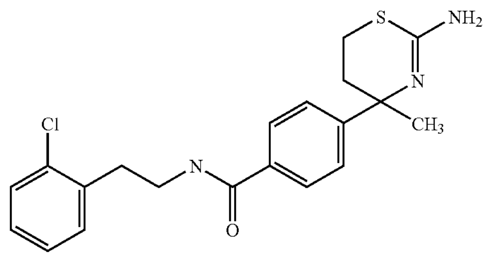 [SMILES: CC1(c2ccc(C(=O)NCCc3ccccc3Cl)cc2)CCSC(N)=N1] |
| 531 | 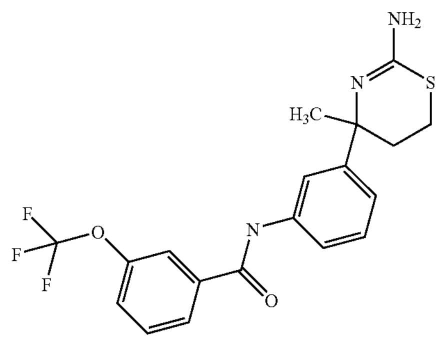 [SMILES: CC1(c2cccc(NC(=O)c3cccc(OC(F)(F)F)c3)c2)CCSC(N)=N1] |
| 532 | 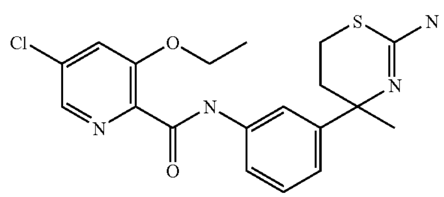 [SMILES: CCOc1cc(Cl)cnc1C(=O)Nc1cccc(C2(C)CCSC(N)=N2)c1] |
| 533 | 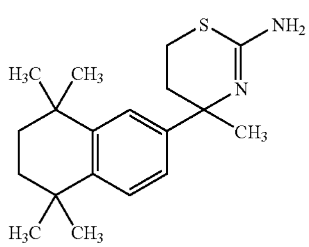 [SMILES: CC1(C)CCC(C)(C)c2cc(C3(C)CCSC(N)=N3)ccc21] |
| 534 | 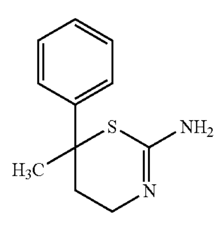 |
| 535 | 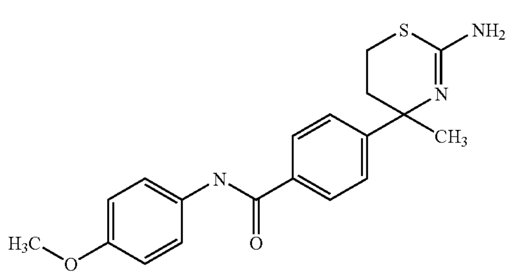 [SMILES: COc1ccc(NC(=O)c2ccc(C3(C)CCSC(N)=N3)cc2)cc1] |

TABLE 57

| No. | Structure |
|---|---|
| 536 | 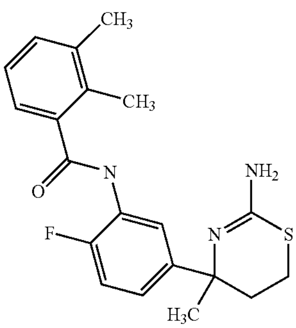 [SMILES: Cc1cccc(C(=O)Nc2cc(C3(C)CCSC(N)=N3)ccc2F)c1C] |
| 537 | 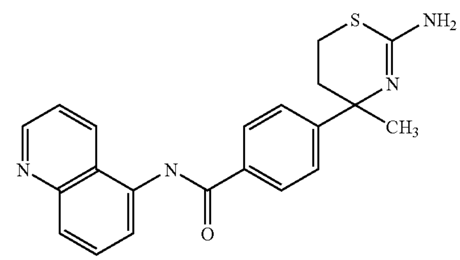 [SMILES: CC1(c2ccc(C(=O)Nc3cccc4ncccc34)cc2)CCSC(N)=N1] |
| 538 | 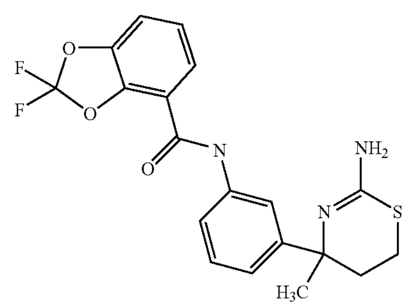 [SMILES: CC1(c2cccc(NC(=O)c3cccc4c3OC(F)(F)O4)c2)CCSC(N)=N1] |
| 539 | 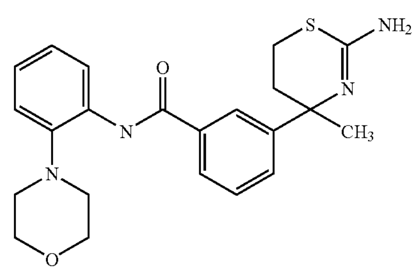 [SMILES: CC1(c2cccc(C(=O)Nc3ccccc3N3CCOCC3)c2)CCSC(N)=N1] |
| 540 | 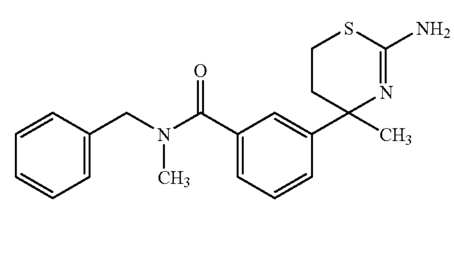 [SMILES: CN(Cc1ccccc1)C(=O)c1cccc(C2(C)CCSC(N)=N2)c1] |

TABLE 57-continued

| No. | Structure |
|---|---|
| 541 | 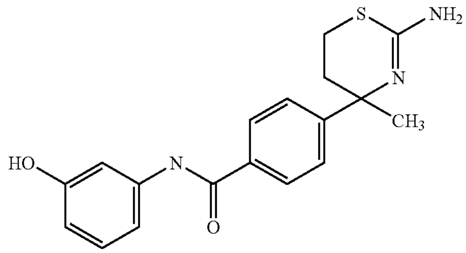 [SMILES: CC1(c2ccc(C(=O)Nc3cccc(O)c3)cc2)CCSC(N)=N1] |
| 542 | 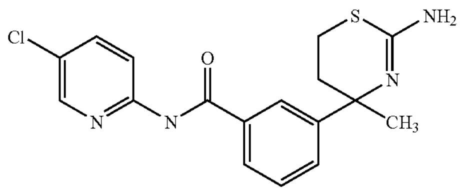 [SMILES: CC1(c2cccc(C(=O)Nc3ccc(Cl)cn3)c2)CCSC(N)=N1] |
| 543 | 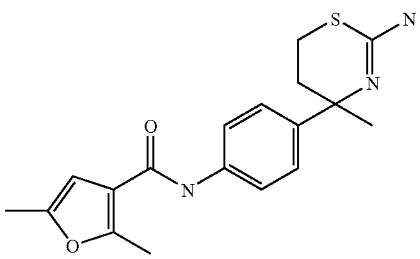 [SMILES: Cc1cc(C(=O)Nc2ccc(C3(C)CCSC(N)=N3)cc2)c(C)o1] |
| 544 | 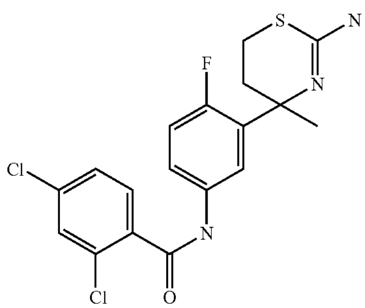 [SMILES: CC1(c2cc(NC(=O)c3ccc(Cl)cc3Cl)ccc2F)CCSC(N)=N1] |
| 545 | 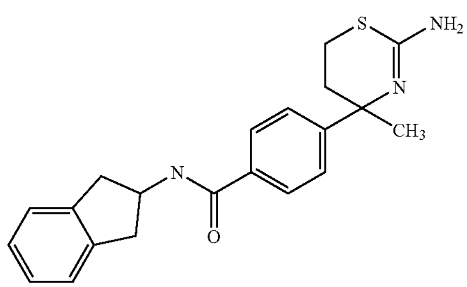 [SMILES: CC1(c2ccc(C(=O)NC3Cc4ccccc4C3)cc2)CCSC(N)=N1] |
| 546 | 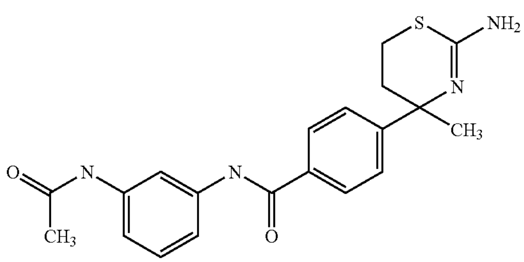 [SMILES: CC(=O)Nc1cccc(NC(=O)c2ccc(C3(C)CCSC(N)=N3)cc2)c1] |

TABLE 58

| No. | Structure |
|---|---|
| 547 | 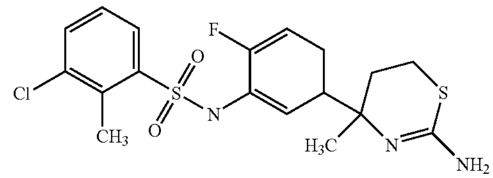 [SMILES: Cc1c(Cl)cccc1S(=O)(=O)NC1=CC(C2(C)CCSC(N)=N2)CC=C1F] |
| 548 | 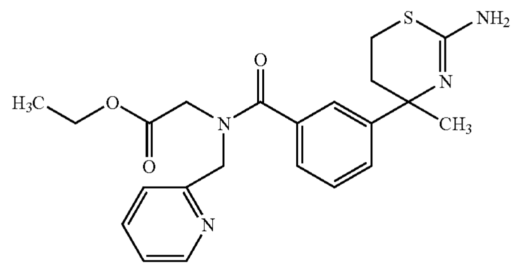 [SMILES: CCOC(=O)CN(Cc1ccccn1)C(=O)c1cccc(C2(C)CCSC(N)=N2)c1] |
| 549 | 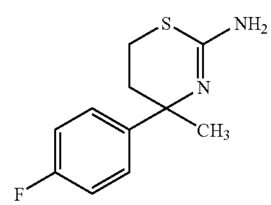 |
| 550 | 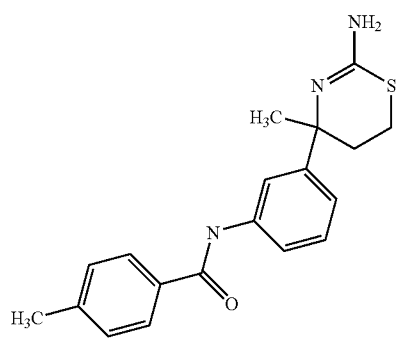 [SMILES: Cc1ccc(C(=O)Nc2cccc(C3(C)CCSC(N)=N3)c2)cc1] |
| 551 | 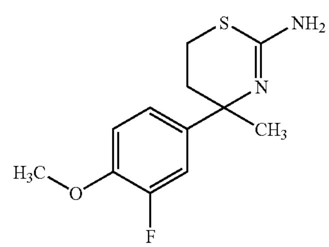 [SMILES: COc1ccc(C2(C)CCSC(N)=N2)cc1F] |

TABLE 58-continued
| No. | Structure |
|---|---|
| 552 | 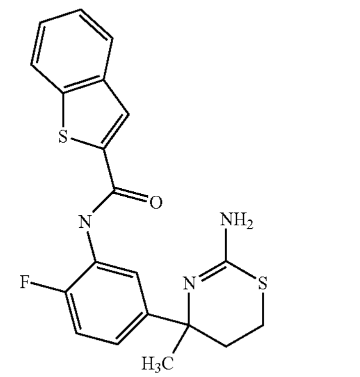 |
| 553 | 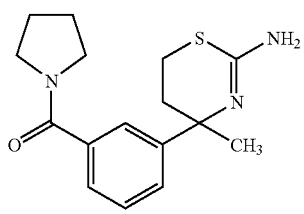 [SMILES: CC1(c2cccc(C(=O)N3CCCC3)c2)CCSC(N)=N1] |
| 554 | 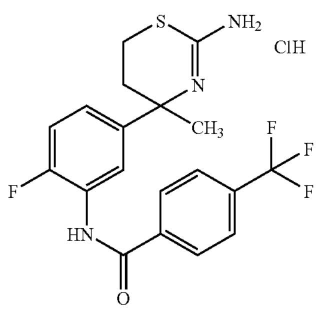 [SMILES: CC1(c2ccc(F)c(NC(=O)c3ccc(C(F)(F)F)cc3)c2)CCSC(N)=N1 ; Cl] |
| 555 | 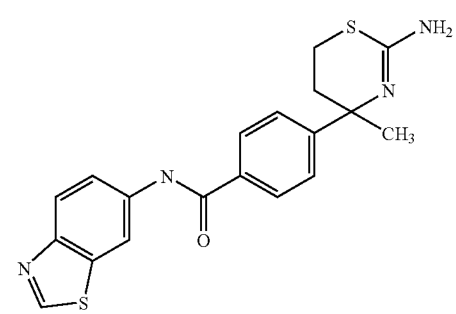 [SMILES: CC1(c2ccc(C(=O)Nc3ccc4ncsc4c3)cc2)CCSC(N)=N1] |
TABLE 59
| No. | Structure |
|---|---|
| 556 | |
| 557 | 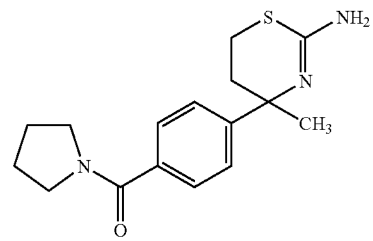 [SMILES: CC1(c2ccc(C(=O)N3CCCC3)cc2)CCSC(N)=N1] |
| 558 | 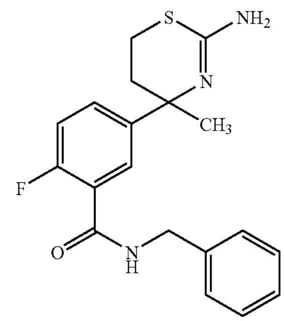 [SMILES: CC1(c2ccc(F)c(C(=O)NCc3ccccc3)c2)CCSC(N)=N1] |
| 559 | 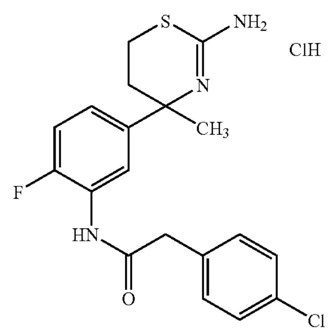 [SMILES: CC1(c2ccc(F)c(NC(=O)Cc3ccc(Cl)cc3)c2)CCSC(N)=N1 ; Cl] |
| 560 | 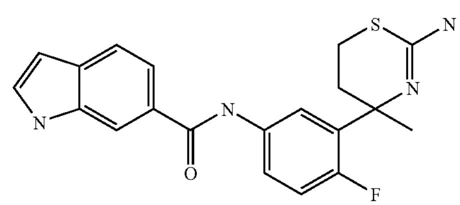 [SMILES: CC1(c2cc(NC(=O)c3ccc4cc[nH]c4c3)ccc2F)CCSC(N)=N1] |
| 561 | 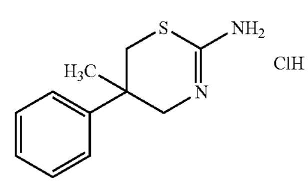 |
| 562 | 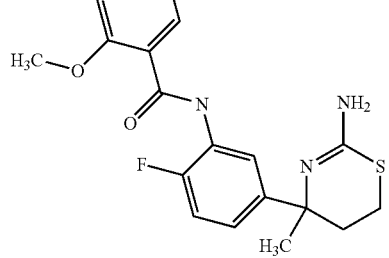 |

TABLE 59-continued
| No. | Structure |
|---|---|
| 563 | 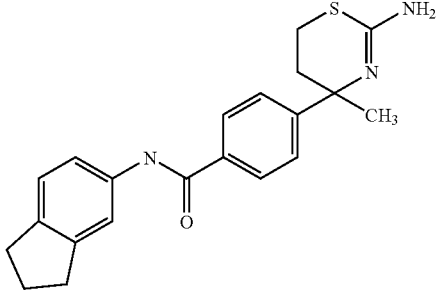 [SMILES: CC1(c2ccc(C(=O)Nc3ccc4c(c3)CCC4)cc2)CCSC(N)=N1] |
| 564 | 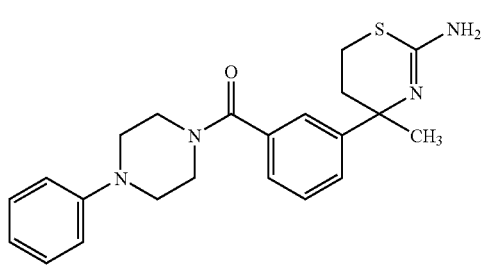 |
| 565 | 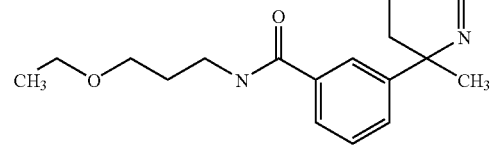 |
| 566 | 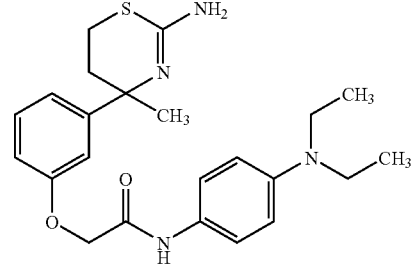 [SMILES: CCN(CC)c1ccc(NC(=O)COc2cccc(C3(C)CCSC(N)=N3)c2)cc1] |
TABLE 60
| No. | Structure |
|---|---|
| 567 | 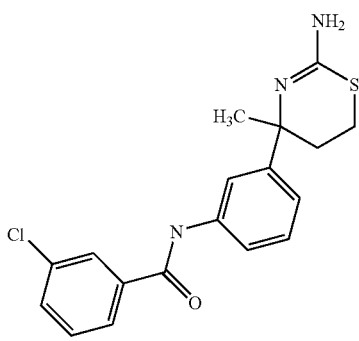 [SMILES: CC1(c2cccc(NC(=O)c3cccc(Cl)c3)c2)CCSC(N)=N1] |
| 568 | 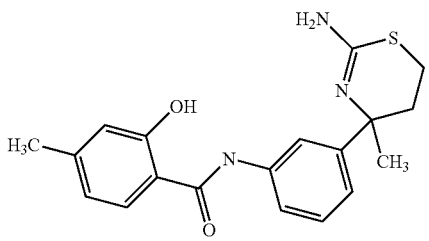 [SMILES: Cc1ccc(C(=O)Nc2cccc(C3(C)CCSC(N)=N3)c2)c(O)c1] |
| 569 | 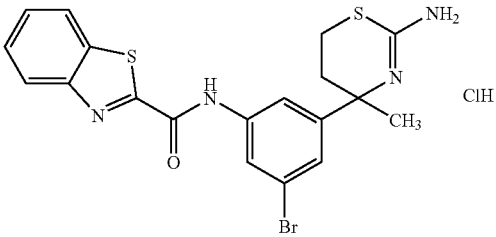 [SMILES: CC1(c2cc(Br)cc(NC(=O)c3nc4ccccc4s3)c2)CCSC(N)=N1 ; Cl] |
| 570 | 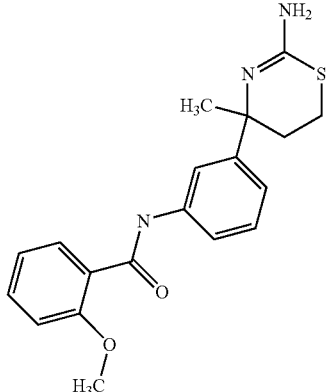 |
| 571 | 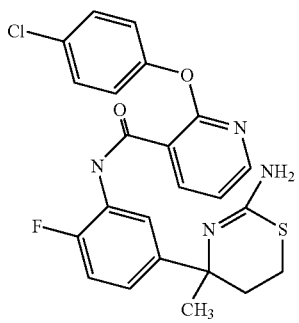 [SMILES: CC1(c2ccc(F)c(NC(=O)c3cccnc3Oc3ccc(Cl)cc3)c2)CCSC(N)=N1] |
| 572 | 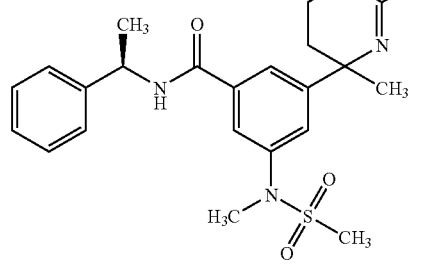 |

TABLE 60-continued

| No. | Structure |
|---|---|
| 573 | 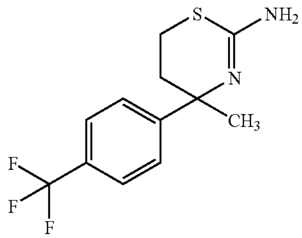 [SMILES: CC1(c2ccc(C(F)(F)F)cc2)CCSC(N)=N1] |
| 574 | 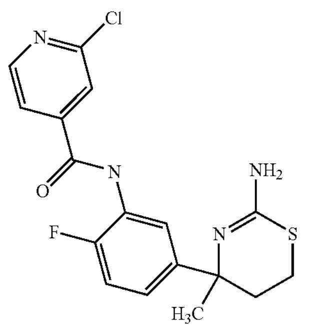 [SMILES: CC1(c2ccc(F)c(NC(=O)c3ccnc(Cl)c3)c2)CCSC(N)=N1] |

TABLE 61

| No. | Structure |
|---|---|
| 575 | 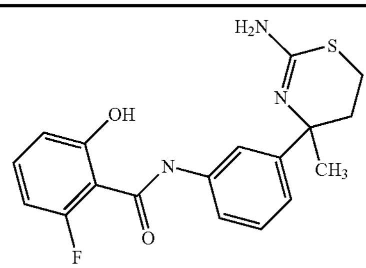 |
| 576 | 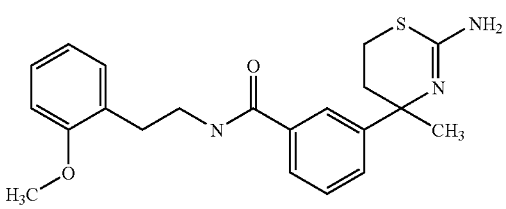 [SMILES: COc1ccccc1CCNC(=O)c1cccc(C2(C)CCSC(N)=N2)c1] |
| 577 | 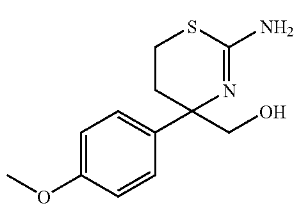 [SMILES: COc1ccc(C2(CO)CCSC(N)=N2)cc1] |
| 578 | 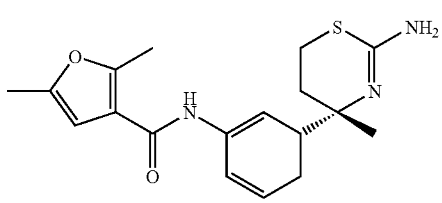 [SMILES: Cc1cc(C(=O)NC2=CC([C@]3(C)CCSC(N)=N3)CC=C2)c(C)o1] |

TABLE 61-continued

| No. | Structure |
|---|---|
| 579 | 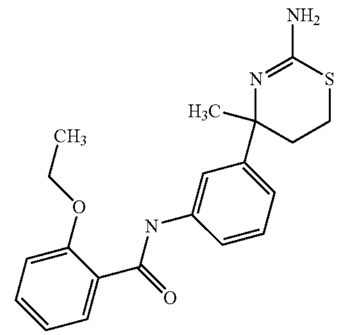 [SMILES: CCOc1ccccc1C(=O)Nc1cccc(C2(C)CCSC(N)=N2)c1] |
| 580 | 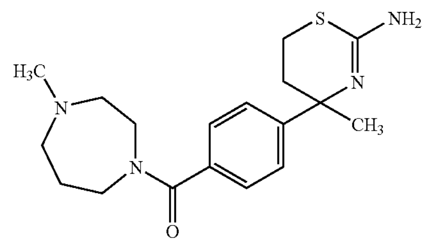 [SMILES: CN1CCCN(C(=O)c2ccc(C3(C)CCSC(N)=N3)cc2)CC1] |
| 581 | 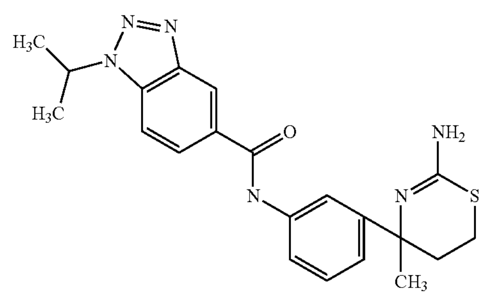 [SMILES: CC(C)n1nnc2cc(C(=O)Nc3cccc(C4(C)CCSC(N)=N4)c3)ccc21] |
| 582 | 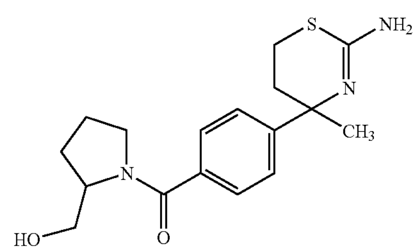 [SMILES: CC1(c2ccc(C(=O)N3CCCC3CO)cc2)CCSC(N)=N1] |
| 583 | 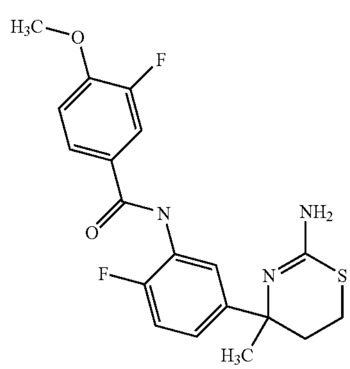 [SMILES: COc1ccc(C(=O)Nc2cc(C3(C)CCSC(N)=N3)ccc2F)cc1F] |

TABLE 61-continued

| No. | Structure |
|---|---|
| 584 | (structure) |

TABLE 62

| No. | Structure |
|---|---|
| 585 | (structure) |
| 586 | (structure) |
| 587 | (structure) |
| 588 | (structure) |

TABLE 62-continued

| No. | Structure |
|---|---|
| 589 | (structure) |
| 590 | (structure) |
| 591 | (structure) |

TABLE 63

| No. | Structure |
|---|---|
| 592 | (structure) |

TABLE 63-continued
| No. | Structure |
|---|---|
| 593 | 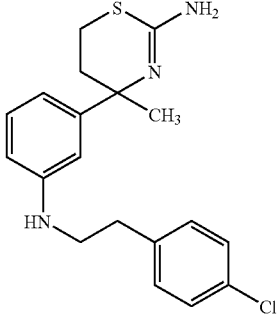 [SMILES: CC1(c2cccc(NCCc3ccc(Cl)cc3)c2)CCSC(N)=N1] |
| 594 | 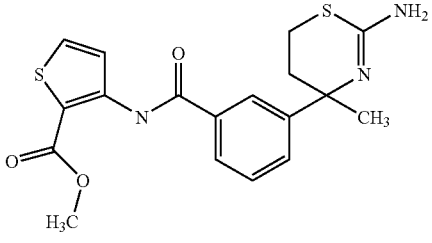 [SMILES: COC(=O)c1sccc1NC(=O)c1cccc(C2(C)CCSC(N)=N2)c1] |
| 595 | 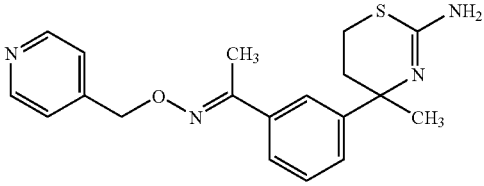 [SMILES: C/C(=N\OCc1ccncc1)c1cccc(C2(C)CCSC(N)=N2)c1] |
| 596 | 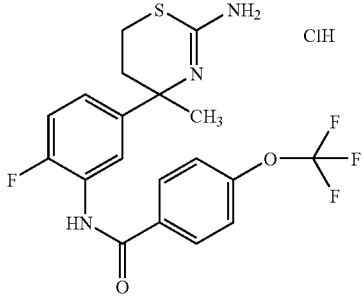 [SMILES: CC1(c2ccc(F)c(NC(=O)c3ccc(OC(F)(F)F)cc3)c2)CCSC(N)=N1 ; Cl] |
| 597 | 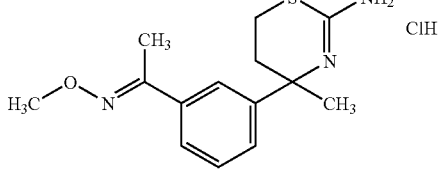 |
| 598 | 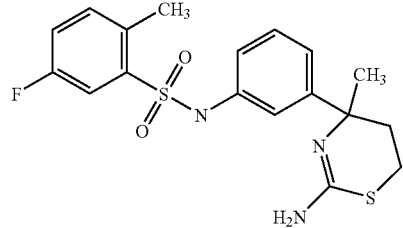 [SMILES: Cc1ccc(F)cc1S(=O)(=O)Nc1cccc(C2(C)CCSC(N)=N2)c1] |
| 599 | 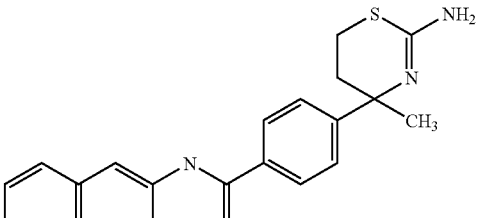 |
| 600 | 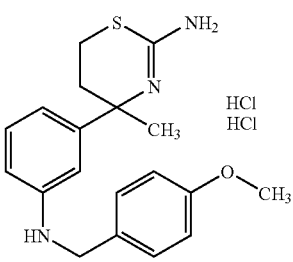 [SMILES: COc1ccc(CNc2cccc(C3(C)CCSC(N)=N3)c2)cc1 ; Cl ; Cl] |
| 601 | 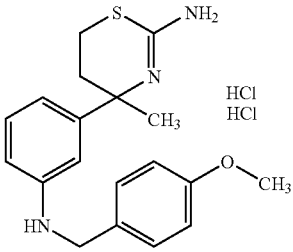 |
| 602 | 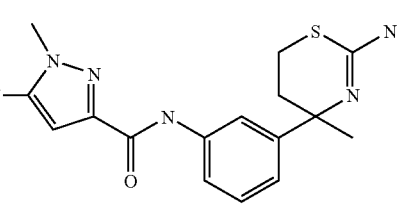 |
TABLE 64
| No. | Structure |
|---|---|
| 603 | 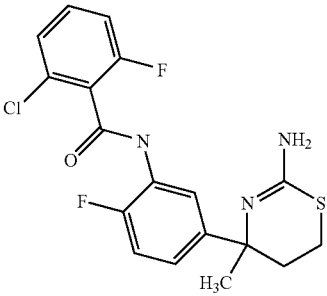 [SMILES: CC1(c2ccc(F)c(NC(=O)c3c(F)cccc3Cl)c2)CCSC(N)=N1] |

TABLE 64-continued

| No. | Structure |
|---|---|
| 604 | 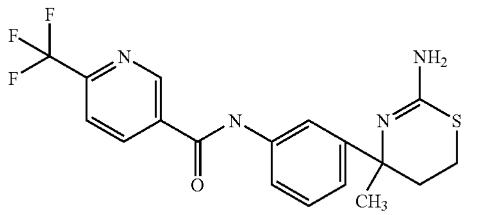 [SMILES: CC1(c2cccc(NC(=O)c3ccc(C(F)(F)F)nc3)c2)CCSC(N)=N1] |
| 605 | 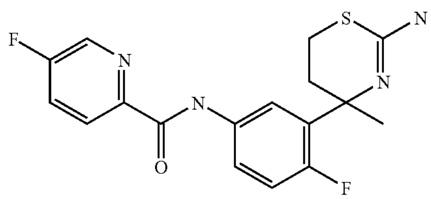 [SMILES: CC1(c2cc(NC(=O)c3ccc(F)cn3)ccc2F)CCSC(N)=N1] |
| 606 | 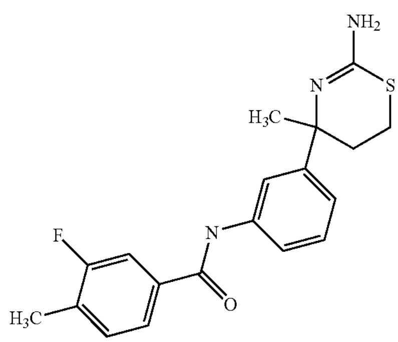 [SMILES: Cc1ccc(C(=O)Nc2cccc(C3(C)CCSC(N)=N3)c2)cc1F] |
| 607 | 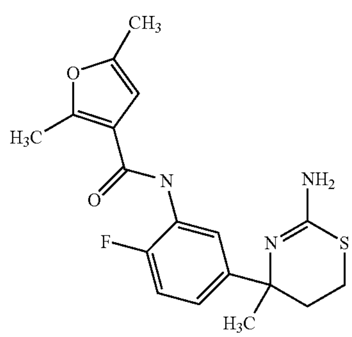 [SMILES: Cc1cc(C(=O)Nc2cc(C3(C)CCSC(N)=N3)ccc2F)c(C)o1] |
| 608 | 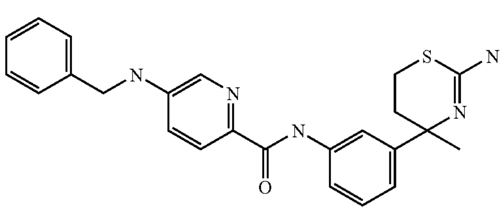 [SMILES: CC1(c2cccc(NC(=O)c3ccc(NCc4ccccc4)cn3)c2)CCSC(N)=N1] |
| 609 | 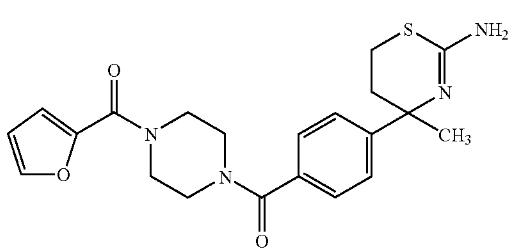 [SMILES: CC1(c2ccc(C(=O)N3CCN(C(=O)c4ccco4)CC3)cc2)CCSC(N)=N1] |

TABLE 64-continued

| No. | Structure |
|---|---|
| 610 | |
| 611 | |
| 612 | |
| 613 | |

TABLE 65

| No. | Structure |
|---|---|
| 614 | 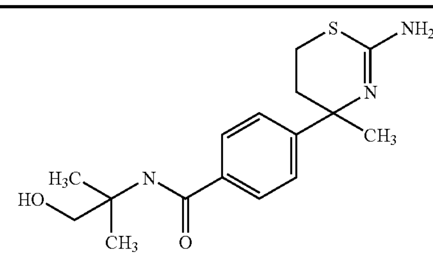 |
| 615 | 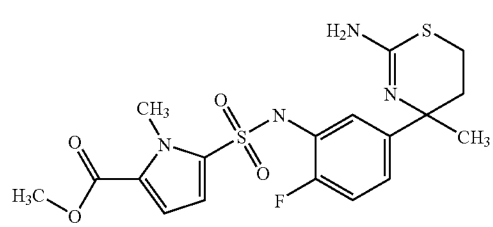 |

TABLE 65-continued
| No. | Structure |
|---|---|
| 616 | 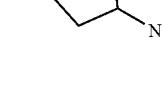 |
| 617 | 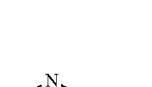 |
| 618 | 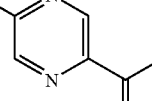 |
| 619 | 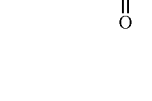 |
| 620 | 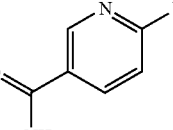 |
TABLE 65-continued
| No. | Structure |
|---|---|
| 621 | |
| 622 | |
| 623 | |
| 624 | |
TABLE 66
| No. | Structure |
|---|---|
| 625 | 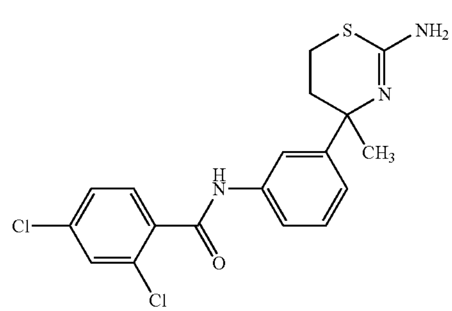 [SMILES: CC1(c2cccc(NC(=O)c3ccc(Cl)cc3Cl)c2)CCSC(N)=N1] |

TABLE 66-continued

| No. | Structure |
|---|---|
| 626 | 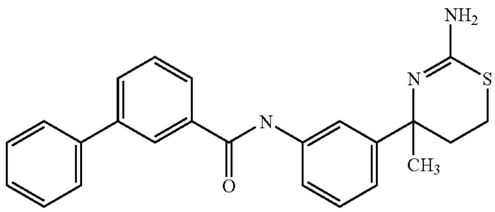 [SMILES: CC1(c2cccc(NC(=O)c3cccc(-c4ccccc4)c3)c2)CCSC(N)=N1] |
| 627 | 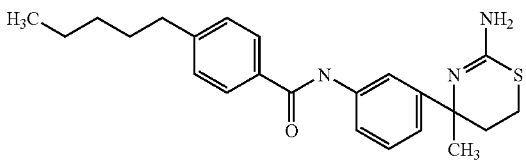 [SMILES: CCCCCc1ccc(C(=O)Nc2cccc(C3(C)CCSC(N)=N3)c2)cc1] |
| 628 | 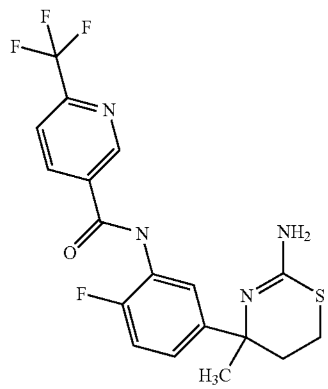 [SMILES: CC1(c2ccc(F)c(NC(=O)c3ccc(C(F)(F)F)nc3)c2)CCSC(N)=N1] |
| 629 | 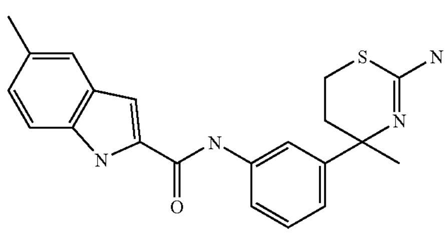 [SMILES: Cc1ccc2[nH]c(C(=O)Nc3cccc(C4(C)CCSC(N)=N4)c3)cc2c1] |
| 630 | 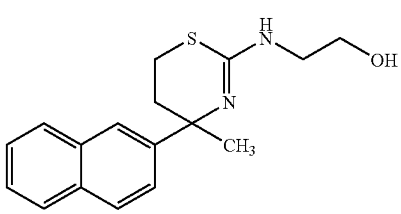 [SMILES: CC1(c2ccc3ccccc3c2)CCSC(NCCO)=N1] |
| 631 | 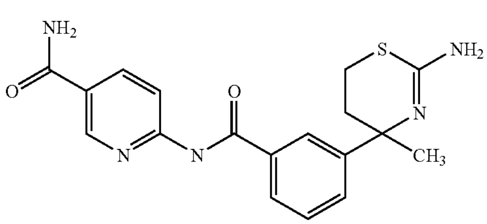 [SMILES: CC1(c2cccc(C(=O)Nc3ccc(C(N)=O)cn3)c2)CCSC(N)=N1] |

TABLE 66-continued

| No. | Structure |
|---|---|
| 632 | 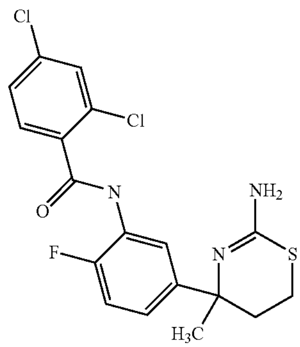 |
| 633 | 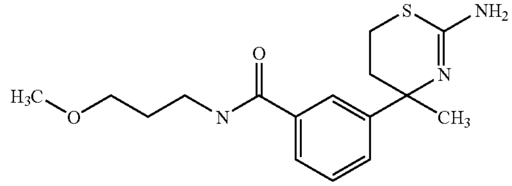 [SMILES: COCCCNC(=O)c1cccc(C2(C)CCSC(N)=N2)c1] |
| 634 | 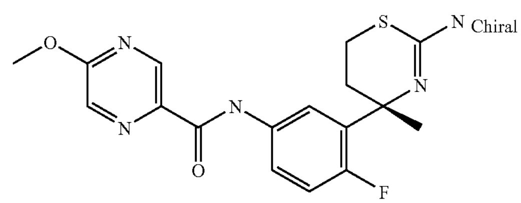 [SMILES: COc1cnc(C(=O)Nc2ccc(F)c([C@]3(C)CCSC(N)=N3)c2)cn1] |
| 635 | 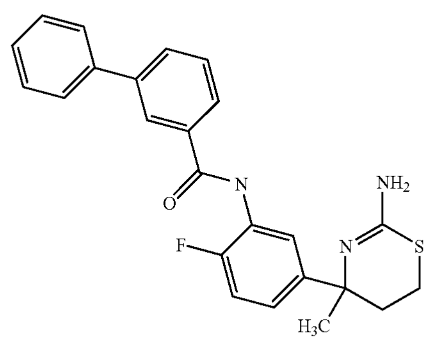 [SMILES: CC1(c2ccc(F)c(NC(=O)c3cccc(-c4ccccc4)c3)c2)CCSC(N)=N1] |

TABLE 67

| No. | Structure |
|---|---|
| 636 | 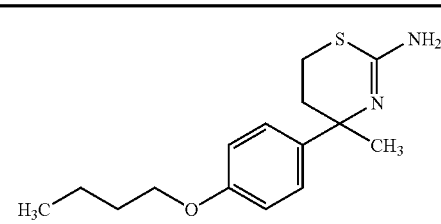 |

TABLE 67-continued
| No. | Structure |
|---|---|
| 637 | 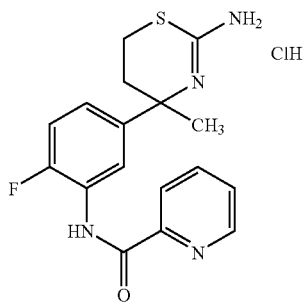 [SMILES: CC1(c2ccc(F)c(NC(=O)c3ccccn3)c2)CCSC(N)=N1 ; Cl] |
| 638 | 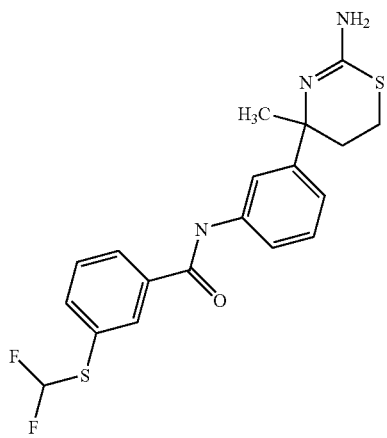 [SMILES: CC1(c2cccc(NC(=O)c3cccc(SC(F)F)c3)c2)CCSC(N)=N1] |
| 639 | 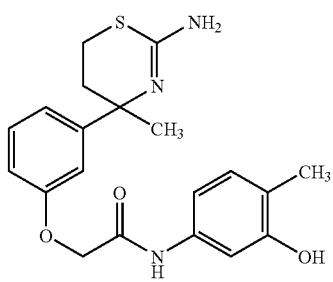 [SMILES: Cc1ccc(NC(=O)COc2cccc(C3(C)CCSC(N)=N3)c2)cc1O] |
| 640 | 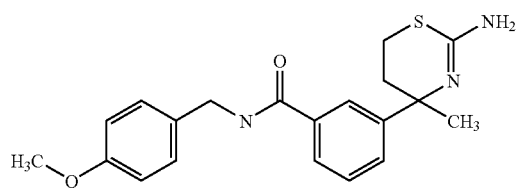 [SMILES: COc1ccc(CNC(=O)c2cccc(C3(C)CCSC(N)=N3)c2)cc1] |
TABLE 67-continued
| No. | Structure |
|---|---|
| 641 | 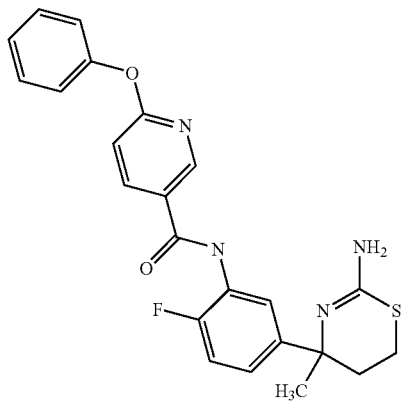 [SMILES: CC1(c2ccc(F)c(NC(=O)c3ccc(Oc4ccccc4)nc3)c2)CCSC(N)=N1] |
| 642 | 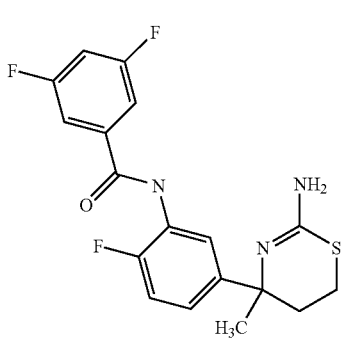 [SMILES: CC1(c2ccc(F)c(NC(=O)c3cc(F)cc(F)c3)c2)CCSC(N)=N1] |
| 643 | 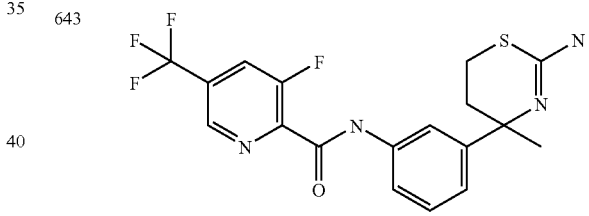 |
TABLE 68
| No. | Structure |
|---|---|
| 644 | 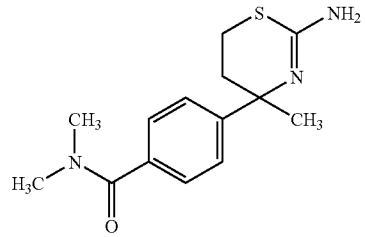 [SMILES: CN(C)C(=O)c1ccc(C2(C)CCSC(N)=N2)cc1] |
| 645 | 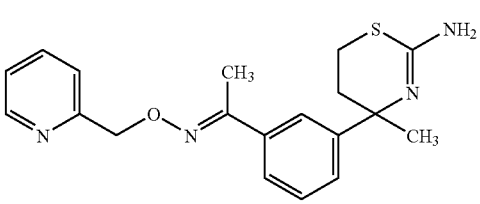 [SMILES: C/C(=N\OCc1ccccn1)c1cccc(C2(C)CCSC(N)=N2)c1] |

TABLE 68-continued

| No. | Structure |
|-----|-----------|
| 646 | (3,5-dichloropyridin-2-yl)-C(=O)-NH-(3-(2-imino-4-methyl-1,3-thiazinan-4-yl)phenyl), Chiral |
| 647 | (2-(hydroxymethyl)pyrrolidin-1-yl)-C(=O)-(3-(2-amino-4-methyl-5,6-dihydro-4H-1,3-thiazin-4-yl)phenyl) |
| 648 | (3-(pyridin-3-yl)phenyl)-C(=O)-NH-(3-(2-amino-4-methyl-5,6-dihydro-4H-1,3-thiazin-4-yl)phenyl) |
| 649 | (3-(2-amino-4-methyl-5,6-dihydro-4H-1,3-thiazin-4-yl)phenyl)-CH₂-morpholine |
| 650 | (4-(2-amino-4-methyl-5,6-dihydro-4H-1,3-thiazin-4-yl)phenyl)-C(=O)-NH-(4-ethoxyphenyl) |
| 651 | (5-cyanopyridin-2-yl)-C(=O)-NH-(3-(2-imino-4-methyl-1,3-thiazinan-4-yl)phenyl) |
| 652 | (benzo[c][1,2,5]oxadiazol-5-yl)-C(=O)-NH-(3-(2-imino-4-methyl-1,3-thiazinan-4-yl)phenyl) |

TABLE 68-continued

| No. | Structure |
|-----|-----------|
| 653 | (5-((dimethylamino)methyl)pyridin-2-yl)-C(=O)-NH-(3-(2-imino-4-methyl-1,3-thiazinan-4-yl)phenyl) |
| 654 | (6-methyl-6-phenyl-5,6-dihydro-4H-1,3-oxazin-2-yl)-NH-tert-butyl |
| 655 | (4-(2-hydroxyethyl)piperidin-1-yl)-C(=O)-(3-(2-amino-4-methyl-5,6-dihydro-4H-1,3-thiazin-4-yl)phenyl) |
| 656 | (2-methoxyethyl)-NH-C(=O)-(3-(2-amino-4-methyl-5,6-dihydro-4H-1,3-thiazin-4-yl)phenyl) |

TABLE 69

| No. | Structure |
|-----|-----------|
| 657 | (3-(2-amino-4-methyl-5,6-dihydro-4H-1,3-thiazin-4-yl)phenyl)-(CH₂)₂-C(=O)-NH-(5-chloropyridin-2-yl), 2 ClH |
| 658 | (naphthalen-2-yl)-S(=O)₂-NH-(2-fluoro-5-(2-amino-4-methyl-5,6-dihydro-4H-1,3-thiazin-4-yl)phenyl) |

TABLE 69-continued
| No. | Structure |
|---|---|
| 659 | 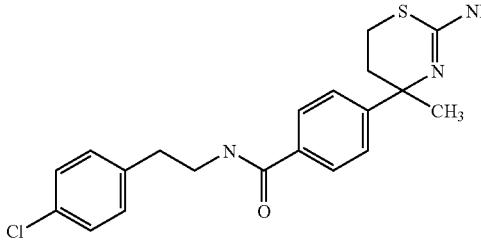 |
| 660 | 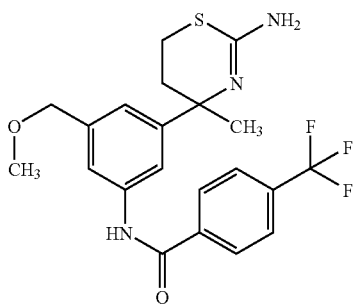 [SMILES: COCc1cc(NC(=O)c2ccc(C(F)(F)F)cc2)cc(C2(C)CCSC(N)=N2)c1] |
| 661 | 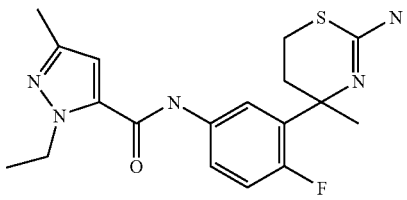 [SMILES: CCn1nc(C)cc1C(=O)Nc1ccc(F)c(C2(C)CCSC(N)=N2)c1] |
| 662 | 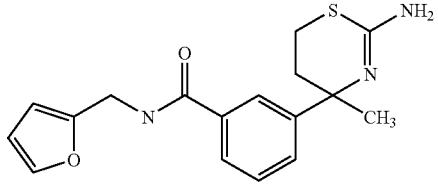 [SMILES: CC1(c2cccc(C(=O)NCc3ccco3)c2)CCSC(N)=N1] |
| 663 | 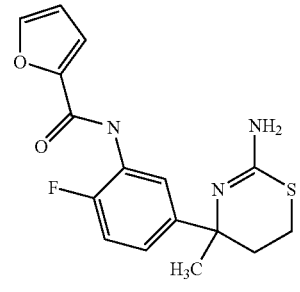 [SMILES: CC1(c2ccc(F)c(NC(=O)c3ccco3)c2)CCSC(N)=N1] |
| 664 | 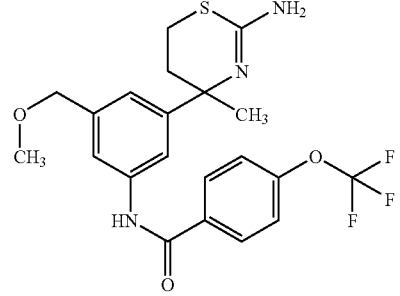 [SMILES: COCc1cc(NC(=O)c2ccc(OC(F)(F)F)cc2)cc(C2(C)CCSC(N)=N2)c1] |
TABLE 69-continued
| No. | Structure |
|---|---|
| 665 | 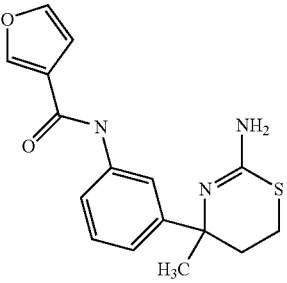 [SMILES: CC1(c2cccc(NC(=O)c3ccoc3)c2)CCSC(N)=N1] |
TABLE 70
| No. | Structure |
|---|---|
| 666 | 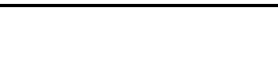 |
| 667 | 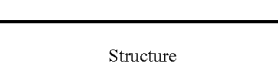 |
| 668 | 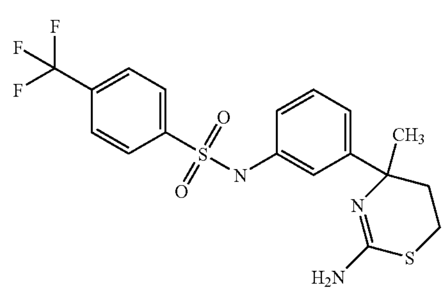 [SMILES: CC1(c2cccc(NS(=O)(=O)c3ccc(C(F)(F)F)cc3)c2)CCSC(N)=N1] |

TABLE 70-continued
| No. | Structure |
|-----|-----------|
| 669 | 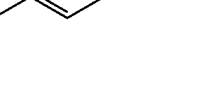 |
| 670 | 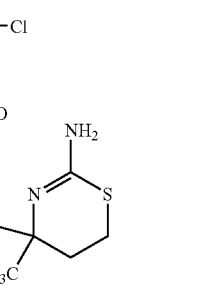 |
| 671 | 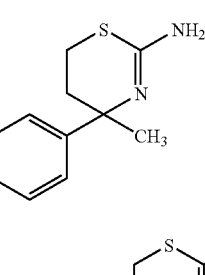 |
| 672 | 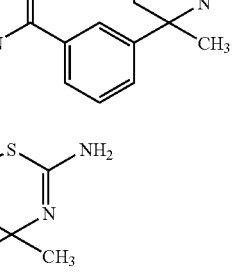 |
| 673 | 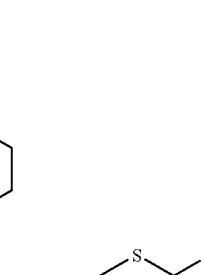 |
| 674 | 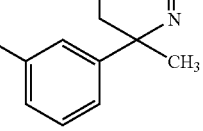 |
TABLE 71
| No. | Structure |
|-----|-----------|
| 675 | 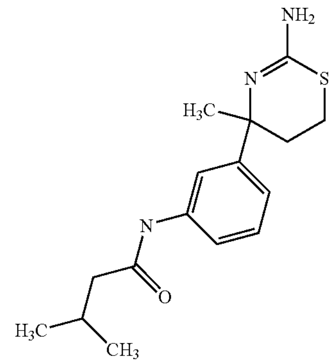 [SMILES: CC(C)CC(=O)Nc1cccc(C2(C)CCSC(N)=N2)c1] |
| 676 | 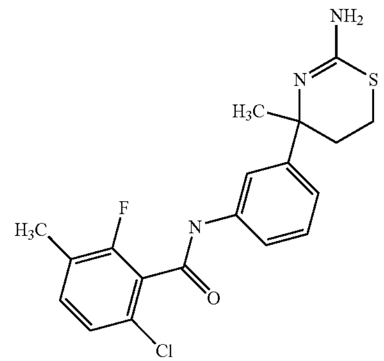 [SMILES: Cc1ccc(Cl)c(C(=O)Nc2cccc(C3(C)CCSC(N)=N3)c2)c1F] |
| 677 | 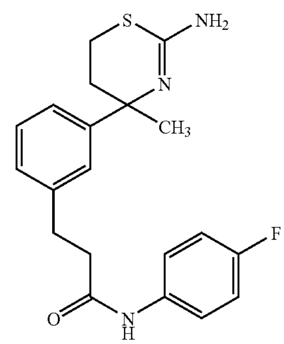 |
| 678 | 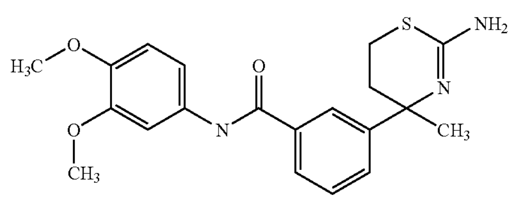 [SMILES: COc1ccc(NC(=O)c2cccc(C3(C)CCSC(N)=N3)c2)cc1OC] |
| 679 | 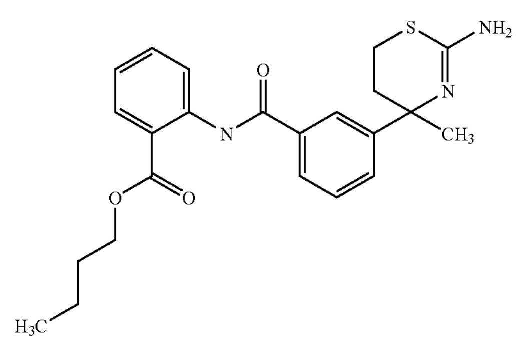 [SMILES: CCCCOC(=O)c1ccccc1NC(=O)c1cccc(C2(C)CCSC(N)=N2)c1] |

TABLE 71-continued
| No. | Structure |
|---|---|
| 680 | 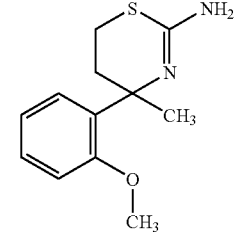 [SMILES: COc1ccccc1C1(C)CCSC(N)=N1] |
| 681 | 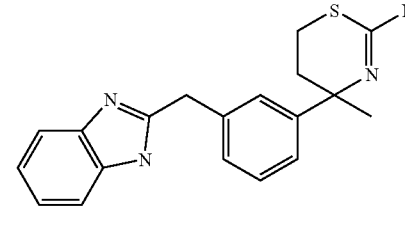 |
| 682 | 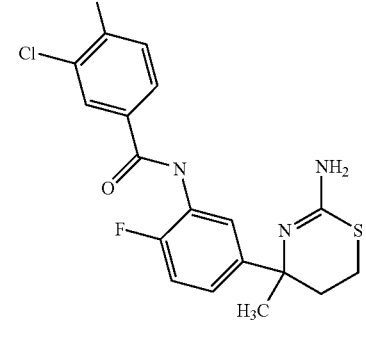 |
| 683 | 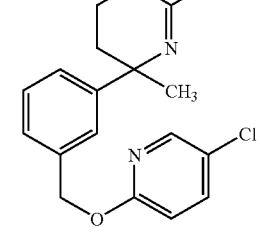 |
TABLE 72
| No. | Structure |
|---|---|
| 684 | 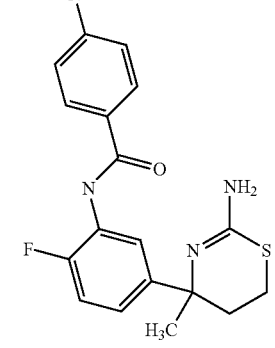 |
TABLE 72-continued
| No. | Structure |
|---|---|
| 685 | 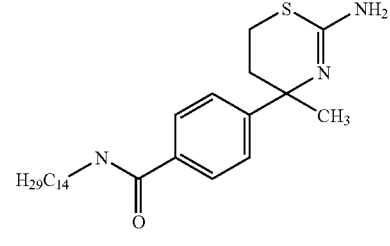 |
| 686 | 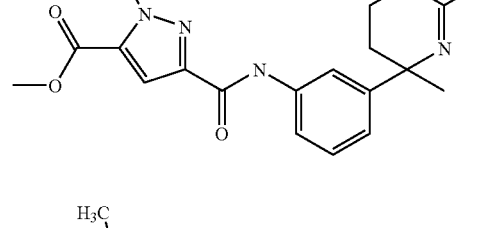 |
| 687 | 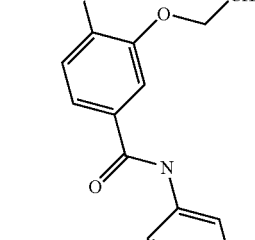 |
| 688 | 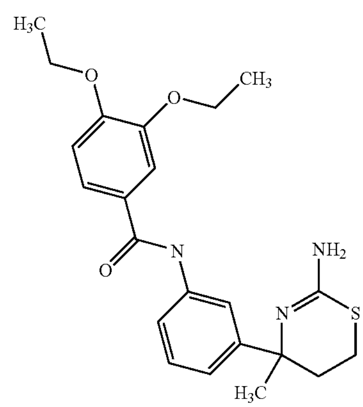 [SMILES: CCOc1ccc(C(=O)Nc2cccc(C3(C)CCSC(N)=N3)c2)cc1OCC] |
| 689 | 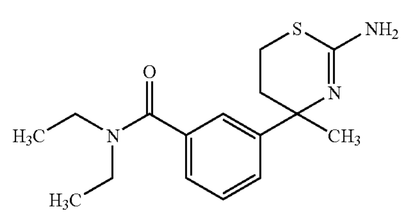 [SMILES: CCN(CC)C(=O)c1cccc(C2(C)CCSC(N)=N2)c1] |

TABLE 72-continued
| No. | Structure |
|---|---|
| 690 | 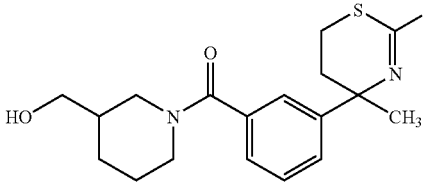 |
| 691 | 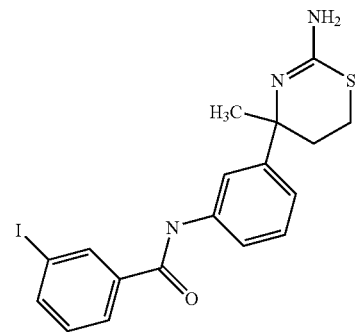 [SMILES: CC1(c2cccc(NC(=O)c3cccc(I)c3)c2)CCSC(N)=N1] |
| 692 | 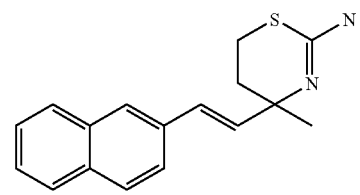 [SMILES: CC1(/C=C/c2ccc3ccccc3c2)CCSC(N)=N1] |
TABLE 73
| No. | Structure |
|---|---|
| 693 | 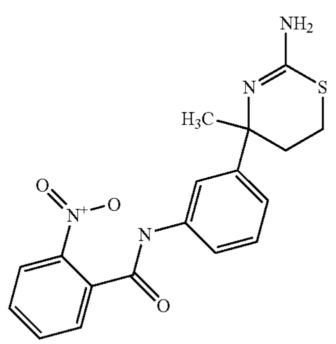 |
| 694 | 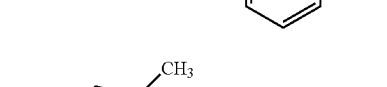 |
TABLE 73-continued
| No. | Structure |
|---|---|
| 695 | 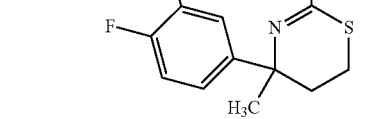 |
| 696 | 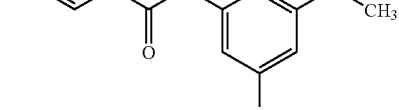 |
| 697 | 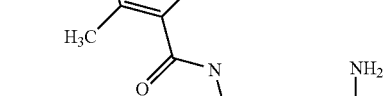 |
| 698 | 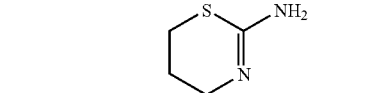 |
| 699 | 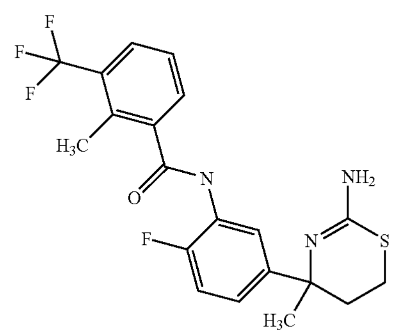 [SMILES: Cc1c(C(=O)Nc2cc(C3(C)CCSC(N)=N3)ccc2F)cccc1C(F)(F)F] |
| 700 | 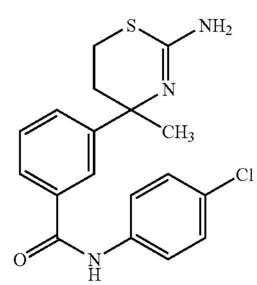 [SMILES: CC1(c2cccc(C(=O)Nc3ccc(Cl)cc3)c2)CCSC(N)=N1] |

TABLE 73-continued

| No. | Structure |
|---|---|
| 701 | 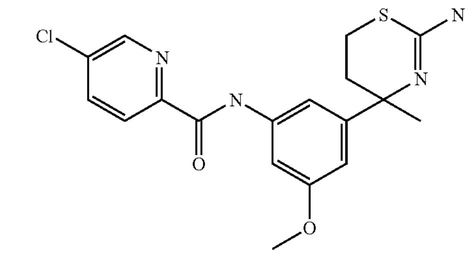 [SMILES: COc1cc(NC(=O)c2ccc(Cl)cn2)cc(C2(C)CCSC(N)=N2)c1] |
| 702 | 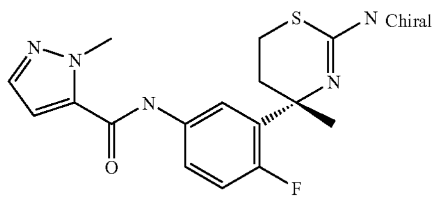 [SMILES: Cn1nccc1C(=O)Nc1ccc(F)c([C@]2(C)CCSC(N)=N2)c1] |

TABLE 74

| No. | Structure |
|---|---|
| 703 | 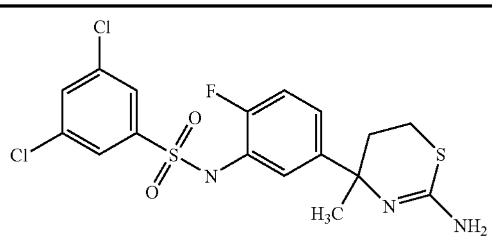 |
| 704 | 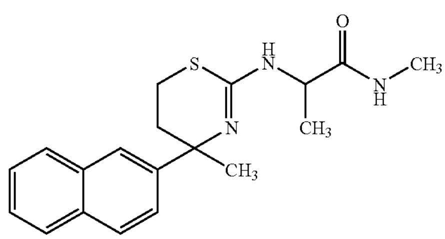 [SMILES: CNC(=O)C(C)NC1=NC(C)(c2ccc3ccccc3c2)CCS1] |
| 705 | 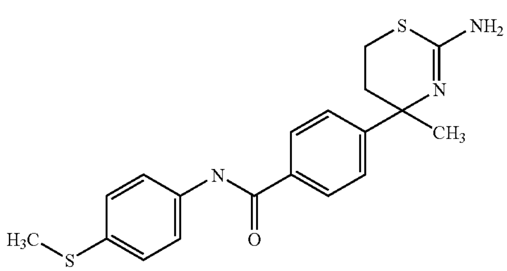 [SMILES: CSc1ccc(NC(=O)c2ccc(C3(C)CCSC(N)=N3)cc2)cc1] |
| 706 | 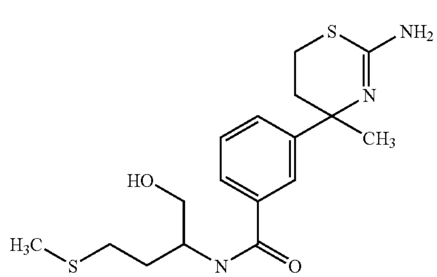 [SMILES: CSCCC(CO)NC(=O)c1cccc(C2(C)CCSC(N)=N2)c1] |

TABLE 74-continued

| No. | Structure |
|---|---|
| 707 | 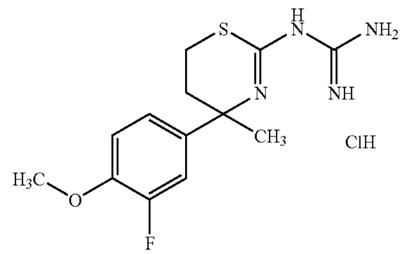 [SMILES: COc1ccc(C2(C)CCSC(NC(=N)N)=N2)cc1F ; Cl] |
| 708 | 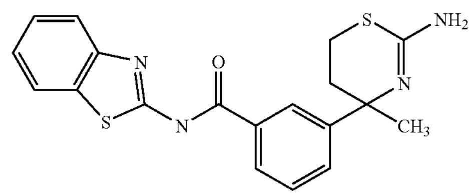 [SMILES: CC1(c2cccc(C(=O)Nc3nc4ccccc4s3)c2)CCSC(N)=N1] |
| 709 | 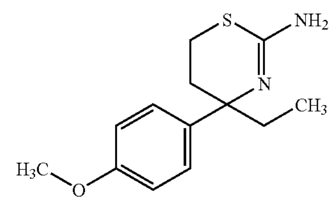 [SMILES: CCC1(c2ccc(OC)cc2)CCSC(N)=N1] |
| 710 | 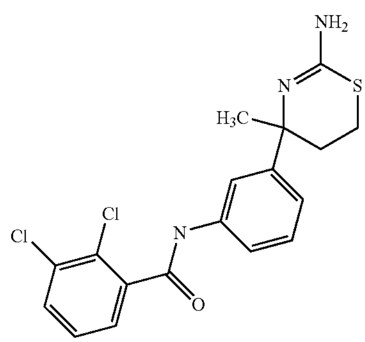 |
| 711 | 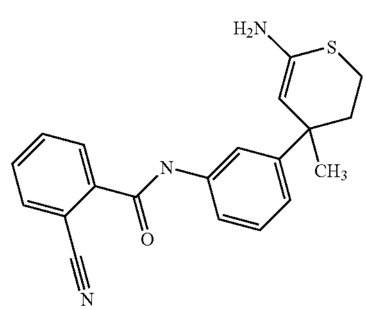 [SMILES: CC1(c2cccc(NC(=O)c3ccccc3C#N)c2)C=C(N)SCC1] |
| 712 | 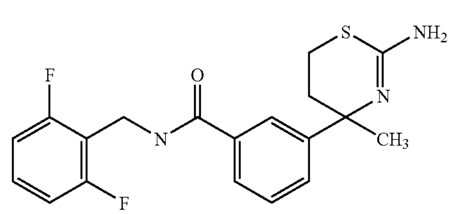 [SMILES: CC1(c2cccc(C(=O)NCc3c(F)cccc3F)c2)CCSC(N)=N1] |

TABLE 75

| No. | Structure |
| --- | --- |
| 713 | (structure) |
| 714 | (structure) |
| 715 | (structure) |
| 716 | (structure) |
| 717 | (structure) |

TABLE 75-continued

| No. | Structure |
| --- | --- |
| 718 | (structure) |
| 719 | (structure) |

TABLE 76

| No. | Structure |
| --- | --- |
| 720 | (structure) |
| 721 | (structure) |
| 722 | (structure) |

TABLE 76-continued
| No. | Structure |
|---|---|
| 723 | 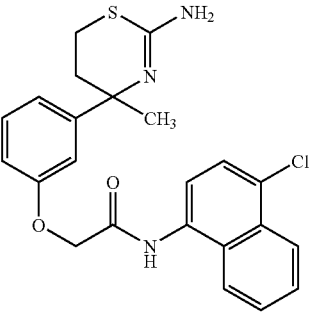 [SMILES: CC1(c2cccc(OCC(=O)Nc3ccc(Cl)c4ccccc34)c2)CCSC(N)=N1] |
| 724 | 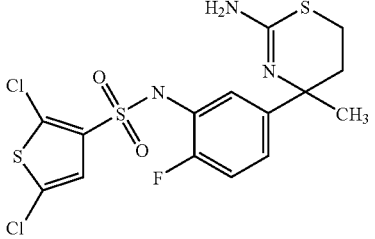 [SMILES: CC1(c2ccc(F)c(NS(=O)(=O)c3cc(Cl)sc3Cl)c2)CCSC(N)=N1] |
| 725 | 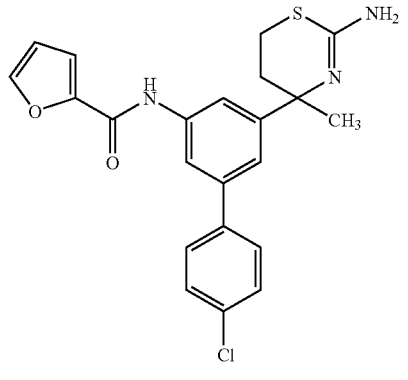 [SMILES: CC1(c2cc(NC(=O)c3ccco3)cc(-c3ccc(Cl)cc3)c2)CCSC(N)=N1] |
| 726 | 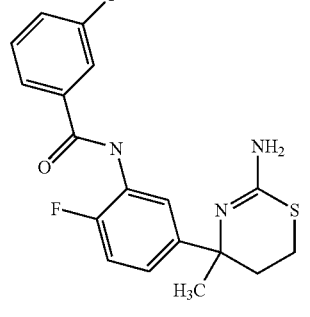 |
| 727 | 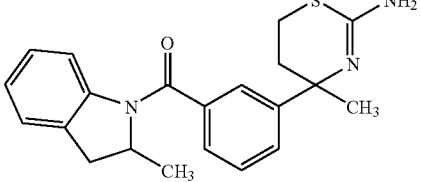 |
TABLE 76-continued
| No. | Structure |
|---|---|
| 728 | 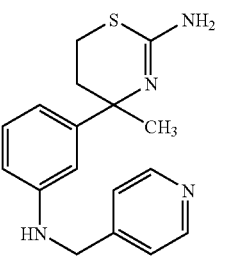 [SMILES: CC1(c2cccc(NCc3ccncc3)c2)CCSC(N)=N1] |
| 729 | 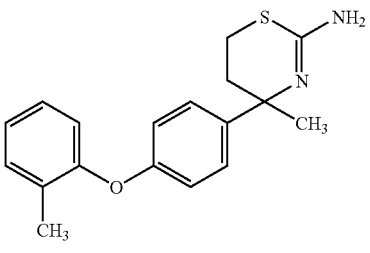 [SMILES: Cc1ccccc1Oc1ccc(C2(C)CCSC(N)=N2)cc1] |
TABLE 77
| No. | Structure |
|---|---|
| 730 | 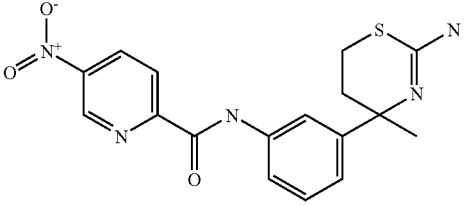 [SMILES: CC1(c2cccc(NC(=O)c3ccc([N+](=O)[O-])cn3)c2)CCSC(N)=N1] |
| 731 | 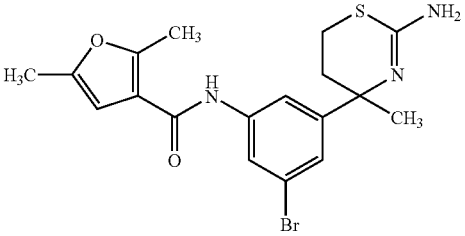 [SMILES: Cc1cc(C(=O)Nc2cc(Br)cc(C3(C)CCSC(N)=N3)c2)c(C)o1] |
| 732 | 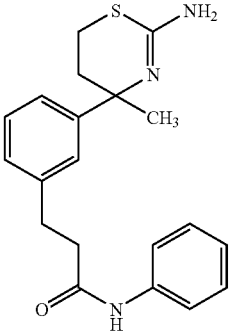 [SMILES: CC1(c2cccc(CCC(=O)Nc3ccccc3)c2)CCSC(N)=N1] |

TABLE 77-continued

| No. | Structure |
|-----|-----------|
| 733 | 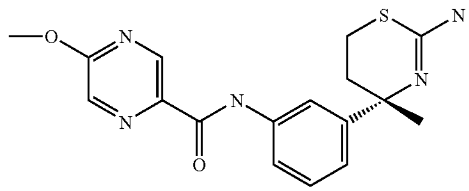 |
| 734 | 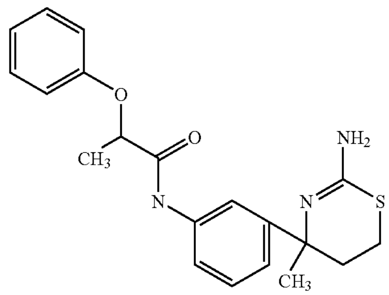 [SMILES: CC(Oc1ccccc1)C(=O)Nc1cccc(C2(C)CCSC(N)=N2)c1] |
| 735 | 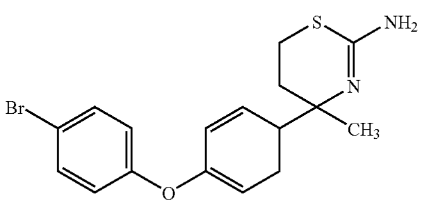 [SMILES: CC1(C2C=CC(Oc3ccc(Br)cc3)=CC2)CCSC(N)=N1] |
| 736 | 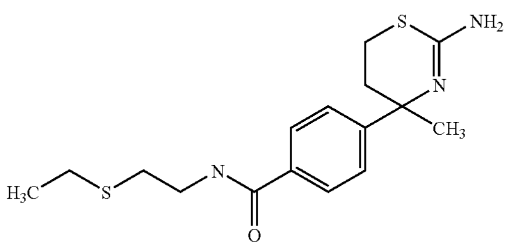 [SMILES: CCSCCNC(=O)c1ccc(C2(C)CCSC(N)=N2)cc1] |
| 737 | 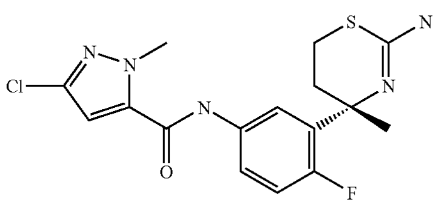 |
| 738 | 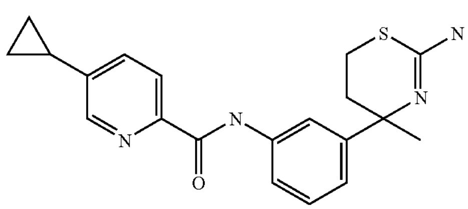 [SMILES: CC1(c2cccc(NC(=O)c3ccc(C4CC4)cn3)c2)CCSC(N)=N1] |
| 739 | 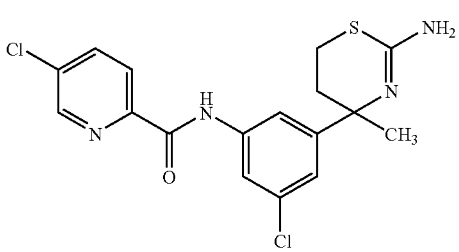 [SMILES: CC1(c2cc(Cl)cc(NC(=O)c3ccc(Cl)cn3)c2)CCSC(N)=N1] |

TABLE 77-continued

| No. | Structure |
|-----|-----------|

TABLE 78

| No. | Structure |
|-----|-----------|
| 740 | 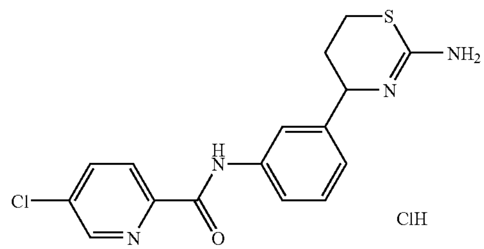 [SMILES: NC1=NC(c2cccc(NC(=O)c3ccc(Cl)cn3)c2)CCS1 ; Cl] |
| 741 | 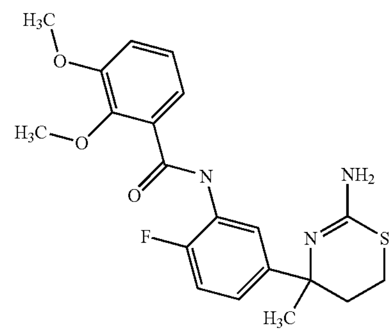 [SMILES: COc1cccc(C(=O)Nc2cc(C3(C)CCSC(N)=N3)ccc2F)c1OC] |
| 742 | 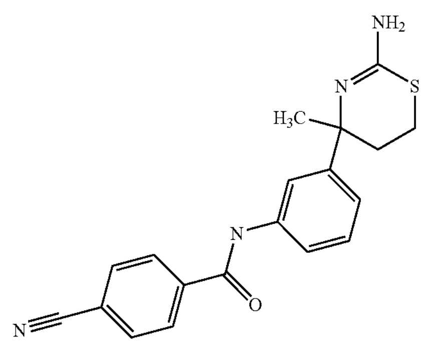 [SMILES: CC1(c2cccc(NC(=O)c3ccc(C#N)cc3)c2)CCSC(N)=N1] |
| 743 | 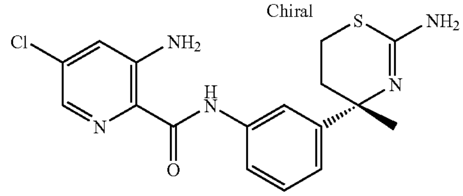 [SMILES: C[C@@]1(c2cccc(NC(=O)c3ncc(Cl)cc3N)c2)CCSC(N)=N1] |
| 744 | 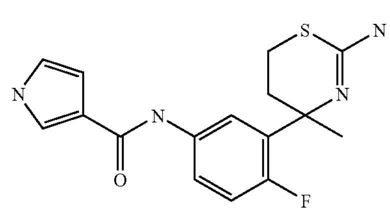 [SMILES: CC1(c2cc(NC(=O)c3cc[nH]c3)ccc2F)CCSC(N)=N1] |

TABLE 78-continued
| No. | Structure |
|---|---|
| 745 | 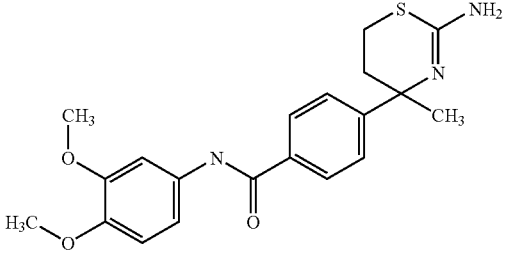 [SMILES: COc1ccc(NC(=O)c2ccc(C3(C)CCSC(N)=N3)cc2)cc1OC] |
| 746 | 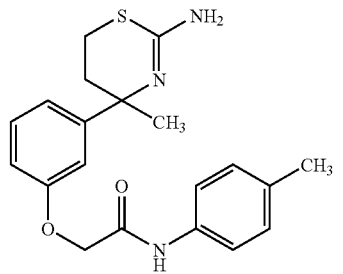 [SMILES: Cc1ccc(NC(=O)COc2cccc(C3(C)CCSC(N)=N3)c2)cc1] |
| 747 | 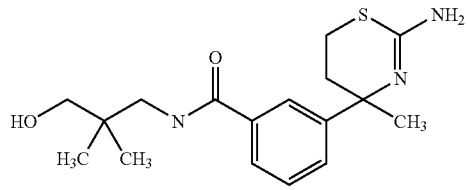 [SMILES: CC(C)(CO)CNC(=O)c1cccc(C2(C)CCSC(N)=N2)c1] |
| 748 | 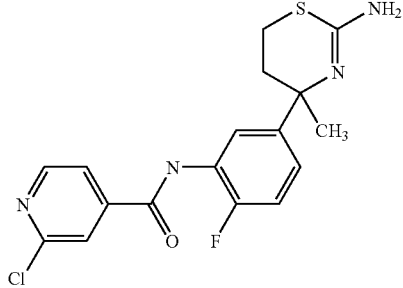 [SMILES: CC1(c2ccc(F)c(NC(=O)c3ccnc(Cl)c3)c2)CCSC(N)=N1] |
| 749 | 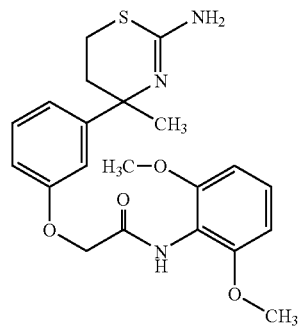 [SMILES: COc1cccc(OC)c1NC(=O)COc1cccc(C2(C)CCSC(N)=N2)c1] |
TABLE 79
| No. | Structure |
|---|---|
| 750 | 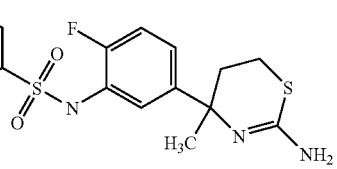 |
| 751 | 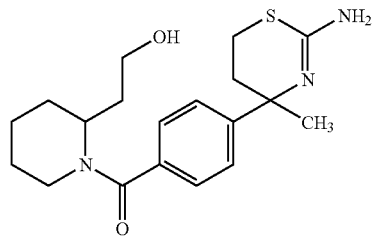 [SMILES: CC1(c2ccc(C(=O)N3CCCCC3CCO)cc2)CCSC(N)=N1] |
| 752 | 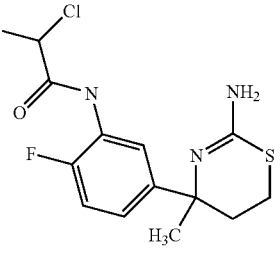 |
| 753 | 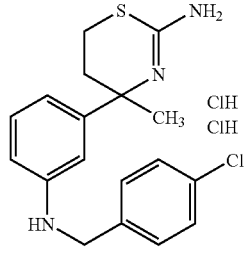 [SMILES: CC1(c2cccc(NCc3ccc(Cl)cc3)c2)CCSC(N)=N1 ; Cl ; Cl] |
| 754 | 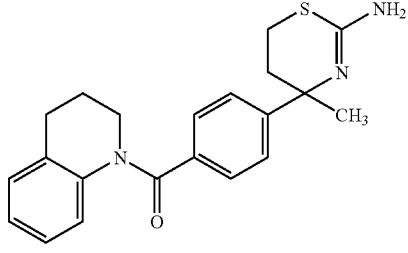 [SMILES: CC1(c2ccc(C(=O)N3CCCc4ccccc43)cc2)CCSC(N)=N1] |

TABLE 79-continued

| No. | Structure |
|---|---|
| 755 | (structure) |
| 756 | (structure) |
| 757 | (structure) |
| 758 | (structure) |
| 759 | (structure) |

TABLE 80

| No. | Structure |
|---|---|
| 760 | (structure) |
| 761 | (structure) |
| 762 | (structure) |
| 763 | (structure) |
| 764 | (structure) |
| 765 | (structure) |

TABLE 80-continued
| No. | Structure |
|---|---|
| 766 | 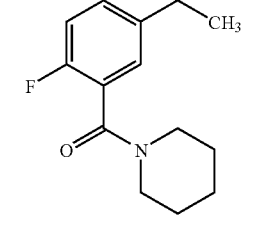 |
| 767 | 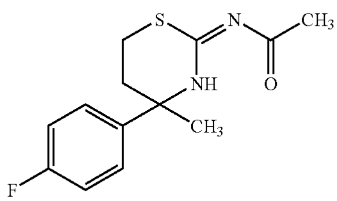 [SMILES: CC(=O)/N=C1\NC(C)(c2ccc(F)cc2)CCS1] |
| 768 | 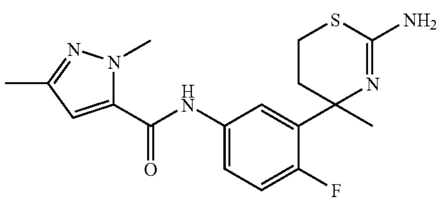 [SMILES: Cc1cc(C(=O)Nc2ccc(F)c(C3(C)CCSC(N)=N3)c2)n(C)n1] |
| 769 | 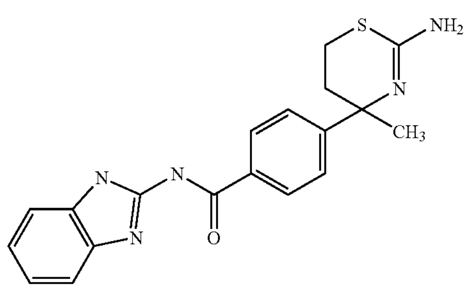 [SMILES: CC1(c2ccc(C(=O)Nc3nc4ccccc4[nH]3)cc2)CCSC(N)=N1] |
TABLE 81
| No. | Structure |
|---|---|
| 770 | 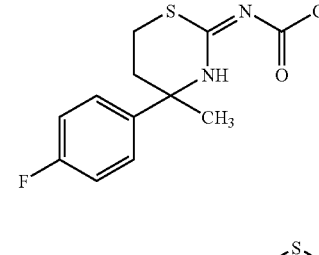 |
TABLE 81-continued
| No. | Structure |
|---|---|
| 771 | 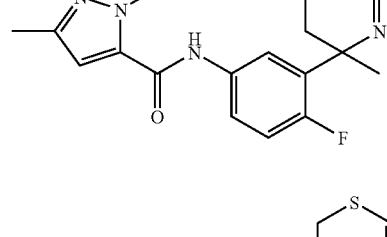 |
| 772 | 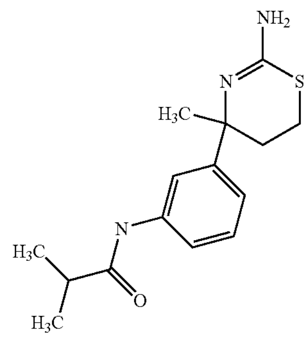 [SMILES: CC(C)C(=O)Nc1cccc(C2(C)CCSC(N)=N2)c1] |
| 773 | 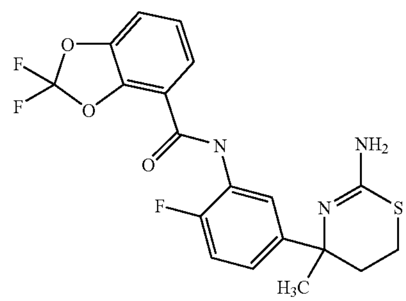 [SMILES: CC1(c2ccc(F)c(NC(=O)c3cccc4c3OC(F)(F)O4)c2)CCSC(N)=N1] |
| 774 | 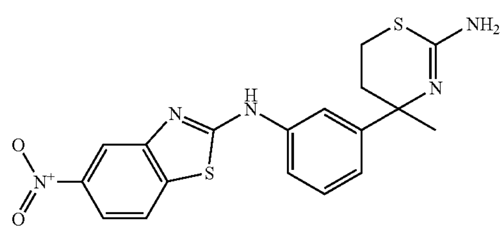 |
| 775 | 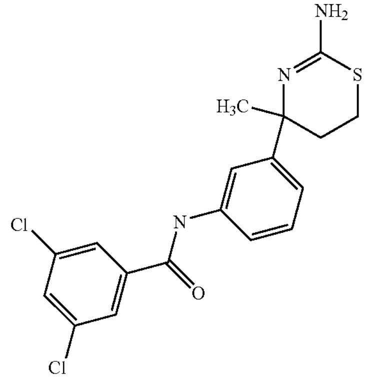 [SMILES: CC1(c2cccc(NC(=O)c3cc(Cl)cc(Cl)c3)c2)CCSC(N)=N1] |

TABLE 81-continued
| No. | Structure |
|---|---|
| 776 | 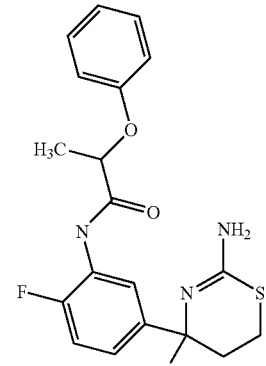 |
| 777 | 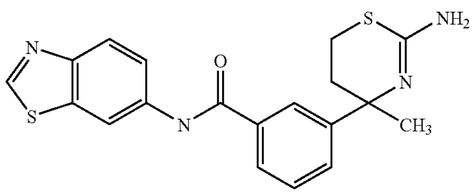 [SMILES: CC1(c2cccc(C(=O)Nc3ccc4ncsc4c3)c2)CCSC(N)=N1] |
TABLE 82
| No. | Structure |
|---|---|
| 778 | |
| 779 | |
| 780 | |
| 781 | 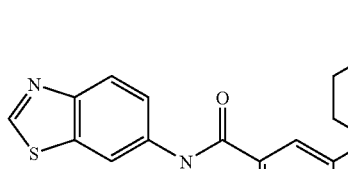 |
| 782 | 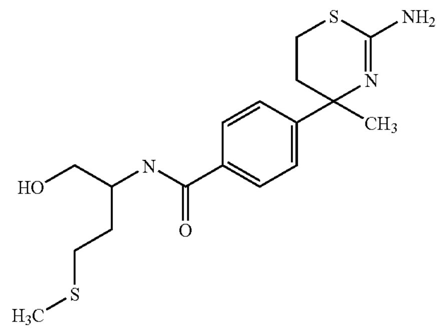 [SMILES: CSCCC(CO)NC(=O)c1ccc(C2(C)CCSC(N)=N2)cc1] |
| 783 | 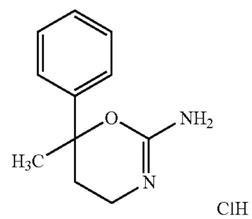 |
| 784 | 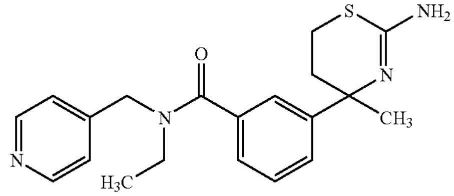 [SMILES: CCN(Cc1ccncc1)C(=O)c1cccc(C2(C)CCSC(N)=N2)c1] |
| 785 | 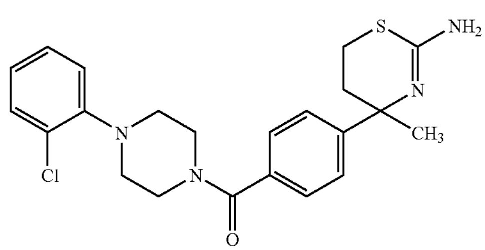 [SMILES: CC1(c2ccc(C(=O)N3CCN(c4ccccc4Cl)CC3)cc2)CCSC(N)=N1] |
| 786 | 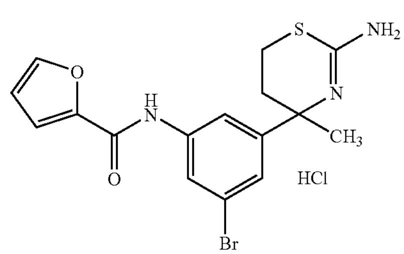 [SMILES: CC1(c2cc(Br)cc(NC(=O)c3ccco3)c2)CCSC(N)=N1 ; Cl] |

TABLE 82-continued

| No. | Structure |
|-----|-----------|
| 787 | 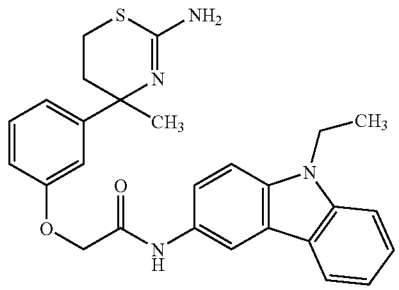 [SMILES: CCn1c2ccccc2c2cc(NC(=O)COc3cccc(C4(C)CCSC(N)=N4)c3)ccc21] |
| 788 | 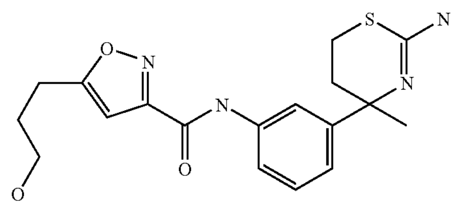 [SMILES: CC1(c2cccc(NC(=O)c3cc(CCCO)on3)c2)CCSC(N)=N1] |
| 789 | 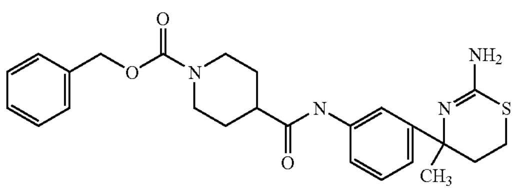 [SMILES: CC1(c2cccc(NC(=O)C3CCN(C(=O)OCc4ccccc4)CC3)c2)CCSC(N)=N1] |

TABLE 83

| No. | Structure |
|-----|-----------|
| 790 | 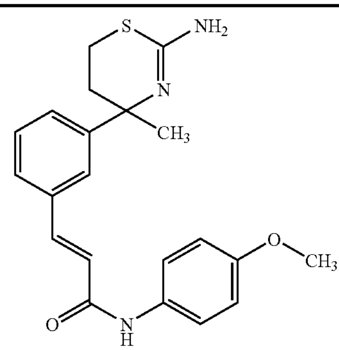 |
| 791 | 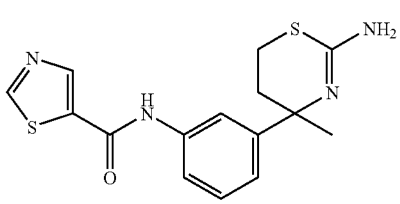 [SMILES: CC1(c2cccc(NC(=O)c3cncs3)c2)CCSC(N)=N1] |
| 792 | 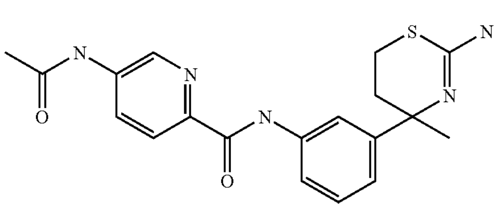 [SMILES: CC(=O)Nc1ccc(C(=O)Nc2cccc(C3(C)CCSC(N)=N3)c2)nc1] |

TABLE 83-continued

| No. | Structure |
|-----|-----------|
| 793 | 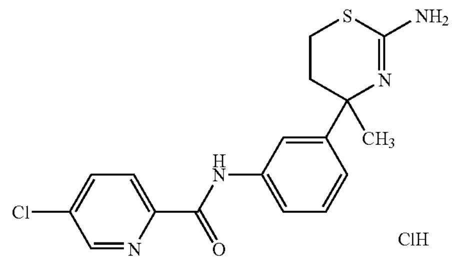 [SMILES: CC1(c2cccc(NC(=O)c3ccc(Cl)cn3)c2)CCSC(N)=N1 ; Cl] |
| 794 | 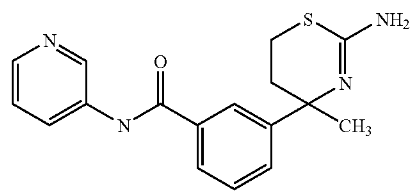 [SMILES: CC1(c2cccc(C(=O)Nc3cccnc3)c2)CCSC(N)=N1] |
| 795 | 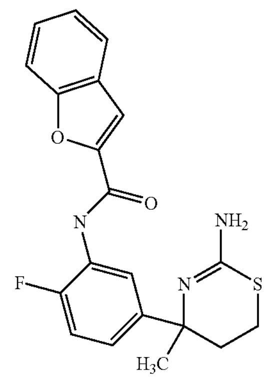 [SMILES: CC1(c2ccc(F)c(NC(=O)c3cc4ccccc4o3)c2)CCSC(N)=N1] |
| 796 | 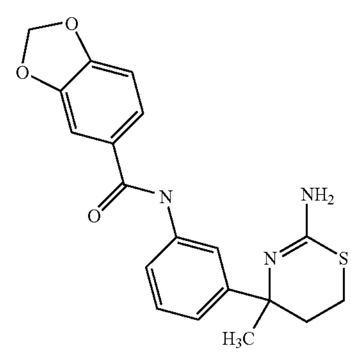 [SMILES: CC1(c2cccc(NC(=O)c3ccc4c(c3)OCO4)c2)CCSC(N)=N1] |
| 797 | 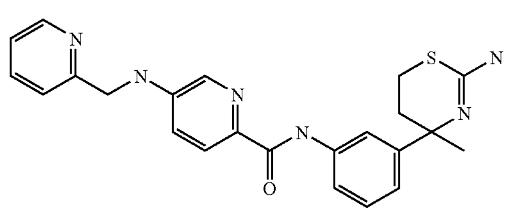 [SMILES: CC1(c2cccc(NC(=O)c3ccc(NCc4ccccn4)cn3)c2)CCSC(N)=N1] |

TABLE 83-continued

| No. | Structure |
|---|---|
| 798 | (structure) |

TABLE 84

| No. | Structure |
|---|---|
| 799 | (structure) ClH, ClH |
| 800 | (structure) |
| 801 | (structure) |
| 802 | (structure) |

TABLE 84-continued

| No. | Structure |
|---|---|
| 803 | (structure) |
| 804 | (structure) |
| 805 | (structure) |
| 806 | (structure) |
| 807 | (structure) |
| 808 | (structure) |

TABLE 84-continued
| No. | Structure |
|---|---|
| 809 | 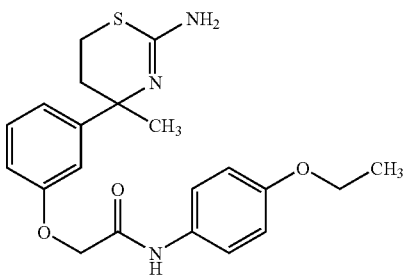 [SMILES: CCOc1ccc(NC(=O)COc2cccc(C3(C)CCSC(N)=N3)c2)cc1] |
TABLE 85
| No. | Structure |
|---|---|
| 810 | 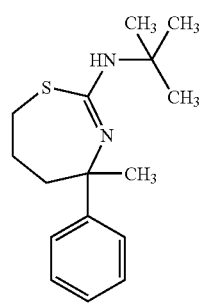 [SMILES: CC(C)(C)NC1=NC(C)(c2ccccc2)CCCS1] |
| 811 | 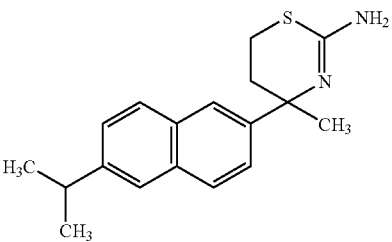 [SMILES: CC(C)c1ccc2cc(C3(C)CCSC(N)=N3)ccc2c1] |
| 812 | 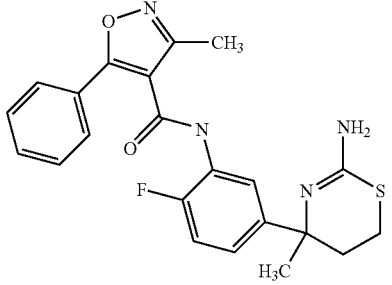 [SMILES: Cc1noc(-c2ccccc2)c1C(=O)Nc1cc(C2(C)CCSC(N)=N2)ccc1F] |
| 813 | 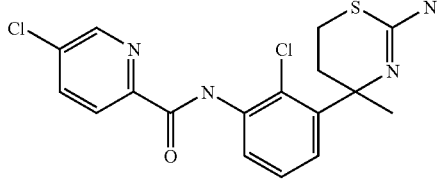 [SMILES: CC1(c2cccc(NC(=O)c3ccc(Cl)cn3)c2Cl)CCSC(N)=N1] |
TABLE 85-continued
| No. | Structure |
|---|---|
| 814 | 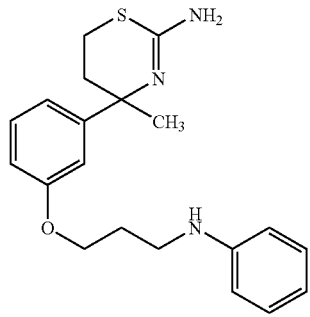 [SMILES: CC1(c2cccc(OCCCNc3ccccc3)c2)CCSC(N)=N1] |
| 815 | 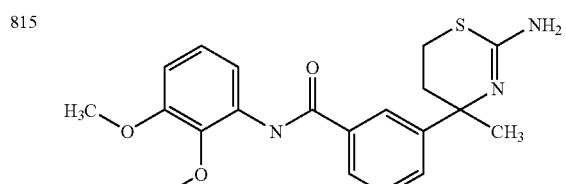 |
| 816 | 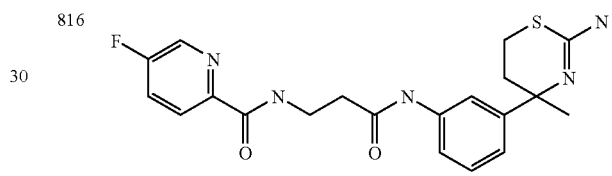 |
| 817 | 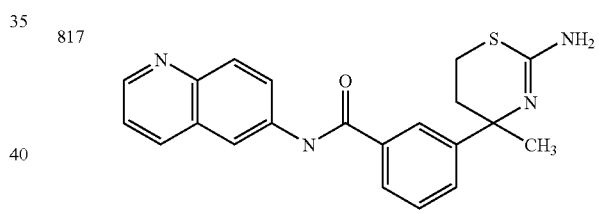 |
| 818 | 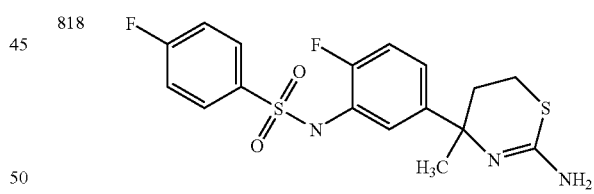 |
TABLE 86
| No. | Structure |
|---|---|
| 819 | 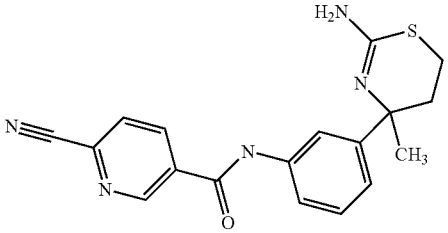 [SMILES: CC1(c2cccc(NC(=O)c3ccc(C#N)nc3)c2)CCSC(N)=N1] |

TABLE 86-continued
| No. | Structure |
|---|---|
| 820 | 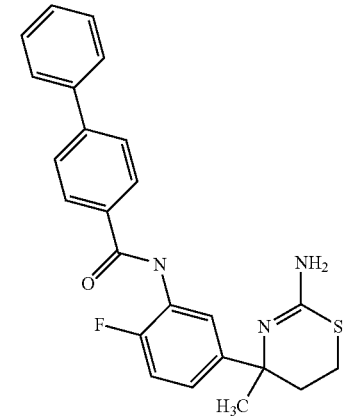 |
| 821 | 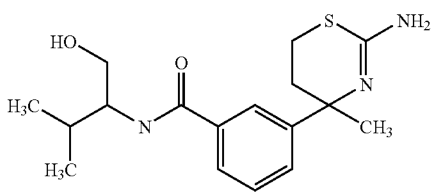 [SMILES: CC(C)C(CO)NC(=O)c1cccc(C2(C)CCSC(N)=N2)c1] |
| 822 | 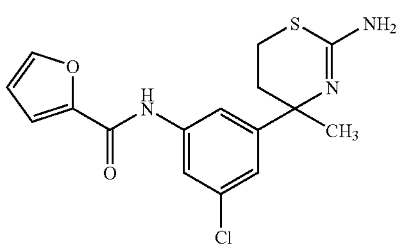 [SMILES: CC1(c2cc(Cl)cc(NC(=O)c3ccco3)c2)CCSC(N)=N1] |
| 823 | 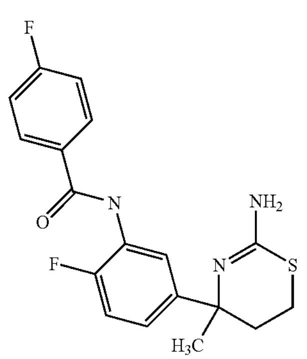 [SMILES: CC1(c2ccc(F)c(NC(=O)c3ccc(F)cc3)c2)CCSC(N)=N1] |
| 824 | 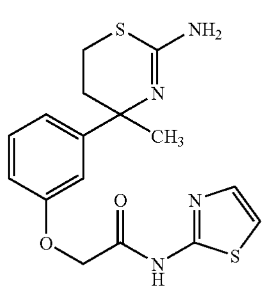 [SMILES: CC1(c2cccc(OCC(=O)Nc3nccs3)c2)CCSC(N)=N1] |
TABLE 86-continued
| No. | Structure |
|---|---|
| 825 | 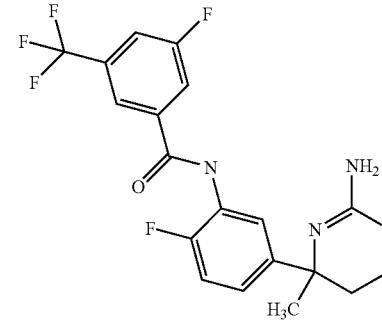 |
| 826 | |
| 827 | |
TABLE 87
| No. | Structure |
|---|---|
| 828 | 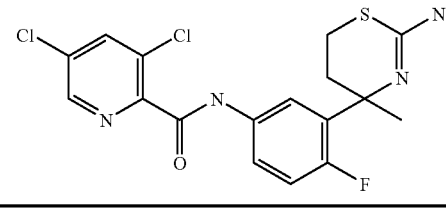 |
| 829 | 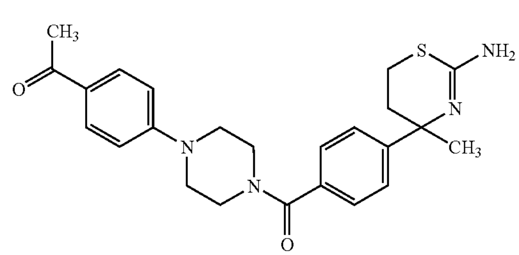 [SMILES: CC(=O)c1ccc(N2CCN(C(=O)c3ccc(C4(C)CCSC(N)=N4)cc3)CC2)cc1] |

TABLE 87-continued

| No. | Structure |
|---|---|
| 830 | 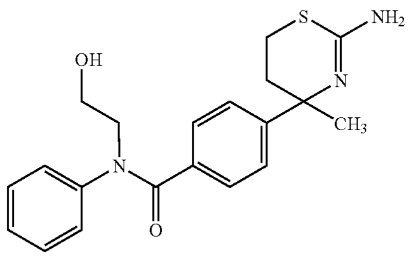 [SMILES: CC1(c2ccc(C(=O)N(CCO)c3ccccc3)cc2)CCSC(N)=N1] |
| 831 | 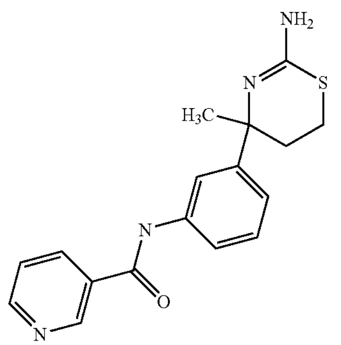 [SMILES: CC1(c2cccc(NC(=O)c3cccnc3)c2)CCSC(N)=N1] |
| 832 | 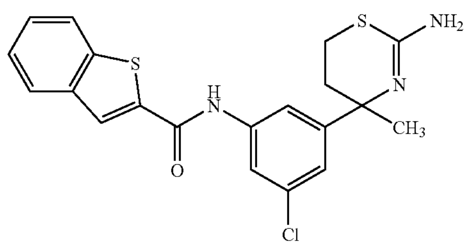 [SMILES: CC1(c2cc(Cl)cc(NC(=O)c3cc4ccccc4s3)c2)CCSC(N)=N1] |
| 833 | 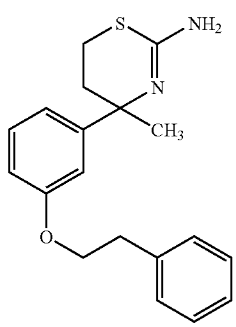 [SMILES: CC1(c2cccc(OCCc3ccccc3)c2)CCSC(N)=N1] |
| 834 | 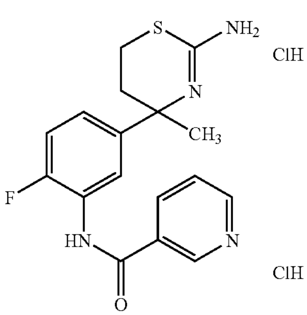 [SMILES: CC1(c2ccc(F)c(NC(=O)c3cccnc3)c2)CCSC(N)=N1 ; Cl ; Cl] |

TABLE 87-continued

| No. | Structure |
|---|---|
| 835 (racemate) | 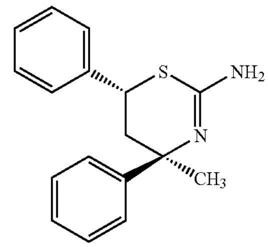 [SMILES: C[C@]1(c2ccccc2)C[C@H](c2ccccc2)SC(N)=N1] |
| 836 | 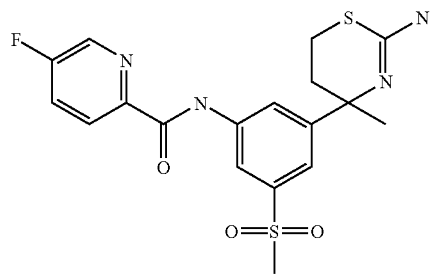 |

TABLE 88

| No. | Structure |
|---|---|
| 837 | 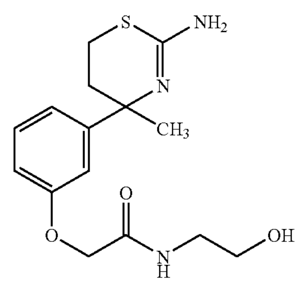 [SMILES: CC1(c2cccc(OCC(=O)NCCO)c2)CCSC(N)=N1] |
| 838 | 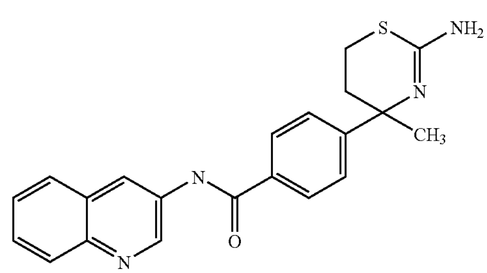 [SMILES: CC1(c2ccc(C(=O)Nc3cnc4ccccc4c3)cc2)CCSC(N)=N1] |
| 839 | 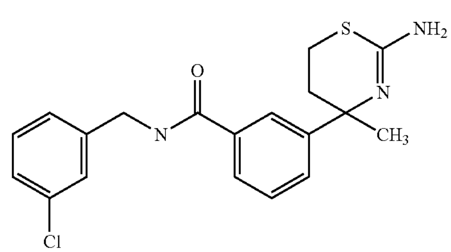 [SMILES: CC1(c2cccc(C(=O)NCc3cccc(Cl)c3)c2)CCSC(N)=N1] |

TABLE 88-continued
| No. | Structure |
|-----|-----------|
| 840 | 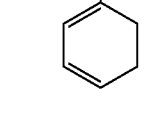 ClH |
| 841 | 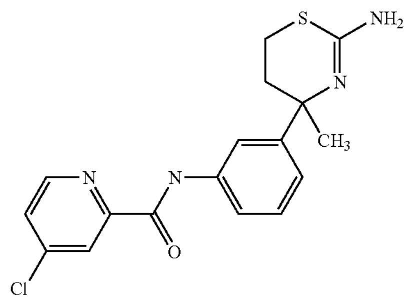 [SMILES: CC1(c2cccc(NC(=O)c3cc(Cl)ccn3)c2)CCSC(N)=N1] |
| 842 | 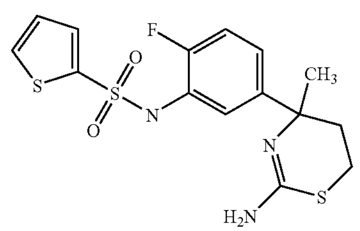 [SMILES: CC1(c2ccc(F)c(NS(=O)(=O)c3cccs3)c2)CCSC(N)=N1] |
| 843 | 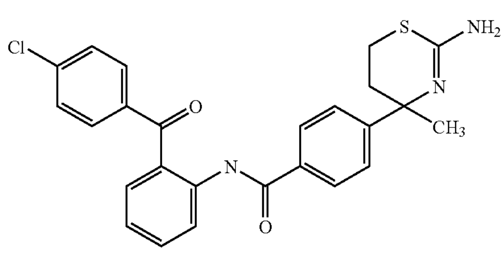 [SMILES: CC1(c2ccc(C(=O)Nc3ccccc3C(=O)c3ccc(Cl)cc3)cc2)CCSC(N)=N1] |
| 844 | 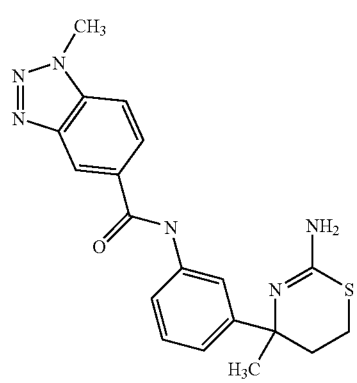 [SMILES: Cn1nnc2cc(C(=O)Nc3cccc(C4(C)CCSC(N)=N4)c3)ccc21] |
TABLE 88-continued
| No. | Structure |
|-----|-----------|
| 845 | 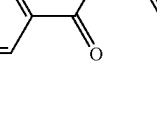 |
TABLE 89
| No. | Structure |
|-----|-----------|
| 846 | 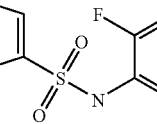 |
| 847 | 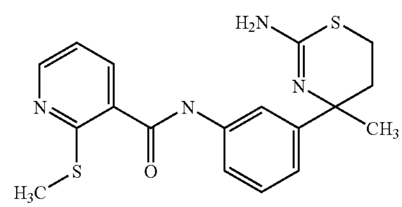 [SMILES: CSc1ncccc1C(=O)Nc1cccc(C2(C)CCSC(N)=N2)c1] |
| 848 | 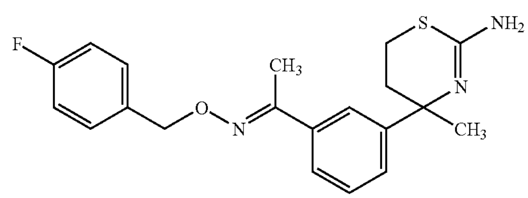 [SMILES: C/C(=N\OCc1ccc(F)cc1)c1cccc(C2(C)CCSC(N)=N2)c1] |
| 849 | ClH |
| 850 | 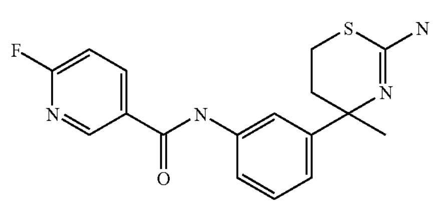 [SMILES: CC1(c2cccc(NC(=O)c3ccc(F)nc3)c2)CCSC(N)=N1] |

TABLE 89-continued

| No. | Structure |
|---|---|
| 851 | 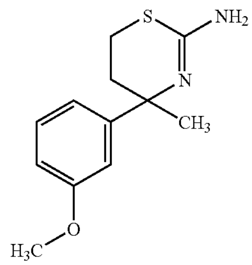 [SMILES: COc1cccc(C2(C)CCSC(N)=N2)c1] |
| 852 | 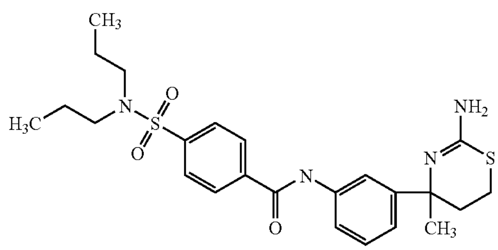 [SMILES: CCCN(CCC)S(=O)(=O)c1ccc(C(=O)Nc2cccc(C3(C)CCSC(N)=N3)c2)cc1] |
| 853 | 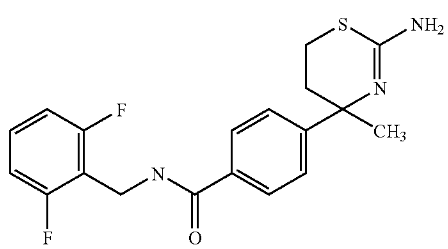 [SMILES: CC1(c2ccc(C(=O)NCc3c(F)cccc3F)cc2)CCSC(N)=N1] |
| 854 | 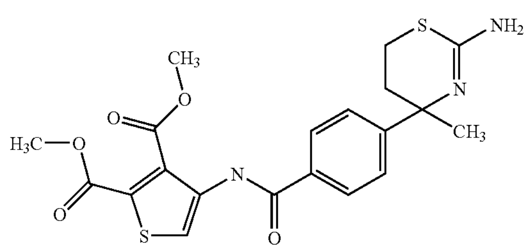 [SMILES: COC(=O)c1scc(NC(=O)c2ccc(C3(C)CCSC(N)=N3)cc2)c1C(=O)OC] |
| 855 | 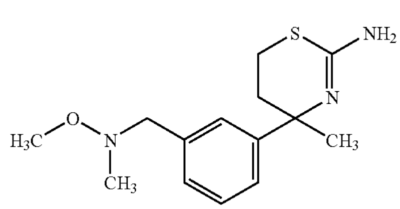 [SMILES: CON(C)Cc1cccc(C2(C)CCSC(N)=N2)c1] |

TABLE 90

| No. | Structure |
|---|---|
| 856 | 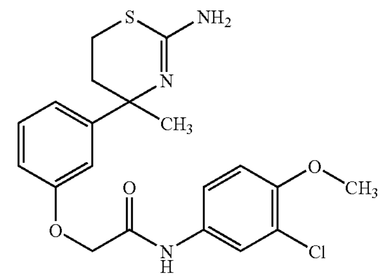 [SMILES: COc1ccc(NC(=O)COc2cccc(C3(C)CCSC(N)=N3)c2)cc1Cl] |
| 857 | 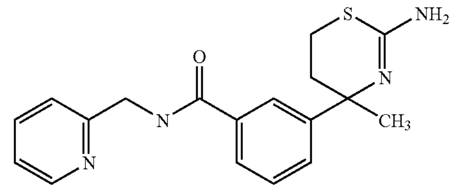 [SMILES: CC1(c2cccc(C(=O)NCc3ccccn3)c2)CCSC(N)=N1] |
| 858 | 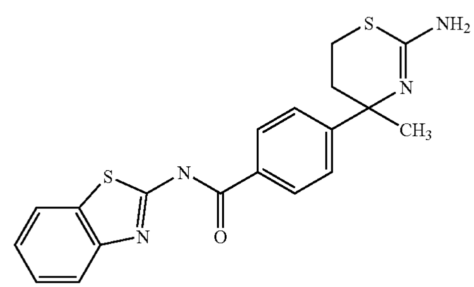 [SMILES: CC1(c2ccc(C(=O)Nc3nc4ccccc4s3)cc2)CCSC(N)=N1] |
| 859 | 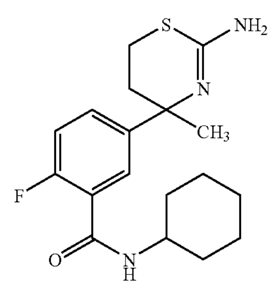 [SMILES: CC1(c2ccc(F)c(C(=O)NC3CCCCC3)c2)CCSC(N)=N1] |
| 860 | 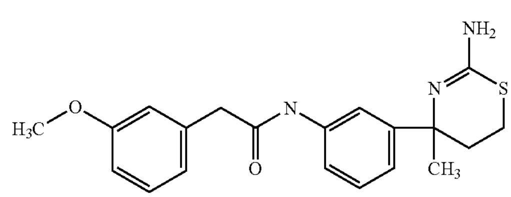 [SMILES: COc1cccc(CC(=O)Nc2cccc(C3(C)CCSC(N)=N3)c2)c1] |
| 861 | 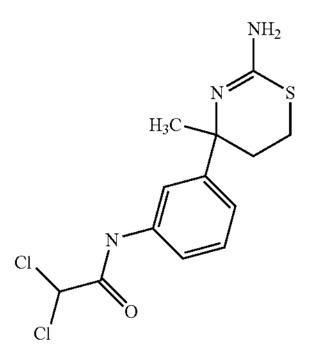 [SMILES: CC1(c2cccc(NC(=O)C(Cl)Cl)c2)CCSC(N)=N1] |

TABLE 90-continued

| No. | Structure |
|---|---|
| 862 | 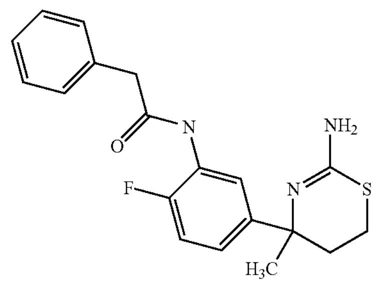 [SMILES: CC1(c2ccc(F)c(NC(=O)Cc3ccccc3)c2)CCSC(N)=N1] |
| 863 | 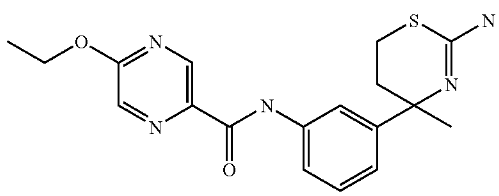 [SMILES: CCOc1cnc(C(=O)Nc2cccc(C3(C)CCSC(N)=N3)c2)cn1] |
| 864 | 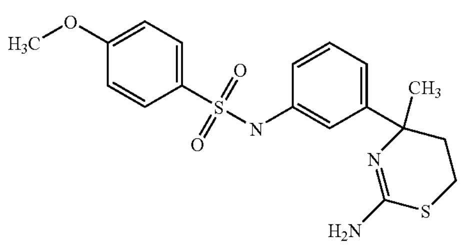 [SMILES: COc1ccc(S(=O)(=O)Nc2cccc(C3(C)CCSC(N)=N3)c2)cc1] |

TABLE 91

| No. | Structure |
|---|---|
| 865 | 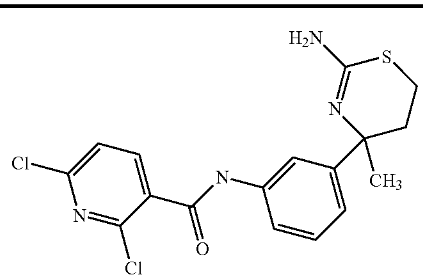 |
| 866 | 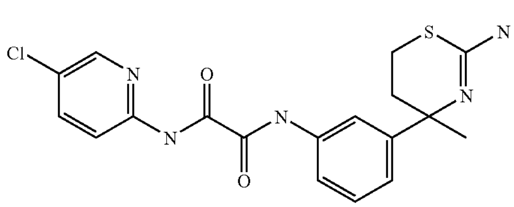 [SMILES: CC1(c2cccc(NC(=O)C(=O)Nc3ccc(Cl)cn3)c2)CCSC(N)=N1] |

TABLE 91-continued

| No. | Structure |
|---|---|
| 867 | 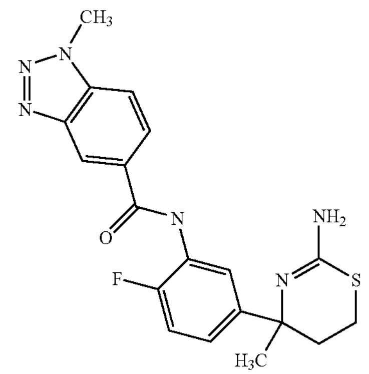 [SMILES: Cn1nnc2cc(C(=O)Nc3cc(C4(C)CCSC(N)=N4)ccc3F)ccc21] |
| 868 | 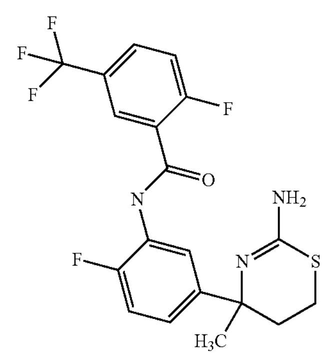 |
| 869 | 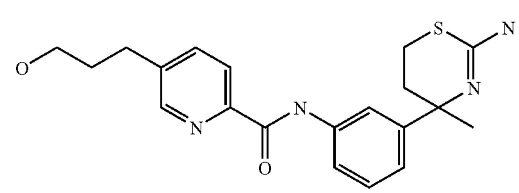 [SMILES: CC1(c2cccc(NC(=O)c3ccc(CCCO)cn3)c2)CCSC(N)=N1] |
| 870 | 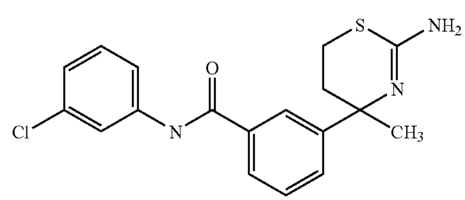 [SMILES: CC1(c2cccc(C(=O)Nc3cccc(Cl)c3)c2)CCSC(N)=N1] |
| 871 | 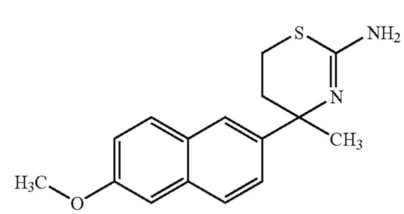 [SMILES: COc1ccc2cc(C3(C)CCSC(N)=N3)ccc2c1] |
| 872 | 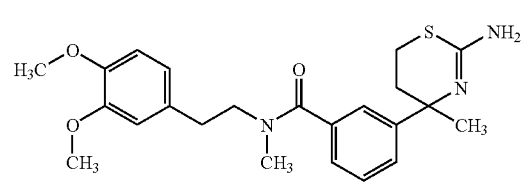 [SMILES: COc1ccc(CCN(C)C(=O)c2cccc(C3(C)CCSC(N)=N3)c2)cc1OC] |

TABLE 91-continued

| No. | Structure |
|-----|-----------|
| 873 | 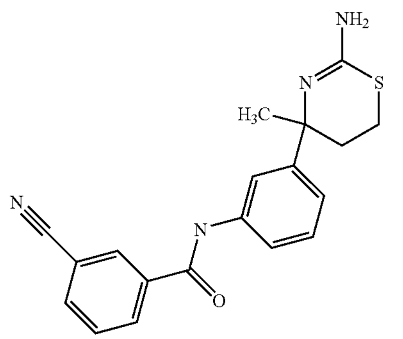 [SMILES: CC1(c2cccc(NC(=O)c3cccc(C#N)c3)c2)CCSC(N)=N1] |
| 874 | 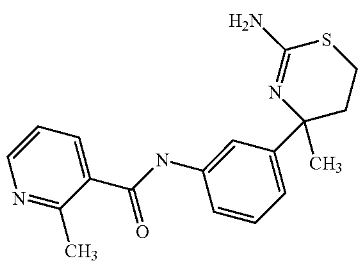 [SMILES: Cc1ncccc1C(=O)Nc1cccc(C2(C)CCSC(N)=N2)c1] |

TABLE 92

| No. | Structure |
|-----|-----------|
| 875 | |
| 876 | |
| 877 | 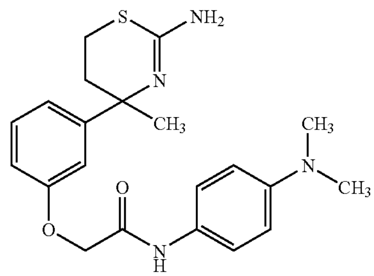 [SMILES: CN(C)c1ccc(NC(=O)COc2cccc(C3(C)CCSC(N)=N3)c2)cc1] |
| 878 | 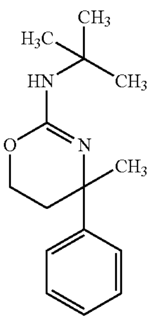 [SMILES: CC(C)(C)NC1=NC(C)(c2ccccc2)CCO1] |
| 879 | 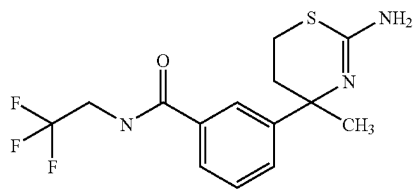 [SMILES: CC1(c2cccc(C(=O)NCC(F)(F)F)c2)CCSC(N)=N1] |
| 880 | 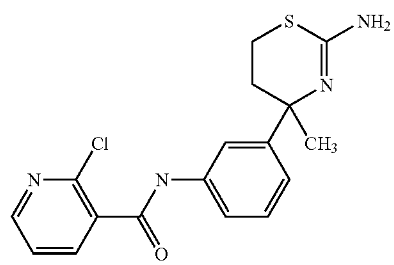 [SMILES: CC1(c2cccc(NC(=O)c3cccnc3Cl)c2)CCSC(N)=N1] |
| 881 | 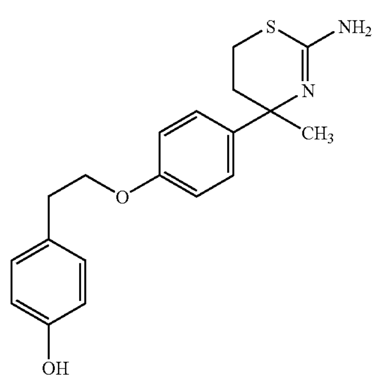 [SMILES: CC1(c2ccc(OCCc3ccc(O)cc3)cc2)CCSC(N)=N1] |

TABLE 92-continued

| No. | Structure |
|-----|-----------|
| 882 | 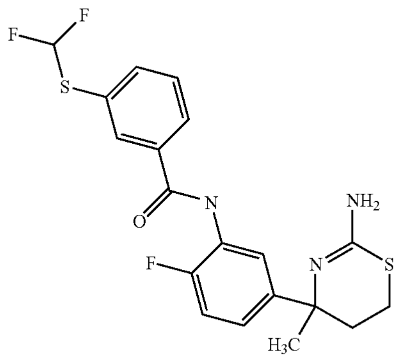 [SMILES: CC1(c2ccc(F)c(NC(=O)c3cccc(SC(F)F)c3)c2)CCSC(N)=N1] |

TABLE 93

| No. | Structure |
|-----|-----------|
| 883 | (Chiral) |
| 884 | 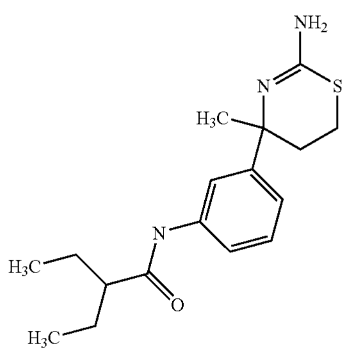 [SMILES: CCC(CC)C(=O)Nc1cccc(C2(C)CCSC(N)=N2)c1] |
| 885 | 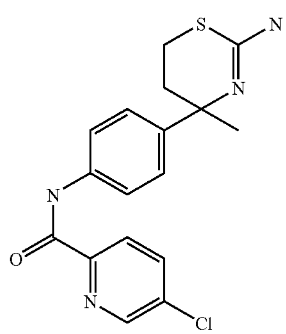 [SMILES: CC1(c2ccc(NC(=O)c3ccc(Cl)cn3)cc2)CCSC(N)=N1] |

TABLE 93-continued

| No. | Structure |
|-----|-----------|
| 886 | 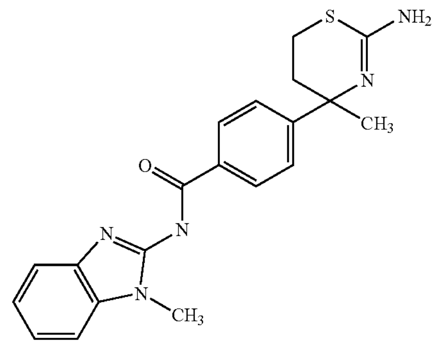 [SMILES: Cn1c(NC(=O)c2ccc(C3(C)CCSC(N)=N3)cc2)nc2ccccc21] |
| 887 | 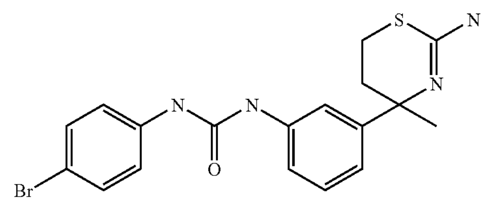 |
| 888 | 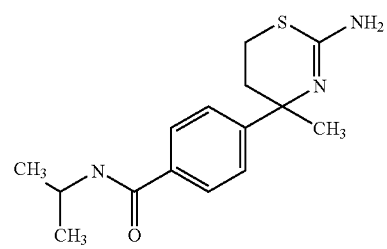 [SMILES: CC(C)NC(=O)c1ccc(C2(C)CCSC(N)=N2)cc1] |
| 889 | 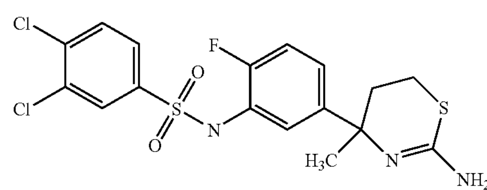 [SMILES: CC1(c2ccc(F)c(NS(=O)(=O)c3ccc(Cl)c(Cl)c3)c2)CCSC(N)=N1] |
| 890 | 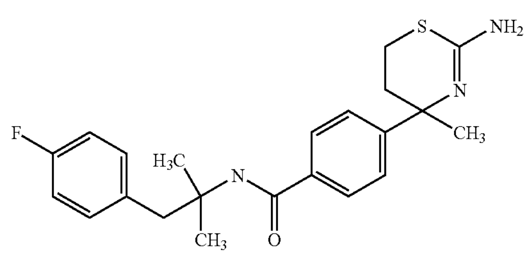 [SMILES: CC(C)(Cc1ccc(F)cc1)NC(=O)c1ccc(C2(C)CCSC(N)=N2)cc1] |
| 891 | 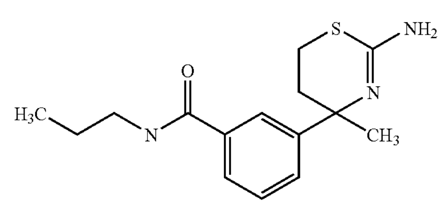 [SMILES: CCCNC(=O)c1cccc(C2(C)CCSC(N)=N2)c1] |

TABLE 94
| No. | Structure |
|---|---|
| 892 | 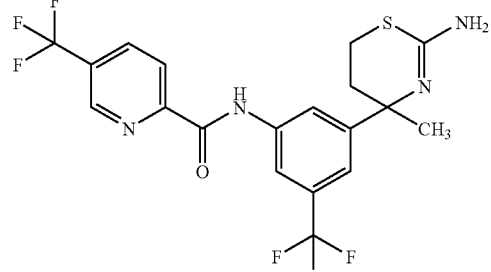 |
| 893 | 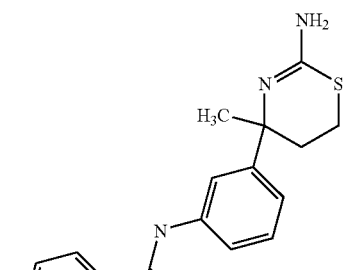 |
| 894 | 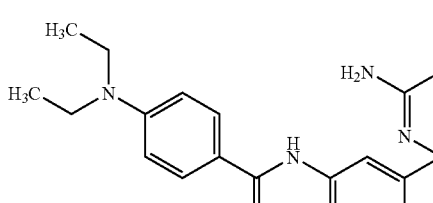 |
| 895 | 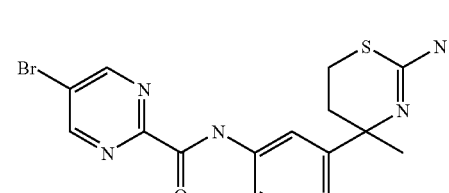 |
| 896 | 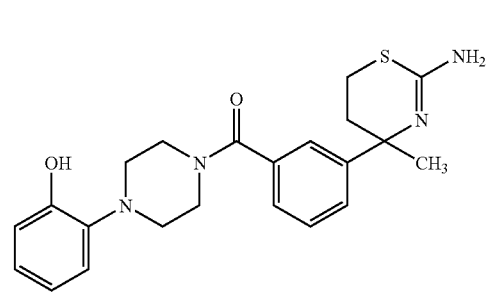 |
TABLE 94-continued
| No. | Structure |
|---|---|
| 897 | 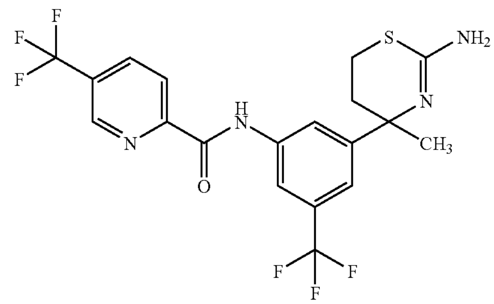 [SMILES: CC1(c2cc(NC(=O)c3ccc(C(F)(F)F)cn3)cc(C(F)(F)F)c2)CCSC(N)=N1] |
| 898 | 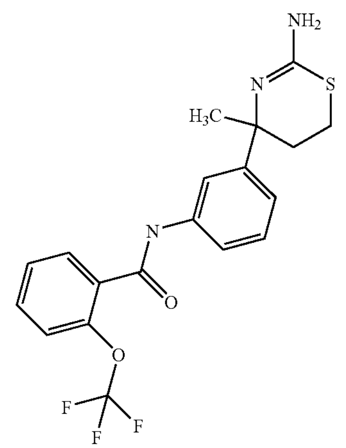 [SMILES: CC1(c2cccc(NC(=O)c3ccccc3OC(F)(F)F)c2)CCSC(N)=N1] |
| 899 | 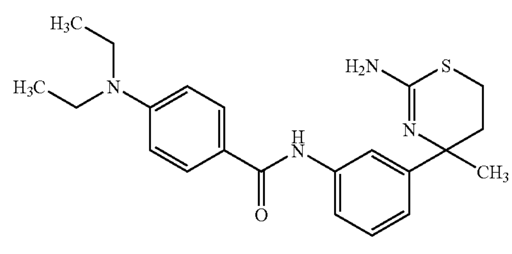 [SMILES: CCN(CC)c1ccc(C(=O)Nc2cccc(C3(C)CCSC(N)=N3)c2)cc1] |
| 900 | 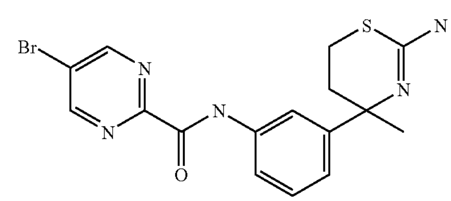 [SMILES: CC1(c2cccc(NC(=O)c3ncc(Br)cn3)c2)CCSC(N)=N1] |
| 901 | 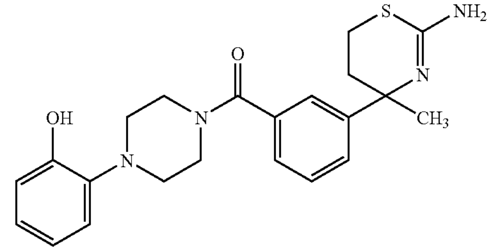 |

TABLE 95

| No. | Structure |
|---|---|
| 902 | 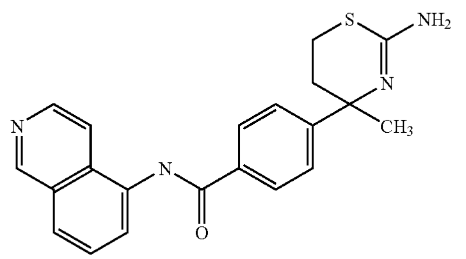 [SMILES: CC1(c2ccc(C(=O)Nc3cccc4cnccc34)cc2)CCSC(N)=N1] |
| 903 | 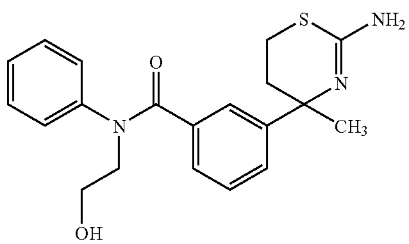 [SMILES: CC1(c2cccc(C(=O)N(CCO)c3ccccc3)c2)CCSC(N)=N1] |
| 904 | 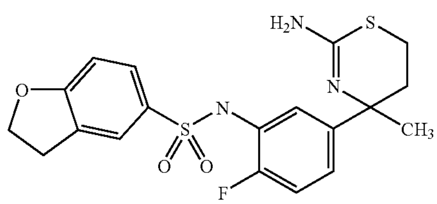 [SMILES: CC1(c2ccc(F)c(NS(=O)(=O)c3ccc4c(c3)CCO4)c2)CCSC(N)=N1] |
| 905 | 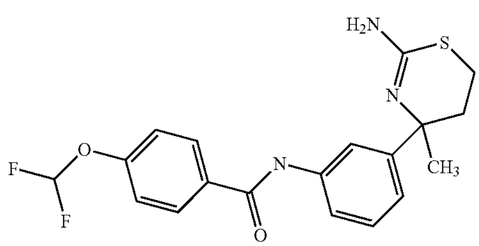 [SMILES: CC1(c2cccc(NC(=O)c3ccc(OC(F)F)cc3)c2)CCSC(N)=N1] |
| 906 | 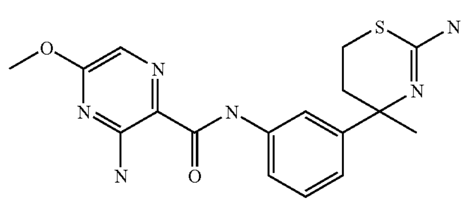 |
| 907 | 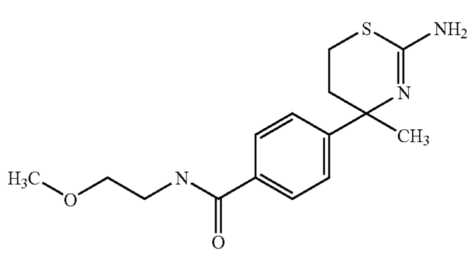 [SMILES: COCCNC(=O)c1ccc(C2(C)CCSC(N)=N2)cc1] |
| 908 | 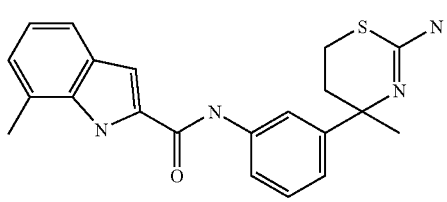 [SMILES: Cc1cccc2cc(C(=O)Nc3cccc(C4(C)CCSC(N)=N4)c3)[nH]c12] |

TABLE 95-continued

| No. | Structure |
|---|---|
| 909 | 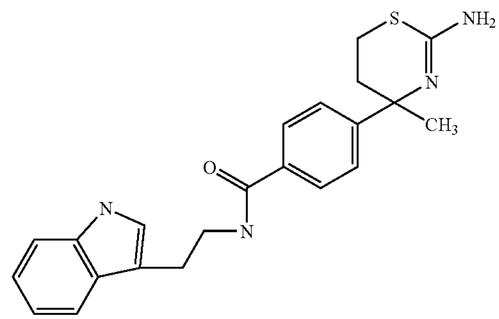 [SMILES: CC1(c2ccc(C(=O)NCCc3c[nH]c4ccccc34)cc2)CCSC(N)=N1] |
| 910 | 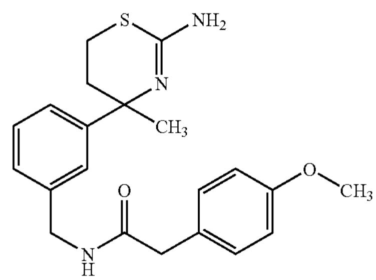 [SMILES: COc1ccc(CC(=O)NCc2cccc(C3(C)CCSC(N)=N3)c2)cc1] |
| 911 | 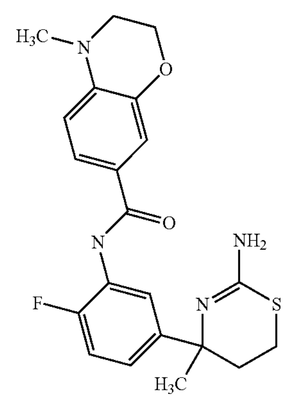 [SMILES: CN1CCOc2cc(C(=O)Nc3cc(C4(C)CCSC(N)=N4)ccc3F)ccc21] |
| 912 | ClH |

TABLE 96
| No. | Structure |
|---|---|
| 913 | 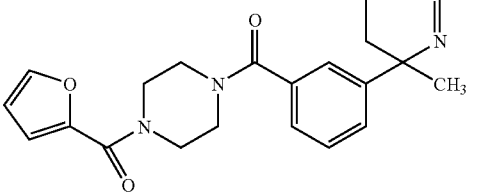 |
| 914 | 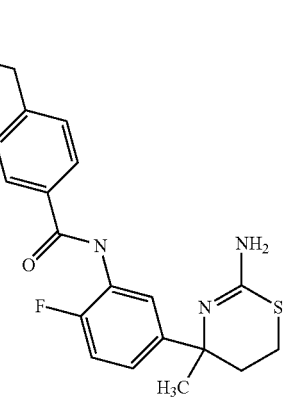 |
| 915 | 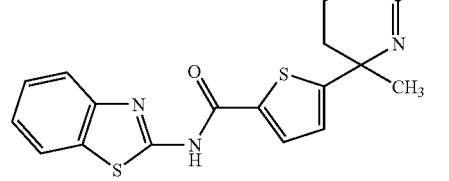 |
| 916 | 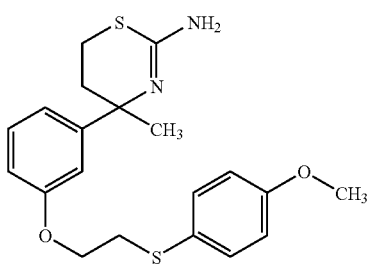 [SMILES: COc1ccc(SCCOc2cccc(C3(C)CCSC(N)=N3)c2)cc1] |
| 917 | 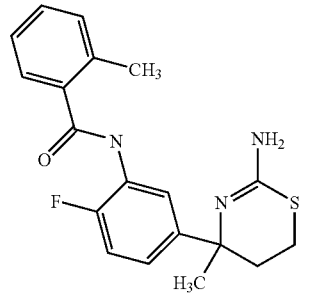 [SMILES: Cc1ccccc1C(=O)Nc1cc(C2(C)CCSC(N)=N2)ccc1F] |
TABLE 96-continued
| No. | Structure |
|---|---|
| 918 | 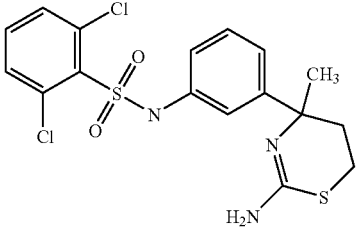 [SMILES: CC1(c2cccc(NS(=O)(=O)c3c(Cl)cccc3Cl)c2)CCSC(N)=N1] |
| 919 | 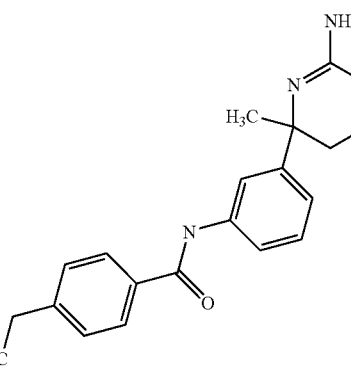 |
| 920 | 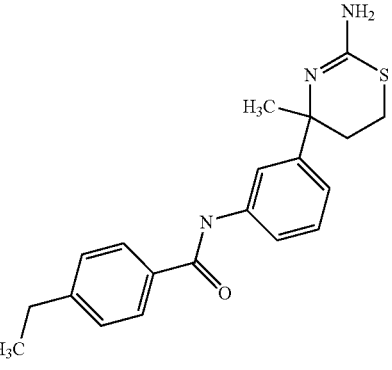 |
TABLE 97
| No. | Structure |
|---|---|
| 921 | 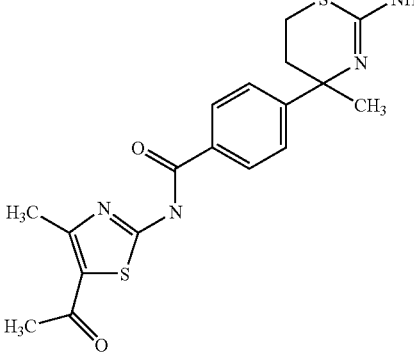 |

TABLE 97-continued

| No. | Structure |
|---|---|
| 922 | 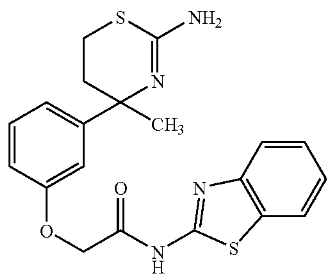 [SMILES: CC1(c2cccc(OCC(=O)Nc3nc4ccccc4s3)c2)CCSC(N)=N1] |
| 923 | 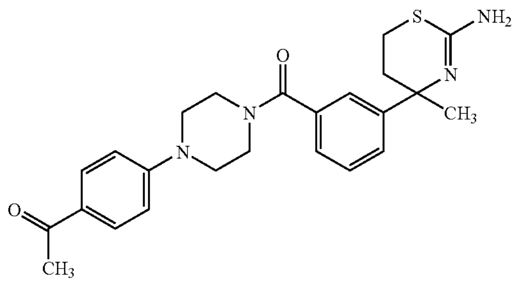 [SMILES: CC(=O)c1ccc(N2CCN(C(=O)c3cccc(C4(C)CCSC(N)=N4)c3)CC2)cc1] |
| 924 | 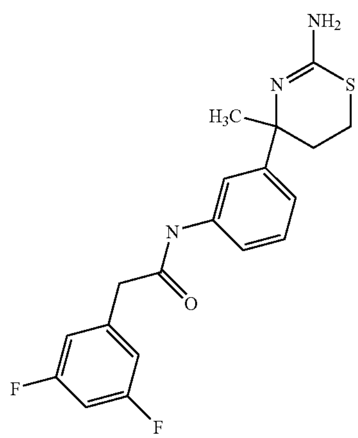 [SMILES: CC1(c2cccc(NC(=O)Cc3cc(F)cc(F)c3)c2)CCSC(N)=N1] |
| 925 | 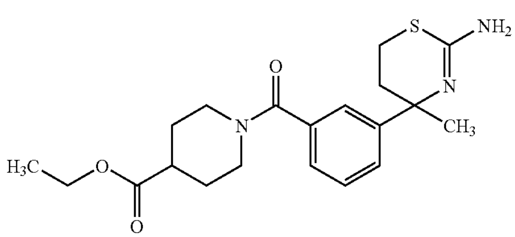 [SMILES: CCOC(=O)C1CCN(C(=O)c2cccc(C3(C)CCSC(N)=N3)c2)CC1] |
| 926 | 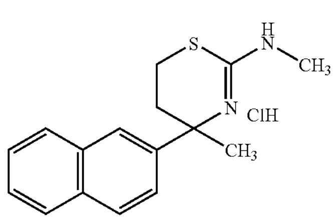 [SMILES: CNC1=NC(C)(c2ccc3ccccc3c2)CCS1 ; Cl] |
| 927 | 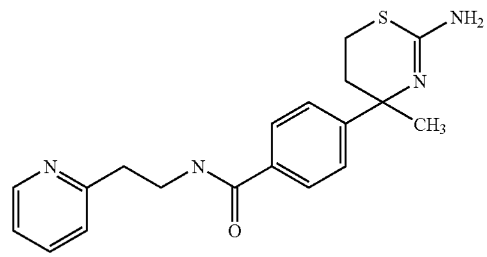 [SMILES: CC1(c2ccc(C(=O)NCCc3ccccn3)cc2)CCSC(N)=N1] |
| 928 | 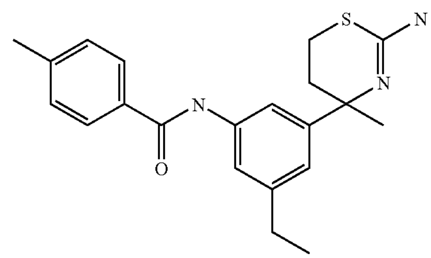 [SMILES: CCc1cc(NC(=O)c2ccc(C)cc2)cc(C2(C)CCSC(N)=N2)c1] |
| 929 | 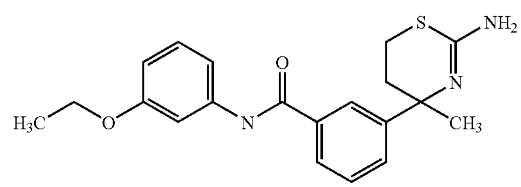 [SMILES: CCOc1cccc(NC(=O)c2cccc(C3(C)CCSC(N)=N3)c2)c1] |
| 930 | 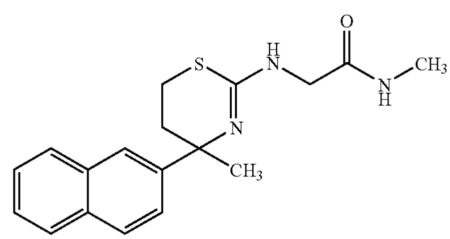 [SMILES: CNC(=O)CNC1=NC(C)(c2ccc3ccccc3c2)CCS1] |

TABLE 98

| No. | Structure |
|---|---|
| 931 | 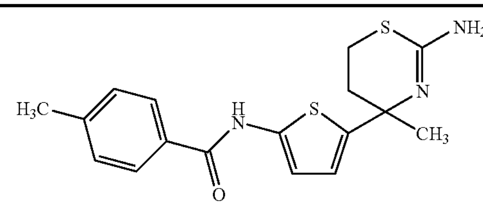 |
| 932 | 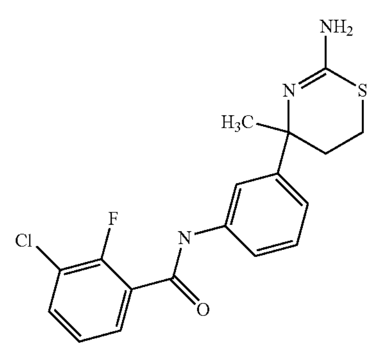 [SMILES: CC1(c2cccc(NC(=O)c3cccc(Cl)c3F)c2)CCSC(N)=N1] |

TABLE 98-continued

| No. | Structure |
|---|---|
| 933 | 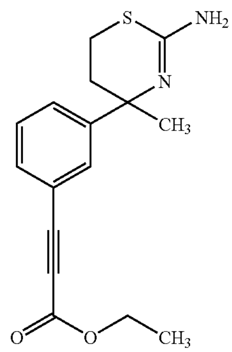 [SMILES: CCOC(=O)C#Cc1cccc(C2(C)CCSC(N)=N2)c1] |
| 934 | 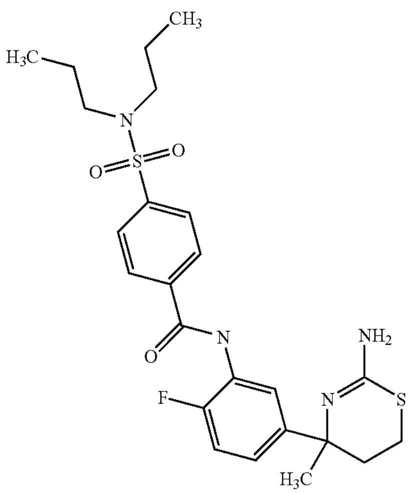 [SMILES: CCCN(CCC)S(=O)(=O)c1ccc(C(=O)Nc2cc(C3(C)CCSC(N)=N3)ccc2F)cc1] |
| 935 | 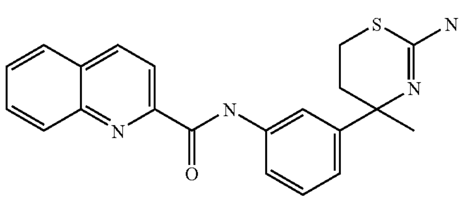 [SMILES: CC1(c2cccc(NC(=O)c3ccc4ccccc4n3)c2)CCSC(N)=N1] |
| 936 | 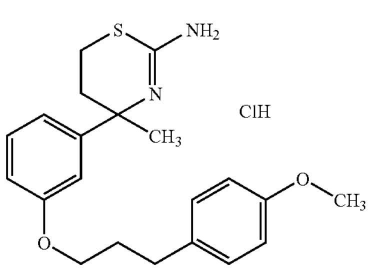 [SMILES: COc1ccc(CCCOc2cccc(C3(C)CCSC(N)=N3)c2)cc1 ; Cl] |

TABLE 98-continued

| No. | Structure |
|---|---|
| 937 | 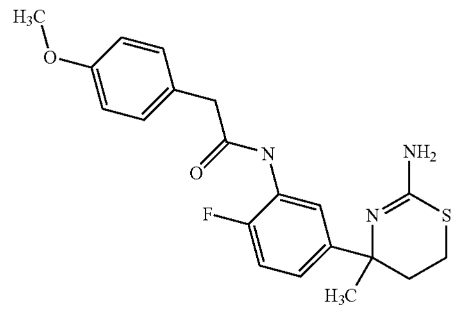 [SMILES: COc1ccc(CC(=O)Nc2cc(C3(C)CCSC(N)=N3)ccc2F)cc1] |
| 938 | 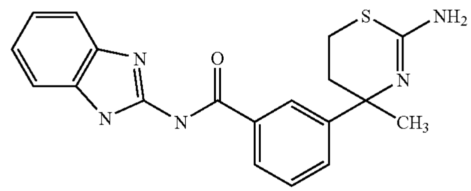 |

TABLE 99

| No. | Structure |
|---|---|
| 939 | 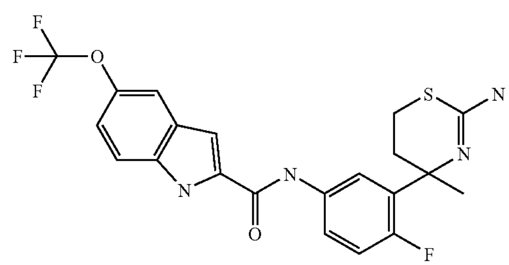 [SMILES: CC1(c2cc(NC(=O)c3cc4cc(OC(F)(F)F)ccc4[nH]3)ccc2F)CCSC(N)=N1] |
| 940 | 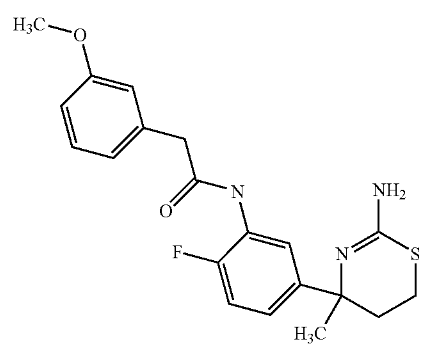 [SMILES: COc1cccc(CC(=O)Nc2cc(C3(C)CCSC(N)=N3)ccc2F)c1] |
| 941 | 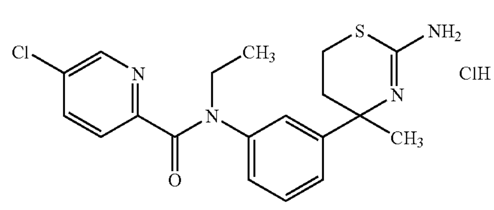 [SMILES: CCN(C(=O)c1ccc(Cl)cn1)c1cccc(C2(C)CCSC(N)=N2)c1 ; Cl] |

TABLE 99-continued
| No. | Structure |
|---|---|
| 942 | 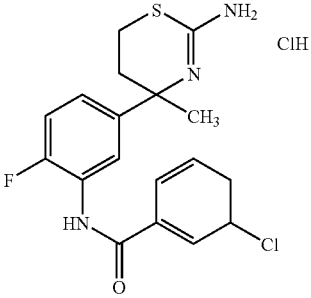 [SMILES: CC1(c2ccc(F)c(NC(=O)C3=CC(Cl)CC=C3)c2)CCSC(N)=N1 ; Cl] |
| 943 | 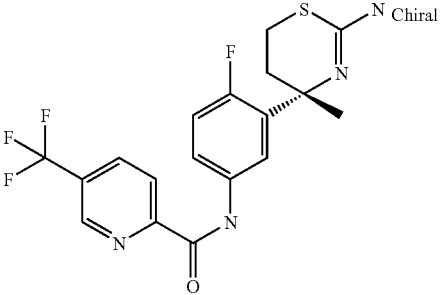 [SMILES: C[C@@]1(c2cc(NC(=O)c3ccc(C(F)(F)F)cn3)ccc2F)CCSC(N)=N1] |
| 944 | 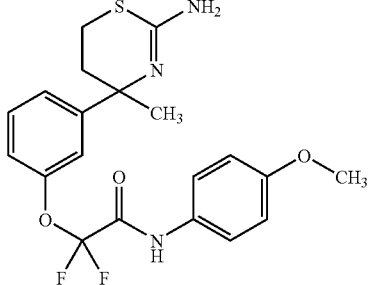 [SMILES: COc1ccc(NC(=O)C(F)(F)Oc2cccc(C3(C)CCSC(N)=N3)c2)cc1] |
| 945 | 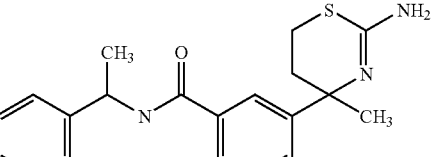 |
| 946 | 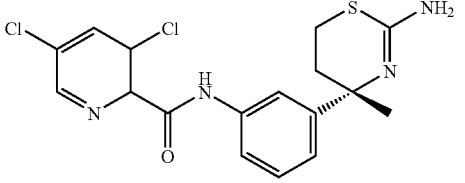 [SMILES: C[C@@]1(c2cccc(NC(=O)C3N=CC(Cl)=CC3Cl)c2)CCSC(N)=N1] |
| 947 | 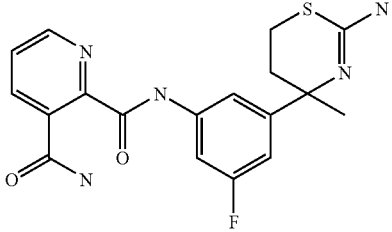 [SMILES: CC1(c2cc(F)cc(NC(=O)c3ncccc3C(N)=O)c2)CCSC(N)=N1] |
TABLE 100
| No. | Structure |
|---|---|
| 948 | 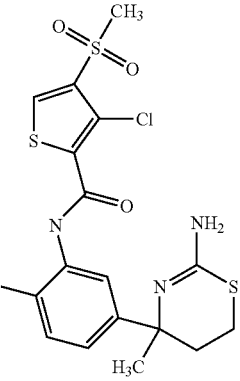 |
| 949 | 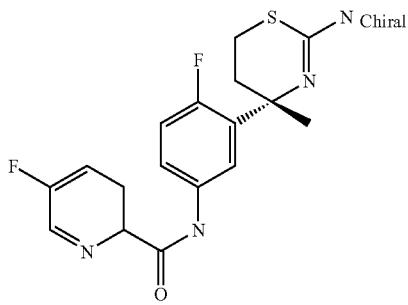 [SMILES: C[C@@]1(c2cc(NC(=O)C3CC=C(F)C=N3)ccc2F)CCSC(N)=N1] |
| 950 | 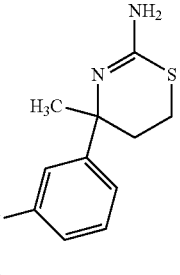 |
| 951 | 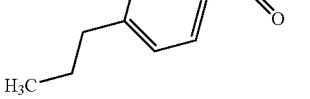 |

TABLE 100-continued
| No. | Structure |
|---|---|
| 952 | 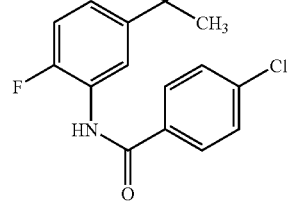 |
| 953 | 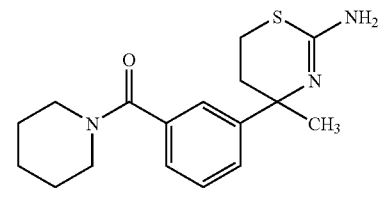 [SMILES: CC1(c2cccc(C(=O)N3CCCCC3)c2)CCSC(N)=N1] |
| 954 | 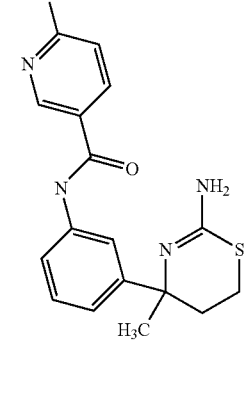 |
| 955 | 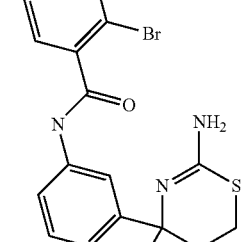 |
TABLE 101
| No. | Structure |
|---|---|
| 956 | 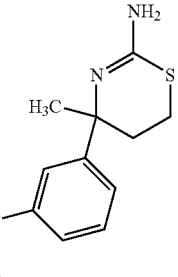 |
| 957 | 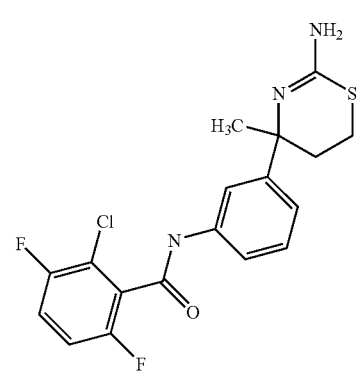 [SMILES: CC1(c2cccc(NC(=O)c3c(F)ccc(F)c3Cl)c2)CCSC(N)=N1] |
| 958 | 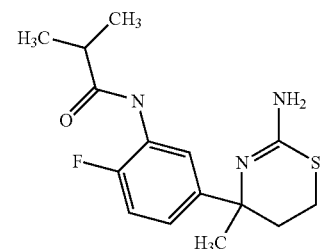 |
| 959 | 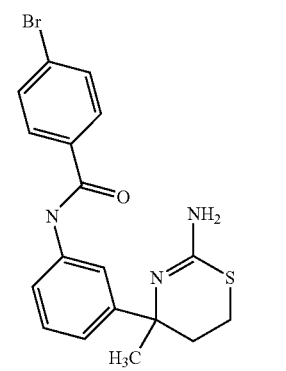 [SMILES: CC1(c2cccc(NC(=O)c3ccc(Br)cc3)c2)CCSC(N)=N1] |
| 960 | 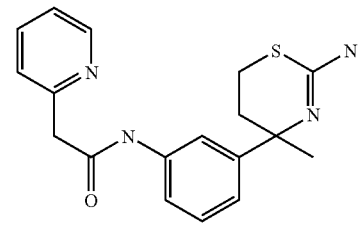 [SMILES: CC1(c2cccc(NC(=O)Cc3ccccn3)c2)CCSC(N)=N1] |

TABLE 101-continued

| No. | Structure |
|---|---|
| 961 | 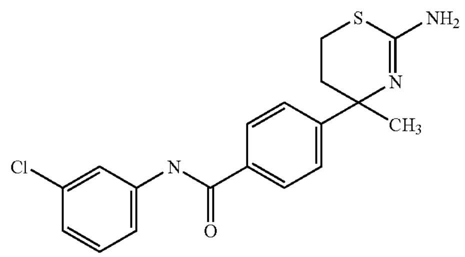 [SMILES: CC1(c2ccc(C(=O)Nc3cccc(Cl)c3)cc2)CCSC(N)=N1] |
| 962 | 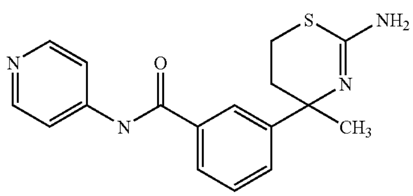 [SMILES: CC1(c2cccc(C(=O)Nc3ccncc3)c2)CCSC(N)=N1] |
| 963 | 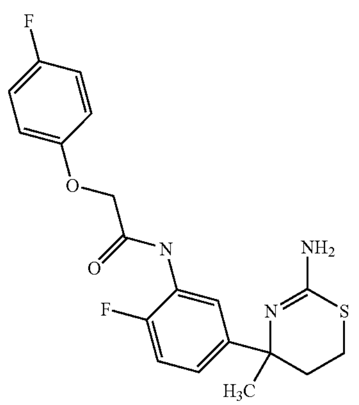 [SMILES: CC1(c2ccc(F)c(NC(=O)COc3ccc(F)cc3)c2)CCSC(N)=N1] |

TABLE 102

| No. | Structure |
|---|---|
| 964 | |｜

TABLE 102-continued

| No. | Structure |
|---|---|
| 965 | 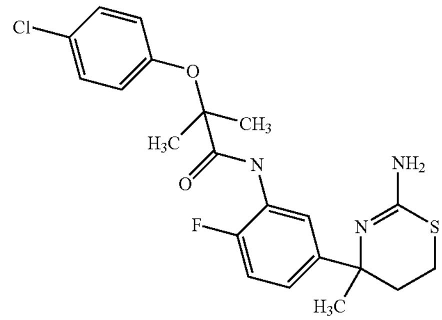 [SMILES: CC(C)(Oc1ccc(Cl)cc1)C(=O)Nc1cc(C2(C)CCSC(N)=N2)ccc1F] |
| 966 | 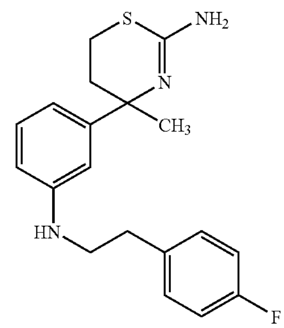 [SMILES: CC1(c2cccc(NCCc3ccc(F)cc3)c2)CCSC(N)=N1] |
| 967 | 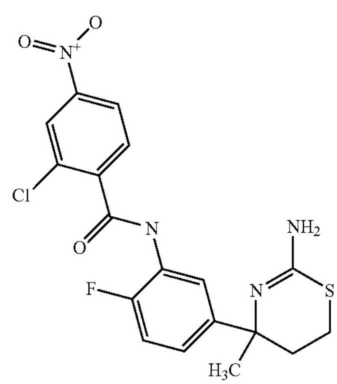 |
| 968 | 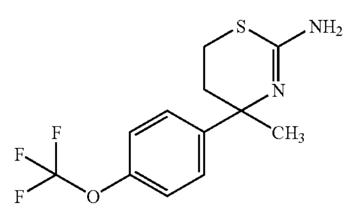 [SMILES: CC1(c2ccc(OC(F)(F)F)cc2)CCSC(N)=N1] |
| 969 | 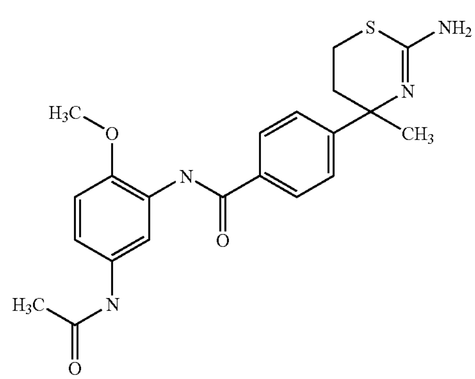 [SMILES: COc1ccc(NC(C)=O)cc1NC(=O)c1ccc(C2(C)CCSC(N)=N2)cc1] |

TABLE 102-continued
| No. | Structure |
|-----|-----------|
| 970 | 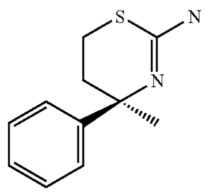 |
TABLE 103
| No. | Structure |
|-----|-----------|
| 971 | 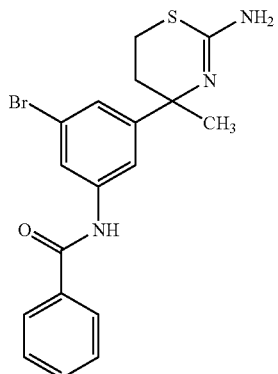 |
| 972 | 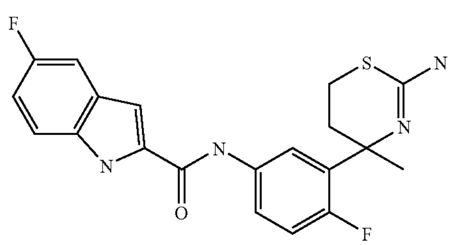 [SMILES: CC1(c2cc(NC(=O)c3cc4cc(F)ccc4[nH]3)ccc2F)CCSC(N)=N1] |
| 973 | 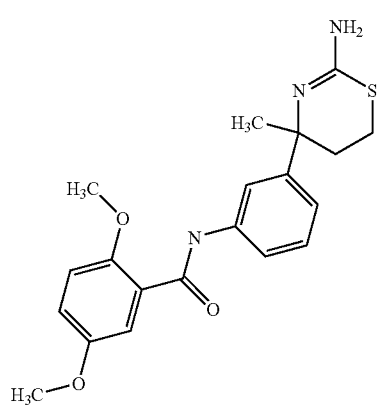 [SMILES: COc1ccc(OC)c(C(=O)Nc2cccc(C3(C)CCSC(N)=N3)c2)c1] |
TABLE 103-continued
| No. | Structure |
|-----|-----------|
| 974 | 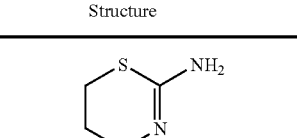 |
| 975 | 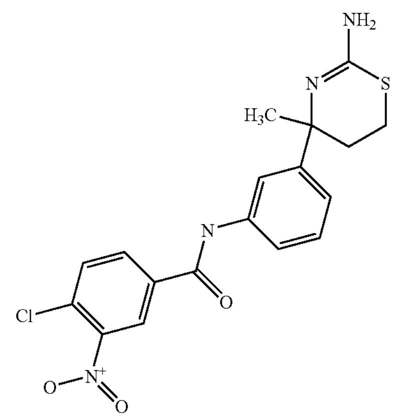 |
| 976 | 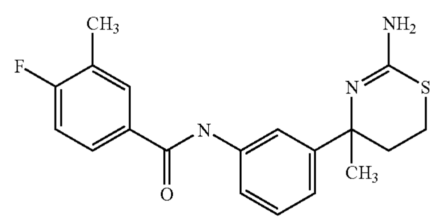 [SMILES: Cc1cc(C(=O)Nc2cccc(C3(C)CCSC(N)=N3)c2)ccc1F] |
| 977 | 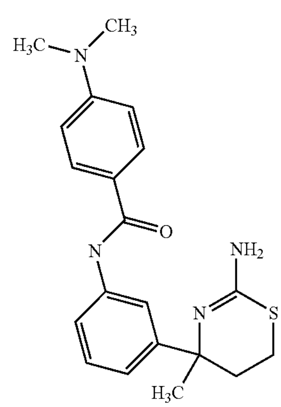 [SMILES: CN(C)c1ccc(C(=O)Nc2cccc(C3(C)CCSC(N)=N3)c2)cc1] |

TABLE 104

| No. | Structure |
|-----|-----------|
| 978 | 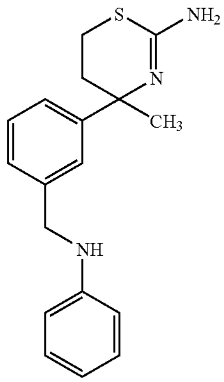 [SMILES: CC1(c2cccc(CNc3ccccc3)c2)CCSC(N)=N1] |
| 979 | 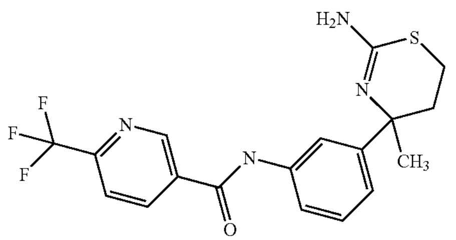 [SMILES: CC1(c2cccc(NC(=O)c3ccc(C(F)(F)F)nc3)c2)CCSC(N)=N1] |
| 980 | 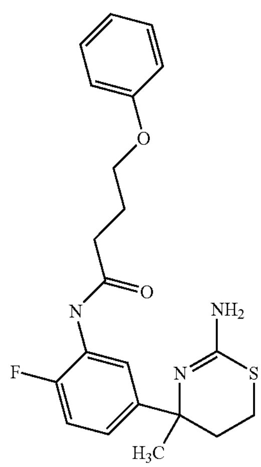 [SMILES: CC1(c2ccc(F)c(NC(=O)CCCOc3ccccc3)c2)CCSC(N)=N1] |
| 981 | 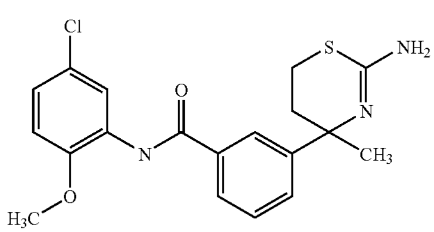 [SMILES: COc1ccc(Cl)cc1NC(=O)c1cccc(C2(C)CCSC(N)=N2)c1] |
| 982 | 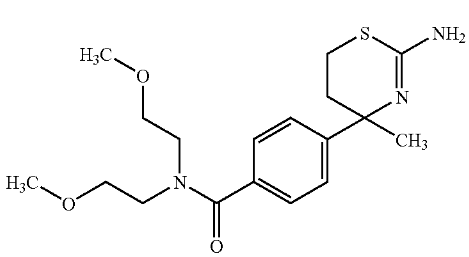 [SMILES: COCCN(CCOC)C(=O)c1ccc(C2(C)CCSC(N)=N2)cc1] |

TABLE 104-continued

| No. | Structure |
|-----|-----------|
| 983 | 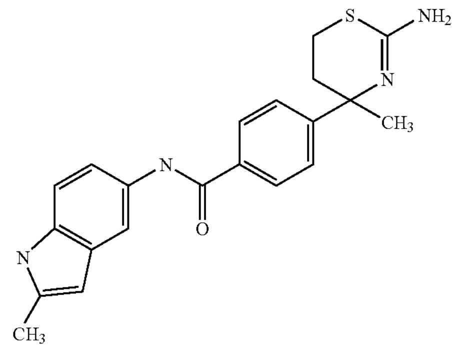 [SMILES: Cc1cc2cc(NC(=O)c3ccc(C4(C)CCSC(N)=N4)cc3)ccc2[nH]1] |
| 984 | 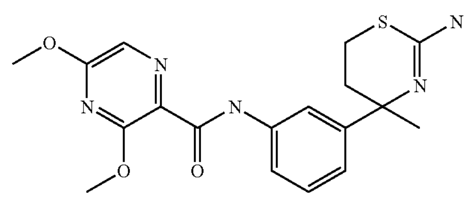 [SMILES: COc1cnc(C(=O)Nc2cccc(C3(C)CCSC(N)=N3)c2)c(OC)n1] |
| 985 | 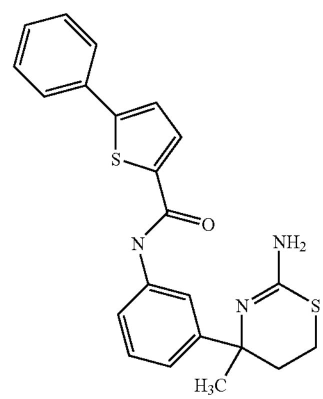 [SMILES: CC1(c2cccc(NC(=O)c3ccc(-c4ccccc4)s3)c2)CCSC(N)=N1] |
| 986 | 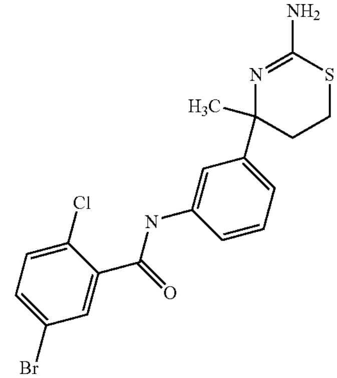 [SMILES: CC1(c2cccc(NC(=O)c3cc(Br)ccc3Cl)c2)CCSC(N)=N1] |

TABLE 105
| No. | Structure |
|---|---|
| 987 | 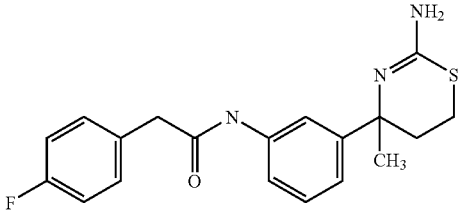 [SMILES: CC1(c2cccc(NC(=O)Cc3ccc(F)cc3)c2)CCSC(N)=N1] |
| 988 | 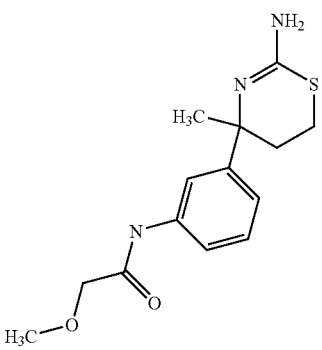 [SMILES: COCC(=O)Nc1cccc(C2(C)CCSC(N)=N2)c1] |
| 989 | 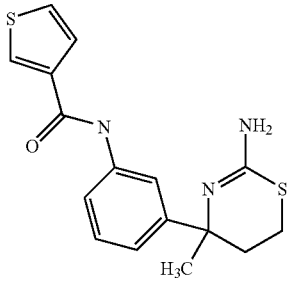 [SMILES: CC1(c2cccc(NC(=O)c3ccsc3)c2)CCSC(N)=N1] |
| 990 | 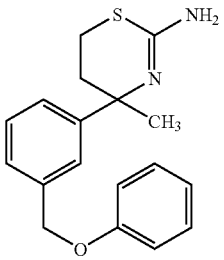 [SMILES: CC1(c2cccc(COc3ccccc3)c2)CCSC(N)=N1] |
| 991 | 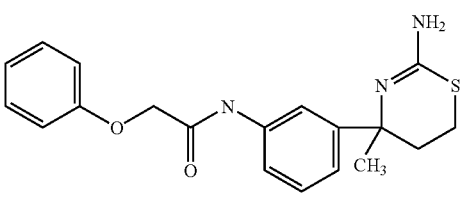 [SMILES: CC1(c2cccc(NC(=O)COc3ccccc3)c2)CCSC(N)=N1] |
TABLE 105-continued
| No. | Structure |
|---|---|
| 992 | 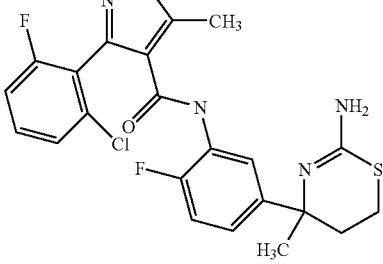 |
| 993 | 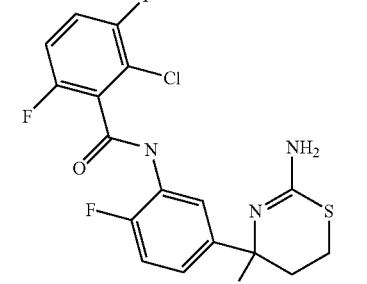 |
| 994 | 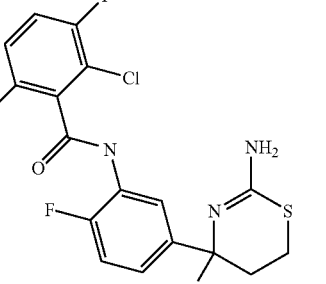 |
| 995 | 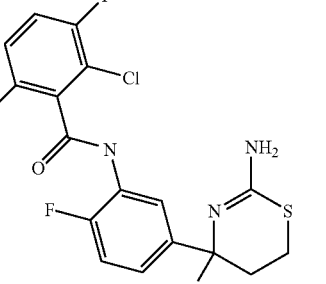 |

TABLE 106

| No. | Structure |
|---|---|
| 996 | 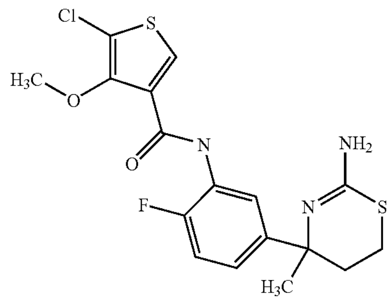 [SMILES: COc1c(C(=O)Nc2cc(C3(C)CCSC(N)=N3)ccc2F)csc1Cl] |
| 997 | 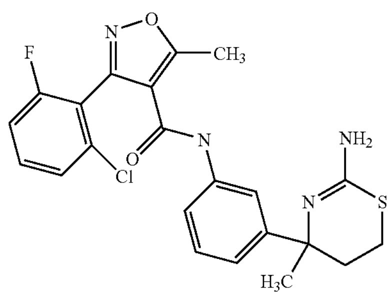 [SMILES: Cc1onc(-c2c(F)cccc2Cl)c1C(=O)Nc1cccc(C2(C)CCSC(N)=N2)c1] |
| 998 | 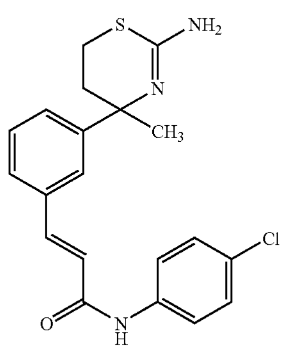 [SMILES: CC1(c2cccc(/C=C/C(=O)Nc3ccc(Cl)cc3)c2)CCSC(N)=N1] |
| 999 | 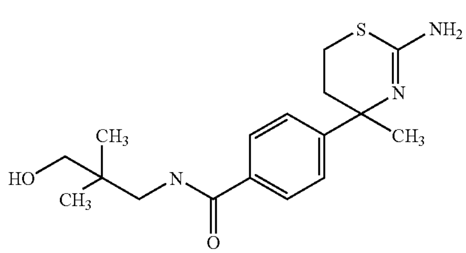 [SMILES: CC(C)(CO)CNC(=O)c1ccc(C2(C)CCSC(N)=N2)cc1] |
| 1000 | 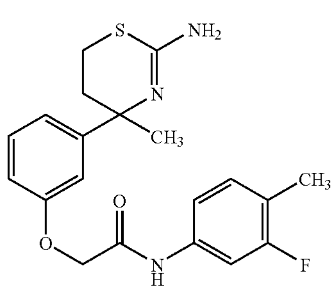 |

TABLE 106-continued

| No. | Structure |
|---|---|
| 1001 | 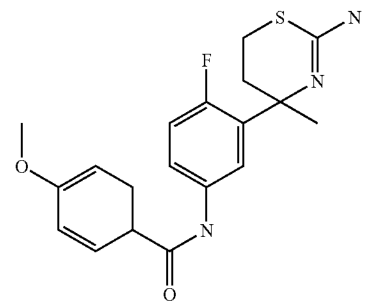 [SMILES: COC1=CCC(C(=O)Nc2ccc(F)c(C3(C)CCSC(N)=N3)c2)C=C1] |
| 1002 | 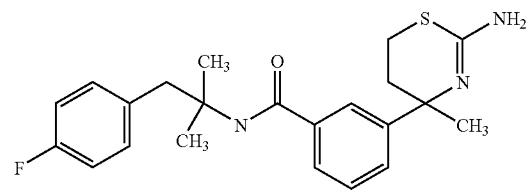 [SMILES: CC(C)(Cc1ccc(F)cc1)NC(=O)c1cccc(C2(C)CCSC(N)=N2)c1] |
| 1003 | 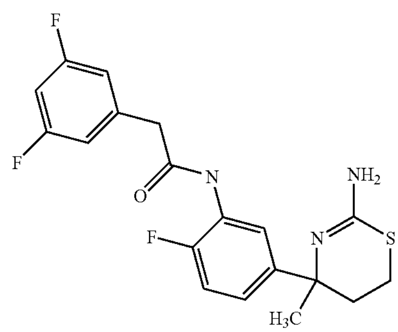 [SMILES: CC1(c2ccc(F)c(NC(=O)Cc3cc(F)cc(F)c3)c2)CCSC(N)=N1] |
| 1004 | 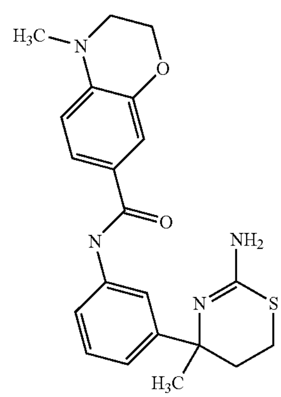 [SMILES: CN1CCOc2cc(C(=O)Nc3cccc(C4(C)CCSC(N)=N4)c3)ccc21] |

TABLE 107

| No. | Structure |
|---|---|
| 1005 | 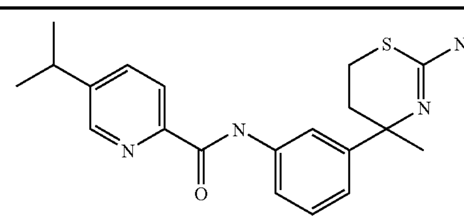 |

TABLE 107-continued

| No. | Structure |
|-----|-----------|
| 1006 | 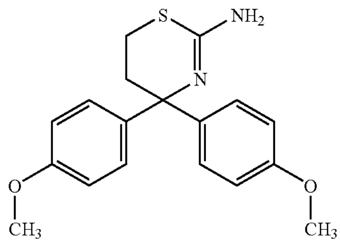 [SMILES: COc1ccc(C2(c3ccc(OC)cc3)CCSC(N)=N2)cc1] |
| 1007 | 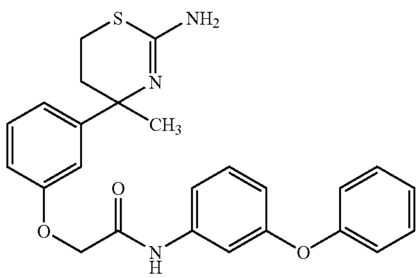 [SMILES: CC1(c2cccc(OCC(=O)Nc3cccc(Oc4ccccc4)c3)c2)CCSC(N)=N1] |
| 1008 | 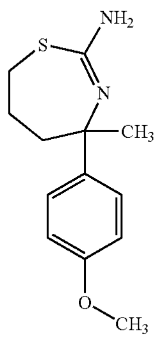 [SMILES: COc1ccc(C2(C)CCCSC(N)=N2)cc1] |
| 1009 | 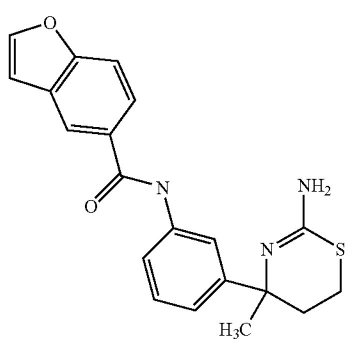 [SMILES: CC1(c2cccc(NC(=O)c3ccc4occc4c3)c2)CCSC(N)=N1] |
| 1010 | 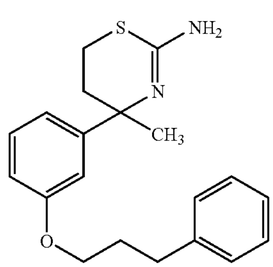 |

TABLE 107-continued

| No. | Structure |
|-----|-----------|
| 1011 | 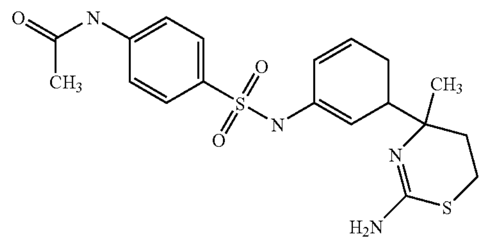 [SMILES: CC(=O)Nc1ccc(S(=O)(=O)NC2=CC(C3(C)CCSC(N)=N3)CC=C2)cc1] |
| 1012 | 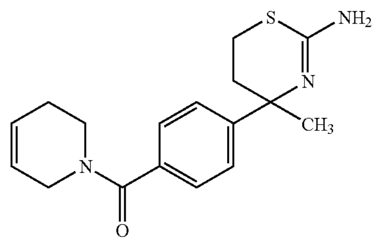 [SMILES: CC1(c2ccc(C(=O)N3CC=CCC3)cc2)CCSC(N)=N1] |
| 1013 | 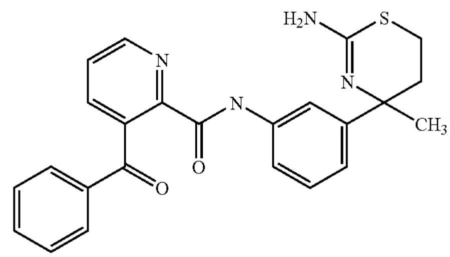 [SMILES: CC1(c2cccc(NC(=O)c3ncccc3C(=O)c3ccccc3)c2)CCSC(N)=N1] |

TABLE 108

| No. | Structure |
|-----|-----------|
| 1014 | ClH |
| 1015 | 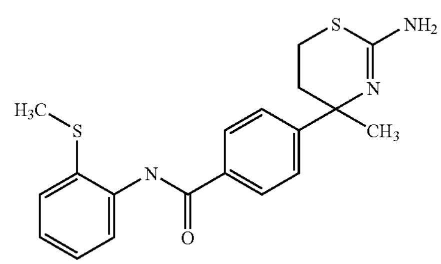 [SMILES: CSc1ccccc1NC(=O)c1ccc(C2(C)CCSC(N)=N2)cc1] |

TABLE 108-continued
| No. | Structure |
|---|---|
| 1016 | 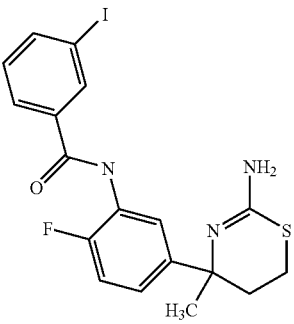 [SMILES: CC1(c2ccc(F)c(NC(=O)c3cccc(I)c3)c2)CCSC(N)=N1] |
| 1017 | 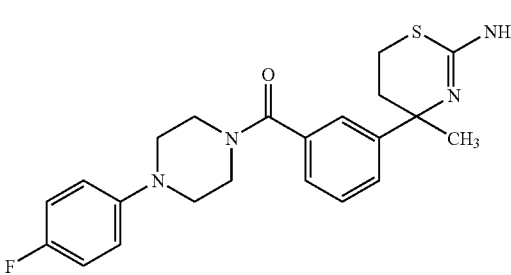 |
| 1018 | 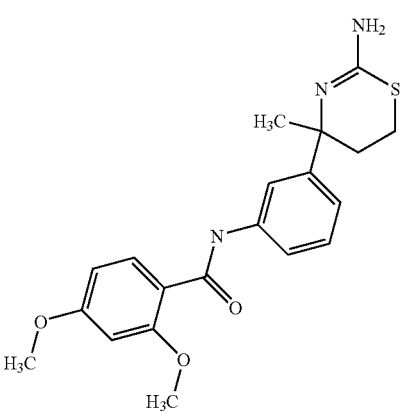 [SMILES: COc1ccc(C(=O)Nc2cccc(C3(C)CCSC(N)=N3)c2)c(OC)c1] |
| 1019 | 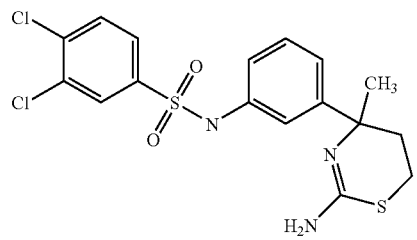 [SMILES: CC1(c2cccc(NS(=O)(=O)c3ccc(Cl)c(Cl)c3)c2)CCSC(N)=N1] |
| 1020 | 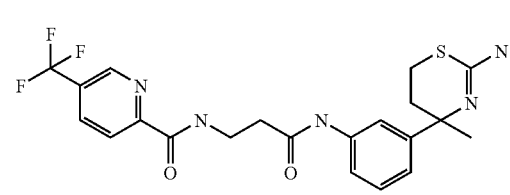 [SMILES: CC1(c2cccc(NC(=O)CCNC(=O)c3ccc(C(F)(F)F)cn3)c2)CCSC(N)=N1] |
TABLE 108-continued
| No. | Structure |
|---|---|
| 1021 | 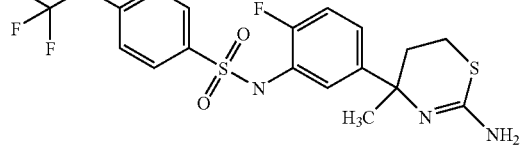 |
TABLE 109
| No. | Structure |
|---|---|
| 1022 | 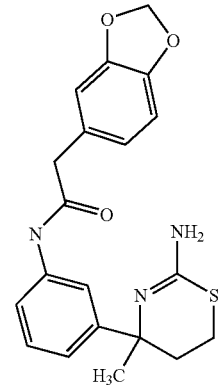 [SMILES: CC1(c2cccc(NC(=O)Cc3ccc4c(c3)OCO4)c2)CCSC(N)=N1] |
| 1023 | 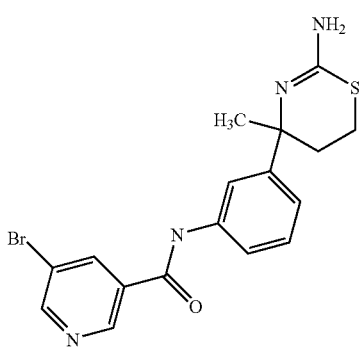 [SMILES: CC1(c2cccc(NC(=O)c3cncc(Br)c3)c2)CCSC(N)=N1] |
| 1024 | 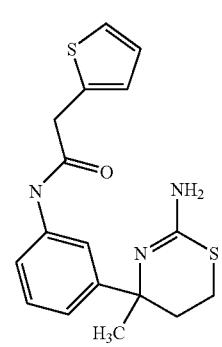 [SMILES: CC1(c2cccc(NC(=O)Cc3cccs3)c2)CCSC(N)=N1] |

TABLE 109-continued

| No. | Structure |
|---|---|
| 1025 | 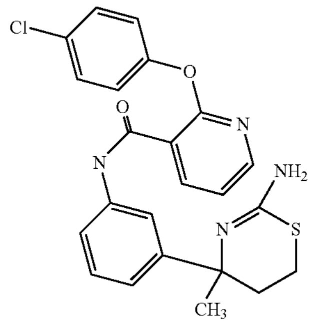 [SMILES: CC1(c2cccc(NC(=O)c3cccnc3Oc3ccc(Cl)cc3)c2)CCSC(N)=N1] |
| 1026 | 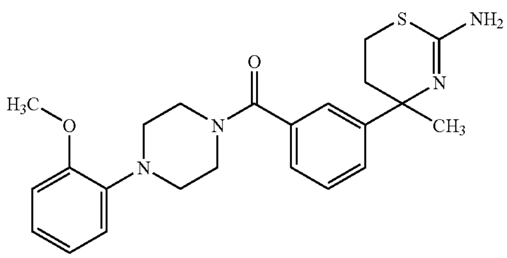 [SMILES: COc1ccccc1N1CCN(C(=O)c2cccc(C3(C)CCSC(N)=N3)c2)CC1] |
| 1027 | 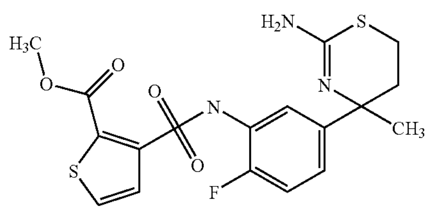 |
| 1028 | 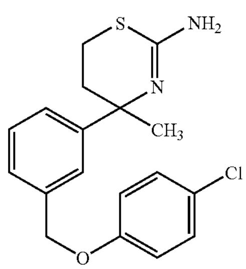 [SMILES: CC1(c2cccc(COc3ccc(Cl)cc3)c2)CCSC(N)=N1] |
| 1029 | 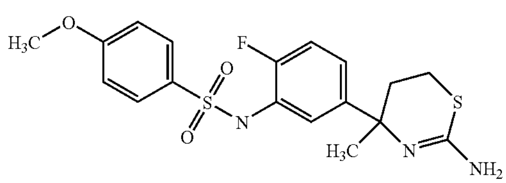 [SMILES: COc1ccc(S(=O)(=O)Nc2cc(C3(C)CCSC(N)=N3)ccc2F)cc1] |
| 1030 | 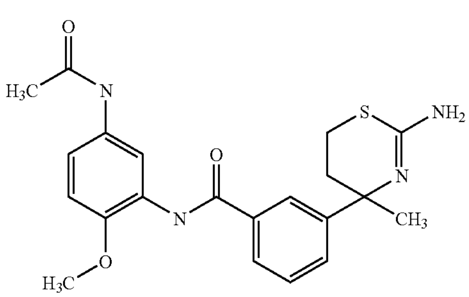 [SMILES: COc1ccc(NC(C)=O)cc1NC(=O)c1cccc(C2(C)CCSC(N)=N2)c1] |

TABLE 110

| No. | Structure |
|---|---|
| 1031 | 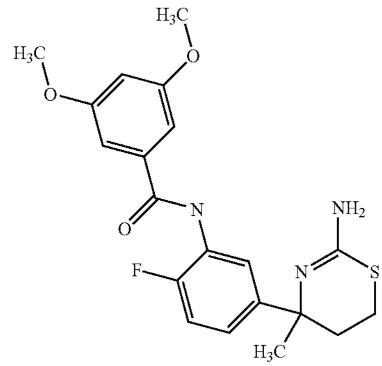 [SMILES: COc1cc(OC)cc(C(=O)Nc2cc(C3(C)CCSC(N)=N3)ccc2F)c1] |
| 1032 | 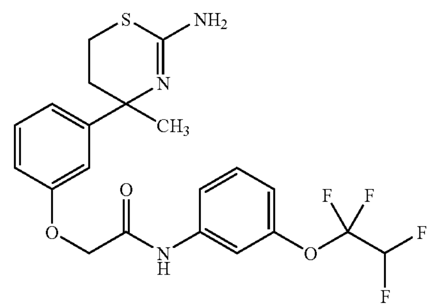 [SMILES: CC1(c2cccc(OCC(=O)Nc3cccc(OC(F)(F)C(F)F)c3)c2)CCSC(N)=N1] |
| 1033 | 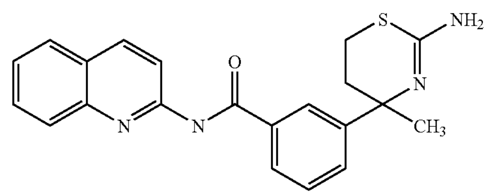 [SMILES: CC1(c2cccc(C(=O)Nc3ccc4ccccc4n3)c2)CCSC(N)=N1] |
| 1034 | 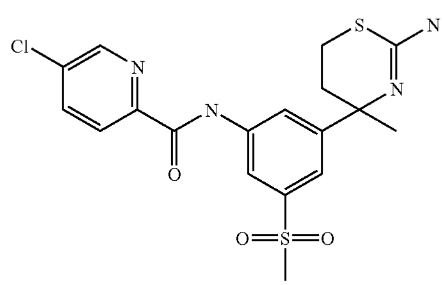 |
| 1035 | 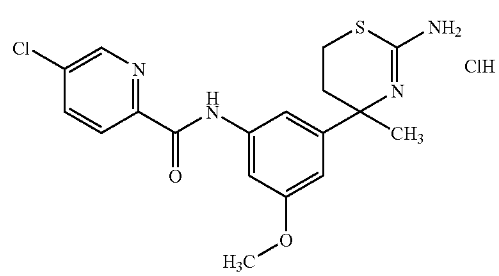 [SMILES: COc1cc(NC(=O)c2ccc(Cl)cn2)cc(C2(C)CCSC(N)=N2)c1 ; Cl] |

TABLE 110-continued
| No. | Structure |
|---|---|
| 1036 | 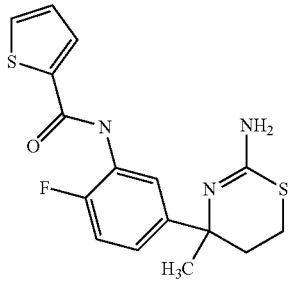 [SMILES: CC1(c2ccc(F)c(NC(=O)c3cccs3)c2)CCSC(N)=N1] |
| 1037 | 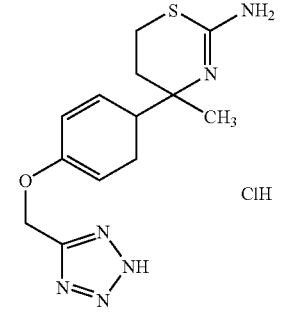 [SMILES: CC1(C2C=CC(OCc3nn[nH]n3)=CC2)CCSC(N)=N1 ; Cl] ClH |
| 1038 | 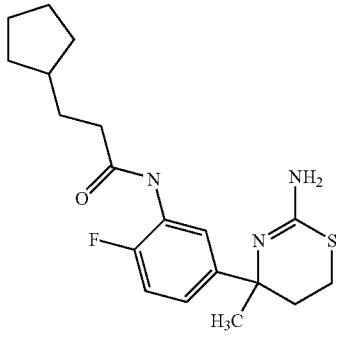 [SMILES: CC1(c2ccc(F)c(NC(=O)CCC3CCCC3)c2)CCSC(N)=N1] |
| 1039 | 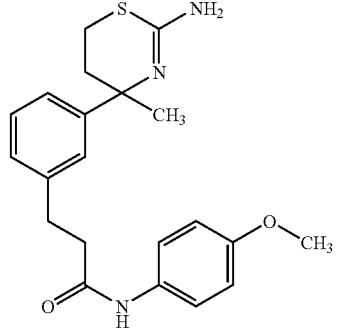 [SMILES: COc1ccc(NC(=O)CCc2cccc(C3(C)CCSC(N)=N3)c2)cc1] |
TABLE 111
| No. | Structure |
|---|---|
| 1040 | 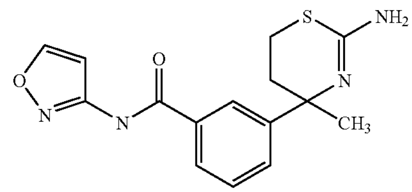 [SMILES: CC1(c2cccc(C(=O)Nc3ccon3)c2)CCSC(N)=N1] |
| 1041 | 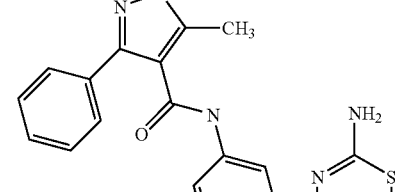 |
| 1042 | 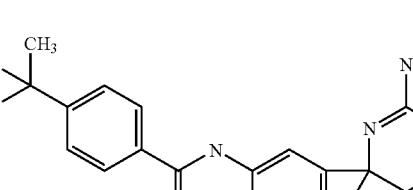 |
| 1043 | 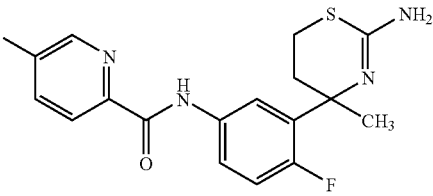 ClH |
| 1044 | 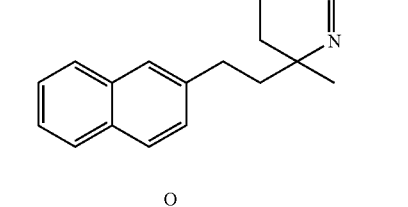 |
| 1045 | 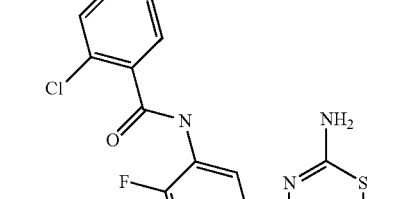 |

TABLE 111-continued

| No. | Structure |
|---|---|
| 1046 | 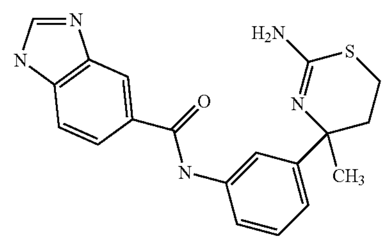 [SMILES: CC1(c2cccc(NC(=O)c3ccc4[nH]cnc4c3)c2)CCSC(N)=N1] |
| 1047 | 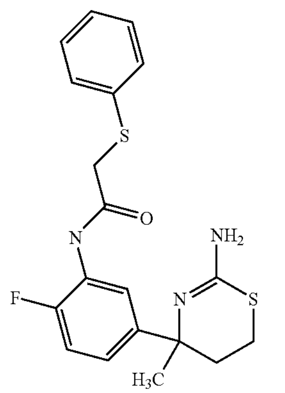 |
| 1048 | 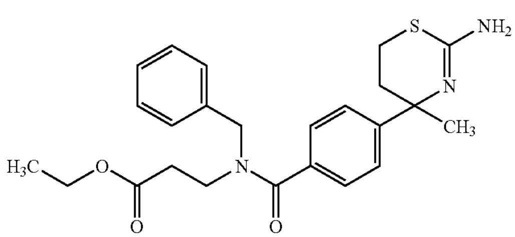 [SMILES: CCOC(=O)CCN(Cc1ccccc1)C(=O)c1ccc(C2(C)CCSC(N)=N2)cc1] |

TABLE 112

| No. | Structure |
|---|---|
| 1049 | |
| 1050 | 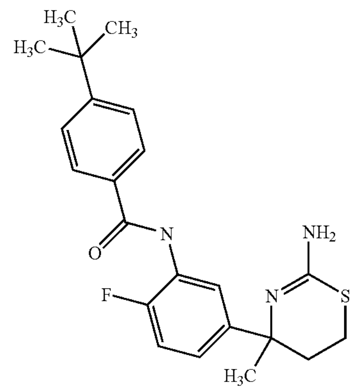 [SMILES: CC(C)(C)c1ccc(C(=O)Nc2cc(C3(C)CCSC(N)=N3)ccc2F)cc1] |
| 1051 | 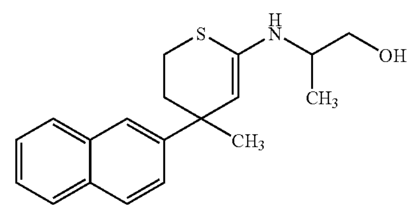 [SMILES: CC(CO)NC1=CC(C)(c2ccc3ccccc3c2)CCS1] |
| 1052 | 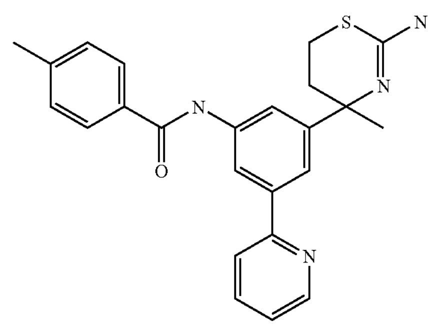 [SMILES: Cc1ccc(C(=O)Nc2cc(-c3ccccn3)cc(C3(C)CCSC(N)=N3)c2)cc1] |
| 1053 | 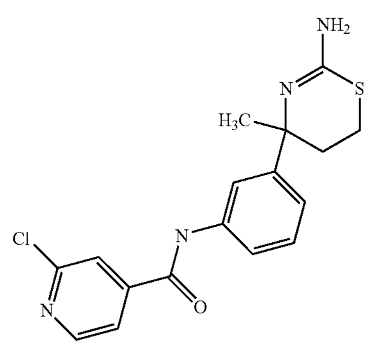 [SMILES: CC1(c2cccc(NC(=O)c3ccnc(Cl)c3)c2)CCSC(N)=N1] |
| 1054 | 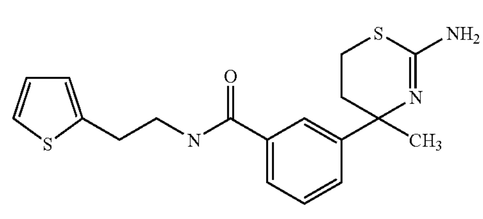 [SMILES: CC1(c2cccc(C(=O)NCCc3cccs3)c2)CCSC(N)=N1] |

TABLE 112-continued
| No. | Structure |
|---|---|
| 1055 | 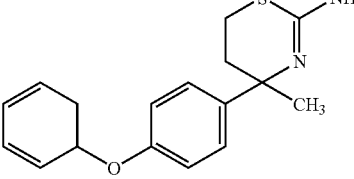 |
| 1056 | 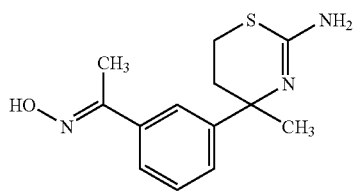 [SMILES: C/C(=N\O)c1cccc(C2(C)CCSC(N)=N2)c1] |
| 1057 | 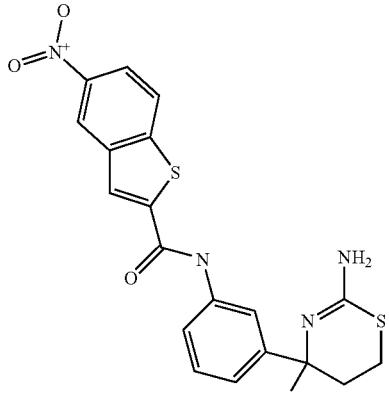 |
TABLE 113
| No. | Structure |
|---|---|
| 1058 | 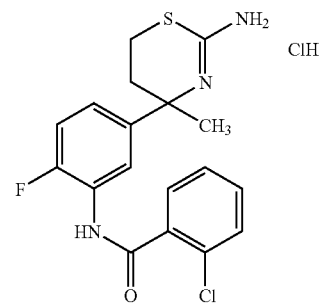 |
| 1059 | 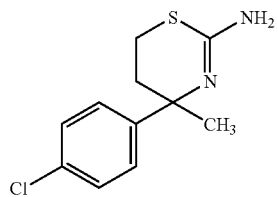 |
| 1060 | 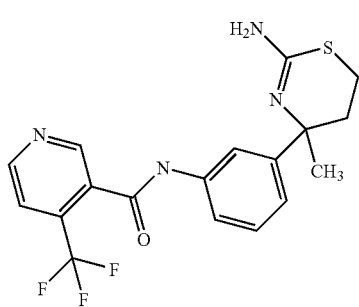 |
TABLE 113-continued
| No. | Structure |
|---|---|
| 1061 | 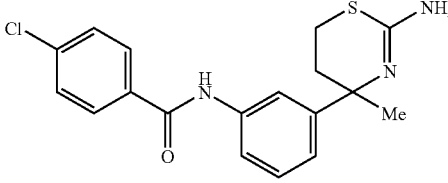 |
| 1062 | 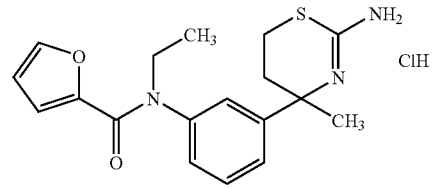 [SMILES: CCN(C(=O)c1ccco1)c1cccc(C2(C)CCSC(N)=N2)c1 ; Cl] |
| 1063 | 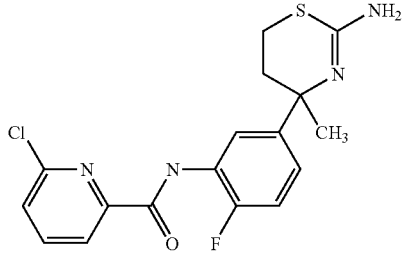 [SMILES: CC1(c2ccc(F)c(NC(=O)c3cccc(Cl)n3)c2)CCSC(N)=N1] |
| 1064 | 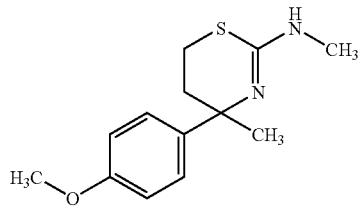 |
| 1065 | 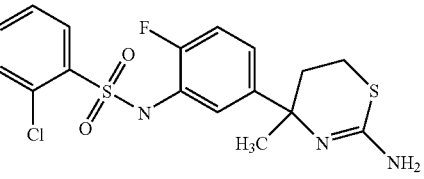 |

TABLE 113-continued

| No. | Structure |
|---|---|
| 1066 | 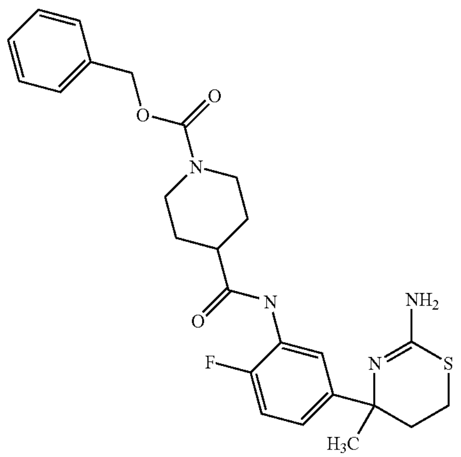 [SMILES: CC1(c2ccc(F)c(NC(=O)C3CCN(C(=O)OCc4ccccc4)CC3)c2)CCSC(N)=N1] |
| 1067 | 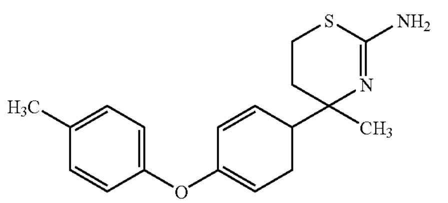 [SMILES: Cc1ccc(OC2=CCC(C3(C)CCSC(N)=N3)C=C2)cc1] |

TABLE 114

| No. | Structure |
|---|---|
| 1068 | 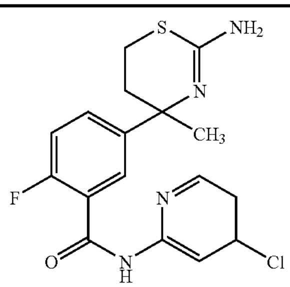 |
| 1069 | ClH |
| 1070 | 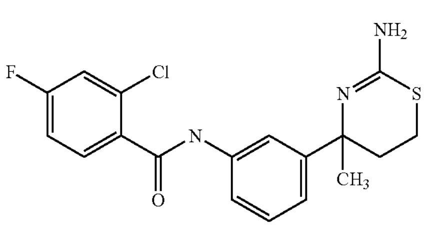 [SMILES: CC1(c2cccc(NC(=O)c3ccc(F)cc3Cl)c2)CCSC(N)=N1] |

TABLE 114-continued

| No. | Structure |
|---|---|
| 1071 | 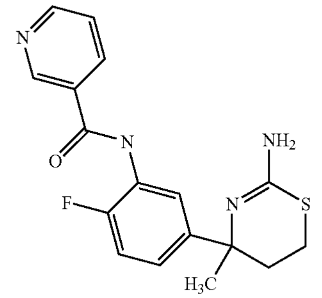 [SMILES: CC1(c2ccc(F)c(NC(=O)c3cccnc3)c2)CCSC(N)=N1] |
| 1072 | 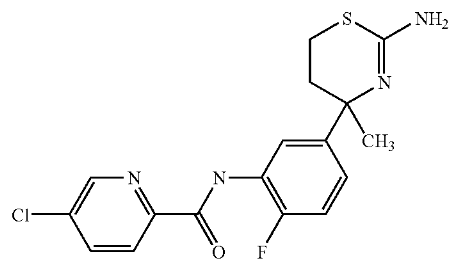 [SMILES: CC1(c2ccc(F)c(NC(=O)c3ccc(Cl)cn3)c2)CCSC(N)=N1] |
| 1073 | 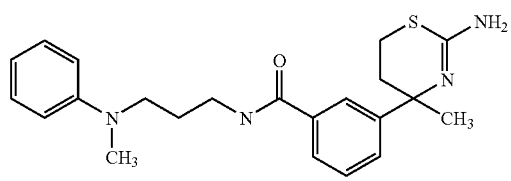 [SMILES: CN(CCCNC(=O)c1cccc(C2(C)CCSC(N)=N2)c1)c1ccccc1] |
| 1074 | 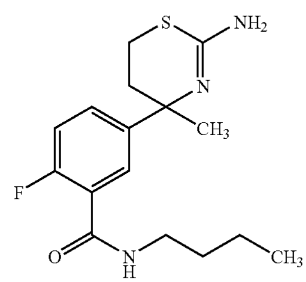 [SMILES: CCCCNC(=O)c1cc(C2(C)CCSC(N)=N2)ccc1F] |
| 1075 | 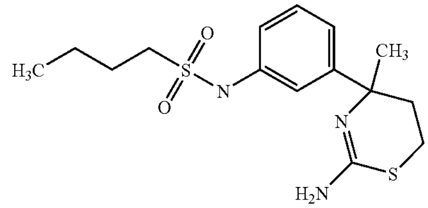 [SMILES: CCCCS(=O)(=O)Nc1cccc(C2(C)CCSC(N)=N2)c1] |

TABLE 115
| No. | Structure |
|---|---|
| 1076 | 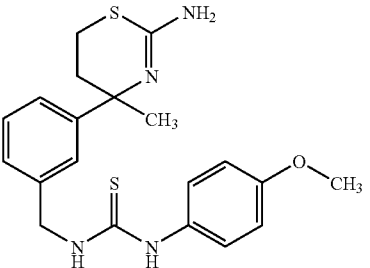 |
| 1077 | 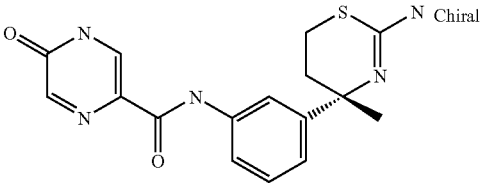 [SMILES: C[C@@]1(c2cccc(NC(=O)c3c[nH]c(=O)cn3)c2)CCSC(N)=N1] |
| 1078 | 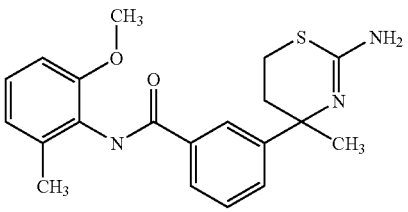 [SMILES: COc1cccc(C)c1NC(=O)c1cccc(C2(C)CCSC(N)=N2)c1] |
| 1079 | 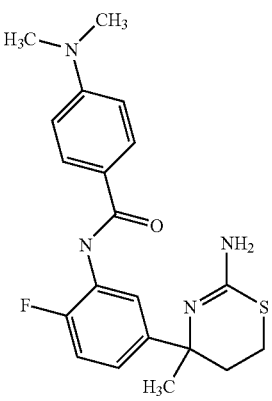 [SMILES: CN(C)c1ccc(C(=O)Nc2cc(C3(C)CCSC(N)=N3)ccc2F)cc1] |
| 1080 | 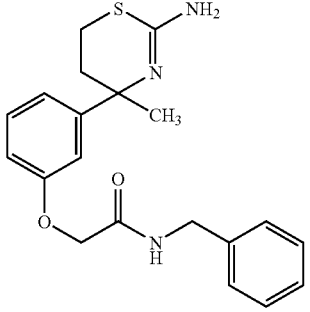 [SMILES: CC1(c2cccc(OCC(=O)NCc3ccccc3)c2)CCSC(N)=N1] |
TABLE 115-continued
| No. | Structure |
|---|---|
| 1081 | 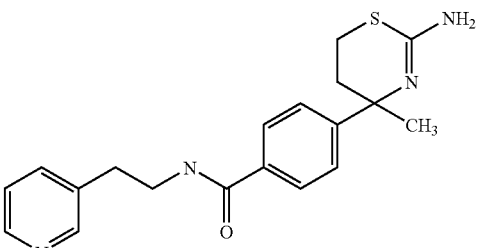 |
| 1082 | 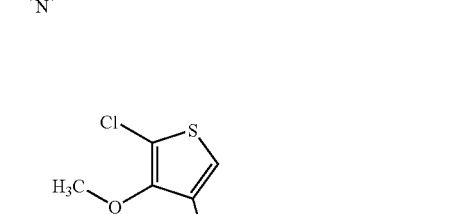 |
| 1083 | 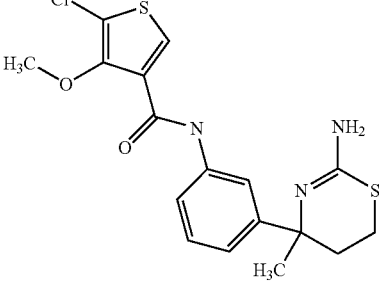 |
| 1084 | 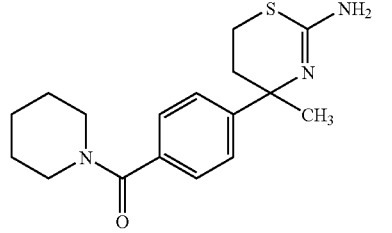 [SMILES: CC1(c2ccc(C(=O)N3CCCCC3)cc2)CCSC(N)=N1] |
| 1085 | 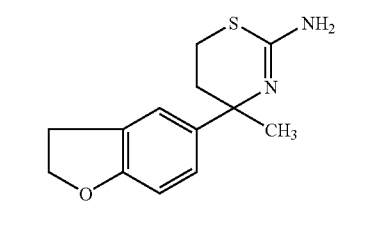 [SMILES: CC1(c2ccc3c(c2)CCO3)CCSC(N)=N1] |

TABLE 116
| No. | Structure |
|---|---|
| 1086 | 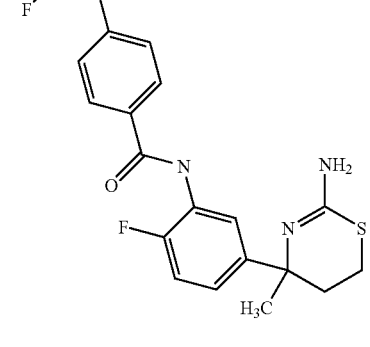 |
| 1087 | 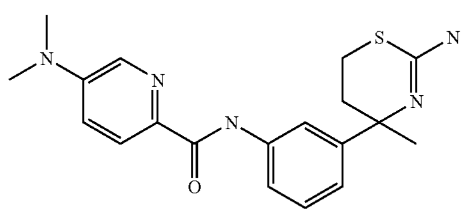 |
| 1088 | 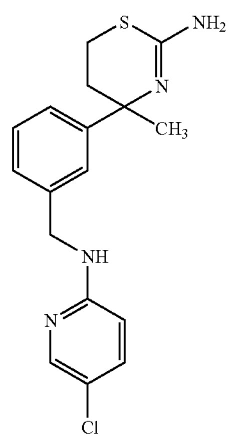 [SMILES: CC1(c2cccc(CNc3ccc(Cl)cn3)c2)CCSC(N)=N1] |
| 1089 | 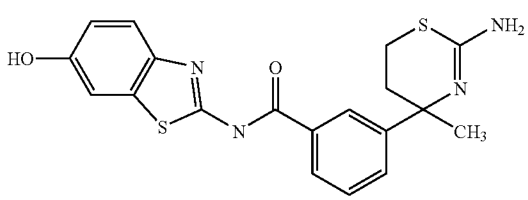 [SMILES: CC1(c2cccc(C(=O)Nc3nc4ccc(O)cc4s3)c2)CCSC(N)=N1] |
| 1090 | 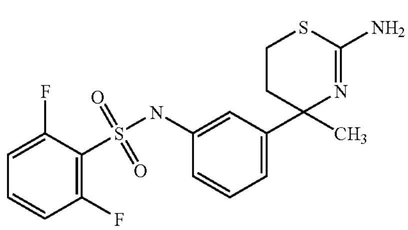 |
TABLE 116-continued
| No. | Structure |
|---|---|
| 1091 | 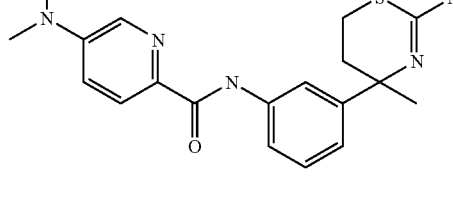 |
| 1092 | 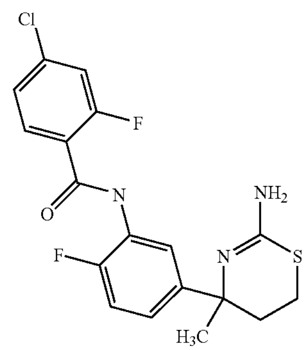 [SMILES: CC1(c2ccc(F)c(NC(=O)c3ccc(Cl)cc3F)c2)CCSC(N)=N1] |
| 1093 | 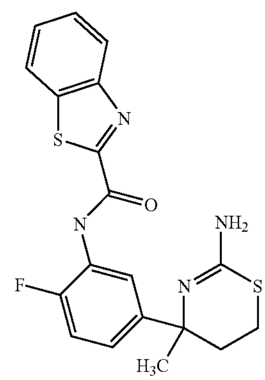 [SMILES: CC1(c2ccc(F)c(NC(=O)c3nc4ccccc4s3)c2)CCSC(N)=N1] |
| 1094 | 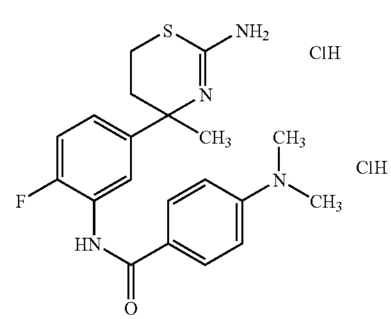 [SMILES: CN(C)c1ccc(C(=O)Nc2cc(C3(C)CCSC(N)=N3)ccc2F)cc1 ; Cl ; Cl] |

TABLE 117

| No. | Structure |
|---|---|
| 1095 | 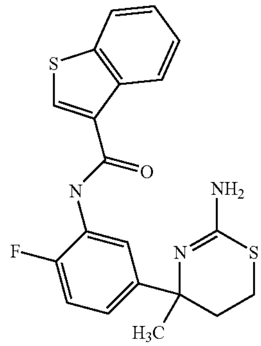 [SMILES: CC1(c2ccc(F)c(NC(=O)c3csc4ccccc34)c2)CCSC(N)=N1] |
| 1096 | 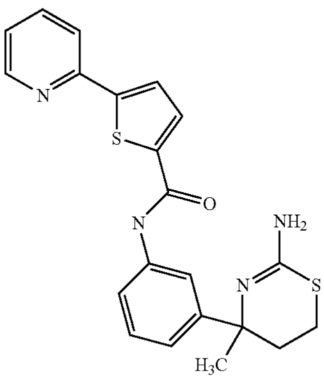 [SMILES: CC1(c2cccc(NC(=O)c3ccc(-c4ccccn4)s3)c2)CCSC(N)=N1] |
| 1097 | 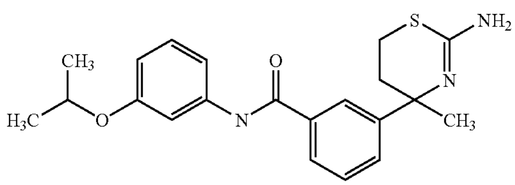 [SMILES: CC(C)Oc1cccc(NC(=O)c2cccc(C3(C)CCSC(N)=N3)c2)c1] |
| 1098 | 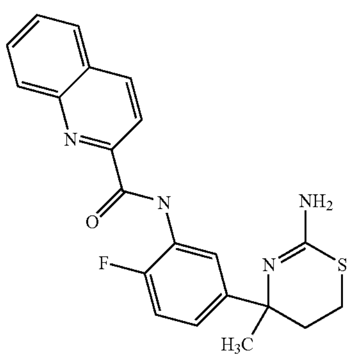 [SMILES: CC1(c2ccc(F)c(NC(=O)c3ccc4ccccc4n3)c2)CCSC(N)=N1] |
| 1099 | 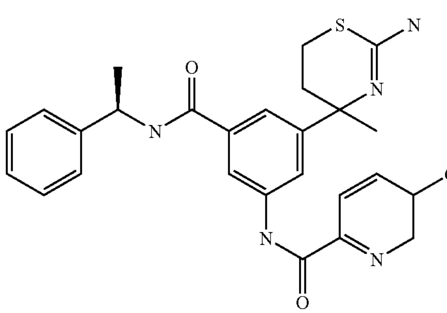 |

TABLE 117-continued

| No. | Structure |
|---|---|
| 1100 | 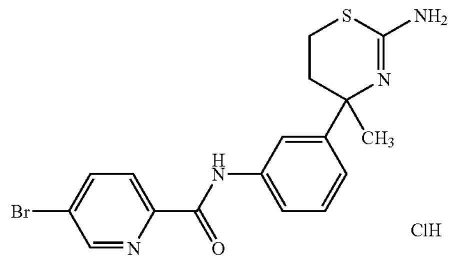 [SMILES: CC1(c2cccc(NC(=O)c3ccc(Br)cn3)c2)CCSC(N)=N1 ; Cl] |
| 1101 | 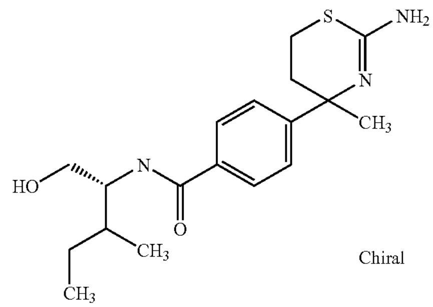 [SMILES: CCC(C)[C@H](CO)NC(=O)c1ccc(C2(C)CCSC(N)=N2)cc1] |
| 1102 | 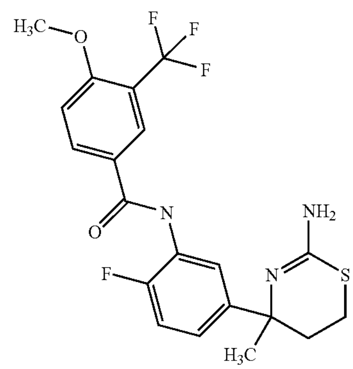 [SMILES: COc1ccc(C(=O)Nc2cc(C3(C)CCSC(N)=N3)ccc2F)cc1C(F)(F)F] |

TABLE 118

| No. | Structure |
|---|---|
| 1103 | 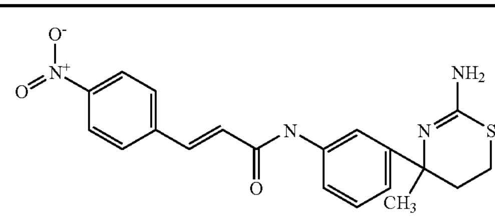 |
| 1104 | 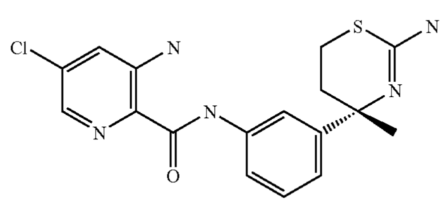 |

TABLE 118-continued
| No. | Structure |
|---|---|
| 1105 | 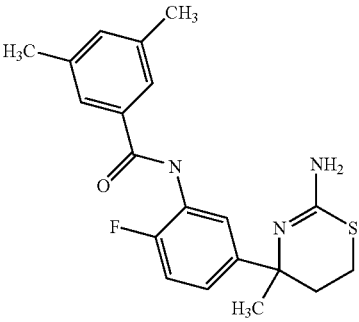 [SMILES: Cc1cc(C)cc(C(=O)Nc2cc(C3(C)CCSC(N)=N3)ccc2F)c1] |
| 1106 | 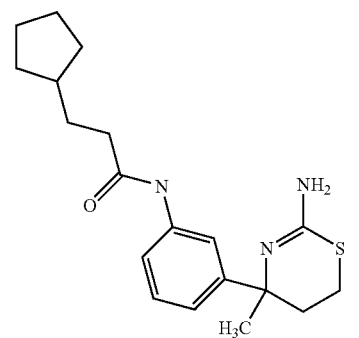 [SMILES: CC1(c2cccc(NC(=O)CCC3CCCC3)c2)CCSC(N)=N1] |
| 1107 | 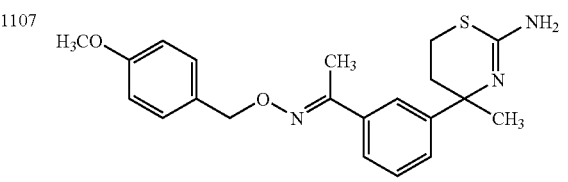 |
| 1108 | 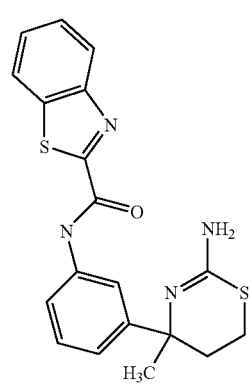 [SMILES: CC1(c2cccc(NC(=O)c3nc4ccccc4s3)c2)CCSC(N)=N1] |
| 1109 | 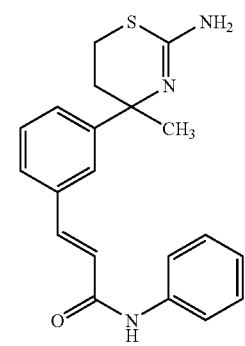 |
TABLE 118-continued
| No. | Structure |
|---|---|
| 1110 | 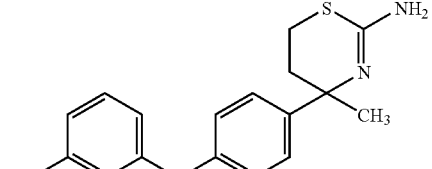 |
| 1111 | 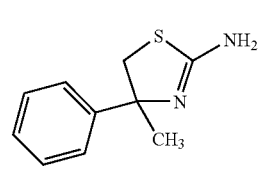 |
TABLE 119
| No. | Structure |
|---|---|
| 1112 | 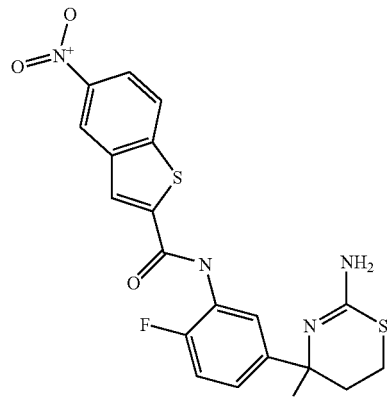 |
| 1113 | 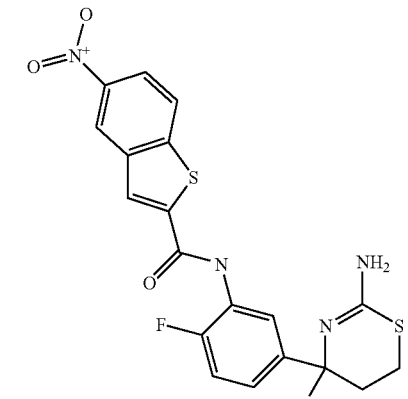 |
| 1114 | 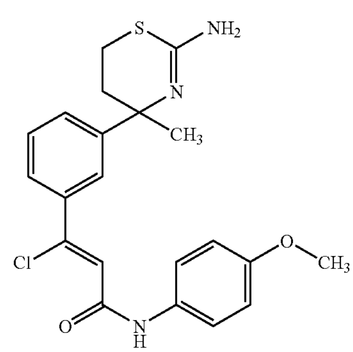 [SMILES: COc1ccc(NC(=O)/C=C(\Cl)c2cccc(C3(C)CCSC(N)=N3)c2)cc1] |

TABLE 119-continued

| No. | Structure |
|---|---|
| 1115 | 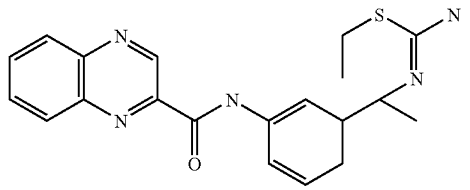 [SMILES: CCS/C(N)=N\C(C)C1C=C(NC(=O)c2cnc3ccccc3n2)C=CC1] |
| 1116 | 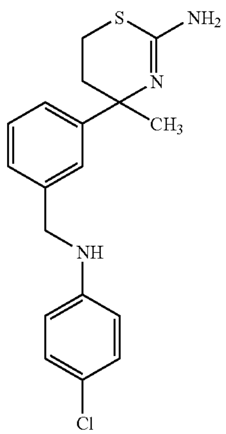 |
| 1117 | 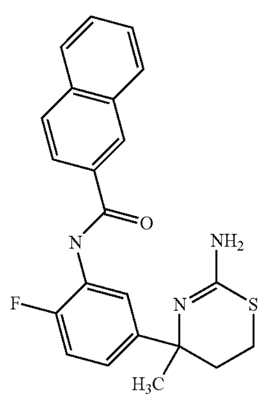 [SMILES: CC1(c2ccc(F)c(NC(=O)c3ccc4ccccc4c3)c2)CCSC(N)=N1] |
| 1118 | 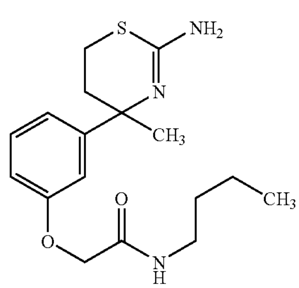 [SMILES: CCCCNC(=O)COc1cccc(C2(C)CCSC(N)=N2)c1] |

TABLE 120

| No. | Structure |
|---|---|
| 1119 | 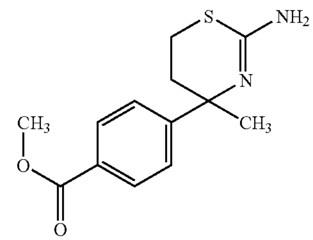 [SMILES: COC(=O)c1ccc(C2(C)CCSC(N)=N2)cc1] |
| 1120 | 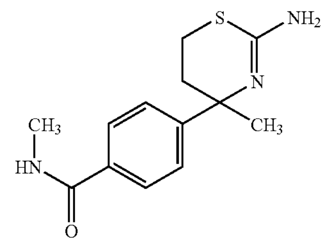 [SMILES: CNC(=O)c1ccc(C2(C)CCSC(N)=N2)cc1] |
| 1121 | 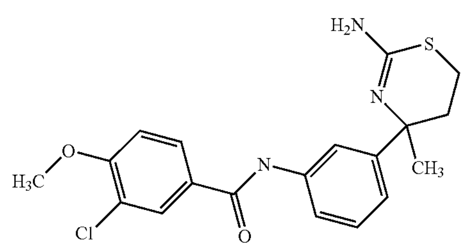 [SMILES: COc1ccc(C(=O)Nc2cccc(C3(C)CCSC(N)=N3)c2)cc1Cl] |
| 1122 | 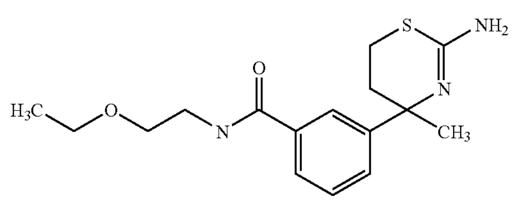 [SMILES: CCOCCNC(=O)c1cccc(C2(C)CCSC(N)=N2)c1] |
| 1123 | 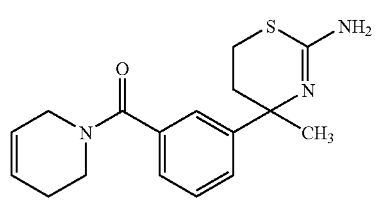 [SMILES: CC1(c2cccc(C(=O)N3CC=CCC3)c2)CCSC(N)=N1] |
| 1124 | 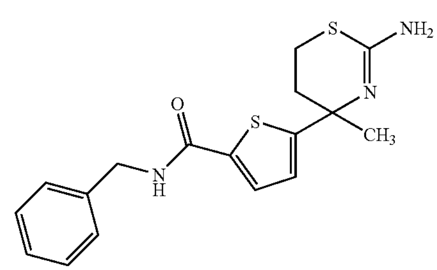 [SMILES: CC1(c2ccc(C(=O)NCc3ccccc3)s2)CCSC(N)=N1] |

TABLE 120-continued

| No. | Structure |
|---|---|
| 1125 | 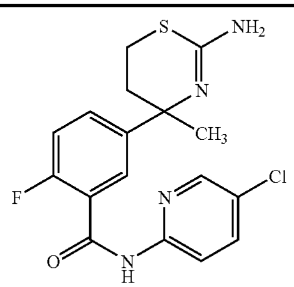 |
| 1126 | 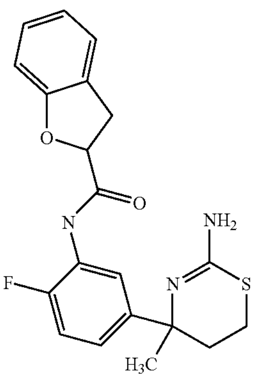 [SMILES: CC1(c2ccc(F)c(NC(=O)C3Cc4ccccc4O3)c2)CCSC(N)=N1] |
| 1127 | 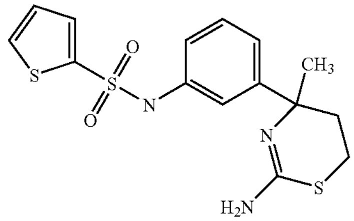 [SMILES: CC1(c2cccc(NS(=O)(=O)c3cccs3)c2)CCSC(N)=N1] |
| 1128 | 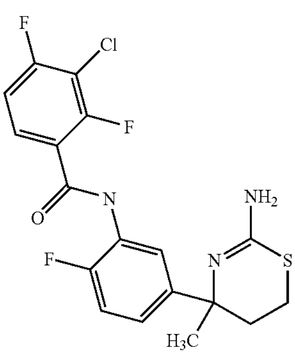 [SMILES: CC1(c2ccc(F)c(NC(=O)c3ccc(F)c(Cl)c3F)c2)CCSC(N)=N1] |

TABLE 121

| No. | Structure |
|---|---|
| 1129 | |
| 1130 | 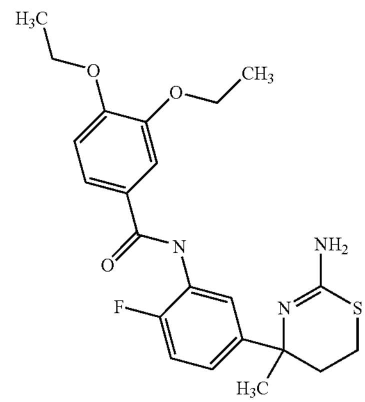 [SMILES: CCOc1ccc(C(=O)Nc2cc(C3(C)CCSC(N)=N3)ccc2F)cc1OCC] |
| 1131 | 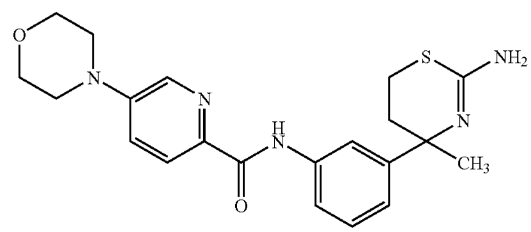 [SMILES: CC1(c2cccc(NC(=O)c3ccc(N4CCOCC4)cn3)c2)CCSC(N)=N1] |
| 1132 | 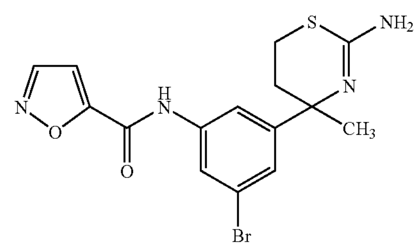 |
| 1133 | 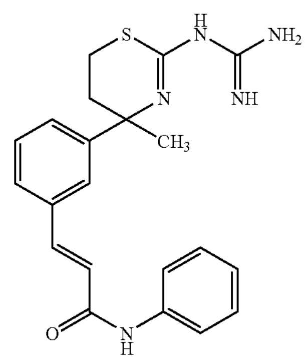 [SMILES: CC1(c2cccc(/C=C/C(=O)Nc3ccccc3)c2)CCSC(NC(=N)N)=N1] |
| 1134 | 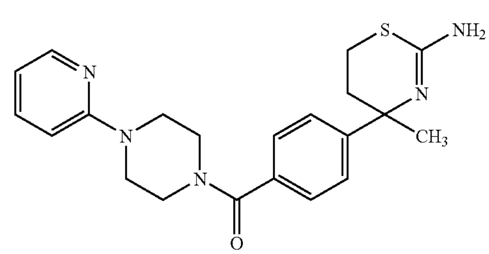 [SMILES: CC1(c2ccc(C(=O)N3CCN(c4ccccn4)CC3)cc2)CCSC(N)=N1] |

TABLE 121-continued
| No. | Structure |
|-----|-----------|
| 1135 | 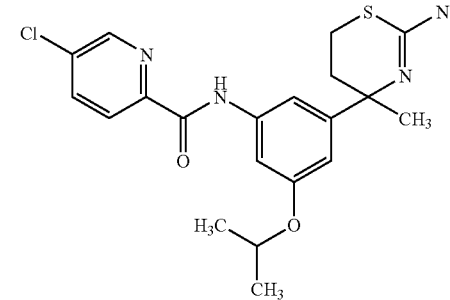 |
| 1136 | 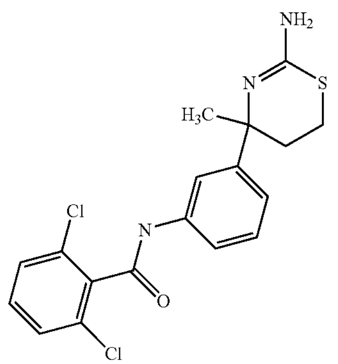 [SMILES: CC1(c2cccc(NC(=O)c3c(Cl)cccc3Cl)c2)CCSC(N)=N1] |
TABLE 122
| No. | Structure |
|-----|-----------|
| 1137 | 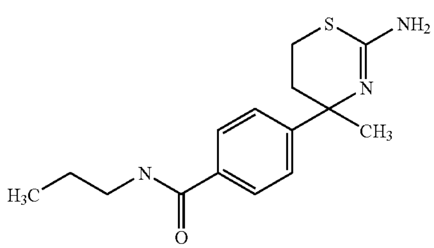 [SMILES: CCCNC(=O)c1ccc(C2(C)CCSC(N)=N2)cc1] |
| 1138 | 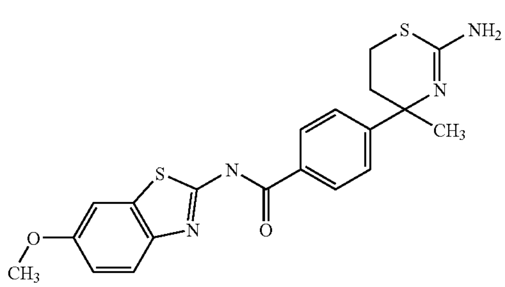 [SMILES: COc1ccc2nc(NC(=O)c3ccc(C4(C)CCSC(N)=N4)cc3)sc2c1] |
TABLE 122-continued
| No. | Structure |
|-----|-----------|
| 1139 | 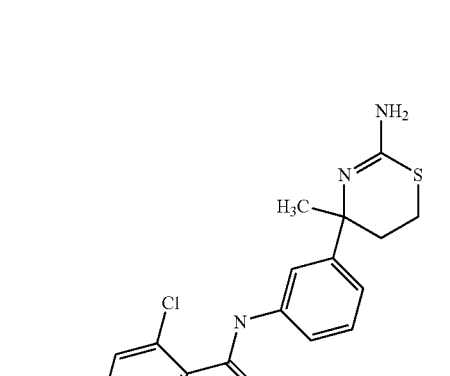 |
| 1140 | 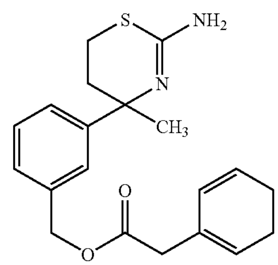 [SMILES: CC1(c2cccc(COC(=O)CC3=CCCC=C3)c2)CCSC(N)=N1] |
| 1141 | 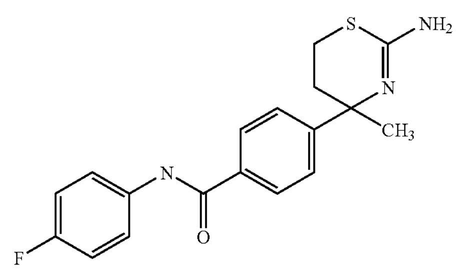 [SMILES: CC1(c2ccc(C(=O)Nc3ccc(F)cc3)cc2)CCSC(N)=N1] |
| 1142 | 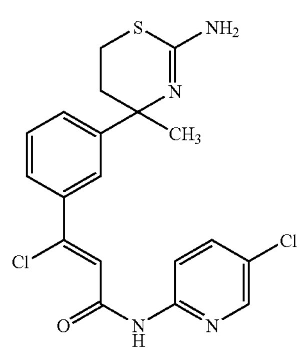 [SMILES: CC1(c2cccc(/C(Cl)=C/C(=O)Nc3ccc(Cl)cn3)c2)CCSC(N)=N1] |
| 1143 | 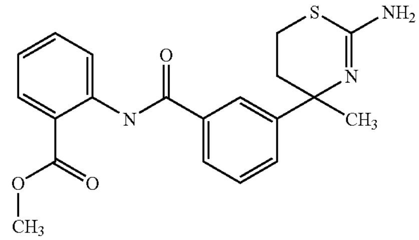 [SMILES: COC(=O)c1ccccc1NC(=O)c1cccc(C2(C)CCSC(N)=N2)c1] |

TABLE 122-continued

| No. | Structure |
|---|---|
| 1144 | (structure) |
| 1145 | (structure) |
| 1146 | (structure) |

TABLE 123

| No. | Structure |
|---|---|
| 1147 | (structure) |
| 1148 | (structure) |
| 1149 | (structure) |

TABLE 123-continued

| No. | Structure |
|---|---|
| 1150 | (structure) |
| 1151 | (structure) |
| 1152 | (structure) |
| 1153 | (structure) |
| 1154 | (structure) |

TABLE 123-continued

| No. | Structure |
|---|---|
| 1155 | 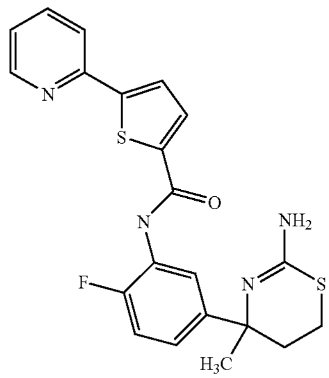 [SMILES: CC1(c2ccc(F)c(NC(=O)c3ccc(-c4ccccn4)s3)c2)CCSC(N)=N1] |
| 1156 | 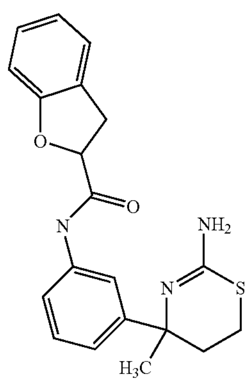 [SMILES: CC1(c2cccc(NC(=O)C3Cc4ccccc4O3)c2)CCSC(N)=N1] |

TABLE 124

| No. | Structure |
|---|---|
| 1157 | |
| 1158 | |
| 1159 | 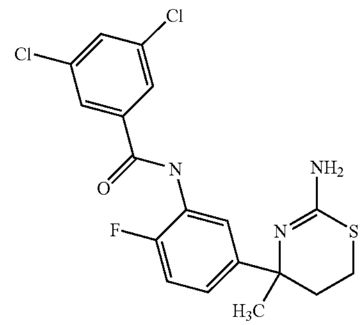 [SMILES: CC1(c2ccc(F)c(NC(=O)c3cc(Cl)cc(Cl)c3)c2)CCSC(N)=N1] |
| 1160 | 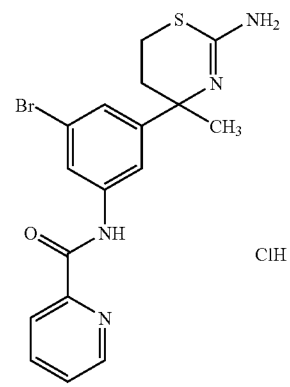 [SMILES: CC1(c2cc(Br)cc(NC(=O)c3ccccn3)c2)CCSC(N)=N1 ; Cl] |
| 1161 | 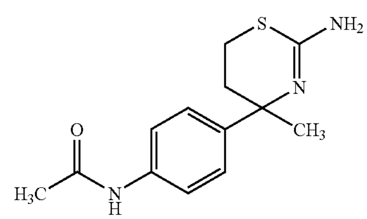 [SMILES: CC(=O)Nc1ccc(C2(C)CCSC(N)=N2)cc1] |
| 1162 | 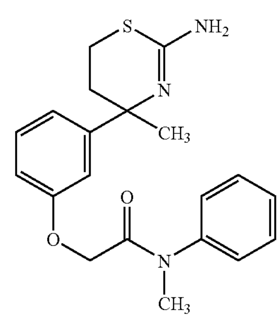 [SMILES: CN(C(=O)COc1cccc(C2(C)CCSC(N)=N2)c1)c1ccccc1] |
| 1163 | 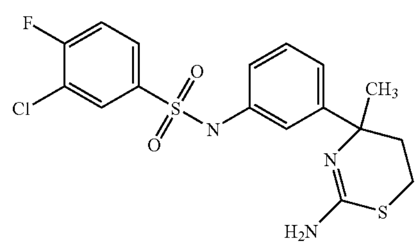 |

TABLE 124-continued

| No. | Structure |
|---|---|
| 1164 | (structure) |

TABLE 125

| No. | Structure |
|---|---|
| 1165 | (structure) |
| 1166 | (structure) |
| 1167 | (structure) |
| 1168 | (structure) |
| 1169 | (structure) |
| 1170 | (structure) |
| 1171 | (structure) |
| 1172 | (structure) |

TABLE 125-continued
| No. | Structure |
|---|---|
| 1173 | 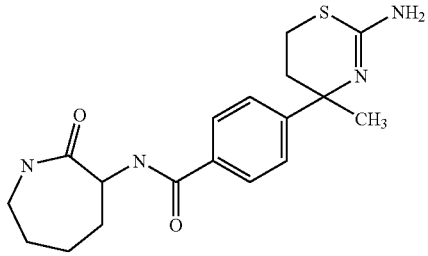 [SMILES: CC1(c2ccc(C(=O)NC3CCCCNC3=O)cc2)CCSC(N)=N1] |
TABLE 126
| No. | Structure |
|---|---|
| 1174 | 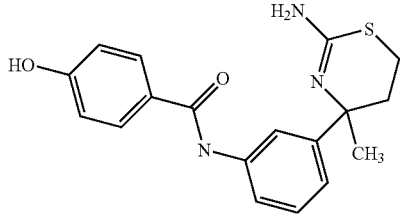 [SMILES: CC1(c2cccc(NC(=O)c3ccc(O)cc3)c2)CCSC(N)=N1] |
| 1175 | 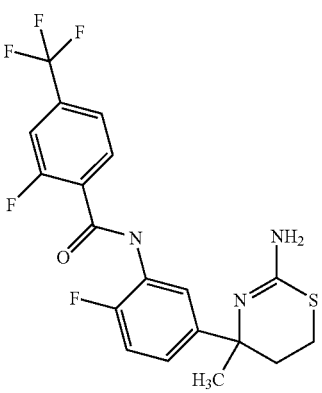 [SMILES: CC1(c2ccc(F)c(NC(=O)c3ccc(C(F)(F)F)cc3F)c2)CCSC(N)=N1] |
| 1176 | 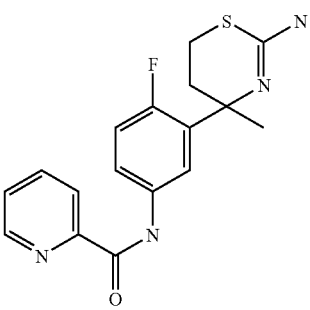 [SMILES: CC1(c2cc(NC(=O)c3ccccn3)ccc2F)CCSC(N)=N1] |
| 1177 | 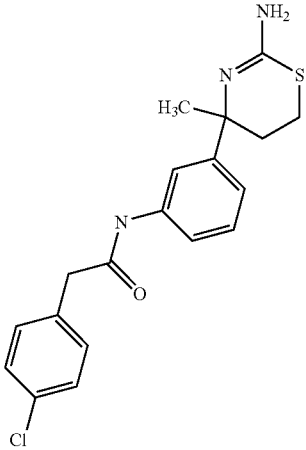 [SMILES: CC1(c2cccc(NC(=O)Cc3ccc(Cl)cc3)c2)CCSC(N)=N1] |
| 1178 | 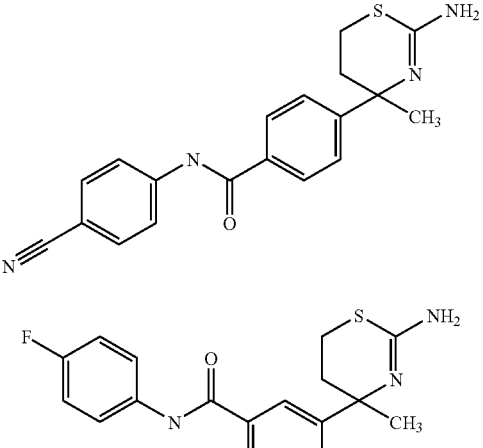 |
| 1179 | 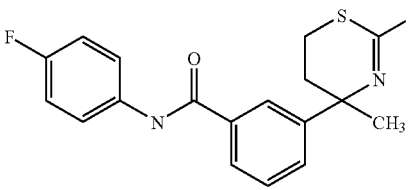 |
| 1180 | 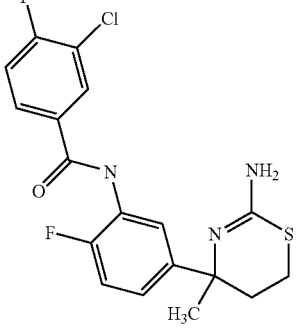 |
| 1181 | 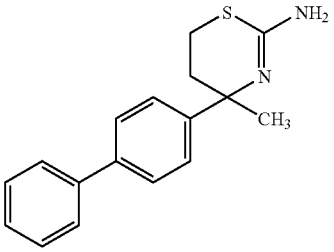 [SMILES: CC1(c2ccc(-c3ccccc3)cc2)CCSC(N)=N1] |

TABLE 126-continued
| No. | Structure |
|---|---|
| 1182 | 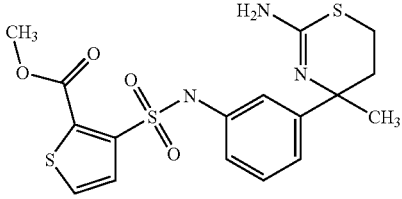 [SMILES: COC(=O)c1sccc1S(=O)(=O)Nc1cccc(C2(C)CCSC(N)=N2)c1] |
| 1183 | 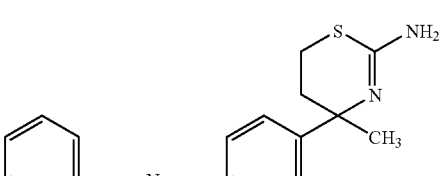 |
TABLE 127
| No. | Structure |
|---|---|
| 1184 | 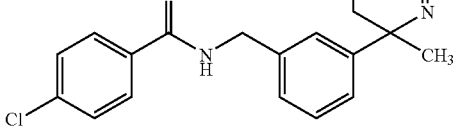 HCl |
| 1185 | 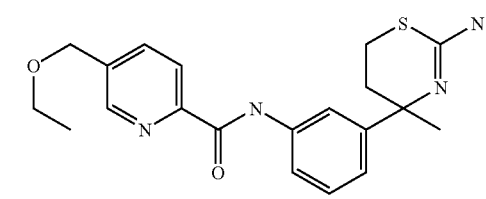 [SMILES: CCOCc1ccc(C(=O)Nc2cccc(C3(C)CCSC(N)=N3)c2)nc1] |
| 1186 | 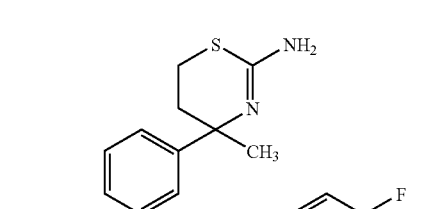 |
TABLE 127-continued
| No. | Structure |
|---|---|
| 1187 | 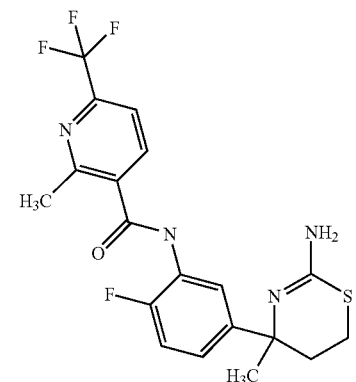 |
| 1188 | 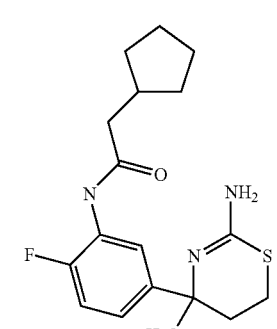 |
| 1189 | 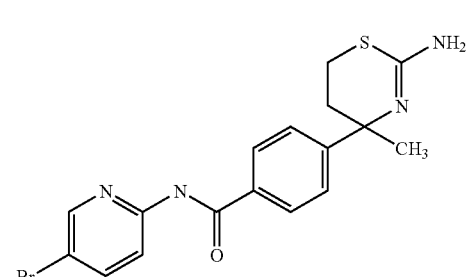 |
| 1190 | 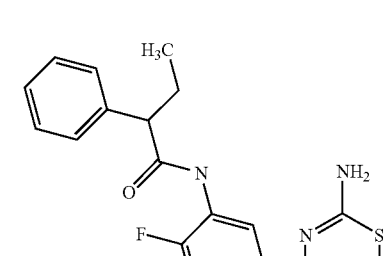 |
| 1191 | 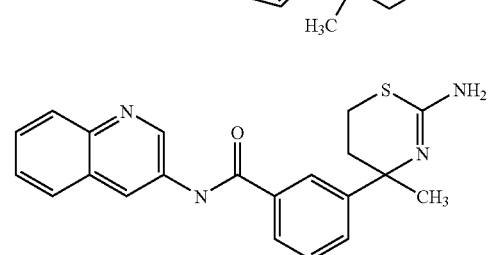 |

TABLE 127-continued
| No. | Structure |
|---|---|
| 1192 | 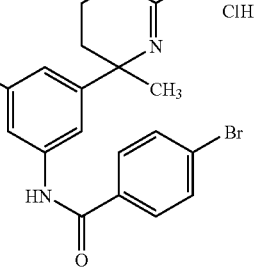 |
| 1193 | 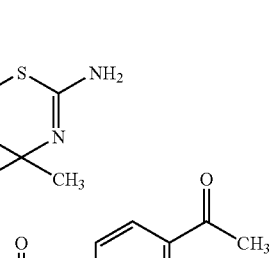 |
| 1194 | 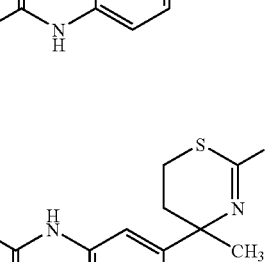 |
TABLE 128
| No. | Structure |
|---|---|
| 1195 | 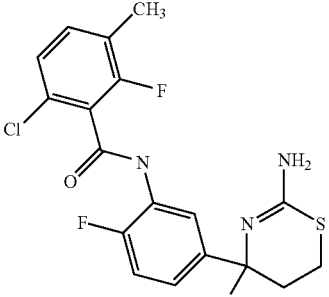 |
| 1196 | 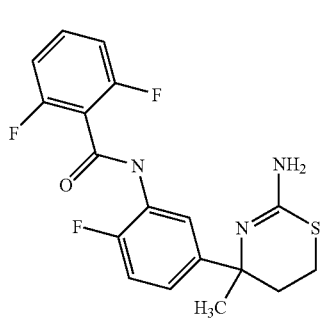 [SMILES: CC1(c2ccc(F)c(NC(=O)c3c(F)cccc3F)c2)CCSC(N)=N1] |
| 1197 | 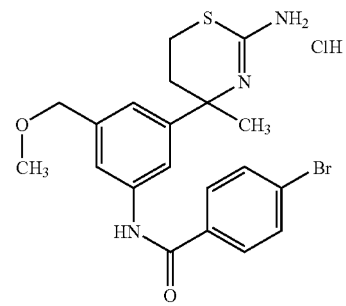 [SMILES: COCc1cc(NC(=O)c2ccc(Br)cc2)cc(C2(C)CCSC(N)=N2)c1 ; Cl] |
| 1198 | 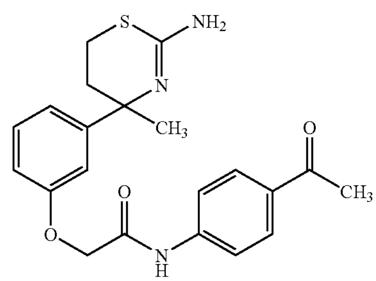 [SMILES: CC(=O)c1ccc(NC(=O)COc2cccc(C3(C)CCSC(N)=N3)c2)cc1] |
| 1199 | 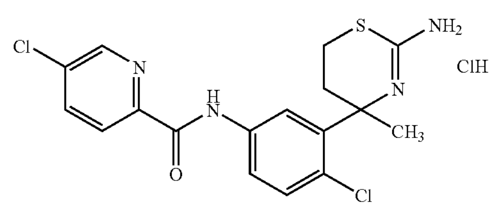 [SMILES: CC1(c2cc(NC(=O)c3ccc(Cl)cn3)ccc2Cl)CCSC(N)=N1 ; Cl] |
| 1200 | 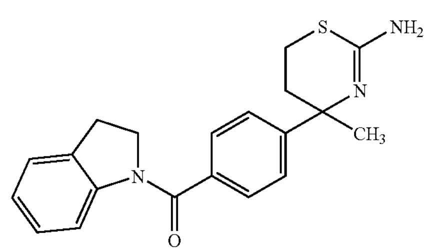 [SMILES: CC1(c2ccc(C(=O)N3CCc4ccccc43)cc2)CCSC(N)=N1] |
| 1201 | 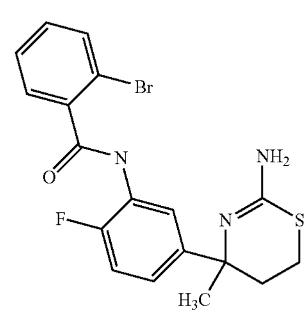 [SMILES: CC1(c2ccc(F)c(NC(=O)c3ccccc3Br)c2)CCSC(N)=N1] |

TABLE 128-continued
| No. | Structure |
|---|---|
| 1202 | 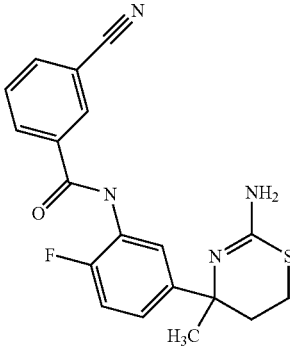 [SMILES: CC1(c2ccc(F)c(NC(=O)c3cccc(C#N)c3)c2)CCSC(N)=N1] |
| 1203 | 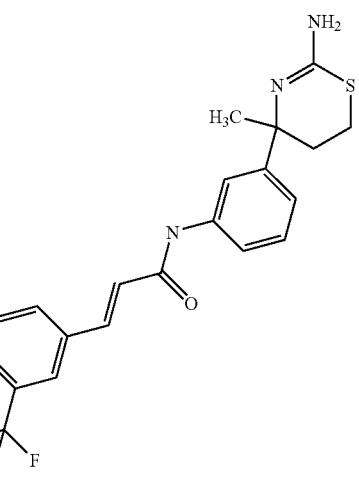 |
TABLE 129
| No. | Structure |
|---|---|
| 1204 | 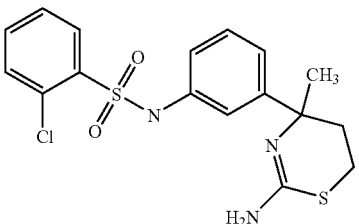 |
| 1205 | 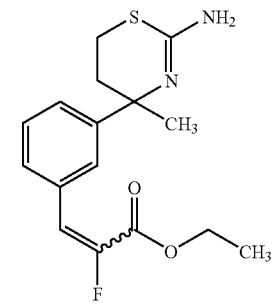 [SMILES: CCOC(=O)C(F)=Cc1cccc(C2(C)CCSC(N)=N2)c1] |
| 1206 | 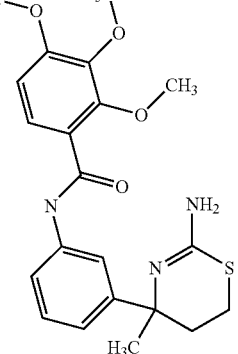 |
| 1207 | 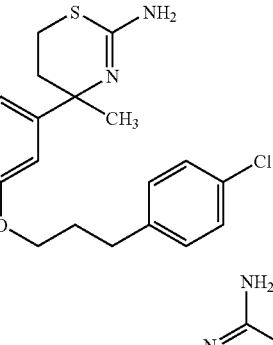 |
| 1208 | 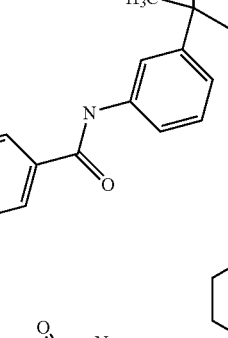 |
| 1209 | 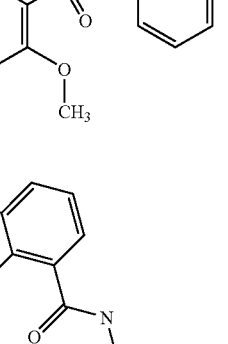 |
| 1210 | 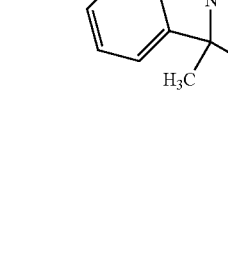 |

TABLE 129-continued
| No. | Structure |
|---|---|
| 1211 | 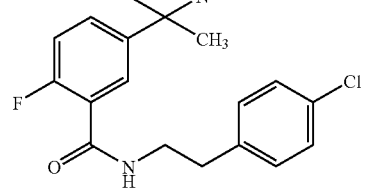 |
| 1212 | 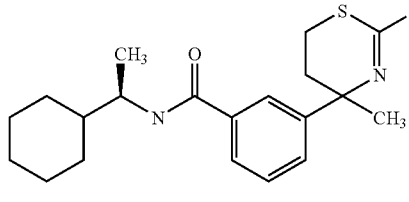 |
TABLE 130
| No. | Structure |
|---|---|
| 1213 | 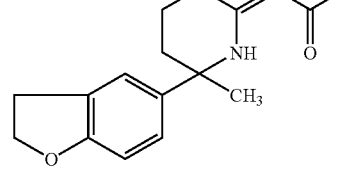 |
| 1214 | 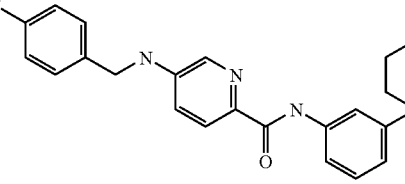 |
| 1215 | 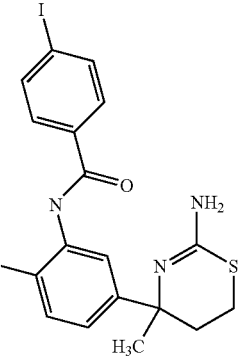 |
| 1216 | 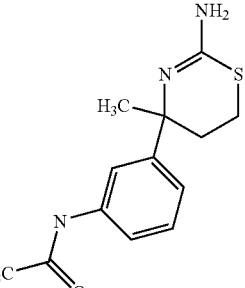 |
TABLE 130-continued
| No. | Structure |
|---|---|
| 1217 | 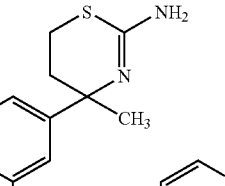 |
| 1218 | 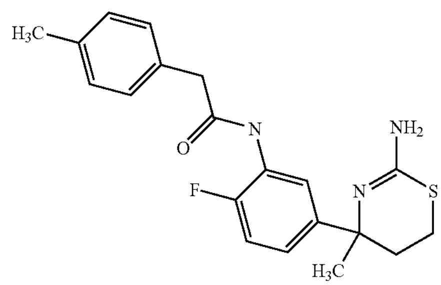 [SMILES: Cc1ccc(CC(=O)Nc2cc(C3(C)CCSC(N)=N3)ccc2F)cc1] |
| 1219 | 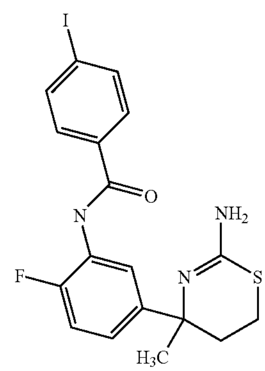 |
| 1220 | 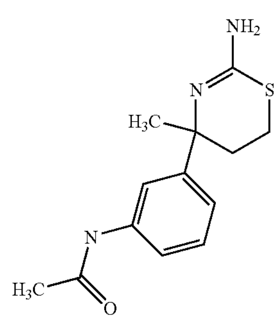 [SMILES: CC(=O)Nc1cccc(C2(C)CCSC(N)=N2)c1] |
| 1221 | 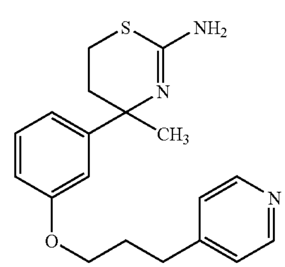 [SMILES: CC1(c2cccc(OCCCc3ccncc3)c2)CCSC(N)=N1] |

TABLE 131

| No. | Structure |
|---|---|
| 1222 | 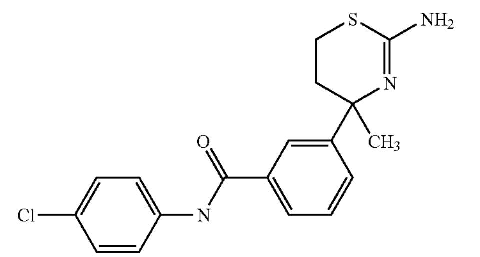 [SMILES: CC1(c2cccc(C(=O)Nc3ccc(Cl)cc3)c2)CCSC(N)=N1] |
| 1223 | 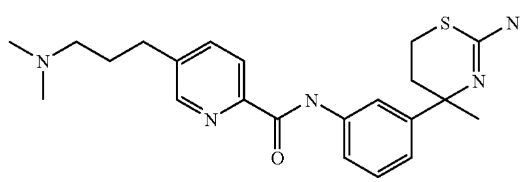 [SMILES: CN(C)CCCc1ccc(C(=O)Nc2cccc(C3(C)CCSC(N)=N3)c2)nc1] |
| 1224 | 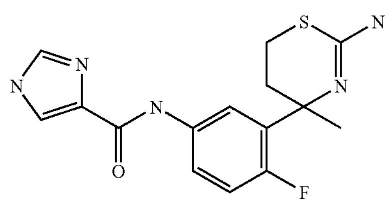 [SMILES: CC1(c2cc(NC(=O)c3c[nH]cn3)ccc2F)CCSC(N)=N1] |
| 1225 | 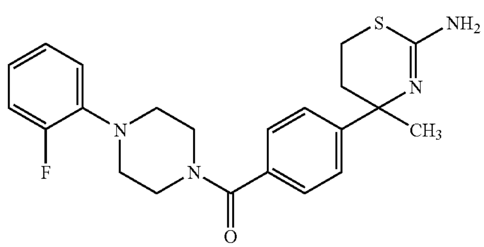 |
| 1226 | 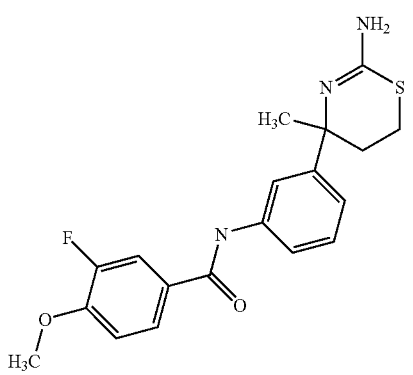 [SMILES: COc1ccc(C(=O)Nc2cccc(C3(C)CCSC(N)=N3)c2)cc1F] |
| 1227 | 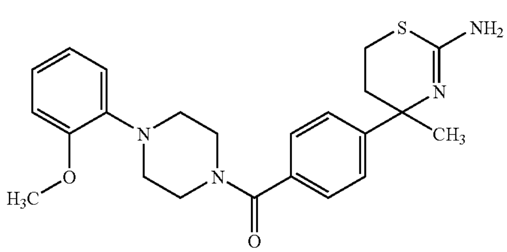 [SMILES: COc1ccccc1N1CCN(C(=O)c2ccc(C3(C)CCSC(N)=N3)cc2)CC1] |

TABLE 131-continued

| No. | Structure |
|---|---|
| 1228 | 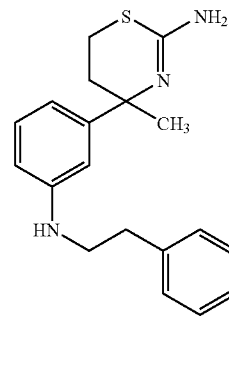 |
| 1229 | 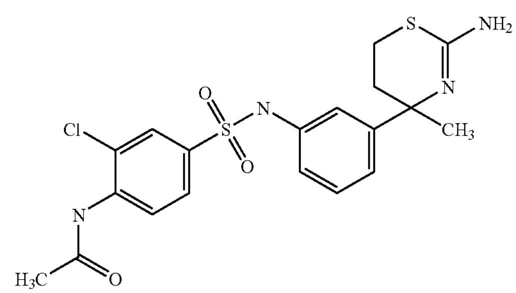 [SMILES: CC(=O)Nc1ccc(S(=O)(=O)Nc2cccc(C3(C)CCSC(N)=N3)c2)cc1Cl] |
| 1230 | 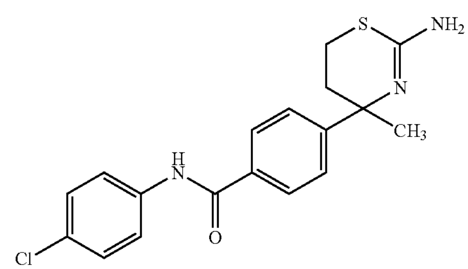 [SMILES: CC1(c2ccc(C(=O)Nc3ccc(Cl)cc3)cc2)CCSC(N)=N1] |
| 1231 | 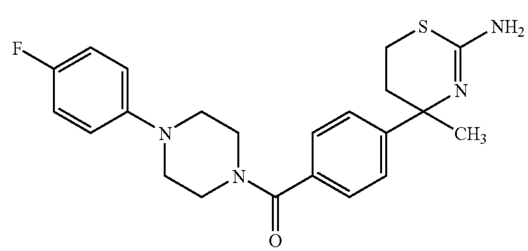 [SMILES: CC1(c2ccc(C(=O)N3CCN(c4ccc(F)cc4)CC3)cc2)CCSC(N)=N1] |

TABLE 132

| No. | Structure |
|---|---|
| 1232 | 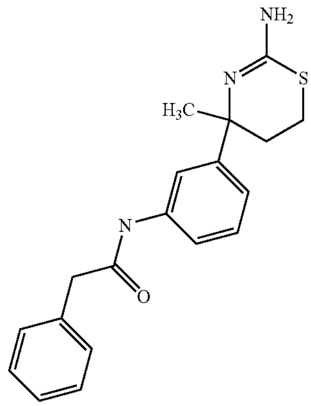 [SMILES: CC1(c2cccc(NC(=O)Cc3ccccc3)c2)CCSC(N)=N1] |
| 1233 | 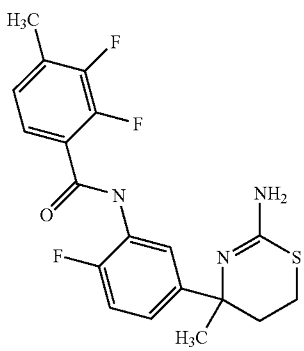 [SMILES: Cc1ccc(C(=O)Nc2cc(C3(C)CCSC(N)=N3)ccc2F)c(F)c1F] |
| 1234 | 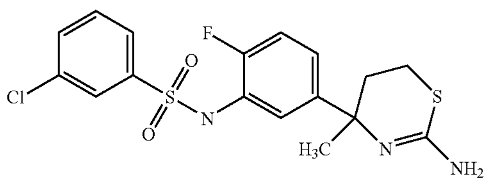 [SMILES: CC1(c2ccc(F)c(NS(=O)(=O)c3cccc(Cl)c3)c2)CCSC(N)=N1] |
| 1235 | 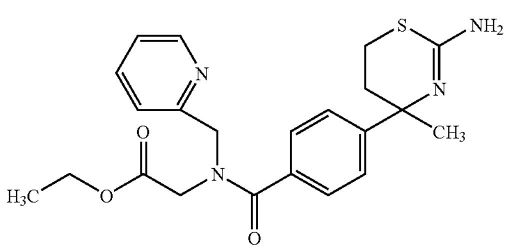 [SMILES: CCOC(=O)CN(Cc1ccccn1)C(=O)c1ccc(C2(C)CCSC(N)=N2)cc1] |
| 1236 | 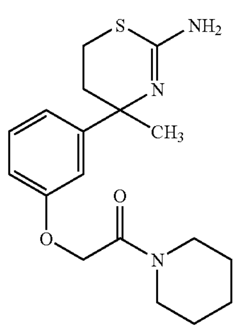 [SMILES: CC1(c2cccc(OCC(=O)N3CCCCC3)c2)CCSC(N)=N1] |

TABLE 132-continued

| No. | Structure |
|---|---|
| 1237 | 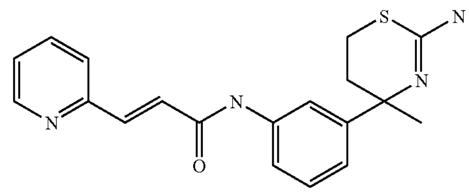 [SMILES: CC1(c2cccc(NC(=O)/C=C/c3ccccn3)c2)CCSC(N)=N1] |
| 1238 | 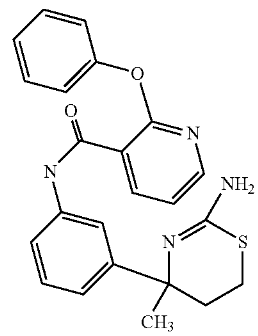 [SMILES: CC1(c2cccc(NC(=O)c3cccnc3Oc3ccccc3)c2)CCSC(N)=N1] |
| 1239 | 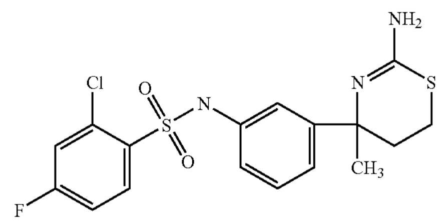 [SMILES: CC1(c2cccc(NS(=O)(=O)c3ccc(F)cc3Cl)c2)CCSC(N)=N1] |
| 1240 | 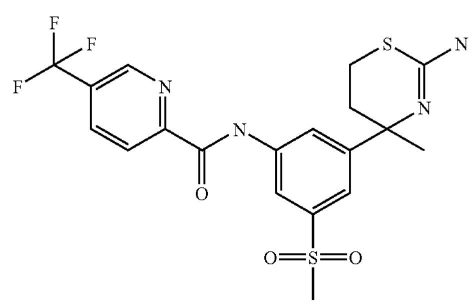 [SMILES: CC1(c2cc(NC(=O)c3ccc(C(F)(F)F)cn3)cc(S(C)(=O)=O)c2)CCSC(N)=N1] |
| 1241 | 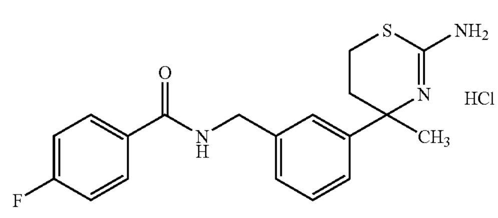 [SMILES: CC1(c2cccc(CNC(=O)c3ccc(F)cc3)c2)CCSC(N)=N1 ; Cl] |
| 1242 | 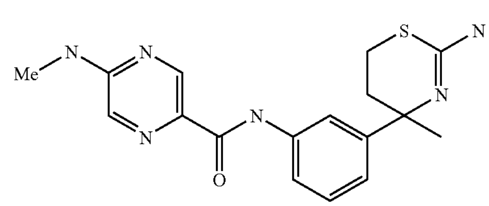 [SMILES: CNc1cnc(C(=O)Nc2cccc(C3(C)CCSC(N)=N3)c2)cn1] |

TABLE 133

| No. | Structure |
|-----|-----------|
| 1243 | 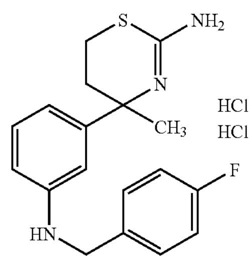 [SMILES: CC1(c2cccc(NCc3ccc(F)cc3)c2)CCSC(N)=N1 ; Cl ; Cl] |
| 1244 | 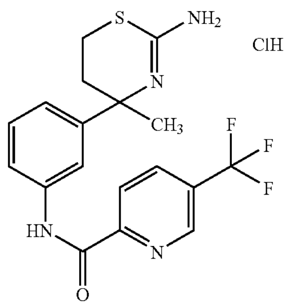 [SMILES: CC1(c2cccc(NC(=O)c3ccc(C(F)(F)F)cn3)c2)CCSC(N)=N1 ; Cl] |
| 1245 | 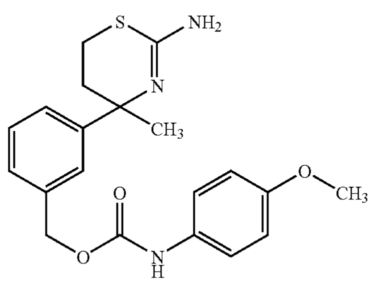 |
| 1246 | 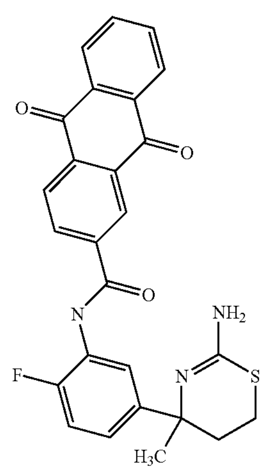 [SMILES: CC1(c2ccc(F)c(NC(=O)c3ccc4c(c3)C(=O)c3ccccc3C4=O)c2)CCSC(N)=N1] |
| 1247 | 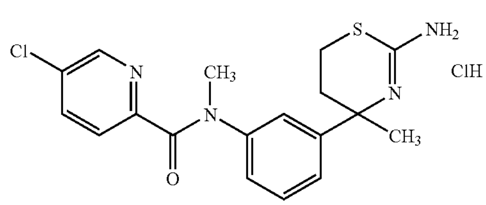 [SMILES: CN(C(=O)c1ccc(Cl)cn1)c1cccc(C2(C)CCSC(N)=N2)c1 ; Cl] |

TABLE 133-continued

| No. | Structure |
|-----|-----------|
| 1248 | 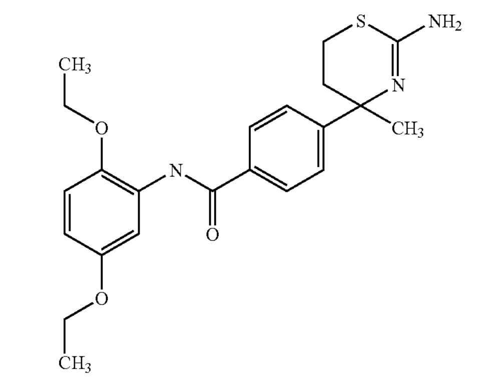 [SMILES: CCOc1ccc(OCC)c(NC(=O)c2ccc(C3(C)CCSC(N)=N3)cc2)c1] |
| 1249 | 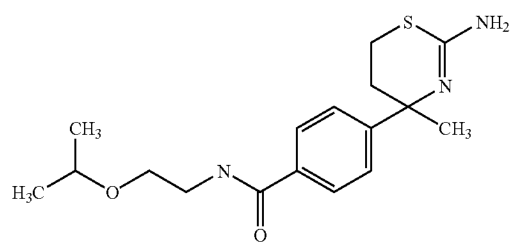 [SMILES: CC(C)OCCNC(=O)c1ccc(C2(C)CCSC(N)=N2)cc1] |
| 1250 | 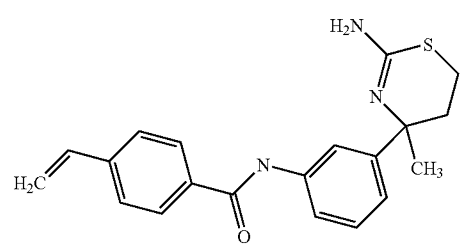 [SMILES: C=Cc1ccc(C(=O)Nc2cccc(C3(C)CCSC(N)=N3)c2)cc1] |
| 1251 | 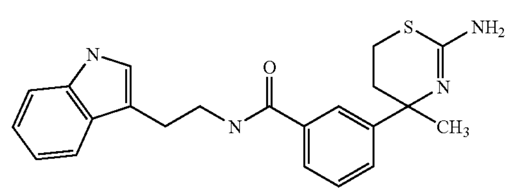 [SMILES: CC1(c2cccc(C(=O)NCCc3c[nH]c4ccccc34)c2)CCSC(N)=N1] |
| 1252 | 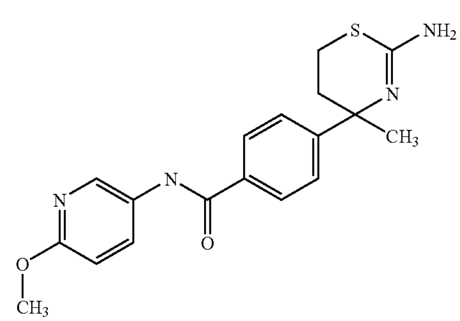 [SMILES: COc1ccc(NC(=O)c2ccc(C3(C)CCSC(N)=N3)cc2)cn1] |

TABLE 134
| No. | Structure |
|---|---|
| 1253 | 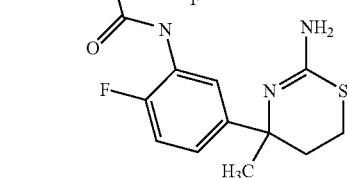 |
| 1254 | 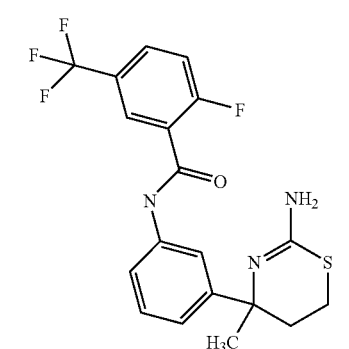 |
| 1255 | 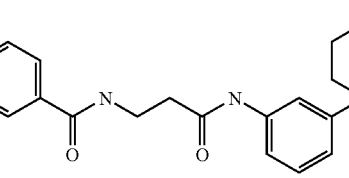 |
| 1256 | 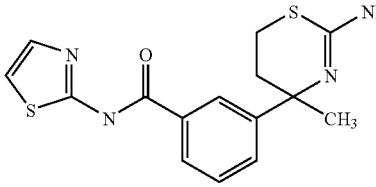 |
| 1257 | 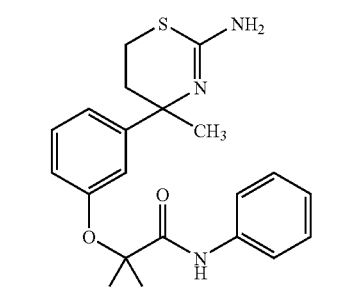 |
| 1258 | 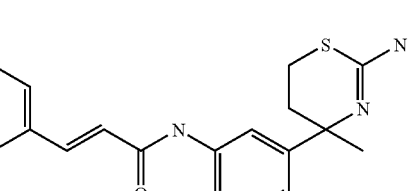 |
TABLE 134-continued
| No. | Structure |
|---|---|
| 1259 | 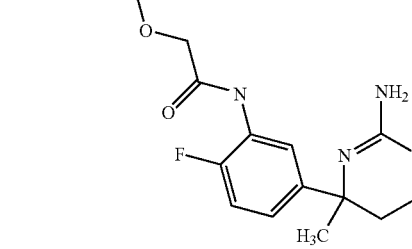 |
| 1260 | 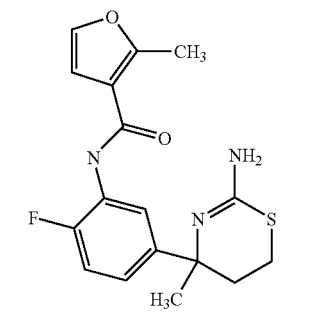 [SMILES: Cc1occc1C(=O)Nc1cc(C2(C)CCSC(N)=N2)ccc1F] |
| 1261 | 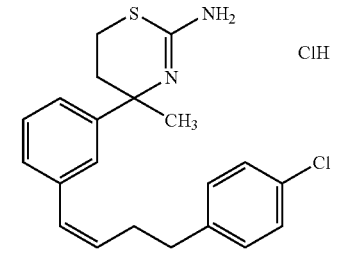 [SMILES: CC1(c2cccc(/C=C\CCc3ccc(Cl)cc3)c2)CCSC(N)=N1 ; Cl] |
TABLE 135
| No. | Structure |
|---|---|
| 1262 | 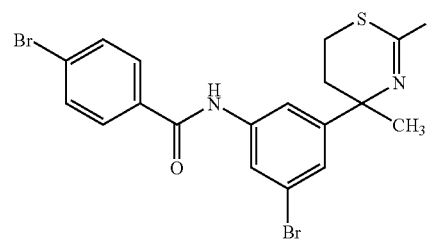 |
| 1263 | 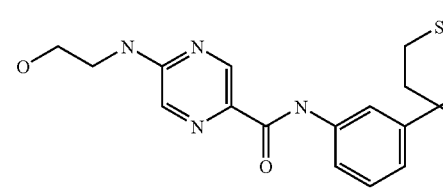 |

TABLE 135-continued

| No. | Structure |
|---|---|
| 1264 | (structure) |
| 1265 | (structure) |
| 1266 | (structure) |
| 1267 | (structure) |
| 1268 | (structure) |
| 1269 | (structure) |
| 1270 | (structure) |
| 1271 | (structure) |
| 1272 | (structure) |
| 1273 | (structure) |

TABLE 136

| No. | Structure |
|---|---|
| 1274 | (structure) |
| 1275 | (structure) |
| 1276 | (structure) |
| 1277 | (structure) |

TABLE 136-continued
| No. | Structure |
|-----|-----------|
| 1278 | 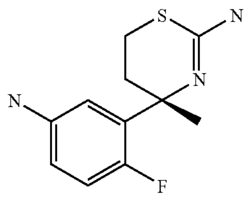 |
| 1279 | 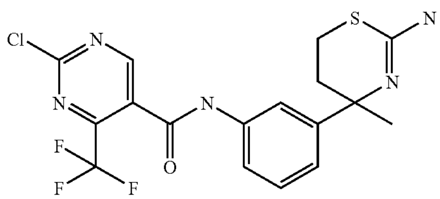 [SMILES: CC1(c2cccc(NC(=O)c3cnc(Cl)nc3C(F)(F)F)c2)CCSC(N)=N1] |
| 1280 | 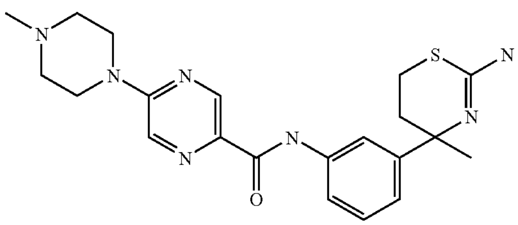 [SMILES: CN1CCN(c2cnc(C(=O)Nc3cccc(C4(C)CCSC(N)=N4)c3)cn2)CC1] |
| 1281 | 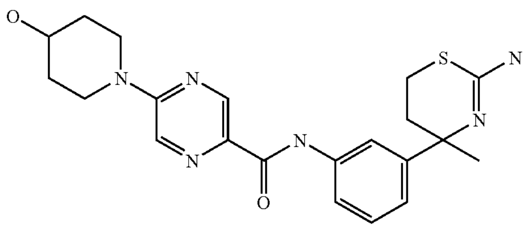 [SMILES: CC1(c2cccc(NC(=O)c3cnc(N4CCC(O)CC4)cn3)c2)CCSC(N)=N1] |
| 1282 |  |
[Chemical formula 83]
in formula, —N— means —NH—,
—N means —NH₂, and
—O means —OH.
TABLE 137
| No. | mp (° C.) | 1H-NMR(δ) | MS (m/z) | UV (λ max: nm) |
|-----|-----------|-----------|----------|----------------|
| 1 | | | | 213.4 |
| | | | | 305.3 |
| 3 | 285 (dec.) | | | |
| 4 | amorphous | | | 219 |
| 5 | | | | 215, 262 |
| 6 | 147-148 | | | |
| 8 | 214-217 | | | |
| 9 | oil | | | 220 |
| 18 | 181-183 | | | |
| 23 | | | | 213.4 |
| | | | | 272.2 |
| | | | | 305.3 |
| 24 | 116-117 | | | |
| 26 | 182-184 | | | |
| 30 | | | | 267.4 |
| 33 | | | | 253.3 |
| | | | | 305.3 |
| 37 | amorphous | | | 219, 275 |
| 38 | 240-244 (dec.) | | | |
| 39 | | | | 285.2 |
| 42 | 187-188 | | | |
| 43 | | | | 218.1 |
| | | | | 275.7 |
| 48 | | | | 230 |
| | | | | 275 |
| 57 | 197-198 | | | |
| 58 | 234-240 | | | |
| 62 | 198-201 | | | |

TABLE 137-continued

| No. | mp (° C.) | 1H-NMR(δ) | MS (m/z) | UV (λ max: nm) |
|---|---|---|---|---|
| 69 | 194-195 | | | |
| 71 | | | | 216.9 |
| | | | | 268.6 |
| 73 | 266-269 | | | |
| 77 | | δ in d20-DMSO: 1.67 (3H, s), 2.13-2.06 (1H, m), 2.63-2.55 (2H, m), 3.16-3.13 (4H, m), 3.65-3.63 (2H, m), 4.76-4.73 (2H, m), 7.15-7.08 (2H, m), 7.30 (1H, t, J = 8.0 Hz), 7.35 (1H, s), 7.42 (1H, t, J = 8.0 Hz), 7.60 (1H, d, J = 8.0 Hz), 7.69 (1H, d, J = 8.0 Hz), 7.73 (1H, brs), 7.86 (1H, d, J = 8.0 Hz), 10.52 (1H, s) | | 422.543 |
| 78 | | $^1$H-NMR (CDCl$_3$) δ: 1.76 (3H, s), 2.02 (1H, s), 2.58 (1H, d, J = 14.1 Hz), 2.78 (2H, d, J = 6.9 Hz), 3.80 (3H, d, J = 13.1 Hz), 4.54 (2H, s), 6.45 (1H, s), 6.55-6.57 (2H, m), 6.66 (1H, d, J = 8.7 Hz), 7.10 (1H, t, J = 7.0 Hz), 7.22 (2H, td, J = 7.7, 1.4 Hz), 7.34 (1H, d, J = 9.1 Hz), 7.56 (1H, d, J = 7.7 Hz). | 365[M + 1] | |
| 80 | | | | 220.4 |
| | | | | 280.4 |

TABLE 138

| No. | mp (° C.) | 1H-NMR(δ) | MS (m/z) | UV (λ max: nm) |
|---|---|---|---|---|
| 85 | 147-148 | 1.54(3H, s), 1.75-1.86(1H, m), 2.08-2.18(1H, m), 2.33(3H, s), 2.63-2.74(1H, m), 2.81-2.90(1H, m), 4.36(2H, br), 7.13(2H, d, J = 8.6 Hz), 7.20(2H, d, J = 8.6 Hz)(solvent: CDCl3) | | |
| 86 | 141-142 | | | |
| 91 | | | 372[M + 1] | 201 |
| | | | 298 | 206 |
| | | | | 216 |
| 96 | | | | 309 |
| 97 | | δ in d13-DMSO: 1.64(3H, s), 2.03-1.97(1H, m), 2.63-2.57(2H, m), 3.28-3.25(1H, m), 7.22(1H, q, J = 12.4, 9.0 Hz), 7.82-7.77(2H, m), 8.60(1H, s), 8.79(1H, s), 10.37(1H, s) | | |
| 99 | 221-224 | | | |
| 101 | 264-265 | | | |
| 104 | amorphous | | | 229, 280 |
| 113 | | 1.58 (s, 3H), 1.88 (ddd, J = 14.1, 10.9, 3.7 Hz, 1H), 2.24 (ddd, J = 14.1, 5.9, 3.5 Hz, 1H), 2.73 (ddd, J = 12.3, 10.9, 3.5 Hz, 1H), 2.88 (ddd, J = 12.3, 5.9, 3.7 Hz, 1H), 3.83 (d, J = 15.4 Hz, 1H), 3.87 (d, J = 15.4 Hz, 1H), 7.02-7.04 (m, 1H), 7.25-7.31 (m, 2H), 7.36 (d, J = 2.0 Hz, 1H), 7.45-7.50 (m, 2H), 8.52 (d, J = 5.2 Hz, 1H), 9.43 (s, 1H) (solvent: CDCl3) | | |
| 114 | | | | 214.5 |
| | | | | 306.5 |
| 115 | | δ in d6-DMSO: 1.47(3H, s), 1.80-1.74(1H, m, 2.22-2.18(1H, m), 2.60-2.55(1H, m), 2.96-2.93(1H, m), 6.14(1H, s), 6.93(1H, s), 7.09-7.04(2H, m), 7.63-7.61(1H, m), 7.68-7.66(1H, m), 9.85(1H, s), 11.63(1H, brs) | | |
| 120 | amorphous | | | 213 |
| 121 | 166-167 | | | |
| 125 | >300 | | | |
| 126 | amorphous | | | 229, 271 |
| 127 | 280-285 | | | |
| 128 | 159-163 | | | |
| 129 | 219-222 | | | |
| 130 | 128-131 | 1.56 (3H, s), 1.83-1.93 (1H, m), 2.16 (1H, dq, J = 13.85, 3.41 Hz), 2.29 (3H, s), 2.72-2.77 (1H, m), 2.90-2.94 (1H, m), 4.13 (3H, s), 6.42 (1H, s), 7.10-7.14 (1H, m), 7.32 (1H, d, J = 7.91 Hz), 7.37-7.38 (1H, m), 7.60-7.63 (1H, m), (solvent: CDCl3) | 344[M + 1] | |
| 132 | 147-150 | | | |
| 134 | | | | 228.5 |

TABLE 139

| No. | mp (° C.) | 1H-NMR(δ) | MS (m/z) | UV (λ max: nm) |
|---|---|---|---|---|
| 139 | 287-290 | 1.77 (s, 3H), 2.10 (ddd, J = 14.0, 10.8, 3.6 Hz, 1H), 2.64-2.70 (4H, m), 2.76 (td, J = 12.8, 3.6 Hz, 1H), 2.90 (dt, J = 12.8, 3.6 Hz, 1H), 7.05 (ddd, J = 8.0, 2.0, 0.8 Hz, 1H), 7.41 (t, J = 8.0 Hz, 1H), 7.69-7.72 (m, 2H), 8.32 (dd, J = 8.0, 0.8 Hz, 1H), 8.40 (dd, J = 8.0, 2.0 Hz, 1H), 9.14 (dd, J = 2.0, 0.8 Hz, 1H) (solvent: CDCl3 + CD3OD) | | |
| 141 | | δ in d17-DMSO: 1.41(3H, s), 1.75-1.70(1H, m), 2.03-1.99(1H, m), 2.62-2.56(1H, m), 2.94-2.89(1H, m), 3.89(3H, s), 6.88(1H, d, J = 8.8 Hz), 7.05(1H, d, J = 7.6 Hz), 7.24(1H, t, J = 8.0 Hz), 7.66-7.63(3H, m), 8.45-8.44(1H, m), 9.90(1H, s) | | |
| 148 | | | 362[M + 1] 286 | 200 208 212 218 262 |
| 149 | 143-145 | | | |
| 157 | | δ in d6-DMSO: 1.20(6H, d, J = 6.6 Hz), 1.41(3H, s), 1.65-1.77(1H, m), 1.96-2.07(1H, m), 2.55-2.63(1H, m), 2.85-2.95(1H, m), 4.04-4.16(1H, m), 5.79(2H, bs), 7.07(1H, d, J = 8.1 Hz), 7.25(1H, t, J = 8.1 Hz), 7.72-7.78(3H, m), 7.93(1H, s), 8.64(1H, s), 9.96(1H, s). | | |
| 159 | amorphous | | | 285 |
| 161 | 247-251 | | | |
| 163 | amorphous | | | |
| 164 | 91-96 | 1.68(s, 3H), 2.07-2.15(m, 1H), 3.13-3.20(m, 1H), 7.12(d, J = 7.6 Hz, 1H), 7.46(t, J = 7.6 Hz, 1H), 7.90-7.94(m, 2H), 8.83(br s, 1H), 8.96(br s, 1H), 9.31(br s, 1H), 10.36(s, 1H), 10.86(s, 1H) | | |
| 165 | 246-248 | | | |
| 166 | amorphous | | | 220, 275 |
| 176 | amorphous | | | 217, 278 |
| 178 | 224-225 | | | |
| 181 | | | | 261.5 |
| 189 | | | | 259 |
| 193 | 266-268 | | | |
| 196 | | | | 212 |
| 202 | 117-118 | 0.85(3H, t, J = 7.3 Hz), 1.02-1.19(1H, m), 1.34-1.54(1H, m), 1.72-1.89(3H, m), 2.04-2.15(1H, m), 2.61-2.82(2H, m), 3.80(3H, s), 4.32(2H, br), 6.85(2H, d, J = 8.9 Hz), 7.18(2H, d, J = 8.9 Hz) (solvent: CDCl3) | | |

TABLE 140

| No. | mp (° C.) | 1H-NMR(δ) | MS (m/z) | UV (λ max: nm) |
|---|---|---|---|---|
| 204 | 205-208 | 1.64 (d, J = 1.2 Hz, 3H), 1.95 (ddd, J = 14.0, 10.8, 3.6 Hz, 1H), 2.45 (ddd, J = 14.0, 6.4, 3.6 Hz, 1H), 2.75 (ddd, J = 12.4, 10.8, 3.6 Hz, 1H), 2.99 (ddd, J = 12.4, 6.4, 3.6 Hz, 1H), 7.09 (dd, J = 11.6, 8.8 Hz, 1H), 7.47 (dd, J = 7.2, 2.8 Hz, 1H), 8.03 (ddd, J = 8.8, 4.4, 2.8 Hz, 1H), 8.89 (s, 2H), 9.75 (s, 1H) (solvent: CDCl3) | | |
| 213 | oil | | | 216, 272 |
| 214 | | | | 212.2 292.3 356.5 |
| 216 | | | | 242.7 |
| 220 | 191-193 | | 363[M + 3] 361[M + 1] 287 285 | |
| 224 | oil | 1.58(3H, s), 1.87(1H, ddd, J = 13.9, 10.5, 3.7), 2.13(1H, ddd, J = 13.9, 6.3, 3.7), 2.25(3H, s), 2.68(1H, ddd, J = 12.1, 10.5, 6.2), 2.89(1H, ddd, J = 12.1, 6.3, 3.7), 5.23(2H, s), 7.28-7.48(4H, m), 7.60(1H, s), 7.75(1H, d, J = 8.0), 8.56(1H, dd, J = 5.0, 1.4), 8.70(1H, d, J = 1.4) (solvent: CDCl3) | | 222 |
| 227 | | | | 213 |

TABLE 140-continued

| No. | mp (° C.) | 1H-NMR(δ) | MS (m/z) | UV (λ max: nm) |
|---|---|---|---|---|
| 232 | | 1H-NMR (CDCl3) δ: 1.59 (3H, s), 1.83-1.90 (1H, m), 2.35-2.47 (4H, m), 2.60-2.67 (1H, m), 2.87-2.92 (1H, m), 4.70 (2H, br s), 6.87-6.98 (2H, m), 7.16 (1H, d, J = 6.6 Hz), 7.27 (2H, d, J = 7.8 Hz), 7.61 (2H, d, J = 8.1 Hz). | 378[M + 1] | |
| 233 | oil | | | 224, 272 |
| 235 | 196-200 | | | |
| 238 | | 1H-NMR (CDCl3) δ: 1.68 (3H, s), 1.97-2.00 (1H, m), 2.53 (1H, dt, J = 14.4, 3.7 Hz), 2.63-2.79 (2H, m), 4.52 (2H, s), 6.56-6.66 (3H, m), 7.17 (1H, t, J = 8.0 Hz), 7.43-7.52 (3H, m), 7.81 (4H, dd, J = 11.6, 5.7 Hz). | 362[M + 1] | |
| 241 | 187-190 | 1H-NMR (DMSO-d6) δ: 1.49 (3H, s), 1.78-1.86 (1H, m), 2.13-2.21 (1H, m), 2.59-2.67 (1H, m), 2.96-3.02 (1H, m), 7.11 (1H, t, J = 10.7 Hz), 7.29 (1H, t, J = 7.8 Hz), 7.45 (1H, t, J = 7.5 Hz), 7.66 (1H, d, J = 8.8 Hz), 7.74-7.78 (1H, m), 7.80-7.83 (1H, m), 8.21 (1H, d, J = 8.6 Hz), 10.25 (1H, s). | | |
| 243 | 182-184 | 1.46(s, 3H), 1.75-1.83(m, 1H), 2.08-2.16(m, 1H), 2.55-2.63(m, 1H), 2.92-2.98(m, 1H), 4.02(s, 3H), 7.11(d, J = 8.0 Hz, 1H), 7.31(t, J = 8.0 Hz, 1H), 7.77(d, J = 8.0 Hz, 1H), 7.82(br s, 1H), 8.41(d, J = 1.2 Hz, 1H), 8.90(d, J = 1.2 Hz, 1H), 10.38(s, 1H) (solvent: CDCl3) | | |

TABLE 141

| No. | mp (° C.) | 1H-NMR(δ) | MS (m/z) | UV (λ max: nm) |
|---|---|---|---|---|
| 244 | 222-224 | | | |
| 251 | | | 351[M + 1] 311 275 | 200 204 215 285 |
| 255 | 238-239 | | | |
| 256 | oil | | | 215, 257 |
| 259 | amorphous | 1.58(3H, s), 2.01(1H, ddd, J = 15.2, 12.2, 3.4), 2.46-2.56(2H, m), 3.07(1H, ddd, J = 13.3, 5.7, 3.5), 4.24(2H, s) 6.53(1H, d, J = 7.6), 6.59-6.61(2H, m), 7.09-7.12(1H, m), 7.11(2H, d, J = 7.6), 7.24(2H, d, J = 7.6), 8.82(2H, br) (solvent: DMSO-d6) | | 229 298 |
| 263 | | | 383[M + 1] 287 | 200 284 |
| 267 | 114-115 | | | |
| 268 | | | | 214.5 298.2 |
| 271 | oil | | | 229, 276 |
| 275 | | (CDCl3) 1.66(3H, d, J = 1.2 Hz), 1.98(1H, ddd, J = 14.0, 10.4, 3.7 Hz), 2.47(1H, ddd, J = 14.0, 6.7, 3.5 Hz), 2.79(1H, ddd, J = 12.0, 10.4, 3.5 Hz), 3.02(1H, ddd, J = 12.0, 6.7, 3.7 Hz), 4.45(2H, br), 6.16(2H, br), 7.04-7.11(2H, m), 7.38(1H, dd, J = 7.2, 2.9 Hz), 7.88(1H, d, J = 2.0 Hz), 7.96(1H, ddd, J = 8.9, 4.2, 2.9 Hz), 9.88(1H, s) | | |
| 277 | | | | 216 228 281 |
| 279 | | | | 214.5 292.3 |
| 281 | amorphous | 1.55(3H, s), 1.83(1H, ddd, J = 13.9, 10.6, 3.9), 2.10(1H, ddd, J = 13.9, 6.5, 3.6), 2.67(1H, ddd, J = 12.2, 10.6, 3.6), 2.87(1H, ddd, J = 12.2, 6.5, 3.9), 4.49(2H, d, J = 5.6), 4.85(1H, br), 6.38(1H, dt, J = 8.5, 0.9), 6.59(1H, ddd, J = 7.2, 5.2, 0.9), 7.21-7.24(2H, m), 7.28-7.32(2H, m), 7.40(1H, ddd, J = 8.5, 7.2, 1.8), 8.11(1H, ddd, J = 5.2, 1.8, 0.8) (solvent: CDCl3) | | 233 301 |
| 282 | 146-147 | | | |
| 284 | 181.5 | | | |

TABLE 141-continued

| No. | mp (° C.) | 1H-NMR(δ) | MS (m/z) | UV (λ max: nm) |
|---|---|---|---|---|
| 293 | | 1.57 (s, 3H), 1.78-1.89 (m, 1H), 2.10-2.19 (m, 1H), 2.69 (ddd, J = 11.9, 10.8, 3.5 Hz, 1H), 2.83-2.91 (m, 1H), 7.15-7.35 (m, 5H) (solvent: CDCl3) | | |
| 299 | | | | 293.5 |

TABLE 142

| No. | mp (° C.) | 1H-NMR(δ) | MS (m/z) | UV (λ max: nm) |
|---|---|---|---|---|
| 301 | | (CDCl3) 1.53(3H, s), 1.80(1H, ddd, J = 14.0, 10.4, 3.6 Hz), 2.12(1H, ddd, J = 14.0, 6.0, 3.6 Hz), 2.75(1H, ddd, J = 12.0, 10.4, 3.6 Hz), 2.85(1H, ddd, J = 12.0, 6.0, 3.6 Hz), 3.64(2H, s), 4.32(2H, br), 6.55(1H, ddd, J = 8.0, 2.0, 0.8 Hz), 6.66(1H, t, J = 2.0 Hz), 6.70(1H, ddd, J = 8.0, 2.0, 0.8 Hz), 7.11(1H, t, J = 8.0 Hz) | | |
| 302 | 122-126 | 1.41(s, 3H), 1.67-1.76(m, 1H), 1.98-2.06(m, 1H), 2.55-2.63(m, 1H), 2.86-2.94(m, 1H), 3.19(s, 6H), 5.75(s, 2H), 7.08(d, J = 8.0 Hz, 1H), 7.26(t, J = 8.0 Hz, 1H), 7.73(d, J = 8.0 Hz, 1H), 7.76(br s, 1H), 8.16(s, 1H), 8.73(s, 1H), 10.00(s, 1H) (solvent: CDCl3) | | |
| 306 | | | | 231, 258, 289 |
| 307 | | 1.83 (ddd, J = 13.9, 10.3, 3.6 Hz, 1H), 2.13 (ddd, J = 13.6, 6.2, 3.5 Hz, 1H), 2.53 (s, 3H), 2.66-2.75 (m, 1H), 2.90 (ddd, J = 12.2, 6.3, 3.8 Hz, 1H), 7.09 (d, J = 7.8 Hz, 1H), 7.32 (t, J = 8.0 Hz, 1H), 7.37 (s, 1H), 7.63 (d, J = 7.8 Hz, 1H), 8.79 (s, 1H) (solvent: CDCl3) | | |
| 308 | 167-188 | | | |
| 309 | 241-244 | | | |
| 319 | | | | 308.9 |
| 329 | 238-239 | | | |
| 330 | | | | 213.4 263.9 |
| 332 | | | | 212.2 |
| 333 | 154-158 | | | |
| 339 | 217-218 | | | |
| 341 | amorphous | | | 216 249 |
| 342 | 184-187 | | | |
| 344 | | (DMSO) 1.49(3H, s), 1.73-1.85(1H, m), 2.15-2.28(1H, m), 2.54-2.66(1H, m), 2.92-3.04(1H, m), 5.86(2H, s), 7.03-7.25(3H, m), 7.40-7.48(2H, m), 7.64-7.78(3H, m), 10.31(1H, s), 11.74(1H, s) | | |
| 353 | | | | 279.3 364.5 |
| 354 | 102-103 | | | |
| 356 | amorphous | 1.73 (s, 3H), 2.09-2.17 (m, 1H), 2.40(s, 3H), 2.65-2.73 (m, 2H), 3.15-3.23 (m, 1H), 3.81(s, 3H), 7.07 (d, J = 7.2 Hz, 2H), 7.29 (br s, 1H), 7.36 (d, J = 8.0 Hz, 2H), 7.61 (d, J = 8.0 Hz, 2H), 7.78 (br s, 1H), 7.90 (d, J = 7.2 Hz, 2H), 8.00 (br s, 1H), 10.32 (s, 1H) (solvent: DMSO-d6) | 267 | |
| 357 | amorphous | | | 224, 298 |

TABLE 143

| No. | mp (° C.) | 1H-NMR(δ) | MS (m/z) | UV (λ max: nm) |
|---|---|---|---|---|
| 358 | | 1.57 (3H, s), 1.80-1.91 (1H, m), 2.15-2.18 (1H, m), 2.70-2.94 (2H, m), 3.94 (3H, s), 4.67 (2H, s), 6.75 (1H, s), 7.05-7.08 (1H, m), 7.31 (1H, t, J = 7.91 Hz), 7.53 (1H, t, J = 1.98 Hz), 7.64-7.67 (1H, m), 8.64 (1H, s). (solvent: CDCl3) | 360[M + 1] | |
| 359 | 212-214 | 1.46(s, 3H), 1.73-1.83(m, 1H), 2.13-2.20(m, 1H), 2.54-2.61(m, 1H), 2.62(s, 3H), 2.93-3.00(m, 1H), 5.84(br s, 2H), 7.12(dd, J = 12.0, 8.8 Hz, 1H), 7.73-7.78(m, 1H), 7.81(dd, J = 7.2, 2.4 Hz, 1H), 8.68 (s, 1H), 9.13(s, 1H), 10.59(s, 1H)(solvent: CDCl3) | | |
| 360 | amorphous | | | 222 |

TABLE 143-continued

| No. | mp (° C.) | 1H-NMR(δ) | MS (m/z) | UV (λ max: nm) |
|---|---|---|---|---|
| 361 | | | | 280.4 |
| 364 | oil | | 344[M + 1] | 227, 271 |
| 367 | | (CDCl3) 1.78(3H, s), 2.07(1H, ddd, J = 14.0, 12.4, 3.6 Hz), 2.61(1H, br d, J = 14.0 Hz), 2.84(1H, td, J = 12.4, 3.2 Hz), 2.94(1H, td, J = 12.4, 3.6 Hz), 4.08(3H, s), 7.07(1H, ddd, J = 8.0, 2.0, 0.8 Hz), 7.40(1H, t, J = 8.0 Hz), 7.63(1H, ddd, J = 8.0, 2.0, 0.8 Hz), 7.74(1H, t, J = 2.0 Hz), 8.18(1H, d, J = 1.2 Hz), 9.02(1H, d, J = 1.2 Hz), 9.56(1H, s) | | |
| 375 | | | | 217 |
| 380 | 181-182 | 0.86 (t, J = 7.2 Hz, 3H), 1.82-1.98 (m, 3H), 2.24 (br, 1H), 2.74 (td, J = 12.0, 3.6 Hz, 1H), 2.84 (dt, J = 12.0, 4.0 Hz, 1H), 7.08 (ddd, J = 8.0, 2.0, 0.8 Hz, 1H), 7.37 (t, J = 8.0 Hz, 1H), 7.58 (t, J = 2.0 Hz, 2H), 7.76 (ddd, J = 8.0, 2.0, 0.8 Hz, 1H), 7.88 (dd, J = 8.4, 2.4 Hz, 1H), 8.25 (dd, J = 8.4, 0.8 Hz, 1H), 8.57 (dd, J = 2.4, 0.8 Hz, 1H), 9.84 (s, 1H) (solvent: CDCl3) | | |
| 383 | oil | | | 225, 269, 288 |
| 389 | amorphous | | | 292 |
| 393 | | | | 213.4 316.0 |
| 395 | amorphous | | | 217, 269 |
| 396 | 211-213 | 1.64 (s, 3H), 1.96 (ddd, J = 14.0, 10.4, 4.0 Hz, 1H), 2.44 (ddd, J = 14.0, 6.8, 3.6 Hz, 1H), 2.75 (ddd, J = 12.4, 10.4, 3.6 Hz, 1H),, 2.99 (ddd, J = 12.4, 6.8, 4.0 Hz, 1H), 4.50 (2H, br), 7.08 (dd, J = 11.6, 8.8 Hz, 1H), 7.45 (dd, J = 6.8, 2.8 Hz, 1H), 8.01 (ddd, J = 8.8, 4.4, 2.8 Hz, 1H), 8.16 (ddd, J = 8.0, 2.0, 0.8 Hz, 1H), 8.43 (d, J = 8.0 Hz, 1H), 8.89 (dd, J = 2.0, 0.8 Hz, 1H), 9.91 (s, 1H) (solvent: CDCl3) | | |
| 401 | 106-107 | | | |

TABLE 144

| No. | mp (° C.) | 1H-NMR(δ) | MS (m/z) | UV (λ max: nm) |
|---|---|---|---|---|
| 405 | 192-194 | 1.41(s, 3H), 1.68-1.77(m, 1H), 1.96-2.05(m, 1H), 2.55-2.63(m, 1H), 2.88-2.95(m, 1H), 4.15(s, 3H), 5.74(s, 2H), 7.13(d, J = 8.0 Hz, 1H), 7.29(t, J = 8.0 Hz, 1H), 7.44(d, J = 8.8 Hz, 1H), 7.75(d, J = 8.0 Hz, 1H), 7.86(br s, 1H), 8.20(d, J = 8.8 Hz, 1H), 10.73(s, 1H) (solvent: CDCl3) | | |
| 406 | | | | 276.9 |
| 408 | 221-224 | 1.74(3H, s), 2.28(2H, m), 2.67(2H, m), 2.91(3H, s), 3.82(3H, s), 6.90(2H, d, J = 9.0), 7.19(2H, d, J = 9.0) (solvent: CDCl3) | | |
| 409 | oil | | | 215 |
| 410 | 178-182 | 1.37(d, J = 6.0 Hz, 6H), 1.42(s, 3H), 1.70-1.78(m, 1H), 2.00-2.08(m, 1H), 2.53-2.61(m, 1H), 2.88-2.95(m, 1H), 5.36(quintet, J = 6.0 Hz, 1H), 7.11(d, J = 8.0 Hz, 1H), 7.29(t, J = 8.0 Hz, 1H), 7.75(d, J = 8.0 Hz, 1H), 7.80(br s, 1H), 8.32(d, J = 1.2 Hz, 1H), 8.87(d, J = 1.2 Hz, 1H), 10.32(s, 1H) (solvent: CDCl3) | | |
| 411 | | | | 218, 264 |
| 413 | 251-254 | | | |
| 415 | amorphous | | | 226, 290 |
| 417 | 137-139 | | | |
| 422 | | (CDCl3) 1.45(3H, s), 1.70-1.84(1H, m), 1.96-2.04(1H, m), 2.88-2.96(1H, m), 3.04-3.14(1H, m), 6.86(1H, d, J = 15.9 Hz), 6.42(1H, d, J = 15.9 Hz), 7.22-7.41(5H, m) | | |
| 426 | | | | 211.0 312.4 |
| 427 | | | | 216 |
| 429 | oil | | | 211 259 |
| 430 | | (DMSO) 1.07(3H, s), 1.53-1.66(4H, m), 2.50-2.70(2H, m), 2.92-3.10(2H, m), 5.48(1H, s), 7.11-7.21(3H, m), 7.23-7.29(2H, m) | | |

TABLE 144-continued

| No. | mp (° C.) | 1H-NMR(δ) | MS (m/z) | UV (λ max: nm) |
|---|---|---|---|---|
| 432 | oil | | | 216, 272 |
| 436 | 254-256 | | | |
| 441 | 181-165 | | | |
| 443 | | ¹H-NMR (CDCl₃) δ: 1.55 (4H, s), 1.74-1.80 (1H, m), 2.13-2.17 (1H, m), 2.68-2.73 (2H, m), 4.33 (1H, br s), 4.48 (2H, d, J = 4.0 Hz), 4.76 (2H, t, J = 20.1 Hz), 6.52 (1H, dd, J = 7.9, 1.8 Hz), 6.63-6.65 (2H, m), 7.13 (1H, t, J = 7.8 Hz), 7.45-7.51 (2H, m), 7.79-7.82 (4H, m). | 362[M + 1] | |

TABLE 145

| No. | mp (° C.) | 1H-NMR(δ) | MS (m/z) | UV (λ max: nm) |
|---|---|---|---|---|
| 444 | 214-215 | 1.41(s, 3H), 1.66-1.76(m, 1H), 1.97-2.05(m, 1H), 2.53-2.62(m, 1H), 2.62(s, 3H), 2.86-2.93(m, 1H), 5.79(br s, 2H), 7.12(d, J = 8.0 Hz, 1H), 7.28(t, J = 8.0 Hz, 1H), 7.74(d, J = 8.0 Hz, 1H), 7.81(br s, 1H), 8.68(s, 1H), 9.14(s, 1H), 10.52(s, 1H) (solvent: CDCl3) | | |
| 445 | 92-93 | | | |
| | | 1.57(3H, s), 1.86(1H, ddd, J = 13.9, 10.4, 3.7), 2.13(1H, ddd, J = 13.9, 6.5, 3.6), 2.25(3H, s), | 219 | 252 |
| 446 | oil | 2.35(3H, s), 2.70(1H, ddd, J = 12.2, 10.4, 3.6), 2.89(1H, ddd, J = 12.2, 6.5, 3.7), 4.35(2H, br), 5.19(2H, s), 7.17(2H, d, J = 8.0), 7.31-7.34(4H, m), 7.50(1H, ddd, J = 5.8, 3.0, 1.8), 7.55-7.60(1H, m) (solvent: CDCl3) | | |
| 448 | | δ in d6-DMSO: 1.41(3H, s), 1.67-1.75(1H, m), 1.98-2.05(1H, m), 2.52-2.61(1H, m), 2.86-2.94(1H, m), 5.79(2H, bs), 7.14(1H, d, J = 7.8 Hz), 7.30(1H, t, J = 7.8 Hz), 7.73(1H, bd, J = 7.8 Hz), 7.81(1H, t, J = 1.8 Hz), 8.94(1H, m), 9.11(1H, m), 10.63(1H, bs). | | |
| 452 | 132-134 | | | |
| 456 | 147-149 | | | |
| 457 | 153-155 | | | |
| 465 | 194.6 | | | |
| 466 | | | | 211 |
| 470 | 281 (dec.) | | | |
| 482 | | 1.60 (s, 3H), 1.91 (ddd, J = 14.0, 10.8, 4.0 Hz, 1H), 2.23 (ddd, J = 14.0, 6.4, 3.6 Hz, 1H), 2.77 (ddd, J = 12.0, 10.8, 3.6 Hz, 1H), 2.93 (ddd, J = 12.0, 6.4, 4.0 Hz, 1H), 7.16 (ddd, J = 8.0, 2.0, 0.8 Hz, 1H), 7.37 (t, J = 8.0 Hz, 1H), 7.61 (t, J = 2.0 Hz, 1H), 7.75 (ddd, J = 8.0, 2.0, 0.8 Hz, 1H), 8.14 (d, J = 1.6 Hz, 1H), 8.80 (d, J = 1.6 Hz, 1H), 9.79 (s, 1H) (solvent: CDCl3) | | |
| 483 | 224-227 | | | 211, 289 |
| 490 | | 1.64 (3H, s) 2.03-2.12 (1H, m) 2.49-2.62 (m) 3.12-3.16 (1H m) 7.22 (1H, dd, J = 4.2 Hz) 7.27 (1H, bs) 7.75 (1H bs) 7.87 (1H, dd, J = 4.2 Hz) 8.04 (1H, s) 8.12 (1H, dd, J = 4.2 Hz) 10.64 (1H, s) 10.72 (1H, s) (solvent: DMSO-d6) | | |
| 491 | | 1.58 (s, 3H), 1.85-1.96 (m, 1H), 2.15-2.24 (m, 1H), 2.50 (s, 3H), 2.67 (s, 3H), 2.71-2.81 (m, 1H), 2.90-2.98 (m, 1H), 7.13 (d, J = 6.2 Hz, 1H), 7.35 (t, J = 8.0 Hz, 1H), 7.40 (s, 1H), 7.55 (d, J = 7.6 Hz, 1H) (solvent: CDCl3) | | |
| 493 | | | | 216 |

TABLE 146

| No. | mp (° C.) | 1H-NMR(δ) | MS (m/z) | UV (λ max: nm) |
|---|---|---|---|---|
| 494 | | δ in d6-DMSO: 1.37(3H, s), 1.62-1.70(1H, m), 2.0-2.12(1H, m), 2.40-2.50(1H, m), 2.79-2.83(1H, m), 3.82(3H, s), 4.52(2H, d, J = 5.4 Hz), 6.19(1H, m), 6.54(1H, d, J = 7.8 Hz), 6.62(1H, d, J = 8.1 Hz), 6.75(1H, s), 7.01(1H, t, J = 8.1 Hz), 7.14-7.25(2H, m), 7.51(1H, d, J = 8.1 Hz), 7.60(1H, d, J = 7.5 Hz). | 366[M + 1] | |
| 496 | 152-154 | | | |
| 497 | | δ in d6-DMSO: 1.48(3H, s), 1.83-1.77(1H, m), 2.61-2.56(1H, m), 2.99-2.95(1H, m), 3.86(3H, s), 6.07(1H, s), 6.95(1H, s), 7.03-7.02(1H, m), 7.09-7.06(1H, m), 7.58-7.57(1H, m), 7.64-7.62(1H, m), 9.83(1H, s) | | |
| 498 | 122-125 | | | |
| 500 | 181-184 | | | |
| 501 | 155-156 | | | |
| 502 | 137-138 | | | |
| 504 | 209-219 | | | |
| 511 | 211-214 | 1.58 (s, 3H), 1.90 (ddd, J = 14.0, 10.0, 3.6 Hz, 1H), 2.15 (ddd, J = 14.0, 6.8, 3.6 Hz, 1H), 2.77 (ddd, J = 12.4, 10.0, 3.6 Hz, 1H), 2.94 (ddd, J = 12.4, 6.8, 3.6 Hz, 1H), 4.34 (2H, br), 7.17 (ddd, J = 8.0, 2.0, 0.8 Hz, 1H), 7.38 (t, J = 8.0 Hz, 1H), 7.50 (d, J = 2.0 Hz, 1H), 7.56 (td, J = 2.0 Hz, 1H), 7.70 (ddd, J = 8.0, 2.0, 0.8 Hz, 1H), 8.08 (d, J = 1.6 Hz), 9.70 (s, 1H) (solvent: CDCl3) | | |
| 515 | 204-206 | 1.61 (s, 3H), 1.90 (ddd, J = 14.0, 10.8, 3.6 Hz, 1H), 2.22 (ddd, J = 14.0, 6.0, 3.6 Hz, 1H), 2.77 (ddd, J = 12.4, 10.8, 3.6 Hz, 1H), 2.93 (ddd, J = 12.4, 60, 3.6 Hz, 1H), 7.15 (ddd, J = 8.0, 2.0, 0.8 Hz, 1H), 7.39 (t, J = 8.0 Hz, 1H), 7.65 (t, J = 2.0 Hz, 1H), 7.80 (ddd, J = 8.0, 2.0, 0.8 Hz, 1H), 8.89 (s, 2H), 9.77 (s, 1H) (solvent: CDCl3) | | |
| 516 | | | | 292.3 |
| 525 | 105-106 | | | |
| 528 | 173-174 | 1.60 (s, 3H), 1.89 (ddd, J = 14.0, 10.8, 3.6 Hz, 1H), 2.22 (ddd, J = 14.0, 6.4, 3.2 Hz, 1H), 2.44 (s, 3H), 2.77 (ddd, J = 12.4, 10.8, 3.2 Hz, 1H), 2.91 (ddd, J = 12.4, 6.4, 3.6 Hz, 1H), 4.50 (br, 2H), 7.11 (ddd, J = 8.0, 2.0, 0.8 Hz, 1H), 7.35 (t, J = 8.0 Hz, 1H), 7.67-7.71 (m, 2H), 7.74 (ddd, J = 8.0, 2.0, 0.8 Hz, 1H), 8.18 (d, J = 8.4 Hz, 1H), 8.44 (d, J = 1.6 Hz, 1H), 9.98 (s, 1H) (solvent: CDCl3) | | |
| 532 | | | | 305.3 |
| 533 | 180-181 | | | |
| 534 | 201-204 | | | |
| 549 | 100-101 | | | |
| 551 | 139-141 | | | |
| 554 | | | | 216 |

TABLE 147

| No. | mp (° C.) | 1H-NMR(δ) | MS (m/z) | UV (λ max: nm) |
|---|---|---|---|---|
| 556 | | (CDCl3) 1.67(3H, d, J = 1.2 Hz), 1.98(1H, ddd, J = 14.0, 10.4, 3.7 Hz), 2.47(1H, ddd, J = 14.0, 6.7, 3.5 Hz), 2.79(1H, ddd, J = 12.0, 10.4, 3.5 Hz), 3.02(1H, ddd, J = 12.0, 6.7, 3.7 Hz), 4.11(3H, s), 4.45(2H, br), 7.10(1H, dd, J = 11.7, 8.8 Hz), 7.41(1H, dd, J = 6.9, 2.8 Hz), 8.04(1H, ddd, J = 8.8, 4.0, 2.8 Hz), 8.20(1H, d, J = 1.4 Hz), 9.06(1H, d, J = 1.4 Hz), 9.51(1H, s) | | |
| 558 | | | 358[M + 1] 282 | 200 |
| 559 | | | | 224 |
| 560 | | δ in d10-DMSO: 1.72(3H, s), 2.12-2.05(1H, m), 2.71-2.61(2H, m), 3.22-3.19(1H, m), 6.52(1H, s), 7.26(1H, q, J = 11.6, 9.2 Hz), 7.55(1H, s), 7.66-7.62(2H, m), 7.79-7.77(1H, m), 7.90-7.88(1H, m), 8.07(1H, s), 10.42(1H, s), 11.55(1H, s) | | |
| 561 | 235-240 | | | |
| 567 | oil | | | 212 |
| 570 | 186-187 | | | |
| 573 | 112-114 | | | |

TABLE 147-continued

| No. | mp (° C.) | 1H-NMR(δ) | MS (m/z) | UV (λ max: nm) |
|---|---|---|---|---|
| 577 | | δ in d19-DMSO: 2.14-2.07(1H, m), 2.88-2.70(3H, m), 3.07, 3.26(2H, abq, J = 12.0 Hz), 3.73(3H, s), 5.40(2H, s), 6.51(1H, s), 6.85(1H, d, J = 12.0 Hz), 7.34(1H, d, J = 8.0 Hz) | | |
| 584 | 152-153 | | | |
| 586 | | δ in d7-DMSO: 1.71(3H, s), 2.10-2.04(1H, m), 2.69-2.59(2H, m), 3.20-3.17(1H, m), 4.00(3H, s), 7.13(1H, d, J = 7.4 Hz), 7.33-7.23(3H, m), 7.55(1H, d, J = 8.4 Hz), 7.72-7.68(1H, m), 7.92-7.90(1H, m), 10.60(1H, s) | | |
| 588 | 155-156 | | | |
| 593 | oil | | | 226 |
| 595 | oil | 1.56(3H, s), 1.86(1H, ddd, J = 13.9, 10.1, 3.7), 2.11(1H, ddd, J = 13.9, 6.6, 3.6), 2.32(3H, s), 2.70(1H, ddd, J = 12.3, 10.1, 3.6), 2.90(1H, ddd, J = 12.3, 6.6, 3.7), 5.25(2H, s), 7.29-7.35(4H, m), 7.47(1H, dt, J = 6.8, 2.0), 7.56-7.58(1H, m), 8.59(2H, d, J = 6.0) (solvent: CDCl3) | | 220 |
| 596 | | | | 215 |
| 597 | 192-194 | | | |
| 600 | 178-180 | | | |
| 601 | 181-192 | 1.59 (3H, s), 1.85-1.95 (1H, m), 2.15-2.22 (1H, m), 2.72-2.78 (1H, m), 2.88-2.96 (1H, m), 4.31 (3H, s), 7.13 (1H, d, J = 7.25 Hz), 7.33 (1H, t, J = 7.91 Hz), 7.59 (1H, s), 7.68 (1H, d, J = 7.91 Hz), 7.75 (1H, s), (solvent: CDCl3) | 375[M + 1] | |
| 602 | 272-285 (dec.) | | | |

TABLE 148

| No. | mp (° C.) | 1H-NMR(δ) | MS (m/z) | UV (λ max: nm) |
|---|---|---|---|---|
| 605 | 230-233 | 1.63 (s, 3H), 1.94 (ddd, J = 14.0, 10.4, 3.6 Hz, 1H), 2.44 (ddd, J = 14.0, 6.4, 3.6 Hz, 1H), 2.75 (ddd, J = 12.4, 10.4, 3.6 Hz, 1H),, 2.98 (ddd, J = 12.4, 6.4, 3.6 Hz, 1H), 4.50 (2H, br), 7.06 (dd, J = 11.6, 8.8 Hz, 1H), 7.40 (dd, J = 7.2, 2.8 Hz, 1H), 7.59 (ddd, J = 8.8, 8.0, 2.8 Hz, 1H), 7.99 (ddd, J = 8.8, 4.4, 2.8 Hz, 1H), 8.33 (dd, J = 8.8, 4.4 Hz, 1H), 8.45 (d, J = 2.8 Hz, 1H), 9.78 (s, 1H) (solvent: CDCl3) | | |
| 608 | | | | 213.4 304.1 |
| 611 | 200-202 | | | |
| 613 | | | | 238 |
| 618 | | 1.74(s, 3H), 1.97-2.07(m, 1H), 2.45-2.55(m, 1H), 2.77-2.85(m, 1H), 2.84(s, 3H), 2.90-2.96(m, 1H), 7.11(d, J = 8.0 Hz, 1H), 7.42(t, J = 8.0 Hz, 1H), 7.57(d, J = 8.8 Hz, 1H), 7.70(d, J = 8.0 Hz, 1H), 7.74(br s, 1H), 8.29(d, J = 8.8 Hz, 1H), 10.12(s, 1H) (solvent: CDCl3) | | |
| 620 | | | | 212, 253 |
| 625 | 107-109 | | | |
| 629 | | δ in d14-DMSO: 1.66(3H, s), 2.11-2.05(1H, m), 2.37(3H, s), 2.63-2.53(2H, m), 3.14-3.11(1H, m), 7.08-7.04(2H, t, J = 7.0 Hz), 7.43-7.35(4H, m), 7.83-7.80(2H, m), 10.39(1H, s), 11.69(1H, s) | | |
| 630 | | 1.28 (3H, t, J = 7.7 Hz), 1.96 (1H, ddd, J = 3.8, 9.9, 13.7 Hz), 2.19 (1H, ddd, J = 3.5, 7.0, 13.7 Hz), 2.74 (1H, ddd, J = 3.6, 9.9, 12.2 Hz), 2.93 (1H, ddd, J = 3.8, 7.0, 12.1 Hz), 4.05-4.49 (4H, m), 7.40-7.50 (3H, m), 7.77-7.86 (1H, m) (solvent: CDCl3) | 301[M + 1] | |
| 634 | | (CDCl3) 1.67(3H, d, J = 1.2 Hz), 1.98(1H, ddd, J = 14.0, 10.4, 3.7 Hz), 2.47(1H, ddd, J = 14.0, 6.7, 3.5 Hz), 2.79(1H, ddd, J = 12.0, 10.4, 3.5 Hz), 3.02(1H, ddd, J = 12.0, 6.7, 3.7 Hz), 4.11(3H, s), 4.45(2H, br), 7.10(1H, dd, J = 11.7, 8.8 Hz), 7.41(1H, dd, J = 6.9, 2.8 Hz), 8.04(1H, ddd, J = 8.8, 4.0, 2.8 Hz), 8.20(1H, d, J = 1.4 Hz), 9.06(1H, d, J = 1.4 Hz), 9.51(1H, s) | | |
| 636 | 118-119 | | | |
| 637 | | | | 229, 275 |
| 643 | 155-157 | 1.60 (s, 3H), 1.90 (ddd, J = 14.0, 10.4, 3.6 Hz, 1H), 2.20 (ddd, J = 14.0, 6.8, 3.6 Hz, 1H), 2.77 (ddd, J = | | |

TABLE 148-continued

| No. | mp (° C.) | 1H-NMR(δ) | MS (m/z) | UV (λ max: nm) |
|---|---|---|---|---|
| | | 12.0, 10.4, 3.6 Hz, 1H),, 2.93 (ddd, J = 12.0, 6.8, 3.6 Hz, 1H), 4.59 (brs, 1H), 7.16 (ddd, J = 8.0, 2.0, 0.8 Hz, 1H), 7.37 (t, J = 8.0 Hz, 1H), 7.67 (t, J = 2.0 Hz, 1H), 7.71 (ddd, J = 8.0, 2.0, 0.8 Hz, 1H), 7.87 (dd, J = 10.0, 1.2 Hz, 1H), 8.73 (d, J = 1.2 Hz, 1H), 9.74 (s, 1H) (solvent: CDCl3) | | |
| 644 | 201-203 | | | |

TABLE 149

| No. | mp (° C.) | 1H-NMR(δ) | MS (m/z) | UV (λ max: nm) |
|---|---|---|---|---|
| 645 | oil | 1.58(3H, s), 1.87(1H, ddd, J = 14.0, 10.4, 3.6), 2.16(1H, ddd, J = 14.0, 6.3, 3.5), 2.34(3H, s), 2.70(1H, ddd, J = 12.3, 10.4, 3.5), 2.90(1H, ddd, J = 12.3, 6.3, 3.6), 5.38(2H, s), 7.18-7.33(3H, m), 7.43(1H, d, J = 8.0), 7.49-7.60(2H, m), 7.69(1H, dt, J = 7.7, 1.9), 8.59(1H, ddd, J = 4.9, 1.9, 1.1) (solvent: CDCl3) | | 222 |
| 649 | 161-162 | | | |
| 651 | 193-196 | 1.59 (s, 3H), 1.90 (ddd, J = 14.0, 10.4, 3.6 Hz, 1H), 2.18 (ddd, J = 14.0, 6.4, 3.6 Hz, 1H), 2.76 (ddd, J = 12.4, 10.4, 3.6 Hz, 1H),, 2.93 (ddd, J = 12.4, 6.4, 3.6 Hz, 1H), 4.42 (br, 2 H), 7.17 (ddd, J = 8.0, 2.0, 0.8 Hz, 1H), 7.38 (t, J = 8.0 Hz, 1H), 7.64 (t, J = 2.0 Hz, 1H), 7.77 (ddd, J = 8.0, 2.0, 0.8 Hz, 1H), 8.20 (dd, J = 8.0, 2.0 Hz, 1H), 8.44 (dd, J = 8.0, 0.8 Hz, 1H), 8.91 (dd, J = 2.0, 0.8 Hz, 1H), 9.87 (s, 1H) (solvent: CDCl3) | | |
| 652 | | δ in d21-DMSO: 1.67(3H, s), 2.14-2.07(1H, m), 2.62-2.57(2H, m), 3.17-3.14(1H, m), 5.74(1H, s), 7.14(1H, d, J = 8.0 Hz), 7.44(1H, t, J = 8.0 Hz), 7.85-7.81(2H, m), 8.01(1H, d, J = 12.0 Hz), 8.16(1H, d, J = 8.0 Hz), 8.77(1H, s), 10.95(1H, s) | | |
| 653 | 193-194 | | | |
| 654 | oil | | | 257 |
| 657 | 199-203 | | | |
| 660 | amorphous | | | 223, 266 |
| 661 | | δ in d9-DMSO: 1.30(3H, t, J = 7.0 Hz), 1.69(3H, s), 2.10-2.04(1H, m), 2.20(3H, s), 2.67-2.62(2H, m), 3.20-3.17(1H, m), 4.40(2H, q, J = 14.0, 7.0 Hz), 6.83(1H, s), 7.25(1H, q, J = 12.0, 9.0 Hz), 7.62-7.61(1H, m), 7.85-7.83(1H, m), 10.42(1H, s) | | |
| 664 | amorphous | | | 225, 267 |
| 667 | amorphous | | | 226 |
| 673 | oil | | | 224 |
| 677 | amorphous | | | 216 |
| 680 | 159-160 | 1.63(3H, s), 1.65-1.80(1H, m), 2.53-2.64(1H, m), 2.75-2.88(2H, m), 3.83(3H, s), 4.32(2H, br), 6.87-6.96(2H, m), 7.19-7.33(2H, m) (solvent: CDCl3) | | |
| 681 | | δ in d6-DMSO: 1.43(3H, s), 1.66-1.74(1H, m), 2.02-2.07(1H, m), 2.56-2.63(1H, m), 2.85-2.90(1H, m), 5.80(2H, bs), 6.91 (1H, d, J = 7.8 Hz), 6.96-6.98(2H, m), 7.25(1H, t, J = 7.8 Hz), 7.2-7.36(2H, m), 7.40(1H, m), 7.89-7.92(1H, m), 9.42(1H, bs), 10.78(1H, bs). | 338[M + 1] | |
| 683 | 166-168 | | | |

TABLE 150

| No. | mp (° C.) | 1H-NMR(δ) | MS (m/z) | UV (λ max: nm) |
|---|---|---|---|---|
| 687 | 164-167 | 1.60 (3H, s), 1.84-1.95 (1H, m), 2.21-2.26 (1H, m), 2.73-2.94 (2H, m), 3.92 (3H, s), 4.25 (3H, s), 7.10 (1H, d, J = 7.58 Hz), 7.34 (1H, t, J = 7.91 Hz), 7.40 (1H, s), 7.57 (1H, br s), 7.66 (1H, d, J = 7.91 Hz), 8.67 (1H, s), (solvent: CDCl3) | 388[M + 1] | |
| 692 | | (CDCl3) 1.50(3H, s), 1.75-1.88(1H, m), 2.00-2.10(1H, m), 2.91-2.99(1H, m), 3.08-3.18(1H, m), 6.21(1H, d, J = 15.9 Hz), 6.59(1H, d, J = 15.9 Hz), 7.42- | | |

TABLE 150-continued

| No. | mp (° C.) | 1H-NMR(δ) | MS (m/z) | UV (λ max: nm) |
|---|---|---|---|---|
| 698 | | 7.47(3H, m), 7.59(1H, dd, J = 8.6, 2.0 Hz), 7.74-7.83(4H, m) | | 269 |
| 700 | 177-178 | | | |
| 701 | | 1.61(s, 3H), 1.90(m, 1H), 2.25(m, 1H), 2.81(m, 1H), 2.92(m, 1H), 3.86(s, 3H), 6.71(t-like, J = 1.8 Hz, 1H), 7.12(t-like, J = 1.8 Hz, 1H), 7.53(t-like, J = 1.8 Hz, 1H), 7.89(dd, J = 8.3 Hz, 2.4 Hz, 1H), 8.24(d, J = 8.3 Hz, 1H), 8.58(d, J = 2.4 Hz, 1H), 9.85(br, 1H) (solvent: CDCl3) | | |
| 702 | | 1H-NMR(CDCl3) δ: 1.65 (3H, s), 1.91-1.98 (1H, m), 2.57-2.62 (1H, m), 2.68-2.75 (1H, m), 2.92-2.97 (1H, m), 4.18 (3H, s), 6.82 (1H, br s), 7.02-7.08 (1H, m), 7.28-7.32 (1H, m), 7.44 (1H, s), 7.92-7.96 (1H, m). | | |
| 707 | 167-174 | | | |
| 709 | 99-100 | 0.82(3H, t, J = 7.3 Hz), 1.72-1.90(3H, m). 2.06-2.15(1H, m), 2.61-2.82(2H, m), 3.80(3H, s), 4.36(2H, br), 6.86(2H, d, J = 8.9 Hz), 7.17(2H, d, J = 8.9 Hz) (solvent: CDCl3) | | |
| 717 | 157-162 | 1.58 (s, 3H), 1.90 (ddd, J = 14.0, 10.4, 3.6 Hz, 1H), 2.15 (ddd, J = 14.0, 6.8, 3.6 Hz, 1H), 2.76 (ddd, J = 12.4, 10.4, 3.6 Hz, 1H), 2.94 (ddd, J = 12.4, 6.8, 3.6 Hz, 1H), 3.49 (1H, S), 3.76 (2H, br), 7.17 (ddd, J = 8.0, 2.0, 0.8 Hz, 1H), 7.36 (t, J = 8.0 Hz, 1H), 7.38 (d, J = 1.6 Hz, 1H), 7.50 (t, J = 2.0 Hz, 1H), 7.73 (ddd, J = 8.0, 2.0, 0.8 Hz, 1H), 8.22 (d, J = 2.4 Hz), 9.26 (d, J = 2.4 Hz, 1H), 10.12 (s, 1H) (solvent: CDCl3) | | |
| 719 | oil | | | 226 254 |
| 720 | 133-138 | | | |
| 725 | amorphous | 1.62 (s, 3H), 1.96-2.03(m, 1H), 2.38-2.49 (m, 1H), 2.63-2.71 (m, 1H), 3.05-3.12 (m, 1H), 6.73 (dd, J = 3.2, 1.6 Hz, 2H), 7.35(d, J = 3.2 Hz, 1H), 7.37 (br s, 1H), 7.57 (d, J = 8.4 Hz, 2H), 7.67 (d, J = 8.4 Hz, 2H), 7.77 (br s, 1H), 7.96(br s, 1H), 8.01(br s, 1H), 10.35 (s, 1H) (solvent: DMSO-d6) | | 265 |
| 728 | 179-182 | | | |
| 729 | 187-169 | | | |

TABLE 151

| No. | mp (° C.) | 1H-NMR(δ) | MS (m/z) | UV (λ max: nm) |
|---|---|---|---|---|
| 730 | | | | 211.0 289.9 |
| 731 | 91-94 | | | |
| 732 | amorphous | | | 211 |
| 735 | 166-168 | | | |
| 737 | | 1H-NMR (CDCl3) δ: 1.59 (3H, s), 1.87-1.94 (1H, m), 2.47-2.53 (1H, m), 2.67-2.73 (1H, m), 2.93-2.99 (1H, m), 4.10 (3H, s), 6.62 (1H, s), 7.04 (1H, t, J = 10.2 Hz), 7.33 (1H, d, J = 4.3 Hz), 7.85 (1H, br s). | | |
| 738 | 181-183 | | | |
| 739 | | | | 285 |
| 740 | 250 (dec.) | | | |
| 743 | 148-150 | 1.60 (s, 3H), 179-2.93 (m, 4H), 4.46 (2H, br), 7.09 (d, J = 2.0 Hz, 1H), 7.12 (ddd, J = 7.6, 2.0, 0.8 Hz, 1H), 7.18 (t, J = 2.0 Hz, 1H), 7.36 (d, J = 7.6, 2.0, 0.8 Hz, 1H), 7.43 (t, J = 7.6 Hz, 1H), 8.21 (d, J = 2.0 Hz) (solvent: CDCl3) | | |
| 744 | | δ in d8-DMSO: 1.47(3H, s), 1.82-1.78(1H, m), 2.22-2.18(1H, m), 2.62-2.56(1H, m), 3.00-2.96(1H, m), 6.79(1H, s), 6.63(1H, s), 7.08-7.03(1H, m), 7.51(1H, s), 7.64-7.57(2H, m), 9.57(1H, s), 11.25(1H, s) | | |
| 753 | amorphous | | | 225, 299 |
| 756 | 110-111 | 1.55(3H, s), 1.76-1.87(1H, m), 2.08-2.17(1H, m), 2.35(3H, s), 2.65-2.76(1H, m), 2.82-2.92(1H, m), 4.35(2H, br), 7.01-7.25(4H, m) (solvent: CDCl3) | | |
| 758 | 156-157 | | | |

TABLE 151-continued

| No. | mp (° C.) | 1H-NMR(δ) | MS (m/z) | UV (λ max: nm) |
|---|---|---|---|---|
| 766 | | | 336[M + 1] 260 | 203 212 |
| 767 | 98-100 | | | |
| 768 | | 1.60 (3H, d, J = 1.3 Hz), 1.89-1.99 (1H, m), 2.29 (3H, s), 2.37-2.42 (1H, m), 2.70-2.75 (1H, m), 2.96-3.00 (1H, m), 4.12 (3H, s), 6.39 (1H, s), 7.04 (1H, dd, J = 11.5, 8.9 Hz), 7.18 (1H, dd, J = 6.9, 2.6 Hz), 7.60 (1H, s), 7.82-7.86 (1H, m), (solvent: CDCl3) | 362[M + 1] | 213 263 |
| 771 | | | 417[M + 1] 341 | 201 |
| 774 | | ¹H-NMR (CDCl₃) δ: 1.77 (3H, s), 2.11-2.21 (1H, m), 2.71-2.80 (1H, m), 2.87-2.99 (2H, m), 6.91 (1H, d, J = 6.9 Hz), 7.28 (2H, s), 7.47 (1H, t, J = 8.1 Hz), 7.75 (1H, t, J = 8.6 Hz), 8.04 (1H, dd, J = 8.6, 2.3 Hz), 8.29 (1H, d, J = 8.2 Hz), 8.46 (1H, d, J = 2.2 Hz). | 400[M + 1] | |

TABLE 151

| No. | mp (° C.) | 1H-NMR(δ) | MS (m/z) | UV (λ max: nm) |
|---|---|---|---|---|
| 781 | | 1.63 (s, 3H), 1.92 (ddd, J = 14.0, 10.8, 4.0 Hz, 1H), 2.29 (m, 1H), 2.78 (ddd, J = 12.4, 10.8, 3.6 Hz, 1H),, 2.91 (ddd, J = 12.4, 6.4, 4.0 Hz, 1H), 3.94 (3H, s), 7.09 (ddd, J = 8.0, 2.0, 0.8 Hz, 1H), 7.34 (dd, J = 8.8, 2.8 Hz, 1H), 7.35 (t, J = 8.0 Hz, 1H), 7.68 (t, J = 2.0 Hz, 1H), 7.71 (ddd, J = 8.0, 2.0, 0.8 Hz, 1H), 8.24 (d, J = 8.8 Hz, 1H), 8.28 (d, J = 2.8 Hz, 1H), 9.86 (s, 1H) (solvent: CDCl3) | | |
| 783 | 205-206 | | | |
| 786 | | 1.66(3H, s), 2.10(1H, m), 2.57-2.64(2H, m), 3.16(1H, m), 6.74(1H, s), 7.30(1H, s), 7.36(1H, s), 7.74(1H, s), 7.98(1H, s), 8.06(1H, s), 10.33(1H, s), 10.47(1H, s) (solvent: DMSO-d6) | | |
| 790 | amorphous | | | 223, 290 |
| 791 | | δ in d18-DMSO: 1.41(3H, s), 1.76-1.69(1H, m), 2.02-1.98(1H, m), 2.62-2.55(1H, m), 2.92-2.89(1H, m), 7.13(1H, d, J = 7.6 Hz), 7.29(1H, t, J = 7.6 Hz), 7.62-7.59(2H, m), 8.71(1H, s), 9.28(1H, s), 10.46(1H, brs) | | |
| 792 | | | | 299.4 |
| 793 | 269 (dec.) | | | |
| 797 | | | | 213.4 312.4 |
| 799 | | | | 215, 240 |
| 800 | | | | 225, 275 |
| 802 | | 1.63 (s, 3H), 1.92 (ddd, J = 14.0, 11.2, 3.6 Hz, 1H), 2.28 (br, 1H), 2.78 (ddd, J = 12.4, 11.2, 3.6 Hz, 1H), 2.81 (3H, s), 2.92 (ddd, J = 12.4, 6.4, 4.0 Hz, 1H), 7.10 (ddd, J = 8.0, 2.0, 0.8 Hz, 1H), 7.35 (t, J = 8.0 Hz, 1H), 7.56 (t, J = 2.0 Hz, 1H), 7.65 (d, J = 2.4 Hz, 1H), 7.74 (ddd, J = 8.0, 2.0, 0.8 Hz, 1H), 8.41 (d, J = 2.4 Hz, 1H), 10.03 (s, 1H) (solvent: CDCl3) | | |
| 803 | | | | 271 |
| 804 | 135-136 | | | |
| 810 | 47-48 | | | |
| 811 | 138-139 | | | |
| 813 | 204-205 | 182 (s, 3H), 1.89-1.94 (m, 1H), 2.78 (ddd, J = 12.4, 6.4, 3.6 Hz, 1H), 4.50 (2H, br), 7.06 (dd, J = 11.6, 8.8 Hz, 1H), 7.40 (dd, J = 7.2, 2.8 Hz, 1H), 7.59 (ddd, J = 8.8, 8.0, 2.8 Hz, 1H), 7.99 (ddd, J = 8.8, 4.4, 2.8 Hz, 1H), 8.33 (dd, J = 8.8, 4.4 Hz, 1H), 8.45 (d, J = 2.8 Hz, 1H), 9.78 (s, 1H)(solvent: CDCl3) | | |
| 814 | oil | | | 218, 272 |
| 816 | | | | 214.5 |

TABLE 152

| No. | mp (° C.) | 1H-NMR(δ) | MS (m/z) | UV (λ max: nm) |
|---|---|---|---|---|
| 820 | | (CDCl3) 1.66(3H, d, J = 1.2 Hz), 1.98(1H, ddd, J = 14.0, 10.4, 3.7 Hz), 2.47(1H, ddd, J = 14.0, 6.7, 3.5 Hz), | | |

TABLE 152-continued

| No. | mp (° C.) | 1H-NMR(δ) | MS (m/z) | UV (λ max: nm) |
|---|---|---|---|---|
|  |  | 2.79(1H, ddd, J = 12.0, 10.4, 3.5 Hz), 3.02(1H, ddd, J = 12.0, 6.7, 3.7 Hz), 4.45(2H, br), 6.16(2H, br), 7.04-7.11(2H, m), 7.38(1H, dd, J = 7.2, 2.9 Hz), 7.88(1H, d, J = 2.0 Hz), 7.96(1H, ddd, J = 8.9, 4.2, 2.9 Hz), 9.88(1H, s) |  |  |
| 822 |  |  |  | 279 |
| 827 | 134-137 |  |  | 214.5 |
|  |  |  |  | 284.0 |
| 832 |  |  |  | 212, 299 |
| 833 | oil |  |  | 212, 273 |
| 834 |  |  |  | 217, 287 |
| 835 | 139-140 |  |  |  |
| 836 |  |  |  | 221.6 |
|  |  |  |  | 279.3 |
| 840 | 223-225 |  |  |  |
| 848 | oil |  |  | 223, 254 |
| 849 | 143-145 |  |  |  |
| 850 |  | δ in d16-DMSO: 1.41(3H, s), 1.75-1.70(1H, m), 2.02-1.99(1H, m), 2.61-2.56(1H, m), 2.93-2.88(1H, m), 7.13(1H, d, J = 8.0), 7.29(1H, t, J = 7.8 Hz), 7.35(1H, q, J = 8.4, 2.4 Hz), 7.66-7.63(2H, m), 8.52-8.47(1H, m), 8.81 (1H, s), 10.44(1H, s) |  |  |
| 851 | 82-83 | 1.55(3H, s), 1.76-1.88(1H, m), 2.10-2.18(1H, m), 2.66-2.77(1H, m), 2.82-2.91(1H, m), 3.81(3H, s), 6.73-6.78(1H, m), 6.88-6.92(2H, m), 7.21-7.29(1H, m) (solvent: CDCl3) |  |  |
| 855 | oil |  |  | 219 |
| 859 |  |  | 350[M + 1] | 200 |
|  |  |  | 274 | 208 |
|  |  |  |  | 254 |
| 863 | 192-194 | 1.39(t, J = 7.2 Hz, 3H), 1.42(s, 3H), 1.71-1.79(m, 1H), 2.02-2.10(m, 1H), 2.55-2.62(m, 1H), 2.88-2.96(m, 1H), 4.47(q, J = 7.2 Hz, 2H), 5.70-6.20(br s, 2H), 7.11(d, J = 8.0 Hz, 1H), 7.29(t, J = 8.0 Hz, 1H), 7.75(d, J = 8.0 Hz, 1H), 7.80(br s, 1H), 8.38(d, J = 1.2 Hz, 1H), 8.87(d, J = 1.2 Hz, 1H), 10.34(s, 1H) (solvent: CDCl3) |  |  |
| 866 |  |  |  | 293.5 |
| 869 |  | 1.65 (s, 3H), 1.90-2.01 (m, 3H), 2.32 (br, 1H), 2.80 (td, J = 12.0, 3.6 Hz, 1H), 2.85 (t, J = 8.0 Hz, 2H), 2.92 (ddd, J = 12.0, 5.6, 3.6, 1H), 3.75 (t, J = 8.0 Hz, 2H), 7.11 (ddd, J = 8.0, 2.0, 0.8 Hz, 1H), 7.37 (t, J = 8.0 Hz, 1H), 7.70 (t, J = 2.0 Hz, 1H), 7.73-7.76 (m, 2H), 8.22 (d, J = 7.6 Hz, 1H), 8.48 (d, J = 2.0 Hz, 1H), 10.00 (s, 1H) (solvent: CDCl3) |  |  |
| 871 | 212-213 |  |  |  |

TABLE 153

| No. | mp (° C.) | 1H-NMR(δ) | MS (m/z) | UV (λ max: nm) |
|---|---|---|---|---|
| 875 | oil |  |  | 222, 271 |
| 876 | oil |  |  | 222 |
| 878 | oil |  |  | 211 |
| 881 | 141-144 |  |  |  |
| 887 |  |  |  | 262.7 |
| 892 | 251 (dec.) |  |  |  |
| 893 |  | δ in d12-DMSO: 1.70(3H, s), 2.10-2.04(1H, m), 2.69-2.59(2H, m), 3.20-3.17(1H, m), 6.80(1H, brs), 7.26-7.20(1H, m), 7.88-7.81(3H, m), 10.35(1H, s)13.53(1H, brs) |  |  |
| 895 |  |  | 378[M + 1] | 202 |
|  |  |  | 302 | 208 |
|  |  |  |  | 216 |
|  |  |  |  | 221 |
|  |  |  |  | 265 |
| 896 | amorphous |  |  | 219, 264 |
| 897 | 212-214 |  |  |  |
| 900 | 205-207 | 1.61 (s, 3H), 1.91 (ddd, J = 14.0, 10.8, 4.0 Hz, 1H), 2.23 (ddd, J = 14.0, 6.4, 3.6 Hz, 1H), 2.77 (ddd, J = 12.4, 10.8, 3.6 Hz, 1H), 2.92 (ddd, J = 12.4, 6.4, 4.0 Hz, 1H), 7.15 (ddd, J = 8.0, 2.0, 0.8 Hz, 1H), 7.38 (t, J = 8.0 Hz, 1H), 7.65 (t, J = 2.0 Hz, 1H), 7.79 (ddd, |  |  |

TABLE 153-continued

| No. | mp (° C.) | 1H-NMR(δ) | MS (m/z) | UV (λ max: nm) |
|---|---|---|---|---|
| | | J = 8.0, 2.0, 0.8 Hz, 1H), 8.99 (s, 2H), 9.78 (s, 1H) (solvent: CDCl3) | | |
| 906 | | | | 212.2 |
| | | | | 273.4 |
| | | | | 350.5 |
| 908 | | δ in d15-DMSO: 1.66(3H, s), 2.11-2.05(1H, m), 2.37(3H, s), 2.63-2.54(2H, m), 3.16-3.11(1H, m), 3.16(3H, s), 7.08-6.96(3H, m), 7.49-7.41(3H, m), 7.85-7.81(2H, m), 10.52(1H, s)11.69(1H, s) | | |
| 910 | oil | | | 211, 276 |
| 916 | 131-132 | | | |
| 926 | | 1.89(3H, s), 2.15(1H, m), 2.71-2.82(2H, m), 2.96(1H, m), 3.04(3H, d, J = 4.9), 7.35(1H, dd, J = 8.7, 1.8), 7.50-7.55(2H, m), 7.74(1H, s), 7.82-7.90(3H, s), 10.40(1H, br), 11.36(1H, Br) (solvent: CDCl$_3$) | | |
| 928 | | 1.20(t, J = 7.6 Hz, 3H), 1.53(br s, 3H), 1.82-1.97(m, 1H), 2.39(s, 3H), 2.61(q, J = 7.6 Hz, 2H), 2.99-3.07(m, 1H), 6.93(br s, 1H), 7.33(d, J = 8.4 Hz, 2H), 7.54-7.58(m, 2H), 7.87(d, J = 8.4 Hz, 2H), 10.13(s, 1H) (solvent: CDCl3) | | |
| 930 | 132.1-134.4 | | 328[M + 1] | |
| 931 | | | | 299 |
| 933 | amorphous | | | 212, 259 |

TABLE 154

| No. | mp (° C.) | 1H-NMR(δ) | MS (m/z) | UV (λ max: nm) |
|---|---|---|---|---|
| 935 | 161-165 | 1.62 (s, 3H), 1.91 (ddd, J = 14.0, 10.4, 4.0 Hz, 1H), 2.24 (ddd, J = 14.0, 6.4, 3.6 Hz, 1H), 2.80 (ddd, J = 12.0, 10.4, 3.6 Hz, 1H), 2.93 (ddd, J = 12.0, 6.4, 4.0 Hz, 1H), 7.15 (ddd, J = 8.0, 2.0, 1.2 Hz, 1H), 7.39 (t, J = 8.0 Hz, 1H), 7.66 (ddd, J = 8.4, 7.2, 1.2 Hz, 1H), 7.75 (t, J = 2.0 Hz, 1H), 7.80-7.84 (m, 2H), 7.93 (ddd, J = 8.0, 2.0, 1.2 Hz), 8.21 (d, J = 8.4 Hz, 1H), 8.38 (d, J = 8.0 Hz, 1H), 8.41 (d, J = 8.0 Hz, 1H), 10.25 (s, 1H) (solvent: CDCl3) | | |
| 936 | 169-170 | | | |
| 939 | | δ in d6-DMSO: 1.72(3H, s), 2.11-2.05(1H, m), 2.70-2.60(2H, m), 3.21-3.18(1H, m), 7.20(1H, d, J = 9.2 Hz), 7.28(1H, q, J = 11.6, 9.2 Hz), 8.56-7.54(2H, m), 7.69(1H, s), 7.90-7.85(2H, m), 10.69(1H, s), 12.17(1H, brs) | | |
| 941 | | | | 220 |
| 944 | amorphous | | | 219, 256 |
| 946 | | 1.61 (s, 3H), 1.91 (ddd, J = 14.0, 10.8, 3.6 Hz, 1H), 2.26 (ddd, J = 14.0, 6.4, 3.6 Hz, 1H), 2.77 (ddd, J = 12.4, 10.8, 3.6 Hz, 1H),, 2.92 (ddd, J = 12.4, 6.4, 3.6 Hz, 1H), 7.13 (ddd, J = 8.0, 2.0, 1.2 Hz, 1H), 7.36 (t, J = 8.0 Hz, 1H), 7.61 (t, J = 2.0 Hz, 1H), 7.72 (ddd, J = 8.0, 2.0, 1.2 Hz, 1H), 7.91 (d, J = 2.4 Hz, 1H), 8.49 (d, J = 2.4 Hz, 1H), 9.75 (s, 1H)(solvent: CDCl3) | | |
| 947 | | | | 215.7 |
| | | | | 276.9 |
| 960 | | | | 261.5 |
| 964 | 185-187 | | | |
| 966 | oil | | | 216 |
| 968 | 107-109 | | | |
| 970 | | 1.57 (s, 3H), 1.78-1.89 (m, 1H), 2.10-2.19 (m, 1H), 2.69 (ddd, J = 11.9, 10.8, 3.5 Hz, 1H), 2.83-2.91 (m, 1H), 7.15-7.35 (m, 5H) (solvent: CDCl3) | | |
| 971 | | (DMSO) 1.49(3H, s), 1.73-1.86(1H, m), 2.16-2.30(1H, m), 2.54-2.65(1H, m), 2.92-3.03(1H, m), 5.86(2H, s), 7.04-7.18(2H, m), 7.38-7.50(3H, m), 7.66-7.78(2H, m), 10.35(1H, s), 11.84(1H, s) | | |
| 972 | | 1.51 (3H, s) 1.91-1.95 (1H, m) 2.37 (3H, s) 3.00-3.05 (1H, m) 7.24 (1H, s) 7.33 (2H, d J = 9.0 Hz) 7.66 (1H, s) 7.85 (2H, d J = 9.0 Hz) 8.03 (1H, s) 10.37 (1H, s) (solvent: DMSO-d6) | | |
| 974 | amorphous | | | 219 |
| 978 | oil | | | 222 |

TABLE 154-continued

| No. | mp (° C.) | 1H-NMR(δ) | MS (m/z) | UV (λ max: nm) |
|---|---|---|---|---|
| 984 | | | | 255.7 |
| | | | | 318.4 |
| 990 | 126-129 | | | |
| 994 | 130-131 | | | |

TABLE 155

| No. | mp (° C.) | 1H-NMR(δ) | MS (m/z) | UV (λ max: nm) |
|---|---|---|---|---|
| 998 | amorphous | | | 229, 290 |
| 1005 | 191-193 | | | |
| 1006 | 88-90 | 2.42-2.47(2H, m), 2.80-2.86(2H, m), 7.78(6H, s), 6.83(4H, d, J = 8.9 Hz), 7.22(4H, d, J = 8.9 Hz) (solvent: CDCl3) | | |
| 1008 | 125-126 | | | |
| 1010 | 90-91 | | | |
| 1014 | 206-210 | | | |
| 1020 | | | | 216.9 |
| | | | | 245.1 |
| 1028 | 105-106 | | | |
| 1034 | | | | 212.2 |
| | | | | 286.4 |
| 1035 | 247-251 (dec.) | | | |
| 1037 | amorphous | | | 224, 272 |
| 1039 | amorphous | | | 217 |
| | | | | 249 |
| 1043 | 277-281 | | | |
| 1044 | | (DMSO) 1.12(3H, s), 1.60(2H, d, J = 6.2 Hz), 1.73(2H, d, J = 8.6 Hz), 2.65-2.90(2H, m), 2.93-3.13(2H, m), 5.55(1H, s), 7.34-7.52(3H, m), 7.68(1H, s), 7.79-7.90(3H, m) | | |
| 1052 | | 1.75(s, 3H), 2.12-2.21(m, 1H), 2.40(s, 3H), 2.65-2.73(m, 2H), 3.17-3.23(m, 1H), 7.37(d, J = 8.4 Hz, 2H), 7.40-7.44(m, 1H), 7.77(br s, 1H), 7.92-7.99(m, 5H), 8.47(br s, 1H), 8.70(d, J = 4.8 Hz, 1H), 10.37(s, 1H), 10.41(s, 1H) (solvent: CDCl3) | | |
| 1055 | 169-170 | 1.56(3H, s), 1.78-1.89(1H, m), 2.04-2.15(1H, m), 2.68-2.79(1H, m), 2.86-2.95(1H, m), 4.32(2H, br), 6.94-7.02(4H, m), 7.05-7.12(1H, m), 7.25-7.37(4H, m)(solvent: CDCl3) | | |
| 1056 | | | | 219 |
| 1059 | 262-287 | | | |
| 1061 | | | | 216 |
| 1062 | 136-137 | 1.53(3H, s), 1.76-1.88(1H, m), 2.03-2.13(1H, m), 2.63-2.73(1H, m), 2.85-2.94(1H, m), 4.35(2H, br), 7.23-7.32(4H, m) (solvent: CDCl3) | | |
| 1064 | 84-85 | 1.52(3H, s), 1.73-1.89(1H, m), 1.97-2.07(1H, m), 2.64-2.81(1H, m), 2.82-2.91(1H, m),2.87(3H, s), 3.77(3H, s), 4.10(1H, brs), 6.84(2H, d, J = 8.9 Hz), 7.28(2H, d, J = 8.6 Hz) (solvent: CDCl3) | | |
| 1067 | 162-165 | | | |
| 1068 | 132-134 | | | 230 |
| 1069 | 194-196 | | | |
| 1074 | | | 324[M + 1] | 200 |
| | | | 248 | 207 |
| 1076 | amorphous | | | 217 |

TABLE 156

| No. | mp (° C.) | 1H-NMR(δ) | MS (m/z) | UV (λ max: nm) |
|---|---|---|---|---|
| 1084 | 146-149 | | | |
| 1087 | | | | 311.2 |
| 1088 | amorphous | 1.55(3H, s), 1.83(1H, ddd, J = 13.9, 10.5, 3.7), 2.09(1H, ddd, J = 13.9, 6.6, 3.6), 2.67(1H, ddd, J = 12.3, 10.5, 3.6), 2.88(1H, ddd, J = 12.3, 6.6, 3.7), 4.48(2H, d, J = 6.0), 4.91(1H, br), 6.33(1H, dd, J = 8.8, 0.8), 7.19(1H, d, J = 7.3, 7.23-7.30(2H, m), | | 229 318 |

TABLE 156-continued

| No. | mp (° C.) | 1H-NMR(δ) | MS (m/z) | UV (λ max: nm) |
|---|---|---|---|---|
|  |  | 7.35(1H, dd, J = 8.8, 2.8), 8.05(1H, dd, J = 2.8, 0.8) (solvent: CDCl3) |  |  |
| 1094 |  |  |  | 216, 322 |
| 1100 | 278 (dec.) |  |  |  |
| 1107 | oil | 1.58(3H, s), 1.90(1H, ddd, J = 13.9, 10.1, 3.7), 2.14(1H, ddd, J = 13.9, 6.8, 3.6), 2.69(1H, ddd, J = 12.2, 10.1, 3.6), 2.94(1H, ddd, J = 12.2, 6.8, 3.7), 3.81(3H, s), 4.62(2H, s), 6.90(2H, d, J = 8.8), 7.30(2H, d, J = 8.8), 7.43(1H, t, J = 7.4), 7.57(1H, ddd, J = 7,4, 1.6, 1.2), 7.81 (1H, ddd, J = 7.6, 1.6, 1.2), 7.95(1H, t, J = 1.6) (solvent : CDCl3) |  | 226 284 |
| 1109 | 134-140 |  |  |  |
| 1110 | 109-110 |  |  |  |
| 1111 | 118-119 |  |  |  |
| 1114 | 121-124 |  |  |  |
| 1115 | 187-170 | 1.63 (s, 3H), 1.93 (ddd, J = 14.0, 10.4, 4.0 Hz, 1H), 2.24 (ddd, J = 14.0, 6.4, 3.6 Hz, 1H), 2.81 (ddd, J = 12.4, 10.4, 3.6 Hz, 1H), 2.96 (ddd, J = 12.4, 6.4, 4.0 Hz, 1H), 4.49 (br, 2 H), 7.19 (ddd, J = 8.0, 2.0, 0.8 Hz, 1H), 7.42 (t, J = 8.0 Hz, 1H), 7.74 (t, J = 2.0 Hz, 1H), 7.84 (ddd, J = 8.0, 2.0, 0.8 Hz, 1H), 7.88-7.95 (m, 2H), 8.22-8.26 (m, 2H), 9.80 (s, 1H), 9.89 (s, 1H) (solvent: CDCl3) |  |  |
| 1116 | oil |  |  | 220, 255, 307 |
| 1119 | 153-157 |  |  |  |
| 1120 | 213-214 |  |  |  |
| 1124 | 169-172 |  |  | 225 |
| 1125 | 195-198 |  |  | 222 256 289 |
| 1131 | 189-191 |  |  |  |
| 1132 | 175-180 (dec) |  |  |  |
| 1133 | amorphous |  |  | 219, 292 |
| 1135 | 255-260 (dec.) |  |  |  |
| 1139 | 140-141 |  |  |  |
| 1140 | oil |  |  | 218 |
| 1142 | 182-186 (dec.) |  |  |  |

TABLE 157

| No. | mp (° C.) | 1H-NMR(δ) | MS (m/z) | UV (λ max: nm) |
|---|---|---|---|---|
| 1147 |  |  |  | 214.5 275.7 |
| 1150 |  |  |  | 221.6 279.3 |
| 1153 | 156-159 |  |  |  |
| 1160 |  | 1.64 (3H, s) 2.02-2.12 (1H, m) 2.54-2.63 (1H, m) 3.11-3.16 (1H, m) 7.28 (1H, s) 7.70 (1H, dd J = 8.1 Hz) 7.85 (1H, s) 8.04-8.17 (2H, m) 8.28 (1H s) 8.74 (1H d J = 5.1 Hz) 10.81 (1H, s) 10.96 (1H, s) (solvent: DMSO-d6) |  |  |
| 1161 | 192-193 |  |  |  |
| 1166 | 290-295 |  | 444[M + 3] 442[M + 1] 368 366 |  |
| 1172 |  | 1.55 (3H, s) 1.94-2.03 (1H, m) 2.18-2.27 (1H, m) 2.32 (3H, s) 3.03-3.07 (1H, m) 7.05 (1H, s) 7.09 (1H, s) 7.14 (1H, s) 7.37 (2H, d J = 9.0 Hz) 7.66 (2H, d, J = 9.0 Hz) 10.65 (1H, s) 10.70 (1H, s) (solvent: DMSO-d6) |  |  |
| 1181 | 194-195 | 1.60(3H, s), 1.81-1.93(1H, m), 2.13-2.22(1H, m), 2.70-2.81(1H, m), 2.86-2.96(1H, m), 4.36(2H, br), 7.29-7.46(5H, m), 7.53-7.61(4H, m) (solvent: CDCl3) |  |  |
| 1184 | 149-150 |  |  |  |
| 1185 |  |  |  | 225.1 280.4 |

TABLE 157-continued

| No. | mp (° C.) | 1H-NMR(δ) | MS (m/z) | UV (λ max: nm) |
|---|---|---|---|---|
| 1193 | 182-183 | | | |
| 1194 | | | 344[M + 1] | 209 |
| | | | 268 | 214 |
| | | | | 261 |
| 1197 | 250-255 (dec.) | | | |
| 1199 | 274-283 | | | |
| 1205 | oil | | | E 213, 273 |
| | | | | Z 219, 275 |
| 1207 | 106-108 | | | |
| 1211 | | 1.77 (s, 3H), 1.98-2.54 (m, 2H), 2.81 (s, 3H), 2.81-2.94 (m, 2H), 3.93 (s, 3H), 7.03 (ddd, J = 8.0, 2.0, 0.8 Hz, 1H), 7.08 (d, J = 2.4 Hz, 1H), 7.36 (t, J = 8.0 Hz, 1H), 7.63 (t, J = 2.0 Hz, 1H), 7.69 (ddd, J = 8.0, 2.0, 0.8 Hz, 1H), 8.14 (d, J = 2.4 Hz, 1H), 10.13 (s, 1H) (solvent: CDCl3) | | |
| 1213 | | | 406[M + 1] | 20 |
| | | | 330 | 209 |
| | | | | 213 |

TABLE 158

| No. | mp (° C.) | 1H-NMR(δ) | MS (m/z) | UV (λ max: nm) |
|---|---|---|---|---|
| 1215 | amorphous | 1.64 (s, 3H), 2.07 (ddd, J = 14.1, 11.5, 3.8 Hz, 1H), 2.17 (s, 3H), 2.39 (ddd, J = 14.1, 5.3, 3.5 Hz, 1H), 2.72 (ddd, J = 12.6, 11.5, 3.5 Hz, 1H), 2.80 (ddd, J = 12.6, 5.3, 3.8 Hz, 1H), 3.21 (t, J = 8.9 Hz, 2H), 4.58 (t, J = 8.9 Hz, 2H), 6.76 (d, J = 8.4 Hz, 1H), 6.97-7.02 (m, 1H), 7.08-7.11 (m, 1H) (solvent: CDCl3) | | |
| 1216 | | | | 305.3 |
| 1217 | 263-266 | | | |
| 1221 | amorphous | | | 220, 253 |
| 1223 | | | | 226.3 |
| | | | | 280.4 |
| 1224 | | δ in d11-DMSO: 1.46(3H, s), 1.83-1.77(1H, m), 2.18-2.15(1H, m), 2.61-2.56(1H, m), 2.99-2.95(1H, m), 7.08(1H, q, J = 12.0, 8.4 Hz), 7.72-7.66(2H, m), 7.79(2H, d, J = 9.2)9.67(1H, s) | | |
| 1228 | oil | | | 224 |
| 1230 | 232-234 | | | |
| 1240 | | | | 216.9 |
| | | | | 285.2 |
| 1241 | 194-195 | | | |
| 1242 | | δ in d21-DMSO: 1.41(3H, m), 1.75-1.68(1H, m), 2.04-1.99(1H, m), 2.61-2.56(1H, m), 2.89(4H, s), 5.75(2H, brs), 7.07(1H, d, J = 4.0 Hz), 7.25(1H, t, J = 8.0 Hz), 7.72(1H, d, J = 8.0 Hz), 7.75(1H, s), 7.83(1H, brs), 7.96(1H, s), 8.67(1H, s), 9.96(1H, s) | | |
| 1243 | amorphous | 1.58(3H, s), 2.00(1H, ddd, J = 14.3, 11.5, 3.1), 2.53(1H, m), 2.56(1H, m), 3.07(1H, dt, J = 12.5, 3.1), 4.26(2H, s), 6.47-6.56(3H, m), 7.07-7.15(1H, m), 7.12(2H, t, J = 8.8), 7.39(2H, dd, J = 8.8, 5.6), 8.76(2H, br) (solvent: DMSO-d6) | | 223 |
| | | | | 299 |
| 1244 | 268-288 | 1.68 (s, 3H), 2.11 (ddd, J = 15.2, 12.0, 4.0 Hz, 1H), 2.57-2.64 (m, 2H), 3.16 (dt, J = 12.0, 4.0 Hz, 1H), 7.13 (ddd, J = 8.0, 2.0, 0.8 Hz, 1H), 7.46 (t, J = 8.0 Hz, 1H), 7.89 (t, J = 2.0 Hz, 1H), 7.97 (ddd, J = 8.0, 2.0, 0.8 Hz, 1H), 8.35 (d, J = 8.0 Hz, 1H), 8.52 (dd, J = 8.0, 2.4 Hz, 1H), 9.12 (d, J = 2.4 Hz, 1H), 10.68 (s, 1H), 10.92 (s, 1H) (solvent: DMSO-d6) | | 219 |
| | | | | 288 |
| 1245 | oil | | | 286 |
| 1247 | | | | 211 |
| 1255 | | | | 242.7 |
| 1257 | amorphous | | | 211 |
| 1258 | | | 352[M + 1] | 228 |
| | | | | 276 |
| | | | | 301 |
| 1261 | 179-180 | | | |
| 1262 | 278-281 | | | |

TABLE 159

| No. | mp (° C.) | 1H-NMR(δ) | MS (m/z) | UV (λ max: nm) |
|---|---|---|---|---|
| 1263 | | 1H-NMR(δ in d6-DMSO): 1.41(3H, s), 1.65-1.77(1H, m), 1.95-2.07(1H, m), 2.54-2.63(1H, m), 2.84-2.94(1H, m), 3.39-3.46(2H, m), 3.53-3.61(2H, m), 4.83(1H, t, J = 5.4 Hz), 5.79(2H, bs), 7.07(1H, d, J = 7.5 Hz), 7.25(1H, t, J = 7.8 Hz), 7.73(1H, d, J = 7.8 Hz), 7.76(1H, m), 7.87-7.93(1H, m), 8.02(1H, d, J = 1.2 Hz), 8.63(1H, d, J = 1.2 Hz), 9.97(1H, s). | 387[M + 1] | |
| 1264 | | 1H-NMR(δ in d6-DMSO): 1.41(3H, s), 1.65-1.77(1H, m), 1.95-2.07(1H, m), 2.53-2.63(1H, m), 2.84-2.95(1H, m), 3.73(8H, s), 5.79(2H, bs), 7.09(1H, d, J = 7.8 Hz), 7.26(1H, t, J = 7.8 Hz), 7.72(1H, d, J = 7.8 Hz), 7.75-7.78(1H, m), 8.34(1H, d, J = 1.2 Hz), 8.76(1H, d, J = 1.2 Hz), 10.08(1H, bs). | 413[M + 1] | |
| 1265 | | 1H-NMR (DMSO-d6) δ: 1.42 (3H, s), 1.70-1.76 (1H, m), 2.02-2.05 (1H, m), 2.56-2.59 (1H, m), 2.87-2.93 (2H, m), 7.07 (1H, d, J = 7.6 Hz), 7.23-7.26 (3H, m), 7.72-7.74 (2H, m), 7.93 (1H, s), 8.60 (1H, s), 9.99 (1H, s). | | |
| 1266 | | 1H-NMR(δ in d6-DMSO): 1.43(3H, s), 1.70-1.81(1H, m), 1.97-2.10(1H, m), 2.55-2.64(1H, m), 2.89-2.95(1H, m), 5.84(2H, bs), 7.17(1H, d, J = 7.8 Hz), 7.33(1H, t, J = 7.8 Hz), 9.98(1H, d, J = 1.2 Hz), 10.01(1H, d, J = 1.2 Hz), 10.74(1H, bs). | 369[M + 1] | |
| 1267 | | 1H-NMR (CDCl3) δ: 1.82-1.91 (1H, m), 2.04 (3H, s), 2.22 (1H, ddd, J = 13.8, 5.2, 3.6 Hz), 2.67 (1H, dt, J = 16.7, 5.8 Hz), 2.80 (1H, dt, J = 12.4, 4.7 Hz), 6.95 (2H, d, J = 8.1 Hz), 7.06 (2H, td, J = 7.8, 1.2 Hz), 7.18 (1H, td, J = 7.6, 1.1 Hz), 7.27 (1H, d, J = 1.7 Hz), 7.32 (1H, d, J = 7.9 Hz), 7.42-7.44 (2H, m), 7.80 (1H, dd, J = 8.0, 1.9 Hz). | 338[M + 1] | |
| 1268 | | 1H-NMR (CDCl3) δ: 1.62 (3H, s), 1.89 (1H, t, J = 12.3 Hz), 2.27-2.30 (1H, m), 2.69-2.76 (1H, m), 2.85-2.88 (1H, m), 7.11 (1H, dd, J = 11.4, 7.7 Hz), 7.30-7.53 (2H, m), 7.63 (1H, s), 7.71 (1H, d, J = 6.9 Hz). | 327[M + 1] | |
| 1269 | | 1H-NMR (DMSO-d6) δ: 1.40 (3H, s), 1.70-1.73 (1H, m), 1.99-2.02 (1H, m), 2.57-2.60 (1H, m), 2.88-2.90 (1H, m), 3.29 (3H, s), 3.52 (4H, s), 5.75 (2H, br s), 7.07 (1H, d, J = 7.6 Hz), 7.25 (1H, t, J = 7.7 Hz), 7.72 (1H, d, J = 8.3 Hz), 7.75 (1H, s), 7.92 (1H, br s), 8.03 (1H, s), 8.64 (1H, s), 9.96 (1H, s). | | |
| 1271 | | 1H-NMR(δ in d6-DMSO): 1.41(3H, s), 1.65-1.75(1H, m), 1.99-2.06(5H, m), 2.52-2.61(1H, m), 2.85-2.93(1H, m), 3.55(4H, t, J = 6.6 Hz), 5.79(2H, bs), 7.05(1H, d, J = 7.8 Hz), 7.25(1H, t, J = 7.8 Hz), 7.70-7.75(1H, m), 7.73-7.77(1H, m), 7.97(1H, d, J = 1.2 Hz), 8.72(1H, d, J = 1.2 Hz), 10.00(1H, s). | 397[M + 1] | |

TABLE 160

| No. | mp (° C.) | 1H-NMR(δ) | MS (m/z) | UV (λ max: nm) |
|---|---|---|---|---|
| 1272 | | (CDCl3) 1.61(3H, s), 1.85-1.96(1H, m), 2.17-2.27(1H, m), 2.69-2.79(1H, m), 2.87-2.97(1H, m), 7.17 (1H, d, J = 8.1 Hz), 7.38 (1H, t, J = 8.1 Hz), 7.48-7.74(5H, m), 8.40(2H, d, J = 7.5 Hz) | | |
| 1273 | | 1H-NMR (CDCl3) δ: 1.58 (3H, s), 1.89 (1H, t, J = 11.2 Hz), 2.27 (1H, s), 2.75-2.82 (2H, m), 6.61 (1H, dd, J = 20.3, 8.4 Hz), 7.10 (1H, d, J = 7.2 Hz), 7.37 (1H, dd, J = 15.0, 8.8 Hz), 7.90 (1H, d, J = 7.6 Hz), 8.10 (1H, d, J = 3.2 Hz), 9.37 (1H, d, J = 4.9 Hz), 9.69 (1H, s). | 395[M + 1] | |
| 1274 | | 1H-NMR (CDCl3) δ: 1.61 (3H, s), 1.84-1.93 (1H, m), 2.30 (1H, t, J = 13.1 Hz), 2.77-2.86 (2H, m), 6.64 (1H, dd, J = 20.6, 8.6 Hz), 7.13 (1H, d, J = 7.9 Hz), 7.38-7.43 (1H, m), 7.93 (1H, d, J = 8.1 Hz), 8.13 (1H, s), 9.40 (1H, d, J = 4.9 Hz), 9.72 (1H, s). | 327[M + 1] | |
| 1275 | | 1H-NMR (DMSO-d6) δ: 1.40 (3H, s), 1.70-1.72 (1H, m), 2.01-2.04 (1H, m), 2.18 (6H, s), 2.44 (2H, t, J = 6.3 Hz), 2.56-2.59 (1H, m), 2.86-2.92 (1H, m), 7.06 (1H, d, J = 7.6 Hz), 7.25 (1H, t, J = 7.7 Hz), 7.71-7.73 (3H, m), 8.02 (1H, s), 8.64 (1H, s), 9.95 (1H, s). | | |

TABLE 160-continued

| No. | mp (° C.) | 1H-NMR(δ) | MS (m/z) | UV (λ max: nm) |
|---|---|---|---|---|
| 1276 | | 1H-NMR (DMSO-d6) δ: 1.70-1.73 (1H, m), 1.99-2.02 (1H, m), 2.57-2.60 (1H, m), 2.88-2.91 (1H, m), 3.04 (3H, s), 3.43 (3H, t, J = 6.3 Hz), 3.79-3.81 (2H, m), 5.75 (3H, br s), 7.08 (1H, d, J = 7.3 Hz), 7.26 (1H, t, J = 7.8 Hz), 7.72 (1H, d, J = 7.8 Hz), 7.76 (1H, s), 8.04 (1H, s), 8.09 (1H, br s), 8.70 (1H, s), 10.01 (1H, s). | | |
| 1279 | | 1H-NMR (CDCl3) δ: 1.73 (3H, s), 2.04 (1H, dt, J = 18.2, 6.5 Hz), 2.45 (1H, d, J = 13.6 Hz), 2.78 (2H, t, J = 11.8 Hz), 2.89 (2H, t, J = 11.5 Hz), 6.60 (1H, s), 6.99 (1H, d, J = 8.2 Hz), 7.34 (1H, t, J = 8.0 Hz), 7.48 (1H, s), 7.70 (1H, d, J = 8.2 Hz). | 328[M + 1] | |
| 1280 | | 1H-NMR(δ in d6-DMSO): 1.42(3H, s), 1.68-1.82(1H, m), 2.02-2.09(1H, m), 2.23(3H, s), 2.43(4H, t, J = 5.1 Hz), 2.53-2.61(1H, m), 2.87-2.95(1H, m), 3.73(4H, t, J = 5.1 Hz), 6.01 (2H, bs), 7.07(1H, d, J = 7.8 Hz), 7.26(1H, t, J = 7.8 Hz), 7.73(1H, d, J = 7.8 Hz), 7.73-7.78(1H, m), 8.33(1H, d, J = 1.2 Hz), 8.72(1H, d, J = 1.2 Hz), 10.06(1H, s). | 426[M + 1] | |
| 1281 | | 1H-NMR(δ in d6-DMSO): 1.40(3H, s), 1.30-1.50(2H, m), 1.69-1.76(1H, m), 1.82-1.88(2H, m), 2.01-2.07(1H, m), 2.52-2.61(1H, m), 2.86-2.94(1H, m), 3.76-3.83(1H, m), 4.10-4.18(2H, m), 4.82(1H, d, J = 4.2 Hz), 5.91(2H, bs), 7.07(1H, d, J = 7.8 Hz), 7.26(1H, t, J = 7.8 Hz), 7.70-7.77(2H, m), 8.33(1H, d, J = 1.2 Hz), 8.70(1H, d, J = 1.2 Hz), 10.02(1H, s). | 427[M + 1] | |

TABLE 161

| 化合物番号 | MS(m/z) |
|---|---|
| 2 | 336[M + 1] |
| 7 | 394[M + 1] |
| 10 | 431[M + 3] |
| | 429[M + 1] |
| 11 | 356[M + 1] |
| 12 | 354[M + 1] |
| 13 | 363[M + 3] |
| | 361[M + 1] |
| 14 | 394[M + 1] |
| 15 | 409[M + 1] |
| 16 | 425[M + 1] |
| 17 | 374[M + 1] |
| 19 | 362[M + 3] |
| | 360[M + 1] |
| 20 | 438[M + 1] |
| 21 | 380[M + 3] |
| | 378[M + 1] |
| 22 | 380[M + 3] |
| | 378[M + 1] |
| 25 | 354[M + 1] |
| 27 | 338[M + 1] |
| 28 | 356[M + 1] |
| 29 | 372[M + 1] |
| 31 | 378[M + 1] |
| 32 | 417[M + 1] |
| 34 | 358[M + 1] |
| 35 | 398[M + 3] |
| | 396[M + 1] |
| 36 | 370[M + 1] |
| 40 | 416[M + 1] |
| | 340 |
| 41 | 414[M + 1] |
| 44 | 362[M + 3] |
| | 360[M + 1] |
| 45 | 365[M + 1] |
| 46 | 362[M + 1] |
| 47 | 416[M + 3] |
| | 414[M + 1] |
| 49 | 394[M + 3] |
| | 392[M + 1] |
| 50 | 292[M + 1] |
| 51 | 388[M + 1] |
| 52 | 360[M + 1] |
| | 284 |
| 53 | 380[M + 1] |
| 54 | 332[M + 1] |
| 55 | 412[M + 3] |
| | 410[M + 1] |
| 56 | 397[M + 1] |
| | 395[M + 1] |
| 59 | 412[M + 1] |
| 60 | 422[M + 1] |
| | 420[M + 1] |
| 61 | 394[M + 1] |
| 63 | 366[M + 1] |
| 64 | 441[M + 1] |
| | 365 |
| 65 | 384[M + 1] |
| 66 | 398[M + 1] |
| 67 | 386[M + 1] |
| | 310 |
| 68 | 376[M + 1] |
| 70 | 372[M + 1] |
| 72 | 330[M + 1] |
| 74 | 322[M + 1] |
| 75 | 412[M + 1] |
| 76 | 363[M + 3] |
| | 361[M + 1] |
| 79 | 310[M + 1] |
| 81 | 386[M + 1] |
| 82 | 306[M + 1] |
| 83 | 336[M + 1] |
| 84 | 380[M + 1] |
| 87 | 415[M + 1] |
| 88 | 426[M + 1] |
| 89 | 370[M + 1] |
| 90 | 354[M + 1] |
| 92 | 417[M + 1] |
| 93 | 407[M + 1] |
| 94 | 350[M + 1] |
| 95 | 406[M + 3] |
| | 404[M + 1] |
| 98 | 398[M + 3] |
| | 396[M + 1] |
| 100 | 332[M + 1] |
| 102 | 424[M + 3] |

TABLE 161-continued

| 化合物番号 | MS(m/z) |
|---|---|
|  | 422[M + 1] |
| 103 | 444[M + 1] |
| 105 | 424[M + 1] |
|  | 348 |
| 106 | 490[M + 1] |
|  | 414 |
| 107 | 414[M + 3] |
|  | 412[M + 1] |
| 108 | 332[M + 1] |
| 109 | 412[M + 1] |
| 110 | 404[M + 1] |
| 111 | 469[M + 1] |
|  | 393 |
| 112 | 377[M + 1] |
| 116 | 408[M + 1] |
| 117 | 413[M + 1] |
| 118 | 372[M + 1] |
| 119 | 424[M + 1] |
| 122 | 338[M + 1] |
| 124 | 471[M + 1] |
| 131 | 412[M + 3] |
|  | 410[M + 1] |
| 133 | 404[M + 1] |
| 135 | 416[M + 1] |
| 136 | 380[M + 1] |
| 137 | 327[M + 1] |
| 138 | 394[M + 1] |
| 140 | 456[M + 1] |
| 142 | 446[M + 1] |
| 143 | 399[M + 1] |
| 144 | 432[M + 1] |
| 145 | 394[M + 3] |
|  | 392[M + 1] |
| 146 | 433[M + 3] |
|  | 431[M + 1] |
| 147 | 324[M + 1] |
| 150 | 418[M + 1] |
| 151 | 458[M + 3] |
|  | 456[M + 1] |
| 152 | 371[M + 1] |
| 153 | 398[M + 1] |
| 154 | 401[M + 1] |
| 155 | 322[M + 1] |
| 156 | 332[M + 3] |
|  | 330[M + 1] |
| 158 | 394[M + 1] |

TABLE 162

| 化合物番号 | MS(m/z) |
|---|---|
| 160 | 427[M + 1] |
| 162 | 416[M + 3] |
|  | 414[M + 1] |
| 167 | 392[M + 3] |
|  | 390[M + 1] |
| 168 | 380[M + 3] |
|  | 378[M + 1] |
| 169 | 346[M + 1] |
| 170 | 356[M + 1] |
| 171 | 334[M + 1] |
| 172 | 376[M + 3] |
|  | 374[M + 1] |
| 173 | 424[M + 3] |
|  | 422[M + 1] |
| 174 | 369[M + 1] |
| 175 | 410[M + 1] |
| 177 | 357[M + 1] |
| 179 | 334[M + 1] |
| 180 | 426[M + 1] |
| 182 | 396[M + 3] |
|  | 394[M + 1] |
| 183 | 372[M + 1] |
| 184 | 346[M + 1] |
| 185 | 330[M + 1] |
| 186 | 393[M + 3] |
|  | 391[M + 1] |

TABLE 162-continued

| 化合物番号 | MS(m/z) |
|---|---|
| 187 | 374[M + 1] |
| 188 | 423[M + 1] |
| 190 | 278[M + 1] |
| 191 | 448[M + 1] |
| 192 | 436[M + 3] |
|  | 434[M + 1] |
| 194 | 384[M + 1] |
| 195 | 369[M + 1] |
| 197 | 382[M + 1] |
| 198 | 355[M + 1] |
| 199 | 361[M + 1] |
| 200 | 356[M + 1] |
|  | 280 |
| 201 | 452[M + 1] |
| 203 | 397[M + 1] |
| 205 | 427[M + 1] |
| 206 | 386[M + 1] |
|  | 310 |
| 207 | 384[M + 1] |
| 208 | 386[M + 3] |
|  | 384[M + 1] |
| 209 | 371[M + 1] |
| 210 | 366[M + 1] |
| 211 | 442[M + 1] |
|  | 366 |
| 212 | 345[M + 1] |
| 215 | 425[M + 3] |
|  | 423[M + 1] |
| 217 | 362[M + 1] |
| 218 | 322[M + 1] |
| 219 | 347[M + 1] |
| 221 | 444[M + 1] |
| 222 | 329[M + 1] |
| 223 | 413[M + 1] |
| 225 | 402[M + 1] |
| 226 | 390[M + 1] |
| 228 | 383[M + 1] |
| 229 | 366[M + 1] |
| 230 | 368[M + 1] |
| 231 | 336[M + 1] |
| 234 | 378[M + 1] |
| 236 | 392[M + 1] |
| 237 | 348[M + 1] |
| 239 | 384[M + 1] |
| 240 | 341[M + 1] |
| 242 | 446[M + 1] |
| 245 | 374[M + 1] |
| 246 | 390[M + 1] |
|  | 314 |
| 247 | 374[M + 1] |
| 248 | 370[M + 1] |
| 249 | 336[M + 1] |
| 250 | 366[M + 1] |
| 252 | 401[M + 1] |
| 253 | 397[M + 1] |
| 254 | 434[M + 1] |
| 257 | 321[M + 1] |
| 258 | 398[M + 1] |
| 260 | 440[M + 1] |
| 261 | 308[M + 1] |
| 262 | 466[M + 3] |
|  | 464[M + 1] |
| 264 | 336[M + 1] |
| 265 | 435[M + 1] |
| 266 | 432[M + 1] |
|  | 430[M + 1] |
| 269 | 372[M + 1] |
|  | 296 |
| 270 | 338[M + 1] |
| 272 | 349[M + 1] |
| 273 | 406[M + 3] |
|  | 404[M + 1] |
| 274 | 380[M + 1] |
| 276 | 398[M + 3] |
|  | 396[M + 1] |
| 278 | 404[M + 1] |
| 280 | 433[M + 3] |
|  | 431[M + 1] |
| 283 | 322[M + 1] |
| 285 | 340[M + 1] |

TABLE 162-continued

| | |
|---|---|
| 286 | 433[M + 3] |
| | 431[M + 1] |
| 287 | 440[M + 1] |
| 288 | 354[M + 1] |
| 289 | 341[M + 1] |
| 290 | 363[M + 3] |
| | 361[M + 1] |
| 291 | 317[M + 1] |
| 292 | 426[M + 1] |
| 294 | 424[M + 3] |
| | 422[M + 1] |
| 295 | 394[M + 3] |
| | 392[M + 1] |
| 296 | 389[M + 1] |
| 297 | 448[M + 3] |
| | 446[M + 1] |
| 298 | 363[M + 3] |
| | 361[M + 1] |
| 300 | 356[M + 1] |
| 303 | 366[M + 1] |
| 304 | 402[M + 1] |
| 305 | 407[M + 3] |
| | 405[M + 1] |
| 310 | 411[M + 1] |

TABLE 163

| | |
|---|---|
| 311 | 388[M + 1] |
| 312 | 428[M + 1] |
| 313 | 453[M + 1] |
| 314 | 368[M + 1] |
| 315 | 322[M + 1] |
| 316 | 386[M + 1] |
| 317 | 328[M + 1] |
| 318 | 362[M + 1] |
| 320 | 327[M + 1] |
| 321 | 392[M + 1] |
| 322 | 404[M + 1] |
| | 328 |
| 323 | 394[M + 1] |
| 324 | 384[M + 1] |
| 325 | 399[M + 1] |
| 326 | 440[M + 1] |
| | 364 |
| 327 | 314[M + 1] |
| 328 | 384[M + 1] |
| 331 | 360[M + 1] |
| 334 | 412[M + 1] |
| 335 | 316[M + 1] |
| 336 | 356[M + 1] |
| 337 | 428[M + 1] |
| 338 | 466[M + 3] |
| | 464[M + 1] |
| 340 | 344[M + 1] |
| 343 | 399[M + 1] |
| 345 | 412[M + 1] |
| 346 | 384[M + 1] |
| 347 | 430[M + 1] |
| 348 | 341[M + 1] |
| 349 | 335[M + 1] |
| 350 | 412[M + 1] |
| 351 | 322[M + 1] |
| 352 | 327[M + 1] |
| 355 | 397[M + 1] |
| 362 | 366[M + 1] |
| 363 | 376[M + 3] |
| | 374[M + 1] |
| 365 | 366[M + 1] |
| 366 | 409[M + 1] |
| 368 | 384[M + 1] |
| 369 | 396[M + 3] |
| | 394[M + 1] |
| 371 | 398[M + 3] |
| | 396[M + 1] |
| 372 | 348[M + 1] |
| 373 | 358[M + 1] |
| 374 | 364[M + 1] |

TABLE 163-continued

| | |
|---|---|
| 376 | 412[M + 1] |
| 377 | 425[M + 1] |
| 378 | 380[M + 3] |
| | 378[M + 1] |
| 379 | 377[M + 1] |
| 381 | 409[M + 1] |
| 382 | 340[M + 1] |
| 384 | 388[M + 1] |
| 385 | 384[M + 1] |
| 386 | 352[M + 1] |
| 387 | 376[M + 1] |
| 388 | 440[M + 1] |
| 390 | 407[M + 1] |
| | 331 |
| 391 | 362[M + 1] |
| 392 | 390[M + 1] |
| 394 | 363[M + 3] |
| | 361[M + 1] |
| 397 | 460[M + 3] |
| | 458[M + 1] |
| 398 | 408[M + 1] |
| 399 | 372[M + 1] |
| 400 | 374[M + 1] |
| 402 | 372[M + 1] |
| | 296 |
| 403 | 436[M + 1] |
| 404 | 376[M + 3] |
| | 374[M + 1] |
| 407 | 449[M + 3] |
| | 447[M + 1] |
| 412 | 410[M + 1] |
| 414 | 331[M + 1] |
| 416 | 282[M + 1] |
| 418 | 322[M + 1] |
| 419 | 420[M + 3] |
| | 418[M + 1] |
| 420 | 332[M + 1] |
| 421 | 388[M + 3] |
| | 386[M + 1] |
| 423 | 412[M + 3] |
| | 410[M + 1] |
| 424 | 370[M + 1] |
| 425 | 380[M + 3] |
| | 378[M + 1] |
| 428 | 350[M + 1] |
| 431 | 391[M + 1] |
| 433 | 454[M + 3] |
| | 452[M + 1] |
| 434 | 448[M + 3] |
| | 446[M + 1] |
| 435 | 431[M + 3] |
| | 429[M + 1] |
| 437 | 382[M + 1] |
| 438 | 400[M + 1] |
| | 324 |
| 439 | 380[M + 1] |
| 440 | 358[M + 1] |
| 442 | 394[M + 1] |
| | 318 |
| 447 | 370[M + 1] |
| 449 | 336[M + 1] |
| 450 | 455[M + 1] |
| 451 | 390[M + 3] |
| | 388[M + 1] |
| 453 | 358[M + 1] |
| 454 | 407[M + 1] |
| | 331 |
| 455 | 296[M + 1] |
| 458 | 382[M + 1] |
| 459 | 392[M + 1] |
| 460 | 431[M + 1] |
| 461 | 369[M + 1] |
| 462 | 381[M + 3] |
| | 379[M + 1] |
| 463 | 440[M + 3] |
| | 438[M + 1] |
| 464 | 338[M + 1] |
| | 262 |
| 467 | 387[M + 1] |
| 468 | 439[M + 1] |

TABLE 163-continued

| | |
|---|---|
| | 363 |
| 469 | 360[M + 1] |
| 471 | 363[M + 3] |
| | 361[M + 1] |

TABLE 164

| | |
|---|---|
| 472 | 376[M + 1] |
| 473 | 414[M + 1] |
| 474 | 334[M + 1] |
| 475 | 317[M + 1] |
| 476 | 324[M + 1] |
| 477 | 437[M + 1] |
| 478 | 379[M + 1] |
| 479 | 394[M + 1] |
| 480 | 370[M + 1] |
| 481 | 431[M + 1] |
| 484 | 314[M + 3] |
| | 312[M + 1] |
| 485 | 448[M + 1] |
| 486 | 350[M + 1] |
| 487 | 338[M + 1] |
| 488 | 306[M + 1] |
| 489 | 335[M + 1] |
| 492 | 380[M + 1] |
| 495 | 334[M + 1] |
| 499 | 370[M + 1] |
| 503 | 412[M + 1] |
| 505 | 363[M + 3] |
| | 361[M + 1] |
| 506 | 386[M + 1] |
| 507 | 400[M + 1] |
| 508 | 372[M + 1] |
| 509 | 414[M + 1] |
| | 338 |
| 510 | 374[M + 1] |
| 512 | 320[M + 1] |
| 513 | 420[M + 3] |
| | 418[M + 1] |
| 514 | 372[M + 1] |
| 517 | 369[M + 1] |
| 518 | 376[M + 1] |
| 519 | 411[M + 1] |
| 520 | 395[M + 1] |
| 521 | 372[M + 1] |
| 522 | 390[M + 1] |
| 523 | 414[M + 1] |
| 524 | 341[M + 1] |
| 526 | 426[M + 1] |
| 527 | 381[M + 3] |
| | 379[M + 1] |
| 529 | 320[M + 1] |
| 530 | 390[M + 3] |
| | 388[M + 1] |
| 531 | 410[M + 1] |
| 535 | 356[M + 1] |
| 536 | 372[M + 1] |
| 537 | 377[M + 1] |
| 538 | 406[M + 1] |
| 539 | 411[M + 1] |
| 540 | 354[M + 1] |
| 541 | 342[M + 1] |
| 542 | 361[M + 1] |
| 543 | 344[M + 1] |
| 544 | 412[M + 1] |
| 545 | 366[M + 1] |
| 546 | 383[M + 1] |
| 547 | 430[M + 1] |
| | 428[M + 1] |
| 548 | 427[M + 1] |
| 550 | 340[M + 1] |
| 552 | 400[M + 1] |
| 553 | 304[M + 1] |
| 555 | 383[M + 1] |
| 557 | 304[M + 1] |
| 562 | 374[M + 1] |
| 563 | 366[M + 1] |

TABLE 164-continued

| | |
|---|---|
| 564 | 395[M + 1] |
| 565 | 336[M + 1] |
| 566 | 427[M + 1] |
| | 351 |
| 568 | 362[M + 3] |
| | 360[M + 1] |
| 569 | 356[M + 1] |
| 571 | 356[M + 1] |
| 572 | 473[M + 3] |
| | 471[M + 1] |
| 574 | 381[M + 3] |
| | 379[M + 1] |
| 575 | 360[M + 1] |
| 576 | 384[M + 1] |
| 578 | 344[M + 1] |
| 579 | 370[M + 1] |
| 580 | 347[M + 1] |
| 581 | 409[M + 1] |
| 582 | 334[M + 1] |
| 583 | 392[M + 1] |
| 585 | 358[M + 1] |
| 587 | 348[M + 1] |
| 589 | 407[M + 3] |
| | 405[M + 3] |
| 590 | 410[M + 3] |
| | 408[M + 1] |
| 591 | 460[M + 1] |
| | 384 |
| 592 | 380[M + 3] |
| | 378[M + 1] |
| 594 | 390[M + 1] |
| 598 | 394[M + 1] |
| 599 | 377[M + 1] |
| 603 | 398[M + 3] |
| | 396[M + 1] |
| 604 | 395[M + 1] |
| 606 | 358[M + 1] |
| 607 | 362[M + 1] |
| 609 | 413[M + 1] |
| 610 | 409[M + 1] |
| 612 | 385[M + 1] |
| 614 | 322[M + 1] |
| 615 | 441[M + 1] |
| 616 | 346[M + 3] |
| | 344[M + 1] |
| | 270 |
| | 268 |
| 617 | 406[M + 3] |
| | 404[M + 1] |
| 619 | 404[M + 1] |
| 621 | 366[M + 1] |
| 623 | 422[M + 1] |
| | 346 |
| 624 | 370[M + 1] |
| 626 | 402[M + 1] |
| 627 | 398[M + 3] |
| | 396[M + 1] |
| 628 | 413[M + 1] |
| 631 | 370[M + 1] |
| 632 | 414[M + 3] |
| | 412[M + 1] |

TABLE 165

| | |
|---|---|
| 633 | 322[M + 1] |
| 635 | 420[M + 1] |
| 638 | 408[M + 1] |
| 639 | 386[M + 1] |
| | 310 |
| 640 | 370[M + 1] |
| 641 | 437[M + 1] |
| 642 | 380[M + 1] |
| 646 | 395[M + 1] |
| 647 | 334[M + 1] |
| 648 | 403[M + 1] |
| 650 | 370[M + 1] |
| 655 | 362[M + 1] |

TABLE 165-continued

| | |
|---|---|
| 656 | 308[M + 1] |
| 658 | 430[M + 1] |
| 659 | 340[M + 3] |
| | 388[M + 1] |
| 662 | 330[M + 1] |
| 663 | 334[M + 1] |
| 665 | 316[M + 1] |
| 666 | 345[M + 1] |
| 668 | 430[M + 1] |
| 669 | 377[M + 1] |
| 670 | 368[M + 3] |
| | 366[M + 1] |
| 671 | 334[M + 1] |
| 672 | 442[M + 1] |
| 674 | 340[M + 1] |
| 675 | 306[M + 1] |
| 676 | 392[M + 1] |
| 678 | 386[M + 1] |
| 679 | 426[M + 1] |
| 682 | 414[M + 3] |
| | 412[M + 1] |
| 684 | 384[M + 1] |
| 685 | 389[M + 1] |
| 686 | 446[M + 1] |
| 688 | 414[M + 1] |
| 689 | 306[M + 1] |
| 690 | 348[M + 1] |
| 691 | 452[M + 1] |
| 693 | 371[M + 1] |
| 694 | 448[M + 1] |
| 695 | 364[M + 1] |
| 696 | 392[M + 3] |
| | 390[M + 1] |
| 697 | 358[M + 1] |
| 699 | 426[M + 1] |
| 703 | 451[M + 3] |
| | 449[M + 1] |
| 704 | 342[M + 1] |
| 705 | 372[M + 1] |
| 706 | 368[M + 1] |
| 708 | 383[M + 1] |
| 710 | 396[M + 3] |
| | 394[M + 1] |
| 711 | 351[M + 1] |
| 712 | 376[M + 1] |
| 713 | 398[M + 3] |
| | 396[M + 1] |
| 714 | 366[M + 1] |
| 715 | 454[M + 1] |
| 716 | 381[M + 3] |
| | 379[M + 1] |
| 718 | 386[M + 1] |
| 721 | 322[M + 1] |
| 722 | 377[M + 1] |
| 723 | 440[M + 1] |
| | 364 |
| 724 | 457[M + 3] |
| | 455[M + 1] |
| 726 | 362[M + 1] |
| 727 | 366[M + 1] |
| 734 | 370[M + 1] |
| 736 | 338[M + 1] |
| 741 | 404[M + 1] |
| 742 | 351[M + 1] |
| 745 | 386[M + 1] |
| 746 | 370[M + 1] |
| | 294 |
| 747 | 336[M + 1] |
| 748 | 381[M + 3] |
| | 379[M + 1] |
| 749 | 416[M + 1] |
| | 340 |
| 750 | 437[M + 1] |
| 751 | 362[M + 1] |
| 752 | 352[M + 3] |
| | 350[M + 1] |
| 754 | 366[M + 1] |
| 755 | 354[M + 1] |
| 757 | 425[M + 1] |
| 759 | 346[M + 1] |

TABLE 165-continued

| | |
|---|---|
| 760 | 344[M + 1] |
| 761 | 402[M + 1] |
| 762 | 251[M + 1] |
| 763 | 355[M + 1] |
| 764 | 362[M + 3] |
| | 360[M + 1] |
| 765 | 392[M + 3] |
| | 390[M + 1] |
| 769 | 366[M + 1] |
| 770 | 372[M + 1] |
| 772 | 292[M + 1] |
| 773 | 424[M + 1] |
| 775 | 396[M + 3] |
| | 394[M + 1] |
| 776 | 388[M + 1] |
| 777 | 383[M + 1] |
| 778 | 404[M + 1] |
| 779 | 398[M + 1] |
| 780 | 368[M + 1] |
| 782 | 368[M + 1] |
| 784 | 369[M + 1] |
| 785 | 431[M + 3] |
| | 429[M + 1] |
| 787 | 473[M + 1] |
| | 397 |
| 788 | 375[M + 1] |
| 789 | 467[M + 1] |
| 794 | 327[M + 1] |
| 795 | 384[M + 1] |
| 796 | 370[M + 1] |
| 798 | 370[M + 1] |
| 801 | 404[M + 3] |
| | 402[M + 1] |
| 805 | 376[M + 1] |
| 806 | 411[M + 1] |
| 807 | 356[M + 1] |

TABLE 166

| | |
|---|---|
| 808 | 354[M + 1] |
| 809 | 400[M + 1] |
| | 324 |
| 812 | 425[M + 1] |
| 815 | 386[M + 1] |
| 817 | 377[M + 1] |
| 818 | 398[M + 1] |
| 819 | 352[M + 1] |
| 821 | 336[M + 1] |
| 823 | 362[M + 1] |
| 824 | 363[M + 1] |
| | 287 |
| 825 | 420[M + 1] |
| 826 | 430[M + 1] |
| 828 | 377[M + 1] |
| 829 | 437[M + 1] |
| 830 | 370[M + 1] |
| 831 | 327[M + 1] |
| 837 | 324[M + 1] |
| | 248 |
| 838 | 377[M + 1] |
| 839 | 376[M + 3] |
| | 374[M + 1] |
| 841 | 363[M + 3] |
| | 361[M + 1] |
| 842 | 386[M + 1] |
| 843 | 466[M + 3] |
| | 464[M + 1] |
| 844 | 381[M + 1] |
| 845 | 324[M + 1] |
| | 248 |
| 846 | 358[M + 1] |
| 847 | 373[M + 1] |
| 852 | 489[M + 1] |
| 853 | 376[M + 1] |
| 854 | 448[M + 1] |
| 856 | 420[M + 1] |
| | 344 |

TABLE 166-continued

| | |
|---|---|
| 857 | 341[M + 1] |
| 858 | 383[M + 1] |
| 860 | 370[M + 1] |
| 861 | 334[M + 3] |
| | 332[M + 1] |
| 862 | 358[M + 1] |
| 864 | 392[M + 1] |
| 865 | 398[M + 3] |
| | 396[M + 1] |
| 867 | 399[M + 1] |
| 868 | 430[M + 1] |
| 870 | 362[M + 3] |
| | 360[M + 1] |
| 872 | 428[M + 1] |
| 873 | 351[M + 1] |
| 874 | 341[M + 1] |
| 877 | 399[M + 1] |
| | 323 |
| 879 | 332[M + 1] |
| 880 | 363[M + 3] |
| | 361[M + 1] |
| 882 | 426[M + 1] |
| 883 | 360[M + 1] |
| 884 | 320[M + 1] |
| 885 | 361[M + 1] |
| 886 | 380[M + 1] |
| 888 | 292[M + 1] |
| 889 | 451[M + 1] |
| | 449[M + 1] |
| 890 | 400[M + 1] |
| 891 | 292[M + 1] |
| 894 | 347[M + 1] |
| 898 | 412[M + 3] |
| | 410[M + 1] |
| 899 | 397[M + 1] |
| 901 | 411[M + 1] |
| 902 | 377[M + 1] |
| 903 | 370[M + 1] |
| 904 | 422[M + 1] |
| 905 | 392[M + 1] |
| 907 | 308[M + 1] |
| 909 | 393[M + 1] |
| 911 | 415[M + 1] |
| 912 | 383[M + 1] |
| 913 | 413[M + 1] |
| 914 | 400[M + 1] |
| 915 | 389[M + 1] |
| | 313 |
| 917 | 358[M + 1] |
| 918 | 433[M + 3] |
| | 431[M + 1] |
| 919 | 354[M + 1] |
| 920 | 381[M + 3] |
| | 379[M + 1] |
| 921 | 389[M + 1] |
| 922 | 413[M + 1] |
| | 337 |
| 923 | 437[M + 1] |
| 924 | 376[M + 1] |
| 925 | 390[M + 1] |
| 927 | 355[M + 1] |
| 929 | 370[M + 1] |
| 932 | 380[M + 3] |
| | 378[M + 1] |
| 934 | 507[M + 1] |
| 937 | 388[M + 1] |
| 938 | 366[M + 1] |
| 940 | 388[M + 1] |
| 942 | 378[M + 1] |
| 943 | 413[M + 1] |
| 945 | 372[M + 1] |
| 948 | 462[M + 1] |
| 949 | 363[M + 1] |
| 950 | 368[M + 1] |
| 951 | 412[M + 1] |
| 952 | 378[M + 1] |
| 953 | 318[M + 1] |
| 954 | 363[M + 3] |
| | 361[M + 1] |
| 955 | 406[M + 3] |
| | 404[M + 1] |
| 956 | 292[M + 1] |
| 957 | 398[M + 3] |
| | 396[M + 1] |
| 958 | 310[M + 1] |
| 959 | 406[M + 3] |
| | 404[M + 1] |
| 961 | 362[M + 3] |
| | 360[M + 1] |
| 962 | 327[M + 1] |
| 963 | 392[M + 1] |

TABLE 167

| | |
|---|---|
| 965 | 438[M + 3] |
| | 436[M + 1] |
| 967 | 425[M + 3] |
| | 423[M + 1] |
| 969 | 413[M + 1] |
| 973 | 386[M + 1] |
| 975 | 407[M + 3] |
| | 405[M + 1] |
| 976 | 358[M + 1] |
| 977 | 369[M + 1] |
| 979 | 395[M + 1] |
| 980 | 402[M + 1] |
| 981 | 392[M + 3] |
| | 390[M + 1] |
| 982 | 366[M + 1] |
| 983 | 379[M + 1] |
| 985 | 408[M + 1] |
| 986 | 440[M + 3] |
| | 438[M + 1] |
| 987 | 358[M + 1] |
| 988 | 294[M + 1] |
| 989 | 332[M + 1] |
| 991 | 356[M + 1] |
| 992 | 477[M + 1] |
| 993 | 416[M + 3] |
| | 414[M + 1] |
| 995 | 425[M + 3] |
| | 423[M + 1] |
| 996 | 416[M + 3] |
| | 414[M + 1] |
| 997 | 363[M + 3] |
| | 361[M + 1] |
| 999 | 336[M + 1] |
| 1000 | 388[M + 1] |
| | 312 |
| 1001 | 374[M + 1] |
| 1002 | 400[M + 1] |
| 1003 | 394[M + 1] |
| 1004 | 397[M + 1] |
| 1007 | 448[M + 1] |
| | 372 |
| 1009 | 366[M + 1] |
| 1011 | 419[M + 1] |
| 1012 | 316[M + 1] |
| 1013 | 431[M + 1] |
| 1015 | 372[M + 1] |
| 1016 | 470[M + 1] |
| 1017 | 413[M + 1] |
| 1018 | 386[M + 1] |
| 1019 | 433[M + 3] |
| | 431[M + 1] |
| 1021 | 464[M + 1] |
| 1022 | 384[M + 1] |
| 1023 | 407[M + 3] |
| | 405[M + 1] |
| 1024 | 346[M + 1] |
| 1025 | 455[M + 3] |
| | 453[M + 1] |
| 1026 | 425[M + 1] |
| 1027 | 444[M + 1] |
| 1029 | 410[M + 1] |
| 1030 | 413[M + 1] |

TABLE 167-continued

| | |
|---|---|
| 1031 | 404[M + 1] |
| 1032 | 472[M + 1] |
| | 396 |
| 1033 | 377[M + 1] |
| 1036 | 350[M + 1] |
| 1038 | 364[M + 1] |
| 1040 | 317[M + 1] |
| 1041 | 407[M + 1] |
| 1042 | 382[M + 1] |
| 1045 | 425[M + 3] |
| | 423[M + 1] |
| 1046 | 366[M + 1] |
| 1047 | 390[M + 1] |
| 1048 | 440[M + 1] |
| 1049 | 396[M + 1] |
| 1050 | 400[M + 1] |
| 1051 | 315[M + 1] |
| 1053 | 363[M + 3] |
| | 361[M + 1] |
| 1054 | 360[M + 1] |
| 1057 | 427[M + 1] |
| 1058 | 360[M + 1] |
| 1060 | 381[M + 3] |
| | 379[M + 1] |
| 1063 | 395[M + 1] |
| 1065 | 451[M + 1] |
| | 449[M + 1] |
| 1066 | 485[M + 1] |
| 1070 | 380[M + 3] |
| | 378[M + 1] |
| 1071 | 345[M + 1] |
| 1072 | 381[M + 3] |
| | 379[M + 1] |
| 1073 | 397[M + 1] |
| 1075 | 342[M + 1] |
| 1077 | 344[M + 1] |
| 1078 | 370[M + 1] |
| 1079 | 387[M + 1] |
| 1080 | 370[M + 1] |
| | 294 |
| 1081 | 355[M + 1] |
| 1082 | 398[M + 3] |
| | 396[M + 1] |
| 1083 | 318[M + 1] |
| 1085 | 439[M + 3] |
| | 437[M + 1] |
| 1086 | 428[M + 1] |
| 1089 | 399[M + 1] |
| 1090 | 398[M + 1] |
| 1091 | 434[M + 3] |
| | 432[M + 1] |
| 1092 | 398[M + 3] |
| | 396[M + 1] |
| 1093 | 401[M + 1] |
| 1095 | 400[M + 1] |
| 1096 | 409[M + 1] |
| 1097 | 384[M + 1] |
| 1098 | 395[M + 1] |
| 1099 | 511[M + 4] |
| | 510[M + 3] |
| | 509[M + 2] |
| | 508[M + 1] |
| 1101 | 350[M + 1] |
| 1102 | 442[M + 1] |
| 1103 | 397[M + 1] |
| 1105 | 372[M + 1] |
| 1106 | 346[M + 1] |
| 1108 | 383[M + 1] |
| 1112 | 445[M + 1] |

TABLE 168

| | |
|---|---|
| 1113 | 358[M + 1] |
| 1117 | 394[M + 1] |
| 1118 | 336[M + 1] |
| | 260 |

TABLE 168-continued

| | |
|---|---|
| 1121 | 392[M + 3] |
| | 390[M + 1] |
| 1122 | 322[M + 1] |
| 1123 | 316[M + 1] |
| 1126 | 386[M + 1] |
| 1127 | 368[M + 1] |
| 1128 | 416[M + 3] |
| | 414[M + 1] |
| 1129 | 341[M + 1] |
| 1130 | 432[M + 1] |
| 1134 | 396[M + 1] |
| 1136 | 396[M + 3] |
| | 394[M + 1] |
| 1137 | 292[M + 1] |
| 1138 | 413[M + 1] |
| 1141 | 344[M + 1] |
| 1143 | 384[M + 1] |
| 1144 | 446[M + 1] |
| 1145 | 390[M + 1] |
| | 314 |
| 1146 | 405[M + 1] |
| 1148 | 380[M + 1] |
| | 304 |
| 1149 | 364[M + 1] |
| 1151 | 442[M + 1] |
| 1152 | 365[M + 1] |
| 1154 | 318[M + 1] |
| 1155 | 427[M + 1] |
| 1156 | 368[M + 1] |
| 1157 | 366[M + 1] |
| 1158 | 415[M + 3] |
| | 413[M + 1] |
| 1159 | 414[M + 3] |
| | 412[M + 1] |
| 1162 | 370[M + 1] |
| | 294 |
| 1163 | 416[M + 3] |
| | 414[M + 1] |
| 1164 | 396[M + 1] |
| | 320 |
| 1165 | 361[M + 1] |
| 1167 | 424[M + 1] |
| | 348 |
| 1168 | 428[M + 1] |
| 1169 | 422[M + 1] |
| 1170 | 411[M + 1] |
| 1171 | 390[M + 3] |
| | 388[M + 1] |
| 1173 | 361[M + 1] |
| 1174 | 342[M + 1] |
| 1175 | 430[M + 1] |
| 1176 | 345[M + 1] |
| 1177 | 376[M + 3] |
| | 374[M + 1] |
| 1178 | 351[M + 1] |
| 1179 | 344[M + 1] |
| 1180 | 398[M + 3] |
| | 396[M + 1] |
| 1182 | 426[M + 1] |
| 1183 | 376[M + 3] |
| | 374[M + 1] |
| 1186 | 374[M + 1] |
| | 298 |
| 1187 | 427[M + 1] |
| 1188 | 350[M + 1] |
| 1189 | 408[M + 3] |
| | 406[M + 1] |
| 1190 | 386[M + 1] |
| 1191 | 377[M + 1] |
| 1192 | 335[M + 1] |
| 1195 | 412[M + 3] |
| | 410[M + 1] |
| 1196 | 380[M + 1] |
| 1198 | 398[M + 1] |
| | 322 |
| 1200 | 352[M + 1] |
| 1201 | 424[M + 3] |
| | 422[M + 1] |
| 1202 | 369[M + 1] |
| 1203 | 420[M + 1] |

TABLE 168-continued

| | |
|---|---|
| 1204 | 398[M + 3] |
| | 396[M + 1] |
| 1206 | 416[M + 1] |
| 1208 | 344[M + 1] |
| 1209 | 422[M + 1] |
| 1210 | 408[M + 1] |
| 1212 | 391[M + 1] |
| 1214 | 360[M + 1] |
| 1218 | 372[M + 1] |
| 1219 | 470[M + 1] |
| 1220 | 264[M + 1] |
| 1222 | 362[M + 3] |
| | 360[M + 1] |
| 1225 | 413[M + 1] |
| 1226 | 374[M + 1] |
| 1227 | 425[M + 1] |
| 1229 | 455[M + 3] |
| | 453[M + 1] |
| 1231 | 413[M + 1] |
| 1232 | 340[M + 1] |
| 1233 | 394[M + 1] |
| 1234 | 416[M + 3] |
| | 414[M + 1] |
| 1235 | 427[M + 1] |
| 1236 | 348[M + 1] |
| | 272 |
| 1237 | 353[M + 1] |
| 1238 | 419[M + 1] |
| 1239 | 416[M + 3] |
| | 414[M + 1] |
| 1246 | 474[M + 1] |
| 1248 | 414[M + 1] |
| 1249 | 336[M + 1] |
| 1250 | 352[M + 1] |
| 1251 | 393[M + 1] |
| 1252 | 357[M + 1] |
| 1253 | 430[M + 1] |
| 1254 | 412[M + 1] |
| 1256 | 333[M + 1] |
| 1259 | 356[M + 1] |
| 1260 | 348[M + 1] |
| 1270 | 374[M + 1] |
| 1282 | 362[M + 1] |

[Chemical formula 84]

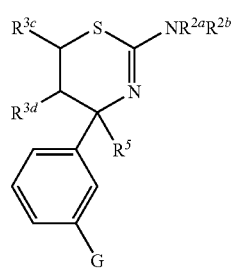
(Ia)

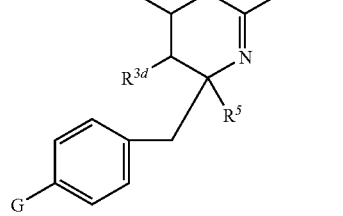
(Ib)

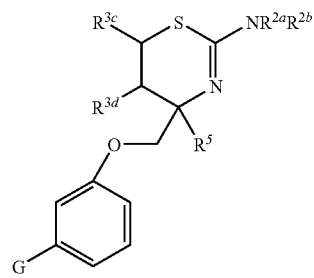
(Ic)

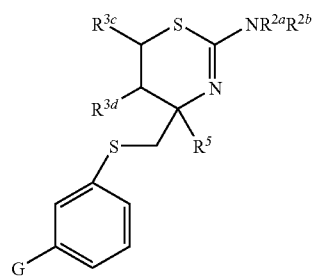
(Id)

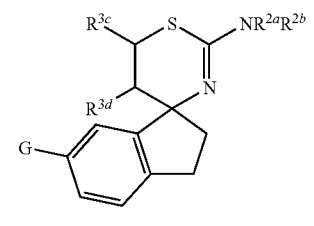
(Ie)

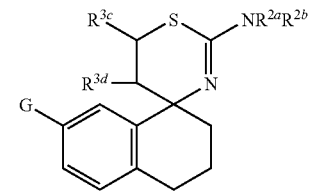
(If)

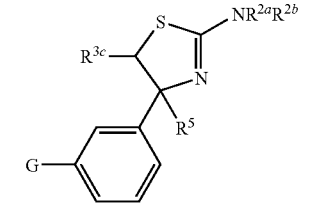
(Ig)

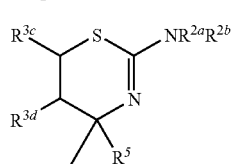
(Ih)

In above structural formula (Ia) to (Ih), the combination of $NR^{2a}R^{2b}$, $R^{3c}$, $R^{3d}$, $R^5$ and G ($NR^{2a}R^{2b}$, $R^{3c}$, $R^{3d}$, $R^5$, G) are the following compounds.
(NHMe,H,H,Me,CONHPh),(NHMe,H,H,Me,CONH-3-pyridyl),(NHMe,H,H,Me,NHCOPh),(NHMe,H,H,Me,NHCO-2-furyl),(NHMe,H,H,Me,NHCONHPh),(NHMe,H,H,Me,NHCOCONHPh),(NHMe,H,H,Et,CONHPh),(NHMe,H,H,Et,CONH-3-pyridyl),(NHMe,H,H,Et, NHCOPh),(NHMe,H,H,Et,NHCO-2-furyl),(NHMe,H,H,Et,NHCONHPh),(NHMe,H,H,Et,NHCOCONHPh),(NHMe,H,H,CH2OH,CONHPh),(NHMe,H,H,CH2OH,CONH-3-pyridyl),(NHMe,H,H,CH2OH,NHCOPh),(NHMe,H,H,CH2OH,NHCO-2-furyl),(NHMe,H,H,CH2OH,NHCONHPh),(NHMe,H,H,CH2OH,NHCOCONHPh),(NHMe,H,Me,Me,CONHPh),(NHMe,H,Me,Me,CONH-3-pyridyl),(NHMe,H,Me,Me,NHCOPh),(NHMe,H,Me,Me,NHCO-2furyl),(NHMe,H,Me,Me,NHCONHPh),(NHMe,H,Me,Me,NHCOCONHPh),(NHMe,H,Me,Et,CONHPh),(NHMe,H,Me,Et,CONH-3-pyridyl),(NHMe,H,Me,Et,NHCOPh),(NHMe,H,Me,Et,NHCO-2-furyl),(NHMe,H,Me,Et,NHCONHPh),(NHMe,H,Me,Et,NHCOCONHPh),(NHMe,H,Me,CH2OH,CONHPh),(NHMe,H,Me,H,Me,CH2OH,CONH-3-pyridyl),(NHMe,H,Me,CH2OH,NHCOPh),(NHMe,H,Me,CH2OH,NHCO-2-furyl),(NHMe,H,Me,CH2OH,NHCONHPh),(NHMe,H,Me,CH2OH,NHCOCONHPh),(NHMe,H,Ph,Me,CONHPh),(NHMe,H,Ph,Me,CONH-3-pyridyl),(NHMe,H,Ph,Me,NHCOPh),(NHMe,H,Ph,Me,NHCO-2furyl),(NHMe,H,Ph,Me,NHCONHPh),(NHMe,H,Ph,Me,NHCOCONHPh),(NHMe,H,Ph,Et,CONHPh),(NHMe,H,Ph,Et,CONH-3-pyridyl),(NHMe,H,Ph,Et,NHCOPh),(NHMe,H,Ph,Et,NHCO-2-furyl),(NHMe,H,Ph,Et,NHCONHPh),(NHMe,H,Ph,Et,NHCOCONHPh),(NHMe,H,Ph,CH2OH,CONHPh),(NHMe,H,Ph,CH2OH,CONH-3-pyridyl),(NHMe,H,Ph,CH2OH,NHCOPh),(NHMe,H,Ph,CH2OH,NHCO-2-furyl),(NHMe,H,Ph,CH2OH,NHCONHPh),(NHMe,H,Ph,CH2OH,NHCOCONHPh),(NHMe,H,OH,Me,CONHPh),(NHMe,H,OH,Me,CONH-3-pyridyl),(NHMe,H,OH,Me,NHCOPh),(NHMe,H,OH,Me,NHCO-2-furyl),(NHMe,H,OH,Me,NHCONHPh),(NHMe,H,OH,Me,NHCOCONHPh),(NHMe,H,OH,Et,CONHPh),(NHMe,H,OH,Et,CONH-3-pyridyl),(NHMe,H,OH,Et,NHCOPh),(NHMe,H,OH,Et,NHCO-2-furyl),(NHMe,H,OH,Et,NHCONHPh),(NHMe,H,OH,Et,NHCOCONHPh),(NHMe,H,OH,CH2OH,CONHPh),(NHMe,H,OH,CH2OH,CONH-3-pyridyl),(NHMe,H,OH,CH2OH,NHCOPh),(NHMe,H,OH,CH2OH,NHCO-2-furyl),(NHMe,H,OH,CH2OH,NHCONHPh),(NHMe,H,OH,CH2OH,NHCOCONHPh),(NHMe,Me,H,Me,CONHPh),(NHMe,Me,H,Me,CONH-3-pyridyl),(NHMe,Me,H,Me,NHCOPh),(NHMe,Me,H,Me,NHCO-2-furyl),(NHMe,Me,H,Me,NHCONHPh),(NHMe,Me,H,Me,NHCOCONHPh),(NHMe,Me,H,Et,CONHPh),(NHMe,Me,H,Et,CONH-3-pyridyl),(NHMe,Me,H,Et,NHCOPh),(NHMe,Me,H,Et,NHCO-2-furyl),(NHMe,Me,H,Et,NHCONHPh),(NHMe,Me,H,Et,NHCOCONHPh),(NHMe,Me,H,CH2OH,CONHPh),(NHMe,Me,H,CH2OH,CONH-3-pyridyl),(NHMe,Me,H,CH2OH,NHCOPh),(NHMe,Me,H,CH2OH,NHCO-2-furyl),(NHMe,Me,H,CH2OH,NHCONHPh),(NHMe,Me,H,CH2OH,NHCOCONHPh),(NHMe,Me,Me,Me,CONHPh),(NHMe,Me,Me,Me,CONH-3-pyridyl),(NHMe,Me,Me,Me,NHCOPh),(NHMe,Me,Me,Me,NHCO-2-furyl),(NHMe,Me,Me,Me,NHCONHPh),(NHMe,Me,Me,Me,NHCOCONHPh),(NHMe,Me,Me,Et,CONHPh),(NHMe,Me,Me,Et,CONH-3-pyridyl),(NHMe,Me,Me,Et,NHCOPh),(NHMe,Me,Me,Et,NHCO-2-furyl),(NHMe,Me,Me,Et,NHCONHPh),(NHMe,Me,Me,Et,NHCOCONHPh),(NHMe,Me,Me,CH2OH,CONHPh),(NHMe,Me,Me,CH2OH,CONH-3-pyridyl),(NHMe,Me,Me,CH2OH,NHCOPh),(NHMe,Me,Me,CH2OH,NHCO-2-furyl),(NHMe,Me,Me,CH2OH,NHCONHPh),(NHMe,Me,Me,CH2OH,NHCOCONHPh),(NHMe,Me,Ph,Me,CONHPh),(NHMe,Me,Ph,Me,CONH-3-pyridyl),(NHMe,Me,Ph,Me,NHCOPh),(NHMe,Me,Ph,Me,NHCO-2-furyl),(NHMe,Me,Ph,Me,NHCONHPh),(NHMe,Me,Ph,Me,NHCOCONHPh),(NHMe,Me,Ph,Et,CONHPh),(NHMe,Me,Ph,Et,CONH-3-pyridyl),(NHMe,Me,Ph,Et,NHCOPh),(NHMe,Me,Ph,Et,NHCO-2-furyl),(NHMe,Me,Ph,Et,NHCONHPh),(NHMe,Me,Ph,Et,NHCOCONHPh),(NHMe,Me,Ph,CH2OH,CONHPh),(NHMe,Me,Ph,CH2OH,CONH-3-pyridyl),(NHMe,Me,Ph,CH2OH,NHCOPh),(NHMe,Me,Ph,CH2OH,NHCO-2-furyl),(NHMe,Me,Ph,CH2OH,NHCONHPh),(NHMe,Me,Ph,CH2OH,NHCOCONHPh),(NHMe,Me,OH,Me,CONHPh),(NHMe,Me,OH,Me,CONH-3-pyridyl),(NHMe,Me,OH,Me,NHCOPh),(NHMe,Me,OH,Me,NHCO-2-furyl),(NHMe,Me,OH,Me,NHCONHPh),(NHMe,Me,OH,Me,NHCOCONHPh),(NHMe,Me,OH,Et,CONHPh),(NHMe,Me,OH,Et,CONH-3-pyridyl),(NHMe,Me,OH,Et,NHCOPh),(NHMe,Me,OH,Et,NHCO-2-furyl),(NHMe,Me,OH,Et,NHCONHPh),(NHMe,Me,OH,Et,NHCOCONHPh),(NHMe,Me,OH,CH2OH,CONHPh),(NHMe,Me,OH,CH2OH,CONH-3-pyridyl),(NHMe,Me,OH,CH2OH,NHCOPh),(NHMe,Me,OH,CH2OH,NHCO-2-furyl),(NHMe,Me,OH,CH2OH,NHCONHPh),(NHMe,Me,OH,CH2OH,NHCOCONHPh),(NHMe,Ph,H,Me,CONHPh),(NHMe,Ph,H,Me,CONH-3-pyridyl),(NHMe,Ph,H,Me,NHCOPh),(NHMe,Ph,H,Me,NHCO-2-furyl),(NHMe,Ph,H,Me,NHCONHPh),(NHMe,Ph,H,Me,NHCOCONHPh),(NHMe,Ph,H,Et,CONHPh),(NHMe,Ph,H,Et,CONH-3-pyridyl),(NHMe,Ph,H,Et,NHCOPh),(NHMe,Ph,H,Et,NHCO-2-furyl),(NHMe,Ph,H,Et,NHCONHPh),(NHMe,Ph,H,Et,NHCOCONHPh),(NHMe,Ph,H,CH2OH,CONHPh),(NHMe,Ph,H,CH2OH,CONH-3-pyridyl),(NHMe,Ph,H,CH2OH,NHCOPh),(NHMe,Ph,H,CH2OH,NHCO-2-furyl),(NHMe,Ph,H,CH2OH,NHCONHPh),(NHMe,Ph,H,CH2OH,NHCOCONHPh),(NHMe,Ph,Me,Me,CONHPh),(NHMe,Ph,Me,Me,CONH-3-pyridyl),(NHMe,Ph,Me,Me,NHCOPh),(NHMe,Ph,Me,Me,NHCO-2-furyl),(NHMe,Ph,Me,Me,NHCONHPh),(NHMe,Ph,Me,Me,NHCOCONHPh),(NHMe,Ph,Me,Et,CONHPh),(NHMe,Ph,Me,Et,CONH-3-pyridyl),(NHMe,Ph,Me,Et,NHCOPh),(NHMe,Ph,Me,Et,NHCO-2-furyl),(NHMe,Ph,Me,Et,NHCONHPh),(NHMe,Ph,Me,Et,NHCOCONHPh),(NHMe,Ph,Me,CH2OH,CONHPh),(NHMe,Ph,Me,CH2OH,CONH-3-pyridyl),(NHMe,Ph,Me,CH2OH,NHCOPh),(NHMe,Ph,Me,CH2OH,NHCO-2-furyl),(NHMe,Ph,Me,CH2OH,NHCONHPh),(NHMe,Ph,Me,CH2OH,NHCOCONHPh),(NHMe,Ph,Ph,Me,CONHPh),(NHMe,Ph,Ph,Me,CONH-3-pyridyl),(NHMe,Ph,Ph,Me,NHCOPh),(NHMe,Ph,Ph,Me,NHCO-2-furyl),(NHMe,Ph,Ph,Me,NHCONHPh),(NHMe,Ph,Ph,Me,NHCOCONHPh),(NHMe,Ph,Ph,Et,CONHPh),(NHMe,Ph,Ph,Et,CONH-3-pyridyl),(NHMe,Ph,Ph,Et,NHCOPh),(NHMe,Ph,Ph,Et,NHCO-2-furyl),(NHMe,Ph,Ph,Et,NHCONHPh),(NHMe,Ph,Ph,Et,NHCOCONHPh),(NHMe,Ph,Ph,CH2OH,CONHPh),(NHMe,Ph,Ph,CH2OH,CONH-3-pyridyl),(NHMe,Ph,Ph,CH2OH,NHCOPh),(NHMe,Ph,Ph,CH2OH,NHCO-2-furyl),(NHMe,Ph,Ph,CH2OH,NHCONHPh),(NHMe,Ph,Ph,CH2OH,NHCOCONHPh),(NHMe,Ph,OH,Me,CONHPh),(NHMe,Ph,OH,Me,CONH-3-pyridyl),(NHMe,Ph,OH,Me,NHCOPh),(NHMe,Ph,OH,Me,NHCO-2-furyl),(NHMe,Ph,OH,Me,NHCONHPh),(NHMe,Ph,OH,Me,NHCOCONHPh),(NHMe,Ph,OH,Et,CONHPh),(NHMe,Ph,OH,Et,CONH-3-pyridyl),(NHMe,Ph,OH,Et,NHCOPh),(NHMe,Ph,OH,Et,NHCO-2-furyl), (NHMe,Ph,OH,Et,NHCONHPh),(NHMe,Ph,OH,Et,
NHCOCONHPh),(NHMe,Ph,OH,CH2OH,CONHPh),
(NHMe,Ph,OH,CH2OH,CONH-3-pyridyl),(NHMe,Ph,
OH,CH2OH,NHCOPh),(NHMe,Ph,OH,CH2OH,NHCO-
2-furyl),(NHMe,Ph,OH,CH2OH,NHCONHPh),(NHMe,
Ph,OH,CH2OH,NHCOCONHPh),
(NHCH2CH2OH,H,H,Me,CONHPh),(NHCH2CH2OH,H,
H,Me,CONH-3-pyridyl),(NHCH2CH2OH,H,Me,NH-
COPh),(NHCH2CH2OH,H,H,Me,NHCO-2-furyl),
(NHCH2CH2OH,H,H,Me,NHCONHPh),
(NHCH2CH2OH,H,H,Me,NHCOCONHPh),
(NHCH2CH2OH,H,H,Et,CONHPh),(NHCH2CH2OH,
H,H,Et,CONH-3-pyridyl),(NHCH2CH2OH,H,H,Et,
NHCOPh),(NHCH2CH2OH,H,H,Et,NHCO-2-furyl),
(NHCH2CH2OH,H,H,Et,NHCONHPh),
(NHCH2CH2OH,H,H,Et,NHCOCONHPh),
(NHCH2CH2OH,H,H,CH2OH,CONHPh),
(NHCH2CH2OH,H,H,CH2OH,CONH-3-pyridyl),
(NHCH2CH2OH,H,H,CH2OH,NHCOPh),
(NHCH2CH2OH,H,H,CH2OH,NHCO-2-furyl),
(NHCH2CH2OH,H,H,CH2OH,NHCONHPh),
(NHCH2CH2OH,H,H,CH2OH,NHCOCONHPh),
(NHCH2CH2OH,H,Me,Me,CONHPh),
(NHCH2CH2OH,H,Me,Me,CONH-3-pyridyl),
(NHCH2CH2OH,H,Me,Me,NHCOPh),
(NHCH2CH2OH,H,Me,Me,NHCO-2-furyl),
(NHCH2CH2OH,H,Me,Me,NHCONHPh),
(NHCH2CH2OH,H,Me,Me,NHCOCONHPh),
(NHCH2CH2OH,H,Me,Et,CONHPh),(NHCH2CH2OH,
H,Me,Et,CONH-3-pyridyl),(NHCH2CH2OH,H,Me,Et,
NHCOPh),(NHCH2CH2OH,H,Me,Et,NHCO-2-furyl),
(NHCH2CH2OH,H,Me,Et,NHCONHPh),
(NHCH2CH2OH,H,Me,Et,NHCOCONHPh),
(NHCH2CH2OH,H,Me,CH2OH,CONHPh),
(NHCH2CH2OH,H,Me,CH2OH,CONH-3-pyridyl),
(NHCH2CH2OH,H,Me,CH2OH,NHCOPh),
(NHCH2CH2OH,H,Me,CH2OH,NHCO-2-furyl),
(NHCH2CH2OH,H,Me,CH2OH,NHCONHPh),
(NHCH2CH2OH,H,Me,CH2OH,NHCOCONHPh),
(NHCH2CH2OH,H,Ph,Me,CONHPh),(NHCH2CH2OH,
H,Ph,Me,CONH-3-pyridyl),(NHCH2CH2OH,H,Ph,Me,
NHCOPh),(NHCH2CH2OH,H,Ph,Me,NHCO-2-furyl),
(NHCH2CH2OH,H,Ph,Me,NHCONHPh),
(NHCH2CH2OH,H,Ph,Me,NHCOCONHPh),
(NHCH2CH2OH,H,Ph,Et,CONHPh),(NHCH2CH2OH,
H,Ph,Et,CONH-3pyridyl),(NHCH2CH2OH,H,Ph,Et,
NHCOPh),(NHCH2CH2OH,H,Ph,Et,NHCO-2-furyl),
(NHCH2CH2OH,H,Ph,Et,NHCONHPh),
(NHCH2CH2OH,H,Ph,Et,NHCOCONHPh),
(NHCH2CH2OH,H,Ph,CH2OH,CONHPh),
(NHCH2CH2OH,H,Ph,CH2OH,CONH-3-pyridyl),
(NHCH2CH2OH,H,Ph,CH2OH,NHCOPh),
(NHCH2CH2OH,H,Ph,CH2OH,NHCO-2-furyl),
(NHCH2CH2OH,H,Ph,CH2OH,NHCONHPh),
(NHCH2CH2OH,H,Ph,CH2OH,NHCOCONHPh),
(NHCH2CH2OH,H,OH,Me,CONHPh),
(NHCH2CH2OH,H,OH,Me,CONH-3-pyridyl),
(NHCH2CH2OH,H,OH,Me,NHCOPh),
(NHCH2CH2OH,H,OH,Me,NHCO-2-furyl),
(NHCH2CH2OH,H,OH,Me,NHCONHPh),
(NHCH2CH2OH,H,OH,Me,NHCOCONHPh),
(NHCH2CH2OH,H,OH,Et,CONHPh),(NHCH2CH2OH,
H,OH,Et,CONH-3-pyridyl),(NHCH2CH2OH,H,OH,Et,
NHCOPh),(NHCH2CH2OH,H,OH,Et,NHCO-2-furyl),
(NHCH2CH2OH,H,OH,Et,NHCONHPh),
(NHCH2CH2OH,H,OH,Et,NHCOCONHPh),
(NHCH2CH2OH,H,OH,CH2OH,CONHPh),
(NHCH2CH2OH,H,OH,CH2OH,CONH-3-pyridyl),
(NHCH2CH2OH,H,OH,CH2OH,NHCOPh),
(NHCH2CH2OH,H,OH,CH2OH,NHCO-2-furyl),
(NHCH2CH2OH,H,OH,CH2OH,NHCONHPh),
(NHCH2CH2OH,H,OH,CH2OH,NHCOCONHPh),
(NHCH2CH2OH,Me,H,Me,CONHPh),
(NHCH2CH2OH,Me,H,Me,CONH-3-pyridyl),
(NHCH2CH2OH,Me,H,Me,NHCOPh),
(NHCH2CH2OH,Me,H,Me,NHCO-2-furyl),
(NHCH2CH2OH,Me,H,Me,NHCONHPh),
(NHCH2CH2OH,Me,H,Me,NHCOCONHPh),
(NHCH2CH2OH,Me,H,Et,CONHPh),(NHCH2CH2OH,
Me,H,Et,CONH-3-pyridyl),(NHCH2CH2OH,Me,H,Et,
NHCOPh),(NHCH2CH2OH,Me,H,Et,NHCO-2-furyl),
(NHCH2CH2OH,Me,H,Et,NHCONHPh),
(NHCH2CH2OH,Me,H,Et,NHCOCONHPh),
(NHCH2CH2OH,Me,H,CH2OH,CONHPh),
(NHCH2CH2OH,Me,H,CH2OH,CONH-3-pyridyl),
(NHCH2CH2OH,Me,H,CH2OH,NHCOPh),
(NHCH2CH2OH,Me,H,CH2OH,NHCO-2-furyl),
(NHCH2CH2OH,Me,H,CH2OH,NHCONHPh),
(NHCH2CH2OH,Me,H,CH2OH,NHCOCONHPh),
(NHCH2CH2OH,Me,Me,Me,CONHPh),
(NHCH2CH2OH,Me,Me,Me,CONH-3-pyridyl),
(NHCH2CH2OH,Me,Me,Me,NHCOPh),
(NHCH2CH2OH,Me,Me,Me,NHCO-2-furyl),
(NHCH2CH2OH,Me,Me,Me,NHCONHPh),
(NHCH2CH2OH,Me,Me,Me,NHCOCONHPh),
(NHCH2CH2OH,Me,Me,Et,CONHPh),
(NHCH2CH2OH,Me,Me,Et,CONH-3-pyridyl),
(NHCH2CH2OH,Me,Me,Et,NHCOPh),
(NHCH2CH2OH,Me,Me,Et,NHCO-2-furyl),
(NHCH2CH2OH,Me,Me,Et,NHCONHPh),
(NHCH2CH2OH,Me,Me,Et,NHCOCONHPh),
(NHCH2CH2OH,Me,Me,CH2OH,CONHPh),
(NHCH2CH2OH,Me,Me,CH2OH,CONH-3-pyridyl),
(NHCH2CH2OH,Me,Me,CH2OH,NHCOPh),CH2OH,
NHCO-2-furyl),(NHCH2CH2OH,Me,Me,CH2OH,
NHCONHPh),(NHCH2CH2OH,Me,Me,CH2OH,
NHCOCONHPh),(NHCH2CH2OH,Me,Ph,Me,
CONHPh),(NHCH2CH2OH,Me,Ph,Me,CONH-3-
pyridyl),(NHCH2CH2OH,Me,Ph,Me,NRCOPh),
(NHCH2CH2OH,Me,Ph,Me,NHCO-2-furyl),
(NHCH2CH2OH,Me,Ph,Me,NHCONHPh),
(NHCH2CH2OH,Me,Ph,Me,NHCOCONHPh),
(NHCH2CH2OH,Me,Ph,Et,CONHPh),(NHCH2CH2OH,
Me,Ph,Et,CONH-3-pyridyl),(NHCH2CH2OH,Me,Ph,Et,
NHCOPh),(NHCH2CH2OH,Me,Ph,Et,NHCO-2-furyl),
(NHCH2CH2OH,Me,Ph,Et,NHCONHPh),
(NRCH2CH2OH,Me,Ph,Et,NHCOCONHPh),
(NHCH2CH2OH,Me,Ph,CH2OH,CONHPh),
(NHCH2CH2OH,Me,Ph,CH2OH,CONH-3-pyridyl),
(NHCH2CH2OH,Me,Ph,CH2OH,NHCOPh),
(NHCH2CH2OH,Me,Ph,CH2OH,NHCO-2-furyl),
(NHCH2CH2OH,Me,Ph,CH2OH,NHCONHPh),
(NHCH2CH2OH,Me,Ph,CH2OH,NHCOCONHPh),
(NHCH2CH2OH,Me,OH,Me,CONHPh),
(NHCH2CH2OH,Me,OH,Me,CONH-3-pyridyl),
(NHCH2CH2OH,Me,OH,Me,NHCOPh),
(NHCH2CH2OH,Me,OH,Me,NHCO-2-furyl),
(NHCH2CH2OH,Me,OH,Me,NHCONHPh),
(NHCH2CH2OH,Me,OH,Me,NHCOCONHPh),
(NHCH2CH2OH,Me,OH,Et,CONHPh),
(NHCH2CH2OH,Me,OH,Et,CONH-3-pyridyl),
(NHCH2CH2OH,Me,OH,Et,NHCOPh),
(NHCH2CH2OH,Me,OH,Et,NHCO-2-furyl),
(NHCH2CH2OH,Me,OH,Et,NHCONHPh), (NHCH2CH2OH,Me,OH,Et,NHCOCONHPh),
(NHCH2CH2OH,Me,OH,CH2OH,CONHPh),
(NHCH2CH2OH,Me,OH,CH2OH,CONH-3-pyridyl),
(NHCH2CH2OH,Me,OH,CH2OH,NHCOPh),
(NHCH2CH2OH,Me,OH,CH2OH,NHCO-2-furyl),
(NHCH2CH2OH,Me,OH,CH2OH,NHCONHPh),
(NHCH2CH2OH,Me,OH,CH2OH,NHCOCONHPh),
(NHCH2CH2OH,Ph,H,Me,CONHPh),(NHCH2CH2OH,
Ph,H,Me,CONH-3-pyridyl),(NHCH2CH2OH,Ph,H,Me,
NHCOPh),(NHCH2CH2OH,Ph,H,Me,NHCO-2-furyl),
(NHCH2CH2OH,Ph,H,Me,NHCONHPh),
(NHCH2CH2OH,Ph,H,Me,NHCOCONHPh),
(NHCH2CH2OH,Ph,H,Et,CONHPh),(NHCH2CH2OH,
Ph,H,Et,CONH-3-pyridyl),(NHCH2CH2OH,Ph,H,Et,
NHCOPh),(NHCH2CH2OH,Ph,H,Et,NHCO-2-furyl),
(NHCH2CH2OH,Ph,H,Et,NHCONHPh),
(NHCH2CH2OH,Ph,H,Et,NHCOCONHPh),
(NHCH2CH2OH,Ph,H,CH2OH,CONHPh),
(NHCH2CH2OH,Ph,H,CH2OH,CONH-3-pyridyl),
(NHCH2CH2OH,Ph,H,CH2OH,NHCOPh),
(NHCH2CH2OH,Ph,H,CH2OH,NHCO-2-furyl),
(NHCH2CH2OH,Ph,H,CH2OH,NHCONHPh),
(NHCH2CH2OH,Ph,H,CH2OH,NHCOCONHPh),
(NHCH2CH2OH,Ph,Me,Me,CONHPh),
(NHCH2CH2OH,Ph,Me,Me,CONH-3-pyridyl),
(NHCH2CH2OH,Ph,Me,Me,NHCOPh),
(NHCH2CH2OH,Ph,Me,Me,NHCO-2-furyl),
(NHCH2CH2OH,Ph,Me,Me,NHCONHPh),
(NHCH2CH2OH,Ph,Me,Me,NHCOCONHPh),
(NHCH2CH2OH,Ph,Me,Et,CONHPh),(NHCH2CH2OH,
Ph,Me,Et,CONH-3-pyridyl),(NHCH2CH2OH,Ph,Me,Et,
NHCOPh),(NHCH2CH2OH,Ph,Me,Et,NHCO-2-furyl),
(NHCH2CH2OH,Ph,Me,Et,NHCONHPh),
(NHCH2CH2OH,Ph,Me,Et,NHCOCONHPh),
(NHCH2CH2OH,Ph,Me,CH2OH,CONHPh),
(NHCH2CH2OH,Ph,Me,CH2OH,CONH-3-pyridyl),
(NHCH2CH2OH,Ph,Me,CH2OH,NHCOPh),
(NHCH2CH2OH,Ph,Me,CH2OH,NHCO-2-furyl),
(NHCH2CH2OH,Ph,Me,CH2OH,NHCONHPh),
(NHCH2CH2OH,Ph,Me,CH2OH,NHCOCONHPh),
(NHCH2CH2OH,Ph,Ph,Me,CONHPh),
(NHCH2CH2OH,Ph,Ph,Me,CONH-3-pyridyl),
(NHCH2CH2OH,Ph,Ph,Me,NHCOPh),
(NHCH2CH2OH,Ph,Ph,Me,NHCO-2-furyl),
(NHCH2CH2OH,Ph,Ph,Me,NHCONHPh),
(NHCH2CH2OH,Ph,Ph,Me,NHCOCONHPh),
(NHCH2CH2OH,Ph,Ph,Et,CONHPh),(NHCH2CH2OH,
Ph,Ph,Et,CONH-3-pyridyl),(NHCH2CH2OH,Ph Ph,Et,
NHCOPh),(NHCH2CH2OH,Ph,Ph,Et,NHCO-2-furyl),
(NHCH2CH2OH,Ph,Ph,Et,NHCONHPh),
(NHCH2CH2OH,Ph,Ph,Et,NHCOCONHPh),
(NHCH2CH2OH,Ph,Ph,CH2OH,CONHPh),
(NHCH2CH2OH,Ph,Ph,CH2OH,CONH-3-pyridyl),
(NHCH2CH2OH,Ph,Ph,CH2OH,NHCOPh),
(NHCH2CH2OH,Ph,Ph,CH2OH,NHCO-2-furyl),
(NHCH2CH2OH,Ph,Ph,CH2OH,NHCONHPh),
(NHCH2CH2OH,Ph,Ph,CH2OH,NHCOCONHPh),
(NHCH2CH2OH,Ph,OH,Me,CONHPh),
(NHCH2CH2OH,Ph,OH,Me,CONH-3-pyridyl),
(NHCH2CH2OH,Ph,OH,Me,NHCOPh),
(NHCH2CH2OH,Ph,OH,Me,NHCO-2-furyl),
(NHCH2CH2OH,Ph,OH,Me,NHCONHPh),
(NHCH2CH2OH,Ph,OH,Me,NHCOCONHPh),
(NHCH2CH2OH,Ph,OH,Et,CONHPh),
(NHCH2CH2OH,Ph,OH,Et,CONH-3-pyridyl),
(NHCH2CH2OH,Ph,OH,Et,NHCOPh),
(NHCH2CH2OH,Ph,OH,Et,NHCO-2-furyl),
(NHCH2CH2OH,Ph,OH,Et,NHCONHPh),
(NHCH2CH2OH,Ph,OH,Et,NHCOCONHPh),
(NHCH2CH2OH,Ph,OH,CH2OH,CONHPh),
(NHCH2CH2OH,Ph,OH,CH2OH,CONH-3-pyridyl),
(NHCH2CH2OH,Ph,OH,CH2OH,NHCOPh),
(NHCH2CH2OH,Ph,OH,CH2OH,NHCO-2-furyl),
(NHCH2CH2OH,Ph,OH,CH2OH,NHCONHPh),
(NHCH2CH2OH,Ph,OH,CH2OH,NHCOCONHPh),
(NHCH2CONH2,H,H,Me,CONHPh),(NHCH2CONH2,H,
H,Me,CONH-3-pyridyl),(NHCH2CONH2,H,H,Me,NH-
COPh),(NHCH2CONH2,H,H,Me,NHCO-2-furyl),
(NHCH2CONH2,H,H,Me,NHCONHPh),
(NHCH2CONH2,H,H,Me,NHCOCONHPh),
(NHCH2CONH2,H,H,Et,CONHPh),(NHCH2CONH2,
H,H,Et,CONH-3-pyridyl),(NHCH2CONH2,H,H,Et,
NHCOPh),(NHCH2CONH2,H,H,Et,NHCO-2-furyl),
(NHCH2CONH2,H,H,Et,NHCONHPh),
(NHCH2CONH2,H,H,Et,NHCOCONHPh),
(NHCH2CONH2,H,H,CH2OH,CONHPh),
(NHCH2CONH2,H,H,CH2OH,CONH-3-pyridyl),
(NHCH2CONH2,H,H,CH2OH,NHCOPh),
(NHCH2CONH2,H,H,CH2OH,NHCO-2-furyl),
(NHCH2CONH2,H,H,CH2OH,NHCONHPh),
(NHCH2CONH2,H,H,CH2OH,NHCOCONHPh),
(NHCH2CONH2,H,Me,Me,CONHPh),
(NHCH2CONH2,H,Me,Me,CONH-3-pyridyl),
(NHCH2CONH2,H,Me,Me,NHCOPh),
(NHCH2CONH2,H,Me,Me,NHCO-2-furyl),
(NHCH2CONH2,H,Me,Me,NHCONHPh),
(NHCH2CONH2,H,Me,Me,NHCOCONHPh),
(NHCH2CONH2,H,Me,Et,CONHPh),(NHCH2CONH2,
H,Me,Et,CONH-3-pyridyl),(NHCH2CONH2,H,Me,Et,
NHCOPh),(NHCH2CONH2,H,Me,Et,NHCO-2-furyl),
(NHCH2CONH2,H,Me,Et,NHCONHPh),
(NHCH2CONH2,H,Me,Et,NHCOCONHPh),
(NHCH2CONH2,H,Me,CH2OH,CONHPh),
(NHCH2CONH2,H,Me,CH2OH,CONH-3-pyridyl),
(NHCH2CONH2,H,Me,CH2OH,NHCOPh),
(NHCH2CONH2,H,Me,CH2OH,NHCO-2-furyl),
(NHCH2CONH2,H,Me,CH2OH,NHCONHPh),
(NHCH2CONH2,H,Me,CH2OH,NHCOCONHPh),
(NHCH2CONH2,H,Ph,Me,CONHPh),(NHCH2CONH2,
H,Ph,Me,CONH-3-pyridyl),(NHCH2CONH2,H,Ph,Me,
NHCOPh),(NHCH2CONH2,H,Ph,Me,NHCO-2-furyl),
(NHCH2CONH2,H,Ph,Me,NHCONHPh),
(NHCH2CONH2,H,Ph,Me,NHCOCONHPh),
(NHCH2CONH2,H,Ph,Et,CONHPh),(NHCH2CONH2,
H,Ph,Et,CONH-3-pyridyl),(NHCH2CONH2,H,Ph,Et,
NHCOPh),(NHCH2CONH2,H,Ph,Et,NHCO-2-furyl),
(NHCH2CONH2,H,Ph,Et,NHCONHPh),
(NHCH2CONH2,H,Ph,Et,NHCOCONHPh),
(NHCH2CONH2,H,Ph,CH2OH,CONHPh),
(NHCH2CONH2,H,Ph,CH2OH,CONH-3-pyridyl),
(NHCH2CONH2,H,Ph,CH2OH,NHCOPh),
(NHCH2CONH2,H,Ph,CH2OH,NHCO-2-furyl),
(NHCH2CONH2,H,Ph,CH2OH,NHCONHPh),
(NHCH2CONH2,H,Ph,CH2OH,NHCOCONHPh),
(NHCH2CONH2,H,OH,Me,CONHPh),
(NHCH2CONH2,H,Me,CONH-3-pyridyl),
(NHCH2CONH2,H,OH,Me,NHCOPh),
(NHCH2CONH2,H,OH,Me,NHCO-2-furyl),
(NHCH2CONH2,H,OH,Me,NHCONHPh),
(NHCH2CONH2,H,OH,Me,NHCOCONHPh),
(NHCH2CONH2,H,OH,Et,CONHPh),(NHCH2CONH2,
H,OH,Et,CONH-3-pyridyl),(NHCH2CONH2,H,OH,Et,
NHCOPh),(NHCH2CONH2,H,OH,Et,NHCO-2-furyl),
(NHCH2CONH2,H,OH,Et,NHCONHPh), (NHCH2CONH2,H,OH,Et,NHCOCONHPh),
(NHCH2CONH2,H,OH,CH2OH,CONHPh),
(NHCH2CONH2,H,OH,CH2OH,CONH-3-pyridyl),
(NHCH2CONH2,H,OH,CH2OH,NHCOPh),
(NHCH2CONH2,H,OH,CH2OH,NHCO-2-furyl),
(NHCH2CONH2,H,OH,CH2OH,NHCONHPh),
(NHCH2CONH2,H,OH,CH2OH,NHCOCONHPh),
(NHCH2CONH2,Me,H,Me,CONHPh),
(NHCH2CONH2,Me,H,Me,CONH-3-pyridyl),
(NHCH2CONH2,Me,H,Me,NHCOPh),
(NHCH2CONH2,Me,H,Me,NHCO-2-furyl),
(NHCH2CONH2,Me,H,Me,NHCONHPh),
(NHCH2CONH2,Me,H,Me,NHCOCONHPh),
(NHCH2CONH2,Me,H,Et,CONHPh),(NHCH2CONH2,Me,H,Et,CONH-3-pyridyl),(NHCH2CONH2,Me,H,Et,NHCOPh),(NHCH2CONH2,Me,H,Et,NHCO-2-furyl),
(NHCH2CONH2,Me,H,Et,NHCONHPh),
(NHCH2CONH2,Me,H,Et,NHCOCONHPh),
(NHCH2CONH2,Me,H,CH2OH,CONHPh),
(NHCH2CONH2,Me,H,CH2OH,CONH-3-pyridyl),
(NHCH2CONH2,Me,H,CH2OH,NHCOPh),
(NHCH2CONH2,Me,H,CH2OH,NHCO-2-furyl),
(NHCH2CONH2,Me,H,CH2OH,NHCONHPh),
(NHCH2CONH2,Me,H,CH2OH,NHCOCONHPh),
(NHCH2CONH2,Me,Me,Me,CONHPh),
(NHCH2CONH2,Me,Me,Me,CONH-3-pyridyl),
(NHCH2CONH2,Me,Me,Me,NHCOPh),
(NHCH2CONH2,Me,Me,Me,NHCO-2-furyl),
(NHCH2CONH2,Me,Me,Me,NHCONHPh),
(NHCH2CONH2,Me,Me,Me,NHCOCONHPh),
(NHCH2CONH2,Me,Me,Et,CONHPh),
(NHCH2CONH2,Me,Me,Et,CONH-3-pyridyl),
(NHCH2CONH2,Me,Me,Et,NHCOPh),
(NHCH2CONH2,Me,Me,Et,NHCO-2-furyl),
(NHCH2CONH2,Me,Me,Et,NHCONHPh),
(NHCH2CONH2,1Me,Me,Et,NHCOCONHPh),
(NHCH2CONH2,Me,Me,CH2OH,CONHPh),
(NHCH2CONH2,Me,Me,CH2OH,CONH-3-pyridyl),
(NHCH2CONH2,Me,Me,CH2OH,NHCOPh),
(NHCH2CONH2,Me,Me,CH2OH,NHCO-2-furyl),
(NHCH2CONH2,Me,Me,CH2OH,NHCONHPh),
(NHCH2CONH2,Me,Me,CH2OH,NHCOCONHPh),
(NHCH2CONH2,Me,Ph,Me,CONHPh),
(NHCH2CONH2,Me,Ph,Me,CONH-3-pyridyl),
(NHCH2CONH2,Me,Ph,Me,NHCOPh),
(NHCH2CONH2,Me,Ph,Me,NHCO-2-furyl),
(NHCH2CONH2,Me,Ph,Me,NHCONHPh),
(NHCH2CONH2,Me,Ph,Me,NHCOCONHPh),
(NHCH2CONH2,Me,Ph,Et,CONHPh),(NHCH2CONH2,Me,Ph,Et,CONH-3-pyridyl),(NHCH2CONH2,Me,Ph,Et,NHCOPh),(NHCH2CONH2,Me,Ph,Et,NHCO-2-furyl),
(NHCH2CONH2,Me,Ph,Et,NHCONHPh),
(NHCH2CONH2,Me,Ph,Et,NHCOCONHPh),
(NHCH2CONH2,Me,Ph,CH2OH,CONHPh),
(NHCH2CONH2,Me,Ph,CH2OH,CONH-3-pyridyl),
(NHCH2CONH2,Me,Ph,CH2OH,NHCOPh),
(NHCH2CONH2,Me,Ph,CH2OH,NHCO-2-furyl),
(NHCH2CONH2,Me,Ph,CH2OH,NHCONHPh),
(NHCH2CONH2,Me,Ph,CH2OH,NHCOCONHPh),
(NHCH2CONH2,Me,OH,Me,CONHPh),
(NHCH2CONH2,Me,OH,Me,CONH-3-pyridyl),
(NHCH2CONH2,Me,OH,Me,NHCOPh),
(NHCH2CONH2,Me,OH,Me,NHCO-2-furyl),
(NHCH2CONH2,Me,OH,Me,NHCONHPh),
(NHCH2CONH2,Me,OH,Me,NHCOCONHPh),
(NHCH2CONH2,Me,OH,Et,CONHPh),
(NHCH2CONH2,Me,OH,Et,CONH-3-pyridyl),
(NHCH2CONH2,Me,OH,Et,NHCOPh),
(NHCH2CONH2,Me,OH,Et,NHCO-2-furyl),
(NHCH2CONH2,Me,OH,Et,NHCONHPh),
(NHCH2CONH2,Me,OH,Et,NHCOCONHPh),
(NHCH2CONH2,Me,OH,CH2OH,CONHPh),
(NHCH2CONH2,Me,OH,CH2OH,CONH-3-pyridyl),
(NHCH2CONH2,Me,OH,CH2OH,NHCOPh),
(NHCH2CONH2,Me,OH,CH2OH,NHCO-2-furyl),
(NHCH2CONH2,Me,OH,CH2OH,NHCONHPh),
(NHCH2CONH2,Me,OH,CH2OH,NHCOCONHPh),
(NHCH2CONH2,Ph,H,Me,CONHPh),(NHCH2CONH2,Ph,H,Me,CONH-3-pyridyl),(NHCH2CONH2,Ph,H,Me,NHCOPh),(NHCH2CONH2,Ph,H,Me,NHCO-2-furyl),
(NHCH2CONH2,Ph,H,Me,NHCONHPh),
(NHCH2CONH2,Ph,H,Me,NHCOCONHPh),
(NHCH2CONH2,Ph,H,Et,CONHPh),(NHCH2CONH2,Ph,H,Et,CONH-3-pyridyl),(NHCH2CONH2,Ph,H,Et,NHCOPh),(NHCH2CONH2,Ph,H,Et,NHCO-2-furyl),
(NHCH2CONH2,Ph,H,Et,NHCONHPh),
(NHCH2CONH2,Ph,H,Et,NHCOCONHPh),
(NHCH2CONH2,Ph,H,CH2OH,CONHPh),
(NHCH2CONH2,Ph,H,CH2OH,CONH-3-pyridyl),
(NHCH2CONH2,Ph,H,CH2OH,NHCOPh),
(NHCH2CONH2,Ph,H,CH2OH,NHCO-2-furyl),
(NHCH2CONH2,Ph,H,CH2OH,NHCONHPh),
(NHCH2CONH2,Ph,H,CH2OH,NHCOCONHPh),
(NHCH2CONH2,Ph,Me,Me,CONHPh),
(NHCH2CONH2,Ph,Me,Me,CONH-3-pyridyl),
(NHCH2CONH2,Ph,Me,Me,NHCOPh),
(NHCH2CONH2,Ph,Me,Me,NHCO-2-furyl),
(NHCH2CONH2,Ph,Me,Me,NHCONHPh),
(NHCH2CONH2,Ph,Me,Me,NHCOCONHPh),
(NHCH2CONH2,Ph,Me,Et,CONHPh),(NHCH2CONH2,Ph,Me,Et,CONH-3-pyridyl),(NHCH2CONH2,Ph,Me,Et,NHCOPh),(NHCH2CONH2,Ph,Me,Et,NHCO-2-furyl),
(NHCH2CONH2,Ph,Me,Et,NHCONHPh),
(NHCH2CONH2,Ph,Me,Et,NHCOCONHPh),
(NHCH2CONH2,Ph,Me,CH2OH,CONHPh),
(NHCH2CONH2,Ph,Me,CH2OH,CONH-3-pyridyl),
(NHCH2CONH2,Ph,Me,CH2OH,NHCOPh),
(NHCH2CONH2,Ph,Me,CH2OH,NHCO-2-furyl),
(NHCH2CONH2,Ph,Me,CH2OH,NHCONHPh),
(NHCH2CONH2,Ph,Me,CH2OH,NHCOCONHPh),
(NHCH2CONH2,Ph,Ph,Me,CONHPh),
(NHCH2CONH2,Ph,Ph,Me,CONH-3-pyridyl),
(NHCH2CONH2,Ph,Ph,Me,NHCOPh),
(NHCH2CONH2,Ph,Ph,Me,NHCO-2-furyl),
(NHCH2CONH2,Ph,Ph,Me,NHCONHPh),
(NHCH2CONH2,Ph,Ph,Me,NHCOCONHPh),
(NHCH2CONH2,Ph,Ph,Et,CONHPh),(NHCH2CONH2,Ph,Ph,Et,CONH-3-pyridyl),(NHCH2CONH2,Ph,Ph,Et,NHCOPh),(NHCH2CONH2,Ph,Ph,Et,NHCO-2-furyl),
(NHCH2CONH2,Ph,Ph,Et,NHCONHPh),
(NHCH2CONH2,Ph,Ph,Et,NHCOCONHPh),
(NHCH2CONH2,Ph,Ph,CH2OH,CONHPh),
(NHCH2CONH2,Ph,Ph,CH2OH,CONH-3-pyridyl),
(NHCH2CONH2,Ph,Ph,CH2OH,NHCOPh),
(NHCH2CONH2,Ph,Ph,CH2OH,NHCO-2-furyl),
(NHCH2CONH2,Ph,Ph,CH2OH,NHCONHPh),
(NHCH2CONH2,Ph,Ph,CH2OH,NHCOCONHPh),
(NHCH2CONH2,Ph,OH,Me,CONHPh),
(NHCH2CONH2,Ph,OH,Me,CONH-3-pyridyl),
(NHCH2CONH2,Ph,OH,Me,NHCOPh),
(NHCH2CONH2,Ph,OH,Me,NHCO-2-furyl),
(NHCH2CONH2,Ph,OH,Me,NHCONHPh),
(NHCH2CONH2,Ph,OH,Me,NHCOCONHPh),
(NHCH2CONH2,Ph,OH,Et,CONHPh), (NHCH2CONH2,Ph,OH,Et,CONH-3-pyridyl),
(NHCH2CONH2,Ph,OH,Et,NHCOPh),
(NHCH2CONH2,Ph,OH,Et,NHCO-2-furyl),
(NHCH2CONH2,Ph,OH,Et,NHCONHPh),
(NHCH2CONH2,Ph,OH,Et,NHCOCONHPh),
(NHCH2CONH2,Ph,OH,CH2OH,CONHPh),
(NHCH2CONH2,Ph,OH,CH2OH,CONH-3-pyridyl),
(NHCH2CONH2,Ph,OH,CH2OH,NHCOPh),
(NHCH2CONH2,Ph,OH,CH2OH,NHCO-2-furyl),
(NHCH2CONH2,Ph,OH,CH2OH,NHCONHPh),
(NHCH2CONH2,Ph,OH,CH2OH,NHCOCONHPh),
(NHCH(Bn)CONH2,H,H,Me,CONHPh),(NHCH(Bn)CONH2,H,H,Me,CONH-3-pyridyl),(NHCH(Bn)CONH2,H,H,Me,NHCOPh),(NHCH(Bn)CONH2,H,H,Me,NHCO-2-furyl),(NHCH(Bn)CONH2,H,H,Me,NHCONHPh),(NHCH(Bn)CONH2,H,H,Me,NHCOCONHPh),(NHCH(Bn)CONH2,H,H,Et,CONHPh),(NHCH(Bn)CONH2,H,H,Et,CONH-3-pyridyl),(NHCH(Bn)CONH2,H,H,Et,NHCOPh),(NHCH(Bn)CONH2,H,H,Et,NHCO-2-furyl),(NHCH(Bn)CONH2,H,H,Et,NHCONHPh),(NHCH(Bn)CONH2,H,H,Et,NHCOCONHPh),(NHCH(Bn)CONH2,H,H,CH2OH,CONHPh),(NHCH(Bn)CONH2,H,H,CH2OH,CONH-3-pyridyl),(NHCH(Bn)CONH2,H,H,CH2OH,NHCOPh),(NHCH(Bn)CONH2,H,H,CH2OH,NHCO-2-furyl),(NHCH(Bn)CONH2,H,H,CH2OH,NHCONHPh),(NHCH(Bn)CONH2,H,H,CH2OH,NHCOCONHPh),(NHCH(Bn)CONH2,H,Me,Me,CONHPh),(NHCH(Bn)CONH2,H,Me,Me,CONH-3-pyridyl),(NHCH(Bn)CONH2,H,Me,Me,NHCOPh),(NHCH(Bn)CONH2,H,Me,Me,NHCO-2-furyl),(NHCH(Bn)CONH2,H,Me,Me,NHCONHPh),(NHCH(Bn)CONH2,H,Me,Me,NHCOCONHPh),(NHCH(Bn)CONH2,H,Me,Et,CONHPh),(NHCH(Bn)CONH2,H,Me,Et,CONH-3-pyridyl),(NHCH(Bn)CONH2,H,Me,Et,NHCOPh),(NHCH(Bn)CONH2,H,Me,Et,NHCO-2-furyl),(NHCH(Bn)CONH2,H,Me,Et,NHCONHPh),(NHCH(Bn)CONH2,H,Me,Et,NHCOCONHPh),(NHCH(Bn)CONH2,H,Me,CH2OH,CONHPh),(NHCH(Bn)CONH2,H,Me,CH2OH,CONH-3-pyridyl),(NHCH(Bn)CONH2,H,Me,CH2OH,NHCOPh),(NHCH(Bn)CONH2,H,Me,CH2OH,NHCO-2-furyl),(NHCH(Bn)CONH2,H,Me,CH2OH,NHCONHPh),(NHCH(Bn)CONH2,H,Me,CH2OH,NHCOCONHPh),(NHCH(Bn)CONH2,H,Ph,Me,CONHPh),(NHCH(Bn)CONH2,H,Ph,Me,CONH-3-pyridyl),(NHCH(Bn)CONH2,H,Ph,Me,NHCOPh),(NHCH(Bn)CONH2,H,Ph,Me,NHCO-2-furyl),(NHCH(Bn)CONH2,H,Ph,Me,NHCONHPh),(NHCH(Bn)CONH2,H,Ph,Me,NHCOCONHPh),(NHCH(Bn)CONH2,H,Ph,Et,CONHPh),(NHCH(Bn)CONH2,H,Ph,Et,CONH-3-pyridyl),(NHCH(Bn)CONH2,H,Ph,Et,NHCOPh),(NHCH(Bn)CONH2,H,Ph,Et,NHCO-2-furyl),(NHCH(Bn)CONH2,H,Ph,Et,NHCONHPh),(NHCH(Bn)CONH2,H,Ph,Et,NHCOCONHPh),(NHCH(Bn)CONH2,H,Ph,CH2OH,CONHPh),(NHCH(Bn)CONH2,H,Ph,CH2OH,CONH-3-pyridyl),(NHCH(Bn)CONH2,H,Ph,CH2OH,NHCOPh),(NHCH(Bn)CONH2,H,Ph,CH2OH,NHCO-2-furyl),(NHCH(Bn)CONH2,H,Ph,CH2OH,NHCONHPh),(NHCH(Bn)CONH2,H,Ph,CH2OH,NHCOCONHPh),(NHCH(Bn)CONH2,H,OH,Me,CONHPh),(NHCH(Bn)CONH2,H,OH,Me,CONH-3-pyridyl),(NHCH(Bn)CONH2,H,OH,Me,NHCOPh),(NHCH(Bn)CONH2,H,OH,Me,NHCO-2-furyl),(NHCH(Bn)CONH2,H,OH,Me,NHCONHPh),(NHCH(Bn)CONH2,H,OH,Me,NHCOCONHPh),(NHCH(Bn)CONH2,H,OH,Et,CONHPh),(NHCH(Bn)CONH2,H,OH,Et,CONH-3-pyridyl),(NHCH(Bn)CONH2,H,OH,Et,NHCOPh),(NHCH(Bn)CONH2,H,OH,Et,NHCO-2-furyl),(NHCH(Bn)CONH2,H,OH,Et,NHCONHPh),(NHCH(Bn)CONH2,H,OH,Et,NHCOCONHPh),(NHCH(Bn)CONH2,H,OH,CH2OH,CONHPh),(NHCH(Bn)CONH2,H,OH,CH2OH,CONH-3-pyridyl),(NHCH(Bn)CONH2,H,OH,CH2OH,NHCOPh),(NHCH(Bn)CONH2,H,OH,CH2OH,NHCO-2-furyl),(NHCH(Bn)CONH2,H,OH,CH2OH,NHCONHPh),(NHCH(Bn)CONH2,H,OH,CH2OH,NHCOCONHPh),(NHCH(Bn)CONH2,Me,H,Me,CONHPh),(NHCH(Bn)CONH2,Me,H,Me,CONH-3-pyridyl),(NHCH(Bn)CONH2,Me,H,Me,NHCOPh),(NHCH(Bn)CONH2,Me,H,Me,NHCO-2-furyl),(NHCH(Bn)CONH2,Me,H,Me,NHCONHPh),(NHCH(Bn)CONH2,Me,Me,NHCOCONHPh),(NHCH(Bn)CONH2,Me,H,Et,CONHPh),(NHCH(Bn)CONH2,Me,H,Et,CONH-3-pyridyl),(NHCH(Bn)CONH2,Me,H,Et,NHCOPh),(NHCH(Bn)CONH2,Me,H,Et,NHCO-2-furyl,(NHCH(Bn)CONH2,Me,H,Et,NHCONHPh),(NHCH(Bn)CONH2,Me,H,Et,NHCOCONHPh),(NHCH(Bn)CONH2,Me,H,CH2OH,CONHPh),(NHCH(Bn)CONH2,Me,H,CH2OH,CONH-3-pyridyl),(NHCH(Bn)CONH2,Me,H,CH2OH,NHCOPh),(NHCH(Bn)CONH2,Me,H,CH2OH,NHCO-2-furyl),(NHCH(Bn)CONH2,Me,H,CH2OH,NHCONHPh),(NHCH(Br)CONH2,Me,H,CH2OH,NHCOCONHPh),(NHCH(Bn)CONH2,Me,Me,Me,CONHPh),(NHCH(Bn)CONH2,Me,Me,Me,CONH-3-pyridyn,(NHCH(Bn)CONH2,Me,Me,Me,NHCOPh),(NHCH(Bn)CONH2,Me,Me,Me,NHCO-2-furyl),(NHCH(Bn)CONH2,Me,Me,Me,NHCONHPh),(NHCH(Bn)CONH2,Me,Me,Me,NHCOCONHPh),(NHCH(Bn)CONH2,Me,Me,Et,CONHPh),(NHCH(Bn)CONH2,Me,Me,Et,CONH-3-pyridyl),(NHCH(Bn)CONH2,Me,Me,Et,NHCOPh),(NHCH(Br)CONH2,Me,Me,Et,NHCO-2-furyl),(NRCH(Bn)CONH2,Me,Me,Et,NHCONHPh),(NHCH(Bn)CONH2,Me,Me,Et,NHCOCONHPh),(NHCH(Bn)CONH2,Me,Me,CH2OH,CONHPh),(NHCH(Bn)CONH2,Me,Me,CH2OH,CONH-3-pyridyl),(NHCH(Bn)CONH2,Me,Me,CH2OH,NHCOPh),(NHCH(Bn)CONH2,Me,Me,CH2OH,NHCO-2-furyl),(NHCH(Bn)CONH2,Me,Me,CH2OH,NHCONHPh),(NHCH(Bn)CONH2,Me,Me,CH2OH,NHCOCONHPh),(NHCH(Bn)CONH2,Me,Ph,Me,CONHPh),(NHCH(Bn)CONH2,Me,Ph,Me,CONH-3-pyridyl),(NHCH(Bn)CONH2,Me,Ph,Me,CONHPh),(NHCH(Bn)CONH2,Me,Ph,Me,NHCO-2-furyl),(NHCH(Bn)CONH2,Me,Ph,Me,NHCONHPh),(NHCH(Bn)CONH2,Me,Ph,Me,NHCOCONHPh),(NHCH(Bn)CONH2,Me,Ph,Et,CONHPh),(NHCH(Bn)CONH2,Me,Ph,Et,CONH-3-pyridyl),(NHCH(Bn)CONH2,Me,Ph,Et,NHCOPh),(NHCH(Bn)CONH2,Me,Ph,Et,NHCO-2-furyl),(NHCH(Bn)CONH2,Me,Ph,Et,NHCONHPh),(NHCH(Bn)CONH2,Me,Ph,Et,NHCOCONHPh),(NHCH(Bn)CONH2,Me,Ph,CH2OH,CONHPh),(NHCH(Bn)CONH2,Me,Ph,CH2OH,CONH-3-pyridyl),(NHCH(Bn)CONH2,Me,Ph,CH2OH,NHCOPh),(NHCH(Bn)CONH2,Me,Ph,CH2OH,NHCO-2-furyl),(NHCH(Bn)CONH2,Me,Ph,CH2OH,NHCONHPh),(NHCH(Bn)CONH2,Me,Ph,CH2OH,NHCOCONHPh),(NHCH(Bn)CONH2,Me,OH,Me,CONHPh),(NHCH(Bn)CONH2,Me,OH,Me,CONH-3-pyridyl),(NHCH(Bn)CONH2,Me,OH,Me,NHCOPh),(NHCH(Bn)CONH2,Me,OH,Me,NHCO-2-furyl,(NHCH(Bn)CONH2,Me,OH,Me,NHCONHPh),(NHCH(Bn)CONH2,Me,OH,Me,NHCOCONHPh),(NHCH(Bn)CONH2,Me,OH,Et,CONHPh),(NHCH(Bn)CONH2,Me,OH,Et,CONH-3-pyridyl),(NHCH(Bn)CONH2,Me,OH,Et,NHCOPh),(NHCH(Bn)CONH2,Me,OH,Et,NHCO-2-furyl),(NHCH(Bn)CONH2,Me,OH,Et,NHCONHPh),(NHCH(Bn)

CONH2,Me,OH,Et,NHCOCONHPh),(NHCH(Bn)
CONH2,Me,OH,CH2OH,CONHPh),(NHCH(Bn)
CONH2,Me,OH,CH2OH,CONH-3-pyridyl),(NHCH(Bn)
CONH2,Me,OH,CH2OH,NHCOPh),(NHCH(Bn)
CONH2,Me,OH,CH2OH,NHCO-2-furyl),(NHCH(Bn)
CONH2,Me,OH,CH2OH,NHCONHPh),(NHCH(Bn)
CONH2,Me,OH,CH2OH,NHCOCONHPh),(NHCH(Bn)
CONH2,Ph,H,Me,CONHPh),(NHCH(Bn)CONH2,Ph,H,
Me,CONH-3-pyridyl),(NHCH(Bn)CONH2,Ph,H,Me,
NHCOPh),(NHCH(Bn)CONH2,Ph,H,Me,NHCO-2-
furyl),(NHCH(Bn)CONH2,Ph,H,Me,NHCONHPh),
(NHCH(Bn)CONH2,Ph,H,Me,NHCOCONHPh),(NHCH
(Bn)CONH2,Ph,H,Et,CONHPh),(NHCH(Bn)CONH2,
Ph,H,Et,CONH-3-pyridyl,(NHCH(Bn)CONH2,Ph,H,Et,
NHCOPh),(NHCH(Bn)CONH2,Ph,H,Et,NHCO-2-furyl),
(NHCH(Bn)CONH2,Ph,H,Et,NHCONHPh),(NHCH(Bn)
CONH2,Ph,H,Et,NHCOCONHPh),(NHCH(Bn)CONH2,
Ph,H,CH2OH,CONHPh),(NHCH(Bn)CONH2,Ph,H,
CH2OH,CONH-3-pyridyl),(NHCH(Bn)CONH2,Ph,H,
CH2OH,NHCOPh),(NHCH(Bn)CONH2,Ph,H,CH2OH,
NHCO-2-furyl),(NHCH(Bn)CONH2,Ph,H,CH2OH,
NHCONHPh),(NHCH(Bn)CONH2,Ph,H,CH2OH,
NHCOCONHPh),(NHCH(Bn)CONH2,Ph,Me,Me,
CONHPh),(NHCH(Bn)CONH2,Ph,Me,Me,CONH-3-
pyridyl),(NHCH(Bn)CONH2,Ph,Me,Me,NHCOPh),
(NHCH(Bn)CONH2,Ph,Me,Me,NHCO-2-furyl),(NHCH
(Bn)CONH2,Ph,Me,Me,NHCONHPh),(NHCH(Bn)
CONH2,Ph,Me,Me,NHCOCONHPh),(NHCH(Bn)
CONH2,Ph,Me,Et,CONHPh),(NHCH(Bn)CONH2,Ph,
Me,Et,CONH-3-pyridyl),(NHCH(Bn)CONH2,Ph,Me,Et,
NHCOPh),(NHCH(Bn)CONH2,Ph,Me,Et,NHCO-2-
furyl),(NHCH(Bn)CONH2,Ph,Me,Et,NHCONHPh),
(NHCH(Bn)CONH2,Ph,Me,Et,NHCOCONHPh),
(NHCH(Bn)CONH2,Ph,Me,CH2OH,CONHPh),(NHCH
(Bn)CONH2,Ph,Me,CH2OH,CONH-3-pyridyl),(NHCH
(Bn)CONH2,Ph,Me,CH2OH,NHCOPh),(NHCH(Bn)
CONH2,Ph,Me,CH2OH,NHCO-2-furyl),(NHCH(Bn)
CONH2,Ph,Me,CH2OH,NHCONHPh),(NHCH(Bn)
CONH2,Ph,Me,CH2OH,NHCOCONHPh),(NHCH(Bn)
CONH2,Ph,Ph,Me,CONHPh),(NHCH(Bn)CONH2,Ph,
Ph,Me,CONH-3-pyridyl),(NHCH(Bn)CONH2,Ph,Ph,
Me,NHCOPh),(NHCH(Bn)CONH2,Ph,Ph,Me,NHCO-2-
furyl),(NHCH(Bn)CONH2,Ph,Ph,Me,NHCONHPh),
(NHCH(Bn)CONH2,Ph,Ph,Me,NHCOCONHPh),
(NHCH(Bn)CONH2,Ph,Ph,Et,CONHPh),(NHCH(Bn)
CONH2,Ph,Ph,Et,CONH-3-pyridyl),(NHCH(Bn)
CONH2,Ph,Ph,Et,NHCOPh),(NHCH(Bn)CONH2,Ph,Ph,
Et,NHCO-2-furyl),(NHCH(Bn)CONH2,Ph,Ph,Et,
NHCONHPh),(NHCH(Bn)CONH2,Ph,Ph,Et,
NHCOCONHPh),(NHCH(Bn)CONH2,Ph,Ph,CH2OH,
CONHPh),(NHCH(Bn)CONH2,Ph,Ph,CH2OH,CONH-
3-pyridyl),(NHCH(Bn)CONH2,Ph,Ph,CH2OH,
NHCOPh),(NHCH(Bn)CONH2,Ph,Ph,CH2OH,NHCO-
2-furyl),(NHCH(Bn)CONH2,Ph,Ph,CH2OH,
NHCONHPh),(NHCH(Bn)CONH2,Ph,Ph,CH2OH,
NHCOCONHPh),(NHCH(Bn)CONH2,Ph,OH,Me,
CONHPh),(NHCH(Bn)CONH2,Ph,OH,Me,CONH-3-
pyridyl),(NHCH(Bn)CONH2,Ph,OH,Me,NHCOPh),
(NHCH(Br)CONH2,Ph,OH,Me,NHCO-2-furyl),(NHCH
(Bn)CONH2,Ph,OH,Me,NHCONHPh),(NHCH(Bn)
CONH2,Ph,OH,Me,NHCOCONHPh),(NHCH(Bn)
CONH2,Ph,OH,Et,CONHPh),(NHCH(Bn)CONH2,Ph,
OH,Et,CONH-3-pyridyl),(NHCH(Bn)CONH2,Ph,OH,
Et,NHCOPh),(NHCH(Bn)CONH2,Ph,OH,Et,NHCO-2-
furyl),(NHCH(Bn)CONH2,Ph,OH,Et,NHCONHPh),
(NHCH(Bn)CONH2,Ph,OH,Et,NHCOCONHPh),
(NHCH(Bn)CONH2,Ph,OH,CH2OH,CONHPh),(NHCH
(Bn)CONH2,Ph,OH,CH2OH,CONH-3-pyridyl),(NHCH
(Bn)CONH2,Ph,OH,CH2OH,NHCOPh),(NHCH(Bn)
CONH2,Ph,OH,CH2OH,NHCO-2-furyl),(NHCH(Bn)
CONH2,Ph,OH,CH2OH,NHCONHPh),(NHCH(Bn)
CONH2,Ph,OH,CH2OH,NHCOCONHPh),
(NHCH(Me)CH2OH,H,H,Me,CONHPh),(NHCH(Me)
CH2OH,H,H,Me,CONH-3-pyridyl),(NHCH(Me)
CH2OH,H,H,Me,NHCOPh),(NHCH(Me)CH2OH,H,H,
Me,NHCO-2-furyl),(NHCH(Me)CH2OH,H,H,Me,
NHCONHPh),(NHCH(Me)CH2OH,H,H,Me,
NHCOCONHPh),(NHCH(Me)CH2OH,H,H,Et,
CONHPh),(NHCH(Me)CH2OH,H,H,Et,CONH-3-
pyridyl),(NHCH(Me)CH2OH,H,H,Et,NHCOPh),(NHCH
(Me)CH2OH,H,H,Et,NHCO-2-furyl),(NHCH(Me)
CH2OH,H,H,Et,NHCONHPh),(NHCH(Me)CH2OH,H,
H,Et,NHCOCONHPh),(NHCH(Me)CH2OH,H,H,
CH2OH,CONHPh),(NHCH(Me)CH2OH,H,H,CH2OH,
CONH-3-pyridyl),(NHCH(Me)CH2OH,H,H,CH2OH,
NHCOPh),(NHCH(Me)CH2OH,H,H,CH2OH,NHCO-2-
furyl),(NHCH(Me)CH2OH,H,H,CH2OH,NHCONHPh),
(NHCH(Me)CH2OH,H,H,CH2OH,NHCOCONHPh,
(NHCH(Me)CH2OH,H,Me,Me,CONHPh),(NHCH(Me)
CH2OH,Me,Me,CONH-3-pyridyl),(NHCH(Me)CH2OH,
H,Me,Me,NHCOPh),(NHCH(Me)CH2OH,H,Me,Me,
NHCO-2-furyl),(NHCH(Me)CH2OH,H,Me,Me,
NHCONHPh),(NHCH(Me)CH2OH,H,Me,Me,
NHCOCONHPh),(NHCH(Me)CH2OH,H,Me,Et,
CONHPh),(NHCH(Me)CH2OH,H,Me,Et,CONH-3-
pyridyl),(NHCH(Me)CH2OH,H,Me,Et,NHCOPh),
(NHCH(Me)CH2OH,H,Me,Et,NHCO-2-furyl),(NHCH
(Me)CH2OH,Me,Et,NHCONHPh),(NHCH(Me)CH2OH,
H,Me,Et,NHCOCONHPh),(NHCH(Me)CH2OH,H,Me,
CH2OH,CONHPh),(NHCH(Me)CH2OH,H,Me,CH2OH,
CONH-3-pyridyl),(NHCH(Me)CH2OH,H,Me,CH2OH,
NHCOPh),(NHCH(Me)CH2OH,H,Me,CH2OH,NHCO-
2-furyl),(NHCH(Me)CH2OH,H,Me,CH2OH,
NHCONHPh),(NHCH(Me)CH2OH,NHCOCONHPh),
(NHCH(Me)CH2OH,H,Ph,Me,CONHPh),(NHCH(Me)
CH2OH,H,Ph,Me,CONH-3-pyridyl),(NHCH(Me)
CH2OH,H,Ph,Me,NHCOPh),(NHCH(Me)CH2OH,H,Ph,
Me,NHCO-2-furyl),(NHCH(Me)CH2OH,H,Ph,Me,
NHCONHPh),(NHCH(Me)CH2OH,H,Ph,Me,
NHCOCONHPh),(NHCH(Me)CH2OH,H,Ph,Et,
CONHPh),(NHCH(Me)CH2OH,H,Ph,Et,CONH-3-
pyridyl),(NHCH(Me)CH2OH,H,Ph,Et,NHCOPh),
(NHCH(Me)CH2OH,H,Ph,Et,NHCO-2-furyl),(NHCH
(Me)CH2OH,Ph,Et,NHCONHPh),(NHCH(Me)CH2OH,
H,Ph,Et,NHCOCONHPh),(NHCH(Me)CH2OH,H,Ph,
CH2OH,CONHPh),(NHCH(Me)CH2OH,H,Ph,CH2OH,
CONH-3-pyridyl),(NHCH(Me)CH2OH,H,Ph,CH2OH,
NHCOPh),(NHCH(Me)CH2OH,H,Ph,CH2OH,NHCO-
2-furyl),(NHCH(Me)CH2OH,H,Ph,CH2OH,
NHCONHPh),(NHCH(Me)CH2OH,H,Ph,CH2OH,
NHCOCONHPh),(NHCH(Me)CH2OH,H,OH,Me,
CONHPh),(NHCH(Me)CH2OH,H,OH,Me,CONH-3-
pyridyl),(NHCH(Me)CH2OH,H,OH,Me,NHCOPh),
(NHCH(Me)CH2OH,H,OH,Me,NHCO-2-furyl),NHCH
(Me)CH2OH,H,OH,Me,NHCONHPh),(NHCH(Me)
CH2OH,H,OH,Me,NHCOCONHPh),(NHCH(Me)
CH2OH,H,OH,Et,CONHPh),(NHCH(Me)CH2OH,H,
OH,Et,CONH-3-pyridyl),(NHCH(Me)CH2OH,H,OH,Et,
NHCOPh),(NHCH(Me)CH2OH,H,OH,Et,NHCO-2-
furyl),(NHCH(Me)CH2OH,H,OH,Et,NHCONHPh),
(NHCH(Me)CH2OH,H,OH,Et,NHCOCONHPh),
(NHCH(Me)CH2OH,H,OH,CH2OH,CONHPh),(NHCH
(Me)CH2OH,H,OH,CH2OH,CONH-3-pyridyl),(NHCH
(Me)CH2OH,H,OH,CH2OH,NHCOPh),(NHCH(Me)

CH2OH,H,OH,CH2OH,NHCO-2-furyl),(NHCH(Me)
CH2OH,H,OH,CH2OH,NHCONHPh),(NHCH(Me)
CH2OH,H,OH,CH2OH,NHCOCONHPh),(NHCH(Me)
CH2OH,Me,H,Me,CONHPh),(NHCH(Me)CH2OH,Me,
H,Me,CONH-3-pyridyl),(NHCH(Me)CH2OH,Me,H,Me,
NHCOPh),(NHCH(Me)CH2OH,Me,H,Me,NHCO-2-
furyl),(NHCH(Me)CH2OH,Me,H,Me,NHCONHPh),
(NHCH(Me)CH2OH,Me,H,Me,NHCOCONHPh),
(NHCH(Me)CH2OH,Me,H,Et,CONHPh),(NHCH(Me)
CH2OH,Me,H,Et,CONH-3-pyridyl),(NHCH(Me)
CH2OH,Me,H,Et,NHCOPh),(NHCH(Me)CH2OH,Me,
H,Et,NHCO-2-furyl),(NHCH(Me)CH2OH,Me,H,Et,
NHCONHPh),(NHCH(Me)CH2OH,Me,H,Et,
NHCOCONHPh),(NHCH(Me)CH2OH,Me,H,CH2OH,
CONHPh),(NHCH(Me)CH2OH,Me,H,CH2OH,CONH-
3-pyridyl),(NHCH(Me)CH2OH,Me,H,CH2OH,
NHCOPh),(NHCH(Me)CH2OH,Me,H,CH2OH,NHCO-
2-furyl),(NHCH(Me)CH2OH,Me,H,CH2OH,
NHCONHPh),(NHCH(Me)CH2OH,Me,H,CH2OH,
NHCOCONHPh),(NHCH(Me)CH2OH,Me,Me,Me,
CONHPh),(NHCH(Me)CH2OH,Me,Me,Me,CONH-3-
pyridyl),(NHCH(Me)CH2OH,Me,Me,Me,NH COPh),
(NHCH(Me)CH2OH,Me,Me,Me,NHCO-2-furyl,(NHCH
(Me)CH2OH,Me,Me,Me,NHCONHPh),(NHCH(Me)
CH2OH,Me,Me,Me,NHCOCONHPh),(NHCH(Me)
CH2OH,Me,Me,Et,CONHPh),(NHCH(Me)CH2OH,Me,
Me,Et,CONH-3-pyridyl),(NHCH(Me)CH2OH,Me,Me,
Et,NHCOPh),(NHCH(Me)CH2OH,Me,Me,Et,NHCO-2-
furyl,(NHCH(Me)CH2OH,Me,Me,Et,NHCONHPh),
(NHCH(Me)CH2OH,Me,Me,Et,NHCOCONHPh),
(NHCH(Me)CH2OH,Me,Me,CH2OH,CONHPh),
(NHCH(Me)CH2OH,Me,Me,CH2OH,CONH-3-pyridyl,
(NHCH(Me)CH2OH,Me,Me,CH2OH,NHCOPh),
(NHCH(Me)CH2OH,Me,Me,CH2OH,NHCO-2-furyl,
(NHCH(Me)CH2OH,Me,Me,CH2OH,NHCONHPh),
(NHCH(Me)CH2OH,Me,Me,CH2OH,NHCOCONHPh),
(NHCH(Me)CH2OH,Me,Ph,Me,CONHPh),(NHCH(Me)
CH2OH,Me,Ph,Me,CONH-3-pyridyl),(NHCH(Me)
CH2OH,Me,Ph,Me,NHCOPh),(NHCH(Me)CH2OH,Me,
Ph,Me,NHCO-2-furyl),(NHCH(Me)CH2OH,Me,Ph,Me,
NHCONHPh),(NHCH(Me)CH2OH,Me,Ph,Me,
NHCOCONHPh),(NHCH(Me)CH2OH,Me,Ph,Et,
CONHPh),(NHCH(Me)CH2OH,Me,Ph,Et,CONH-3-
pyridyl),(NHCH(Me)CH2OH,Me,Ph,Et,NHCOPh),
(NHCH(Me)CH2OH,Me,Ph,Et,NHCO-2-furyl),(NHCH
(Me)CH2OH,Me,Ph,Et,NHCONHPh),(NHCH(Me)
CH2OH,Me,Ph,Et,NHCOCONHPh),(NHCH(Me)
CH2OH,Me,Ph,CH2OH,CONHPh),(NHCH(Me)
CH2OH,Me,Ph,CH2OH,CONH-3-pyridyl),(NHCH(Me)
CH2OH,Me,Ph,CH2OH,NHCOPh),(NHCH(Me)
CH2OH,Me,Ph,CH2OH,NHCO-2-furyl),(NHCH(Me)
CH2OH,Me,Ph,CH2OH,NHCONHPh),(NHCH(Me)
CH2OH,Me,Ph,CH2OH,NHCOCONHPh),(NHCH(Me)
CH2OH,Me,OH,Me,CONHPh),(NHCH(Me)CH2OH,
Me,OH,Me,CONH-3-pyridyl),(NHCH(Me)CH2OH,Me,
OH,Me,NHCOPh),(NHCH(Me)CH2OH,Me,OH,Me,
NHCO-2-furyl),(NHCH(Me)CH2OH,Me,OH,Me,
NHCONHPh),(NHCH(Me)CH2OH,Me,OH,Me,
NHCOCONHPh),(NHCH(Me)CH2OH,Me,OH,Et,
CONHPh),(NHCH(Me)CH2OH,Me,OH,Et,CONH-3-
pyridyl),(NHCH(Me)CH2OH,Me,OH,Et,NHCOPh),
(NHCH(Me)CH2OH,Me,OH,Et,NHCO-2-furyl),(NHCH
(Me)CH2OH,Me,OH,Et,NHCONHPh),(NHCH(Me)
CH2OH,Me,OH,Et,NHCOCONHPh),(NHCH(Me)CH2OH,
Me,OH,CH2OH,CONHPh),(NHCH(Me)CH2OH,Me,
OH,CH2OH,CONH-3-pyridyl),(NHCH(Me)CH2OH,
Me,OH,CH2OH,NHCOPh),(NHCH(Me)CH2OH,Me,
OH,CH2OH,NHCO-2-furyl),(NHCH(Me)CH2OH,Me,
OH,CH2OH,NHCONHPh),(NHCH(Me)CH2OH,Me,
OH,CH2OH,NHCOCONHPh),(NHCH(Me)CH2OH,Ph,
H,Me,CONHPh),(NHCH(Me)CH2OH,Ph,H,Me,CONH-
3-pyridyl),(NHCH(Me)CH2OH,Ph,H,Me,NHCOPh),
(NHCH(Me)CH2OH,Ph,H,Me,NHCO-2-furyl),(NHCH
(Me)CH2OH,Ph,H,Me,NHCONHPh),(NHCH(Me)
CH2OH,Ph,H,Me,NHCOCONHPh),(NHCH(Me)
CH2OH,Ph,H,Et,CONHPh),(NHCH(Me)CH2OH,Ph,H,
Et,CONH-3-pyridyl),(NHCH(Me)CH2OH,Ph,H,Et,
NHCOPh),(NHCH(Me)CH2OH,Ph,H,Et,NHCO-2-
furyl),(NHCH(Me)CH2OH,Ph,H,Et,NHCONHPh),
(NHCH(Me)OCH2OH,Ph,B,Et,NHCOCONHPh),
(NHCH(Me)CH2OH,Ph,H,CH2OH,CONHPh),(NHCH
(Me)CH2OH,Ph,H,CH2OH,CONH-3-pyridyl),(NHCH
(Me)CH2OH,Ph,H,CH2OH,NHCOPh),(NHCH(Me)
CH2OH,Ph,H,CH2OH,NHCO-2-furyl),(NHCH(Me)
CH2OH,Ph,H,CH2OH,NHCONHPh),(NHCH(Me)
CH2OH,Ph,H,CH2OH,NHCOCONHPh),(NHCH(Me)
CH2OH,Ph,Me,Me,CONHPh),(NHCH(Me)CH2OH,Ph,
Me,Me,CONH-3-pyridyl),(NHCH(Me)CH2OH,Ph,Me,
Me,NHCOPh),(NHCH(Me)CH2OH,Ph,Me,Me,NHCO-
2-furyl),(NHCH(Me)CH2OH,Ph,Me,Me,NHCONHPh),
(NHCH(Me)CH2OH,Ph,Me,Me,NHCOCONHPh),
(NHCH(Me)CH2OH,Ph,Me,Et,CONHPh),(NHCH(Me)
CH2OH,Ph,Me,Et,CONH-3-pyridyl),(NHCH(Me)
CH2OH,Ph,Me,Et,NHCOPh),(NHCH(Me)CH2OH,Ph,
Me,Et,NHCO-2-furyl),(NHCH(Me)CH2OH,Ph,Me,Et,
NHCONHPh),(NHCH(Me)CH2OH,Ph,Me,Et,
NHCOCONHPh),(NHCH(Me)CH2OH,Ph,Me,CH2OH,
CONHPh),(NHCH(Me)CH2OH,Ph,Me,CH2OH,CONH-
3-pyridyl),(NHCH(Me)CH2OH,Ph,Me,CH2OH,
NHCOPh),(NHCH(Me)CH2OH,Ph,Me,CH2OH,NHCO-
2-furyl),(NHCH(Me)CH2OH,Ph,Me,CH2OH,
NHCONHPh),(NHCH(Me)CH2OH,Ph,Me,CH2OH,
NHCOCONHPh),(NHCH(Me)CH2OH,Ph,Ph,Me,
CONHPh),(NHCH(Me)CH2OH,Ph,Ph,Me,CONH-3-
pyridyl),(NHCH(Me)CH2OH,Ph,Ph,Me,NHCOPh),
NHCH(Me)CH2OH,Ph,Ph,Me,NHCO-2-furyl),(NHCH
(Me)CH2OH,Ph,Ph,Me,NHCONHPh),(NHCH(Me)
CH2OH,Ph,Ph,Me,NHCOCONHPh),(NHCH(Me)
CH2OH,Ph,Ph,Et,CONHPh),(NHCH(Me)CH2OH,Ph,
Ph,Et,CONH-3-pyridyl),(NHCH(Me)CH2OH,Ph,Ph,Et,
NHCOPh),(NHCH(Me)CH2OH,Ph,Ph,Et,NHCO-2-
furyl),(NHCH(Me)CH2OH,Ph,Ph,Et,NHCONHPh),
(NHCH(Me)CH2OH,Ph,Ph,Et,NHCOCONHPh),(NHCH
(Me)CH2OH,Ph,Ph,CH2OH,CONHPh),(NHCH(Me)
CH2OH,Ph,Ph,CH2OH,CONH-3-pyridyl),(NHCH(Me)
CH2OH,Ph,Ph,CH2OH,NHCOPh),(NHCH(Me)CH2OH,
Ph,Ph,CH2OH,NHCO-2-furyl),(NHCH(Me)CH2OH,Ph,
Ph,CH2OH,NHCONHPh),(NHCH(Me)CH2OH,Ph,Ph,
CH2OH,NHCOCONHPh),(NHCH(Me)CH2OH,Ph,OH,
Me,CONHPh),(NHCH(Me)CH2OH,Ph,OH,Me,CONH-
3-pyridyl),(NHCH(Me)CH2OH,Ph,OH,Me,NHCOPh),
(NHCH(Me)CH2OH,Ph,OH,Me,NHCO-2-furyl),
(NHCH(Me)CH2OH,OH,Me,NHCONHPh),(NHCH
(Me)CH2OH,Ph,OH,Me,NHCOCONHPh),(NHCH(Me)
CH2OH,Ph,OH,Et,CONHPh),(NHCH(Me)CH2OH,Ph,
OH,Et,CONH-3-pyridyl),(NHCH(Me)CH2OH)Ph,OH,
Et,NHCOPh),(NHCH(Me)CH2OH,Ph,OH,Et,NHCO-2-
furyl),(NHCH(Me)CH2OH,Ph,OH,Et,NHCONHPh),
(NHCH(Me)CH2OH,Ph,OH,Et,NHCOCONHPh),
(NHCH(Me)CH2OH,Ph,OH,CH2OH,CONHPh),(NHCH
(Me)CH2OH,Ph,OH,CH2OH,CONH-3-pyridyl),(NHCH
(Me)CH2OH,Ph,OH,CH2OH,NHCOPh),(NHCH(Me)
CH2OH,Ph,OH,CH2OH,NHCO-2-furyl),(NHCH(Me)

CH2OH,Ph,OH,CH2OH,NHCONHPh),(NHCH(Me)
CH2OH,Ph,OH,CH2OH,NHCOCONHPh),
(NHCH(Me)CONHMe,H,H,Me,CONHPh),(NHCH(Me)
CONHMe,H,H,Me,CONH-3-pyridyl),(NHCH(Me)
CONHMe,H,H,Me,NHCOPh),(NHCH(Me)CONHMe,H,
H,Me,NHCO-2-furyl),(NHCH(Me)CONHMe,H,H,Me,
NHCONHPh),(NHCH(Me)CONHMe,H,H,Me,
NHCOCONHPh),(NHCH(Me)CONHMe,H,H,Et,
CONHPh),(NHCH(Me)CONHMe,H,H,Et,CONH-3-
pyridyl),(NHCH(Me)CONHMe,H,H,Et,NHCOPh),
(NHCH(Me)CONHMe,H,H,Et,NHCO-2-furyl),(NHCH
(Me)CONHMe,H,H,Et,NHCONHPh),(NHCH(Me)
CONHMe,H,H,Et,NHCOCONHPh),(NHCH(Me)
CONHMe,H,H,CH2OH,CONHPh),(NHCH(Me)
CONHMe,H,H,CH2OH,CONH-3-pyridyl),(NHCH(Me)
CONHMe,H,H,CH2OH,NHCOPh),(NHCH(Me)
CONHMe,H,H,CH2OH,NHCO-2-furyl),(NHCH(Me)
CONHMe,H,H,CH2OH,NHCONHPh),(NHCH(Me)
CONHMe,H,H,CH2OH,NHCOCONHPh),(NHCH(Me)
CONHMe,H,Me,Me,CONHPh),(NHCH(Me)CONHMe,
H,Me,Me,CONH-3-pyridyl),(NHCH(Me)CONHMe,H,
Me,Me,NHCOPh),(NHCH(Me)CONHMe,H,Me,Me,
NHCO-2-furyl),(NHCH(Me)CONHMe,H,Me,Me,
NHCONHPh),(NHCH(Me)CONHMe,H,Me,Me,
NHCOCONHPh),(NHCH(Me)CONHMe,H,Me,Et,
CONHPh),(NHCH(Me)CONHMe,H,Me,Et,CONH-3-
pyridyl),(NHCH(Me)CONHMe,H,Me,Et,NHCOPh),
(NHCH(Me)CONHMe,Me,Et,NHCO-2-furyl),(NHCH
(Me)CONHMe,H,Me,Et,NHCONHPh),(NHCH(Me)
CONHMe,H,Me,Et,NHCOCONHPh),(NHCH(Me)
CONHMe,H,Me,CH2OH,CONHPh),(NHCH(Me)
CONHMe,H,Me,CH2OH,CONH-3-pyridyl),(NHCH
(Me)CONHMe,H,Me,CH2OH,NHCOPh),(NHCH(Me)
CONHMe,H,Me,CH2OH,NHCO-2-furyl),(NHCH(Me)
CONHMe,H,Me,CH2OH,    NHCONHPh),(NHCH(Me)
CONHMe,H,Me,CH2OH,NHCOCONHPh),(NHCH
(Me)CONHMe,H,Ph,Me,CONHPh),(NHCH(Me)
CONHMe,H,Ph,Me,CONH-3-pyridyl),(NHCH(Me)
CONHMe,H,Ph,Me,NHCOPh),(NHCH(Me)CONHMe,
H,Ph,Me,NHCO-2-furyl),(NHCH(Me)CONHMe,H,Ph,
Me,NHCONHPh),(NHCH(Me)CONHMe,H,Ph,Me,
NHCOCONHPh),(NHCH(Me)CONHMe,H,Ph,Et,
CONHPh),(NHCH(Me)CONHMe,H,Ph,Et,CONH-3-
pyridyl),(NHCH(Me)CONHMe,H,Ph,Et,NHCOPh),
(NHCH(Me)CONHMe,H,Ph,EtNHCO-2-furyl),(NHCH
(Me)CONHMe,H,Ph,Et,NHCONHPh),(NHCH(Me)
CONHMe,H,Ph,Et,NHCOCONHPh),(NHCH(Me)
CONHMe,H,Ph,CH2OH,CONHPh),(NHCH(Me)
CONHMe,H,Ph,CH2OH,CONH-3-pyridyl),(NHCH(Me)
CONHMe,H,Ph,CH2OH,NHCOPh),(NHCH(Me)
CONHMe,H,Ph,CH2OH,NHCO-2-furyl),(NHCH(Me)
CONHMe,H,Ph,CH2OH,NHCONHPh),(NHCH(Me)
CONHMe,H,Ph,CH2OH,NHCOCONHPh),(NHCH(Me)
CONHMe,H,OH,Me,CONHPh),(NHCH(Me)CONHMe,
H,OH,Me,CONH-3-pyridyl),(NHCH(Me)CONHMe,H,
OH,Me,NHCOPh),(NHCH(Me)CONHMe,H,Me,
NHCO-2-furyl),(NHCH(Me)CONHMe,H,OH,Me,
NHCONHPh),(NHCH(Me)CONHMe,H,OH,Me,
NHCOCONHPh),(NHCH(Me)CONHMe,H,OH,Et,
CONHPh),(NHCH(Me)CONHMe,H,OH,Et,CONH-3-
pyridyl),(NHCH(Me)CONHMe,H,OH,Et,NHCOPh),
(NHCH(Me)CONHMe,H,OH,Et,NHCO-2-furyl),
(NHCH(Me)CONHMe,H,OH,Et,NHCONHPh),(NHCH
(Me)CONHMe,H,OH,Et,NHCOCONHPh),(NHCH(Me)
CONHMe,H,OH,CH2OH,CONHPh),(NHCH(Me)
CONHMe,H,OH,CH2OH,CONH-3-pyridyl),(NHCH
(Me)CONHMe,H,OH,CH2OH,NHCOPh),(NHCH(Me)

CONHMe,H,OH,CH2OH,NHCO-2-furyl),(NHCH(Me)
CONHMe,H,OH,CH2OH,NHCONHPh),(NHCH(Me)
CONHMe,H,OH,CH2OH,NHCOCONHPh),(NHCH
(Me)CONHMe,Me,H,Me,CONHPh),(NHCH(Me)
CONHMe,Me,H,Me,CONH-3-pyridyl),(NHCH(Me)
CONHMe,Me,H,Me,NHCOPh),(NHCH(Me)CONHMe,
Me,H,Me,NHCO-2-furyl),(NHCH(Me)CONHMe,Me,H,
Me,NHCONHPh),(NHCH(Me)CONHMe,Me,H,Me,
NHCOCONHPh),(NHCH(Me)CONHMe,Me,H,Et,
CONHPh),(NHCH(Me)CONHMe,Me,H,Et,CONH-3-
pyridyl),(NHCH(Me)CONHMe,Me,H,Et,NHCOPh),
(NHCH(Me)CONHMe,Me,H,Et,NHCO-2-furyl),(NHCH
(Me)CONHMe,Me,H,Et,NHCONHPh),(NHCH(Me)
CONHMe,Me,H,Et,NHCOCONHPh),(NHCH(Me)
CONHMe,Me,H,CH2OH,CONHPh),(NHCH(Me)
CONHMe,Me,H,CH2OH,CONH-3-pyridyl),(NHCH
(Me)CONHMe,Me,H,CH2OH,NHCOPh),(NHCH(Me)
CONHMe,Me,H,CH2OH,NHCO-2-furyl),(NHCH(Me)
CONHMe,Me,H,CH2OH,NHCONHPh),(NHCH(Me)
CONHMe,Me,Me,H,CH2OH,NHCOCONHPh),(NHCH
(Me)CONHMe,Me,Me,Me,CONHPh),(NHCH(Me)
CONHMe,Me,Me,Me,CONH-3-pyridyl),(NHCH(Me)
CONHMe,Me,Me,Me,NHCOPh),(NHCH(Me)
CONHMe,Me,Me,Me,NHCO-2-furyl),(NHCH(Me)
CONHMe,Me,Me,Me,NHCONHPh),(NHCH(Me)
CONHMe,Me,Me,Me,NHCOCONHPh),(NHCH(Me)
CONHMe,Me,Me,Et,CONHPh),(NHCH(Me)CONHMe,
Me,Me,Et,CONH-3-pyridyl),(NHCH(Me)CONHMe,Me,
Me,Et,NHCOPh),(NHCH(Me)CONHMe,Me,Me,Et,
NHCO-2-furyl),(NHCH(Me)CONHMe,Me,Me,Et,
NHCONHPh),(NHCH(Me)CONHMe,Me,Me,Et,
NHCOCONHPh),(NHCH(Me)CONHMe,Me,Me,
CH2OH,CONHPh),(NHCH(Me)CONHMe,Me,Me,
CH2OH,CONH-3-pyridyl),(NHCH(Me)CONHMe,Me,
Me,CH2OH,NHCOPh),(NHCH(Me)CONHMe,Me,Me,
CH2OH,NHCO-2-furyl),(NHCH(Me)CONHMe,Me,Me,
CH2OH,NHCONHPh),(NHCH(Me)CONHMe,Me,Me,
CH2OH,NHCOCONHPh),(NHCH(Me)CONHMe,Me,
Ph,Me,CONHPh),(NHCH(Me)CONHMe,Me,Ph,Me,
CONH-3-pyridyl),(NHCH(Me)CONHMe,Me,Ph,Me,
NHCOPh),(NHCH(Me)CONHMe,Me,Ph,Me,NHCO-2-
furyl),(NHCH(Me)CONHMe,Me,Ph,Me,NHCONHPh),
(NHCH(Me)CONHMe,Me,Ph,Me,NHCOCONHPh),
(NHCH(Me)CONHMe,Me,Ph,Et,CONHPh),(NHCH
(Me)CONHMe,Me,Ph,Et,CONH-3-pyridyl),(NHCH
(Me)CONHMe,Me,Ph,Et,NHCOPh),(NHCH(Me)
CONHMe,Me,Ph,Et,NHCO-2-furyl),(NHCH(Me)
CONHMe,Me,Ph,Et,NHCONHPh),(NHCH(Me)
CONHMe,Me,Ph,Et,NHCOCONHPh),(NHCH(Me)
CONHMe,Me,Ph,CH2OH,CONHPh),(NHCH(Me)
CONHMe,Me,Ph,CH2OH,CONH-3-pyridyl),(NHCH
(Me)CONHMe,Me,Ph,CH2OH,NHCOPh),(NHCH(Me)
CONHMe,Me,Ph,CH2OH,NHCO-2-furyl),(NHCH(Me)
CONHMe,Me,Ph,CH2OH,NHCONHPh),(NHCH(Me)
CONHMe,Me,Ph,CH2OH,NHCOCONHPh),(NHCH
(Me)CONHMe,Me,OH,Me,CONHPh),(NHCH(Me)
CONHMe,Me,OH,Me,CONH-3-pyridyl),(NHCH(Me)
CONHMe,Me,OH,Me,NHCOPh),(NHCH(Me)
CONHMe,Me,OH,Me,NHCO-2-furyl),(NHCH(Me)
CONHMe,Me,OH,Me,NHCONHPh),(NHCH(Me)
CONHMe,Me,OH,Me,NHCOCONHPh),(NHCH(Me)
CONHMe,Me,OH,Et,CONHPh),(NHCH(Me)CONHMe,
Me,OH,Et,CONH-3-pyridyl),(NHCH(Me)CONHMe,
Me,OH,Et,NHCOPh),(NHCH(Me)NHMe,Me,OH,Et,
NHCO-2-furyl),(NHCH(Me)CONHMe,Me,OH,Et,
NHCONHPh),(NHCH(Me)CONHMe,Me,OH,Et,
NHCOCONHPh),(NHCH(Me)CONHMe,Me,OH, CH2OH,CONHPh),(NHCH(Me)CONHMe,Me,OH, CH2OH,CONH-3-pyridyl),(NHCH(Me)CONHMe,Me, OH,CH2OH,NHCOPh),(NHCH(Me)CONHMe,Me,OH, CH2OH,NHCO-2-furyl),(NHCH(Me)CONHMe,Me,OH, CH2OH,NHCONHPh),(NHCH(Me)CONHMe,Me,OH, CH2OH,NHCOCONHPh),(NHCH(Me)CONHMe,Ph,H, Me,CONHPh),(NHCH(Me)CONHMe,Ph,H,Me,CONH-3-pyridyl),(NHCH(Me)CONHMe,Ph,H,Me,NHCOPh), (NHCH(Me)CONHMe,Ph,H,Me,NHCO-2-furyl), (NHCH(Me)CONHMe,Ph,H,Me,NHCONHPh),(NHCH (Me)CONHMe,Ph,H,Me,NHCOCONHPh),(NHCH(Me) CONHMe,Ph,H,Et,CONHPh),(NHCH(Me)CONHMe, Ph,H,Et,CONH-3-pyridyl),(NHCH(Me)CONHMe,Ph,H, Et,NHCOPh),(NHCH(Me)CONHMe,Ph,H,Et,NHCO-2-furyl),(NHCH(Me)CONHMe,Ph,H,Et,NHCONHPh), (NHCH(Me)CONHMe,Ph,H,Et,NHCOCONHPh), (NHCH(Me)CONHMe,Ph,H,CH2OH,CONHPh), (NHCH(Me)CONHMe,Ph,H,CH2OH,CONH-3-pyridyl), (NHCH(Me)CONHMe,Ph,H,CH2OH,NHCOPh), (NHCH(Me)CONHMe,Ph,H,CH2OH,NHCO-2-furyl), (NHCH(Me)CONHMe,Ph,H,CH2OH,NHCONHPh), (NHCH(Me)CONHMe,Ph,H,CH2OH,NHCOCONHPh), (NHCH(Me)CONHMe,Ph,Me,Me,CONHPh),(NHCH (Me)CONHMe,Ph,Me,Me,CONH-3-pyridyl),(NHCH (Me)CONHMe,Ph,Me,Me,NHCOPh),(NHCH(Me) CONHMe,Ph,Me,Me,NHCO-2-furyl),(NHCH(Me) CONHMe,Ph,Me,Me,NHCONHPh),(NHCH(Me) CONHMe,Ph,Me,Me,NHCOCONHPh),(NHCH(Me) CONHMe,Ph,Me,Et,CONHPh),(NHCH(Me)CONHMe, Ph,Me,Et,CONH-3-pyridyl),(NHCH(Me)CONHMe,Ph, Me,Et,NHCOPh),(NHCH(Me)CONHMe,Ph,Me,Et, NHCO-2-furyl),(NHCH(Me)CONHMe,Ph,Me,Et, NHCONHPh),(NHCH(Me)CONHMe,Ph,Me,Et, NHCOCONHPh),(NHCH(Me)CONHMe,Ph,Me, CH2OH,CONHPh),(NHCH(Me)CONHMe,Ph,Me, CH2OH,CONH-3-pyridyl),(NHCH(Me)CONHMe,Ph, Me,CH2OH,NHCOPh),(NHCH(Me)CONHMe,Ph,Me, CH2OH,NHCO-2-furyl),(NHCH(Me)CONHMe,Ph,Me, CH2OH,NHCONHPh),(NHCH(Me)CONHMe,Ph,Me, CH2OH,NHCOCONHPh),(NHCH(Me)CONHMe,Ph, Ph,Me,CONHPh),(NHCH(Me)CONHMe,Ph,Ph,Me, CONH-3-pyridyl),(NHCH(Me)CONHMe,Ph,Ph,Me, NHCOPh),(NHCH(Me)CONHMe,Ph,Ph,Me,NHCO-2-furyl),(NHCH(Me)CONHMe,Ph,Ph,Me,NHCONHPh), (NHCH(Me)CONHMe,Ph,Ph,Me,NHCOCONHPh), (NHCH(Me)CONHMe,Ph,Ph,Et,CONHPh),(NHCH (Me)CONHMe,Ph,Ph,Et,CONH-3-pyridyl),(NHCH(Me) CONHMe,Ph,Ph,Et,NHCOPh),(NHCH(Me)CONHMe, Ph,Ph,Et,NHCO-2-furyl),(NHCH(Me)CONHMe,Ph,Ph, Et,NHCONHPh),(NHCH(Me)CONHMe,Ph,Ph,Et, NHCOCONHPh),(NHCH(Me)CONHMe,Ph,Ph, CH2OH,CONHPh),(NHCH(Me)CONHMe,Ph,Ph, CH2OH,CONH-3-pyridyl),(NHCH(Me)CONHMe,Ph, Ph,CH2OH,NHCOPh),(NHCH(Me)CONHMe,Ph,Ph, CH2OH,NHCO-2-furyl),(NHCH(Me)CONHMe,Ph,Ph, CH2OH,NHCONHPh),(NHCH(Me)CONHMe,Ph,Ph, CH2OH,NHCOCONHPh),(NHCH(Me)CONHMe,Ph, OH,Me,CONHPh),(NHCH(Me)CONHMe,Ph,OH,Me, CONH-3-pyridyl),(NHCH(Me)CONHMe,Ph,OH,Me, NHCOPh),(NHCH(Me)CONHMe,Ph,OH,Me,NHCO-2-furyl),(NHCH(Me)CONHMe,Ph,OH,Me,NHCONHPh), (NHCH(Me)CONHMe,Ph,OH,Me,NHCOCONHPh), (NHCH(Me)CONHMe,Ph,OH,Et,CONHPh),(NHCH (Me)CONHMe,Ph,OH,Et,CONH-3-pyridyl),(NHCH (Me)CONHMe,Ph,OH,Et,NHCOPh),(NHCH(Me) CONHMe,Ph,OH,Et,NHCO-2-furyl),(NHCH(Me) CONHMe,Ph,OH,Et,NHCONHPh),(NHCH(Me) CONHMe,Ph,OH,Et,NHCOCONHPh),(NHCH(Me) CONHMe,Ph,OH,CH2OH,CONHPh),(NHCH(Me) CONHMe,Ph,OH,CH2OH,CONH-3-pyridyl),(NHCH (Me)CONHMe,Ph,OH,CH2OH,NHCOPh),(NHCH(Me) CONHMe,Ph,OH,CH2OH,NHCO-2-furyl),(NHCH(Me) CONHMe,Ph,OH,CH2OH,NHCONHPh),(NHCH(Me) CONHMe,Ph,OH,CH2OH,NHCOCONHPh), (NHCOCH(iPr)OH,H,H,Me,CONHPh),(NHCOCH(iPr) OH,H,H,Me,CONH-3-pyridyl),(NHCOCH(iPr)OH,H,H, Me,NHCOPh),(NHCOCH(iPr)OH,H,H,Me,NHCO-2-furyl),(NHCOCH(iPr)OH,H,H,Me,NHCONHPh), (NHCOCH(iPr)OH,H,H,Me,NHCOCONHPh), (NHCOCH(iPr)OH,H,H,Et,CONHPh),(NHCOCH(iPr) OH,H,H,Et,CONH-3-pyridyl),(NHCOCH(iPr)OH,H,Et, NHCOPh),(NHCOCH(iPr)OH,H,H,Et,NHCO-2-furyl), (NHCOCH(iPr)OH,H,H,Et,NHCONHPh),(NHCOCH (iPr)OH,H,H,Et,NHCOCONHPh),(NHCOCH(iPr)OH,H, H,CH2OH,CONHPh),(NHCOCH(iPr)OH,H,H,CH2OH, CONH-3-pyridyl),(NHCOCH(iPr)OH,H,H,CH2OH, NHCOPh),(NHCOCH(iPr)OH,H,H,CH2OH,NHCO-2-furyl),(NHCOCH(iPr)OH,H,H,CH2OH,NHCONHPh), (NHCOCH(iPr)OH,H,H,CH2OH,NHCOCONHPh), (NHCOCH(iPr)OH,H,Me,Me,CONHPh),(NHCOCH (iPr)OH,H,H,Me,Me,CONH-3-pyridyl),(NHCOCH(iPr) OH,H,Me,Me,NHCOPh),(NHCOCH(iPr)OH,H,Me,Me, NHCO-2-furyl),(NHCOCH(iPr)OH,H,Me,Me, NHCONHPh),(NHCOCH(iPr)OH,H,Me,Me, NHCOCONHPh),(NHCOCH(iPr)OH,H,Me,Et, CONHPh),(NHCOCH(iPr)OH,H,Me,Et,CONH-3-pyridyl),(NHCOCH(iPr)OH,H,Me,Et,NHCOPh), (NHCOCH(iPr)OH,H,Me,Et,NHCO-2-furyl),(NHCOCH (iPr)OH,H,H,Me,Et,NHCONHPh),(NHCOCH(iPr)OH, H,Me,Et,NHCOCONHPh),(NHCOCH(iPr)OH,H,Me, CH2OH,CONHPh),(NHCOCH(iPr)OH,H,Me,CH2OH, CONH-3-pyridyl),(NHCOCH(iPr)OH,H,Me,CH2OH, NHCOPh),(NHCOCH(iPr)OH,Me,CH2OH,NHCO-2-furyl),(NHCOCH(iPr)OH,H,Me,CH2OH,NHCONHPh), (NHCOCH(iPr)OH,H,Me,CH2OH,NHCOCONHPh), (NHCOCH(iPr)OH,H,Ph,Me,CONHPh),(NHCOCH(iPr) OH,H,Ph,Me,CONH-3-pyridyl),(NHCOCH(iPr)OH,H, Ph,Me,NHCOPh),(NHCOCH(iPr)OH,H,Ph,Me,NHCO-2-furyl),(NHCOCH(iPr)OH,H,Ph,Me,NHCONHPh), (NHCOCH(iPr)OH,H,Ph,Me,NHCOCONHPh), (NHCOCH(iPr)OH,H,Ph,Et,CONHPh),(NHCOCH(iPr) OH,H,Ph,Et,CONH-3-pyridyl,(NHCOCH(iPr)OH,H,Ph, Et,NHCOPh),(NHCOCH(iPr)OH,H,Ph,Et,NHCO-2-furyl),(NHCOCH(iPr)OH,H,Ph,Et,NHCONHPh), (NHCOCH(iPr)OH,H,Ph,Et,NHCOCONHPh), (NHCOCH(iPr)OH,Ph,CH2OH,CONHPh),(NHCOCH (iPr)OH,Ph,CH2OH,CONH-3-pyridyl),(NHCOCH(iPr) OH,H,Ph,CH2OH,NHCOPh),(NHCOCH(iPr)OH,H,Ph, CH2OH,NHCO-2-furyl),(NHCOCH(iPr)OH,H,Ph, CH2OH,NHCONHPh),(NHCOCH(iPr)OH,H,Ph, CH2OH,NHCOCONHPh),(NHCOCH(iPr)OH,H,OH, Me,CONHPh),(NHCOCH(iPr)OH,H,OH,Me,CONH-3-pyridyl),(NHCOCH(iPr)OH,H,OH,Me,NHCOPh), (NHCOCH(iPr)OH,H,OH,Me,NHCO-2-furyl), (NHCOCH(iPr)OH,H,OH,Me,NHCONHPh),(NHCOCH (iPr)OH,H,OH,Me,NHCOCONHPh),(NHCOCH(iPr) OH,H,OH,Et,CONHPh),(NHCOCH(iPr)OH,H,OH,Et, CONH-3-pyridyl),(NHCOCH(iPr)OH,H,OH,Et, NHCOPh),(NHCOCH(iPr)OH,H,OH,Et,NHCO-2-furyl), (NHCOCH(iPr)OH,H,OH,Et,NHCONHPh),(NHCOCH (iPr)OH,H,OH,Et,NHCOCONHPh),(NHCOCH(iPr)OH, H,OH,CH2OH,CONHPh),(NHCOCH(iPr)OH,H,OH, CH2OH,CONH-3-pyridyl),(NHCOCH(iPr)OH,H,OH, CH2OH,NHCOPh),(NHCOCH(iPr)OH,H,OH,CH2OH, NHCO-2-furyl),(NHCOCH(iPr)OH,H,OH,CH2OH,
NHCONHPh),(NHCOCH(iPr)OH,H,OH,CH2OH,
NHCOCONHPh),(NHCOCH(iPr)OH,Me,H,Me,
CONHPh),(NHCOCH(iPr)OH,Me,H,Me,CONH-3-
pyridyl),(NHCOCH(iPr)OH,Me,H,Me,NHCOPh),
(NHCOCH(iPr)OH,Me,H,Me,NHCO-2-furyl),
(NHCOCH(iPr)OH,Me,H,Me,NHCONHPh),(NHCOCH
(iPr)OH,Me,H,Me,NHCOCONHPh),(NHCOCH(iPr)
OH,Me,H,Et,CONHPh),(NHCOCH(iPr)OH,Me,H,Et,
CONH-3-pyridyl),(NHCOCH(iPr)OH,Me,H,Et,
NHCOPh),(NHCOCH(iPr),OH,Me,H,Et,NHCO-2-
furyl),(NHCOCH(iPr)OH,Me,H,Et,NHCONHPh),
(NHCOCH(iPr)OH,Me,H,Et,NHCOCONHPh),
(NHCOCH(iPr)OH,Me,H,CH2OH,CONHPh),
(NHCOCH(iPr)OH,Me,H,CH2OH,CONH-3-pyridyl),
(NHCOCH(iPr)OH,Me,H,CH2OH,NHCOPh),
(NHCOCH(iPr)OH,Me,H,CH2OH,NHCO-2-furyl),
(NHCOCH(iPr)OH,Me,H,CH2OH,NHCONHPh),
(NHCOCH(iPr)OH,Me,H,CH2OH,NHCOCONHPh),
(NHCOCH(iPr)OH,Me,Me,Me,CONHPh),(NHCOCH
(iPr)OH,Me,Me,Me,CONH-3-pyridyl),(NHCOCH(iPr)
OH,Me,Me,Me,NHCOPh),(NHCOH(iPr)OH,Me,Me,
Me,NHCO-2-furyl),(NHCOCH(iPr)OH,Me,Me,Me,
NHCONHPh),(NHCOCH(iPr)OH,Me,Me,Me,
NHCOCONHPh),(NHCOCH(iPr)OH,Me,Me,Et,
CONHPh),(NHCOCH(iPr)OOH,Me,Me,Et,CONH-3-
pyridyl),(NHCOCH(iPr)OH,Me,Me,Et,NHCOPh),
(NHCOCH(iPr)OH,Me,Me,Et,NHCO-2-furyl),
(NHCOCH(iPr)OH,Me,Me,Et,NHCONHPh),(NHCOCH
(iPr)OH,Me,Me,Et,NHCOCONHPh),(NHCOCH(iPr)
OH,Me,Me,CH2OH,CONHPh),(NHCOCH(iPr)OH,Me,
Me,CH2OH,CONH-3-pyridyl),(NHCOCH(iPr)OH,Me,
Me,CH2OH,NHCOPh),(NHCOCH(iPr)OH,Me,Me,
CH2OH,NHCO-2-furyl),(NHCOCH(iPr)OH,Me,Me,
CH2OH,NHCONHPh),(NHCOC(iPr)OH,Me,Me,
CH2OH,NHCOCONHPh),(NHCOCH(iPr)OH,Me,Ph,
Me,CONHPh),(NHCOCH(iPr)OH,Me,Ph,Me,CONH-3-
pyridyl),(NHCOCH(iPr)OH,Me,Ph,Me,NHCOPh),
(NHCO(iPr)OH,Me,Ph,Me,NHCO-2-furyl),(NHCOCH
(iPr)OH,Me,Ph,Me,NHCONHPh),(NHCOCH(iPr)OH,
Me,Ph,Me,NHCOCONHPh),(NHCOCH(iPr)OH,Me,Ph,
Et,CONHPh),(NHCOCH(iPr)OH,Me,Ph,Et,CONH-3-
pyridyl),(NHCOCH(iPr)OH,Me,Ph,Et,NHCOPh),
(NHCOCH(iPr)OH,Me,Ph,Et,NHCO-2-furyl),
(NHCOCH(iPr)OH,Me,Ph,Et,NHCONHPh),(NHCOCH
(iPr)OH,Me,Ph,Et,NHCOCONHPh),(NHCOCH(iPr)OH,
Me,Ph,CH2OH,CONHPh),(NHCOCH(iPr)OH,Me,Ph,
CH2OH,CONH-3-pyridyl),(NHCOCH(iPr)OH,Me,Ph,
CH2OH,NHCOPh),(NHCOCH(iPr)OH,Me,Ph,CH2OH,
NHCO-2-furyl),(NHCOCH(iPr)OH,Me,Ph,CH2OH,
NHCONHPh),(NHCOCH(iPr)OH,Me,Ph,CH2OH,
NHCOCONHPh),(NHCOCH(iPr)OH,Me,OH,Me,
CONHPh),(NHCOCH(iPr)OH,Me,OH,Me,CONH-3-
pyridyl),(NHCOCH(iPr)OH,Me,OH,Me,NHCOPh),
(NHCOCH(iPr)OH,Me,OH,Me,NHCO-2-furyl),
(NHCOCH(iPr)OH,Me,OH,Me,NHCONHPh),
(NHCOCH(iPr)OH,Me,OH,Me,NHCOCONHPh),
(NHCOCH(iPr)OH,Me,OH,Et,CONHPh),(NHCOCH
(iPr)OH,Me,OH,Et,CONH-3-pyridyl),(NHCOCH(iPr)
OH,Me,OH,Et,NHCOPh),(NHCOCH(iPr)OH,Me,OH,
Et,NHCO-2-furyl),(NHCOCH(iPr)OH,Me,OH,Et,
NHCONHPh),(NHCOCH(iPr)OH,Me,OH,Et,
NHCOCONHPh),(NHCOCH(iPr)OH,Me,OH,CH2OH,
CONHPh),(NHCOCH(iPr)OH,Me,OH,CH2OH,CONH-
3-pyridyl),(NHCOCH(iPr)OH,Me,OH,CH2OH,
NHCOPh),(NHCOCH(iPr)OH,Me,OH,CH2OH,NHCO-
2-furyl),(NHCOCH(iPr)OH,Me,OH,CH2OH,
NHCONHPh),(NHCOCH(iPr)OH,Me,OH,CH2OH,
NHCONHPh),(NHCOCH(iPr)OH,Me,OH,CH2OH,
NHCOCONHPh),(NHCOCH(iPr)OH,Ph,H,Me,
CONHPh),(NHCOCH(iPr)OH,Ph,H,Me,CONH-3-
pyridyl),(NHCOCH(iPr)OH,Ph,H,Me,NHCOPh),
(NHCOCH(iPr)OH,Ph,H,Me,NHCO-2-furyl),
(NHCOCH(iPr)OH,Ph,H,Me,NHCONHPh),(NHCOCH
(iPr)OH,Ph,H,Me,NHCOCONHPh),(NHCOCH(iPr)OH,
Ph,H,Et,CONHPh),(NHCOCH(iPr)OH,Ph,H,Et,CONH-
3-pyridyl),(NHCOCH(iPr)OH,Ph,H,Et,NHCOPh),
(NHCOCH(iPr)OH,Ph,H,Et,NHCO-2-furyl),(NHCOCH
(iPr)OH,Ph,H,Et,NHCONHPh),(NHCOCH(iPr)OH,Ph,
H,Et,NHCOCONHPh),(NHCOCH(iPr)OH,Ph,H,
CH2OH,CONHPh),(NHCOCH(iPr)OH,Ph,H,CH2OH,
CONH-3-pyridyl),(NHCOCH(iPr)OH,Ph,H,CH2OH,
NHCOPh),(NHCOCH(iPr)OH,Ph,CH2OH,NHCO-2-
furyl),(NHCOCH(iPr)OH,Ph,H,CH2OH,NHCONHPh),
(NHCOCH(iPr)OH,Ph,H,CH2OH,NHCOCONHPh),
(NHCOCH(iPr)OH,Ph,Me,Me,CONHPh),(NHCOCH
(iPr)OH,Ph,Me,Me,CONH-3-pyridyl),(NHCOCH(iPr)
OH,Ph,Me,Me,NHCOPh),(NHCOCH(iPr)OH,Ph,Me,
Me,NHCO-2-furyl),(NHCOCH(iPr)OH,Ph,Me,Me,
NHCONHPh),(NHCOCH(iPr)OH,Ph,Me,Me,
NHCOCONHPh),(NHCOCH(iPr)OH,Ph,Me,Et,
CONHPh),(NHCOCH(iPr)OH,Ph,Me,Et,CONH-3-
pyridyl),(NHCOCH(iPr)OH,Ph,Me,Et,NHCOPh),
(NHCOCH(iPr)OH,Ph,Me,Et,NHCO-2-furyl),
(NHCOCH(iPr)OH,Ph,Me,Et,NHCONHPh),(NHCOCH
(iPr)OH,Ph,Me,Et,NHCOCONHPh),(NHCOCH(iPr)OH,
Ph,Me,CH2OH,CONHPh),(NHCOCH(iPr)OH,Ph,Me,
CH2OH,CONH-3-pyridyl),(NHCOCH(iPr)OH,Ph,Me,
CH2OH,NHCOPh),(NHCOCH(iPr)OH,Ph,Me,CH2OH,
NHCO-2-furyl),(NHCOCH(iPr)OH,Ph,Me,CH2OH,
NHCONHPh),(NHCOCH(iPr)OH,Ph,Me,CH2OH,
NHCOCONHPh),(NHCOCH(iPr)OH,Ph,Ph,Me,
CONHPh),(NHCOCH(iPr)OH,Ph,Ph,Me,CONH-3-
pyridyl),(NHCOCH(iPr)OH,Ph,Ph,Me,NHCOPh),
(NHCOCH(iPr)OH,Ph,Ph,Me,NHCO-2-furyl),
(NHCOCH(iPr)OH,Ph,Ph,Me,NHCONHPh),(NHCOCH
(iPr)OH,Ph,Ph,Me,NHCOCONHPh),(NHCOCH(iPr)
OH,Ph,Ph,Et,CONHPh),(NHCOCH(iPr)OH,Ph,Ph,Et,
CONH-3-pyridyl),(NHCOCH(iPr)OH,Ph,Ph,Et,
NHCOPh),(NHCOCH(iPr)OH,Ph,Ph,Et,NHCO-2-furyl),
(NHCOCH(iPr)OH,Ph,Ph,Et,NHCONHPh),(NHCOCH
(iPr)OH,Ph,Ph,Et,NHCOCONHPh),(NHCOCH(iPr)OH,
Ph,Ph,CH2OH,CONHPh),(NHCOCH(iPr)OH,Ph,Ph,
CH2OH,CONH-3-pyridyl),(NHCOCH(iPr),OH,Ph,Ph,
CH2OH,NHCOPh),(NHCOCH(iPr)OH,Ph,Ph,CH2OH,
NHCO-2-furyl),(NHCOCH(iPr)OH,Ph,Ph,CH2OH,
NHCONHPh),(NHCOCH,(iPr)OH,Ph,Ph,CH2OH,
NHCOCONHPh),(NHCOCH(iPr)OH,Ph,OH,Me,
CONHPh),(NHCOCH(iPr)OH,Ph,OH,Me,CONH-3-
pyridyl),(NHCOCH(iPr)OH,Ph,OH,Me,NHCOPh),
(NHCOCH(iPr)OH,Ph,OH,Me,NHCO-2-furyl),
(NHCOCH(iPr)OH,Ph,OH,Me,NHCONHPh),
(NHCOCH(iPr)OH,Ph,OH,Me,NHCOCONHPh),
(NHCOCH(iPr)OH,Ph,OH,Et,CONHPh),(NHCOCH
(iPr)OH,Ph,OH,Et,CONH-3-pyridyl),(NHCOCH(iPr)
OH,Ph,OH,Et,NHCOPh),(NHCOCH(iPr)OH,Ph,OH,Et,
NHCO-2-furyl),(NHCOCH(iPr)OH,Ph,OH,Et,
NHCONHPh),(NHCOCH(iPr)OH,Ph,OH,Et,
NHCOCONHPh,(NHCOCH(iPr)OH,Ph,OH,CH2OH,
CONHPh),(NHCOCH(iPr)OH,Ph,OH,CH2OH,CONH-
3-pyridyl),(NHCOCH(iPr)OH,Ph,OH,CH2OH,
NHCOPh),(NHCOCH(iPr)OH,Ph,OH,CH2OH,NHCO-
2-furyl),(NHCOCH(iPr)OH,Ph,OH,CH2OH,
NHCONHPh),(NHCOCH(iPr)OH,Ph,OH,CH2OH,
NHCOCONHPh), (NHSO2Me,H,H,Me,CONHPh),(NHSO2Me,H,H,Me,CONH-3-pyridyl),(NHSO2Me,H,H,Me,NHCOPh),(NHSO2Me,H,H,Me,NHCO-2-furyl),(NHSO2Me,H,H,Me,NHCONHPh),(NHSO2Me,H,H,Me,NHCOCONHPh),(NHSO2Me,H,H,Et,CONHPh),(NHSO2Me,H,H,Et,CONH-3-pyridyl),(NHSO2Me,H,H,Et,NHCOPh),(NHSO2Me,H,H,Et,NHCO-2-furyl),(NHSO2Me,H,H,Et,NHCONHPh),(NHSO2Me,H,H,Et,NHCOCONHPh),(NHSO2Me,H,H,CH2OH,CONHPh),(NHSO2Me,H,H,CH2OH,CONH-3-pyridyl),(NHSO2Me,H,H,CH2OH,NHCOPh),(NHSO2Me,H,H,CH2OH,NHCO-2-furyl),(NHSO2Me,H,H,CH2OH,NHCONHPh),(NHSO2Me,H,H,CH2OH,NHCOCONHPh),(NHSO2Me,H,Me,Me,CONHPh),(NHSO2Me,H,Me,Me,CONH-3-pyridyl),(NHSO2Me,H,Me,Me,NHCOPh),(NHSO2Me,H,Me,Me,NHCO-2-furyl),(NHSO2Me,H,Me,Me,NH,CONHPh),(NHS2Me,H,Me,Me,NHCOCONHPh),(NHSO2Me,H,Me,Et,CONHPh),(NHSO2Me,H,Me,Et,CONH-3-pyridyl),(NHSO2Me,H,Me,Et,NHCOPh),(NHSO2Me,H,Me,Et,NHCO-2-furyl),(NHSO2Me,H,Me,Et,NHCONHPh),(NHSO2Me,H,Me,Et,NHCOCONHPh),(NHSO2Me,H,Me,CH2OH,CONHPh),(NHSO2Me,H,Me,CH2OH,CONH-3-pyridyl),(NHSO2Me,H,Me,CH2OH,NHCOPh),(NHSO2Me,H,Me,CH2OH,NHCO-2-furyl),(NHSO2Me,H,Me,CH2OH,NHCONHPh),(NHSO2Me,H,Me,CH2OH,NHCOCONHPh),(NHSO2Me,H,Ph,Me,CONHPh),(NHSO2Me,H,Ph,Me,CONH-3-pyridyl),(NHSO2Me,H,Ph,Me,NHCOPh),(NHSO2Me,H,Ph,Me,NHCO-2-furyl),(NHSO2Me,H,Ph,Me,NHCONHPh),(NHSO2Me,H,Ph,Me,NHCOCONHPh),(NHSO2Me,H,Ph,Et,CONHPh),(NHSO2Me,H,Ph,Et,CONH-3-pyridyl),(NHSO2Me,H,Ph,Et,NHCOPh),(NHSO2Me,H,Ph,Et,NHCO-2-furyl),(NHSO2Me,H,Ph,Et,NHCONHPh),(NHSO2Me,H,Ph,Et,NHCOCONHPh),(NHSO2Me,H,Ph,CH2OH,CONHPh),(NHSO2Me,H,Ph,CH2OH,CONH-3-pyridyl),(NHSO2Me,H,Ph,CH2OH,NHCOPh),(NHSO2Me,H,Ph,CH2OH,NHCO-2-furyl),(NHSO2Me,H,Ph,CH2OH,NHCONHPh),(NHSO2Me,H,Ph,CH2OH,NHCOCONHPh),(NHSO2Me,H,OH,Me,CONHPh),(NHSO2Me,H,OH,Me,CONH-3-pyridyl),(NHSO2Me,H,OH,Me,NHCOPh),(NHSO2Me,H,OH,Me,NHCO-2-furyl),(NHSO2Me,H,OH,Me,NHCONHPh),(NHSO2Me,H,OH,Et,NHCOCONHPh),(NHSO2Me,H,OH,Et,CONHPh),(NHSO2Me,H,OH,Et,CONH-3-pyridyl),(NHSO2Me,H,OH,Et,NHCOPh),(NHSO2Me,H,OH,Et,NHCO-2-furyl),(NHSO2Me,H,OH,Et,NHCONHPh),(NHSO2Me,H,OH,Et,NHCOCONHPh),(NHSO2Me,H,OH,CH2OH,CONHPh),(NHSO2Me,H,OH,CH2H,CONH-3-pyridyl),(NHSO2Me,H,OH,CH2OH,NHCOPh),(NHSO2Me,H,OH,CH2OH,NHCO-2-furyl),(NHSO2Me,H,OH,CH2OH,NHCONHPh),(NHSO2Me,H,OH,CH2OH,NHCOCONHPh),(NHSO2Me,Me,H,Me,CONHPh),(NHSO2Me,Me,H,Me,CONH-3-pyridyl),(NHSO2Me,Me,H,Me,NHCOPh),(NHSO2Me,Me,H,Me,NHCO-2-furyl),(NHSO2Me,Me,H,Me,NHCONHPh),(NHSO2Me,Me,H,Me,NHCOCONHPh),(NHSO2Me,Me,H,Et,CONHPh),(NHSO2Me,Me,H,Et,CONH-3-pyridyl),(NHSO2Me,Me,H,Et,NHCOPh),(NHSO2Me,Me,H,Et,NHCO-2-furyl),(NHSO2Me,Me,H,Et,NHCONHPh),(NHSO2Me,Me,H,Et,NHCOCONHPh),(NHSO2Me,Me,H,CH2OH,CONHPh),(NHSO2Me,Me,H,CH2OH,CONH-3-pyridyl),(NHSO2Me,Me,H,CH2OH,NHCOPh),(NHSO2Me,Me,H,CH2OH,NHCO-2-furyl),(NHSO2Me,Me,H,CH2OH,NHCONHPh),(NHSO2Me,Me,H,CH2OH,NHCOCONHPh),(NHSO2Me,Me,Me,Me,CONHPh),(NHSO2Me,Me,Me,Me,CONH-3-pyridyl),(NHSO2Me,Me,Me,Me,NHCOPh),(NHSO2Me,Me,Me,Me,NHCO-2-furyl),(NHSO2Me,Me,Me,Me,NHCONHPh),(NHSO2Me,Me,Me,Me,NHCOCONHPh),(NHSO2Me,Me,Me,Et,CONHPh),(NHSO2Me,Me,Me,Et,CONH-3-pyridyl),(NHSO2Me,Me,Me,Et,NHCOPh),(NHSO2Me,Me,Me,Et,NHCO-2-furyl),(NHSO2Me,Me,Me,Et,NHCONHPh),(NHSO2Me,Me,Me,Et,NHCOCONHPh),(NHSO2Me,Me,Me,CH2OH,CONHPh),(NHSO2Me,Me,Me,CH2OH,CONH-3-pyridyl),(NHSO2Me,Me,Me,CH2OH,NHCOPh),(NHSO2Me,Me,Me,CH2OH,NHCO-2-furyl),(NHSO2Me,Me,Me,CH2OH,NHCONHPh),(NHSO2Me,Me,Me,CH2OH,NHCOCONHPh),(NHSO2Me,Me,Ph,Me,CONHPh),(NHSO2Me,Me,Ph,Me,CONH-3-pyridyl),(NHSO2Me,Me,Ph,Me,NHCOPh),(NHSO2Me,Me,Ph,Me,NHCO-2-furyl),(NHSO2Me,Me,Ph,Me,NHCONHPh),(NHSO2Me,Me,Ph,Me,NHCOCONHPh),(NHSO2Me,Me,Ph,Et,CONHPh),(NHSO2Me,Me,Ph,Et,CONH-3-pyridyl),(NHSO2Me,Me,Ph,Et,NHCOPh),(NHSO2Me,Me,Ph,Et,NHCO-2-furyl),(NHSO2Me,Me,Ph,Et,NHCONHPh),(NHSO2Me,Me,Ph,Et,NHCOCONHPh),(NHSO2Me,Me,Ph,CH2OH,CONHPh),(NHSO2Me,Me,Ph,CH2OH,CONH-3-pyridyl),(NHSO2Me,Me,Ph,CH2OH,NHCOPh),(NHSO2Me,Me,Ph,CH2OH,NHCO-2-furyl),(NHSO2Me,Me,Ph,CH2OH,NHCONHPh),(NHSO2Me,Me,Ph,CH2OH,NHCOCONHPh),(NHSO2Me,Me,OH,Me,CONHPh),(NHSO2Me,Me,OH,Me,CONH-3-pyridyl),(NHSO2Me,Me,OH,Me,NHCOPh),(NHSO2Me,Me,OH,Me,NHCO-2-furyl),(NHSO2Me,Me,OH,Me,NHCONHPh),(NHSO2Me,Me,OH,Me,NHCOCONHPh),(NHSO2Me,Me,OH,Et,CONHPh),(NHSO2Me,Me,OH,Et,CONH-3-pyridyl),(NHSO2Me,Me,OH,Et,NHCOPh),(NHSO2Me,Me,OH,Et,NHCO-2-furyl),(NHSO2Me,Me,OH,Et,NHCONHPh),(NHSO2Me,Me,OH,Et,NHCOCONHPh),(NHSO2Me,Me,OH,CH2OH,CONHPh),(NHSO2Me,Me,OH,CH2OH,CONH-3-pyridyl),(NHSO2Me,Me,OH,CH2OH,NHCOPh),(NHSO2Me,Me,OH,CH2OH,NHCO-2-furyl),(NHSO2Me,Me,OH,CH2OH,NHCONHPh),(NHSO2Me,Me,OH,CH2OH,NHCOCONHPh),(NHSO2Me,Ph,H,Me,CONHPh),(NHSO2Me,Ph,H,Me,CONH-3-pyridyl),(NHSO2Me,Ph,H,Me,NHCOPh),(NHSO2Me,Ph,H,Me,NHCO-2-furyl),(NHSO2Me,Ph,H,Me,NHCONHPh),(NHSO2Me,Ph,H,Me,NHCOCONHPh),(NHSO2Me,Ph,H,Et,CONHPh),(NHSO2Me,Ph,H,Et,CONH-3-pyridyl),(NHSO2Me,Ph,H,Et,NHCOPh),(NHSO2Me,Ph,H,Et,NHCO-2-furyl),(NHSO2Me,Ph,H,Et,NHCONHPh),(NHSO2Me,Ph,H,Et,NHCOCONHPh),(NHSO2Me,Ph,H,CH2OH,CONHPh),(NHSO2Me,Ph,H,CH2OH,CONH-3-pyridyl),(NHSO2Me,Ph,H,CH2OH,NHCOPh),(NHSO2Me,Ph,H,CH2OH,NHCO-2-furyl),(NHSO2Me,Ph,H,CH2OH,NHCONHPh),(NHSO2Me,Ph,H,CH2OH,NHCOCONHPh),(NHSO2Me,Ph,Me,Me,CONHPh),(NHSO2Me,Ph,Me,Me,CONH-3-pyridyl),(NHSO2Me,Ph,Me,Me,NHCOPh),(NHSO2Me,Ph,Me,Me,NHCO-2-furyl),(NHSO2Me,Ph,Me,Me,NHCONHPh),(NHSO2Me,Ph,Me,Me,NHCOCONHPh),(NHSO2Me,Ph,Me,Et,CONHPh),(NHSO2Me,Ph,Me,Et,CONH-3-pyridyl),(NHSO2Me,Ph,Me,Et,NHCOPh),(NHSO2Me,Ph,Me,Et,NHCO-2-furyl),(NHSO2Me,Ph,Me,Et,NHCONHPh),(NHSO2Me,Ph,Me,Et,NHCOCONHPh),(NHSO2Me,Ph,Me,CH2OH,CONHPh),(NHSO2Me,Ph,Me,CH2OH,CONH-3-pyridyl),(NHSO2Me,Ph,Me,CH2OH,NHCOPh),(NHSO2Me,Ph,Me,CH2OH,NHCO- 2-furyl),(NHSO2Me,Ph,Me,CH2OH,NHCONHPh),
(NHSO2Me,Ph,Me,CH2OH,NHCOCONHPh),
(NHSO2Me,Ph,Ph,Me,CONHPh),(NHSO2Me,Ph,Ph,
Me,CONH-3-pyridyl),(NHSO2Me,Ph,Ph,Me,NHCOPh),
(NHSO2Me,Ph,Ph,Me,NHCO-2-furyl),(NHSO2Me,Ph,
Ph,Me,NHCONHPh),(NHSO2Me,Ph,Ph,Me,
NHCOCONHPh),(NHSO2Me,Ph,Ph,Et,CONHPh),
(NHSO2Me,Ph,Ph,Et,CONH-3-pyridyl),(NHSO2Me,Ph,
Ph,Et,NHCOPh),(NHSO2Me,Ph,Ph,Et,NHCO-2-furyl),
(NHSO2Me,Ph,Ph,Et,NHCONHPh),(NHSO2Me,Ph,Ph,
Et,NHCOCONHPh),(NHSO2Me,Ph,Ph,CH2OH,
CONHPh),(NHSO2Me,Ph,Ph,CH2OH,CONH-3-
pyridyl),(NHSO2Me,Ph,Ph,CH2OH,NHCOPh),
(NHSO2Me,Ph,Ph,CH2OH,NHCO-2-furyl),(NHSO2Me,
Ph,Ph,CH2OH,NHCONHPh),(NHSO2Me,Ph,Ph,
CH2OH,NHCOCONHPh),(NHSO2Me,Ph,OH,Me,
CONHPh),(NHSO2Me,Ph,OH,Me,CONH-3-pyridyl),
(NHSO2Me,Ph,OH,Me,NHCOPh),(NHSO2Me,Ph,OH,
Me,NHCO-2-furyl),(NHSO2Me,Ph,OH,Me,
NHCONHPh),(NHSO2Me,Ph,OH,Me,NHCOCONHPh),
(NHSO2Me,Ph,OH,Et,CONHPh),(NHSO2Me,Ph,OH,
Et,CONH-3-pyridyl),(NHSO2Me,Ph,OH,Et,NHCOPh),
(NHSO2Me,Ph,OH,Et,NHCO-2-furyl),(NHSO2Me,Ph,
OH,Et,NHCONHPh),(NHSO2Me,Ph,OH,Et,
NHCOCONHPh),(NHSO2Me,Ph,OH,CH2OH,
CONHPh),(NHSO2Me,Ph,OH,CH2OH,CONH-3-
pyridyl),(NHSO2Me,Ph,OH,CH2OH,NHCOPh),
(NHSO2Me,Ph,OH,CH2OH,NHCO-2-furyl),
(NHSO2Me,Ph,OH,CH2OH,NHCONHPh),(NHSO2Me,
Ph,OH,CH2OH,NHCOCONHPh),
(NH2,H,H,Me,CONHPh),(NH2,H,H,Me,CONH-3-py-
ridyl),(NH2,H,H,Me,NHCOPh),(NH2,H,H,Me,NHCO-
2-furyl),(NH2,H,H,Me,NHCONHPh),(NH2,H,H,Me,
NHCOCONHPh),(NH2,H,H,Et,CONHPh),(NH2,H,H,Et,
CONH-3-pyridyl),(NH2,H,H,Et,NHCOPh),(NH2,H,H,
Et,NHCO-2-furyl),(NH2,H,H,Et,NHCONHPh),(NH2,H,
H,Et,NHCOCONHPh),(NH2,H,H,CH2OH,CONHPh),
(NH2,H,H,CH2OH,CONH-3-pyridyl),(NH2,H,H,
CH2OH,NHCONHPh),(NH2,H,H,CH2OH,
NHCOCONHPh),(NH2,H,Me,Me,CONHPh),(NH2,H,
Me,Me,CONH-3-pyridyl),(NH2,H,Me,Me,
NHCONHPh),(NH2,H,Me,Me,NHCOCONHPh),(NH2,
H,Me,Et,CONHPh),(NH2,H,Me,Et,CONH-3-pyridyl),
(NH2,H,Me,Et,NHCOPh),(NH2,H,Me,Et,NHCO-2-
furyl),(NH2,H,Me,Et,NHCONHPh),(NH2,H,Me,Et,
NHCOCONHPh),(NH2,H,Me,CH2OH,CONHPh),(NH2,
H,Me,CH2OH,CONH-3-pyridyl),(NH2,H,Me,CH2OH,
NHCONHPR(NH2,H,Me,CH2OH,NHCOCONHPh),
(NH2,H,Ph,Me,CONHPh),(NH2,H,Ph,Me,CONH-3-
pyridyl),(NH2,H,Ph,Me,NHCONHPh),(NH2,H,Ph,Me,
NHCOCONHPh),(NH2,H,Ph,Et,CONHPh),(NH2,H,Ph,
Et,CONH-3-pyridyl),(NH2,H,Ph,Et,NHCOPh),(NH2,H,
Ph,Et,NHCO-2-furyl),(NH2,H,Ph,Et,NHCONHPh),
(NH2,H,Ph,Et,NHCOCONHPh),(NH2,H,Ph,CH2OH,
CONHPh),(NH2,H,Ph,CH2OH,CONH-3-pyridyl),(NH2,
H,Ph,CH2OH,NHCONHPh),(NH2,H,Ph,CH2OH,
NHCOCONHPh),(NH2,H,OH,Me,CONHPh),(NH2,H,
OH,Me,CONH-3-pyridyl),(NH2,H,OH,Me,
NHCONHPh),(NH2,H,OH,Me,NHCOCONHPh),(NH2,
H,OH,Et,CONHPh),(NH2,H,OH,Et,CONH-3-pyridyl),
(NH2,H,OH,Et,NHCOPh),(NH2,H,OH,Et,NHCO-2-
furyl),(NH2,H,OH,Et,NHCONHPh),(NH2,H,OH,Et,
NHCOCONHPh),(NH2,H,OH,CH2OH,CONHPh),
(NH2,H,OH,CH2OH,CONH-3-pyridyl),(NH2,H,OH,
CH2OH,NHCONHPh),(NH2,H,OH,CH2OH,
NHCOCONHPh),(NH2,Me,H,Me,CONHPh),(NH2,Me,
H,Me,CONH-3-pyridyl),(NH2,Me,H,Me,NHCONHPh),
(NH2Me,H,Me,NHCOCONHPh),(NH2,Me,H,Et,
CONHPh),(NH2,Me,H,Et,CONH-3-pyridyl),(NH2,Me,
H,Et,NHCOPh),(NH2,Me,H,Et,NHCO-2-furyl),(NH2,
Me,H,Et,NHCONHPh),(NH2,Me,H,Et,
NHCOCONHPh),(NH2,Me,H,CH2OH,CONHPh),(NH2,
Me,H,CH2OH,CONH-3-pyridyl),(NH2,Me,H,CH2OH,
NHCONHPh),(NH2,Me,H,CH2OH,NHCOCONHPh),
(NH2,Me,Me,Me,CONHPh),(NH2,Me,Me,Me,CONH-
3-pyridyl),(NH2,Me,Me,Me,NHCONHPh),(NH2,Me,
Me,Me,NHCOCONHPh),(NH2,Me,Me,Et,CONHPh),
(NH2,Me,Me,Et,CONH-3-pyridyl),(NH2,Me,Me,Et,
NHCOPh),(NH2,Me,Me,Et,NHCO-2-furyl),(NH2,Me,
Me,Et,NHCONHPh),(NH2,Me,Me,Et,NHCOCONHPh),
(NH2,Me,Me,CH2OH,CONHPh),(NH2,Me,Me,
CH2OH,CONH-3-pyridyl),(NH2,Me,Me,CH2OH,
NHCONHPh),(NH2,Me,Me,CH2OH,NHCOCONHPh),
(NH2,Me,Ph,Me,CONHPh),(NH2,Me,Ph,Me,CONH-3-
pyridyl),(NH2,Me,Ph,Me,NHCOPh),(NH2,Me,Ph,Me,
NHCO-2-furyl),(NH2,Me,Ph,Me,NHCONHPh),(NH2,
Me,Ph,Me,NHCOCONHPh),(NH2,Me,Ph,Et,CONHPh),
(NH2,Me,Ph,Et,CONH-3-pyridyl),(NH2,Me,Ph,Et,
NHCOPh),(NH2,Me,Ph,Et,NHCO-2-furyl),(NH2,Me,Ph,
Et,NHCONHPh),(NH2,Me,Ph,Et,NHCOCONHPh),
(NH2,Me,Ph,CH2OH,CONHPh),(NH2,Me,Ph,CH2OH,
CONH-3-pyridyl),(NH2,Me,Ph,CH2OH,NHCONHPh),
(NH2,Me,Ph,CH2OH,NHCOCONHPh),(NH2,Me,OH,
Me,CONHPh),(NH2,Me,OH,Me,CONH-3-pyridyl),
(NH2,Me,OH,Me,NHCONHPh),(NH2,Me,OH,Me,
NHCOCONHPh),(NH2,Me,OH,Et,CONHPh),(NH2,Me,
OH,Et,CONH-3-pyridyl),(NH2,Me,OH,Et,NHCOPh),
(NH2,Me,OH,Et,NHCO-2-furyl),(NH2,Me,OH,Et,
NHCONHPh),(NH2,Me,OH,Et,NHCOCONHPh),(NH2,
Me,OH,CH2OH,CONHPh),(NH2,Me,OH,CH2OH,
CONH-3-pyridyl),(NH2,Me,OH,CH2OH,NHCONHPh),
(NH2,Me,OH,CH2OH,NHCOCONHPh),(NH2,Ph,H,
Me,CONHPh),(NH2,Ph,H,Me,CONH-3-pyridyl),(NH2,
Ph,H,Me,NHCONHPh),(NH2,Ph,H,Me,
NHCOCONHPh),(NH2,Ph,H,Et,CONHPh),(NH2,Ph,H,
Et,CONH-3-pyridyl),(NH2,Ph,H,Et,NHCOPh),(NH2,Ph,
H,Et,NHCO-2-furyl),(NH2,Ph,H,Et,NHCONHPh),
(NH2,Ph,H,Et,NHCOCONHPh),(NH2,Ph,H,CH2OH,
CONHPh),(NH2,Ph,H,CH2OH,CONH-3-pyridyl),(NH2,
Ph,H,(H2OH,NHCONHPh),(NH2,Ph,H,CH2OH,
NHCOCONHPh),(NH2,Ph,Me,Me,CONHPh),(NH2,Ph,
Me,Me,CONH-3-pyridyl),(NH2,Ph,Me,Me,
NHCONHPh),(NH2,Ph,Me,Me,NHCOCONHPh),(NH2,
Ph,Me,Et,CONHPh),(NH2,Ph,Me,Et,CONH-3-pyridyl),
(NH2,Ph,Me,Et,NHCOPh),(NH2,Ph,Me,Et,NHCO-2-
furyl),(NH2,Ph,Me,Et,NHCONHPh),(NH2,Ph,Me,Et,
NHCOCONHPh),(NH2,Ph,Me,CH2OH,CONHPh),
(NH2,Ph,Me,CH2OH,CONH-3-pyridyl),(NH2,Ph,Me,
CH2OH,NHCONHPh),(NH2,Ph,Me,CH2OH,
NHCOCONHPh),(NH2,Ph,Ph,Me,CONHPh),(NH2,Ph,
Ph,Me,CONH-3-pyridyl),(NH2,Ph,Ph,Me,NHCOPh),
(NH2,Ph,Ph,Me,NHCO-2-furyl),(NH2,Ph,Ph,Me,
NHCONHPh),(NH2,Ph,Ph,Me,NHCOCONHPh),(NH2,
Ph,Ph,Et,CONHPh),(NH2,Ph,Ph,CONH-3-pyridyl),
(NH2,Ph,Ph,Et,NHCOPh),(NH2,Ph,Ph,Et,NHCO-2-
furyl),(NH2,Ph,Ph,Et,NHCONHPh),(NH2,Ph,Ph,Et,
NHCOCONHPh),(NH2,Ph,Ph,CH2OH,CONHPh),
(NH2,Ph,Ph,CH2OH,CONH-3-pyridyl),(NH2,Ph,Ph,
CH2OH,NHCOPh),(NH2,Ph,Ph,CH2OH,NHCO-2-
furyl),(NH2,Ph,Ph,CH2OH,NHCONHPh),(NH2,Ph,Ph,
CH2OH,NHCOCONHPh),(NH2,Ph,OH,Me,CONHPh),
(NH2,Ph,OH,Me,CONH-3-pyridyl),(NH2,Ph,OH,Me,
NHCONHPh),(NH2,Ph,OH,Me,NHCOCONHPh),(NH2,
Ph,OH,Et,CONHPh),(NH2,Ph,OH,Et,CONH-3-pyridyl), (NH2,Ph,OH,Et,NHCOPh),(NH2,Ph,OH,Et,NHCO-2-furyl),(NH2,Ph,OH,Et,NHCONHPh),(NH2,Ph,OH,Et,NHCOCONHPh),(NH2,Ph,OH,CH2OH,CONHPh),(NH2,Ph,OH,CH2OH,CONH-3-pyridyl),(NH2,Ph,OH,CH2OH,NHCOPh),(NH2,Ph,OH,CH2OH,NHCO-2-furyl),(NH2,Ph,OH,CH2OH,NHCONHPh),(NH2,Ph,OH,CH2OH,NHCOCONHPh),
(NHCH2CH(OH)CH2OH,H,H,Me,CONHPh),(NHCH2CH(OH)CH2OH,H,H,Me,CONH-3-pyridyl),(NHCH2CH(OH)CH2OH,H,H,Me,NHCOPh),(NHCH2CH(OH)CH2OH,H,H,Me,NHCO-2-furyl),(NHCH2CH(OH)CH2OH,H,H,Me,NHCONHPh),(NHCH2CH(OH)CH2OH,H,H,Me,NHCOCONHPh),(NHCH2CH(OH)CH2OMe,H,H,Me,CONHPh),(NHCH2CH(OH)CH2OMe,H,H,Me,CONH-3-pyridyl),(NHCH2CH(OH)CH2OMe,H,H,Me,NHCOPh),(NHCH2CH(OH)CH2OMe,H,H,Me,NHCO-2-furyl),(NHCH2CH(OH)CH2OMe,H,H,Me,NHCONHPh),(NHCH2CH(OH)CH2OMe,H,H,Me,NHCOCONHPh),(NHCH2CH(OH)CH2NH2,H,H,Me,CONHPh),(NHCH2CH(OH)CH2NH2,H,H,Me,CONH-3-pyridyl),(NHCH2CH(OH)CH2NH2,H,H,Me,NHCOPh),(NHCH2CH(OH)CH2NH2,H,H,Me,NHCO-2-furyl),(NHCH2CH(OH)CH2NH2,H,H,Me,NHCONHPh),(NHCH2CH(OH)CH2NH2,H,H,Me,NHCOCONHPh),(NHCH2CH(OH)CH2NHMe,H,H,Me,CONHPh),(NHCH2CH(OH)CH2NHMe,H,H,Me,CONH-3-pyridyl),(NHCH2CH(OH)CH2NHMe,H,Me,NHCOPh),(NHCH2CH(OH)CH2NHMe,H,H,Me,NHCO-2-furyl),(NHCH2CH(OH)CH2NHMe,H,H,Me,NHCONHPh),(NHCH2CH(OH)CH2NHMe,H,H,Me,NHCOCONHPh),(NHCH2CH(OH)CH2NHCOMe,H,H,Me,CONHPh),(NHCH2CH(OH)CH2NHCOMe,H,H,Me,CONH-3-pyridyl),(NHCH2CH(OH)CH2NHCOMe,H,H,Me,NHCOPh),(NHCH2CH(OH)CH2NHCOMe,H,H,Me,NHCO-2-furyl),(NHCH2CH(OH)CH2NHCOMe,H,H,Me,NHCONHPh),(NHCH2CH(OH)CH2NHCOMe,H,H,Me,NHCOCONHPh),(NHCH2CH(OH)CH2N(Me)Me,H,H,Me,CONHPh),(NHCH2CH(OH)CH2N(Me)Me,H,H,Me,CONH-3-pyridyl),(NHCH2CH(OH)CH2N(Me)Me,H,H,Me,NHCOPh),(NHCH2CH(OH)CH2N(Me)Me,H,H,Me,NHCO-2-furyl),(NHCH2CH(OH)CH2N(Me)Me,H,H,Me,NHCONHPh),(NHCH2CH(OH)CH2N(Me)Me,H,H,Me,NHCOCONHPh),(NHC(O)C(O)NH2,H,H,Me,CONHPh),(NHC(O)C(O)NH2,H,H,Me,CONH-3-pyridyl),(NHC(O)C(O)NH2,H,Me,NHCOPh),(NHC(O)C(O)NH2,H,H,Me,NHCO-2-furyl),(NHC(O)C(O)NH2,H,H,Me,NHCONHPh),(NHC(O)C(O)NH2,H,H,Me,NHCOCONHPh),(NHC(O)C(O)NHMe,H,H,Me,CONHPh),(NHC(O)C(O)NHMe,H,H,Me,CONH-3-pyridyl),(NHC(O)C(O)NHMe,H,H,Me,NHCOPh),(NHC(O)C(O)NHMe,H,H,Me,NHCO-2-furyl),(NHC(O)C(O)NHMe,H,H,Me,NHCONHPh),(NHC(O)C(O)NHMe,H,H,Me,NHCOCONHPh),(NHC(O)C(O)N(Me)Me,H,H,Me,CONHPh),(NHC(O)C(O)N(Me)Me,H,H,Me,CONH-3-pyridyl),(NHC(O)C(O)N(Me)Me,H,H,Me,NHCOPh),(NHC(O)C(O)N(Me)Me,H,H,Me,NHCO-2-furyl),(NHC(O)C(O)N(Me)Me,H,H,Me,NHCONHPh),(NHC(O)C(O)N(Me)Me,H,H,Me,NHCOCONHPh),

[Chemical formula 85]

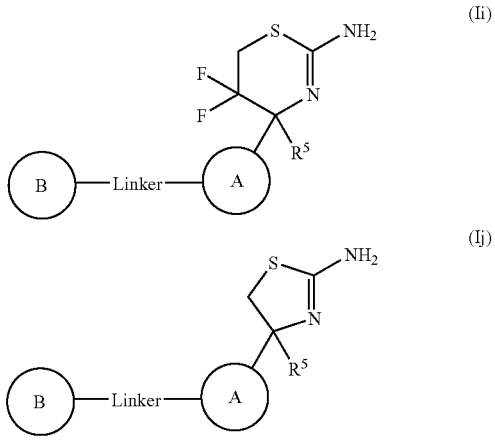

In above structural formula (Ii) or (Ij), the combination of B, Linker, A, $R^5$ (B, Linker, A, $R^5$) are the following compounds.

TABLE 169

| | B | | Linker | | A | | R5 | |
|---|---|---|---|---|---|---|---|---|
| B1 | Ph- | L1 | (C(=S)NH) | A1 | (pyrimidine) | R51 | —CN |
| B2 | 2-pyridyl- | L2 | (NHC(=S)) | A2 | (pyrimidine) | R52 | —C≡CH |
| B3 | 4-Me-Ph- | L3 | (CH2C(=O)) | A3 | (cyclohexane) | R53 | —C≡CMe |

TABLE 169-continued

| B | | Linker | A | | R5 | |
|---|---|---|---|---|---|---|
| B4 | cHex- | L4 (CH2-C(=O)-CH2) | A4 (piperidine-3,5-diyl, NH) | | R54 | —CF3 |
| B5 | cHex-CH2— | L5 (C(=O)-C(=O)) | A5 (1,3-phenylene) | | R55 | —CH2Cl |
| | | | | | R56 | CHCl2 |

(B, Linker, A, R⁵)=(B1,L1,A1,R51),(B1,L1,A1,R52),(B1,L1,A1,R53),(B1,L1,A1,R54),(B1,L1,A1,R55),(B1,L1,A1,R56),(B1,L1,A2,R51),(B1,L1,A2,R52),(B1,L1,A2,R53),(B1,L1,A2,R54),(B1,L1,A2,R55),(B1,L1,A2,R56),(B1,L1,A3,R51),(B1,L1,A3,R52),(B1,L1,A3,R53),(B1,L1,A3,R54),(B1,L1,A3,R55),(B1,L1,A3,R56),(B1,L1,A4,R51),(B1,L1,A4,R52),(B1,L1,A4,R53),(B1,L1,A4,R54),(B1,L1,A4,R55),(B1,L1,A4,R56),(B1,L1,A5,R51),(B1,L1,A5,R52),(B1,L1,A5,R53),(B1,L1,A5,R54),(B1,L1,A5,R55),(B1,L1,A5,R56),(B1,L2,A1,R51),(B1,L2,A1,R52),(B1,L2,A1,R53),(B1,L2,A1,R54),(B1,L2,A1,R55),(B1,L2,A1,R56),(B1,L2,A2,R51),(B1,L2,A2,R52),(B1,L2,A2,R53),(B1,L2,A2,R54),(B1,L2,A2,R55),(B1,L2,A2,R56),(B1,L2,A3,R51),(B1,L2,A3,R52),(B1,L2,A3,R53),(B1,L2,A3,R54),(B1,L2,A3,R55),(B1,L2,A3,R56),(B1,L2,A4,R51),(B1,L2,A4,R52),(B1,L2,A4,R53),(B1,L2,A4,R54),(B1,L2,A4,R55),(B1,L2,A4,R56),(B1,L2,A5,R51),(B1,L2,A5,R52),(B1,L2,A5,R53),(B1,L2,A5,R54),(B1,L2,A5,R55),(B1,L2,A5,R56),(B1,L3,A1,R51),(B1,L3,A1,R52),(B1,L3,A1,R53),(B1,L3,A1,R54),(B1,L3,A1,R55),(B1,L3,A1,R56),(B1,L3,A2,R51),(B1,L3,A2,R52),(B1,L3,A2,R53),(B1,L3,A2,R54),(B1,L3,A2,R55),(B1,L3,A2,R56),(B1,L3,A3,R51),(B1,L3,A3,R52),(B1,L3,A3,R53),(B1,L3,A3,R54),(B1,L3,A3,R55),(B1,L3,A3,R56),(B1,L3,A4,R51),(B1,L3,A4,R52),(B1,L3,A4,R53),(B1,L3,A4,R54),(B1,L3,A4,R55),(B1,L3,A4,R56),(B1,L3,A5,R51),(B1,L3,A5,R52),(B1,L3,A5,R53),(B1,L3,A5,R54),(B1,L3,A5,R55),(B1,L3,A5,R56),(B1,L4,A1,R51),(B1,L4,A1,R52),(B1,L4,A1,R53),(B1,L4,A1,R54),(B1,L4,A1,R55),(B1,L4,A1,R56),(B1,L4,A2,R51),(B1,L4,A2,R52),(B1,L4,A2,R53),(B53),(B1,L4,A2,R54),(B1,L4,A2,R55),(B1,L4,A2,R56),(B1,L4,A3,R51),(B1,L4,A3,R52),(B1,L4,A3,R53),(B1,L4,A3,R54),(B1,L4,A3,R55),(B1,L4,A3,R56),(B1,L4,A4,R51),(B1,L4,A4,R52),(B1,L4,A4,R53),(B1,L4,A4,R54),(B1,L4,A4,R55),(B1,L4,A4,R56),(B1,L4,A5,R51),(B1,L4,A5,R52),(B1,L4,A5,R53),(B1,L4,A5,R54),(B1,L4,A5,R55),(B1,L4,A5,R56),(B1,L5,A1,R51),(B1,L5,A1,R52),(B1,L5,A1,R53),(B1,L5,A1,R54),(B1,L5,A1,R55),(B1,L5,A1,R56),(B1,L5,A2,R51),(B1,L5,A2,R52),(B1,L5,A2,R53),(B1,L5,A2,R54),(B1,L5,A2,R55),(B1,L5,A2,R56),(B1,L5,A3,R51),(B1,L5,A3,R52),(B1,L5A3,R53),(B1,L5,A3,R54),(B1,L5,A3,R55),(B1,L5,A3,R56),(B1,L5,A4,R51),(B1,,L5,A4,R52),(B1,L5,A4,R53),(B1,L5,A4,R54),(B1,L5,A4,R55),(B1,L5,A4,R56),(B1,L5,A5,R51),(B1,L5,A5,R52),(B1,L5,A5,R53),(B1,L5,A5,R54),(B1,L5,A5,R55),(B1,L5,A5,R56),(B2,L1,A1,R51),(B2,L1,A1,R52),(B2,L1,A1,R53),(B2,L1,A1,R54),(B2,L1,A1,R55),(B2,L1,A1,R56),(B2,L1,A2,R51),(B2,L1,A2,R52),(B2,L1,A2,R53),(B2,L1,A2,R54),(B2,L1,A2,R55),(B2,L1,A2,R56),(B2,L1,A3,R51),(B2,L1,A3,R52),(B2,L1,A3,R53),(B2,L1,A3,R54),(B2,L1,A3,R55),(B2,L1,A3,R56),(B2,L1,A4,R51),(B2,L1,A4,R52),(B2,L1,A4,R53),(B2,L1,A4,R54),(B2,L1,A4,R55),(B2,L1,A4,R56),(B2,L1,A5,R51),(B2,L1,A5,R52),(B2,L1,A5,R53),(B2,L1,A5,R54),(B2,L1,A5,R55),(B2,L1,A5,R56),(B2,L2,A1,R51),(B2,L2,A1,R52),(B2,L2,A1,R53),(B2,L2,A1,R54),(B2,L2,A1,R55),(B2,L2,A1,R56),(B2,L2,A2,R51),(B2,L2,A2,R52),(B2,L2,A2,R53),(B2,L2,A2,R54),(B2,L2,A2,R55),(B2,L2,A2,R56),(B2,L2,A3,R51),(B2,L2,A3,R52),(B2,L2,A3,R53),(B2,L2,A3,R54),(B2,L2,A3,R55),(B2,L2,A3,R56),(B2,L2,A4,R51),(B2,L2,A4,R52),(B2,L2,A4,R53),(B2,L2,A4,R54),(B2,L2,A4,R55),(B2,L2,A4,R56),(B2,L2,A5,R51),(B2,L2,A5,R52),(B2,L2,A5,R53),(B2,L2,A5,R54),(B2,L2,A5,R55),(B2,L2,A5,R56),(B2,L3,A1,R51),(B2,L3,A1,R52),(B2,L3,A1,R53),(B2,L3,A1,R54),(B2,L3,A1,R55),(B2,L3,A1,R56),(B2,L3,A2,R51),(B2,L3,A2,R52),(B2,L3,A2,R53),(B2,L3,A2,R54),(B2,L3,A2,R55),(B2,L3,A2,R56),(B2,L3,A3,R51),(B2,L3,A3,R52),(B2,L3,A3,R53),(B2,L3,A3,R54),(B2,L3,A3R55),(B2,L3,A3,R56),(B2,L3,A4,R51),(B2,L3,A4,R52),(B2,L3,A4,R53),(B2,L3,A4,R54),(B2,L3,A4,R55),(B2,L3,A4,R56),(B2,L3,A5,R51),(B2,L3,A5,R52),(B2,L3,A5,R53),(B2,L3,A5,R54),(B2,L3,A5,R55),(B2,L3,A5,R56),(B2,L4,A1,R51),(B2,L4,A1,R52),(B2,L4,A1,R53),(B2,L4,A1,R54),(B2,L4,A1,R55),(B2,L4,A1,R56),(B2,L4,A2,R51),(B2,L4,A2,R52),(B2,L4,A2,R53),(B2,L4,A2,R54),(B2,L4,A2,R55),(B2,L4,A2,R56),(B2,L4,A3,R51),(B2,L4,A3,R52),(B2,L4,A3,R53),(B2,L4,A3,R54),(B2,L4,A3,R55),(B2,L4,A3,R56),(B2,L4,A4,R51),(B2,L4,A4,R52),(B2,L4,A4,R53),(B2,L4,A4,R54),(B2,L4,A4,R55),(B2,L4,A4,R56),(B2,L4,A5,R51),(B2,L4,A5,R52),(B2,L4,A5,R53),(B2,L4,A5,R54),(B2,L4,A5,R55),(B2,L4,A5,R56),(B2,L5,A1,R51),(B2,L5,A1,R52),(B2,L5,A1,R53),(B2,L5,A1,R54),(B2,L5,A1,R55),(B2,L5,A1,R56),(B2,L5,A2,R51),(B2,L5A2,R52),(B2,L5,A2,R53),(B2,L5,A2,R54),(B2,L5,A2,R55),(B2,L5,A2,R56),(B2,L5,A3,R51),(B2,L5,A3,R52),(B2,L5,A3,R53),(B2,L5,A3,R54),(B2,L5,A3,R55),(B2,L5,A3,R56),(B2,L5,A4,R51),(B2,L5,A4,R52),(B2,L5,A4,R53),(B2,L5,A4,R54),(B2,L5,A4,R55),(B2,L5,A4,R56),(B2,L5,A5,R51),(B2,L5,A5,R52),(B2,L5,A5,R53),(B2,L5,A5,R54),(B2,L5,A5,R55),(B2,L5,A5,R56),(B3,L1,A1,R51),(B3,L1,A1,R52),(B3,L1,A1,R53),(B3,L1,A1,R54),(B3, L1,A1,R55),(B3,L1,A1,R56),(B3,L1,A2,R51),(B3,L1, A2,R52),(B3,L1,A2,R53),(B3,L1,A2,R54),(B3,L1,A2, R55),(B3,L1,A2,R56),(B3,L1,A3,R51),(B3,L1,A3,R52), (B3,L1,A3,R53),(B3,L1,A3,R54),(B3,L1,A3,R55),(B3, L1,A3,R56),(B3,L1,A4,R51),(B3,L1,A4,R52),(B3,L1, A4,R53),(B3,L1,A4,R54),(B3,L1,A4,R55),(B3,L1,A4, R56),(B3,L1,A5,R51),(B3,L1,A5,R52),(B3,L1,A5,R53), (B3,L1,A5,R54),(B3,L1,A5,R55),(B3,L1,A5,R56),(B3, L2,A1,R51),(B3,L2,A1,R52),(B3,L2,A1,R53),(B3,L2, A1,R54),(B3,L2,A1,R55),(B3,L2,A1,R56),(B3,L2,A2, R51),(B3,L2,A2,R52),(B3,L2,A2,R53),(B3,L2,A2,R54), (B3,L2,A2,R55),(B3,L2,A2,R56),(B3,L2,A3,R51),(B3, L2,A3,R52),(B3,L2,A3,R53),(B3,L2,A3,R54),(B3,L2, A3,R55),(B3,L2,A3,R56),(B3,L2,A4,R51),(B3,L2,A4, R52),(B3,L2,A4,R53),(B3,L2,A4,R54),(B3,L2,A4,R55), (B3,L2,A4,R56),(B3,L2,A5,R51),(B3,L2,A5,R52),(B3, L2,A5,R53),(B3,L2,A5,R54),(B3,L2,A5,R55),(B3,L2, A5,R56),(B3,L3,A1,R51),(B3,L3,A1,R52),(B3,L3,A1, R53),(B3,L3,A1,R54),(B3,L3,A1,R55),(B3,L3,A1,R56), (B3,L3,A2,R51),(B3,L3,A2,R52),(B3,L3,A2,R53),(B3, L3,A2,R54),(B3,L3,A2,R55),(B3,L3,A2,R56),(B3,L3, A3,R51),(B3,1,3,A3,R52),(B3,L3,A3,R53),(B3,L3,A3, R54),(B3,L3,A3,R55),(B3,L3,A3,R56),(B3,L3,A4,R51), (B3,L3,A4,R52),(B3,L3,A4,R53),(B3,L3,A4,R54),(B3, L3,A4,R55),(B3,L3,A4,R56),(B3,L3,A5,R51),(B3,L3, A5,R52),(B3,L3,A5,R53),(B3,L3,A5,R54),(B3,L3,A5, R55),(B3,L3,A5,R56),(B3,L4,A1,R51),(B3,L4,A1,R52), (B3,L4,A1,R53),(B3,L4,A1,R54),(B3,L4,A1,R55),(B3, L4,A1,R56),(B3,L4,A2,R51),(B3,L4,A2,R52),(B3,L4, A2,R53),(B3,L4,A2,R54),(B3,L4,A2,R55),(B3,L4,A2, R56),(B3,L4,A3,R51),(B3,L4,A3,R52),(B3,L4,A3,R53), (B3,L4,A3,R54),(B3,L4,A3,R55),(B3,L4,A3,R56),(B3, L4,A4,R51),(B3,L4,A4,R52),(B3,L4,A4,R53),(B3,L4, A4,R54),(B3,L4,A4,R55),(B3,L4,A4,R56),(B3,L4,A5, R51),(B3,L4,A5,R52),(B3,L4,A5,R53),(B3,L4,A5,R54), (B3,L4,A5,R55),(B3,L4,A5,R56),(B3,L5,A1,R51),(B3, L5,A1,R52),(B3,L5,A1,R53),(B3,L5,A1,R54),(B3,L5, A1,R55),(B3,L5,A1,R56),(B3,L5,A2,R51),(B3,L5,A2, R52),(B3,L5,A2,R53),(B3,L5,A2,R54),(B3,L5,A2,R55), (B3,L5,A2,R56),(B3,L5,A3,R51),(B3,L5,A3,R52),(B3, L5,A3,R53),(B3,L5,A3,R54),(B3,L5,A3,R55),(B3,L5, A3,R56),(B3,L5,A4,R51),(B3,L5,A4,R52),(B3,L5,A4, R53),(B3,L5,A4,R54),(B3,L5,A4,R55),(B3,L5,A4,R56), (B3,L5,A5,R51),(B3,L5,A5,R52),(B3,L5,A5,R53),(B3, L5,A5,R54),(B3,L5,A5,R55),(B3,L5,A5,R56),(B4,L1, A1,R51),(B4,L1,A1,R52),(B4,L1,A1,R53),(B4,L1,A1, R54),(B4,L1,A1,R55),(B4,L1,A1,R56),(B4,L1,A2,R51), (B4,L1,A2,R52),(B4,L1,A2,R53),(B4,L1,A2,R54),(B4, L1,A2,R55),(B4,L1,A2,R56),(B4,L1,A3,R51),(B4,L1, A3,R52),(B4,L1,A3,R53),(B4,L1,A3,R54),(B4,L1,A3, R55),(B4,L1,A3,R56),(B4,L1,A4,R51),(B4,L1,A4,R52), (B4,L1,A4,R53),(B4,L1,A4,R54),(B4,L1,A4,R55),(B4, L1,A4,R56),(B4,L1,A5,R51),(B4,L1,A5,R52),(B4,L1, A5,R53),(B4,L1,A5,R54),(B4,L1,A5,R55),(B4,L1,A5, R56),(B4,L2,A1,R51),(B4,L2,A1,R52),(B4,L2,A1,R53), (B4,L2,A1,R54),(B4,L2,A 1,R55),(B4,L2,A1,R56),(B4, L2,A2,R51),(B4,L2,A2,R52),(B4,L2,A2,R53),(B4,L2, A2,R54),(B4,L2,A2,R55),(B4,L2,A2,R56),(B4,L2,A3, R51),(B4,L2,A3,R52),(B4,L2,A3,R53),(B4,L2,A3,R54), (B4,L2,A3,R55),(B4,L2,A3,R56),(B4,L2,A4,R51),(B4, L2,A4,R52),(B4,L2,A4,R53),(B4,L2,A4,R54),(B4,L2, A4,R55),(B4,L2,A4,R56),(B4,L2,A5,R51),(B4,L2,A5, R52),(B4,L2,A5,R53),(B4,L2,A5,R54),(B4,L2,A5,R55), (B4,L2,A5,R56),(B4,L3,A1,R51),(B4,L3,A1,R52),(B4, L3,A1,R53),(B4,L3,A1,R54),(B4,L3,A1,R55),(B4,L3, A1,R56),(B4,L3,A2,R51),(B4,L3,A2,R52),(B4,L3,A2, R53),(B4,L3,A2,R54),(B4,L3,A2,R55),(B4,L3,A2,R56), (B4,L3,A3,R51),(B4,L3,A3,R52),(B4,L3,A3,R53),(B4, L3,A3,R54),(B4,L,3,A3,R55),(B4,L3,A3,R56),(B4,L3, A4,R51),(B4,L3,A4,R52),(B4,L3,A4,R53),(B4,L3,A4, R54),(B4,L3,A4,R55),(B4,L3,A4,R56),(B4,L3,A5,R51), (B4,L3,A5,R52),(B4,L3,A5,R53),(B4,L3,A5,R54),(B4, L3,A5,R55),(B4,L3,A5,R56),(B4,L4,A1,R51),(B4,L4, A1,R52),(B4,L4,A1,R53),(B4,L4,A1,R54),(B4,L4,A1, R55),(B4,L4,A1,R56),(B4,L4,A2,R51),(B4,L4,A2,R52), (B4,L4,A2,R53),(B4,L4,A2,R54),(B4,L4,A2,R55),(B4, L4,A2,R56),(B4,L4,A3,R51),(B4,L4,A3,R52),(B4,L4, A3,R53),(B4,L4,A3,R54),(B4,L4,A3,R55),(B4,L4,A3, R56),(B4,L4,A4,R51),(B4,L4,A4,R52),(B4,L4,A4,R53), (B4,L4,A4,R54),(B4,L4,A4,R55),(B4,L4,A4,R56),(B4, L4,A5,R51),(B4,L4,A5,R52),(B4,L4,A5,R53),(B4,L4, A5,R54),(B4,L4,A5,R55),(B4,L4,A5,R56),(B4,L5,A1, R51),(B4,L5,A1,R52),(B4,L5,A1,R53),(B4,L5,A1,R54), (B4,L5,A1,R55),(B4,L5,A1,R56),(B4,L5,A2,R51),(B4, L5,A2,R52),(B4,L5,A2,R53),(B4,L5,A2,R54),(B4,L5, A2,R55),(B4,L5,A2,R56),(B4,L5,A3,R51),(B4,L5,A3, R52),(B4,L5,A3,R53),(B4,L5,A3,R54),(B4,L5,A3,R55), (B4,L5,A3,R56),(B4,L5,A4,R51),(B4,L5,A4,R52),(B4, L5,A4,R53),(B4,L5,A4,R54),(B4,L5,A4,R55),(B4,L5, A4,R56),(B4,L5,A5,R51),(B4,L5,A5,R52),(B4,L5,A5, R53),(B4,L5,A5,R54),(B4,L5,A5,R55),(B4,L5,A5,R56), (B5,L1,A1,R51),(B5,L1,A1,R52),(B5,L1,A1,R53),(B5, L1,A1,R54),(B5,L1,A 1,R55),(B5,L1,A1,R56),(B5,L1, A2,R51),(B5,L1,A2,R52),(B5,L1,A2,R53),(B5,L1,A2, R54),(B5,L1,A2,R55),(B5,L1,A2,R56),(B5,L1,A3,R51), (B5,L1,A3,R52),(B5,L1,A3,R53),(B5,L1,A3,R54),(B5, L1,A3,R55),(B5,L1,A3,R56),(B5,L1,A4,R51),(B5,L1, A4,R52),(B5,L1,A4,R53),(B5,L1,A4,R54),(B5,L1,A4, R55),(B5,L1,A4,R56),(B5,L1,A5,R51),(B5,L1,A5,R52), (B5,L1,A5,R53),(B5,L1,A5,R54),(B5,L1,A5,R55),(B5, L1,A5,R56),(B5,L2,A1,R51),(B5,L2,A1,R52),(B5,L2, A1,R53),(B5,L2,A1,R54),(B5,L2,A1,R55),(B5,L2,A1, R56),(B5,L2,A2,R51),(B5,L2,A2,R52),(B5,L2,A2,R53), (B5,L2,A2,R54),(B5,L2,A2,R55),(B5,L2,A2,R56),(B5, L2,A3,R51),(B5,L2,A3,R52),(B5,L2,A3,R53),(B5,L2, A3,R54),(B5,L2,A3,R55),(B5,L2,A3,R56),(B5,L2,A4, R51),(B5,L2,A4,R52),(B5,L2,A4,R53),(B5,L2,A4,R54), (B5,L2,A4,R55),(B5,L2,A4,R56),(B5,L2,A5,R51),(B5, L2,A5,R52),(B5,L2,A5,R53),(B5,L2,A5,R54),(B5,L2, A5,R55),(B5,L2,A5,R56),(B5,L3,A1,R51),(B5,L3,A1, R52),(B5,L3,A1,R53),(B5,L3,A1,R54),(B5,L3,A1,R55), (B5,L3,A1,R56),(B5,L3,A2,R51),(B5,L3,A2,R52),(B5, L3,A2,R53),(B5,L3,A2,R54),(B5,L3,A2,R55),(B5,L3, A2,R56),(B5,L3,A3,R51),(B5,L3,A3,R52),(B5,L3,A3, R53),(B5,L3,A3,R54),(B5,L3,A3,R55),(B5,L3,A3,R56), (B5,L3,A4,R51),(B5,L3,A4,R52),(B5,L3,A4,R53),(B5, L3,A4,R54),(B5,L3,A4,R55),(B5,L3,A4,R56),(B5,L3, A5,R51),(B5,L3,A5,R52),(B5,L3,A5,R53),(B5,L3,A5, R54),(B5,L3,A5,R55),(B5,L3,A5,R56),(B5,L4,A1,R51), (B5,L4,A1,R52),(B5,L4,A1,R53),(B5,L4,A1,R54),(B5, L4,A1,R55),(B5,L4,A1,R56),(B5,L4,A2,R51),(B5,L4, A2,R52),(B5,L4,A2,R53),(B5,L4,A2,R54),(B5,L4,A2, R55),(B5,L4,A2,R56),(B5,L4,A3,R51),(B5,L4,A3,R52), (B5,L4,A3,R53),(B5,L4,A3,R54),(B5,L4,A3,R55),(B5, L4,A3,R56),(B5,L4,A4,R51),(B5,L4,A4,R52),(B5,L4, A4,R53),(B5,L4,A4,R54),(B5,L4,A4,R55),(B5,L4,A4, R56),(B5,L4,A5,R51),(B5,L4,A5,R52),(B5,L4,A5,R53), (B5,L4,A5,R54),(B5,L4,A5,R55),(B5,L4,A5,R56),(B5, L5,A1,R51),(B5,L5,A1,R52),(B5,L5,A1,R53),(B5,L5, A1,R54),(B5,L5,A1,R55),(B5,L5,A1,R56),(B5,L5,A2, R51),(B5,L5,A2,R52),(B5,L5,A2,R53),(B5,L5,A2,R54), (B5,L5,A2,R55),(B5,L5,A2,R56),(B5,L5,A3,R51),(B5, L5,A3,R52),(B5,L5,A3,R53),(B5,L5,A3,R54),(B5,L5, A3,R55),(B5,L5,A3,R56),(B5,L5,A4,R51),(B5,L5,A4, R52),(B5,L5,A4,R53),(B5,L5,A4,R54),(B5,L5,A4,R55), (B5,L5,A4,R56),(B5,L5,A5,R51),(B5,L5,A5,R52),(B5, L5,A5,R53),(B5,L5,A5,R54),(B5,L5,A5,R55),(B5,L5, A5,R56).

Test Example 1

Lowering Effect on Brain β Amyloid in Rats

A test compound was suspended in 0.5% methylcellulose, the final concentration was adjusted to 2 mg/mL, and this was orally administered to male Crg:SD rat (7 to 9 week old) at 10 mg/kg. In a vehicle control group, only 0.5% methylcellulose was administered, and an administration test was performed at 3 to 8 animals per group. A brain was isolated 3 hours after administration, a cerebral hemisphere was isolated, a weight thereof was measured, the hemisphere was rapidly frozen in liquid nitrogen, and stored at −80° C. until the day for extraction. The frozen cerebral hemisphere was transferred to a homogenizer manufactured by Teflon (registered trade mark) under ice cooling, a 5-fold volume of a weight of an extraction buffer (containing 1% CHAPS ({3-[(3-chloroamidopropyl) dimethylammonio]-1-propanesulfonate}), 20 mM Tris-HCl (pH 8.0), 150 mM NaCl, Complete (Roche) protease inhibitor) was added, up and down movement was repeated, and this was homogenized to solubilize for 2 minutes. The suspension was transferred to a centrifugation tube, allowed to stand on an ice for 3 hours or more and, thereafter centrifuged at 100,000×g and 4° C. for 20 minutes. After centrifugation, the supernatant was transferred to an ELISA plate (product No. 27730, Immuno-Biological Laboratories) for measuring β amyloid 1-40. ELISA measurement was performed according to the attached instruction. The lowering effect was calculated as a ratio compared to the brain b amyloid 1-40 level of vehicle control group.

TABLE 170

| Compound No. | % of vehicle control group |
| --- | --- |
| 634 | 21.1 |
| 622 | 50.1 |

Compound No. 733, 359, 39, 212, 793, 204, 243, 482 and 1282 also lowered the brain β amyloid 1-40 with approximately 60 to 90% reduction compared to those of a vehicle control group.

Therefore, it is shown that Compound (I) lowers the brain β amyloid 1-40 in rats.

Test Example 2

Lowering Effect on Brain β Amyloid in Mice

A test compound was suspended in 0.5% methylcellulose, the final concentration was adjusted to 10 mg/mL, and this was subcutaneously administered to back of male Crlj:CD-1 (ICR) mouse (7 to 8 week old) at 100 mg/kg. In a vehicle control group, only 0.5% methylcellulose was administered. A test was performed at 4 to 8 animals per group. A brain was isolated 3 hours after administration. The subsequent operations were the same as in the above test in rat.

TABLE 171

| Compound No. | % of vehicle control group |
| --- | --- |
| 1199 | 14.1 |
| 1043 | 15.0 |
| 1100 | 20.2 |
| 127 | 25.2 |
| 605 | 36.5 |
| 396 | 38.4 |
| 1244 | 50.1 |
| 651* | 52.3 |

(*3 hours after 30 mg/kg of subcutaneous administration)

Compounds 309, 165, 739, 1266, 900, 220, 964, 1262 and 1014 also lowered the brain β amyloid 1-40 with approximately 60 to 90% reduction compared to those of vehicle control group.

Therefore, it is shown that Compound (I) lowers the brain β amyloid 1-40 in mice.

Formulation Example 1

A granule containing the following ingredients is prepared.

| Ingredient | Compound represented by formula (I) | 10 mg |
| --- | --- | --- |
| | Lactose | 700 mg |
| | Corn starch | 274 mg |
| | HPC-L | 16 mg |
| | | 1000 mg |

The compound represented by the formula (I) and lactose are passed through a 60 mesh sieve. Corn starch is passed through a 120 mesh sieve. These are mixed with a V-type mixer, to a mixed powder is added a HPC-L (lower viscosity hydroxypropylcellulose) aqueous solution, the materials are kneaded, granulated (extrusion granulation, pore diameter 0.5 to 1 mm), and dried. The resulting dry granule is passed through a sieve using a vibration sieve (12/60 mesh) to obtain a granule.

Formulation Example 2

A granule for filling into a capsule containing the following ingredients is prepared.

| Ingredient | Compound represented by formula (I) | 15 mg |
| --- | --- | --- |
| | Lactose | 90 mg |
| | Corn starch | 42 mg |
| | HPC-L | 3 mg |
| | | 150 mg |

The compound represented by the formula (I) and lactose are passed through a 60 mesh sieve. Corn starch is passed through a 120 mesh sieve. These are mixed, to a mixed powder is added a HPC-L solution, the materials are kneaded, granulated., and dried. The resulting dry granule is size-adjusted, 150 mg of which is filled into a No. 4 hard gelatin capsule.

Formulation Example 3

A tablet containing the Mowing ingredients is prepared.

| Ingredient | Compound represented by the formula (I) | 10 mg |
|---|---|---|
| | Lactose | 90 mg |
| | Microcrystalline cellulose | 30 mg |
| | CMC-Na | 15 mg |
| | Magnesium stearate | 5 mg |
| | | 150 mg |

The compound represented by the formula (I), lactose, microcrystalline cellulose, CMC-Na (carboxymethylcellulose sodium salt) are passed through a 60 mesh sieve, and mixed. Into a mixed powder is mixed magnesium stearate to obtain a mixed powder for tabletting. The present mixed powder is compressed to obtain 150 mg of a tablet.

Formulation Example 4

The following ingredients are warmed, mixed, and sterilized to obtain an injectable.

| Ingredient | Compound represented by the formula (I) | 3 mg |
|---|---|---|
| | Nonionic surfactant | 15 mg |
| | Purified water for injection | 1 ml |

INDUSTRIAL APPLICABILITY

The pharmaceutical composition of the present invention can be a useful medicament for treating disease induced by production, secretion and/or deposition o β amyloid, especially Alzheimer's disease.

The invention claimed is:

1. A method for treating Alzheimer's disease, comprising: administering a composition in an amount effective for treating Alzheimer's disease to a subject in need thereof, wherein the composition contains a compound represented by the general formula (I):

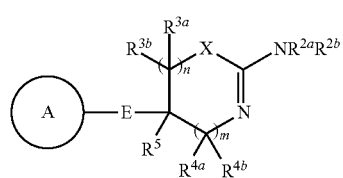

(I)

wherein ring A is

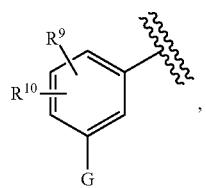

$R^9$ and $R^{10}$ are each independently a hydrogen atom, halogen, hydroxy, cyano, nitro, mercapto, optionally substituted lower alkyl, optionally substituted lower alkoxy, optionally substituted lower alkenyl, optionally substituted lower alkynyl, optionally substituted acyl, optionally substituted acyloxy, carboxy, optionally substituted lower alkoxycarbonyl, optionally substituted lower alkoxycarbonyloxy, optionally substituted lower aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl, optionally substituted lower alkyl sulfinyl, optionally substituted arylsulfinyl, optionally substituted lower alkylsulfonyloxy, optionally substituted arylsulfonyloxy, optionally substituted sulfamoyl, an optionally substituted carbocyclic group, optionally substituted carbocyclicoxy, an optionally substituted heterocyclic group, or optionally substituted heterocyclicoxy;

G is

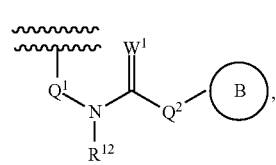

(ii)

wherein $Q^1$ and $Q^2$ are each independently a bond, optionally substituted lower alkylene, or optionally substituted lower alkenylene;

$W^1$ is O or S;

$R^{12}$ is a hydrogen atom, lower alkyl, hydroxy lower alkyl, lower alkoxy lower alkyl, lower alkoxycarbonyl lower alkyl, carbocyclic lower alkyl, or acyl;

ring B is an optionally substituted carbocyclic group or an optionally substituted heterocyclic group,

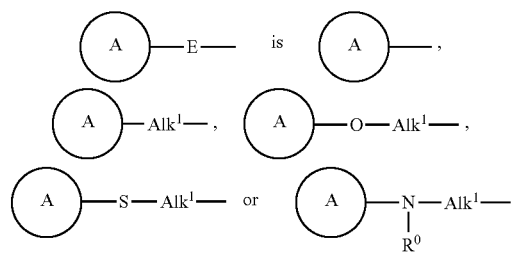

wherein $Alk^1$ is lower alkylene or lower alkenylene;

$R^0$ is a hydrogen atom, lower alkyl, or acyl;

X is S, O, or $NR^1$;

$R^1$ is a hydrogen atom or lower alkyl;

each of $R^{2a}$ and $R^{2b}$ is a hydrogen atom, $R^{3a}$, $R^{3b}$, $R^{4a}$, and $R^{4b}$ are each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group, or an optionally substituted heterocyclic group;

n is 2 and m is 0;

each $R^{3a}$, each $R^{3b}$, each $R^{4a}$, and each $R^{4b}$ may be independently different;

$R^5$ is optionally substituted lower alkyl;

its pharmaceutically acceptable salt, or a solvate thereof as an active ingredient.

2. The method for treating Alzheimer's disease according to claim 1, wherein X is S.

3. The method for treating Alzheimer's disease according to claim 1, wherein E is a bond.

4. The method for treating Alzheimer's disease according to claim 1, wherein ring B is aryl optionally substituted with one or more substituents selected from the group consisting of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy, and an optionally substituted heterocyclic group or heteroaryl optionally substituted with one or more substituents selected from the group consisting of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy, and an optionally substituted heterocyclic group.

5. The method for treating Alzheimer's disease according to claim 1, wherein G is represented by the formula:

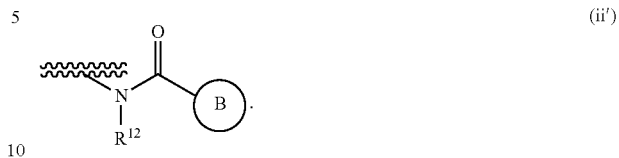

(ii')

6. The method for treating Alzheimer's disease according to claim 1, wherein $R^5$ is C1 to C3 alkyl.

7. The method for treating Alzheimer's disease according to claim 1, wherein $R^5$ is methyl.

8. The method for treating Alzheimer's disease according to claim 1, wherein $R^{3a}$ and $R^{3b}$ are each independently a hydrogen atom, halogen, hydroxy, optionally substituted lower alkyl, optionally substituted lower alkoxy, or optionally substituted aryl.

9. The method for treating Alzheimer's disease according to claim 1, wherein all of $R^{3a}$ and all of $R^{3b}$ are hydrogen atoms.

* * * * *